United States Patent
Kamenecka et al.

(10) Patent No.: US 9,499,517 B2
(45) Date of Patent: *Nov. 22, 2016

(54) SUBSTITUTED PROLINES / PIPERIDINES AS OREXIN RECEPTOR ANTAGONISTS

(71) Applicant: Eolas Therapeutics, Inc., Carlsbad, CA (US)

(72) Inventors: Theodore M. Kamenecka, Palm Beach Gardens, FL (US); Yuanjun He, Palm Beach Gardens, FL (US); William Nguyen, Jupiter, FL (US); Rong Jiang, Millersville, MD (US); Xinyi Song, Bristol, PA (US); Robert Jason Herr, Voorheesville, NY (US); Qin Jiang, Latham, NY (US)

(73) Assignee: Eolas Therapeutics, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/179,432

(22) Filed: Feb. 12, 2014

(65) Prior Publication Data

US 2014/0364432 A1    Dec. 11, 2014

Related U.S. Application Data

(63) Continuation-in-part of application No. PCT/US2013/024903, filed on Feb. 6, 2013.

(60) Provisional application No. 61/596,062, filed on Feb. 7, 2012.

(51) Int. Cl.
| | |
|---|---|
| *A61K 31/445* | (2006.01) |
| *C07D 401/02* | (2006.01) |
| *C07D 401/12* | (2006.01) |
| *A61K 31/40* | (2006.01) |
| *C07D 401/14* | (2006.01) |
| *C07D 417/06* | (2006.01) |
| *C07D 417/14* | (2006.01) |

(52) U.S. Cl.
CPC ............ *C07D 401/12* (2013.01); *A61K 31/40* (2013.01); *A61K 31/445* (2013.01); *C07D 401/14* (2013.01); *C07D 417/06* (2013.01); *C07D 417/14* (2013.01)

(58) Field of Classification Search
CPC .......................... A61K 31/445; C07D 401/02
USPC .................... 546/181, 192; 514/315, 326
See application file for complete search history.

(56) References Cited

U.S. PATENT DOCUMENTS

| | | |
|---|---|---|
| 2008/0132490 A1 | 6/2008 | Bergman et al. |
| 2009/0012073 A1 | 1/2009 | Branch et al. |
| 2009/0203736 A1 | 8/2009 | Knust et al. |
| 2010/0168134 A1 | 7/2010 | Breslin et al. |
| 2010/0184808 A1 | 7/2010 | Aissaoui et al. |
| 2011/0003835 A1 | 1/2011 | Mueller et al. |
| 2011/0263643 A1 | 10/2011 | Cox et al. |
| 2012/0165339 A1 | 6/2012 | Terauchi et al. |
| 2012/0295921 A1 | 11/2012 | Breslin et al. |
| 2014/0364433 A1 | 12/2014 | Kamenecka et al. |

FOREIGN PATENT DOCUMENTS

| | | |
|---|---|---|
| EP | 2161266 A1 | 3/2010 |
| JP | 2010155827 A | 7/2010 |
| WO | WO-9958533 A1 | 11/1999 |
| WO | WO-0047576 A1 | 8/2000 |
| WO | WO-0047577 A1 | 8/2000 |
| WO | WO-0047580 A2 | 8/2000 |
| WO | WO-0185693 A1 | 11/2001 |
| WO | WO-0196302 A1 | 12/2001 |
| WO | WO-0244172 A1 | 6/2002 |
| WO | WO-02051232 A2 | 7/2002 |
| WO | WO-02051838 A1 | 7/2002 |
| WO | WO-02089800 A2 | 11/2002 |
| WO | WO-02090355 A1 | 11/2002 |
| WO | WO-03002559 A2 | 1/2003 |
| WO | WO-03032991 A1 | 4/2003 |
| WO | WO-03037847 A1 | 5/2003 |

(Continued)

OTHER PUBLICATIONS

Heifetz et al., Study of Human Orexin-1 and -2 G-Protein-Coupled Receptors with Novel and Published Antagonists by Modeling, Molecular Dynamics Simulations, and Site-Directed Mutagenesis; Biochemistry, (2012), 3178-3179.

(Continued)

*Primary Examiner* — Golam M M Shameem

(74) *Attorney, Agent, or Firm* — Ropes & Gray LLP

(57) ABSTRACT

The present invention is directed to compounds that modulate the bioactivity of an orexin receptor such as $OX_1$ or $OX_2$, or both; to pharmaceutical compositions and combinations comprising a compound of the invention; to methods of treatment of malconditions in patients wherein modulation of an orexin receptor is medically indicated; and to methods of preparation of compounds of the invention. For example, orexin receptor-modulatory compounds of the present invention can be used in treatment of an eating disorder, obesity, alcoholism or an alcohol-related disorder, drug abuse or addiction including addiction to cocaine, opiates, amphetamines, or nicotine, a sleep disorder, a cognitive dysfunction in a psychiatric or neurologic disorder, depression, anxiety, panic disorder, schizophrenia, Alzheimer's disease, Parkinson's disease, Huntington's chorea, headache, migraine, pain, gastrointestinal diseases, epilepsy, inflammations, immune-related diseases, endocrine-related diseases, cancer, hypertension, behavior disorder, mood disorder, manic depression, dementia, sex disorder, psychosexual disorder, or renal disease.

12 Claims, 2 Drawing Sheets

(56) References Cited

FOREIGN PATENT DOCUMENTS

| | | |
|---|---|---|
| WO | WO-03041711 A1 | 5/2003 |
| WO | WO-03051368 A1 | 6/2003 |
| WO | WO-03051872 A1 | 6/2003 |
| WO | WO-03051873 A1 | 6/2003 |
| WO | WO-2004004733 A1 | 1/2004 |
| WO | WO-2004026866 A1 | 4/2004 |
| WO | WO-2004033418 A2 | 4/2004 |
| WO | WO-2004041791 A1 | 5/2004 |
| WO | WO-2004041807 A1 | 5/2004 |
| WO | WO-2004041816 A1 | 5/2004 |
| WO | WO-2004052876 A1 | 6/2004 |
| WO | WO-2004085403 A1 | 10/2004 |
| WO | WO-2004096780 A1 | 11/2004 |
| WO | WO-2005060959 A1 | 7/2005 |
| WO | WO-2005075458 A1 | 8/2005 |
| WO | WO-2005118548 A1 | 12/2005 |
| WO | WO-2006067224 A2 | 6/2006 |
| WO | WO-2006110626 A1 | 10/2006 |
| WO | WO-2006127550 A1 | 11/2006 |
| WO | WO-2007008276 A2 | 1/2007 |
| WO | WO-2007019234 A2 | 2/2007 |
| WO | WO-2007025069 A2 | 3/2007 |
| WO | WO-2007061763 A2 | 5/2007 |
| WO | WO-2007/085718 A1 | 8/2007 |
| WO | WO-2007/088276 A2 | 8/2007 |
| WO | WO-2007085178 A1 | 8/2007 |
| WO | WO-2007116374 A1 | 10/2007 |
| WO | WO-2007122591 A2 | 11/2007 |
| WO | WO-2007126934 A2 | 11/2007 |
| WO | WO-2007143856 A1 | 12/2007 |
| WO | WO-2008008517 A2 | 1/2008 |
| WO | WO-2008008518 A1 | 1/2008 |
| WO | WO-2008008551 A2 | 1/2008 |
| WO | WO-2008020405 A2 | 2/2008 |
| WO | WO-2008026149 A1 | 3/2008 |
| WO | WO-2008038251 A2 | 4/2008 |
| WO | WO-2008065626 A2 | 6/2008 |
| WO | WO-2008078291 A1 | 7/2008 |
| WO | WO-2008081399 A2 | 7/2008 |
| WO | WO-2008087611 A2 | 7/2008 |
| WO | WO-2008107335 A1 | 9/2008 |
| WO | WO-2008108991 A1 | 9/2008 |
| WO | WO-2008110488 A1 | 9/2008 |
| WO | WO-2008117241 A2 | 10/2008 |
| WO | WO-2008122513 A1 | 10/2008 |
| WO | WO-2008/143856 A1 | 11/2008 |
| WO | WO-2008139416 A1 | 11/2008 |
| WO | WO-2008147518 A1 | 12/2008 |
| WO | WO-2008150364 A1 | 12/2008 |
| WO | WO-2009004584 A1 | 1/2009 |
| WO | WO-2009016087 A1 | 2/2009 |
| WO | WO-2009016560 A2 | 2/2009 |
| WO | WO-2009016564 A2 | 2/2009 |
| WO | WO-2009020642 A1 | 2/2009 |
| WO | WO-2009022311 A2 | 2/2009 |
| WO | WO-2009040730 A2 | 4/2009 |
| WO | WO-2009058238 A1 | 5/2009 |
| WO | WO-2009079637 A1 | 6/2009 |
| WO | WO-2009080533 A1 | 7/2009 |
| WO | WO-2009092642 A1 | 7/2009 |
| WO | WO-2009104155 A1 | 8/2009 |
| WO | WO-2009124956 A1 | 10/2009 |
| WO | WO-2009150614 A1 | 12/2009 |
| WO | WO-2009153180 A1 | 12/2009 |
| WO | WO-2009156951 A2 | 12/2009 |
| WO | WO-2010004507 A1 | 1/2010 |
| WO | WO-2010012620 A1 | 2/2010 |
| WO | WO-2010017260 A1 | 2/2010 |
| WO | WO-2010044054 A1 | 4/2010 |
| WO | WO-2010048010 A1 | 4/2010 |
| WO | WO-2010048012 A1 | 4/2010 |
| WO | WO-2010048013 A1 | 4/2010 |
| WO | WO-2010048014 A1 | 4/2010 |
| WO | WO-2010048016 A1 | 4/2010 |
| WO | WO-2010048017 A1 | 4/2010 |
| WO | WO-2010051236 A1 | 5/2010 |
| WO | WO-2010051237 A1 | 5/2010 |
| WO | WO-2010051238 A1 | 5/2010 |
| WO | WO-2010060470 A1 | 6/2010 |
| WO | WO-2010060471 A1 | 6/2010 |
| WO | WO-2010060472 A1 | 6/2010 |
| WO | WO-2010063662 A1 | 6/2010 |
| WO | WO-2010063663 A1 | 6/2010 |
| WO | WO-2010072722 A1 | 7/2010 |
| WO | WO-2010086366 A1 | 8/2010 |
| WO | WO-2010122151 A1 | 10/2010 |
| WO | WO-2011005636 A1 | 1/2011 |
| WO | WO-2011006960 A1 | 1/2011 |
| WO | WO-2011023578 A1 | 3/2011 |
| WO | WO-2011023585 A1 | 3/2011 |
| WO | WO-2011050198 A1 | 4/2011 |
| WO | WO-2011050200 A1 | 4/2011 |
| WO | WO-2011050202 A1 | 4/2011 |
| WO | WO-2011053522 A1 | 5/2011 |
| WO | WO-2011061318 A1 | 5/2011 |
| WO | WO-2011073316 A1 | 6/2011 |
| WO | WO-2011076744 A1 | 6/2011 |
| WO | WO-2011076747 A1 | 6/2011 |
| WO | WO-2011138265 A2 | 11/2011 |
| WO | WO-2011138266 A1 | 11/2011 |
| WO | WO-2012081692 A1 | 6/2012 |
| WO | WO-2012085852 A1 | 6/2012 |
| WO | WO-2012085857 A1 | 6/2012 |
| WO | WO-2012089606 A1 | 7/2012 |
| WO | WO-2012089607 A1 | 7/2012 |
| WO | WO-2012101487 A1 | 8/2012 |
| WO | WO-2012110986 A1 | 8/2012 |
| WO | WO-2012114252 A1 | 8/2012 |
| WO | WO-2012145581 A1 | 10/2012 |
| WO | WO-2012153729 A1 | 11/2012 |
| WO | WO-2013005755 A1 | 1/2013 |
| WO | WO-2013050938 A1 | 4/2013 |
| WO | WO-2013059163 A1 | 4/2013 |
| WO | WO-2013059222 A1 | 4/2013 |
| WO | WO-2013062857 A1 | 5/2013 |
| WO | WO-2013062858 A1 | 5/2013 |
| WO | WO-2013068935 A1 | 5/2013 |
| WO | WO-2013092893 A1 | 6/2013 |
| WO | WO-2013119639 A1 | 8/2013 |
| WO | WO-2013123240 A1 | 8/2013 |
| WO | WO-2013127913 A1 | 9/2013 |
| WO | WO-2013139730 A1 | 9/2013 |
| WO | WO-2015/123355 A1 | 8/2015 |

OTHER PUBLICATIONS

Hirose et al., N-Acyl 6,7-Dimethoxy-1,2,3,4-tetrahydroisoquinoline: The First Orexin-2 Receptor Selective Non-peptidic Antagonist; Bioorganic & Medicinal Chemistry Letters, (2003) 4497-4499.

Jiang, et al., Disubstituted piperidines as potent orexin (hypocretin) receptor antagonists; Bioorganic & Medicinal Chemistry Letters 22 (2012) 3890-3893.

Whitman et al., Discovery of a Potent, CNS-Penetrant Orexin Receptor Antagonist Based on an N,N-Disubstituted-1,4-diazepane Scaffold that Promotes Sleep in Rats; ChemMedChem (2009),1069-1074.

Di Fabio, et al. "Discovery process and pharmacological characterization of a novel dual orexin 1 and orexin 2 receptor antagonist useful for treatment of sleep disorders", Bioorganic & Medicinal Chemistry Letters, Elsevier Ltd., 21 (18):5562-5567 (2011).

Gatfield, et al., "Orexin Receptor Antagonists: A New Concept in CNS Disorders?", ChemMedChem 5(8):1197-1214 (2010).

1A

1B

1C

1D

2A

2B

SUBSTITUTED PROLINES / PIPERIDINES AS OREXIN RECEPTOR ANTAGONISTS

CROSS-REFERENCE TO RELATED APPLICATIONS

This application claims priority to PCT Application No. PCT/US2013/024903, filed Feb. 6, 2013, which claims priority to U.S. provisional application Ser. No. 61/596,062, filed Feb. 7, 2012, the content of each of which is incorporated herein by reference in its entirety.

STATEMENT OF GOVERNMENT SUPPORT

This invention was made with government support under Grant Numbers 5 RO1 DA023915 and 1 PO1 DA033622 awarded by the National Institutes of Health. The government has certain rights in this invention.

BACKGROUND

Orexins are a family of homologous peptides including species orexin A, or OR-A, and orexin B, or OR-B. Orexin A is a 33 amino acid peptide and orexin B is a 28 amino acid peptide (Sakurai T. et al., Cell (1998), 92, 573-585). Orexins are produced in neurons of the lateral hypothalamus and bind to at least two distinct G-protein-coupled receptors, termed $OX_1$ and $OX_2$ receptors. The receptor $OX_1$ is selective for OR-A, while the receptor $OX_2$ can bind both OR-A and OR-B. Orexins are found to stimulate food consumption, regulate states of sleep and wakefulness, and may be involved in neural mechanisms of drug abuse and addiction.

SUMMARY

The present invention is directed to compounds that can modulate the bioactivity of an orexin receptor such as $OX_1$ or $OX_2$, or both; to pharmaceutical compositions and combinations comprising a compound of the invention; to methods of treatment of malconditions in patients wherein modulation of an orexin receptor is medically indicated; and to methods of preparation of compounds of the invention.

In various embodiments, the invention provides receptor-modulatory non-peptidic small molecules that can activate or inhibit one or more classes of orexin receptors in the human nervous system. In various embodiments, the invention provides a compound of formula (I),

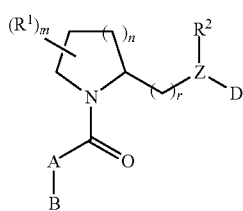

(I)

wherein
A comprises aryl or heteroaryl;
B is absent, or comprises aryl, aryloxy, heteroaryl, or heteroaryloxy;
wherein A or B or both can each independently be unsubstituted or can each independently be mono- or multi-substituted with J or with R', or both;
D comprises aryl, aroyl, heteroaryl, or heteroaroyl, wherein D can be unsubstituted or can be mono- or independently multi-substituted with J or with R', or with both;
Z is N or O, provided that when Z is O, $R^2$ is absent
$R^1$ comprises independently at each occurrence halo, oxo, hydroxy, cyano, $(C_{1-4})$alkyl, $(C_{1-4})$alkoxy, $(C_{1-4})$acyloxy, $(C_{1-4})$acylamido, haloalkyl, haloalkoxy, $NR^aR^b$, $C(=O)NR^aR^b$, $C(=O)OR^a$, $SO_2R^a$, $SO_2NR^aR^b$, cycloalkyl, heterocyclyl, aryl, aralkyl, or heteroaryl;
or one or more $R^1$ groups together with the ring to which they are bonded form a bicyclo[2.2.2], bicyclo[3.3.0], or bicyclo[4.3.0] ring system, wherein any bicyclo ring system can be cis-fused or trans-fused, wherein any alkyl, alkoxy, bicyclo ring system, cycloalkyl, heterocyclyl, aryl, aralkyl, or heteroaryl can be mono- or independently multi-substituted with J or with R', or with both;
$R^a$ and $R^b$ are independently at each occurrence H, $(C_{1-4})$alkyl, aralkyl, $(C_{1-5})$acyl, or $R^a$ and $R^b$ together with the nitrogen atom to which they are bonded form a 4-7 membered ring optionally further comprising 1 or 2 $NR^c$, O, S, SO, or $SO_2$, wherein $R^c$ is H or $(C_{1-4})$alkyl, wherein any $R^a$, $R^b$, or $R^c$ can be mono- or independently multi-substituted with J or with R', or both;
$R^2$ comprises H, $(C_{1-4})$alkyl, or $(C_{1-5})$acyl, or $R^2$ together with D and the nitrogen atom to which they are bonded form a phthalimido group, wherein any alkyl, acyl, or phthalimido group is optionally mono- or independently multi-substituted with J or with R', or with both;
J is halogen, (C1-C6)alkyl, OR', CN, $CF_3$, $OCF_3$, =O, =S, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}C(O)N(R')_2$, $(CH_2)_{0-p}C(S)N(R')_2$, $(CH_2)_{0-p}NH\text{—}C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;
wherein, each R' is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$ cycloalkyl or $(C_3-C_{10})$-cycloalkenyl]-[$(C_1-C_{12})$-alkyl or $(C_2-C_{12})$-alkenyl or $(C_2-C_{12})$-alkynyl], $(C_6-C_{10})$-aryl, $(C_6-C_{10})$-aryl-[$(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-[$(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-[$(C_1-C_{12})$-alkyl or $(C_2-C_{12})$-alkenyl or $(C_2-C_{12})$-alkynyl], wherein R' is substituted with 0-3 substituents selected independently from $J^R$;
or, when two R' are bound to a nitrogen atom or to two adjacent nitrogen atoms, the two R' groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N, NR', O, S, S(O) and $S(O)_2$, wherein each ring is substituted with 0-3 substituents selected independently from $J^R$; wherein, in any bicyclic or tricyclic ring system, each ring is linearly fused, bridged, or spirocyclic, wherein each ring is either aromatic or nonaromatic, wherein each ring can be fused to a $(C_6-C_{10})$aryl, mono- or bicyclic 5-10 membered heteroaryl, $(C_3-C_{10})$cycloalkyl or mono- or bicyclic 3-10 membered heterocyclyl;

$J^R$ is halogen, OR, CN, CF$_3$, OCF$_3$, =O, =S, C(O), S(O), methylenedioxy, ethylenedioxy, $(CH_2)_{0-p}N(R)_2$, $(CH_2)_{0-p}SR$, $(CH_2)_{0-p}S(O)R$, $(CH_2)_{0-p}S(O)_2R$, $(CH_2)_{0-p}S(O)_2N(R)_2$, $(CH_2)_{0-p}SO_3R$, $(CH_2)_{0-p}C(O)R$, $(CH_2)_{0-p}C(O)C(O)R$, $(CH_2)_{0-p}C(O)CH_2C(O)R$, $(CH_2)_{0-p}C(S)R$, $(CH_2)_{0-p}C(O)OR$, $(CH_2)_{0-p}C(O)R$, $(CH_2)_{0-p}C(O)N(R)_2$, $(CH_2)_{0-p}C(O)N(R)_2$, $(CH_2)_{0-p}C(S)N(R)_2$, $(CH_2)_{0-p}NH-C(O)R$, $(CH_2)_{0-p}N(R)N(R)C(O)R$, $(CH_2)_{0-p}N(R)N(R)C(O)OR$, $(CH_2)_{0-p}N(R)N(R)CON(R)_2$, $(CH_2)_{0-p}N(R)SO_2R$, $(CH_2)_{0-p}N(R)SO_2N(R)_2$, $(CH_2)_{0-p}N(R)C(O)OR$, $(CH_2)_{0-p}N(R)C(O)R$, $(CH_2)_{0-p}N(R)C(S)R$, $(CH_2)_{0-p}N(R)C(O)N(R)_2$, $(CH_2)_{0-p}N(R)C(S)N(R)_2$, $(CH_2)_{0-p}N(COR)COR$, $(CH_2)_{0-p}N(OR)R$, $(CH_2)_{0-p}C(=NH)N(R)_2$, $(CH_2)_{0-p}C(O)N(OR)R$, or $(CH_2)_{0-p}C(=NOR)R$; and, R is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$cycloalkyl or $(C_3-C_{10})$-cycloalkenyl]-$[(C_1-C_{12})$-alkyl or $(C_2-C_{12})$-alkenyl or $(C_2-C_{12})$-alkynyl], $(C_6-C_{10})$-aryl, $(C_6-C_{10})$-aryl-$[(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-$[(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-$[(C_1-C_{12})$-alkyl or $(C_2-C_{12})$-alkenyl or $(C_2-C_{12})$-alkynyl];

m is 0, 1, 2, 3, 4, 5, or 6; n is 1, 2, or 3; p=0, 1, or 2; r=0, 1, 2, or 3;

or any salt or hydrate thereof.

In various embodiments, the invention provides pharmaceutical compositions comprising a compound of the invention and a pharmaceutically acceptable excipient.

In various embodiments, the invention provides a method of modulating an orexin receptor, such as $OX_1$ or $OX_2$, or both, comprising contacting the receptor with an effective amount or concentration of a compound of the invention.

In various embodiments, the invention provides a method of treating a malcondition in a patient wherein modulation of an orexin receptor is medically indicated, comprising administering to the patient a compound of the invention in a dose, at a frequency, and for a duration to provide a beneficial effect to the patient. The orexin receptor can be $OX_1$, or can be $OX_2$. In various embodiments, the malcondition can comprise an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, head ache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. Drug abuse and addiction can include abuse of or addiction to cocaine, opiates, amphetamines, ethanol, cannabis/marijuana, or nicotine.

BRIEF DESCRIPTION OF THE FIGURES

FIG. 1A shows the food acquisition results for knock-out (KO) and wild-type (WT) mice. FIG. 1B shows the food acquisition results for Example 11. FIG. 1C shows the results for mice that were given a virus to site-specifically restore Hcrt-1R expression or an empty vector (control) in the dorsal thalamus three weeks prior to the initiation of the experiment. FIG. 1D shows that lentiviral restoration of Hcrt-1R expression in the dorsal thalamus of KO mice restored nicotine self-administration.

FIG. 2A shows the effect of the test compound on food self-administration. FIG. 2B shows the results for JNJ10397049 in the nicotine self-administration arm.

DETAILED DESCRIPTION

Figure 1:
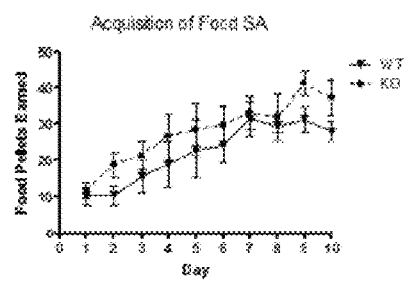
FIG. 1 shows the results of testing Example 11 in a food and nicotine self-administration assay.
Figure 1:
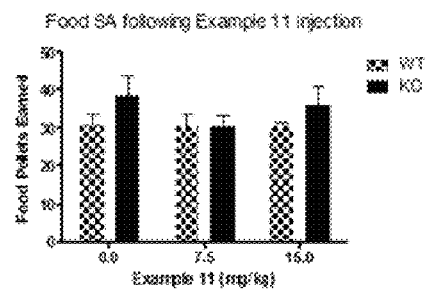
Figure 1:
Figure 1:
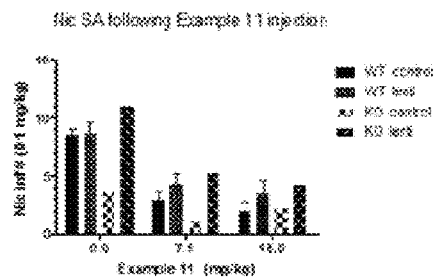

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein an orexin receptor plays a role in the biochemical mechanisms involved in the disease or malcondition such that a therapeutically beneficial effect can be achieved by acting on the receptor. "Acting on" an orexin receptor can include binding to the orexin receptor and/or inhibiting the bioactivity of the orexin receptor.

The expression "effective amount", when used to describe therapy to an individual suffering from a disorder, refers to the amount of a compound of the invention that is effective to inhibit or otherwise act on an orexin receptor in the individual's tissues wherein the orexin receptor involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention. In various embodiments, the invention can provide enantiomerically pure forms of the claimed compounds, or racemic mixtures, or enantiomerically enriched mixtures, or (when more than a single chiral center is present), diastereomerically pure compounds, or diastereomeric mixtures in any relative proportions.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium (1H), deuterium (2H), or tritium (3H) in any combination. Similarly, any carbon atom or set thereof in a molecule can be any of the isotopic form of carbons, such as 11C, 12C, 13C, or 14C, or any nitrogen atom or set thereof in a molecule can be any of the isotopic forms of nitrogen, such as 13N, 14N, or 15N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or 14C radiolabeled sample where only some fraction of the set of molecules making up the macroscopic sample contains a radioactive atom. It is also understood that many elements that are not artificially isotopically enriched themselves are mixtures of naturally occurring isotopic forms, such as 14N and 15N, 32S and 34S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, 14C and 3H can be prepared using neutrons generated in a nuclear reactor. Following nuclear transformation, 14C and 3H are incorporated into precursor molecules, followed by further elaboration as needed.

Additional isotopically labeled forms include isotopes of hydrogen, carbon, nitrogen, oxygen, phosphorous, fluorine, chlorine, and iodine, such as 2H, 3H, 11C, 13C, 14C, 15N, 18O, 17O, 31P, 32P, 35S, 18F, 36Cl, and 125I, respectively. Such isotopically labeled compounds are useful in metabolic studies (preferably with 14C), reaction kinetic studies (with, for example 2H or 3H), detection or imaging techniques [such as positron emission tomography (PET) or single-photon emission computed tomography (SPECT)] including drug or substrate tissue distribution assays, or in radioactive treatment of patients. In particular, an 18F or 11C labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," NeuroRx 2005, 2(2), 226-236, and references cited therein. Further, substitution with heavier isotopes such as deuterium (i.e., 2H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

A "carboxyl-activating" group or procedure, as the term is used herein, refers to a group replacing the hydroxyl group of a carboxyl to form a species that more readily undergoes reactions with nucleophilic reagents such as alcohols and amines. An example is an acyl halide, such as an acid chloride, that is activated for reactions leading to the formation of esters and amides. Another example is an N-hydroxy ester of a carboxylic acid, such as an N-hydroxysuccinimide ester, or an N-hydroxybenztriazole ester. Another example is a carbodiimide that reacts with the hydroxyl group of a carboxyl group to form an O-acylisourea, that is thus activated for subsequent reaction with a nucleophile.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')2, CN, NO, NO2, ONO2, azido, CF3, OCF3, R', O (oxo), S (thiono), C(O), S(O), methylenedioxy, ethylenedioxy, N(R')$_2$, SR', SOR', SO2R', SO2N(R')2, SO3R', C(O)R', C(O)C(O)R', C(O)CH2C(O)R', C(S)R', C(O)OR', OC(O)R', C(O)N(R')2, OC(O)N(R')2, C(S)N(R')2, (CH2)0-2N(R')C(O)R', (CH2)0-2N(R')N(R')2, N(R')N(R')C(O)R', N(R')N(R')C(O)OR', N(R')N(R')CON(R')2, N(R')SO2R', N(R')SO2N(R')2, N(R') C(O)OR', N(R')C(O)R', N(R')C(S)R', N(R')C(O)N(R')2, N(R')C(S)N(R')2, N(COR')COR', N(OR')R', C(=NH)N(R') 2, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)2 can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH2)n or (CR'2)n wherein n is 1, 2, 3, or more, and each R' is independently selected.

C(O) and S(O)2 groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)2 group is bound to one carbon and one nitrogen atom, the resulting unit is termed a "sulfonamide." When a S(O)2 group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyamines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH(CH3), —CH═C(CH3)2, —C(CH3)═CH2, —C(CH3)═CH(CH3), —C(CH2CH3)═CH2, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C (CH₃), —C≡C(CH2CH3), —CH2C≡CH, —CH2C≡C (CH3), and —CH2C≡C(CH2CH3) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH2-CH2-CH3, —CH2-CH2CH2-OH, —CH2-CH2-NH—CH3, —CH2-S—CH2-CH3, —CH2CH2-S(=O)—CH3, and —CH2CH2-O—CH2CH2-O—CH3. Up to two heteroatoms may be consecutive, such as, for example, —CH2-NH—OCH3, or —CH2-CH2-S—S—CH3.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH3, —CH=CH—CH2-OH, —CH2-CH=N—OCH3, —CH=CH—N(CH3)-CH3, —CH2-CH=CH—CH2-SH, and —CH=CH—O—CH2CH2-O—CH3.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

An "aroyl" group, as the term is used herein, refers to an aryl group bonded via an exocyclic carbonyl group, such as a benzoyl group.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C2-heterocyclyl can be a 5-ring with two carbon atoms and three heteroatoms, a 6-ring with two carbon atoms and four heteroatoms and so forth. Likewise a C4-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzodioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. In some embodiments, heteroaryl groups have 5, 6, 8, 9, or 10 ring members. A heteroaryl group is a variety of a heterocyclyl group that possesses an aromatic electronic structure. A heteroaryl group designated as a C2-heteroaryl can be a 5-ring with two carbon atoms and three heteroatoms, a 6-ring with two carbon atoms and four heteroatoms and so forth. Likewise a C4-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, imidazolyl, triazolyl, tetrazolyl, oxazolyl, isoxazolyl, thiazolyl, isothiazolyl, oxadiazolyl, thiadiazolyl, pyridinyl, pyrimidinyl, pyridazinyl, pyrazinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

A "heteroaroyl" group, as the term is used herein, refers to a heteroaryl group bonded via an exocyclic carbonyl group, analogous to a benzoyl group but wherein the phenyl ring of the benzoyl group is replaced by a heteroaryl group.

Various synonyms can be used throughout in the naming of heteroaryl groups, among others. As used herein, the term "pyridyl" is synonymous with "pyridinyl," the term "quinolyl" is synonymous with the term "quinolinyl," and so forth. The term "phthalimidoyl" or "phthalimido" refers to a phthalimide group bonded by its nitrogen atom. The term "pyridoyl" refers to a pyridylcarbonyl group; the term "quinoloyl" refers to a quinolylcarbonyl group, and so forth. The carbonyl group can be disposed at any position; for example, for "pyridoyl", any of the following structures are indicated:

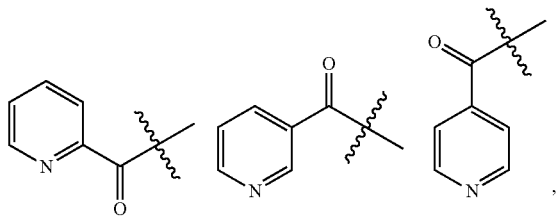 [SMILES: *C(=O)c1ccccn1 ; *C(=O)c1cccnc1 ; *C(=O)c1ccncc1 ; ","]

wherein a wavy line indicates a point of attachment. Similarly, the term "quinoloyl" refers to a quinoline ring bearing a carbonyl group at any chemically feasible position of substitution, the term "isoquinoloyl" refers to an isoquinoline ring bearing a carbonyl group at any chemically feasible position of substitution, and so forth.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "(Cx-Cy)perfluoroalkyl," wherein x<y, means an alkyl group with a minimum of x carbon atoms and a maximum of y carbon atoms, wherein all hydrogen atoms are replaced by fluorine atoms. Preferred is —(C1-C6) perfluoroalkyl, more preferred is —(C1-C3)perfluoroalkyl, most preferred is —CF3.

The term "(Cx-Cy)perfluoroalkylene," wherein x<y, means an alkyl group with a minimum of x carbon atoms and a maximum of y carbon atoms, wherein all hydrogen atoms are replaced by fluorine atoms. Preferred is —(C1-C6)perfluoroalkylene, more preferred is —(C1-C3)perfluoroalkylene, most preferred is —CF2-.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—NH2, for example, alkylamines, arylamines, alkylarylamines; R2NH wherein each R is independently selected, such as dialkylamines, diarylamines, aralkylamines, heterocyclylamines and the like; and R3N wherein each R is independently selected, such as trialkylamines, dialkylarylamines, alkyldiarylamines, triarylamines, and the like. The term "amine" also includes ammonium ions as used herein.

An "amino" group is a substituent of the form —NH2, —NHR, —NR2, —NR3+, wherein each R is independently selected, and protonated forms of each, except for —NR3+, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion NH4+, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)NR2, and —NRC(O)R groups, respectively. Amide groups therefore include but are not limited to primary carboxamide groups (—C(O)NH2) and formamide groups (—NHC(O)H). A "carboxamido" group is a group of the formula C(O)NR2, wherein R can be H, alkyl, aryl, etc.

The term "azido" refers to an N3 group. An "azide" can be an organic azide or can be a salt of the azide (N3-) anion. The term "nitro" refers to an NO2 group bonded to an organic moiety. The term "nitroso" refers to an NO group bonded to an organic moiety. The term nitrate refers to an ONO2 group bonded to an organic moiety or to a salt of the nitrate (NO3-) anion.

The term "urethane" ("carbamoyl" or "carbamyl") includes N- and O-urethane groups, i.e., —NRC(O)OR and —OC(O)NR2 groups, respectively.

The term "sulfonamide" (or "sulfonamido") includes S- and N-sulfonamide groups, i.e., —SO2NR2 and —NRSO2R groups, respectively. Sulfonamide groups therefore include but are not limited to sulfamoyl groups (—SO2NH2). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)NR2. Typically, an amidino group is —C(NH)NH2.

The term "guanidine" or "guanidino" includes groups of the formula —NRC(NR)NR2. Typically, a guanidino group is —NHC(NH)NH2.

The invention can provide a salt form of a compound of the invention, i.e., a structure as shown, but in the form of a salt, such as a salt of an amine and an acid. Compounds of the invention can be amines, and as such can form salts with organic or inorganic acids. Salts can be used either as dosing forms for patients, in which case the salts are "pharmaceutically acceptable salts", or can be salts formed with any acid that is useful, e.g., in chemical processing. A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH4+ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

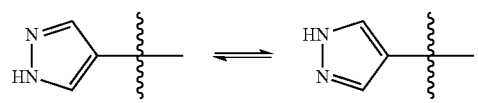 [SMILES: *c1cn[nH]c1 ; *c1cn[nH]c1]

Such tautomerism can also occur with substituted pyrazoles such as 3-methyl, 5-methyl, or 3,5-dimethylpyrazole, and the like. Another example of tautomerism is amidoimido (lactam-lactim when cyclic) tautomerism, such as is seen in heterocyclic compounds bearing a ring oxygen atom adjacent to a ring nitrogen atom. For example, the equilibrium:

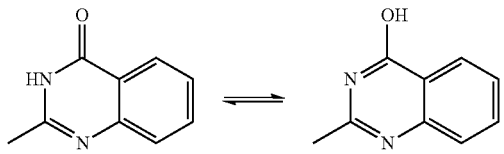

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

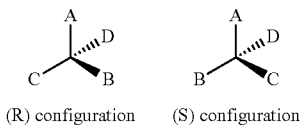

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight. Compounds of the present invention are provided in any of these degrees of enantiomeric purity, e.g., a racemic mixture of enantiomers (50% enantiomerically pure), or 80% enantiomerically pure, or 90% enantiomerically pure, or 98% enantiomerically pure, or 99+% enantiomerically pure.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Isolated optical isomers (enantiomerically pure compounds) can also be prepared by the use of chiral intermediates or catalysts in synthesis. When a chiral synthetic intermediate is used, the optical center (chiral center) can be preserved without racemization throughout the remainder of the preparative procedure, as is well known in the art. Chiral catalyst can be used to impart at least some degree of enantiomeric purity to products of reactions catalyzed by the chiral catalyst. And, in some cases, compounds having at least some degree of enantiomeric enrichment can be obtained by physical processes such as selective crystallization of salts or complexes formed with chiral adjuvants.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

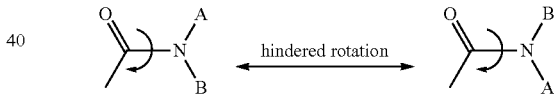

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

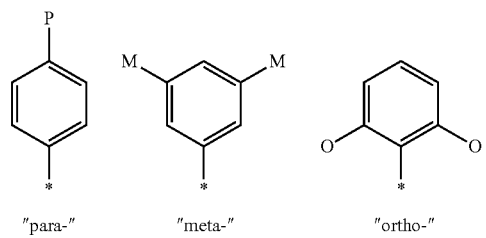

In various embodiments, a compound as shown in any of the Examples, or among the exemplary compounds, is provided.

Provisos may apply to any of the disclosed categories or embodiments wherein any one or more of the other above disclosed embodiments or species may be excluded from such categories or embodiments.

In various embodiments, the compound or set of compounds, such as are used in the inventive methods, can be any one of any of the combinations and/or sub-combinations of the above-listed embodiments.

DESCRIPTION

In various embodiments, the invention provides a compound of formula (I),

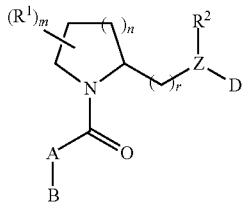

(I)

wherein
A comprises aryl or heteroaryl;
B is absent, or comprises aryl, aryloxy, heteroaryl, or heteroaryloxy;
wherein A or B or both can each independently be unsubstituted or can each independently be mono- or multi-substituted with J or with R', or with both;
D comprises aryl, aroyl, heteroaryl, or heteroaroyl, wherein D can be unsubstituted or can be mono- or independently multi-substituted with J or with R', or with both;
Z is N or O, provided that when Z is O, $R^2$ is absent
$R^1$ comprises independently at each occurrence halo, oxo, hydroxy, cyano, $(C_{1-4})$alkyl, $(C_{1-4})$alkoxy, $(C_{1-4})$acyloxy, $(C_{1-4})$acylamido, haloalkyl, haloalkoxy, $NR^aR^b$, $C(=O)NR^aR^b$, $C(=O)OR^a$, $SO_2R^a$, $SO_2NR^aR^b$, cycloalkyl, heterocyclyl, aryl, aralkyl, or heteroaryl;
or one or more $R^1$ groups together with the ring to which they are bonded form a bicyclo[2.2.2], bicyclo[3.3.0], or bicyclo[4.3.0] ring system, wherein any bicyclo ring system can be cis-fused or trans-fused, wherein any alkyl, alkoxy, bicyclo ring system, cycloalkyl, heterocyclyl, aryl, aralkyl, or heteroaryl can be mono- or independently multi-substituted with J or with R', or with both;
$R^a$ and $R^b$ are independently at each occurrence H, $(C_{1-4})$alkyl, aralkyl, $(C_{1-5})$acyl, or $R^a$ and $R^b$ together with the nitrogen atom to which they are bonded form a 4-7 membered ring optionally further comprising 1 or 2 $NR^c$, O, S, SO, or $SO_2$, wherein $R^c$ is H or $(C_{1-4})$alkyl, wherein any $R^a$, $R^b$, or $R^c$ can be mono- or independently multi-substituted with J or with R', or with both;
$R^2$ comprises H, $(C_{1-4})$alkyl, or $(C_{1-5})$acyl, or $R^2$ together with D and the nitrogen atom to which they are bonded form a phthalimido group, wherein any alkyl, acyl, or phthalimido group is optionally mono- or independently multi-substituted with J or with R', or with both;
J is halogen, (C1-C6)alkyl, OR', CN, $CF_3$, $OCF_3$, =O, =S, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)C(O)R'$, $(CH_2)_{0-p}C(O)CH_2C(O)R$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R')_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$;
wherein, each R' is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$cycloalkyl or $(C_3-C_{10})$-cycloalkenyl]-$[(C_1-C_{12})$-alkyl or $(C_2-C_{12})$-alkenyl or $(C_2-C_{12})$-alkynyl], $(C_6-C_{10})$-aryl, $(C_6-C_{10})$-aryl-$[(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-$[(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-$[(C_1-C_{12})$-alkyl or $(C_2-C_{12})$-alkenyl or $(C_2-C_{12})$-alkynyl], wherein R' is substituted with 0-3 substituents selected independently from $J^R$;
or, when two R' are bound to a nitrogen atom or to two adjacent nitrogen atoms, the two R' groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N, NR', O, S, S(O) and $S(O)_2$, wherein each ring is substituted with 0-3 substituents selected independently from $J^R$; wherein, in any bicyclic or tricyclic ring system, each ring is linearly fused, bridged, or spirocyclic, wherein each ring is either aromatic or nonaromatic, wherein each ring can be fused to a $(C_6-C_{10})$aryl, mono- or bicyclic 5-10 membered heteroaryl, $(C_3-C_{10})$cycloalkyl or mono- or bicyclic 3-10 membered heterocyclyl;
$J^R$ is halogen, OR, CN, $CF_3$, $OCF_3$, =O, =S, C(O), S(O), methylenedioxy, ethylenedioxy, $(CH_2)_{0-p}N(R)_2$, $(CH_2)_{0-p}SR$, $(CH_2)_{0-p}S(O)R$, $(CH_2)_{0-p}S(O)_2R$, $(CH_2)_{0-p}S(O)_2N(R)_2$, $(CH_2)_{0-p}SO_3R$, $(CH_2)_{0-p}C(O)R$, $(CH_2)_{0-p}C(O)C(O)R$, $(CH_2)_{0-p}C(O)CH_2C(O)R$, $(CH_2)_{0-p}C(S)R$, $(CH_2)_{0-p}C(O)OR$, $(CH_2)_{0-p}OC(O)R$, $(CH_2)_{0-p}C(O)N(R)_2$, $(CH_2)_{0-p}OC(O)N(R)_2$, $(CH_2)_{0-p}C(S)N(R)_2$, $(CH_2)_{0-p}NH—C(O)R$, $(CH_2)_{0-p}N(R)N(R)C(O)R$, $(CH_2)_{0-p}N(R)N(R)C(O)OR$, $(CH_2)_{0-p}N(R)N(R)CON(R)_2$, $(CH_2)_{0-p}N(R)SO_2R$, $(CH_2)_{0-p}N(R)SO_2N(R)_2$, $(CH_2)_{0-p}N(R)C(O)OR$, $(CH_2)_{0-p}N(R)C(O)R$, $(CH_2)_{0-p}N(R)C(S)R$, $(CH_2)_{0-p}N(R)C(O)N(R)_2$, $(CH_2)_{0-p}N(R)C(S)N(R)_2$, $(CH_2)_{0-p}N(COR)COR$, $(CH_2)_{0-p}N(OR)R$, $(CH_2)_{0-p}C(=NH)N(R)_2$, $(CH_2)_{0-p}C(O)N(OR)R$, or $(CH_2)_{0-p}C(=NOR)R$; and,
R is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$cycloalkyl or $(C_3-C_{10})$-cycloalkenyl]-$[(C_1-C_{12})$-alkyl or $(C_2-C_{12})$-alkenyl or $(C_2-C_{12})$-alkynyl], $(C_6-C_{10})$-aryl, $(C_6-C_{10})$-aryl-$[(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-$[(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-$[(C_1-C_{12})$-alkyl or $(C_2-C_{12})$-alkenyl or $(C_2-C_{12})$-alkynyl];
m is 0, 1, 2, 3, 4, 5, or 6; n is 1, 2, or 3; p=0, 1, or 2; r=0, 1, 2, or 3;
or any salt or hydrate thereof.

In various embodiments, Z can be a nitrogen atom, substituted with $R^2$ as defined herein. When D comprises a carbonyl group (e.g., pyridoyl, quinoloyl, benzofuranoyl, and the like), then Z as a nitrogen atom forms an amide bond with the D group. When D does not comprise a carbonyl group in the bonding position (pyridyl, quinolyl, benzofuranyl, and the like), then Z as a nitrogen atom forms an amine bond with the D group.

In other embodiments, Z can be an oxygen atom, in which case $R^2$ is absent. When D comprises a carbonyl group (e.g., pyridoyl, quinoloyl, benzofuranoyl, and the like), Z as an oxygen atom forms an ester bond with the D group. When D does not comprise a carbonyl group in the bonding position (pyridyl, quinolyl, benzofuranyl, and the like), then Z as an oxygen atom forms an ether bond with the D group.

In various embodiments, the invention provides a compound of formula (I) wherein A comprises phenyl, thiazolyl, pyrazolyl, pyridyl, or quinolyl, wherein A can each independently be unsubstituted or can each independently be mono- or multi-substituted with J or with R', or both; or any salt or hydrate thereof.

In various embodiments, the invention provides a compound of formula (I) wherein B comprises phenyl, pyridyl, pyrazidinyl, pyrimidinyl, pyrazinyl, pyrolyl, pyrazolyl, oxazolyl, imidazolyl, oxadiazolyl, (1,2,3)-triazolyl, (1,2,4)-triazolyl, wherein B can each independently be unsubstituted or can each independently be mono- or multi-substituted with J or with R', or both; or any salt or hydrate thereof.

In various embodiments, the invention provides a compound of formula (I) wherein D comprises pyridyl, pyridoyl, pyridazinyl, pyridazinoyl, pyrimidinyl, pyrimidinoyl, pyrazinyl, pyrazinoyl, quinolyl, quinoloyl, benzofuranyl, benzofuranoyl, benzoxazolyl, benzoxazoloyl, benzthiazolyl, or benzthiazoloyl; or wherein D combined with R2 and the nitrogen atom to which they are bonded comprises phthalimidoyl, wherein D can be unsubstituted or can be mono- or independently multi-substituted with J or with R', or both; or any salt or hydrate thereof.

In various embodiments, the invention provides a compound of formula (I) comprising a bicyclic compound of any of formulas (IIA) or (IIB)

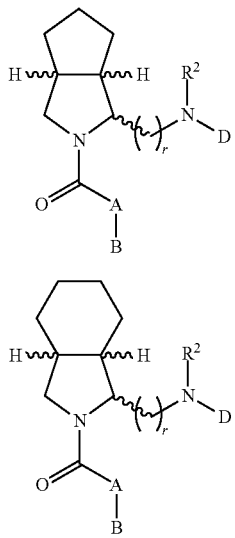

or any salt or hydrate thereof. Formula (IIA) is a bicyclo [3.3.0] system, and formula (IIB) is a bicyclo[4.3.0] system, and in both formulas (IIA) and (IIB), Z of formula (I) is nitrogen. The bicyclo ring junction can be cis-fused or trans-fused, and the sidechain can be of any relative orientation stereochemically in any of formulas (IIA) through (IID). The invention can provide mixed or pure diastereomeric forms, any one of which can be racemic or enantiomerically enriched. Alternatively, these bicyclo ring systems can be included in analogous structures wherein Z of formula (I) is oxygen. In various embodiments, the invention can provide a compound of formula (IIC), a bicyclo[3.3.0] system, or of formula (IID), a bicyclo[4.3.0] system:

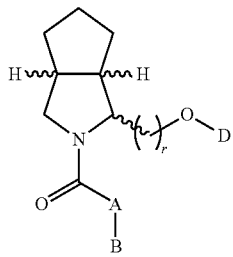

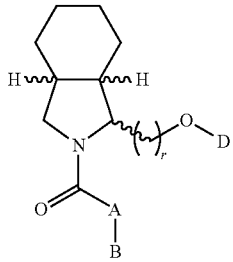

In various embodiments, the invention provides a compound of formula (I) comprising any of formulas (IIIA), (IIIB), (IIIC), (IIID), (IIIE), or (IIIF):

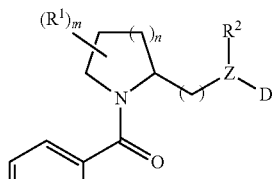

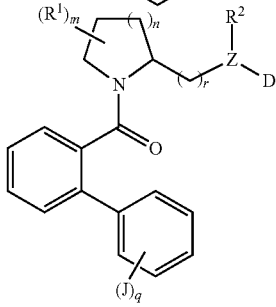

-continued

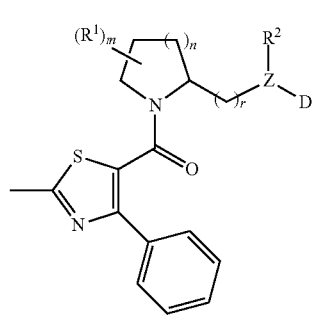
(IIIC)

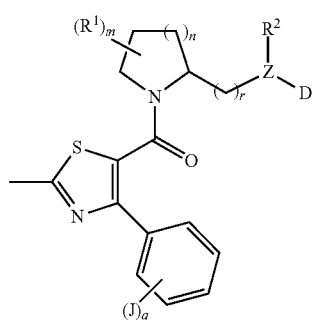
(IIID)

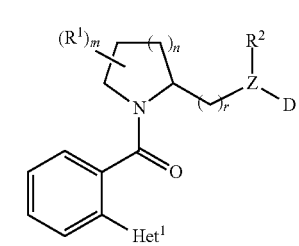
(IIIE)

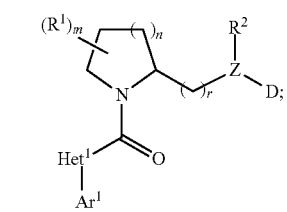
(IIIF)

wherein Z, D, R¹, m, and R² are as defined for Formula (I), n is 1 or 2, q=1, 2, or 3, r=1 or 2; Het¹ is an unsubstituted or J-substituted pyrrolyl, pyrazolyl, imidazolyl, oxazolyl, thiazolyl, trizolyl, pyrimidinyl, or pyridyl; Ar¹ is an unsubstituted or J-substituted phenyl; wherein J-substituted indicates the presence of 1-3 J substituents; or any salt or hydrate thereof. In various embodiments, each J is independently selected from the set consisting of F, Cl, and methoxy. More specifically, the invention provides a compound of any of formulas (IIIA), (IIIB), (IIIC), (IIID), (IIIE), or (IIIF), wherein n=1 or 2 (i.e., a pyrrolidine (proline), or a piperidine), and wherein m=1 or 2. In various embodiments, R¹ is F, oxo, methyl, trifluoromethyl, hydroxy, acetoxy, methoxy, NH₂, N-methylamino, N-ethylamino, N,N-dimethylamino, N-isopropylamino, N-benzylamino, hydroxyethylamino, or acetamido; or any salt or hydrate thereof. More specifically, the invention provides in various embodiments a compound of any of formulas (IIIA), (IIIB), (IIIC), (IIID), (IIIE), or (IIIF) wherein D comprises pyridyl, pyridoyl, quinolyl, quinoloyl, or benzofuranyl, or wherein D combined with R² and the nitrogen atom to which they are bonded comprises phthalimidoyl; or any salt or hydrate thereof.

In various embodiments, the invention provides a compound of formula (I) comprising a compound of formula (IVA)

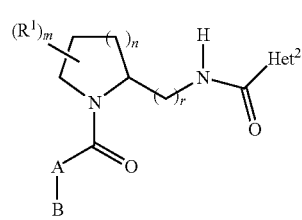
(IVA)

or a compound of formula (IVB)

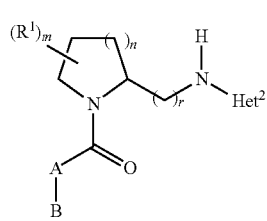
(IVB)

or a compound of formula (IVC)

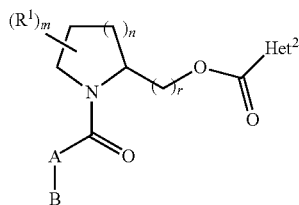

or a compound of formula (IVD)

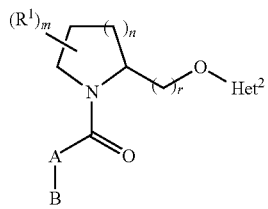

wherein A, B, and R¹, are as defined herein, wherein m=1 or 2, n=1 or 2; r=1 or 2; and r=1 or 2; and Het² is an unsubstituted or J-substituted quinolyl, pyridyl, pyrimidyl, benzoxazolyl, benzimidazolyl, or benzthiazolyl; wherein J-substituted indicates the presence of 1-3 J substituents; or any salt or hydrate thereof.

In various embodiments, the invention can provide a compound of formula (VA) or of formula (VB):

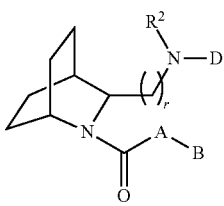

(VA)

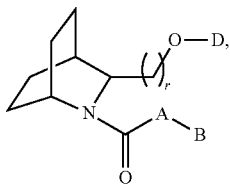

(VB)

wherein A, B, D, R², are as defined herein, and r=1 or 2; or any salt or hydrate thereof.

In some embodiments, compounds as described herein are of Formula (VI):

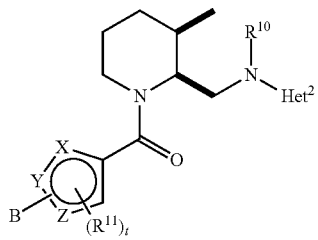

(VI)

wherein
R$^{10}$ is H or methyl;
Het² is a monocyclic heteroaryl comprising one N and one or two additional heteroatoms selected from the group consisting of NH, O, and S;
  wherein Het² is optionally substituted with one, two, or three substituents independently selected from the group consisting of halo, C$_{1-4}$alkyl, C$_{1-4}$alkoxy, —CN, —CF$_3$, and C$_{3-6}$cycloalkyl, wherein said cycloalkyl is optionally substituted with halo, methyl, or cyano; or two adjacent substituents taken together with the atoms to which they are attached form a fused phenyl or monocyclic heteroaryl;
X, Y, and Z are defined as in (a), (b), or (c), wherein:
  (a) X is N, Y is CH, and Z is S;
  (b) X is N, Y is CHCH, and Z is CH; and
  (c) X is CH, Y is CHCH, and Z is CH;
each R$^{11}$ is independently selected from the group consisting of methyl, cyano, chloro, fluoro, and methoxy;
t is 0, 1, or 2;
B is phenyl or a monocyclic heteroaryl comprising one N and one or two additional heteroatoms selected from the group consisting of NH, O, and S;
  wherein ring B is optionally substituted with one or two substituents independently selected from the group consisting of C$_{1-4}$alkyl, C$_{1-4}$alkoxy, halo, —CN, and —CF$_3$;
or a pharmaceutically acceptable salt thereof.

In some embodiments of Formula (VI), compounds are racemic at the stereocenters shown. In other embodiments, compounds of Formula (VI) are have one stereoisomer at the stereocenters shown. In other embodiments, compounds are the (2S), (3R) stereoisomer at the stereocenters shown.

In some embodiments of Formula (VI), the compound is not: Example 11, 12, 15-24, 72-73, 75-78, 82-88, 91, 97-98, 103-108, 112-117, 119-121, 123, 142-144, 146-161, 163, or 170-177, or a pharmaceutically acceptable salt thereof, or any combination thereof.

In some embodiments, compounds are of Formula (VIA):

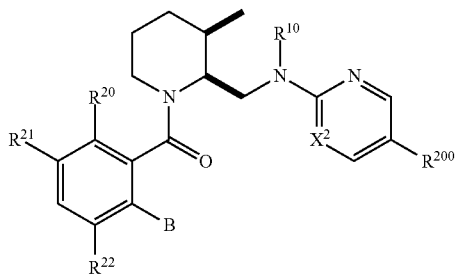

wherein
B is phenyl, pyridyl, and pyrimidinyl, each unsubstituted or substituted with one or two substituents selected from the group consisting of methyl, cyano, chloro, fluoro, and methoxy;
X² is CH or N;
R$^{10}$ is H or methyl;
R$^{200}$ is H, —CF$_3$, or chloro; and
(a) one of R$^{20}$ and R$^{22}$ is methyl, chloro, or fluoro, the other of R$^{20}$ and R$^{22}$ is H, and R$^{21}$ is H; or
(b) R$^{21}$ is H, chloro, or fluoro, and R$^{20}$ and R$^{22}$ are both H;
or a pharmaceutically acceptable salt thereof.

In some embodiments of Formula (VIA), compounds are racemic at the stereocenters shown. In other embodiments, compounds of Formula (VIA) are single isomers at the stereocenters shown. In other embodiments, compounds are the (2S), (3R) stereoisomer at the stereocenters shown.

In other embodiments, compounds as described herein are of Formula (VII):

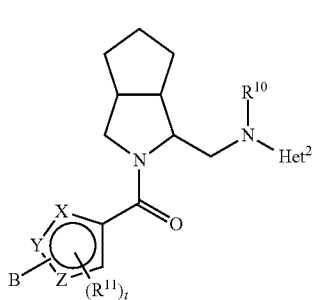

(VII)

wherein
R$^{10}$ is H or methyl;
Het² is a monocyclic heteroaryl comprising one N and one or two additional heteroatoms selected from the group consisting of NH, O, and S;
  wherein Het² is optionally substituted with one, two, or three substituents independently selected from the group consisting of halo, C$_{1-4}$alkyl, C$_{1-4}$alkoxy, —CN, —CF$_3$, and C$_{3-6}$cycloalkyl, wherein said cycloalkyl is optionally substituted with halo, methyl, or cyano; or two adjacent substituents taken together with the atoms to which they are attached form a fused phenyl or monocyclic heteroaryl;

X, Y, and Z are defined as in (a), (b), or (c), wherein:
(a) X is N, Y is CH, and Z is S;
(b) X is N, Y is CHCH, and Z is CH; and
(c) X is CH, Y is CHCH, and Z is CH;

each $R^{11}$ is independently selected from the group consisting of methyl, cyano, chloro, fluoro, and methoxy;

t is 0, 1, or 2;

B is phenyl or a monocyclic heteroaryl comprising one N and one or two additional heteroatoms selected from the group consisting of NH, O, and S;

wherein ring B is optionally substituted with one or two substituents independently selected from the group consisting of $C_{1-4}$alkyl, $C_{1-4}$alkoxy, halo, —CN, and —CF$_3$;

or a pharmaceutically acceptable salt thereof.

In some embodiments of Formula (VII), the compound is not: Example 99, 100, or 164-169, or a pharmaceutically acceptable salt thereof, or any combination thereof.

Some embodiments of Formula (VII) are compounds of Formula (VIIA):

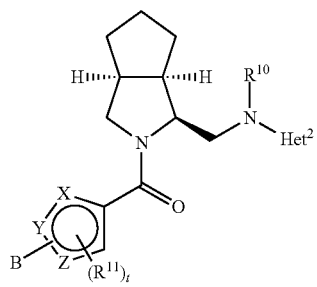

(VIIA)

where each variable is as defined above. In some embodiments, compounds of Formula (VIIA) are racemic at the stereocenters shown. In other embodiments, are non-racemic or single stereoisomeric forms at the stereocenters shown.

In some embodiments, compounds as described herein are of Formula (VIII):

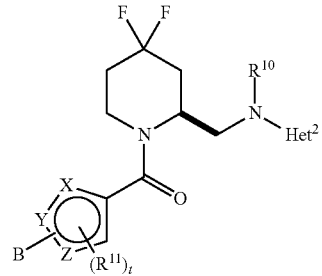

(VIII)

wherein
$R^{10}$ is H or methyl;
Het$^2$ is a monocyclic heteroaryl comprising one N and one or two additional heteroatoms selected from the group consisting of NH, O, and S;
wherein Het$^2$ is optionally substituted with one, two, or three substituents independently selected from the group consisting of halo, $C_{1-4}$alkyl, $C_{1-4}$alkoxy, —CN, —CF$_3$, and $C_{3-6}$cycloalkyl, wherein said cycloalkyl is optionally substituted with halo, methyl, or cyano; or two adjacent substituents taken together with the atoms to which they are attached form a fused phenyl or monocyclic heteroaryl;

X, Y, and Z are defined as in (a), (b), or (c), wherein:
(a) X is N, Y is CH, and Z is S;
(b) X is N, Y is CHCH, and Z is CH; and
(c) X is CH, Y is CHCH, and Z is CH;

each $R^{11}$ is independently selected from the group consisting of methyl, cyano, chloro, fluoro, and methoxy;

t is 0, 1, or 2;

B is phenyl or a monocyclic heteroaryl comprising one N and one or two additional heteroatoms selected from the group consisting of NH, O, and S;

wherein ring B is optionally substituted with one or two substituents independently selected from the group consisting of $C_{1-4}$alkyl, $C_{1-4}$alkoxy, halo, —CN, and —CF$_3$;

or a pharmaceutically acceptable salt thereof.

In some embodiments of Formula (VIII), compounds are racemic at the stereocenter shown. In other embodiments, compounds have the "R" configuration at the stereocenter shown.

In some embodiments, compounds as described herein are of Formula (IX):

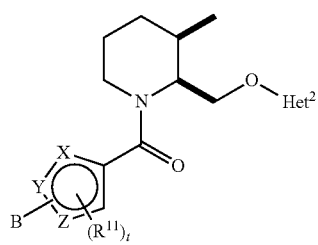

(IX)

wherein
Het$^2$ is a monocyclic heteroaryl comprising one N and one or two additional heteroatoms selected from the group consisting of NH, O, and S;
wherein Het$^2$ is optionally substituted with one, two, or three substituents independently selected from the group consisting of halo, $C_{1-4}$alkyl, $C_{1-4}$alkoxy, —CN, —CF$_3$, and $C_{3-6}$cycloalkyl, wherein said cycloalkyl is optionally substituted with halo, methyl, or cyano; or two adjacent substituents taken together with the atoms to which they are attached form a fused phenyl or monocyclic heteroaryl;

X, Y, and Z are defined as in (a), (b), or (c), wherein:
(a) X is N, Y is CH, and Z is S;
(b) X is N, Y is CHCH, and Z is CH; and
(c) X is CH, Y is CHCH, and Z is CH;

each $R^{11}$ is independently selected from the group consisting of methyl, cyano, chloro, fluoro, and methoxy;

t is 0, 1, or 2;

B is phenyl or a monocyclic heteroaryl comprising one N and one or two additional heteroatoms selected from the group consisting of NH, O, and S;

wherein ring B is optionally substituted with one or two substituents independently selected from the group consisting of $C_{1-4}$alkyl, $C_{1-4}$alkoxy, halo, —CN, and —CF$_3$;

or a pharmaceutically acceptable salt thereof.

In some embodiments of Formula (IX), the compound is not: Example 79-81, or 89-90, or a pharmaceutically acceptable salt thereof, or any combination thereof.

In some embodiments of Formula (IX), compounds are racemic at the stereocenters shown. In other embodiments, compounds of Formula (IX) are single isomers at the stereocenters shown. In other embodiments, compounds are the (2S), (3R) stereoisomer at the stereocenters shown.

In some embodiments of Formulae (VI), (VII), and (VIII), R10 is H. In other embodiments, R10 is methyl.

In some embodiments of Formulae (VI), (VII), (VIII), and (IX), Het2 is pyrrolyl, pyrazolyl, imidazolyl, oxazolyl, isoxazolyl, thiazolyl, isothiazolyl, oxadiazolyl, thiadiazolyl, triazolyl, tetrazolyl, pyridyl, pyrimidinyl, pyridazinyl, or pyrazinyl, each optionally fused to phenyl or a monocyclic heteroaryl, and each optionally substituted with one or two substituents Rx. In some embodiments, Het2 is thiazolyl, thiadiazolyl, pyridyl, pyrimidinyl, pyridazinyl, benzoxazolyl, quinazolinyl, or triazolo-pyrimidinyl, each optionally substituted with one or two substituents Rx. In some embodiments, Het2 is attached to —N(R10) at the 2-position of the monocyclic heteroaryl. In other embodiments, Het2 is attached to —N(R10) at a position alpha to an N in the monocyclic heteroaryl ring. In other embodiments, Het2 is benzoxazolyl. In other embodiments, Het2 is pyridyl. In some embodiments, each Rx is independently selected from the group consisting of —F, —Cl, —Br, methyl, methoxy, —CN, —CF3, cyclopropyl, and cyano-cyclopropyl. In some embodiments, Rx is —CF3 or —Cl.

In some embodiments, X is N, Y is CH, and Z is S. In other embodiments, X is N, Y is CHCH, and Z is CH. In still other embodiments, X is CH, Y is CHCH, and Z is CH. In each case, the CH groups are optionally substituted with B and (R11)t as shown.

In some embodiments, each R11 is independently methyl, chloro, fluoro, or —CN. In some embodiment, R11 is chloro or fluoro. In some embodiments, t is 0. In other embodiments, t is 1. In still other embodiments, t is 2. In some embodiments, the group (XX):

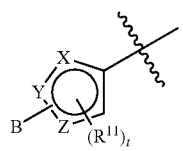

(XX)

is a group of Formula (Xa), or is a group of Formula (Xb), or is a group of Formula (Xc):

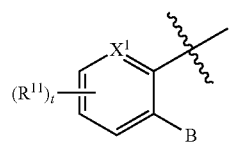

(Xa)

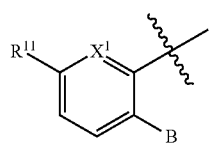

(Xb)

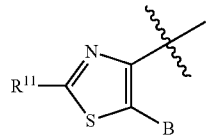

(Xc)

wherein $X^1$ is CH or N and B is unsubstituted or is substituted as described for Formula (VI), (VII), (VIII), or (IX). In some embodiments, $X^1$ is CH or $CR^{11}$. In other embodiments, $X^1$ is N. In other embodiments, the group (XX) is a group of Formula (Xd):

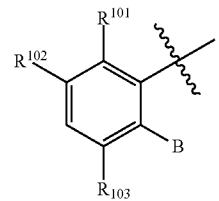

(Xd)

where (a) one of $R^{101}$ and $R^{103}$ is methyl, chloro, or fluoro, the other of $R^{101}$ and $R^{103}$ is H, and $R^{102}$ is H; or (b) $R^{102}$ is H, chloro, or fluoro, and $R^{101}$ and $R^{103}$ are both H.

In some embodiments, ring B is phenyl, or is pyrrolyl, pyrazolyl, imidazolyl, oxazolyl, isoxazolyl, thiazolyl, isothiazolyl, oxadiazolyl, thiadiazolyl, triazolyl, tetrazolyl, pyridyl, pyrimidinyl, pyridazinyl, or pyrazinyl, each optionally substituted with one or two substituents Ry. In some embodiments, ring B is phenyl, pyrrolyl, triazolyl, pyrimidinyl, pyridyl, pyrrolyl, isoxazolyl, pyrazinyl, imidazolyl, tetrazolyl, thiazolyl, pyridazinyl, each optionally substituted with one or two substituents Ry. In some embodiments, ring B is pyrazolyl or triazolyl. In some embodiments, each Ry is independently methyl, ethyl, propyl, isopropyl, butyl, isobutyl, methoxy, ethoxy, isopropoxy, —F, —Cl, —Br, —CN, or —$CF_3$. In other embodiments, there is one Ry. In other embodiments, Ry is methyl, ethyl, isopropyl, methoxy, —F, or —CF3.

In various embodiments, the invention provides any of the compounds as listed below in "Table 1: Exemplary Compounds of the Invention," or any salt or hydrate thereof, or in Table 1A, or any salt or hydrate thereof. Compounds of the invention can possess bioactivity as orexin receptor modulators, e.g., as orexin receptor antagonists, as described in greater detail below.

Pharmaceutical Methods and Uses

"Treating" or "treatment" within the meaning herein refers to an alleviation of symptoms associated with a disorder or disease, or inhibition of further progression or worsening of those symptoms, or prevention or prophylaxis of the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: The Science and Practice of Pharmacy, 19th Ed., 1995, incorporated by reference herein. The compositions can appear in conventional forms, for example capsules, tablets, aerosols, solutions, suspensions or topical applications.

The compounds described herein may be administered simultaneously or sequentially with one or more other active pharmaceutical ingredients. Additional active ingredients may be administered separately or in a combination formulation with one or more compounds described herein. Exemplary additional active ingredients include those that target the same disease or disorder as the disclosed compounds, or a symptom of that disease or disorder. For example, additional active ingredients include those that are known to be useful for enhancing sleep quality and preventing and treating sleep disorders and sleep disturbances, anti-diabetic agents, cardiovascular therapies, anti-obesity agents, other orexin receptor antagonists, pain medications, anti-depressants, anti-anxiety agents, cognition-enhancing agents, anti-Alzheimer's Disease therapies, and other active ingredients. Exemplary active pharmaceutical ingredients and other therapies that are suitable for combination with the presently described compounds include those listed in PCT Publ. No. WO2008/147518 at pages 23-29, which are hereby incorporated by reference.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is nonvolatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

In various embodiments, the invention provides a pharmaceutical composition comprising a compound of the invention and a pharmaceutically acceptable excipient, as described above.

In various embodiments, compounds of the invention can be used to modulate, such as to activate (agonist), or to block activation of (antagonist), an orexin receptor. Accordingly, in various embodiments, the invention provides a method of modulating an orexin receptor comprising contacting the receptor with an effective amount or concentration of a compound of the invention. The orexin receptor can be OX1 or OX2. In various embodiments, the compound of the invention is an antagonist of an orexin receptor such as OX1 or OX2, or both, and can be a selective inhibitor of one or the other. In various embodiments, contacting can take place in vivo within tissues of a patient, such as a human patient.

In various embodiments, the invention provides a method of treating a malcondition in a patient wherein modulation of an orexin receptor is medically indicating, comprising administering to the patient a compound of the invention in a dose, at a frequency, and for a duration to provide a beneficial effect to the patient. Modulation, such as agonism or antagonism, of an orexin receptor can be medically indicated in treatment of a malcondition wherein the orexin receptor plays a metabolic or regulatory role. Certain malconditions can be treated by selective modulation of a single class of orexin receptor, such as modulation of OX1 while OX2 is not influenced by administration of the compound of the invention at the dose provided. In various embodiments, compounds of the invention can be orexin-1 antagonists, and some of those are selective orexin-1 antagonists with respect to orexin-2. By "selective" is meant that one receptor is modulated at concentrations of the compound at least 10 times lower than the concentrations at which the comparative receptor is modulated by that compound. Accordingly, in various embodiments, the compound of the invention can be a selective modulator, e.g., an antagonist, of orexin receptor OX1. Or, the compound of the invention can be a selective modulator (e.g., antagonist) of an orexin receptor OX2. Or the compound of the invention can further modulate other types or classes of receptors having affinity for one of more forms of the orexin class of natural peptidic ligands.

In various embodiments, modulation of an orexin receptor, for example, antagonism of orexin-1, by a compound of the invention can be used to treat a malcondition in a patient wherein the malcondition comprises an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, head ache, migraine, pain, gastrointestinal diseases, epilepsy, inflammations, immune-related diseases, endocrine-related diseases, cancer, hypertension, behavior disorder, mood disorder, manic depression, dementia, sex disorder, psychosexual disorder, and renal disease. Drug abuse and addiction can include abuse of or addiction to cocaine, opiates, amphetamines, or nicotine. Drug abuse and/or addiction can also include abuse of and/or addiction to alcohol, cannabis, or heroin.

In various embodiments, the invention provides a use of a compound of the invention for treatment of a malcondition in a patient. For example, a compound of the invention can be used in the preparation of a medicament for administration to a patient suffering from a malcondition. More specifically, the malcondition can comprise an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, head ache, migraine, pain, gastrointestinal diseases, epilepsy, inflammations, immune-related diseases, endocrine-related diseases, cancer, hypertension, behavior disorder, mood disorder, manic depression, dementia, sex disorder, psychosexual disorder, and renal disease. Drug abuse and addiction can include abuse of or addiction to cocaine, opiates, amphetamines, or nicotine. Drug abuse and/or addiction can also include abuse of and/or addiction to alcohol, cannabis, or heroin.

In other embodiments, the malcondition is narcolepsy, insomnia, learning disorders, memory disorders, depression, anxiety, addiction, obsessive compulsive disorder, affective neurosis, depressive neurosis, anxiety neurosis, dysthymic disorder, behavior disorder, mood disorder, sexual dysfunction, psychosexual dysfunction, sex disorder, schizophrenia, manic depression, delirium, dementia, severe mental retardation or dyskinesias (such as Huntington's Disease or Tourette Syndrome), eating disorders (such as anorexia, bulimia, cachexia, or obesity), addictive feeding behaviors, binge/purge feeding behaviours, cardiovascular diseases, diabetes, appetite/taste disorders, emesis, vomiting, nausea, asthma, cancer, Parkinson's Disease, Cushing's Syndrome/Disease, basophil adenoma, prolactinoma, hyperprolactinemia, hypophysis tumor/adenoma, hypothalamic diseases, inflammatory bowel disease, gastric dyskinesia, gastric ulcers, Froehlich's Syndrome, adrenohypophysis disease, hypophysis diseases, adrenohypophysis hypofunction, adrenohypophysis hyperfunction, hypothalamic hypogonadism, Kallman's syndrome (anosmia, hyposmia), functional or psychogenic amenorrhea, hypopituitarism, hypothalamic hypothyroidism, hypothalamic-adrenal dysfunction, idiopathic hyperprolactinemia, hypothalamic disorders of growth hormone deficiency, idiopathic growth deficiency, dwarfism, gigantism, acromegaly, disturbed biological and circadian rhythms, sleep disturbances associated with disease such as neurological disorders, neuropathic pain, diabetic neuropathy, and restless leg syndroms, heart and lung diseases, acute and congestive heart failure, hypotension, hypertension, urinary retention, osteoporosis, angina pectoris, myocardial infarction, ischemic or hemorrhagic stroke, subsrachnoic hemorrhage, ulcers, allergies, benign prostatic hypertrophy, chronic renal failure, renal disease, impaired glucose tolerance, migraine, episodic migraine, headache disorders (such as tension-type headache, cluster headache, other trigeminal autonomic cephalalgias, other primary headaches such as hemicranias continua, secondary headaches, cranial neuralgia, or central or primary facial pain), hyperalgesia, pain, enhanced or exaggerated sensitivity to pain such as hyperalgesia, causalgia, or allodynia, acute pain, burn pain, atypical facial pain, neuropathic pain, back pain, complex regional pain syndrome I or II, arthritic pain, sports injury pain, pain related to infection (e.g., HIV), post-chemotherapy pain, post-stroke pain, post-operative pain, neuralgia, emesis, nausea, vomiting, conditions associated with visceral pain (such as irritable bowel syndrome or angina), urinary bladder incontinence (e.g., urge incontinence), tolerance to narcotics or withdrawal from narcotics, sleep disorders, sleep apnea, parasomnia, jet lag syndrome, neurodegenerative disorders, disinhibition-dementia-parkinsonism-amyotrophy complex, pallido-ponto-nigral degeneration, epilepsy, seizure disorders, or other diseases related to general orexin system dysfunction.

In still other embodiments, the compounds described herein are useful in a method of treating disorders including, but not limited to, sleep disorders, sleep disturbances, including enhancing sleep quality, improving sleep quality, increasing sleep efficiency, augmenting sleep maintenance; increasing the ratio of the time that a subject sleeps relative to the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent waking during sleep; decreasing nocturnal arousals; decreasing the time spent awake following the initial onset of sleep; increasing the total amount of sleep; reducing the fragmentation of sleep; altering the timing, frequency, or duration of REM sleep bouts; altering the timing, frequency, or duration of slow wave (such as stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease, or cognitive impairment, as well as sleep walking and enuresis, and sleep disorders that accompany aging; Alzheimer's sundowning; conditions associated with circadian rhythmically as well as mental and physical disorders associated with travel across time zones and with rotating shift-work schedules, conditions due to drugs that cause reductions in REM sleep as a side effect; fibromyalgia; syndromes that are manifested by non-restorative sleep and muscle pain; sleep apnea that is associated with respiratory disturbances during sleep; conditions that result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis, or schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder, and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics, or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

It is believed that antagonism of orexin-1, in particular, is medically indicated for the treatment of the above-listed conditions. By antagonism is meant blocking a receptor, in this case an orexin receptor, without causing it to transduce a signal. That is, antagonism results in blocking an endogenous or exogenous ligand from activating, or causing agonism, of the receptor.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day, or 25 to 200 mg per day, or 50 to 100 mg per day, or less than 100 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage. In other embodiments, a unit dosage form includes from about 10 to about 200 mg of active ingredient.

Usually, dosage forms suitable for oral, nasal, pulmonal or transdermal administration include from about 125 g to about 1250 mg, preferably from about 250 g to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician. In some embodiments, dosage form are administered once or twice daily.

It is within ordinary skill to evaluate any compound disclosed and claimed herein for effectiveness in modulation of an orexin receptor and in the various cellular assays using the procedures described above or found in the scientific literature. Accordingly, the person of ordinary skill can prepare and evaluate any of the claimed compounds without undue experimentation.

Any compound found to be an effective modulator, agonist or antagonist, can likewise be tested in animal models and in human clinical studies using the skill and experience of the investigator to guide the selection of dosages and treatment regimens.

Preparation of Compounds of the Invention

Compounds of the invention can be synthesized according to established literature procedures for analogous compounds and general techniques and reactions well known to persons of ordinary skill in the art.

As shown in General Synthetic Scheme A, below, a 2-(aminomethyl)pyrrolidine, 2-(aminomethyl)piperidine, or aminomethylaziridine precursor (i.e., wherein n=1, 2, or 3), appropriately substituted with R1 groups, can be coupled sequentially with the B-A-C(=O) fragment and the D fragment to provide a compound of the invention. The coupling steps can be carried out in either order, if necessary using appropriate protecting groups for functional R1 or J groups with which the reactants can be substituted. General synthetic scheme I details a synthesis for compounds wherein group Z is nitrogen.

General Synthetic Scheme I

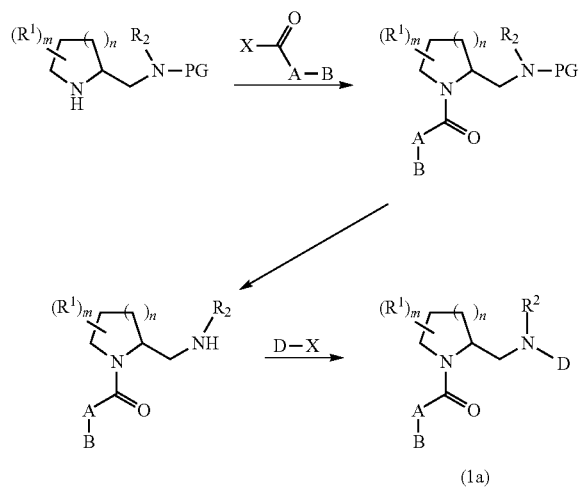

(1a)

For a compound of formula (I) wherein R2 is hydrogen and Z is N (formula (1a)), the compound can be prepared from an appropriately protected aminomethylpyrrolidine, aminomethylpiperidine, or aminomethylaziridine, as shown. The group PG designates an N-protecting group, as are well-known in the art, to allow selective acylation of the ring nitrogen to occur for reaction with an activated B-A-C(=O)OH carboxylic acid, wherein X represents a carboxyl-activating group, e.g., an N-hydroxy ester, or a O-acylisourea, or a halogen. The carboxylic acid can be activated by any method known in the art, for example using HATU as is described below in General Synthetic Procedure A in the Examples, below. Then, the acylated intermediate can undergo deprotection of the aminomethyl protecting group (PG) using techniques suitable for the particular protecting group, and the amino group then reacted with an activated form of group D. For example, if D comprises a carboxylic acid group which is coupled with the aminomethyl group to form an amide, the carboxylic acid group can be activated using the techniques described above to form activated species D-X, which then forms the final product. For cases where D is an aryl, heteroaryl, or heterocyclic ring, the aminomethyl group can react with the corresponding aryl, heteroaryl or heterocyclic halide through a displacement reaction in the presence of a base or through standard metal mediated procedures (Buchwald, Ulmann) known to those skilled in the art. For further elaboration of R2, the nitrogen atom can be reacted with an appropriate reagent; e.g. by alkylation, to provide compounds of formula (1a) wherein R2 is other than hydrogen.

It is understood that the synthesis can proceed in an alternative sequence by starting with an aminomethylpyrrolidine, aminomethylpiperidine, or aminomethylaziridine precursor wherein the protecting group is on the ring nitrogen atom and the exocyclic aminomethyl group is unprotected. Condensation with the D fragment, followed by deprotection of the ring nitrogen atom and coupling with the activated carboxylic acid B-A-C(=O)—X can provide the compound of formula (I).

When the group Z of formula (I) is an oxygen atom, by coupling group D bearing an appropriate leaving group with a compound analogous to the penultimate intermediate shown in Scheme I, above, but bearing a hydroxyl group instead of an amino group on the sidechain.

Alternatively, synthesis of a compound of formula (I) can be achieved according General Synthetic Scheme II, below, wherein a D-NH2 fragment is coupled with an activated 2-methylpyrrolidine or piperidine, which can be derivatized with the B-A-C(=O)OH fragment either prior to or following the coupling.

For the embodiments of structure wherein group Z of formula (I) is an oxygen atom, a D-OH fragment can be coupled with an appropriately activated B-A-C fragment, either bearing a carboxyl group (to form an ester) or a leaving group (for form an ether).

General Synthetic Scheme II

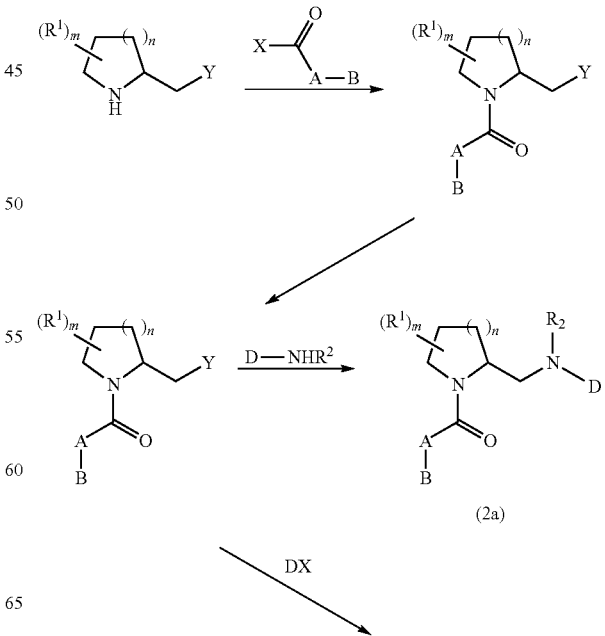

(2a)

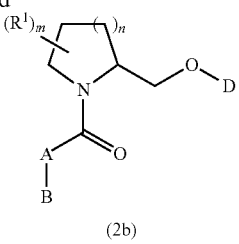

(2b)

An appropriately substituted pyrrolidine or piperidine or aziridine can bear a group Y for eventual displacement in a nucleophilic substitution reaction by amine D-NHR2, particularly when the D group is not bonded to the nitrogen atom via a carbonyl group, e.g., when D is pyridyl instead of pyridoyl, quinolyl instead of quinoloyl, etc. For example, when D is pyridyl and R2 is hydrogen, the D-NHR2 reagent can be an aminopyridine, such as 2-, 3-, or 4-aminopyridine. For example Y can be a halo, or Y can be a hydroxyl. It is understood that Y can be in a protected form for the first step, if necessary, then deprotected and activated for the coupling with DNHR2. For example, Y can be a protected hydroxyl group in the coupling of the first reagent with the activated B-A-C(=O)—X carboxylic acid, which is then converted to Y being a free hydroxyl group, followed by activation for nucleophilic displacement, e.g., as a sulfonate ester, to provide the third reagent above that is then condensed with the D-NHR2 reagent to provide the compound of formula (I). Y may also be a carboxaldehyde group and coupled with DNHR2 by reductive amination. In the final product (2a) or (2b) in Synthetic Scheme II, above, the atom labeled Y becomes the Z group of formula (I).

In Synthetic Scheme II, it is also understood that the sequence can proceed in an alternative order of steps, i.e., coupling of the D-NHR2 reagent with the activated Y-bearing ring system (with the ring nitrogen atom optionally protected as needed), followed by ring nitrogen deprotection and coupling with the activated B-A-C(=O)—X carboxylic acid.

Alternatively, when Y=OH, the alcohol may be coupled to DX (X=halogen or some other leaving group) to afford the ether product II. This can be done using any inorganic (for instance, Cs2CO3, K2CO3, etc.) or organic (for instance, Et3N, iPr2Net, DBU, etc) base in the appropriate solvent and at the appropriate temperature.

Appropriately substituted pyrrolidine, piperidine, and aziridine precursors can be prepared according to literature procedures and upon disclosed synthetic approaches described below in the Examples, using the knowledge of ordinary practitioners of organic synthetic chemistry.

General Synthetic Scheme III

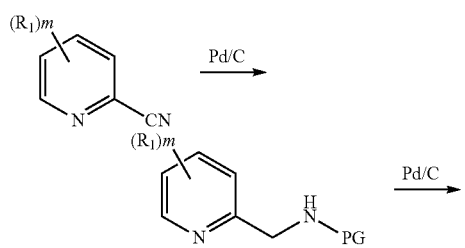

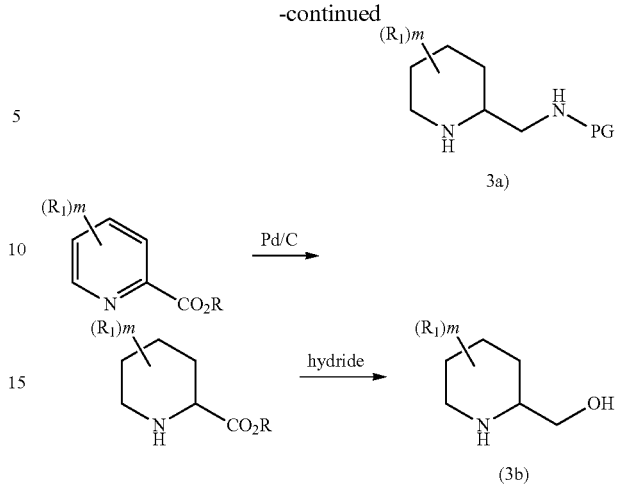

An appropriately substituted piperidine may be synthesized according to the protocol generally described in Synthetic Scheme III. A substituted 2-cyanopyridine can be reduced to the 2-aminomethyl pyridine and protected with a suitable protecting group. Further reduction of the ring provides the differentially protected 2-aminomethyl piperidine 3a. Alternatively, a 2-carboxypyridine (protected as the ester or as the acid) can be reduced to the substituted pipecolic acid and then reduced (using borane, or LAH, for instance) to the amino alcohol. Further functionalization to final products can follow protocols outlined in Schemes I and II above.

General Synthetic Scheme IV

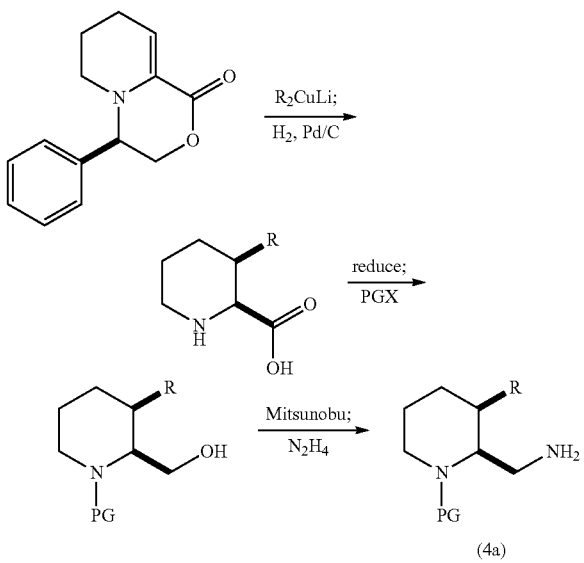

Enantiomerically pure 3-substituted 2-aminomethyl piperidines or 2-hydroxymethyl piperidines can be made as described in Synthetic Scheme IV. The 3-substituted pipecolic acids can be made as described in the literature in Royer et al., *J. Org. Chem.* 1994, 59, 3769, and Royer et al., *Tetrahedron Lett.* 1999, 40, 3699. R can be alkyl, alkenyl, alkynyl, haloalkyl, aryl, heteroaryl, or the like. Reduction of the carboxylic acid with lithium aluminum hydride or borane or other suitable reducing agent provides the primary alcohol after protecting the piperidine nitrogen atom with a suitable protecting group. Conversion of the primary alcohol to the primary amine can be done by several standard approaches as described in the literature and known to those skilled in the art. One such way would be through Mitsunobu reaction with phthalamide and triphenylphosphine and diisopropylazodicarboxylate, followed by cleavage of the phthalimide group with hydrazine to give intermediate 4a. Further functionalization to final products can follow protocols outlined in Schemes I and II above.

One of ordinary skill in the art will recognize that compounds of Formulae (VI), (VII), and (VIII) are prepared using the approaches outlined in the above schemes.

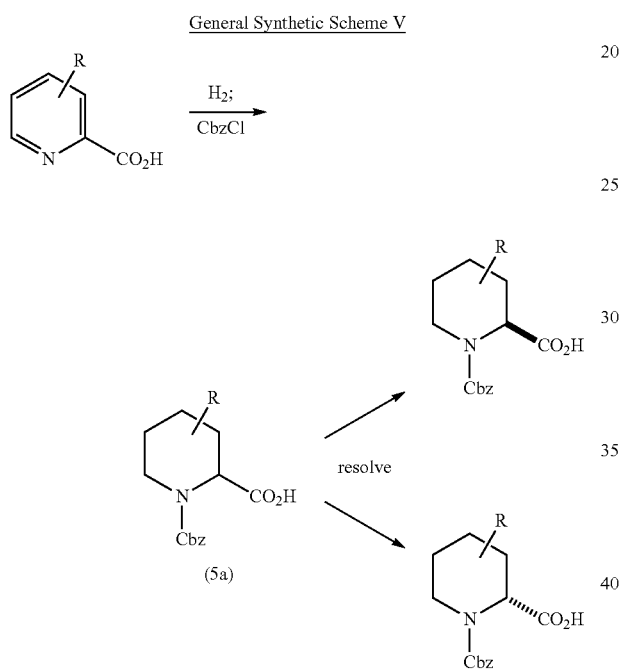

Enantiomerically pure 3-substituted 2-aminomethyl piperidines can be made as described in Synthetic Scheme V. Hydrogenation of an appropriately substituted pyridine carboxylic acid followed by amino group protection affords pipecolic acid derivatives (5a). Resolution of the acid into its enantiomers can be accomplished with a variety of commercially available or synthetically prepared enantiomerically pure amines via their diasteriomeric salts. Alternatively, the enantiomers of (5a) can be separated on a chiral column. Further functionalization to final products can follow protocols outlined in Schemes I-IV above.

EXAMPLES

The following examples of the compounds of the invention further demonstrate features and aspects of specific embodiments of the invention. The parameters and characteristics of the compounds of the invention are set forth by the foregoing text. In some embodiments are contemplated compounds as in Table 1.

TABLE 1

Exemplary Compounds of the Invention

| Example # | Structure |
|---|---|
| Example 1 | 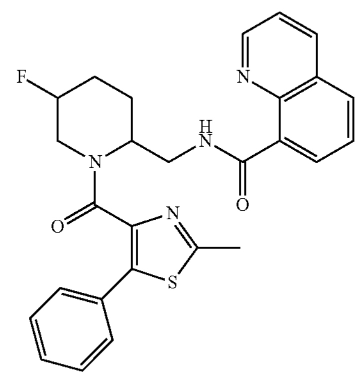 [SMILES: Cc1nc(C(=O)N2CC(F)CCC2CNC(=O)c2cccc3cccnc23)c(-c2ccccc2)s1] |
| Example 2 | 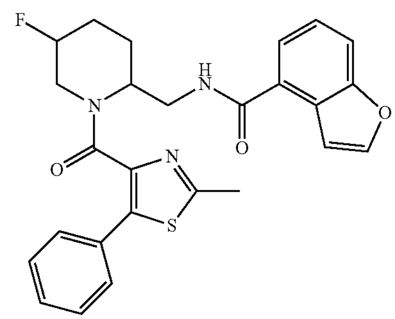 [SMILES: Cc1nc(C(=O)N2CC(F)CCC2CNC(=O)c2cccc3occc23)c(-c2ccccc2)s1] |
| Example 3 | 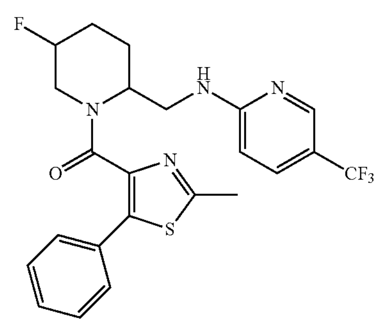 [SMILES: Cc1nc(C(=O)N2CC(F)CCC2CNc2ccc(C(F)(F)F)cn2)c(-c2ccccc2)s1] |
| Example 4 | 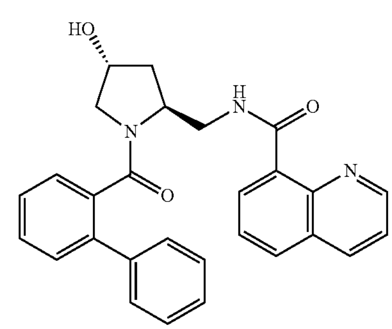 |

TABLE 1-continued

Exemplary Compounds of the Invention

| Example # | Structure |
|---|---|
| Example 5 | (structure) |
| Example 6 | (structure) |
| Example 7 | (structure) |
| Example 8 | (structure) |
| Example 9 | (structure) |
| Example 10 | (structure) |
| Example 11 | (structure) |
| Example 12 | (structure) |
| Example 13 | (structure) |

TABLE 1-continued
Exemplary Compounds of the Invention
| Example # | Structure |
|---|---|
| Example 14 | 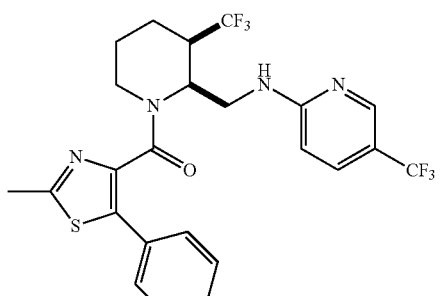 |
| Example 15 | 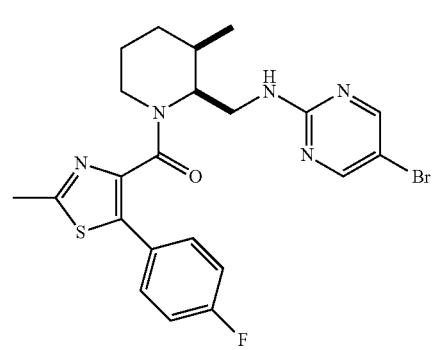 [SMILES: Cc1nc(C(=O)N2CCC[C@@H](C)[C@H]2CNc2ncc(Br)cn2)c(-c2ccc(F)cc2)s1] |
| Example 16 | 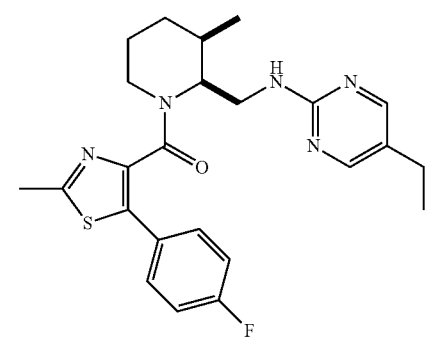 |
| Example 17 | 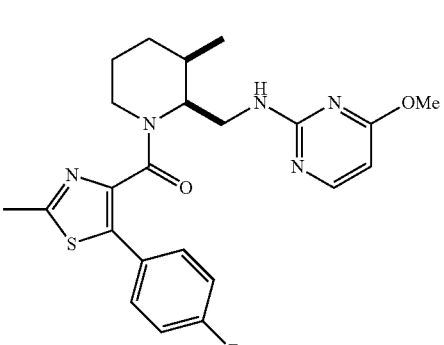 |
TABLE 1-continued
Exemplary Compounds of the Invention
| Example # | Structure |
|---|---|
| Example 18 | 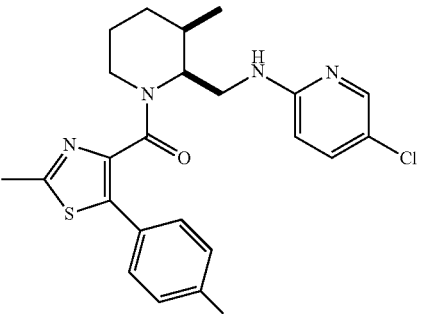 |
| Example 19 | 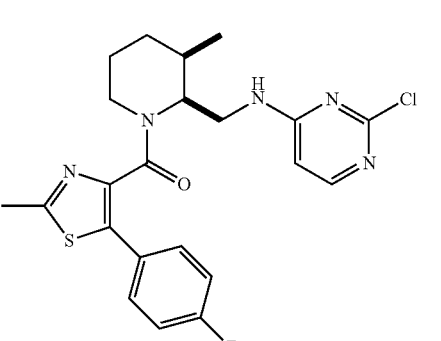 |
| Example 20 | 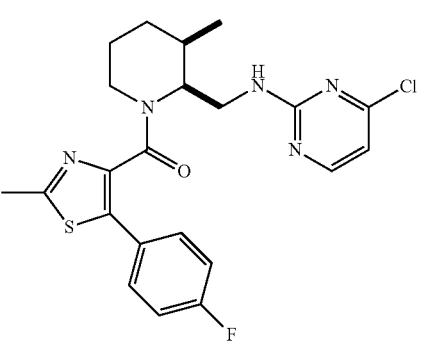 [SMILES: Cc1nc(C(=O)N2CCC[C@@H](C)[C@H]2CNc2nccc(Cl)n2)c(-c2ccc(F)cc2)s1] |
| Example 21 | 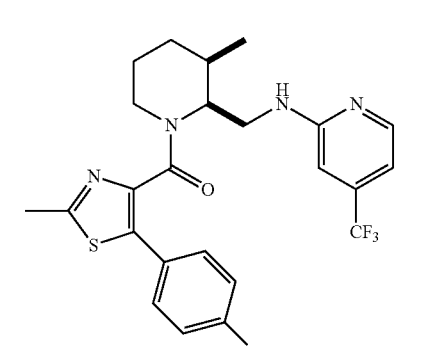 |

TABLE 1-continued
Exemplary Compounds of the Invention
| Example # | Structure |
|---|---|
| Example 22 | 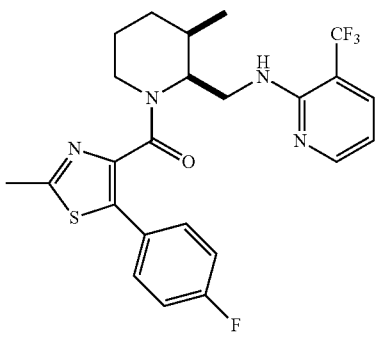 [SMILES: Cc1nc(C(=O)N2CCC[C@@H](C)[C@H]2CNc2ncccc2C(F)(F)F)c(-c2ccc(F)cc2)s1] |
| Example 23 | 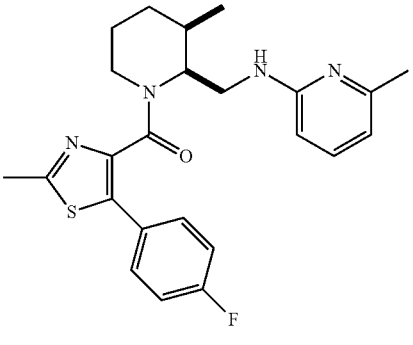 |
| Example 24 | 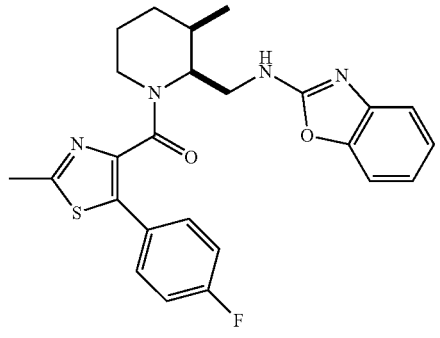 [SMILES: Cc1nc(C(=O)N2CCC[C@@H](C)[C@H]2CNc2nc3ccccc3o2)c(-c2ccc(F)cc2)s1] |
| Example 25 | 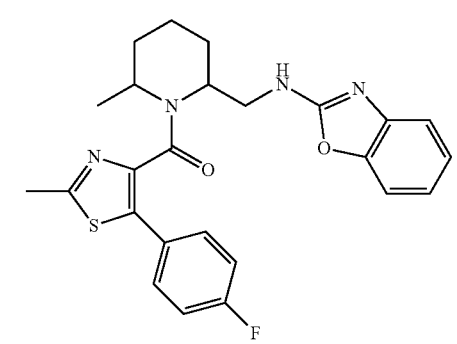 [SMILES: Cc1nc(C(=O)N2C(C)CCCC2CNc2nc3ccccc3o2)c(-c2ccc(F)cc2)s1] |
| Example 26 | 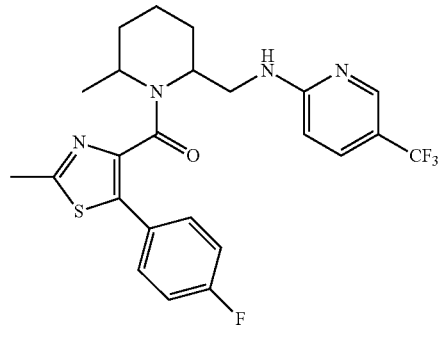 |
| Example 27 | 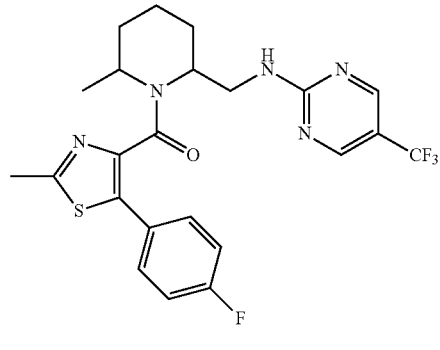 |
| Example 28 | 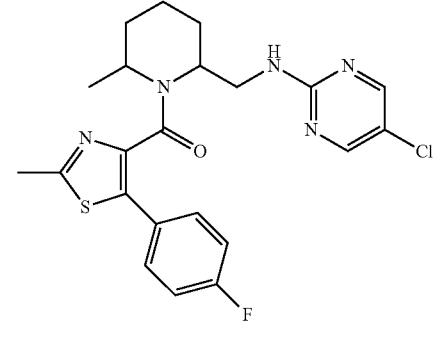 [SMILES: Cc1nc(C(=O)N2C(C)CCCC2CNc2ncc(Cl)cn2)c(-c2ccc(F)cc2)s1] |
| Example 29 | 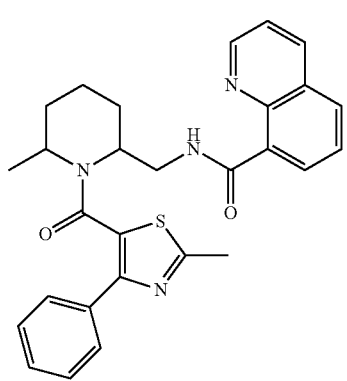 [SMILES: Cc1nc(-c2ccccc2)c(C(=O)N2C(C)CCCC2CNC(=O)c2cccc3cccnc23)s1] |

TABLE 1-continued

Exemplary Compounds of the Invention

| Example # | Structure |
|---|---|
| Example 30 | (structure) |
| Example 31 | (structure) |
| Example 32 | (structure) |
| Example 33 | (structure) |
| Example 34 | (structure) |
| Example 35 | (structure) |
| Example 36 | (structure) |
| Example 37 | (structure) |

TABLE 1-continued

Exemplary Compounds of the Invention

| Example # | Structure |
|---|---|
| Example 38 | 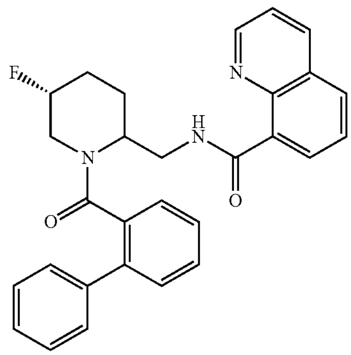 [SMILES: O=C(NCC1CC[C@@H](F)CN1C(=O)c1ccccc1-c1ccccc1)c1cccc2cccnc12] |
| Example 39 | 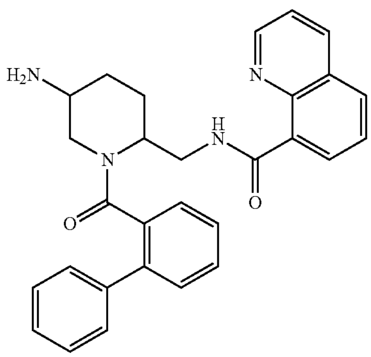 [SMILES: NC1CCC(CNC(=O)c2cccc3cccnc23)N(C(=O)c2ccccc2-c2ccccc2)C1] |
| Example 40 | 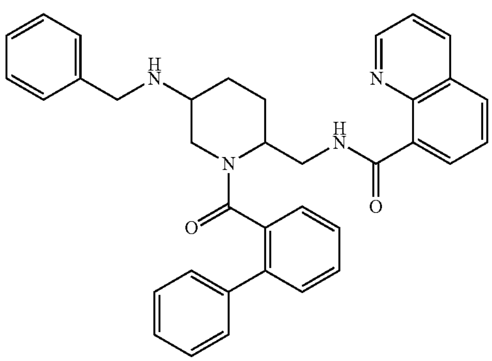 [SMILES: O=C(NCC1CCC(NCc2ccccc2)CN1C(=O)c1ccccc1-c1ccccc1)c1cccc2cccnc12] |
| Example 41 | 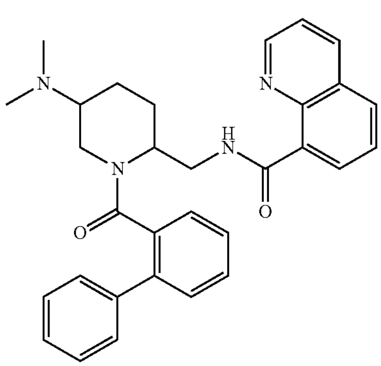 [SMILES: CN(C)C1CCC(CNC(=O)c2cccc3cccnc23)N(C(=O)c2ccccc2-c2ccccc2)C1] |
| Example 42 | |
| Example 43 | |
| Example 44 | |
| Example 45 | |

TABLE 1-continued

Exemplary Compounds of the Invention

| Example # | Structure |
|---|---|
| Example 46 | 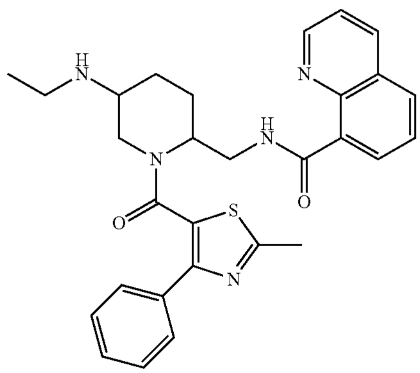 [SMILES: CCNC1CCC(CNC(=O)c2cccc3cccnc23)N(C(=O)c2sc(C)nc2-c2ccccc2)C1] |
| Example 47 | 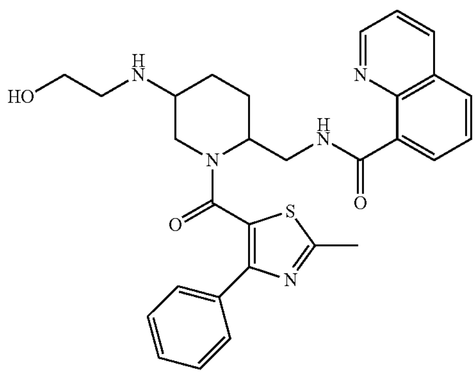 [SMILES: Cc1nc(-c2ccccc2)c(C(=O)N2CC(NCCO)CCC2CNC(=O)c2cccc3cccnc23)s1] |
| Example 48 | 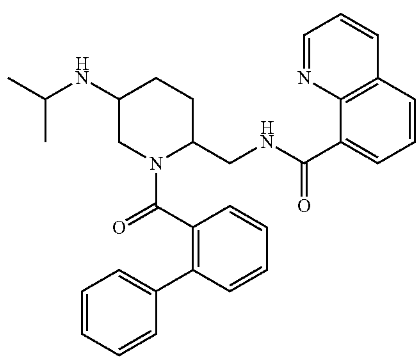 [SMILES: CC(C)NC1CCC(CNC(=O)c2cccc3cccnc23)N(C(=O)c2ccccc2-c2ccccc2)C1] |
| Example 49 | 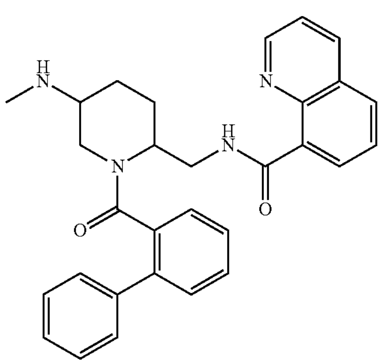 [SMILES: CNC1CCC(CNC(=O)c2cccc3cccnc23)N(C(=O)c2ccccc2-c2ccccc2)C1] |
| Example 50 | |
| Example 51 | |
| Example 52 | |

TABLE 1-continued

Exemplary Compounds of the Invention

| Example # | Structure |
|---|---|
| Example 53 | 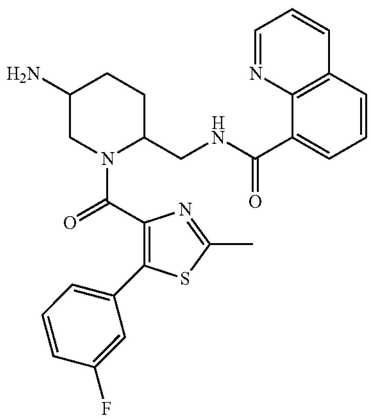 [SMILES: Cc1nc(C(=O)N2CC(N)CCC2CNC(=O)c2cccc3cccnc23)c(-c2cccc(F)c2)s1] |
| Example 54 | 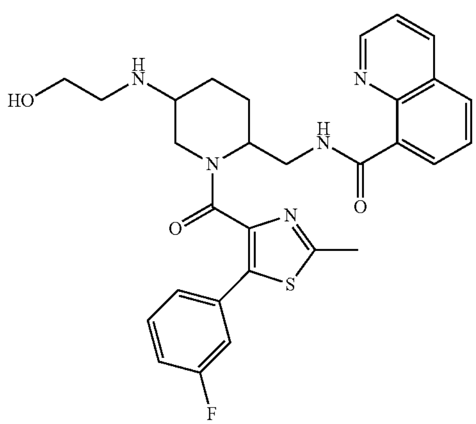 [SMILES: Cc1nc(C(=O)N2CC(NCCO)CCC2CNC(=O)c2cccc3cccnc23)c(-c2cccc(F)c2)s1] |
| Example 55 | 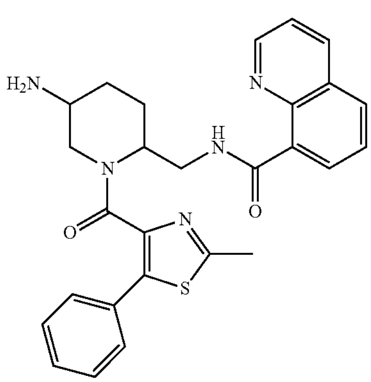 [SMILES: Cc1nc(C(=O)N2CC(N)CCC2CNC(=O)c2cccc3cccnc23)c(-c2ccccc2)s1] |
| Example 56 | 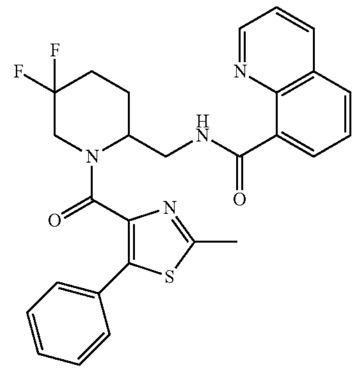 |
| Example 57 | 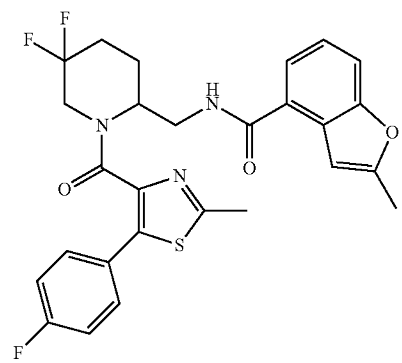 [SMILES: Cc1cc2c(C(=O)NCC3CCC(F)(F)CN3C(=O)c3nc(C)sc3-c3ccc(F)cc3)cccc2o1] |
| Example 58 | 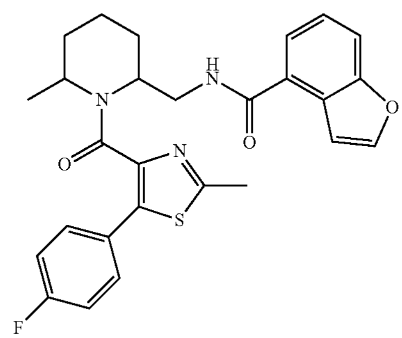 [SMILES: Cc1nc(C(=O)N2C(C)CCCC2CNC(=O)c2cccc3occc23)c(-c2ccc(F)cc2)s1] |
| Example 59 | 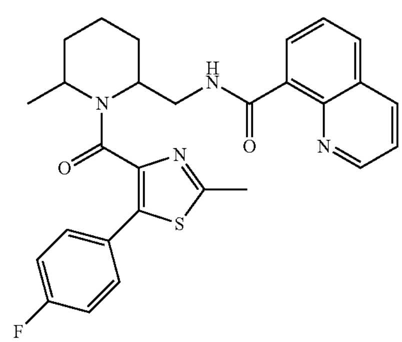 [SMILES: Cc1nc(C(=O)N2C(C)CCCC2CNC(=O)c2cccc3cccnc23)c(-c2ccc(F)cc2)s1] |

TABLE 1-continued

Exemplary Compounds of the Invention

| Example # | Structure |
|---|---|
| Example 60 | 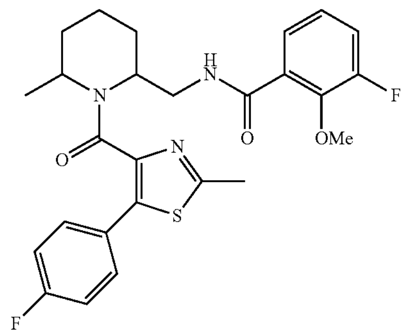 [SMILES: COc1c(F)cccc1C(=O)NCC1CCCC(C)N1C(=O)c1nc(C)sc1-c1ccc(F)cc1] |
| Example 61 | 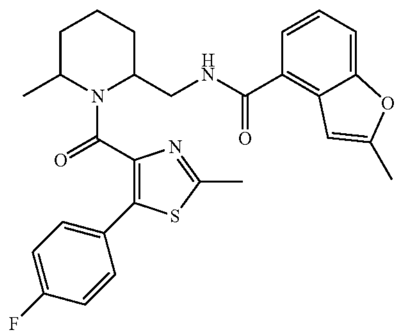 [SMILES: Cc1cc2c(C(=O)NCC3CCCC(C)N3C(=O)c3nc(C)sc3-c3ccc(F)cc3)cccc2o1] |
| Example 62 | 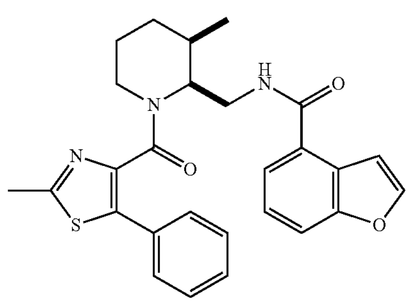 [SMILES: Cc1nc(C(=O)N2CCC[C@@H](C)[C@H]2CNC(=O)c2cccc3occc23)c(-c2ccccc2)s1] |
| Example 63 | 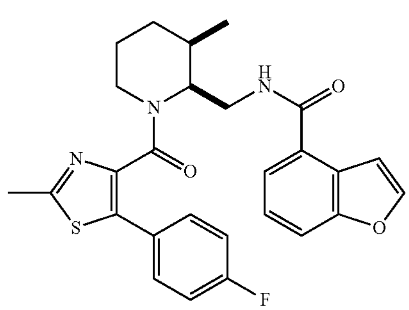 [SMILES: Cc1nc(C(=O)N2CCC[C@@H](C)[C@H]2CNC(=O)c2cccc3occc23)c(-c2ccc(F)cc2)s1] |
| Example 64 | |
| Example 65 | |
| Example 66 | |
| Example 67 | |

TABLE 1-continued

Exemplary Compounds of the Invention

| Example # | Structure |
|---|---|
| Example 68 | (structure) |
| Example 69 | (structure) |
| Example 70 | (structure) |
| Example 71 | (structure) |
| Example 72 | (structure) |
| Example 73 | (structure) |
| Example 74 | (structure) |
| Example 75 | (structure) |

TABLE 1-continued
Exemplary Compounds of the Invention
| Example # | Structure |
|---|---|
| Example 76 | 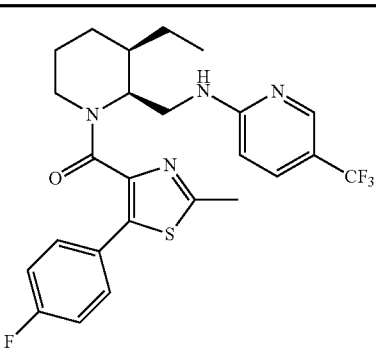 |
| Example 77 | 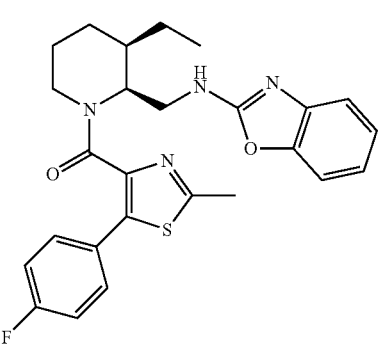 [SMILES: CC[C@@H]1CCCN(C(=O)c2nc(C)sc2-c2ccc(F)cc2)[C@@H]1CNc1nc2ccccc2o1] |
| Example 78 | 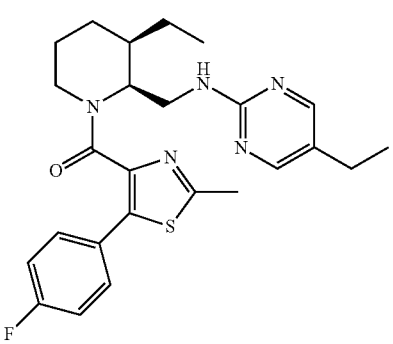 [SMILES: CCc1cnc(NC[C@@H]2[C@H](CC)CCCN2C(=O)c2nc(C)sc2-c2ccc(F)cc2)nc1] |
| Example 79 | 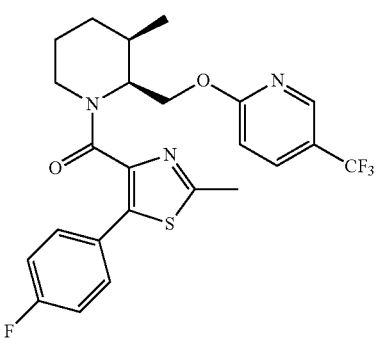 [SMILES: Cc1nc(C(=O)N2CCC[C@@H](C)[C@H]2COc2ccc(C(F)(F)F)cn2)c(-c2ccc(F)cc2)s1] |
| Example 80 | 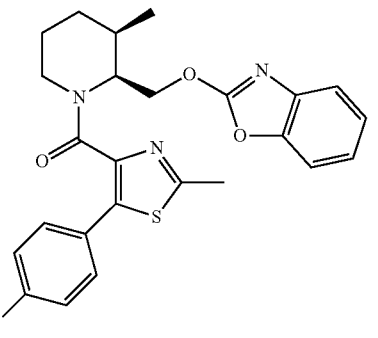 |
| Example 81 | 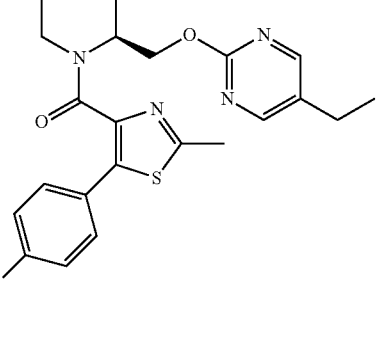 |
| Example 82 | 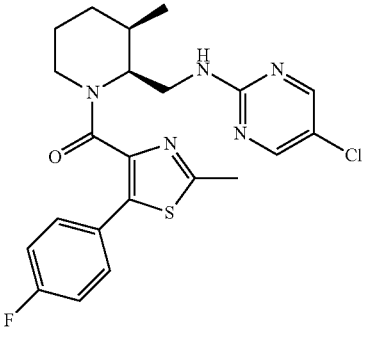 [SMILES: Cc1nc(C(=O)N2CCC[C@@H](C)[C@H]2CNc2ncc(Cl)cn2)c(-c2ccc(F)cc2)s1] |
| Example 83 | 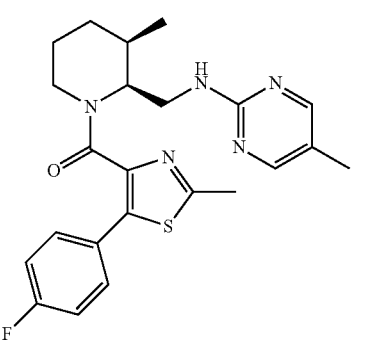 [SMILES: Cc1cnc(NC[C@@H]2[C@H](C)CCCN2C(=O)c2nc(C)sc2-c2ccc(F)cc2)nc1] |

TABLE 1-continued
Exemplary Compounds of the Invention
| Example # | Structure |
|---|---|
| Example 84 | 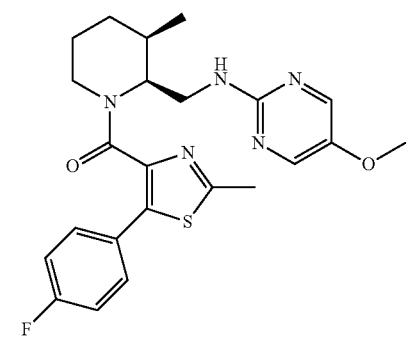 |
| Example 85 | 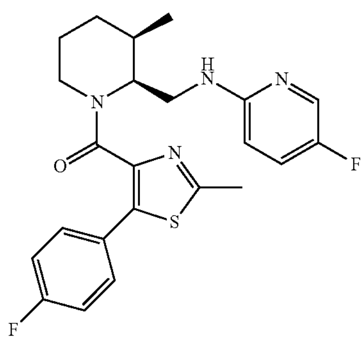 [SMILES: Cc1nc(C(=O)N2CCC[C@@H](C)[C@H]2CNc2ccc(F)cn2)c(-c2ccc(F)cc2)s1] |
| Example 86 | 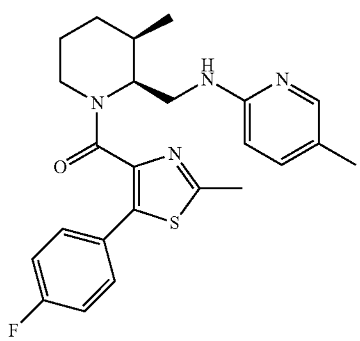 [SMILES: Cc1ccc(NC[C@@H]2[C@H](C)CCCN2C(=O)c2nc(C)sc2-c2ccc(F)cc2)nc1] |
| Example 87 | 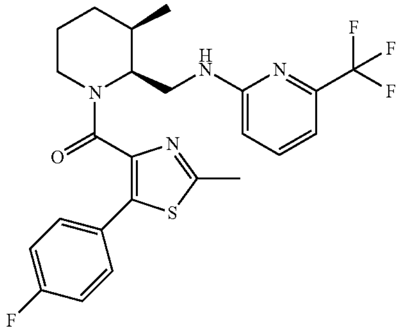 [SMILES: Cc1nc(C(=O)N2CCC[C@@H](C)[C@H]2CNc2cccc(C(F)(F)F)n2)c(-c2ccc(F)cc2)s1] |
| Example 88 | 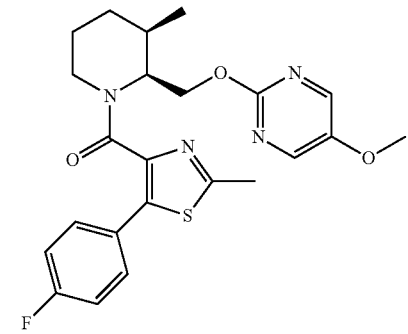 [SMILES: COc1cnc(OC[C@@H]2[C@H](C)CCCN2C(=O)c2nc(C)sc2-c2ccc(F)cc2)nc1] |
| Example 89 | |
| Example 90 | |
| Example 91 | |

TABLE 1-continued
Exemplary Compounds of the Invention
| Example # | Structure |
|---|---|
| Example 92 | 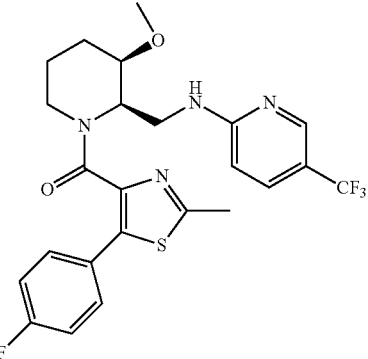 |
| Example 93 | 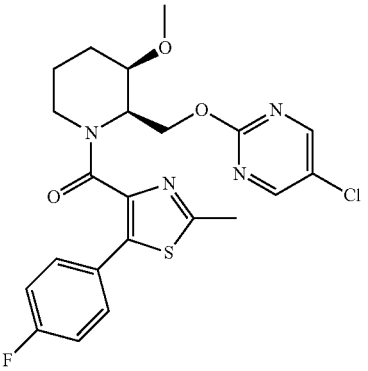 [SMILES: CO[C@@H]1CCCN(C(=O)c2nc(C)sc2-c2ccc(F)cc2)[C@@H]1COc1ncc(Cl)cn1] |
| Example 94 | 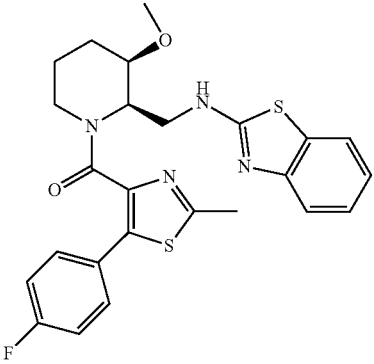 [SMILES: CO[C@@H]1CCCN(C(=O)c2nc(C)sc2-c2ccc(F)cc2)[C@@H]1CNc1nc2ccccc2s1] |
| Example 95 | 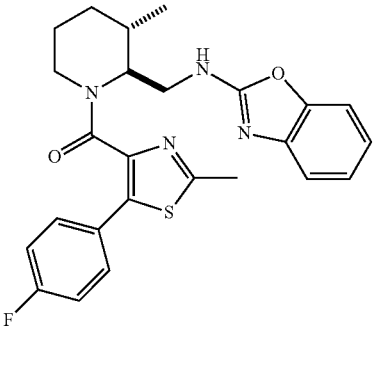 [SMILES: Cc1nc(C(=O)N2CCC[C@H](C)[C@H]2CNc2nc3ccccc3o2)c(-c2ccc(F)cc2)s1] |
| Example 96 | 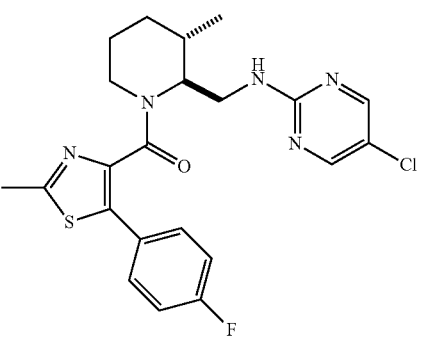 [SMILES: Cc1nc(C(=O)N2CCC[C@H](C)[C@H]2CNc2ncc(Cl)cn2)c(-c2ccc(F)cc2)s1] |
| Example 97 | 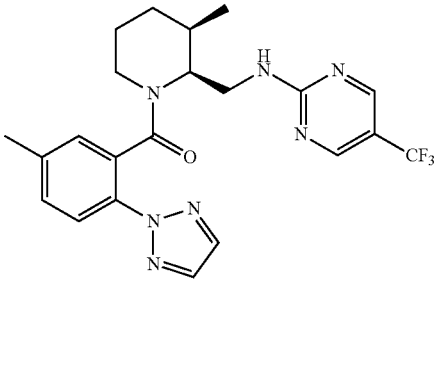 [SMILES: Cc1ccc(-n2nccn2)c(C(=O)N2CCC[C@@H](C)[C@H]2CNc2ncc(C(F)(F)F)cn2)c1] |
| Example 98 | 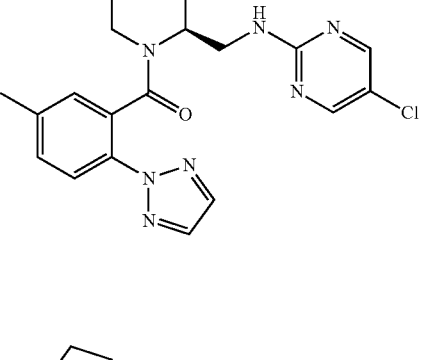 |
| Example 99 | 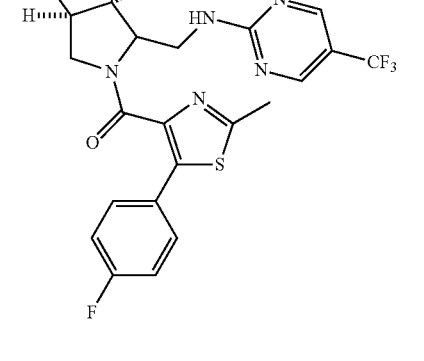 |

TABLE 1-continued

Exemplary Compounds of the Invention

| Example # | Structure |
|---|---|
| Example 100 | |
| Example 101 | |
| Example 102 | |
| Example 103 | |
| Example 104 | 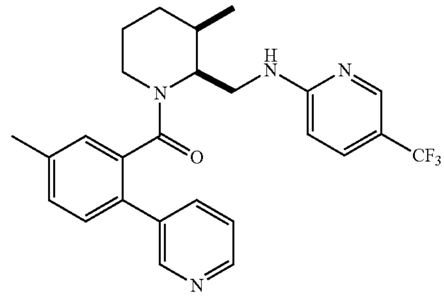 [SMILES: Cc1ccc(-c2cccnc2)c(C(=O)N2CCC[C@@H](C)[C@H]2CNc2ccc(C(F)(F)F)cn2)c1] |
| Example 105 | 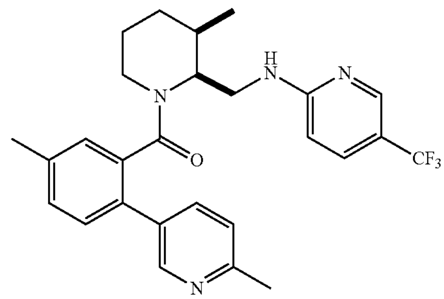 [SMILES: Cc1ccc(-c2ccc(C)nc2)c(C(=O)N2CCC[C@@H](C)[C@H]2CNc2ccc(C(F)(F)F)cn2)c1] |
| Example 106 | 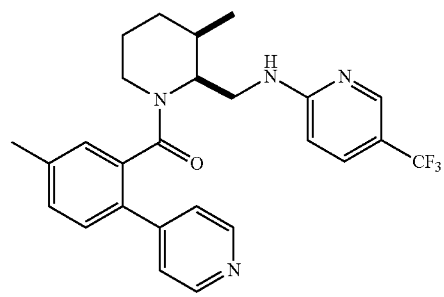 [SMILES: Cc1ccc(-c2ccncc2)c(C(=O)N2CCC[C@@H](C)[C@H]2CNc2ccc(C(F)(F)F)cn2)c1] |
| Example 107 | 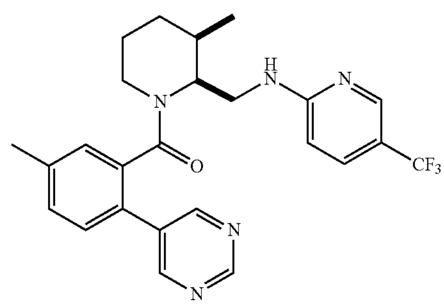 [SMILES: Cc1ccc(-c2cncnc2)c(C(=O)N2CCC[C@@H](C)[C@H]2CNc2ccc(C(F)(F)F)cn2)c1] |
| Example 108 | 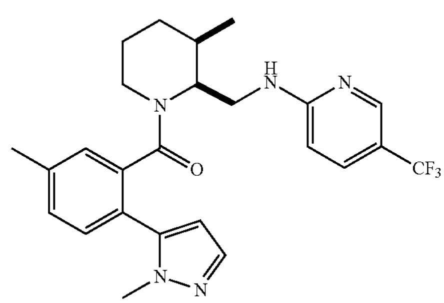 [SMILES: Cc1ccc(-c2ccnn2C)c(C(=O)N2CCC[C@@H](C)[C@H]2CNc2ccc(C(F)(F)F)cn2)c1] |

TABLE 1-continued

Exemplary Compounds of the Invention

| Example # | Structure |
|---|---|
| Example 109 | |
| Example 110 | |
| Example 111 | |
| Example 112 | |
| Example 113 | 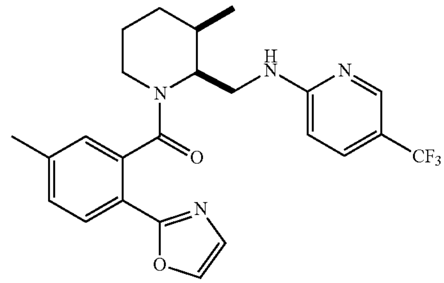 [SMILES: Cc1ccc(-c2ncco2)c(C(=O)N2CCC[C@@H](C)[C@H]2CNc2ccc(C(F)(F)F)cn2)c1] |
| Example 114 | 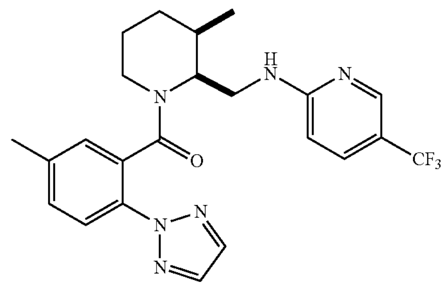 [SMILES: Cc1ccc(-n2nccn2)c(C(=O)N2CCC[C@@H](C)[C@H]2CNc2ccc(C(F)(F)F)cn2)c1] |
| Example 115 | 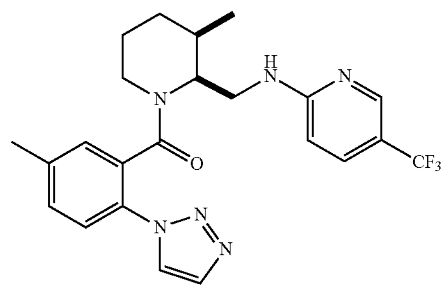 [SMILES: Cc1ccc(-n2ccnn2)c(C(=O)N2CCC[C@@H](C)[C@H]2CNc2ccc(C(F)(F)F)cn2)c1] |
| Example 116 | 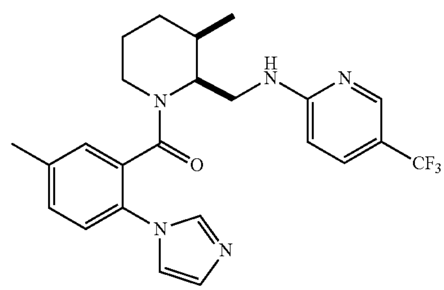 [SMILES: Cc1ccc(-n2ccnc2)c(C(=O)N2CCC[C@@H](C)[C@H]2CNc2ccc(C(F)(F)F)cn2)c1] |
| Example 117 | 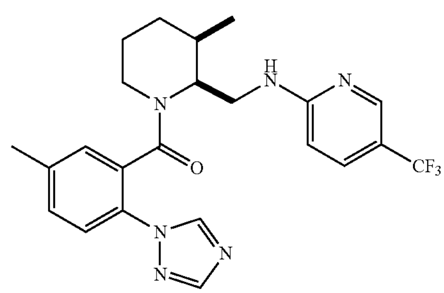 [SMILES: Cc1ccc(-n2cncn2)c(C(=O)N2CCC[C@@H](C)[C@H]2CNc2ccc(C(F)(F)F)cn2)c1] |

TABLE 1-continued

Exemplary Compounds of the Invention

| Example # | Structure |
|---|---|
| Example 118 | 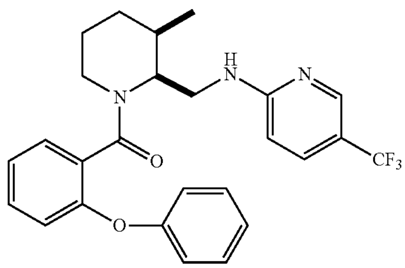 [SMILES: C[C@@H]1CCCN(C(=O)c2ccccc2Oc2ccccc2)[C@@H]1CNc1ccc(C(F)(F)F)cn1] |
| Example 119 | 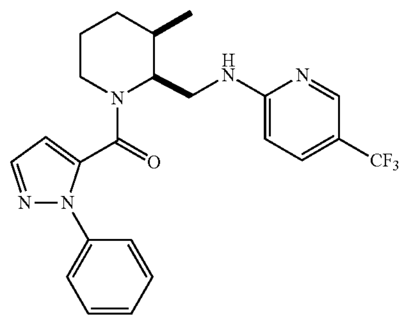 [SMILES: C[C@@H]1CCCN(C(=O)c2ccnn2-c2ccccc2)[C@@H]1CNc1ccc(C(F)(F)F)cn1] |
| Example 120 | 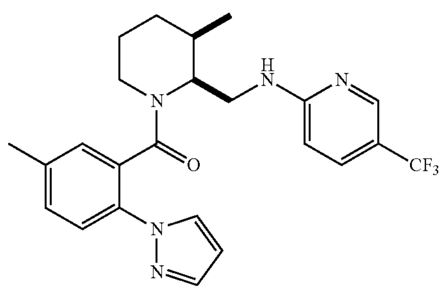 [SMILES: Cc1ccc(-n2cccn2)c(C(=O)N2CCC[C@@H](C)[C@H]2CNc2ccc(C(F)(F)F)cn2)c1] |
| Example 121 | 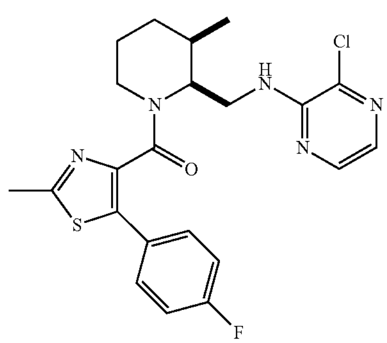 [SMILES: Cc1nc(C(=O)N2CCC[C@@H](C)[C@H]2CNc2nccnc2Cl)c(-c2ccc(F)cc2)s1] |
| Example 122 | 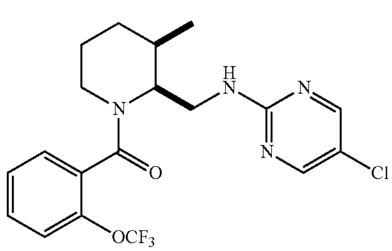 [SMILES: C[C@@H]1CCCN(C(=O)c2ccccc2OC(F)(F)F)[C@@H]1CNc1ncc(Cl)cn1] |
| Example 123 | |
| Example 124 | |
| Example 125 | |
| Example 126 | |

TABLE 1-continued

Exemplary Compounds of the Invention

| Example # | Structure |
|---|---|
| Example 127 | (structure) |
| Example 128 | (structure) |
| Example 129 | (structure) |
| Example 130 | (structure) |
| Example 131 | (structure) |
| Example 132 | (structure) |
| Example 133 | (structure) |
| Example 134 | (structure) |

TABLE 1-continued
Exemplary Compounds of the Invention
| Example # | Structure |
|---|---|
| Example 135 | 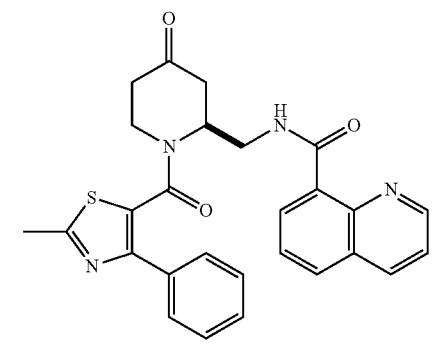 |
| Example 136 | |
| Example 137 | |
| Example 138 | |
| Example 139 | 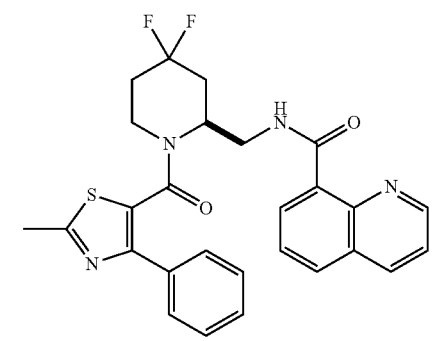 |
| Example 140 | 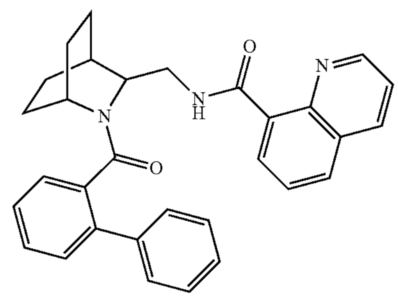 [SMILES: O=C(NCC1C2CCC(CC2)N1C(=O)c1ccccc1-c1ccccc1)c1cccc2cccnc12] |
| Example 141 | 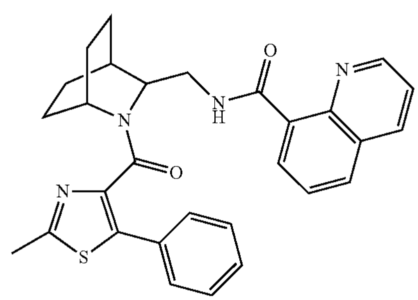 [SMILES: Cc1nc(C(=O)N2C3CCC(CC3)C2CNC(=O)c2cccc3cccnc23)c(-c2ccccc2)s1] |
| Example 142 P | 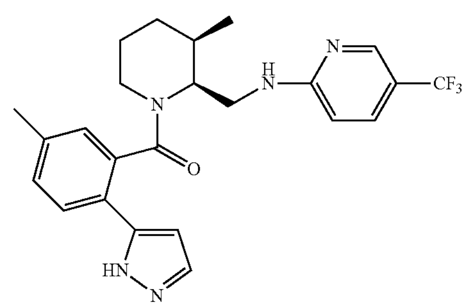 [SMILES: Cc1ccc(-c2ccn[nH]2)c(C(=O)N2CCC[C@@H](C)[C@H]2CNc2ccc(C(F)(F)F)cn2)c1] |
| Example 143 P | 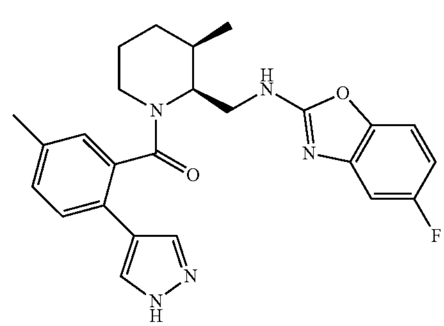 [SMILES: Cc1ccc(-c2cn[nH]c2)c(C(=O)N2CCC[C@@H](C)[C@H]2CNc2nc3cc(F)ccc3o2)c1] |

TABLE 1-continued

Exemplary Compounds of the Invention

| Example # | Structure |
|---|---|
| Example 144 P (See Ex A104 below) | 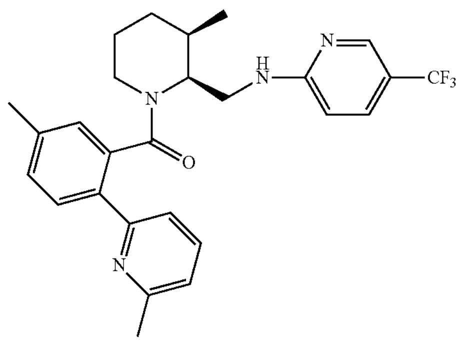 [SMILES: Cc1ccc(-c2cccc(C)n2)c(C(=O)N2CCC[C@@H](C)[C@H]2CNc2ccc(C(F)(F)F)cn2)c1] |
| Example 145 P | 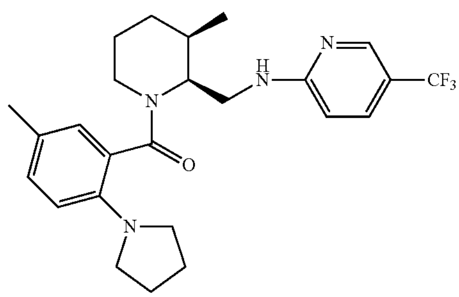 [SMILES: Cc1ccc(N2CCCC2)c(C(=O)N2CCC[C@@H](C)[C@H]2CNc2ccc(C(F)(F)F)cn2)c1] |
| Example 146 P | 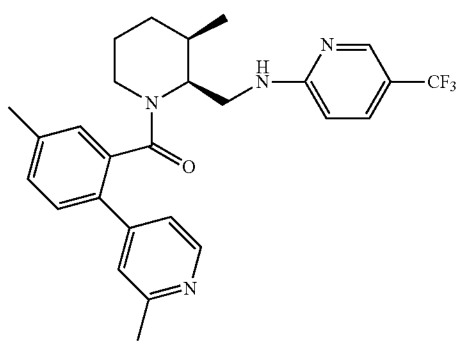 [SMILES: Cc1ccc(-c2ccnc(C)c2)c(C(=O)N2CCC[C@@H](C)[C@H]2CNc2ccc(C(F)(F)F)cn2)c1] |
| Example 147 P (See Ex A108 below) | 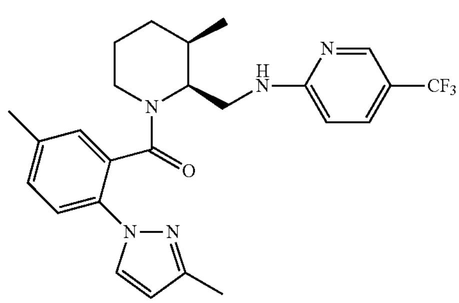 [SMILES: Cc1ccc(-n2ccc(C)n2)c(C(=O)N2CCC[C@@H](C)[C@H]2CNc2ccc(C(F)(F)F)cn2)c1] |
| Example 148 P | 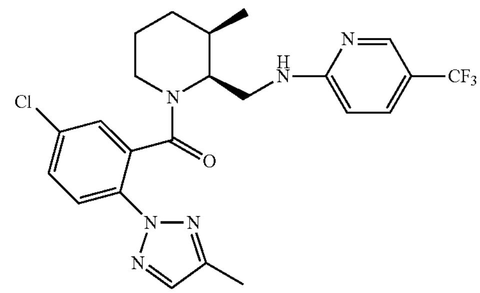 [SMILES: Cc1cnn(-c2ccc(Cl)cc2C(=O)N2CCC[C@@H](C)[C@H]2CNc2ccc(C(F)(F)F)cn2)n1] |
| Example 149 P | 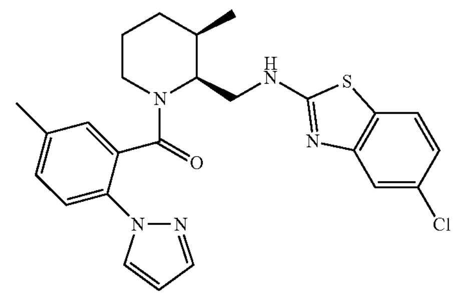 [SMILES: Cc1ccc(-n2cccn2)c(C(=O)N2CCC[C@@H](C)[C@H]2CNc2nc3cc(Cl)ccc3s2)c1] |
| Example 150 P (See Ex A29 below) | 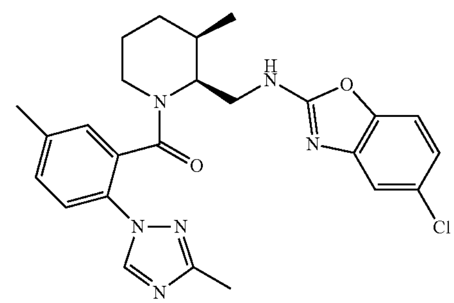 [SMILES: Cc1ccc(-n2cnc(C)n2)c(C(=O)N2CCC[C@@H](C)[C@H]2CNc2nc3cc(Cl)ccc3o2)c1] |
| Example 151 P | 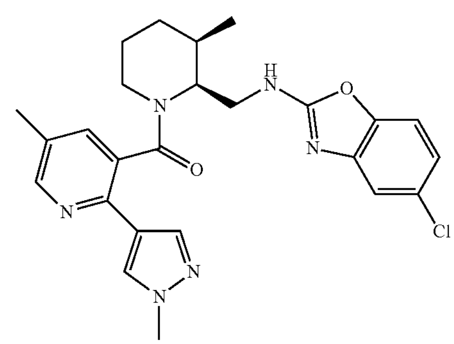 [SMILES: Cc1cnc(-c2cnn(C)c2)c(C(=O)N2CCC[C@@H](C)[C@H]2CNc2nc3cc(Cl)ccc3o2)c1] |
| Example 152 P | 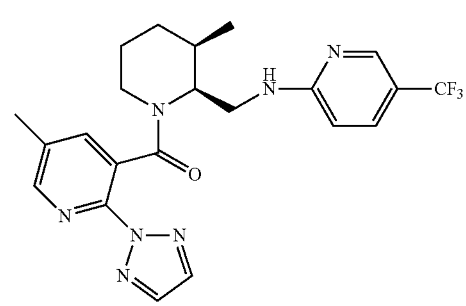 [SMILES: Cc1cnc(-n2nccn2)c(C(=O)N2CCC[C@@H](C)[C@H]2CNc2ccc(C(F)(F)F)cn2)c1] |

TABLE 1-continued
Exemplary Compounds of the Invention
| Example # | Structure |
|---|---|
| Example 153 P | 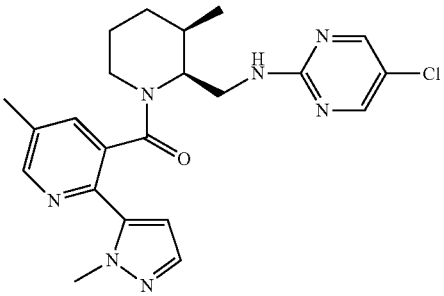 [SMILES: Cc1cnc(-c2ccnn2C)c(C(=O)N2CCC[C@@H](C)[C@H]2CNc2ncc(Cl)cn2)c1] |
| Example 154 P | 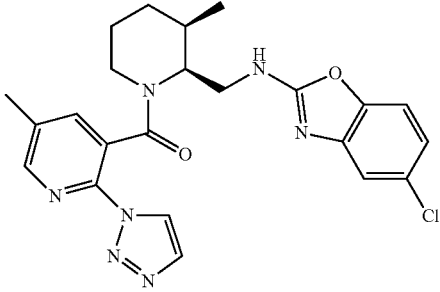 [SMILES: Cc1cnc(-n2ccnn2)c(C(=O)N2CCC[C@@H](C)[C@H]2CNc2nc3cc(Cl)ccc3o2)c1] |
| Example 155 P | 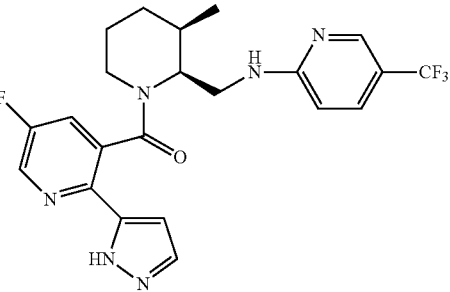 |
| Example 156 P (See Ex A12 below) | 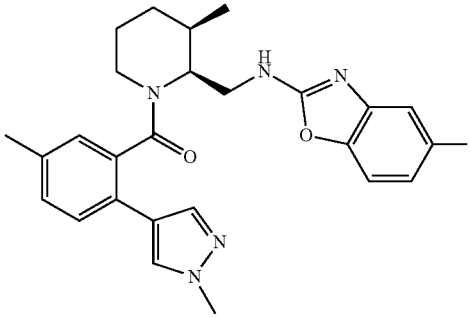 |
| Example 157 P | 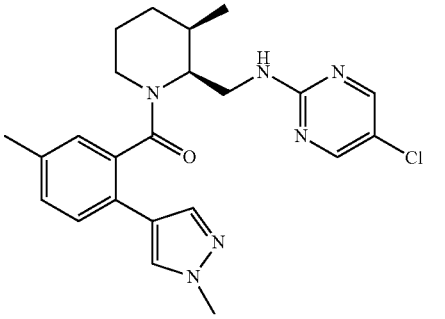 [SMILES: Cc1ccc(-c2cnn(C)c2)c(C(=O)N2CCC[C@@H](C)[C@H]2CNc2ncc(Cl)cn2)c1] |
| Example 158 P (See Ex A11 below) | 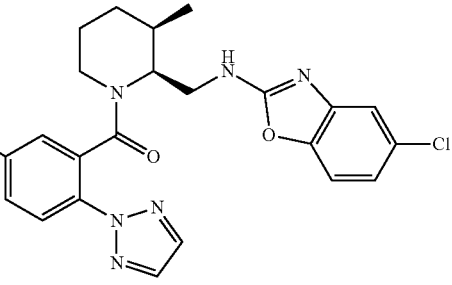 |
| Example 159 P (See Ex A14 below) | 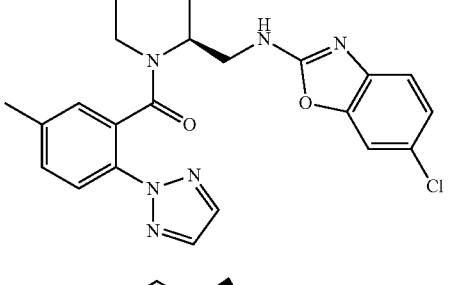 |
| Example 160 P | 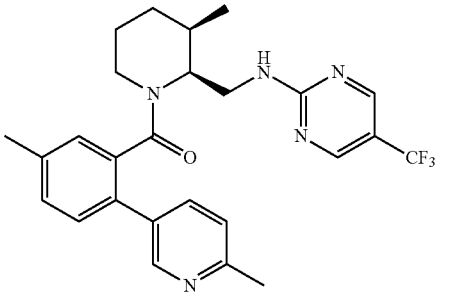 [SMILES: Cc1ccc(-c2ccc(C)nc2)c(C(=O)N2CCC[C@@H](C)[C@H]2CNc2ncc(C(F)(F)F)cn2)c1] |
| Example 161 P | 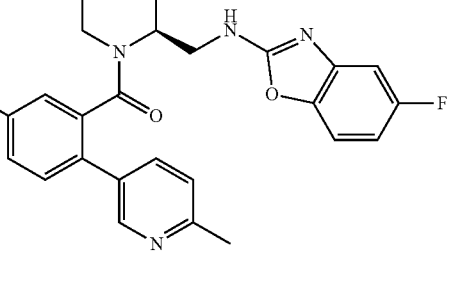 |

TABLE 1-continued
Exemplary Compounds of the Invention
| Example # | Structure |
|---|---|
| Example 162 P | 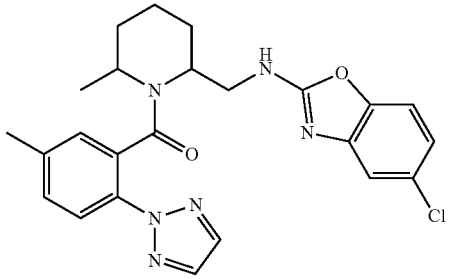 [SMILES: Cc1ccc(-n2nccn2)c(C(=O)N2C(C)CCCC2CNc2nc3cc(Cl)ccc3o2)c1] |
| Example 163 P | 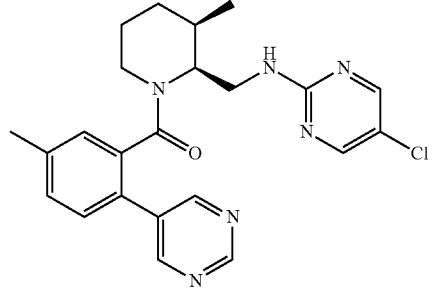 [SMILES: Cc1ccc(-c2cncnc2)c(C(=O)N2CCC[C@@H](C)[C@H]2CNc2ncc(Cl)cn2)c1] |
| Example 164 P | 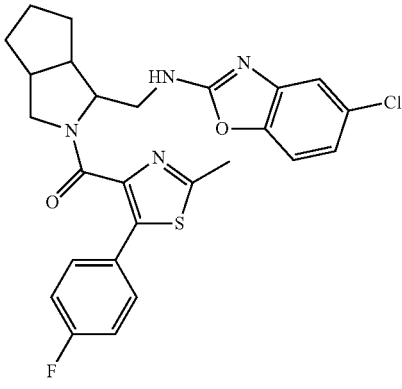 [SMILES: Cc1nc(C(=O)N2CC3CCCC3C2CNc2nc3cc(Cl)ccc3o2)c(-c2ccc(F)cc2)s1] |
| Example 165 P (See Ex A69 below) | 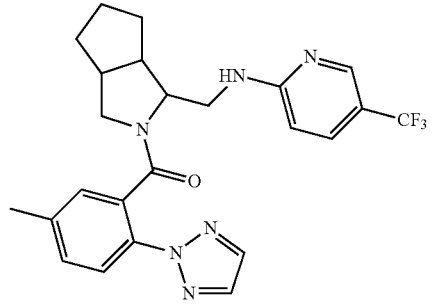 [SMILES: Cc1ccc(-n2nccn2)c(C(=O)N2CC3CCCC3C2CNc2ccc(C(F)(F)F)cn2)c1] |
| Example 166 P | 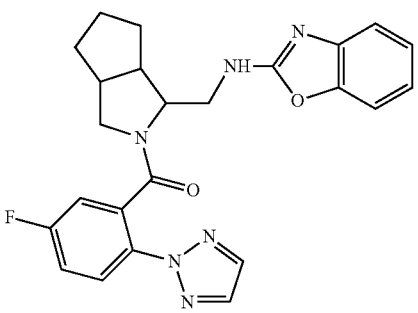 [SMILES: O=C(c1cc(F)ccc1-n1nccn1)N1CC2CCCC2C1CNc1nc2ccccc2o1] |
| Example 167 P | 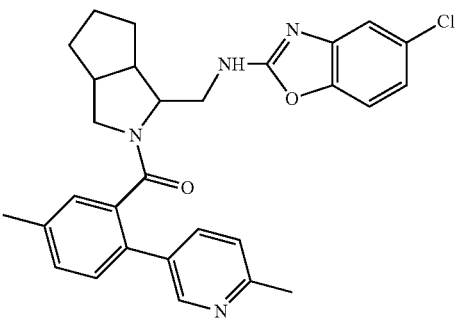 [SMILES: Cc1ccc(-c2ccc(C)nc2)c(C(=O)N2CC3CCCC3C2CNc2nc3cc(Cl)ccc3o2)c1] |
| Example 168 P | 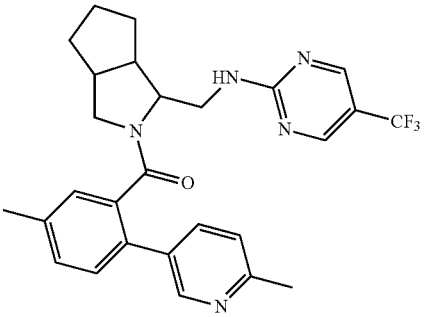 [SMILES: Cc1ccc(-c2ccc(C)nc2)c(C(=O)N2CC3CCCC3C2CNc2ncc(C(F)(F)F)cn2)c1] |
| Example 169 P (See Ex A70 below) | 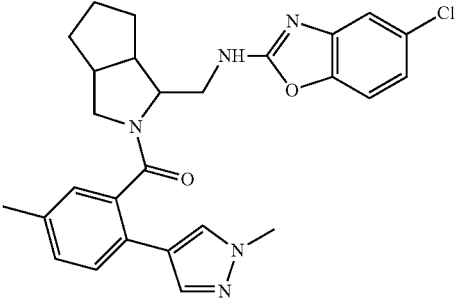 [SMILES: Cc1ccc(-c2cnn(C)c2)c(C(=O)N2CC3CCCC3C2CNc2nc3cc(Cl)ccc3o2)c1] |

TABLE 1-continued
Exemplary Compounds of the Invention
| Example # | Structure |
|---|---|
| Example 170 P | 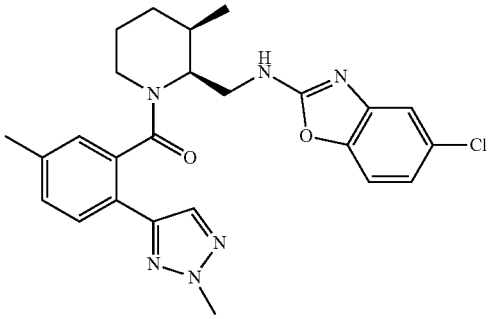 [SMILES: Cc1ccc(-c2cnn(C)n2)c(C(=O)N2CCC[C@@H](C)[C@H]2CNc2nc3cc(Cl)ccc3o2)c1] |
| Example 171 P | 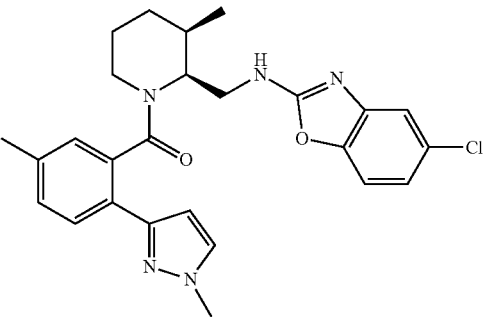 [SMILES: Cc1ccc(-c2ccn(C)n2)c(C(=O)N2CCC[C@@H](C)[C@H]2CNc2nc3cc(Cl)ccc3o2)c1] |
| Example 172 P | 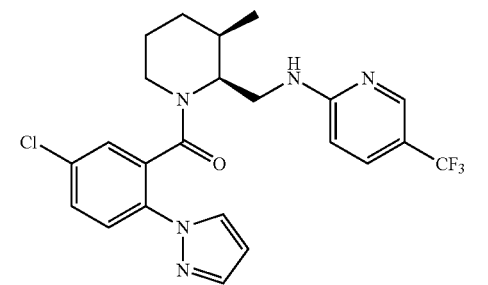 [SMILES: C[C@@H]1CCCN(C(=O)c2cc(Cl)ccc2-n2cccn2)[C@@H]1CNc1ccc(C(F)(F)F)cn1] |
| Example 173 P | 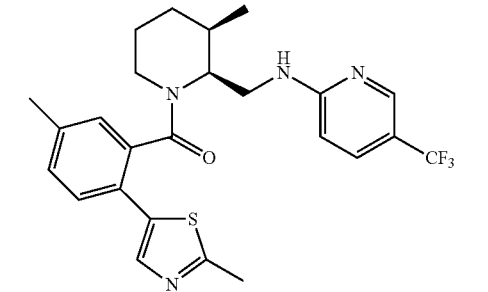 [SMILES: Cc1ccc(-c2cnc(C)s2)c(C(=O)N2CCC[C@@H](C)[C@H]2CNc2ccc(C(F)(F)F)cn2)c1] |
| Example 174 P | 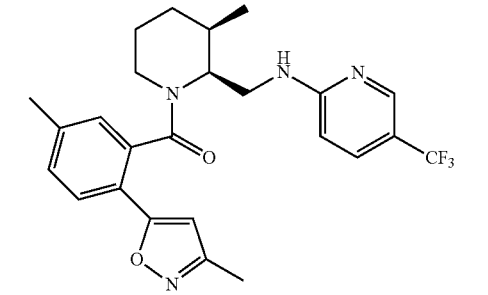 [SMILES: Cc1ccc(-c2cc(C)no2)c(C(=O)N2CCC[C@@H](C)[C@H]2CNc2ccc(C(F)(F)F)cn2)c1] |
| Example 175 P | 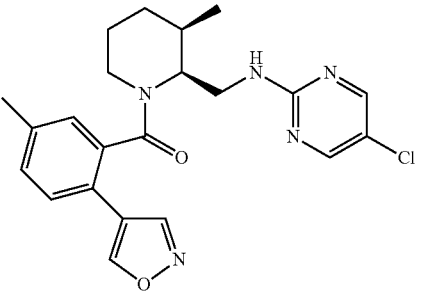 [SMILES: Cc1ccc(-c2cnoc2)c(C(=O)N2CCC[C@@H](C)[C@H]2CNc2ncc(Cl)cn2)c1] |
| Example 176 P | 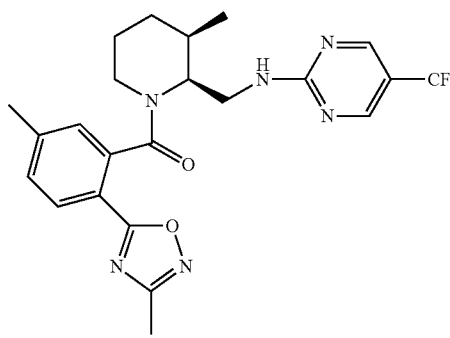 |
| Example 177 P | 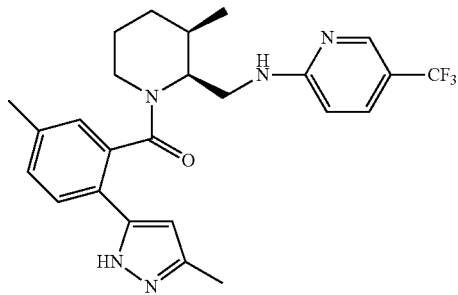 [SMILES: Cc1ccc(-c2cc(C)n[nH]2)c(C(=O)N2CCC[C@@H](C)[C@H]2CNc2ccc(C(F)(F)F)cn2)c1] |
| Example 178 P | 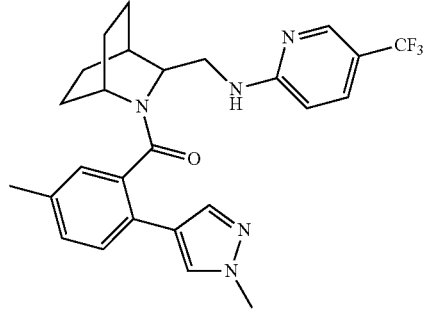 [SMILES: Cc1ccc(-c2cnn(C)c2)c(C(=O)N2C3CCC(CC3)C2CNc2ccc(C(F)(F)F)cn2)c1] |

TABLE 1-continued

Exemplary Compounds of the Invention

| Example # | Structure |
|---|---|
| Example 179 P | 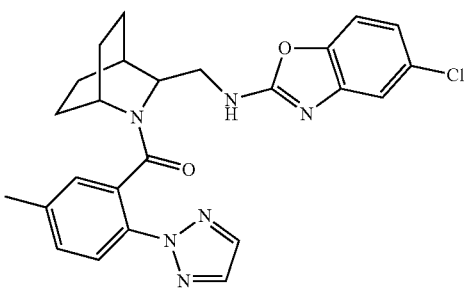 [SMILES: Cc1ccc(-n2nccn2)c(C(=O)N2C3CCC(CC3)C2CNc2nc3cc(Cl)ccc3o2)c1] |
| Example 180 P | 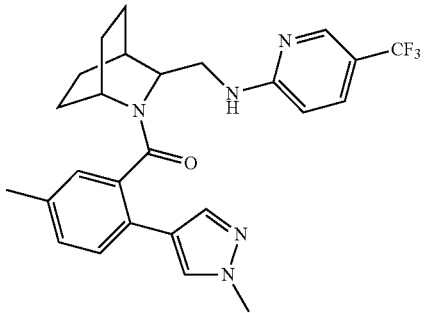 [SMILES: Cc1ccc(-c2cnn(C)c2)c(C(=O)N2C3CCC(CC3)C2CNc2ccc(C(F)(F)F)cn2)c1] |

P=prophetic example (compounds with a "P" designation and a reference to an Example in Table 1A have been prepared).

Further exemplary compounds are shown in Table 1A. In some embodiments are contemplated compounds as in Table 1A. In still other embodiments are contemplated compounds as in Table 1A, except for compounds A11, A12, A14, A29, A69, A70, A104, and A108.

TABLE 1A

| Ex. # | Structure |
|---|---|
| Ex. A1 | 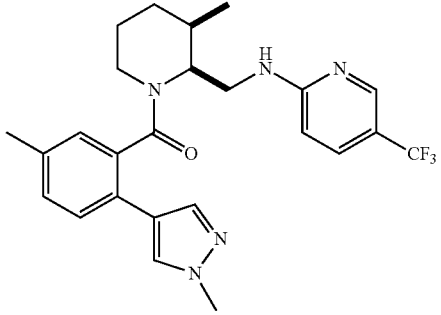 |

TABLE 1A-continued

| Ex. # | Structure |
|---|---|
| Ex. A2 | 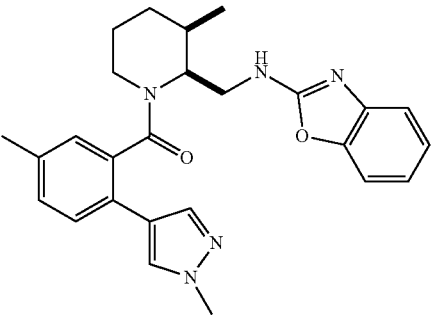 [SMILES: Cc1ccc(-c2cnn(C)c2)c(C(=O)N2CCC[C@@H](C)[C@H]2CNc2nc3ccccc3o2)c1] |
| Ex. A3 | 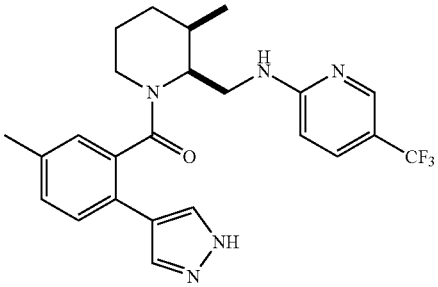 [SMILES: Cc1ccc(-c2cn[nH]c2)c(C(=O)N2CCC[C@@H](C)[C@H]2CNc2ccc(C(F)(F)F)cn2)c1] |
| Ex. A4 | 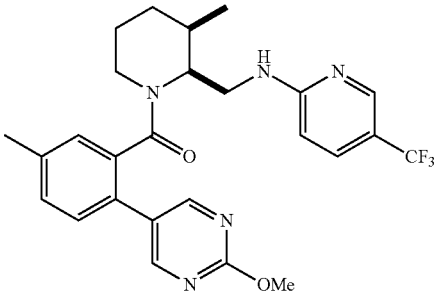 [SMILES: COc1ncc(-c2ccc(C)cc2C(=O)N2CCC[C@@H](C)[C@H]2CNc2ccc(C(F)(F)F)cn2)cn1] |
| Ex. A5 | 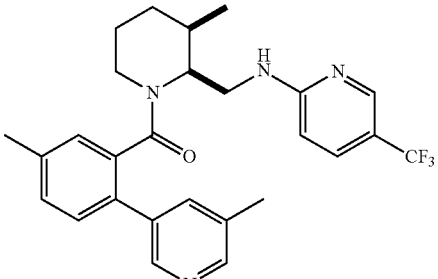 |
| Ex. A6 | 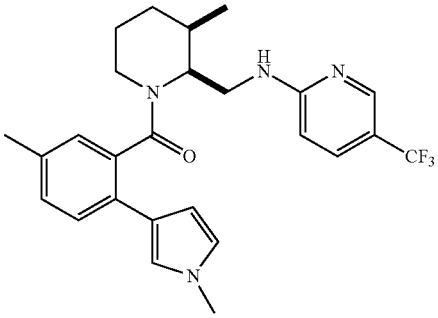 |

TABLE 1A-continued

| Ex. # | Structure |
|---|---|
| Ex. A7 | 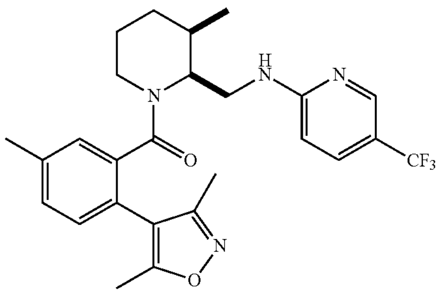 [SMILES: Cc1ccc(-c2c(C)noc2C)c(C(=O)N2CCC[C@@H](C)[C@H]2CNc2ccc(C(F)(F)F)cn2)c1] |
| Ex. A8 | 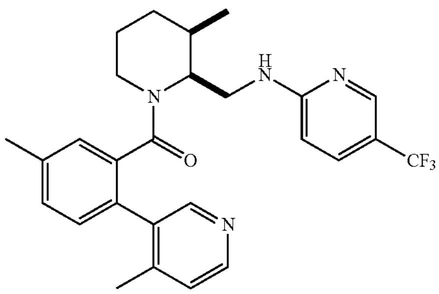 [SMILES: Cc1ccc(-c2cnccc2C)c(C(=O)N2CCC[C@@H](C)[C@H]2CNc2ccc(C(F)(F)F)cn2)c1] |
| Ex. A9 | 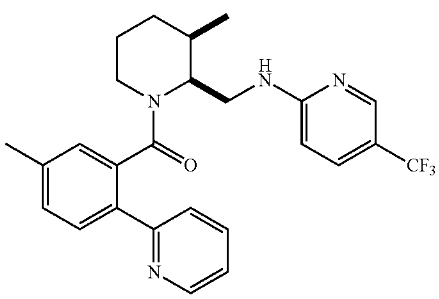 [SMILES: Cc1ccc(-c2ccccn2)c(C(=O)N2CCC[C@@H](C)[C@H]2CNc2ccc(C(F)(F)F)cn2)c1] |
| Ex. A10 | 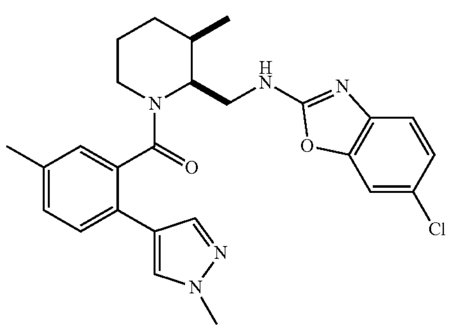 [SMILES: Cc1ccc(-c2cnn(C)c2)c(C(=O)N2CCC[C@@H](C)[C@H]2CNc2nc3ccc(Cl)cc3o2)c1] |
| Ex. A11 | 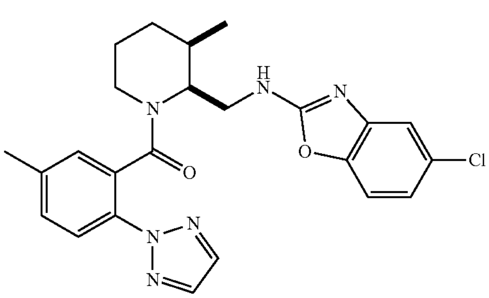 [SMILES: Cc1ccc(-n2nccn2)c(C(=O)N2CCC[C@@H](C)[C@H]2CNc2nc3cc(Cl)ccc3o2)c1] |
| Ex. A12 | |
| Ex. A13 | |
| Ex. A14 | |
| Ex. A15 | |
| Ex. A16 | |

TABLE 1A-continued

| Ex. # | Structure |
|---|---|
| Ex. A17 | 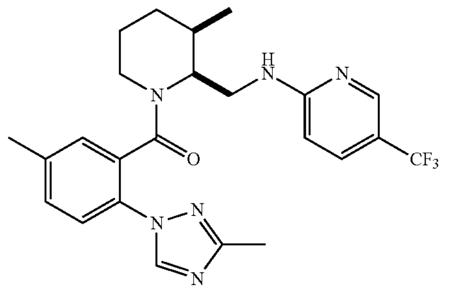 [SMILES: Cc1ccc(-n2cnc(C)n2)c(C(=O)N2CCC[C@@H](C)[C@H]2CNc2ccc(C(F)(F)F)cn2)c1] |
| Ex. A18 | 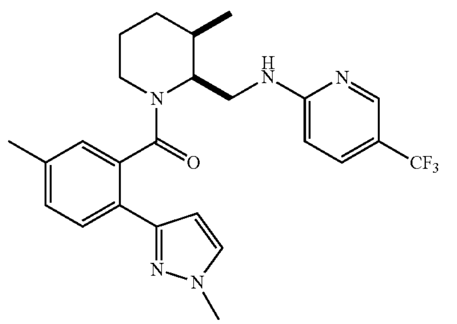 |
| Ex. A19 | 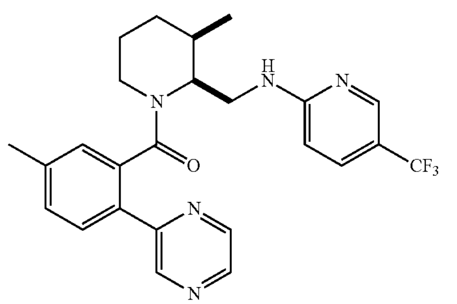 [SMILES: Cc1ccc(-c2cnccn2)c(C(=O)N2CCC[C@@H](C)[C@H]2CNc2ccc(C(F)(F)F)cn2)c1] |
| Ex. A20 | 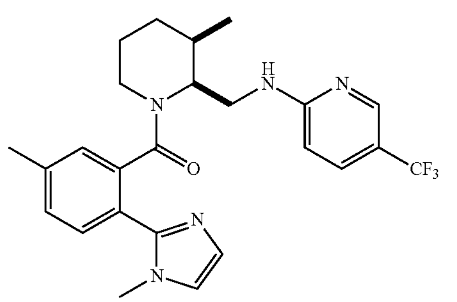 [SMILES: Cc1ccc(-c2nccn2C)c(C(=O)N2CCC[C@@H](C)[C@H]2CNc2ccc(C(F)(F)F)cn2)c1] |
| Ex. A21 | 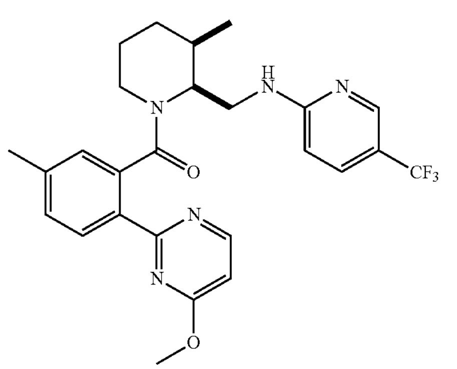 [SMILES: COc1ccnc(-c2ccc(C)cc2C(=O)N2CCC[C@@H](C)[C@H]2CNc2ccc(C(F)(F)F)cn2)n1] |
| Ex. A22 | |
| Ex. A23 | |
| Ex. A24 | |
| Ex. A25 | |
| Ex. A26 | |

TABLE 1A-continued

| Ex. # | Structure |
|---|---|
| Ex. A27 | 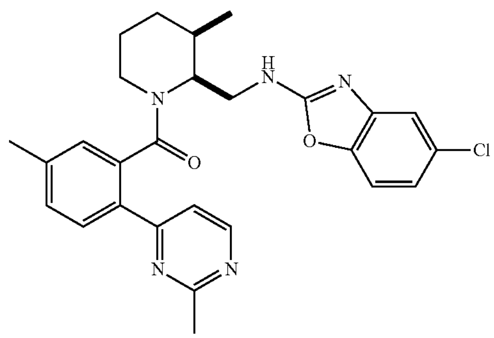 [SMILES: Cc1ccc(-c2ccnc(C)n2)c(C(=O)N2CCC[C@@H](C)[C@H]2CNc2nc3cc(Cl)ccc3o2)c1] |
| Ex. A28 | 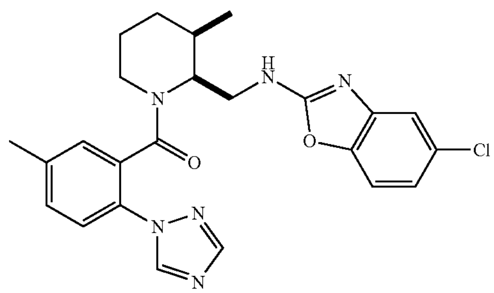 [SMILES: Cc1ccc(-n2cncn2)c(C(=O)N2CCC[C@@H](C)[C@H]2CNc2nc3cc(Cl)ccc3o2)c1] |
| Ex. A29 | 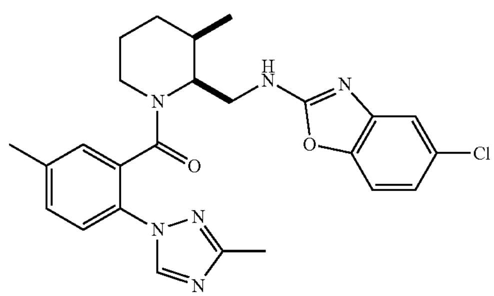 [SMILES: Cc1ccc(-n2cnc(C)n2)c(C(=O)N2CCC[C@@H](C)[C@H]2CNc2nc3cc(Cl)ccc3o2)c1] |
| Ex. A30 | 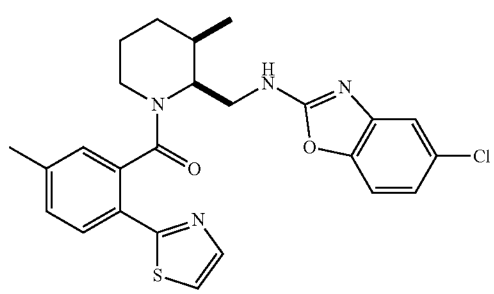 [SMILES: Cc1ccc(-c2nccs2)c(C(=O)N2CCC[C@@H](C)[C@H]2CNc2nc3cc(Cl)ccc3o2)c1] |
| Ex. A31 | 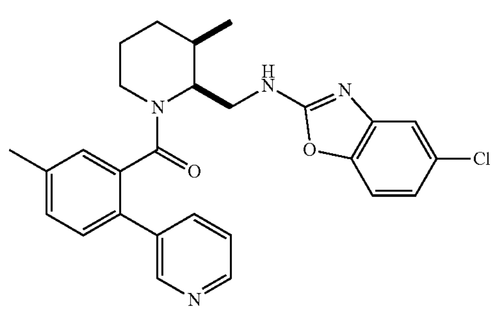 [SMILES: Cc1ccc(-c2cccnc2)c(C(=O)N2CCC[C@@H](C)[C@H]2CNc2nc3cc(Cl)ccc3o2)c1] |
| Ex. A32 | |
| Ex. A33 | |
| Ex. A34 | |
| Ex. A35 | |
| Ex. A36 | |

TABLE 1A-continued

| Ex. # | Structure |
|---|---|
| Ex. A37 | 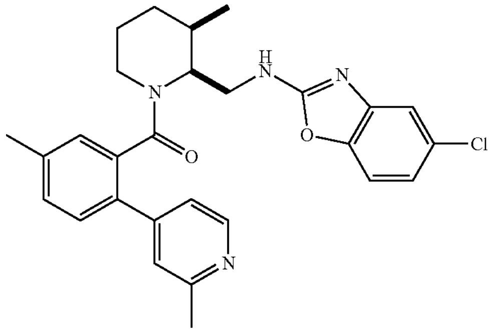 |
| Ex. A38 | 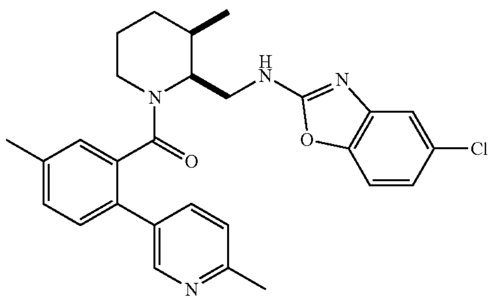 [SMILES: Cc1ccc(-c2ccc(C)nc2)c(C(=O)N2CCC[C@@H](C)[C@H]2CNc2nc3cc(Cl)ccc3o2)c1] |
| Ex. A39 | 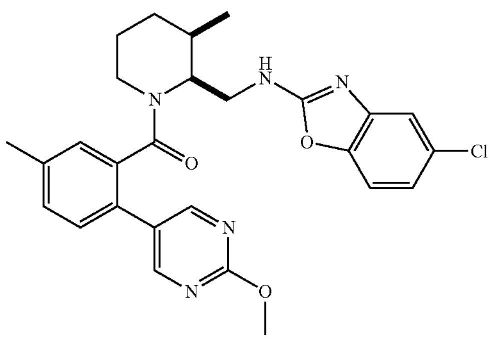 [SMILES: COc1ncc(-c2ccc(C)cc2C(=O)N2CCC[C@@H](C)[C@H]2CNc2nc3cc(Cl)ccc3o2)cn1] |
| Ex. A40 | 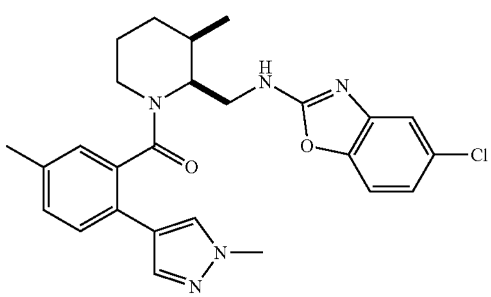 [SMILES: Cc1ccc(-c2cnn(C)c2)c(C(=O)N2CCC[C@@H](C)[C@H]2CNc2nc3cc(Cl)ccc3o2)c1] |
| Ex. A41 | 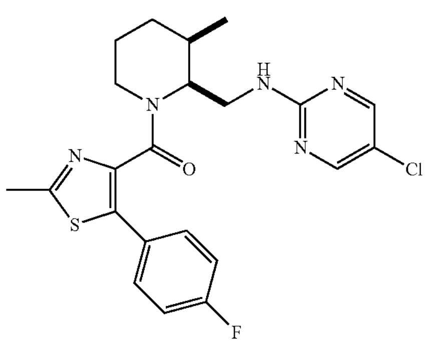 [SMILES: Cc1nc(C(=O)N2CCC[C@@H](C)[C@H]2CNc2ncc(Cl)cn2)c(-c2ccc(F)cc2)s1] |
| Ex. A42 | 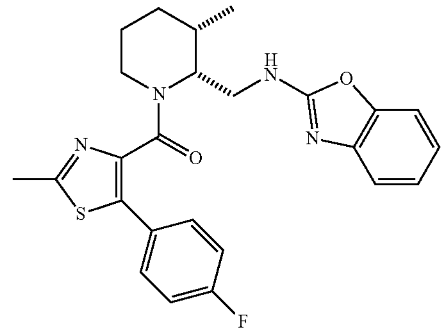 [SMILES: Cc1nc(C(=O)N2CCC[C@H](C)[C@@H]2CNc2nc3ccccc3o2)c(-c2ccc(F)cc2)s1] |
| Ex. A43 | 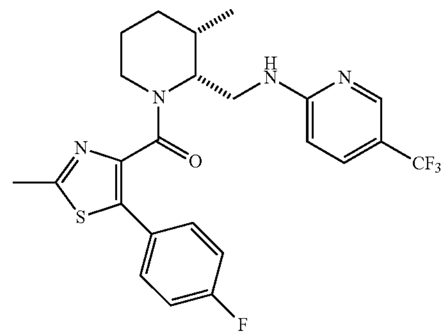 [SMILES: Cc1nc(C(=O)N2CCC[C@H](C)[C@@H]2CNc2ccc(C(F)(F)F)cn2)c(-c2ccc(F)cc2)s1] |
| Ex. A44 | 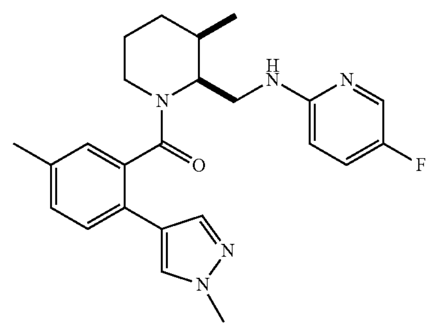 [SMILES: Cc1ccc(-c2cnn(C)c2)c(C(=O)N2CCC[C@@H](C)[C@H]2CNc2ccc(F)cn2)c1] |
| Ex. A45 | 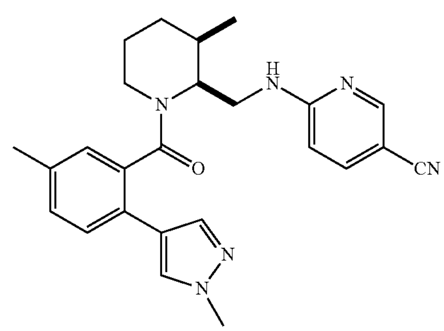 [SMILES: Cc1ccc(-c2cnn(C)c2)c(C(=O)N2CCC[C@@H](C)[C@H]2CNc2ccc(C#N)cn2)c1] |

TABLE 1A-continued

| Ex. # | Structure |
|---|---|
| Ex. A46 | 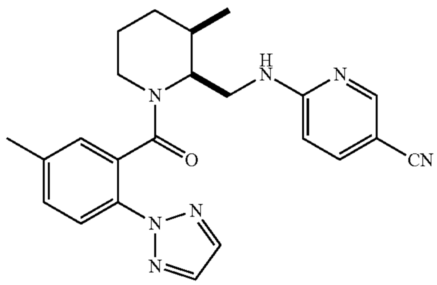 |
| Ex. A47 | 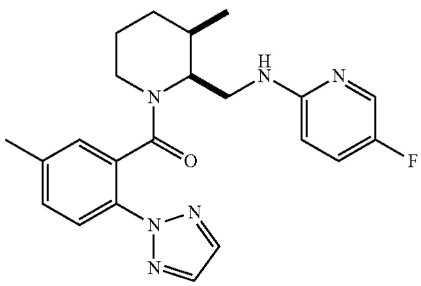 [SMILES: Cc1ccc(-n2nccn2)c(C(=O)N2CCC[C@@H](C)[C@H]2CNc2ccc(F)cn2)c1] |
| Ex. A48 | 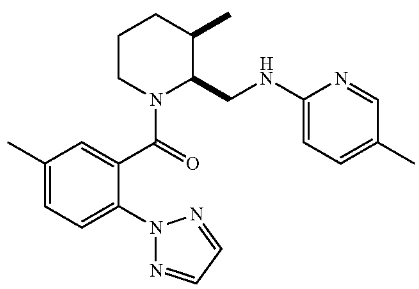 |
| Ex. A49 | 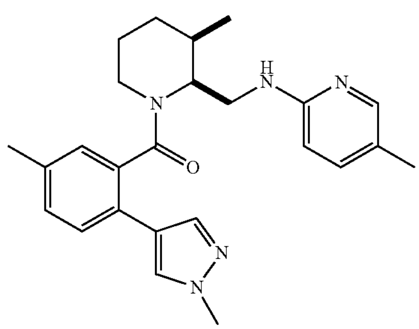 |
| Ex. A50 | 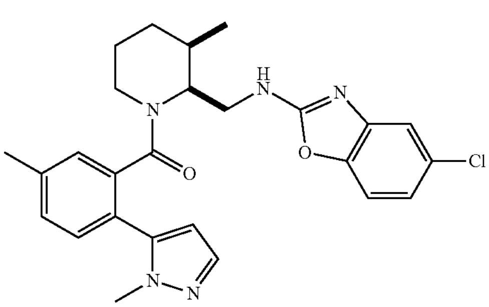 [SMILES: Cc1ccc(-c2ccnn2C)c(C(=O)N2CCC[C@@H](C)[C@H]2CNc2nc3cc(Cl)ccc3o2)c1] |

TABLE 1A-continued

| Ex. # | Structure |
|---|---|
| Ex. A51 | 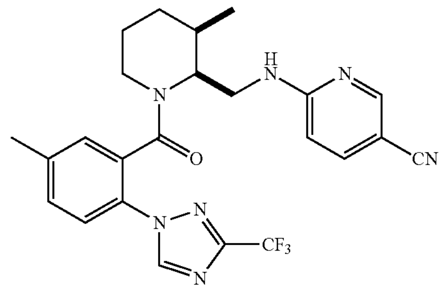 [SMILES: Cc1ccc(-n2cnc(C(F)(F)F)n2)c(C(=O)N2CCC[C@@H](C)[C@H]2CNc2ccc(C#N)cn2)c1] |
| Ex. A52 | 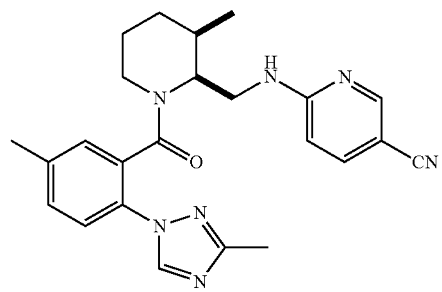 [SMILES: Cc1ccc(-n2cnc(C)n2)c(C(=O)N2CCC[C@@H](C)[C@H]2CNc2ccc(C#N)cn2)c1] |
| Ex. A53 | 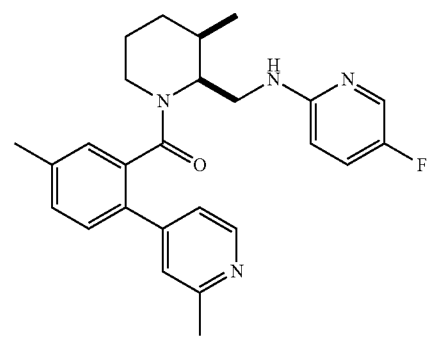 [SMILES: Cc1ccc(-c2ccnc(C)c2)c(C(=O)N2CCC[C@@H](C)[C@H]2CNc2ccc(F)cn2)c1] |
| Ex. A54 | 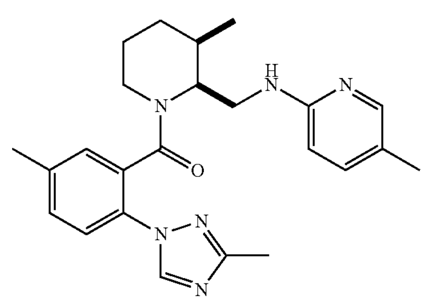 |
| Ex. A55 | 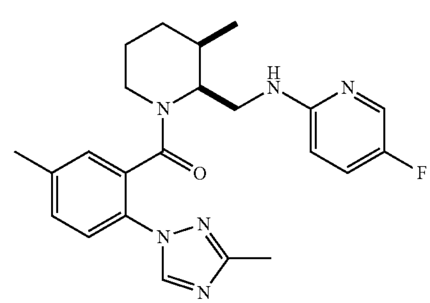 [SMILES: Cc1ccc(-n2cnc(C)n2)c(C(=O)N2CCC[C@@H](C)[C@H]2CNc2ccc(F)cn2)c1] |

TABLE 1A-continued

| Ex. # | Structure |
|---|---|
| Ex. A56 | (structure) |
| Ex. A57 | (structure) |
| Ex. A58 | (structure) |
| Ex. A59 | (structure) |
| Ex. A60 | (structure) |
| Ex. A61 | (structure) |
| Ex. A62 | (structure) |
| Ex. A63 | (structure) |
| Ex. A64 | (structure) |
| Ex. A65 | (structure) |

TABLE 1A-continued
| Ex. # | Structure |
|---|---|
| Ex. A66 | 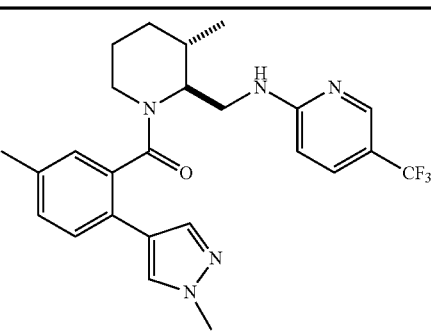 |
| Ex. A67 | 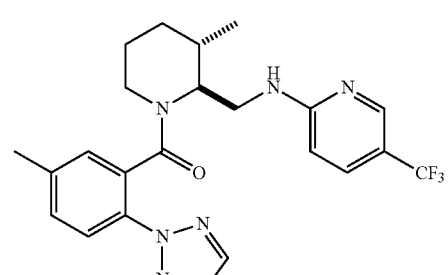 |
| Ex. A68 | 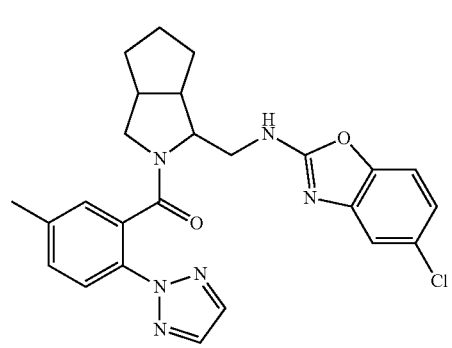 [SMILES: Cc1ccc(-n2nccn2)c(C(=O)N2CC3CCCC3C2CNc2nc3cc(Cl)ccc3o2)c1] |
| Ex. A69 | 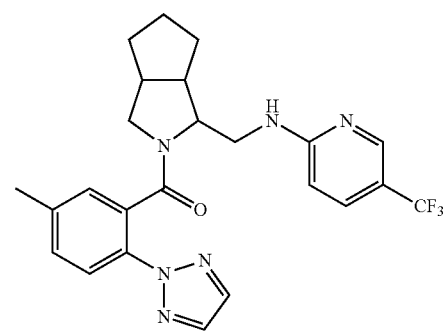 [SMILES: Cc1ccc(-n2nccn2)c(C(=O)N2CC3CCCC3C2CNc2ccc(C(F)(F)F)cn2)c1] |
| Ex. A70 | 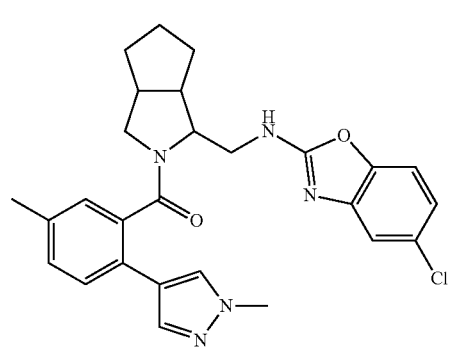 [SMILES: Cc1ccc(-c2cnn(C)c2)c(C(=O)N2CC3CCCC3C2CNc2nc3cc(Cl)ccc3o2)c1] |
| Ex. A71 | 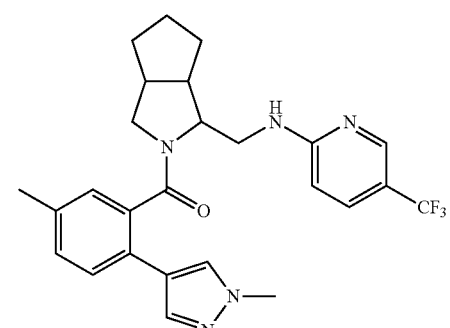 |
| Ex. A72 | 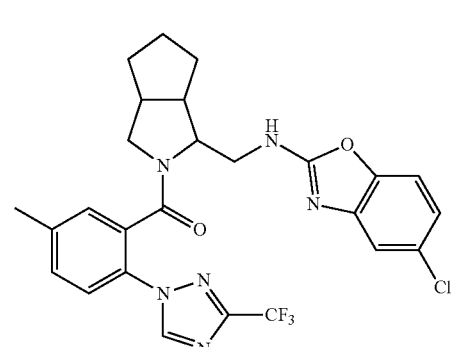 |
| Ex. A73 | 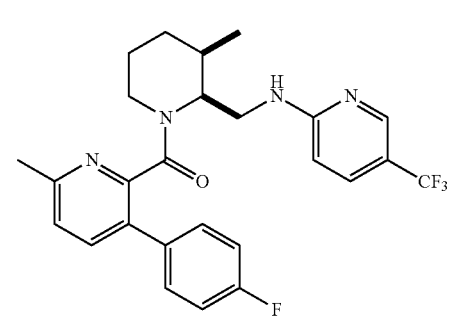 |
| Ex. A74 | 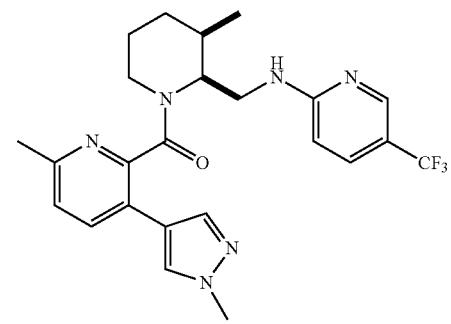 |
| Ex. A75 | 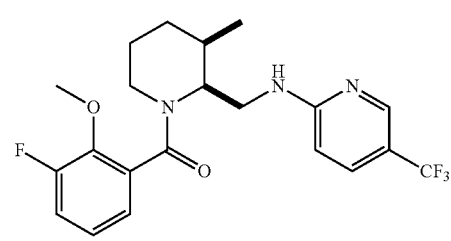 [SMILES: COc1c(F)cccc1C(=O)N1CCC[C@@H](C)[C@H]1CNc1ccc(C(F)(F)F)cn1] |

TABLE 1A-continued
| Ex. # | Structure |
|---|---|
| Ex. A76 | 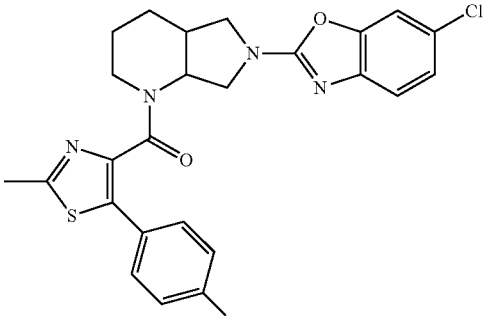 |
| Ex. A77 | 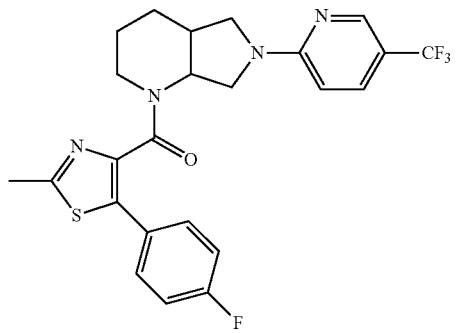 [SMILES: Cc1nc(C(=O)N2CCCC3CN(c4ccc(C(F)(F)F)cn4)CC32)c(-c2ccc(F)cc2)s1] |
| Ex. A78 | 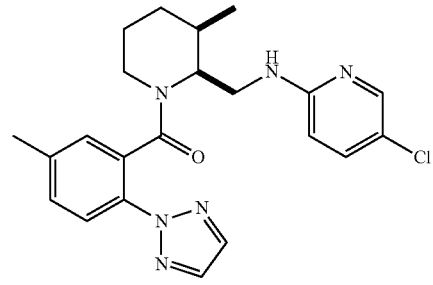 |
| Ex. A79 | 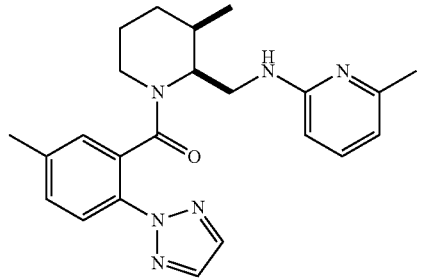 |
| Ex. A80 | 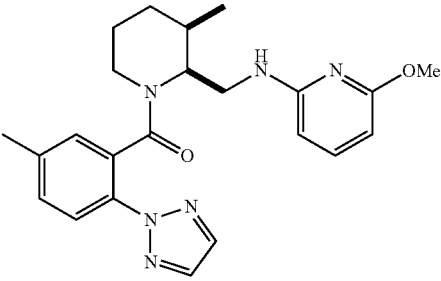 [SMILES: COc1cccc(NC[C@@H]2[C@H](C)CCCN2C(=O)c2cc(C)ccc2-n2nccn2)n1] |
| Ex. A81 | 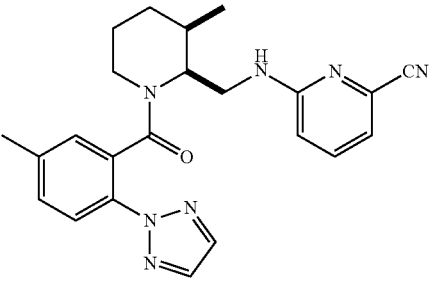 [SMILES: Cc1ccc(-n2nccn2)c(C(=O)N2CCC[C@@H](C)[C@H]2CNc2cccc(C#N)n2)c1] |
| Ex. A82 | 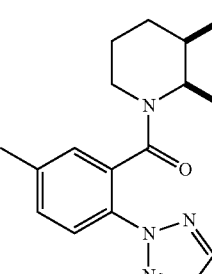 |
| Ex. A83 | 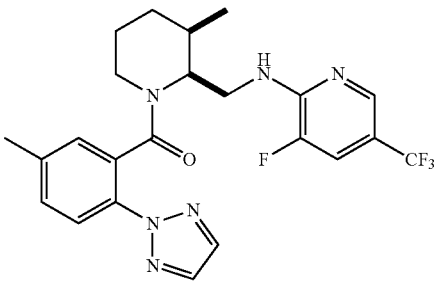 |
| Ex. A84 | 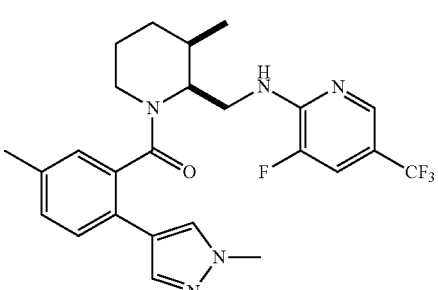 |
| Ex. A85 | 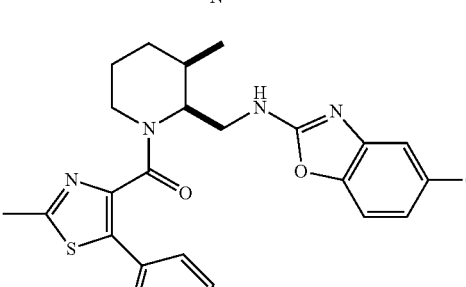 |

TABLE 1A-continued

| Ex. # | Structure |
|---|---|
| Ex. A86 | 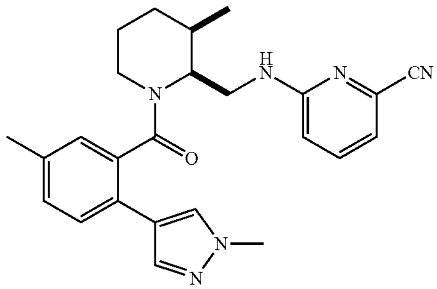 [SMILES: Cc1ccc(-c2cnn(C)c2)c(C(=O)N2CCC[C@@H](C)[C@H]2CNc2cccc(C#N)n2)c1] |
| Ex. A87 | 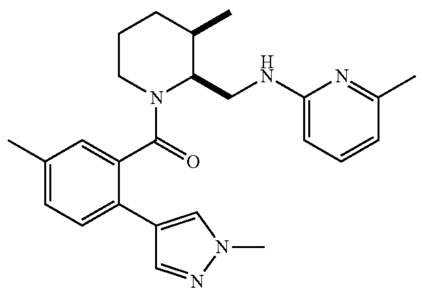 |
| Ex. A88 | 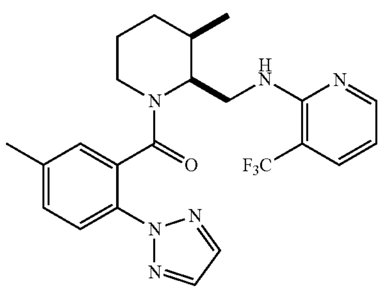 [SMILES: Cc1ccc(-n2nccn2)c(C(=O)N2CCC[C@@H](C)[C@H]2CNc2ncccc2C(F)(F)F)c1] |
| Ex. A89 | 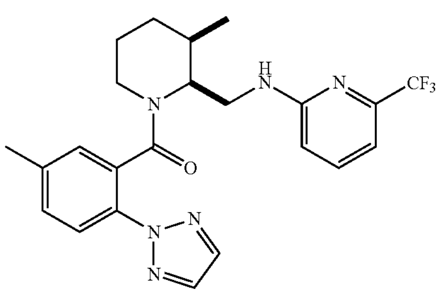 |
| Ex. A90 | 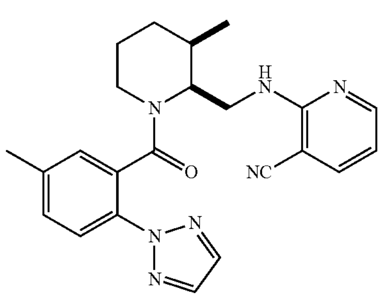 [SMILES: Cc1ccc(-n2nccn2)c(C(=O)N2CCC[C@@H](C)[C@H]2CNc2ncccc2C#N)c1] |
| Ex. A91 | |
| Ex. A92 | |
| Ex. A93 | |
| Ex. A94 | |
| Ex. A95 | |

TABLE 1A-continued

| Ex. # | Structure |
|---|---|
| Ex. A96 | 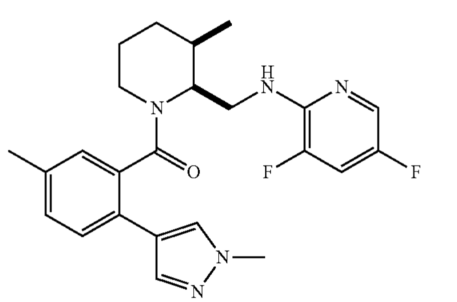 [SMILES: Cc1ccc(-c2cnn(C)c2)c(C(=O)N2CCC[C@@H](C)[C@H]2CNc2ncc(F)cc2F)c1] |
| Ex. A97 | 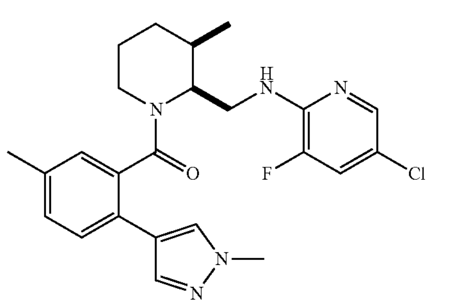 [SMILES: Cc1ccc(-c2cnn(C)c2)c(C(=O)N2CCC[C@@H](C)[C@H]2CNc2ncc(Cl)cc2F)c1] |
| Ex. A98 | 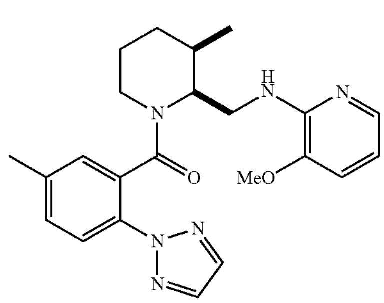 [SMILES: COc1cccnc1NC[C@@H]1[C@H](C)CCCN1C(=O)c1cc(C)ccc1-n1nccn1] |
| Ex. A99 | 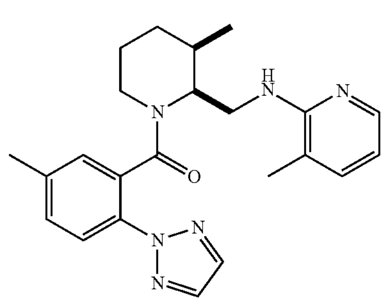 [SMILES: Cc1ccc(-n2nccn2)c(C(=O)N2CCC[C@@H](C)[C@H]2CNc2ncccc2C)c1] |
| Ex. A100 | 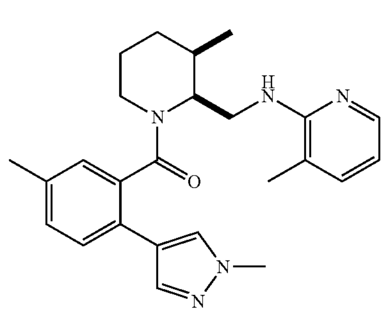 [SMILES: Cc1ccc(-c2cnn(C)c2)c(C(=O)N2CCC[C@@H](C)[C@H]2CNc2ncccc2C)c1] |

TABLE 1A-continued

| Ex. # | Structure |
|---|---|
| Ex. A101 | 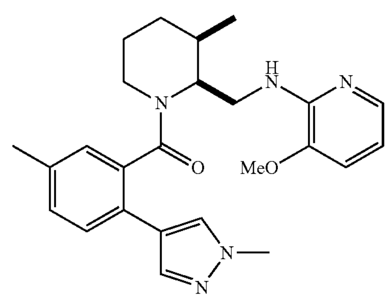 [SMILES: COc1cccnc1NC[C@@H]1[C@H](C)CCCN1C(=O)c1cc(C)ccc1-c1cnn(C)c1] |
| Ex. A102 | 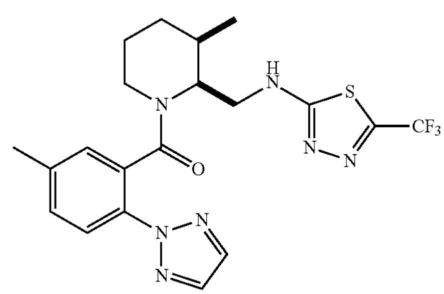 [SMILES: Cc1ccc(-n2nccn2)c(C(=O)N2CCC[C@@H](C)[C@H]2CNc2nnc(C(F)(F)F)s2)c1] |
| Ex. A103 | 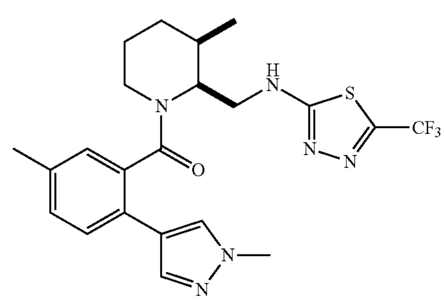 [SMILES: Cc1ccc(-c2cnn(C)c2)c(C(=O)N2CCC[C@@H](C)[C@H]2CNc2nnc(C(F)(F)F)s2)c1] |
| Ex. A104 | 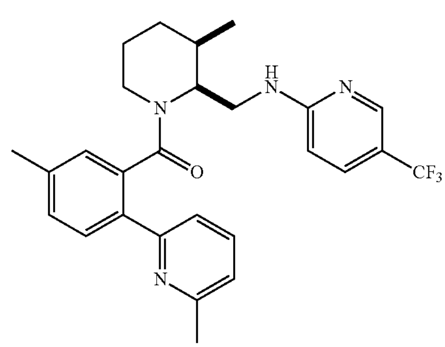 [SMILES: Cc1ccc(-c2cccc(C)n2)c(C(=O)N2CCC[C@@H](C)[C@H]2CNc2ccc(C(F)(F)F)cn2)c1] |
| Ex. A105 | 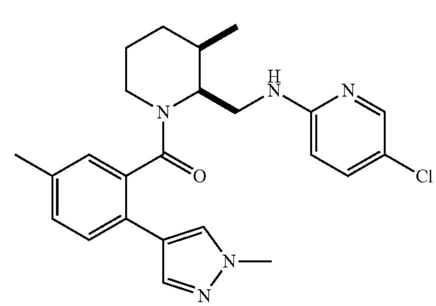 [SMILES: Cc1ccc(-c2cnn(C)c2)c(C(=O)N2CCC[C@@H](C)[C@H]2CNc2ccc(Cl)cn2)c1] |

TABLE 1A-continued

| Ex. # | Structure |
|---|---|
| Ex. A106 | (structure) |
| Ex. A107 | (structure) |
| Ex. A108 | (structure) |
| Ex. A109 | (structure) |
| Ex. A110 | (structure) |
| Ex. A111 | (structure) |
| Ex. A112 | (structure) |
| Ex. A113 | (structure) |
| Ex. A114 | (structure) |
| Ex. A115 | (structure) |

TABLE 1A-continued

| Ex. # | Structure |
|---|---|
| Ex. A116 | 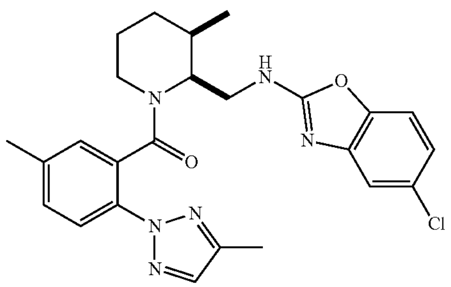 [SMILES: Cc1ccc(-n2ncc(C)n2)c(C(=O)N2CCC[C@@H](C)[C@H]2CNc2nc3cc(Cl)ccc3o2)c1] |
| Ex. A117 | 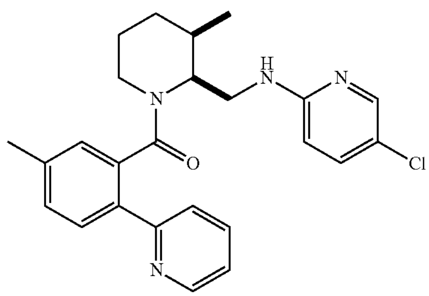 [SMILES: Cc1ccc(-c2ccccn2)c(C(=O)N2CCC[C@@H](C)[C@H]2CNc2ccc(Cl)cn2)c1] |
| Ex. A118 | 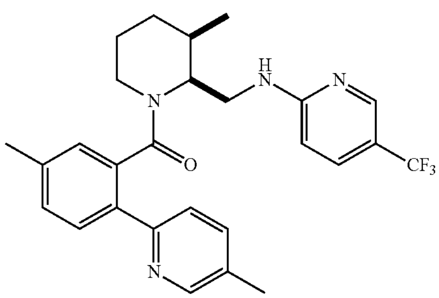 |
| Ex. A119 | 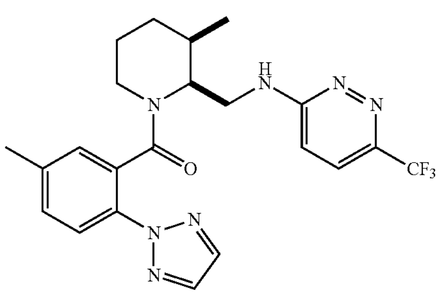 |
| Ex. A120 | 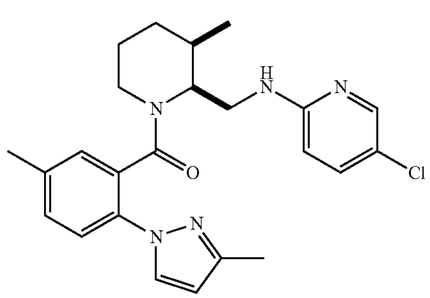 |
| Ex. A121 | |
| Ex. A122 | |
| Ex. A123 | |
| Ex. A124 | |
| Ex. A125 | |

TABLE 1A-continued
| Ex. # | Structure |
|---|---|
| Ex. A126 | 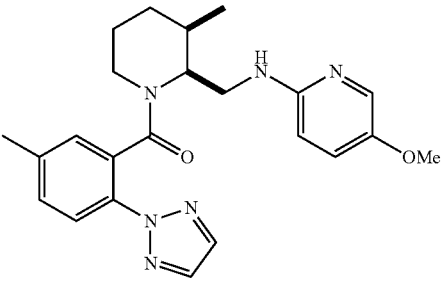 [SMILES: COc1ccc(NC[C@@H]2[C@H](C)CCCN2C(=O)c2cc(C)ccc2-n2nccn2)nc1] |
| Ex. A127 | 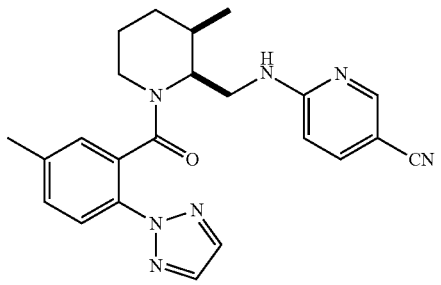 |
| Ex. A128 | 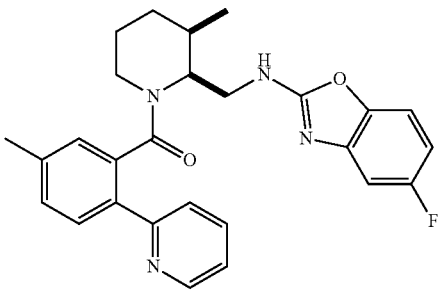 |
| Ex. A129 | 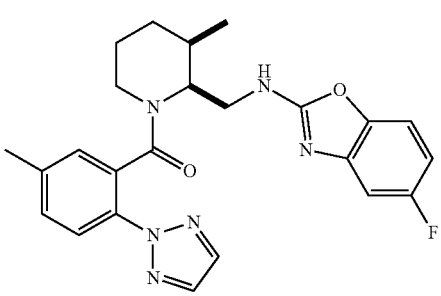 [SMILES: Cc1ccc(-n2nccn2)c(C(=O)N2CCC[C@@H](C)[C@H]2CNc2nc3cc(F)ccc3o2)c1] |
| Ex. A130 | 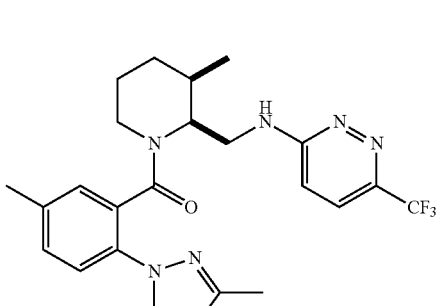 |
| Ex. A131 | 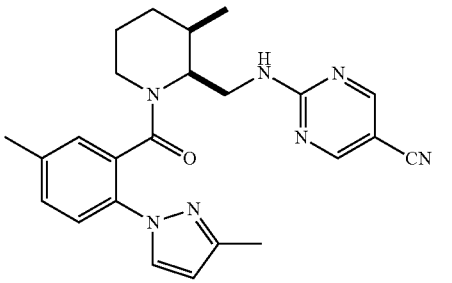 [SMILES: Cc1ccc(-n2ccc(C)n2)c(C(=O)N2CCC[C@@H](C)[C@H]2CNc2ncc(C#N)cn2)c1] |
| Ex. A132 | 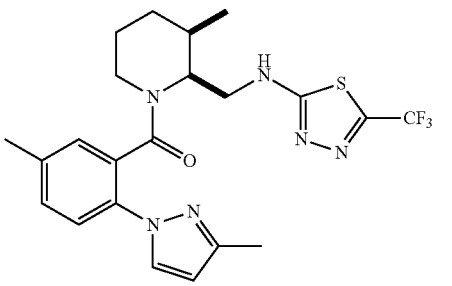 |
| Ex. A133 | 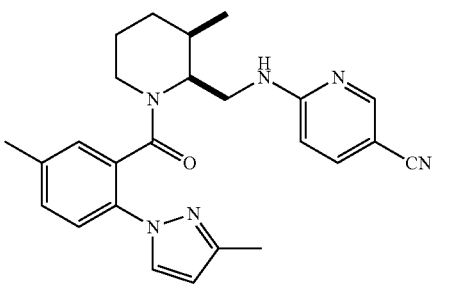 |
| Ex. A134 | 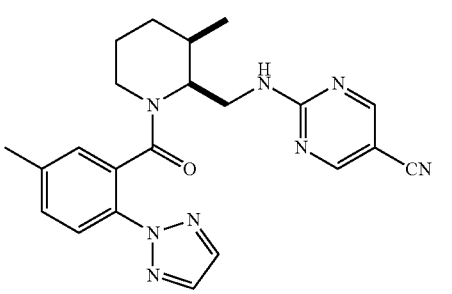 |
| Ex. A135 | 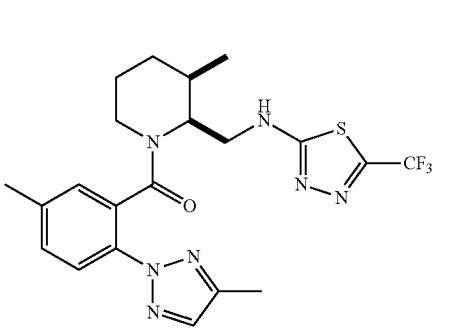 |

TABLE 1A-continued

| Ex. # | Structure |
|---|---|
| Ex. A136 | |
| Ex. A137 | |
| Ex. A138 | |
| Ex. A138 | |
| Ex. A140 | |
| Ex. A141 | 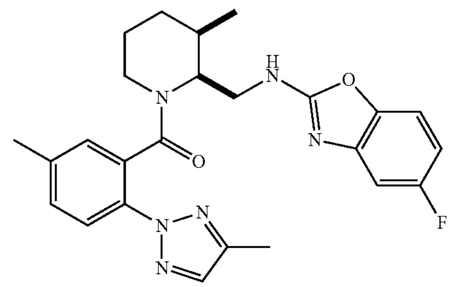 [SMILES: Cc1ccc(-n2ncc(C)n2)c(C(=O)N2CCC[C@@H](C)[C@H]2CNc2nc3cc(F)ccc3o2)c1] |
| Ex. A142 | 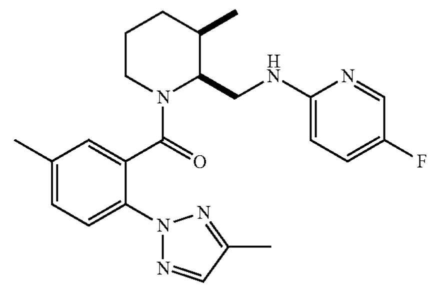 [SMILES: Cc1ccc(-n2ncc(C)n2)c(C(=O)N2CCC[C@@H](C)[C@H]2CNc2ccc(F)cn2)c1] |
| Ex. A143 | 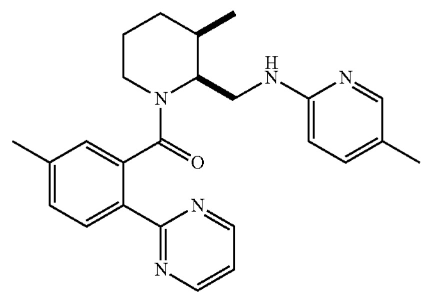 |
| Ex. A144 | 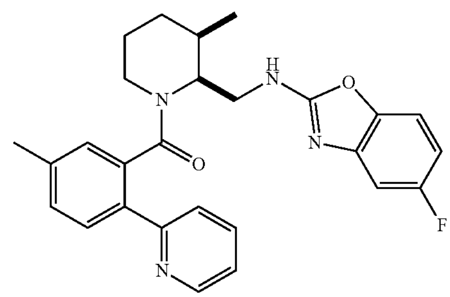 [SMILES: Cc1ccc(-c2ccccn2)c(C(=O)N2CCC[C@@H](C)[C@H]2CNc2nc3cc(F)ccc3o2)c1] |
| Ex. A145 | 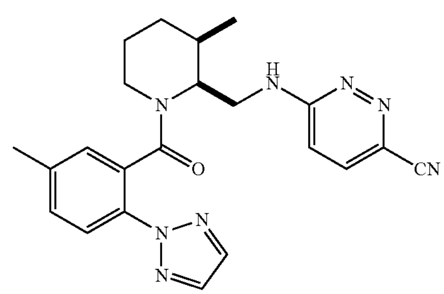 |

TABLE 1A-continued
| Ex. # | Structure |
|---|---|
| Ex. A146 | 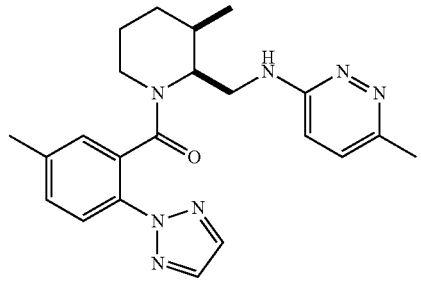 |
| Ex. A147 | 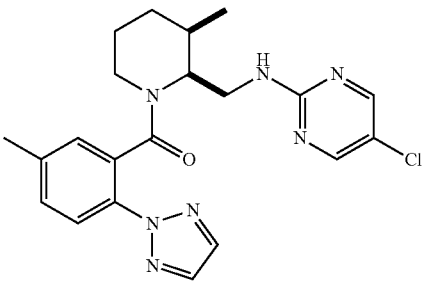 |
| Ex. A148 | 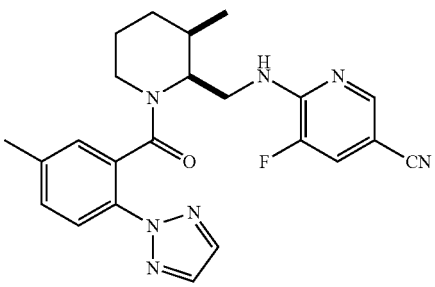 |
| Ex. A149 | 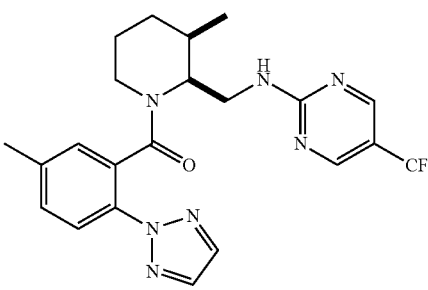 |
| Ex. A150 | 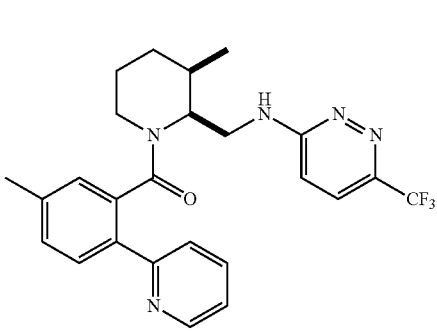 |
| Ex. A151 | 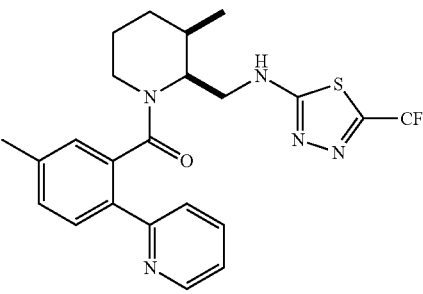 |
| Ex. A152 | 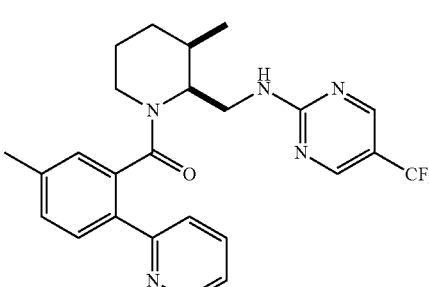 |
| Ex. A153 | 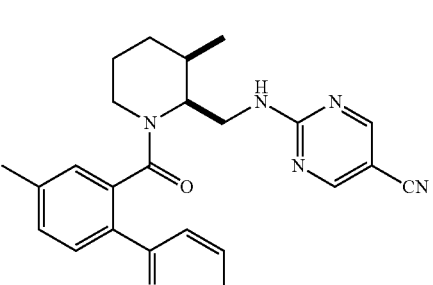 |
| Ex. A154 | 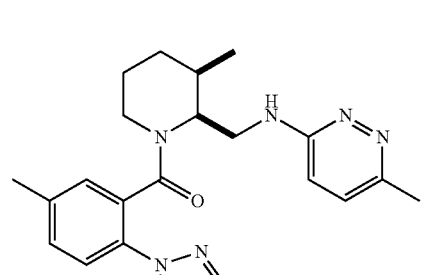 |
| Ex. A155 | 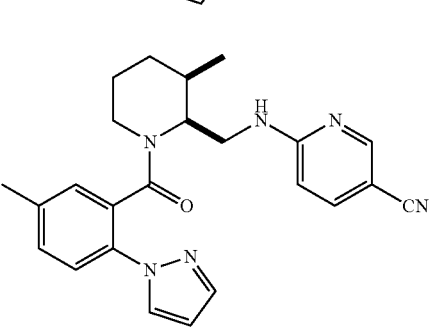 |

TABLE 1A-continued

| Ex. # | Structure |
|---|---|
| Ex. A156 | 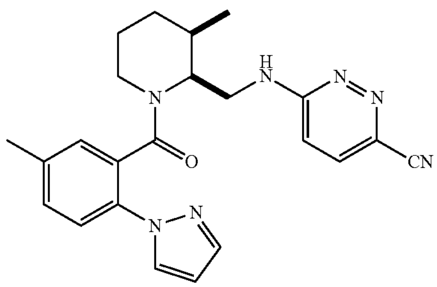 |
| Ex. A157 | 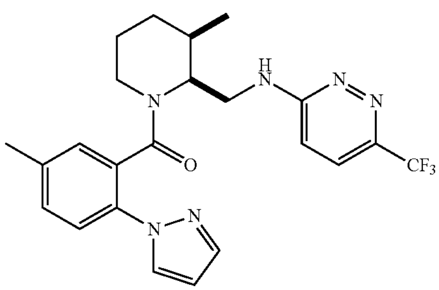 |
| Ex. A158 | 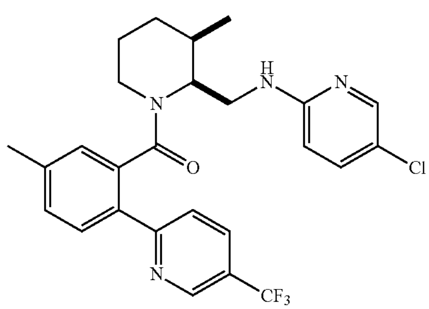 [SMILES: Cc1ccc(-c2ccc(C(F)(F)F)cn2)c(C(=O)N2CCC[C@@H](C)[C@H]2CNc2ccc(Cl)cn2)c1] |
| Ex. A159 | 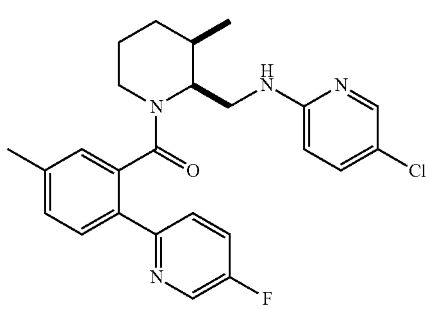 [SMILES: Cc1ccc(-c2ccc(F)cn2)c(C(=O)N2CCC[C@@H](C)[C@H]2CNc2ccc(Cl)cn2)c1] |
| Ex. A160 | 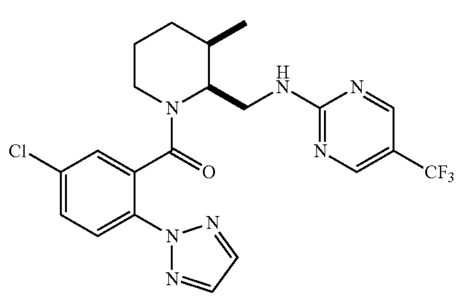 [SMILES: C[C@@H]1CCCN(C(=O)c2cc(Cl)ccc2-n2nccn2)[C@@H]1CNc1ncc(C(F)(F)F)cn1] |
| Ex. A161 | |
| Ex. A162 | |
| Ex. A163 | |
| Ex. A164 | |
| Ex. A165 | |

TABLE 1A-continued

| Ex. # | Structure |
|---|---|
| Ex. A166 | 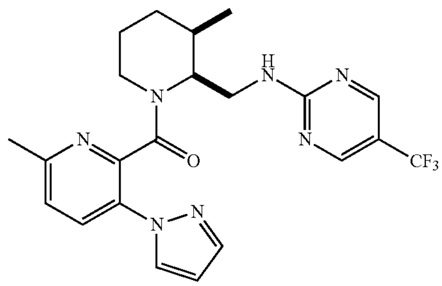 |
| Ex. A167 | 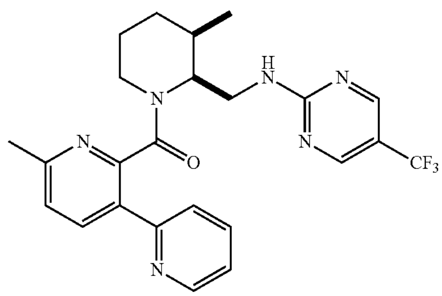 |
| Ex. A168 | 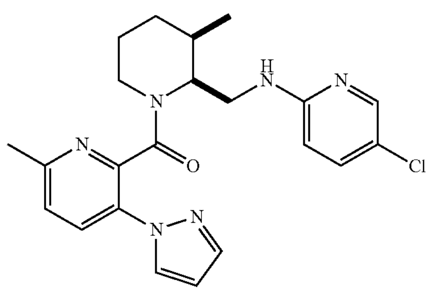 |
| Ex. A169 | 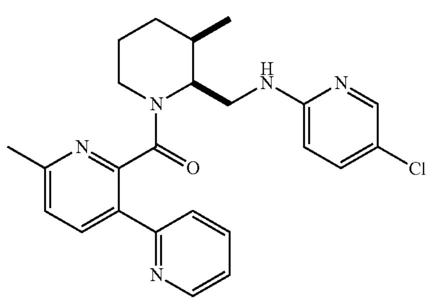 |
| Ex. A170 | 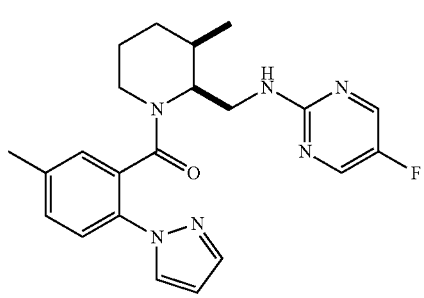 [SMILES: Cc1ccc(-n2cccn2)c(C(=O)N2CCC[C@@H](C)[C@H]2CNc2ncc(F)cn2)c1] |
| Ex. A171 | |
| Ex. A172 | |
| Ex. A173 | |
| Ex. A174 | |
| Ex. A175 | |

TABLE 1A-continued

| Ex. # | Structure |
|---|---|
| Ex. A176 | |
| Ex. A177 | 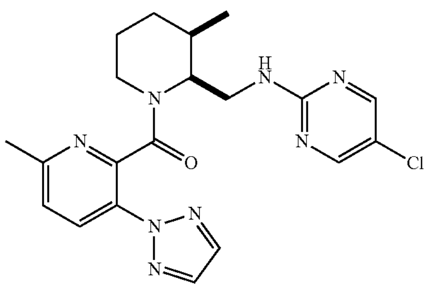 |
| Ex. A176 | |
| Ex. A179 | 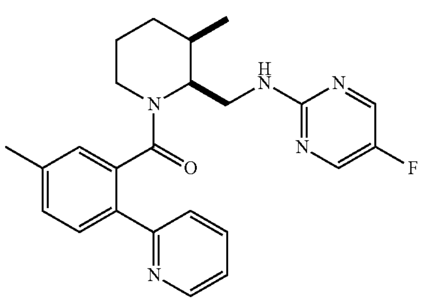 |
| Ex. A180 | 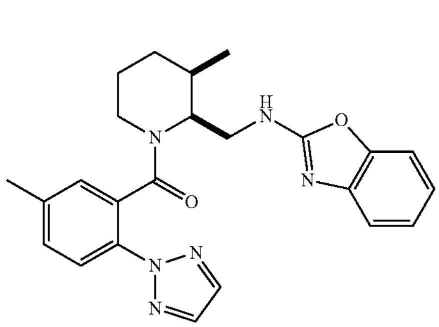 [SMILES: Cc1ccc(-n2nccn2)c(C(=O)N2CCC[C@@H](C)[C@H]2CNc2nc3ccccc3o2)c1] |

TABLE 1A-continued

| Ex. # | Structure |
|---|---|
| Ex. A181 | 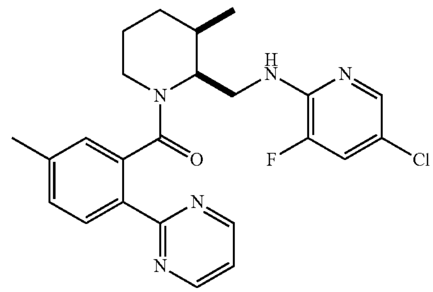 [SMILES: Cc1ccc(-c2ncccn2)c(C(=O)N2CCC[C@@H](C)[C@H]2CNc2ncc(Cl)cc2F)c1] |
| Ex. A182 | 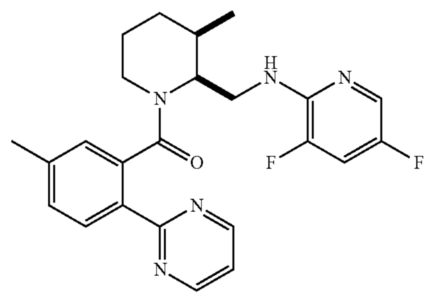 [SMILES: Cc1ccc(-c2ncccn2)c(C(=O)N2CCC[C@@H](C)[C@H]2CNc2ncc(F)cc2F)c1] |
| Ex. A183 | 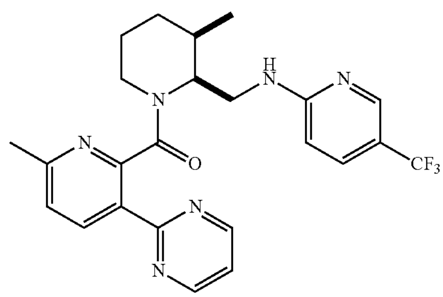 |
| Ex. A184 | 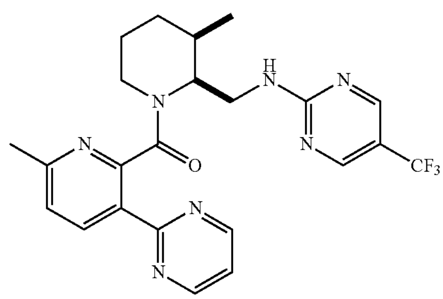 |
| Ex. A185 | 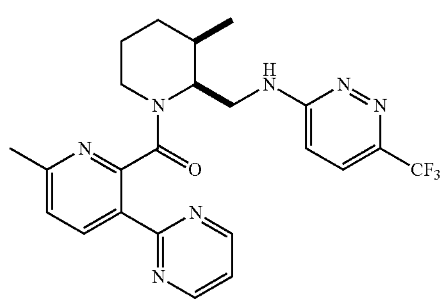 [SMILES: Cc1ccc(-c2ncccn2)c(C(=O)N2CCC[C@@H](C)[C@H]2CNc2ccc(C(F)(F)F)nn2)n1] |

TABLE 1A-continued
| Ex. # | Structure |
|---|---|
| Ex. A186 | 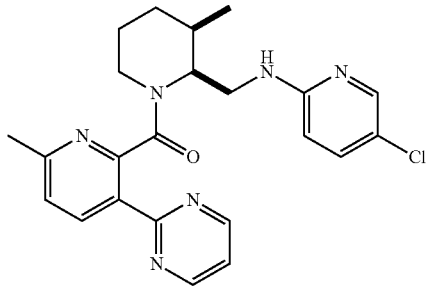 [SMILES: Cc1ccc(-c2ncccn2)c(C(=O)N2CCC[C@@H](C)[C@H]2CNc2ccc(Cl)cn2)n1] |
| Ex. A187 | 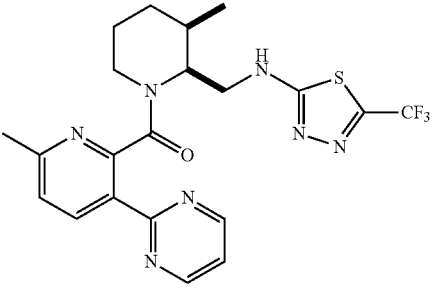 [SMILES: Cc1ccc(-c2ncccn2)c(C(=O)N2CCC[C@@H](C)[C@H]2CNc2nnc(C(F)(F)F)s2)n1] |
| Ex. A188 | 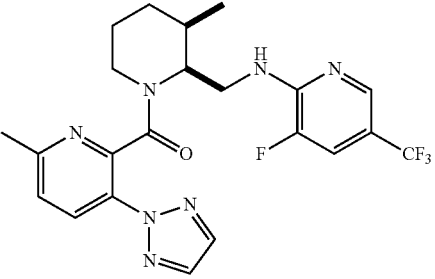 [SMILES: Cc1ccc(-n2nccn2)c(C(=O)N2CCC[C@@H](C)[C@H]2CNc2ncc(C(F)(F)F)cc2F)n1] |
| Ex. A189 | 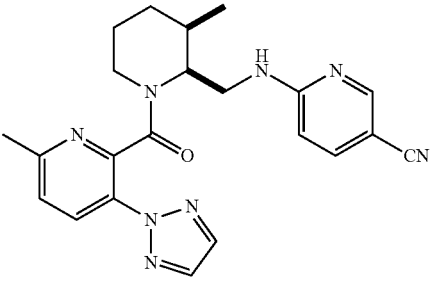 |
| Ex. A190 | 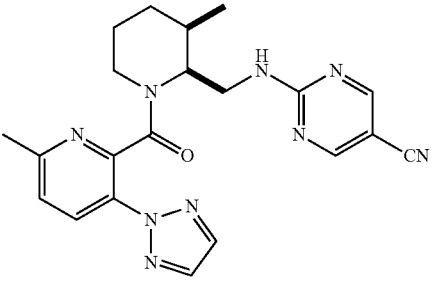 |
| Ex. A191 | 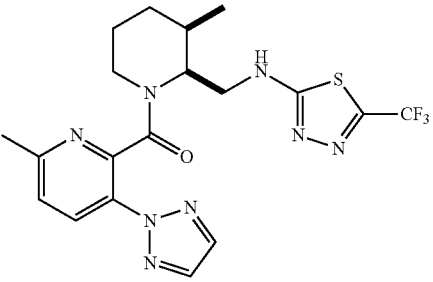 |
| Ex. A192 | 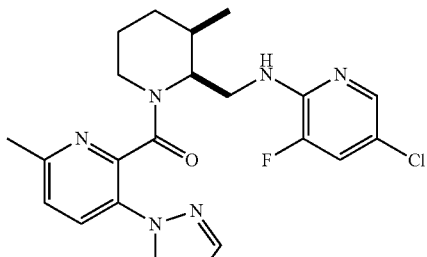 |
| Ex. A193 | 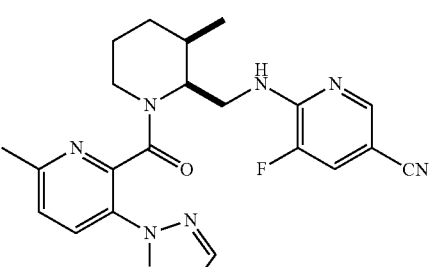 |
| Ex. A194 | 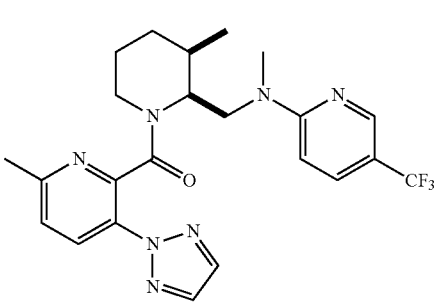 [SMILES: Cc1ccc(-n2nccn2)c(C(=O)N2CCC[C@@H](C)[C@H]2CN(C)c2ccc(C(F)(F)F)cn2)n1] |
| Ex. A195 | 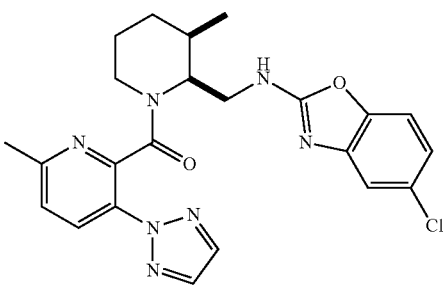 [SMILES: Cc1ccc(-n2nccn2)c(C(=O)N2CCC[C@@H](C)[C@H]2CNc2nc3cc(Cl)ccc3o2)n1] |

TABLE 1A-continued

| Ex. # | Structure |
|---|---|
| Ex. A196 | 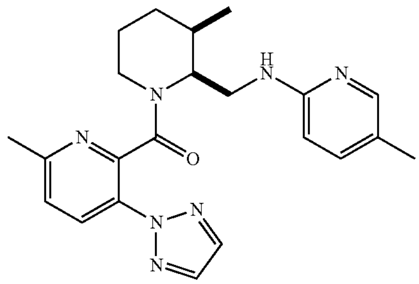 |
| Ex. A197 | 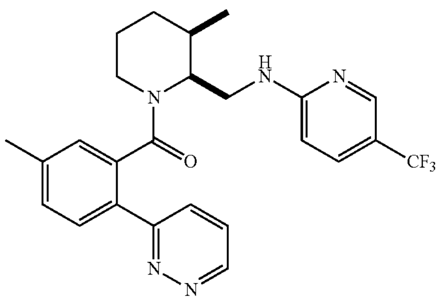 |
| Ex. A198 | 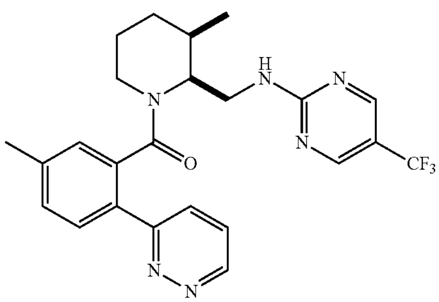 |
| Ex. A199 | 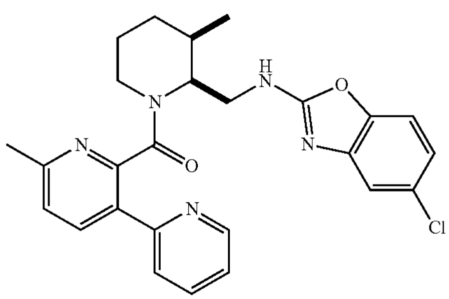 [SMILES: Cc1ccc(-c2ccccn2)c(C(=O)N2CCC[C@@H](C)[C@H]2CNc2nc3cc(Cl)ccc3o2)n1] |
| Ex. A200 | 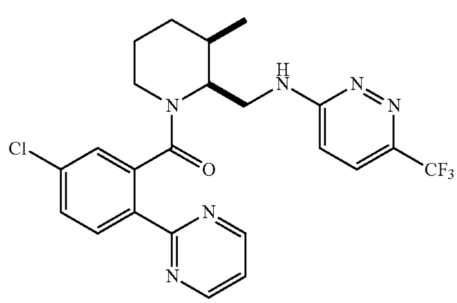 [SMILES: C[C@@H]1CCCN(C(=O)c2cc(Cl)ccc2-c2ncccn2)[C@@H]1CNc1ccc(C(F)(F)F)nn1] |
| Ex. A201 | |
| Ex. A202 | |
| Ex. A203 | |
| Ex. A204 | |
| Ex. A205 | |

TABLE 1A-continued
| Ex. # | Structure |
|---|---|
| Ex. A206 | 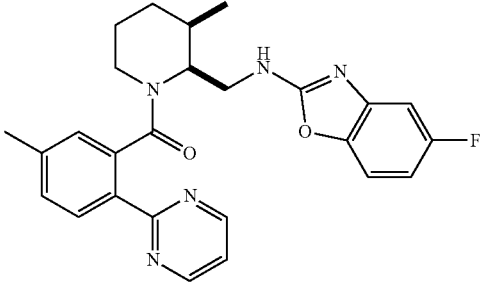 [SMILES: Cc1ccc(-c2ncccn2)c(C(=O)N2CCC[C@@H](C)[C@H]2CNc2nc3cc(F)ccc3o2)c1] |
| Ex. A207 | 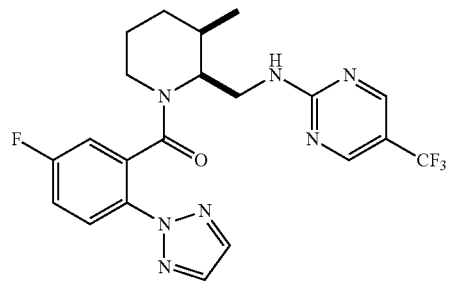 [SMILES: C[C@@H]1CCCN(C(=O)c2cc(F)ccc2-n2nccn2)[C@@H]1CNc1ncc(C(F)(F)F)cn1] |
| Ex. A208 | 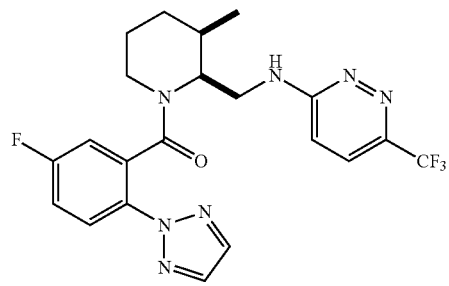 [SMILES: C[C@@H]1CCCN(C(=O)c2cc(F)ccc2-n2nccn2)[C@@H]1CNc1ccc(C(F)(F)F)nn1] |
| Ex. A209 | 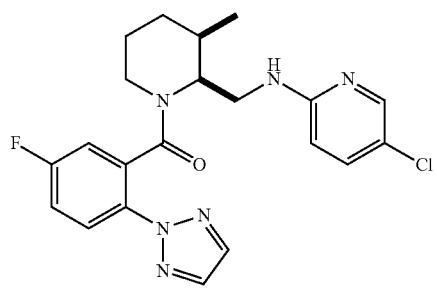 |
| Ex. A210 | 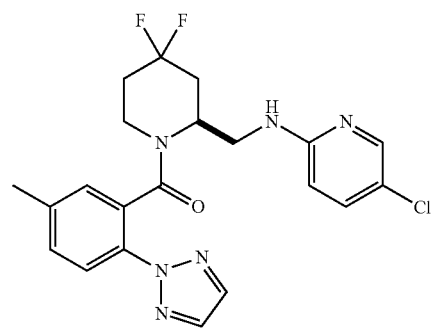 [SMILES: Cc1ccc(-n2nccn2)c(C(=O)N2CCC(F)(F)C[C@H]2CNc2ccc(Cl)cn2)c1] |
| Ex. A211 | 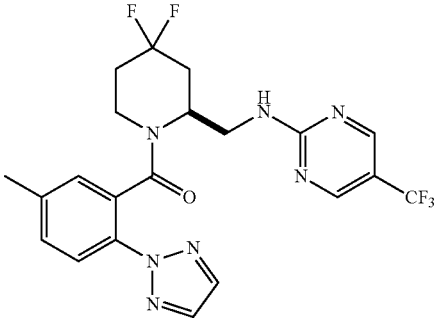 [SMILES: Cc1ccc(-n2nccn2)c(C(=O)N2CCC(F)(F)C[C@H]2CNc2ncc(C(F)(F)F)cn2)c1] |
| Ex. A212 | 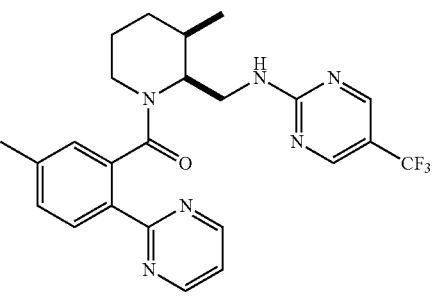 |
| Ex. A213 | 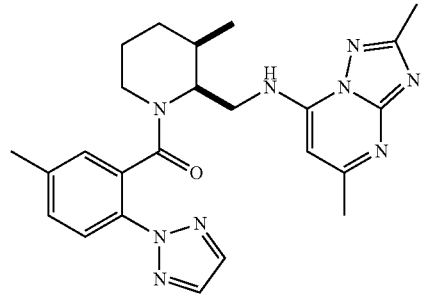 |
| Ex. A214 | 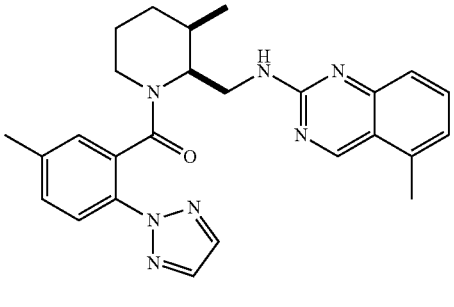 [SMILES: Cc1ccc(-n2nccn2)c(C(=O)N2CCC[C@@H](C)[C@H]2CNc2ncc3c(C)cccc3n2)c1] |
| Ex. A215 | 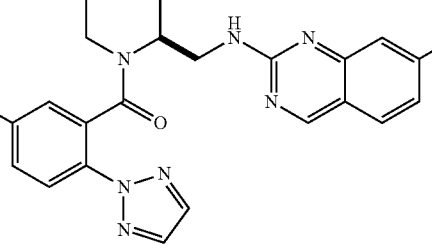 |

TABLE 1A-continued
| Ex. # | Structure |
|---|---|
| Ex. A216 | 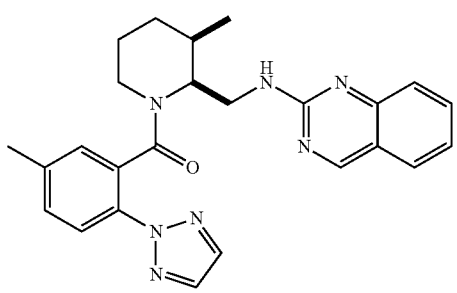 [SMILES: Cc1ccc(-n2nccn2)c(C(=O)N2CCC[C@@H](C)[C@H]2CNc2ncc3ccccc3n2)c1] |
| Ex. A217 | 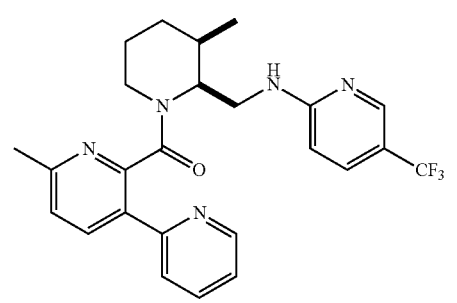 |
| Ex. A218 | 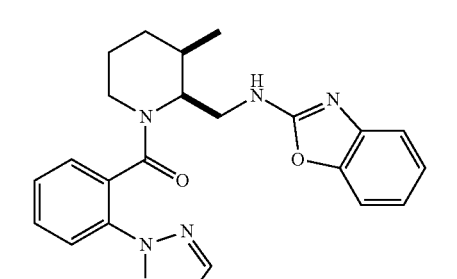 |
| Ex. A219 | 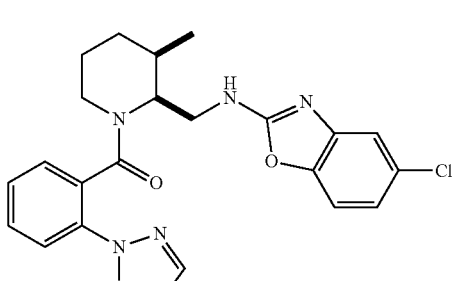 |
| Ex. A220 | 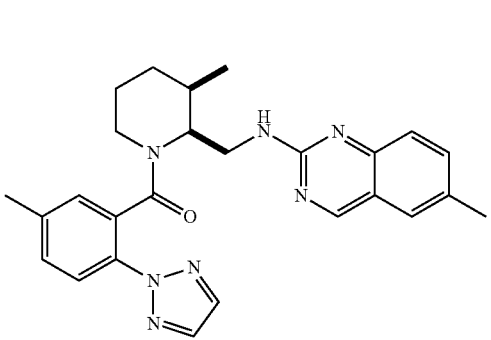 |
| Ex. A221 | 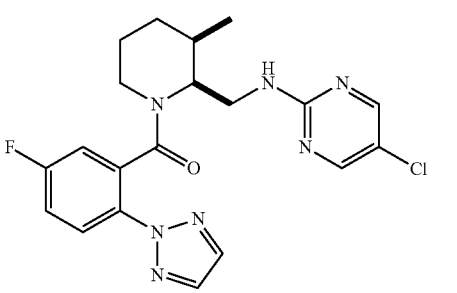 [SMILES: C[C@@H]1CCCN(C(=O)c2cc(F)ccc2-n2nccn2)[C@@H]1CNc1ncc(Cl)cn1] |
| Ex. A222 | 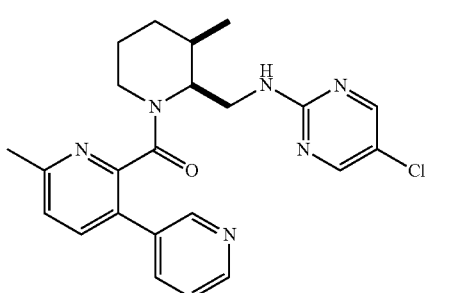 |
| Ex. A223 | 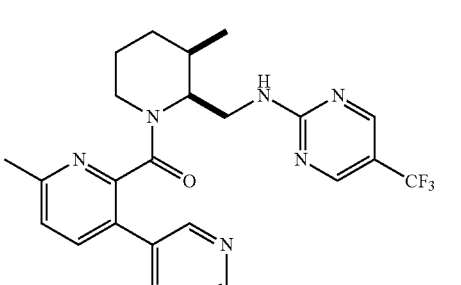 |
| Ex. A224 | 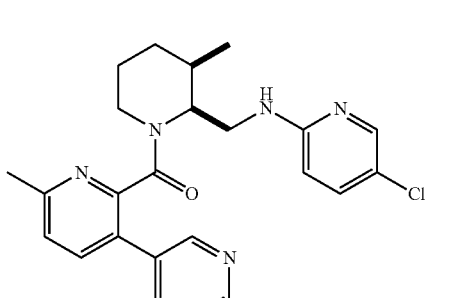 |
| Ex. A225 | 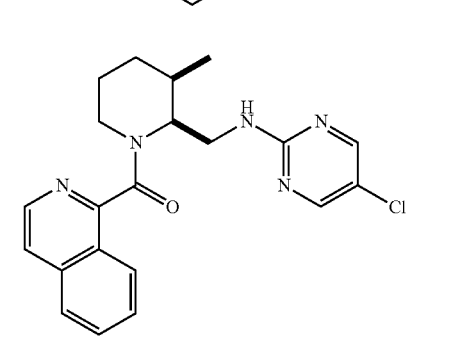 |

TABLE 1A-continued

| Ex. # | Structure |
|---|---|
| Ex. A226 | (structure) |
| Ex. A227 | (structure) |
| Ex. A228 | (structure) |
| Ex. A229 | (structure) |
| Ex. A230 | (structure) |
| Ex. A231 | (structure) |
| Ex. A232 | (structure) |
| Ex. A233 | (structure) |
| Ex. A234 | (structure) |
| Ex. A235 | (structure) |

TABLE 1A-continued

| Ex. # | Structure |
|---|---|
| Ex. A236 | 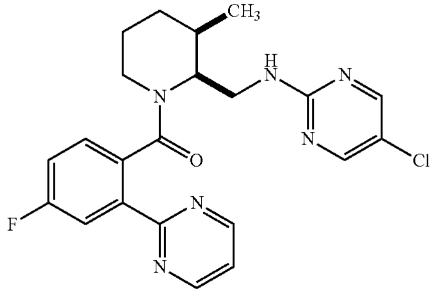 [SMILES: C[C@@H]1CCCN(C(=O)c2ccc(F)cc2-c2ncccn2)[C@@H]1CNc1ncc(Cl)cn1] |
| Ex. A237 | 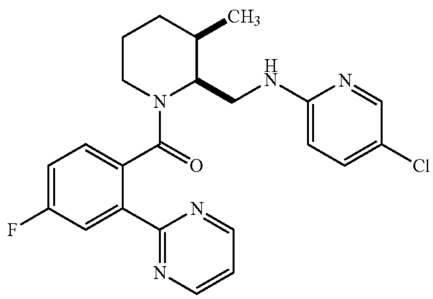 [SMILES: C[C@@H]1CCCN(C(=O)c2ccc(F)cc2-c2ncccn2)[C@@H]1CNc1ccc(Cl)cn1] |
| Ex. A238 P | 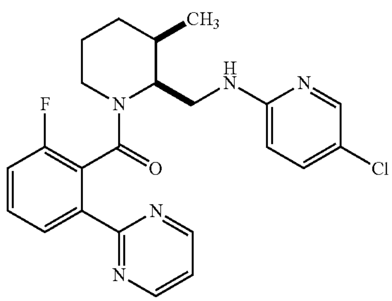 |
| Ex. A239 | 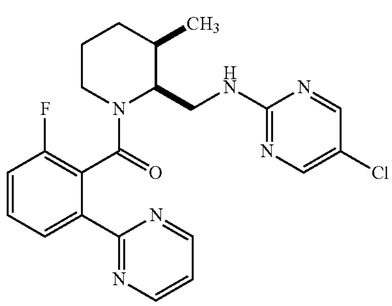 [SMILES: C[C@@H]1CCCN(C(=O)c2c(F)cccc2-c2ncccn2)[C@@H]1CNc1ncc(Cl)cn1] |
| Ex. A240 | 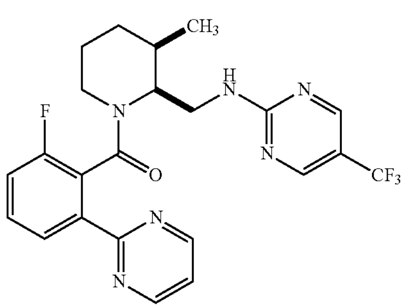 [SMILES: C[C@@H]1CCCN(C(=O)c2c(F)cccc2-c2ncccn2)[C@@H]1CNc1ncc(C(F)(F)F)cn1] |
| Ex. A241 | |
| Ex. A242 | |
| Ex. A243 | |
| Ex. A244 | |
| Ex. A245 P | |

TABLE 1A-continued
| Ex. # | Structure |
|---|---|
| Ex. A246 | 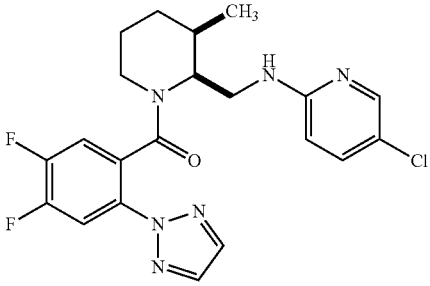 [SMILES: C[C@@H]1CCCN(C(=O)c2cc(F)c(F)cc2-n2nccn2)[C@@H]1CNc1ccc(Cl)cn1] |
| Ex. A247 | 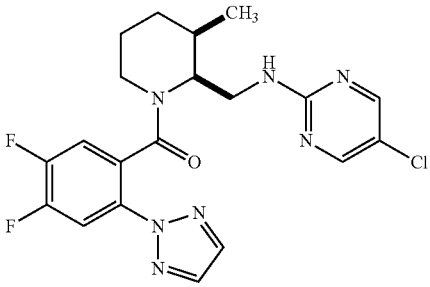 [SMILES: C[C@@H]1CCCN(C(=O)c2cc(F)c(F)cc2-n2nccn2)[C@@H]1CNc1ncc(Cl)cn1] |
| Ex. A248 | 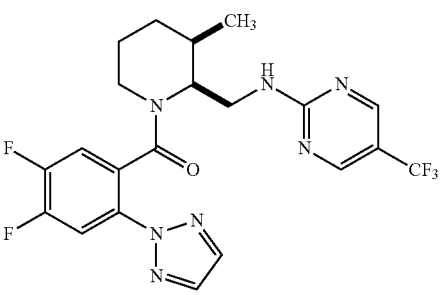 |
| Ex. A249 | 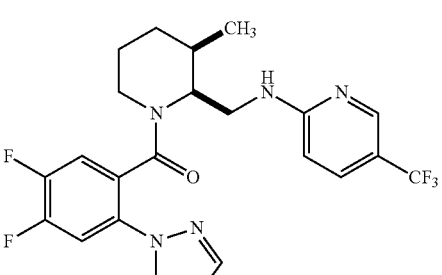 |
| Ex. A250 | 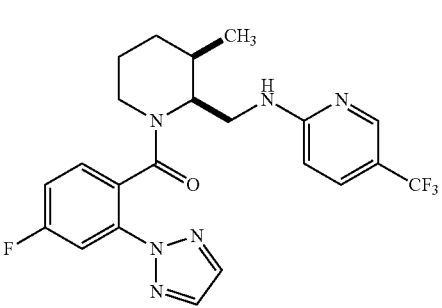 [SMILES: C[C@@H]1CCCN(C(=O)c2ccc(F)cc2-n2nccn2)[C@@H]1CNc1ccc(C(F)(F)F)cn1] |
| Ex. A251 | 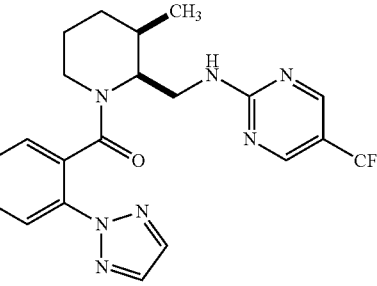 |
| Ex. A252 P | 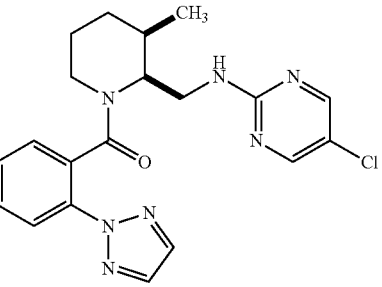 |
| Ex. A253 P | 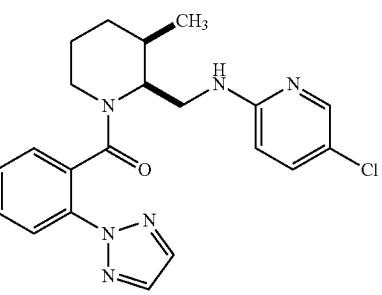 |
| Ex. A254 | 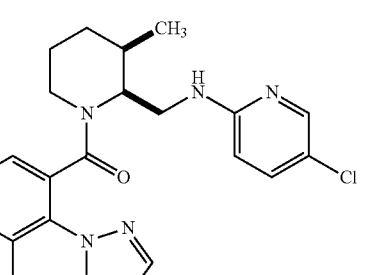 |
| Ex. A255 | 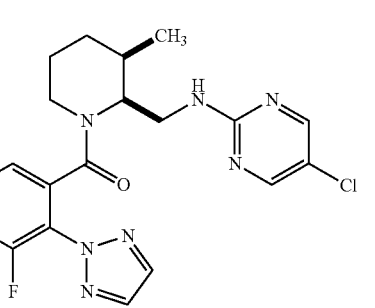 |

TABLE 1A-continued

| Ex. # | Structure |
|---|---|
| Ex. A256 | 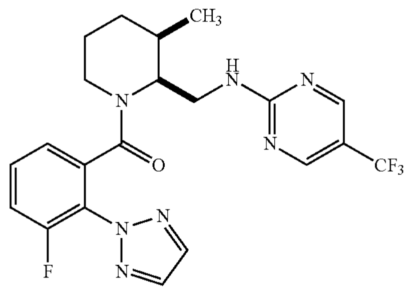 |
| Ex. A257 | 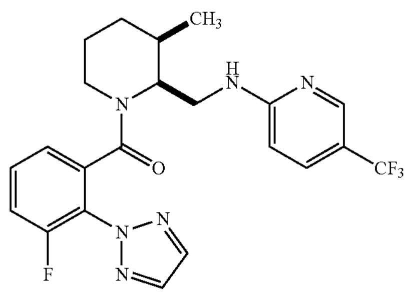 |
| Ex. A258 | 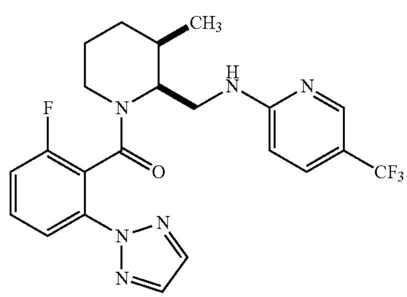 |
| Ex. A259 | 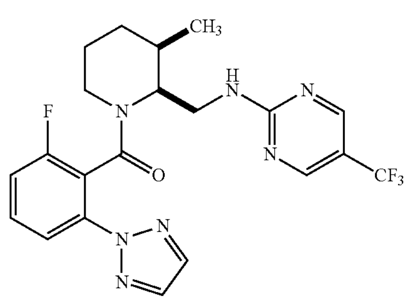 [SMILES: C[C@@H]1CCCN(C(=O)c2c(F)cccc2-n2nccn2)[C@@H]1CNc1ncc(C(F)(F)F)cn1] |
| Ex. A260 | 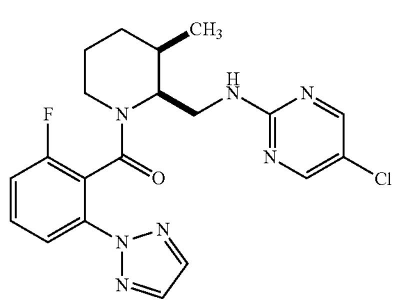 [SMILES: C[C@@H]1CCCN(C(=O)c2c(F)cccc2-n2nccn2)[C@@H]1CNc1ncc(Cl)cn1] |

TABLE 1A-continued

| Ex. # | Structure |
|---|---|
| Ex. A261 | |
| Ex. A262 P | |
| Ex. A263 P | |
| Ex. A264 | |
| Ex. A265 | |

TABLE 1A-continued

| Ex. # | Structure |
|---|---|
| Ex. A266 | 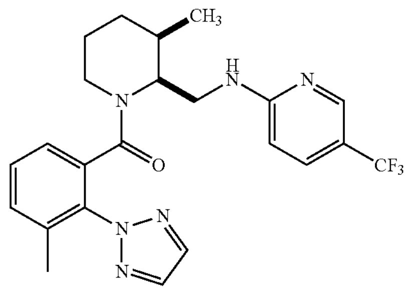 [SMILES: Cc1cccc(C(=O)N2CCC[C@@H](C)[C@H]2CNc2ccc(C(F)(F)F)cn2)c1-n1nccn1] |
| Ex. A267 | 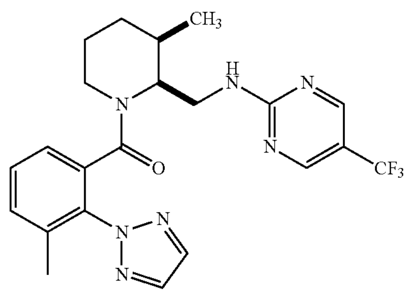 [SMILES: Cc1cccc(C(=O)N2CCC[C@@H](C)[C@H]2CNc2ncc(C(F)(F)F)cn2)c1-n1nccn1] |
| Ex. A268 | 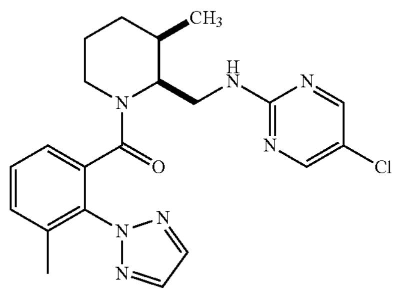 [SMILES: Cc1cccc(C(=O)N2CCC[C@@H](C)[C@H]2CNc2ncc(Cl)cn2)c1-n1nccn1] |
| Ex. A269 P | 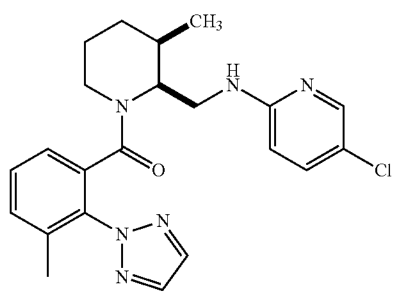 [SMILES: Cc1cccc(C(=O)N2CCC[C@@H](C)[C@H]2CNc2ccc(Cl)cn2)c1-n1nccn1] |
| Ex. A270 P | 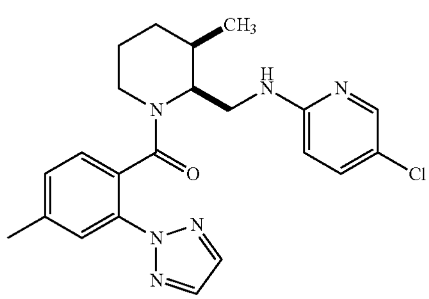 [SMILES: Cc1ccc(C(=O)N2CCC[C@@H](C)[C@H]2CNc2ccc(Cl)cn2)c(-n2nccn2)c1] |
| Ex. A271 | |
| Ex. A272 | |
| Ex. A273 | |
| Ex. A274 P | |
| Ex. A275 P | |

TABLE 1A-continued

| Ex. # | Structure |
|---|---|
| Ex. A276 P | 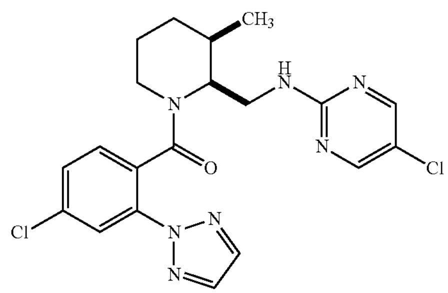 [SMILES: C[C@@H]1CCCN(C(=O)c2ccc(Cl)cc2-n2nccn2)[C@@H]1CNc1ncc(Cl)cn1] |
| Ex. A277 P | 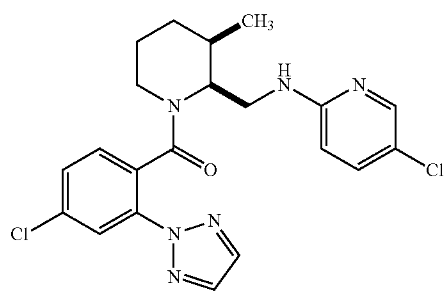 |
| Ex. A278 P | 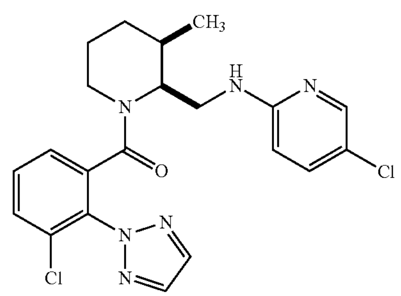 |
| Ex. A279 P | 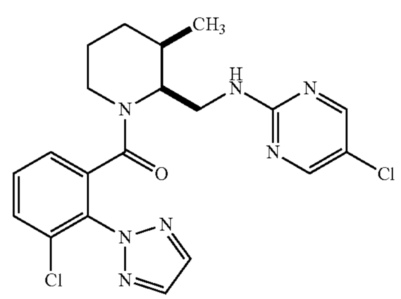 [SMILES: C[C@@H]1CCCN(C(=O)c2cccc(Cl)c2-n2nccn2)[C@@H]1CNc1ncc(Cl)cn1] |
| Ex. A280 P | 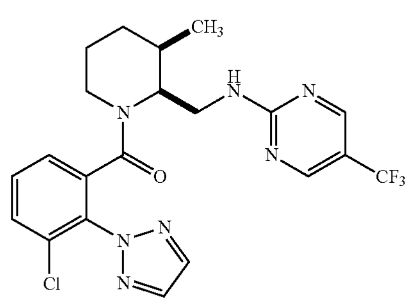 [SMILES: C[C@@H]1CCCN(C(=O)c2cccc(Cl)c2-n2nccn2)[C@@H]1CNc1ncc(C(F)(F)F)cn1] |

| Ex. # | Structure |
|---|---|
| Ex. A281 P | 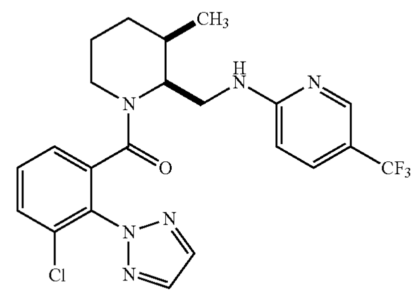 [SMILES: C[C@@H]1CCCN(C(=O)c2cccc(Cl)c2-n2nccn2)[C@@H]1CNc1ccc(C(F)(F)F)cn1] |
| Ex. A282 P | 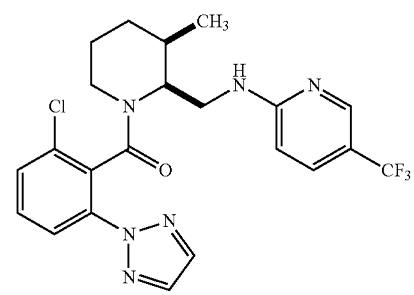 [SMILES: C[C@@H]1CCCN(C(=O)c2c(Cl)cccc2-n2nccn2)[C@@H]1CNc1ccc(C(F)(F)F)cn1] |
| Ex. A283 P | 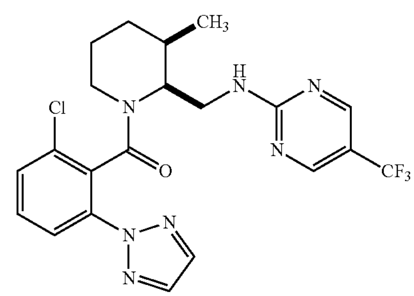 [SMILES: C[C@@H]1CCCN(C(=O)c2c(Cl)cccc2-n2nccn2)[C@@H]1CNc1ncc(C(F)(F)F)cn1] |
| Ex. A284 P | 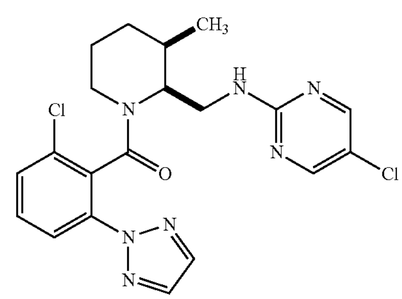 [SMILES: C[C@@H]1CCCN(C(=O)c2c(Cl)cccc2-n2nccn2)[C@@H]1CNc1ncc(Cl)cn1] |
| Ex. A285 P | 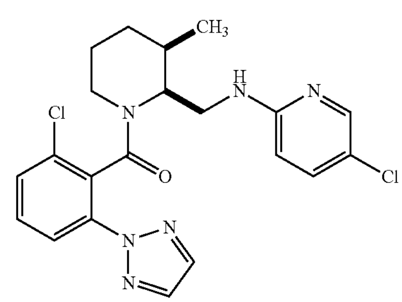 |

TABLE 1A-continued

| Ex. # | Structure |
|---|---|
| Ex. A286 P | (structure) |
| Ex. A287 P | (structure) |
| Ex. A288 P | (structure) |
| Ex. A289 P | (structure) |
| Ex. A290 P | (structure) |
| Ex. A291 P | (structure) |
| Ex. A292 P | (structure) |
| Ex. A293 P | (structure) |
| Ex. A294 P | (structure) |
| Ex. A295 P | (structure) |

TABLE 1A-continued

| Ex. # | Structure |
|---|---|
| Ex. A296 P | (structure) |
| Ex. A297 P | (structure) |
| Ex. A298 | (structure) |
| Ex. A299 | (structure) |
| Ex. A300 P | (structure) |
| Ex. A301 P | (structure) |
| Ex. A302 P | (structure) |
| Ex. A303 P | (structure) |
| Ex. A304 P | (structure) |
| Ex. A305 P | (structure) |

TABLE 1A-continued

| Ex. # | Structure |
|---|---|
| Ex. A306 | 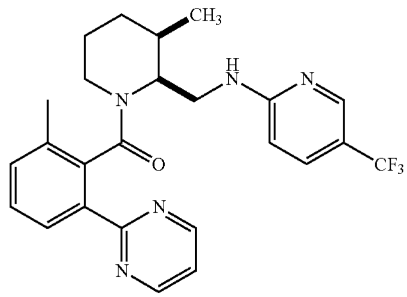 |
| Ex. A307 | 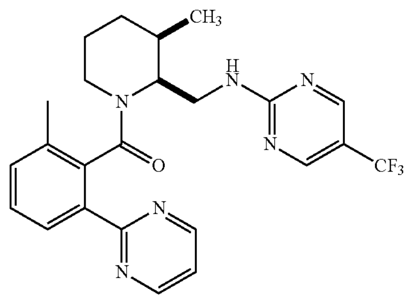 [SMILES: C[C@@H]1CCCN(C(=O)c2c(Cl)cccc2-c2ncccn2)[C@@H]1CNc1ncc(C(F)(F)F)cn1] |
| Ex. A308 P | 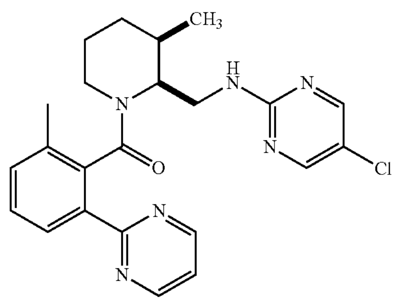 [SMILES: Cc1cccc(-c2ncccn2)c1C(=O)N1CCC[C@@H](C)[C@H]1CNc1ncc(Cl)cn1] |
| Ex. A309 P | 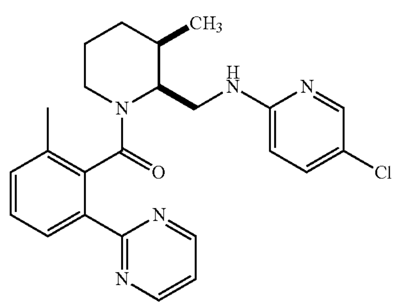 |
| Ex. A310 | 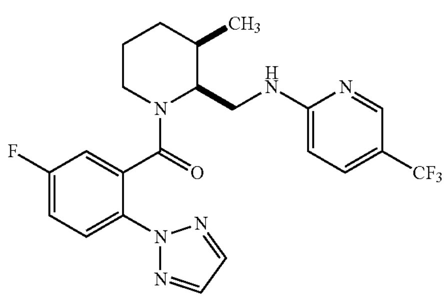 [SMILES: C[C@@H]1CCCN(C(=O)c2cc(F)ccc2-n2nccn2)[C@@H]1CNc1ccc(C(F)(F)F)cn1] |
| Ex. A311 | |
| Ex. A312 | |
| Ex. A313 | |
| Ex. A314 | |
| Ex. A315 | |

TABLE 1A-continued
| Ex. # | Structure |
|---|---|
| Ex. A316 | 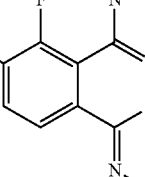 |
| Ex. A317 | 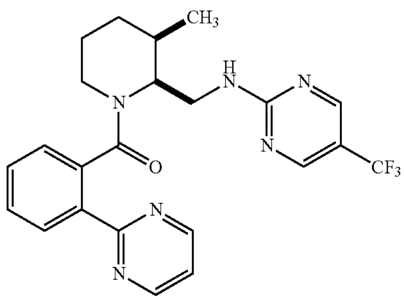 [SMILES: C[C@@H]1CCCN(C(=O)c2ccccc2-c2ncccn2)[C@@H]1CNc1ncc(C(F)(F)F)cn1] |
| Ex. A318 | 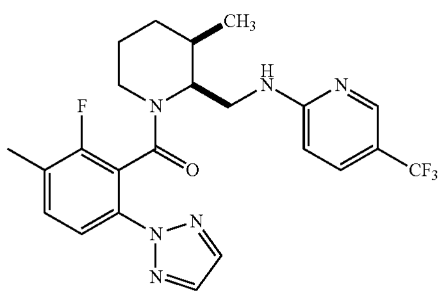 [SMILES: Cc1ccc(-n2nccn2)c(C(=O)N2CCC[C@@H](C)[C@H]2CNc2ccc(C(F)(F)F)cn2)c1F] |
| Ex. A319 | 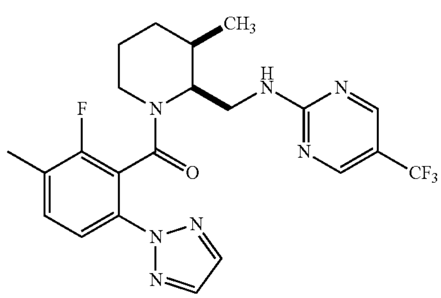 [SMILES: Cc1ccc(-n2nccn2)c(C(=O)N2CCC[C@@H](C)[C@H]2CNc2ncc(C(F)(F)F)cn2)c1F] |
| Ex. A320 P | 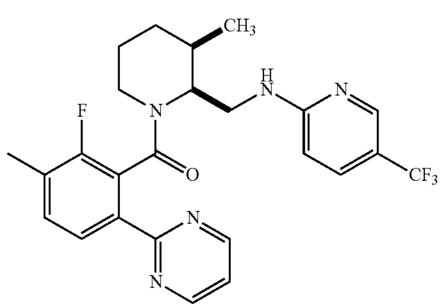 [SMILES: Cc1ccc(-c2ncccn2)c(C(=O)N2CCC[C@@H](C)[C@H]2CNc2ccc(C(F)(F)F)cn2)c1F] |
| Ex. A321 P | 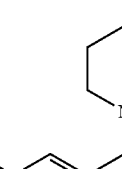 |
| Ex. A322 | |
| Ex. A323 | |
| Ex. A324 P | |
| Ex. A325 P | |

TABLE 1A-continued
| Ex. # | Structure |
|---|---|
| Ex. A326 P | 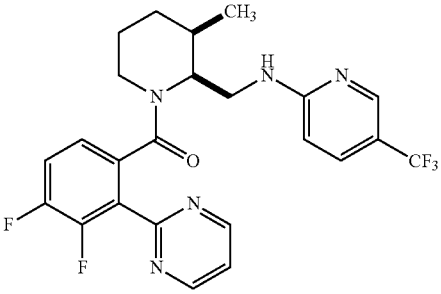 [SMILES: C[C@@H]1CCCN(C(=O)c2ccc(F)c(F)c2-c2ncccn2)[C@@H]1CNc1ccc(C(F)(F)F)cn1] |
| Ex. A327 P | 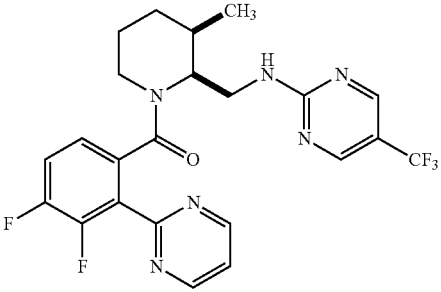 [SMILES: C[C@@H]1CCCN(C(=O)c2ccc(F)c(F)c2-c2ncccn2)[C@@H]1CNc1ncc(C(F)(F)F)cn1] |
| Ex. A328 P | 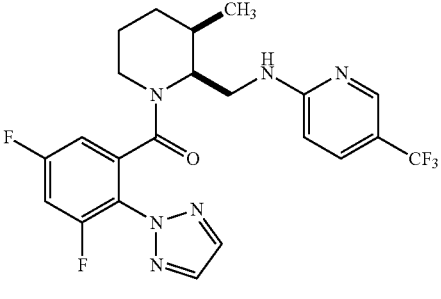 |
| Ex. A329 P | 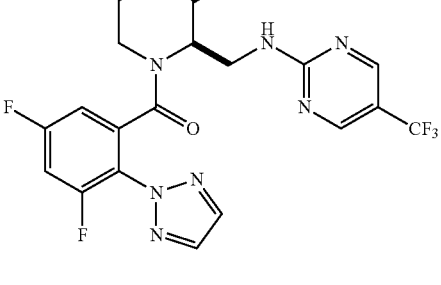 |
| Ex. A330 P | 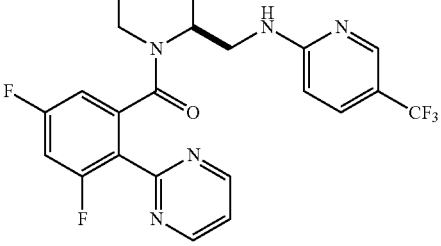 |
| Ex. A331 P | 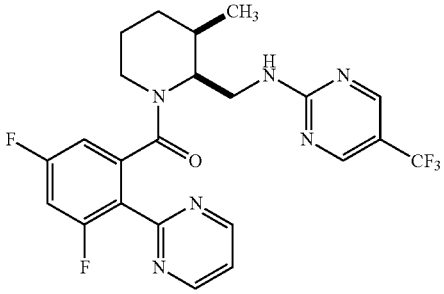 [SMILES: C[C@@H]1CCCN(C(=O)c2cc(F)cc(F)c2-c2ncccn2)[C@@H]1CNc1ncc(C(F)(F)F)cn1] |
| Ex. A332 P | 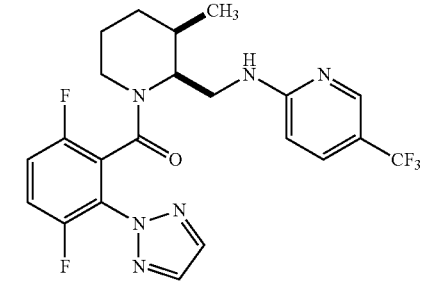 [SMILES: C[C@@H]1CCCN(C(=O)c2c(F)ccc(F)c2-n2nccn2)[C@@H]1CNc1ccc(C(F)(F)F)cn1] |
| Ex. A333 P | 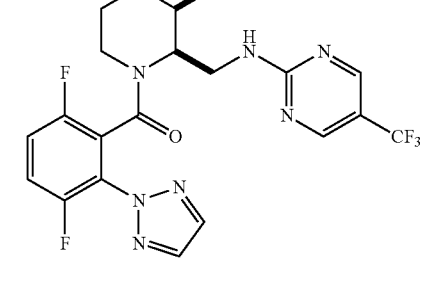 |
| Ex. A334 P | 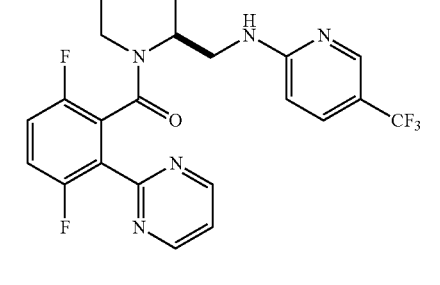 |
| Ex. A335 P | 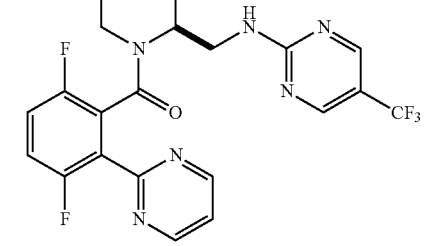 |

TABLE 1A-continued

| Ex. # | Structure |
|---|---|
| Ex. A336 | (structure) |
| Ex. A337 | (structure) |
| Ex. A338 | (structure) |
| Ex. A339 | (structure) |
| Ex. A340 P | (structure) |
| Ex. A341 P | (structure) |
| Ex. A342 P | (structure) |
| Ex. A343 P | (structure) |
| Ex. A344 P | (structure) |
| Ex. A345 P | (structure) |

TABLE 1A-continued

| Ex. # | Structure |
|---|---|
| Ex. A346 P | (structure) |
| Ex. A347 P | (structure) |
| Ex. A348 P | (structure) |
| Ex. A349 P | (structure) |
| Ex. A350 P | (structure) |
| Ex. A351 P | (structure) |
| Ex. A352 P | (structure) |
| Ex. A353 P | (structure) |
| Ex. A354 P | (structure) |
| Ex. A355 P | (structure) |

TABLE 1A-continued

| Ex. # | Structure |
|---|---|
| Ex. A356 P | 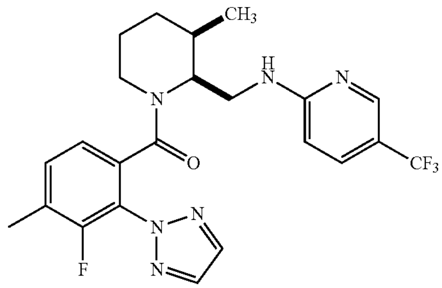 [SMILES: Cc1ccc(C(=O)N2CCC[C@@H](C)[C@H]2CNc2ccc(C(F)(F)F)cn2)c(-n2nccn2)c1F] |
| Ex. A357 P | 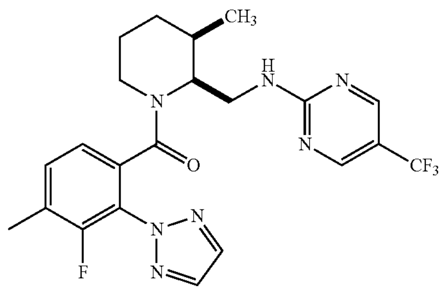 [SMILES: Cc1ccc(C(=O)N2CCC[C@@H](C)[C@H]2CNc2ncc(C(F)(F)F)cn2)c(-n2nccn2)c1F] |
| Ex. A358 P | 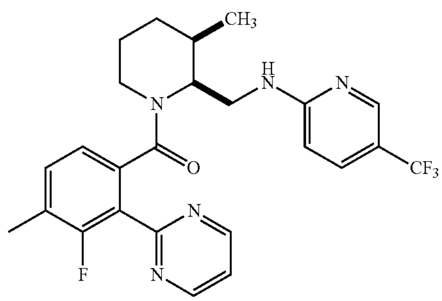 [SMILES: Cc1ccc(C(=O)N2CCC[C@@H](C)[C@H]2CNc2ccc(C(F)(F)F)cn2)c(-c2ncccn2)c1F] |
| Ex. A359 P | 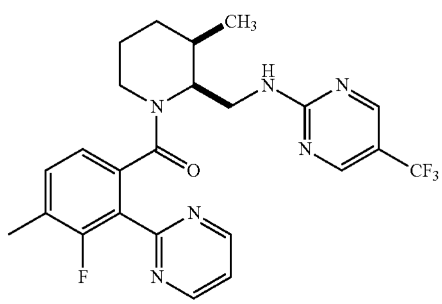 [SMILES: Cc1ccc(C(=O)N2CCC[C@@H](C)[C@H]2CNc2ncc(C(F)(F)F)cn2)c(-c2ncccn2)c1F] |
| Ex. A360 P | 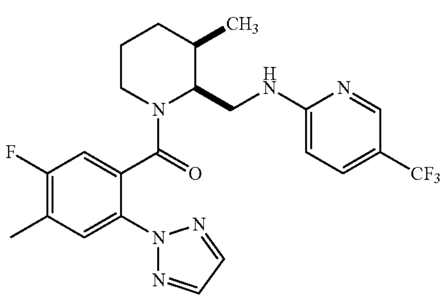 [SMILES: Cc1cc(-n2nccn2)c(C(=O)N2CCC[C@@H](C)[C@H]2CNc2ccc(C(F)(F)F)cn2)cc1F] |
| Ex. A361 P | |
| Ex. A362 P | |
| Ex. A363 P | |
| Ex. A364 P | |
| Ex. A365 P | |

TABLE 1A-continued

| Ex. # | Structure |
|---|---|
| Ex. A366 P | (structure) |
| Ex. A367 P | (structure) |
| Ex. A368 P | (structure) |
| Ex. A369 P | (structure) |
| Ex. A370 P | (structure) |
| Ex. A371 P | (structure) |
| Ex. A372 P | (structure) |
| Ex. A373 P | (structure) |
| Ex. A374 P | (structure) |
| Ex. A375 P | (structure) |

TABLE 1A-continued
| Ex. # | Structure |
|---|---|
| Ex. A376 P | 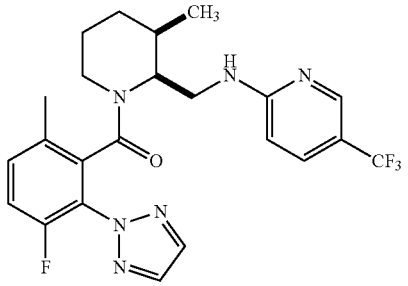 [SMILES: Cc1ccc(F)c(-n2nccn2)c1C(=O)N1CCC[C@@H](C)[C@H]1CNc1ccc(C(F)(F)F)cn1] |
| Ex. A377 P | 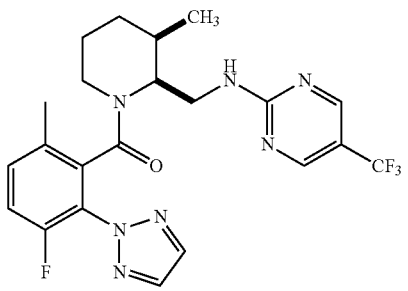 [SMILES: Cc1ccc(F)c(-n2nccn2)c1C(=O)N1CCC[C@@H](C)[C@H]1CNc1ncc(C(F)(F)F)cn1] |
| Ex. A378 P | 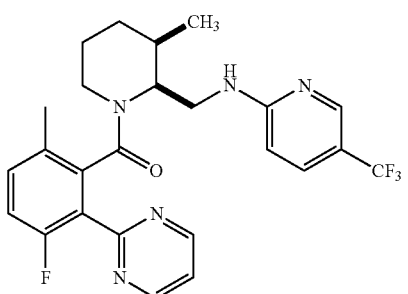 |
| Ex. A379 P | 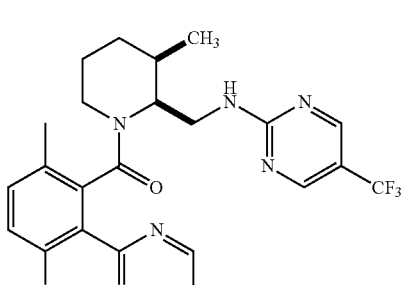 |
| Ex. A380 P | 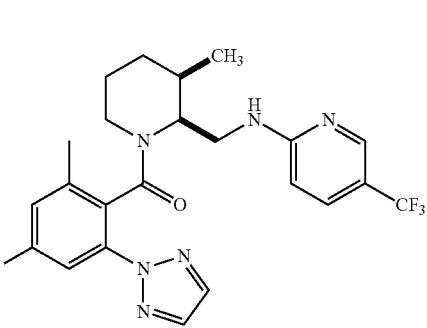 |
| Ex. A381 P | 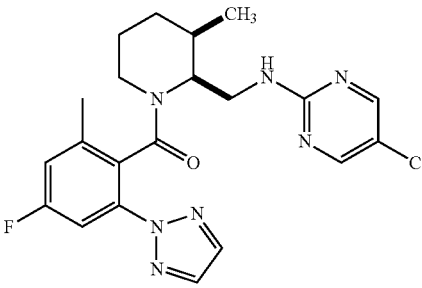 |
| Ex. A382 P | 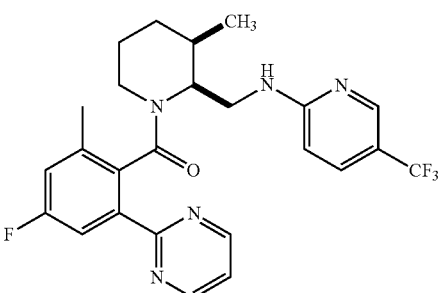 |
| Ex. A383 P | 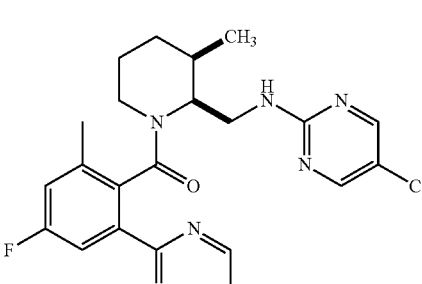 |
| Ex. A384 P | 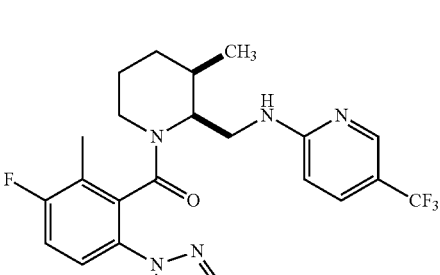 |
| Ex. A385 P | 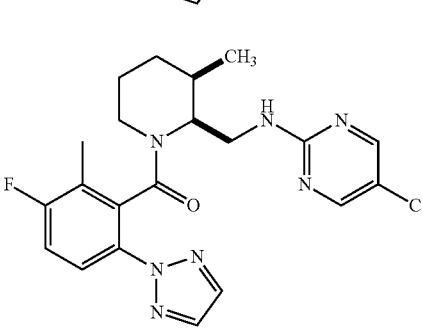 |

TABLE 1A-continued

| Ex. # | Structure |
|---|---|
| Ex. A386 P | (structure) |
| Ex. A387 P | (structure) |
| Ex. A388 P | (structure) |
| Ex. A389 P | (structure) |

Synthetic Examples

Example 1 rac-N-((5-fluoro-1-(2-methyl-5-phenylthiazole-4-carbonyl)piperidin-2-yl)methyl)quinoline-8-carboxamide tert-Butyl (5-fluoropyridin-2-yl)methylcarbamate A solution of (Boc)$_2$O (1.11 g, 5.16 mmol) in CH$_2$Cl$_2$ (3 mL) was added to a mixture of (5-fluoropyridin-2-yl)methanamine (0.64 g, 3.44 mmol) in CH$_2$Cl$_2$ dropwise at room temperature. The resulting mixture was stirred at room temperature overnight and quenched with saturated NaHCO$_3$. The organic portion was separated, dried with MgSO$_4$ and concentrated in vacuo to give desired tert-butyl (5-fluoropyridin-2-yl)methylcarbamate in 83% yield. $^1$H NMR (MeOH-d4, 400 MHz) δ 8.39 (d, 1H), 7.63-7.58 (m, 1H), 7.44-7.40 (m, 1H), 4.35 (s, 2H), 1.53 (s, 2H), 1.48 (s, 7H). MS (ESI) 227 (M+H).

1-Benzyl-2-((tert-butoxycarbonylamino)methyl)-5-fluoropyridinium bromide

A mixture of benzyl bromide (4.21 mmol, 0.5 mL), tert-butyl (5-fluoropyridin-2-yl)methylcarbamate (3.49 mmol, 0.79 g) and acetone (4 mL) in a sealed tube was heated to 80° C. overnight. According to analytical HPLC, around 50% of the starting material remained. Additional benzyl bromide (33.68 mmol, 4.0 mL) was added and the reaction was continued for extra 8 hours. The reaction mixture was concentrated in vacuo and loaded on a pad of silica which was rinsed with ether until benzyl bromide was gone. Then, the silica pad was rinsed with MeOH. Removal of MeOH in vacuo afforded desired product 1-benzyl-2-((tert-butoxycarbonylamino)methyl)-5-fluoropyridinium bromide as light orange solid in 43% yield. MS (ESI) 317 (M+H)

rac-tert-Butyl (1-benzyl-5-fluoro-1,2,3,4-tetrahydropyridin-2-yl)methylcarbamate

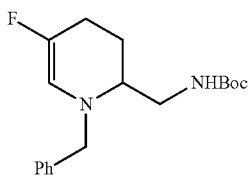

NaBH$_4$ (5.56 mmol, 0.21 g) was added to a solution of 1-benzyl-2-((tert-butoxycarbonylamino)methyl)-5-fluoropyridinium bromide (1.40 mmol, 0.60 g) in MeOH at 0° C. The resulting mixture was stirred at 0° C. for 40 min. An aliquot was checked by analytical HPLC and some of the starting material remained. Additional NaBH$_4$ (5.56 mmol, 0.21 g) was added at 0° C. and the resulting mixture was stirred for extra 40 min. The reaction mixture was diluted with EtOAc and washed with brine. EtOAc layer was separated, dried with MgSO$_4$ and concentrated in vacuo to give desired tert-butyl (1-benzyl-5-fluoro-1,2,3,4-tetrahydropyridin-2-yl)methylcarbamate in 62% yield which was used for next step without further purification. MS (ESI) 321 (M+H).

rac-tert-Butyl (5-fluoropiperidin-2-yl)methylcarbamate

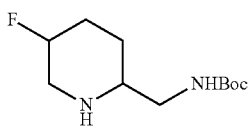

The above described tert-butyl (1-benzyl-5-fluoro-1,2,3,4-tetrahydropyridin-2-yl)methylcarbamate and 10% Pd/C in MeOH was stirred at room temperature under a hydrogen balloon overnight. The reaction mixture was filtered through Celite and concentrated in vacuo to provide the desired product tert-butyl (5-fluoropiperidin-2-yl)methylcarbamate in quantitative yield which was used for next step without further purification. $^1$H NMR (CDCl$_3$, 400 MHz) δ 4.56-4.47 (m, 1H), 3.34-3.17 (m, 2H), 3.02-2.95 (m, 1H), 2.67-2.60 (m, 2H), 2.19-2.14 (m, 1H), 1.81-1.76 (m, 1H), 1.59-1.45 (m, 2H), 1.45 (s, 9H).

rac-(2-(Aminomethyl)-5-fluoropiperidin-1-yl)(2-methyl-5-phenylthiazol-4-yl)methanone

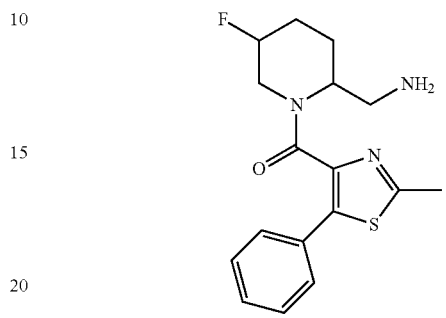

General Procedure A: Amide Coupling Using HATU as Coupling Agent

A mixture of tert-butyl (5-fluoropiperidin-2-yl)methylcarbamate (0.43 mmol, 0.1 g), 2-methyl-5-phenyl-1,3-thiazole-4-carboxylic acid (made as described in the literature: see for instance, WO2008020405, 0.47 mmol, 0.1 g), diisopropyl ethyl amine (0.47 mmol, 0.08 mL) and HATU (0.47 mmol, 0.18 g) in dimethyl acetamide (2 mL) was stirred at room temperature overnight. The reaction mixture was diluted with EtOAc and washed with 1N NaOH and brine successively. The organic layer was separated, dried with MgSO$_4$ and concentrated in vacuo to provide desired tert-butyl (5-fluoro-1-(2-methyl-5-phenylthiazole-4-carbonyl)piperidin-2-yl)methylcarbamate which was used for next step without further purification.

The above described tert-butyl (5-fluoro-1-(2-methyl-5-phenylthiazole-4-carbonyl)piperidin-2-yl)methylcarbamate was stirred in CH$_2$Cl$_2$ (5 mL) and TFA (5 mL) overnight and concentrated in vacuo. The resulting residue was taken in EtOAc and washed with saturated NaHCO$_3$. EtOAc layer was separated, dried with MgSO$_4$ and concentrated in vacuo to afford desired (2-(aminomethyl)-5-fluoropiperidin-1-yl)(2-methyl-5-phenylthiazol-4-yl)methanone in 42% yield over two steps.

The final product N-((5-fluoro-1-(2-methyl-5-phenylthiazole-4-carbonyl)piperidin-2-yl)methyl)quinoline-8-carboxamide was prepared by following general procedure A using (2-(aminomethyl)-5-fluoropiperidin-1-yl)(2-methyl-5-phenylthiazol-4-yl)methanone and quinoline-8-carboxylic acid. The NMR of desired product indicated the presence of two rotamers in ½ ratio. $^1$H NMR (DMSO-d$_6$, 400 MHz) δ 11.02-10.99 (m, 0.33H), 10.73-10.70 (m, 0.67H), 9.05-9.03 (m, 0.33H), 8.98-8.97 (m, 0.67H), 8.62-8.59 (m, 1.33H), 8.52-8.50 (M, 0.67 h), 8.24-8.19 (m, 1H), 7.81-7.74 (m, 1.33H), 7.72-7.68 (m, 0.67H), 7.47-7.43 (m, 0.67H), 7.34-7.32 (m, 2.33H), 7.19-7.10 (m, 2H), 5.08-4.67 (m, 2H) 3.98-3.34 (m, 4H), 2.65 (s, 1H), 2.23 (s, 2H), 2.12-1.69 (m, 2.67H), 1.41-1.39 (m, 1.33H). MS (ESI) 489 (M+H).

Example 2 rac-N-((5-fluoro-1-(2-methyl-5-phenylthiazole-4-carbonyl)piperidin-2-yl)methyl)benzofuran-4-carboxamide

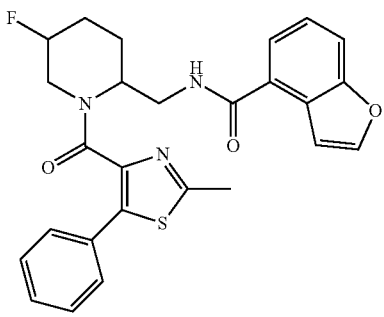 [SMILES: Cc1nc(C(=O)N2CC(F)CCC2CNC(=O)c2cccc3occc23)c(-c2ccccc2)s1]

N-((5-fluoro-1-(2-methyl-5-phenylthiazole-4-carbonyl)piperidin-2-yl)methyl)benzofuran-4-carboxamide was prepared by following general procedure A using (2-(aminomethyl)-5-fluoropiperidin-1-yl)(2-methyl-5-phenylthiazol-4-yl)methanone and benzofuran-4-carboxylic acid. MS (ESI) 478 (M+H).

Example 3 rac-(5-Fluoro-2-((5-(trifluoromethyl)pyridin-2-ylamino)methyl)piperidin-1-yl)(2-methyl-5-phenylthiazol-4-yl)methanone

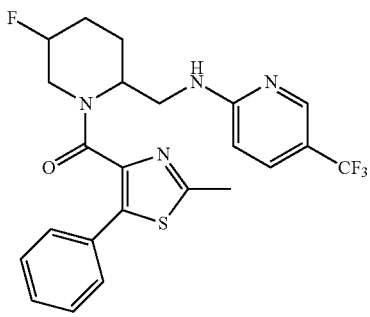 [SMILES: Cc1nc(C(=O)N2CC(F)CCC2CNc2ccc(C(F)(F)F)cn2)c(-c2ccccc2)s1]

General Procedure B: Amination of 2-chloro-5-(trifluoromethyl)pyridine

A mixture of (2-(aminomethyl)-5-fluoropiperidin-1-yl)(2-methyl-5-phenylthiazol-4-yl)methanone (0.18 mmol, 0.06 g), 2-chloro-5-(trifluoromethyl)pyridine (0.38 mmol, 0.07 g) and $Cs_2CO_3$ in DMF (1.5 mL) was stirred at 120° C. overnight. The reaction mixture was diluted with EtOAc and washed with brine. The organic layer was separated, dried with $MgSO_4$ and concentrated in vacuo. The desired (5-fluoro-2-((5-(trifluoromethyl)pyridin-2-ylamino)methyl)piperidin-1-yl) (2-methyl-5-phenylthiazol-4-yl)methanone was isolated by preparative HPLC. MS (ESI) 479 (M+H).

Example 4

N-(((2S,4R)-1-(Biphenylcarbonyl)-4-hydroxypyrrolidin-2-yl)methyl)quinoline-8-carboxamide

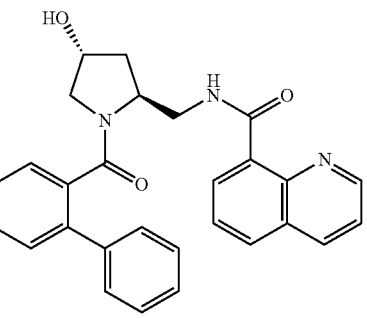

Biphenyl-2-yl((2S,4R)-4-hydroxy-2-(hydroxymethyl)pyrrolidin-1-yl)methanone

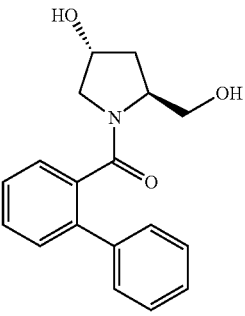 [SMILES: O=C(c1ccccc1-c1ccccc1)N1C[C@H](O)C[C@H]1CO]

Formation of the amide bond was carried out using an adaptation of General Method A, above. A mixture of commercially available (2S,4R)-tert-butyl 4-hydroxy-2-(hydroxymethyl)pyrrolidine-1-carboxylate (3.26 g, 15 mmol) in 50 mL of DCM/TFA (3:2, v/v) was stirred at r.t. for 4 hrs, concentrated in vacuo to give a brown oil as a crude TFA salt of (3R,5S)-5-(hydroxymethyl)pyrrolidin-3-ol, which was dissolved in DMF (28 mL), added with biphenyl-2-carboxylic acid (3.05 g, 15.4 mmol) and HATU (5.86 g, 15.4 mmol). The resulting solution was cooled to 0° C., added with $Et_3N$ (8.8 mL, 63 mmol) dropwise and was allowed to warm to r.t. gradually and stirred overnight. 2M NaOH (aq.) was added and the mixture was extracted with EtOAc (3×). The combined EtOAc solution was washed with brine, dried over $MgSO_4$ and concentrated in vacuo to a brown oil, which was purified by column chromatography on silica gel (10% MeOH in EtOAc) to provide biphenyl-2-yl((2S,4R)-4-hydroxy-2-(hydroxymethyl)pyrrolidin-1-yl)methanone as an off-white solid (2.0 g, 45% yield over two steps). $^1H$ NMR ($CDCl_3$, 400 MHz) δ 7.59-7.57 (m, 2H), 7.54-7.40 (m, 7H), 4.44 (brs, 1H), 4.10 (s, 1H), 3.77-3.72 (m, 1H), 3.62 (brs, 1H), 3.32 (brs, 1H), 3.04-2.96 (m, 1H), 2.60 (brs, 1H), 2.00-1.95 (m, 1H), 1.61 (brs, 2H). MS (ESI) 298.04 (M+H).

2-(((2S,4R)-1-(Biphenylcarbonyl)-4-hydroxypyrrolidin-2-yl)methyl)isoindoline-1,3-dione

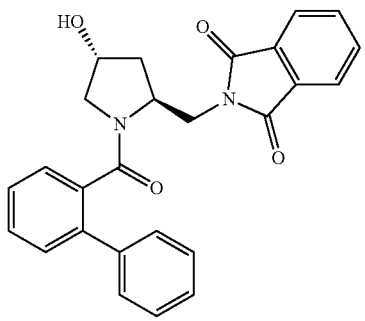 [SMILES: O=C1c2ccccc2C(=O)N1C[C@@H]1C[C@@H](O)CN1C(=O)c1ccccc1-c1ccccc1]

General Procedure C: Converting Hydroxyl Group to Amino Group by Mitsunobu Protocol and Hydrazine Cleavage A solution of biphenyl-2-yl((2S,4R)-4-hydroxy-2-(hydroxymethyl)pyrrolidin-1-yl)methanone (1.67 g, 5.6 mmol), phthalimide (1.24 g, 8.4 mmol) and triphenylphosphine (2.20 g, 8.4 mmol) in THF (56 mL) was cooled to 0° C. and added with DIAD (1.63 mL, 8.4 mmol) dropwise. The resulting suspension was allowed to warm to r.t. gradually and stirred overnight, concentrated in vacuo to a brown oil which was eluted on silica gel column (70% EtOAc in Hexanes) to provide 2-(((2S,4R)-1-(biphenylcarbonyl)-4-hydroxypyrrolidin-2-yl)methyl)isoindoline-1,3-dione as a white solid contaminated with triphenylphosphine oxide and used as-is.

((2S,4R)-2-(aminomethyl)-4-hydroxypyrrolidin-1-yl)(biphenyl-2-yl)methanone

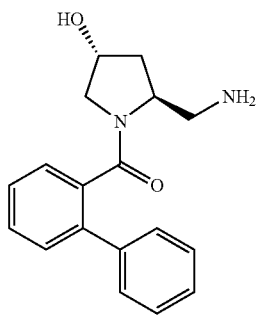 [SMILES: NC[C@@H]1C[C@@H](O)CN1C(=O)c1ccccc1-c1ccccc1]

A mixture of the above mentioned 2-(((2S,4R)-1-(biphenylcarbonyl)-4-hydroxypyrrolidin-2-yl)methyl)isoindoline-1,3-dione (~5.6 mmol) and hydrazine monohydrate (0.65 mL, 10 mmol) in MeOH was stirred at 70° C. for 4 hrs. The resulting white suspension was cooled to r.t., filtered and the filtrate was concentrated in vacuo to a white solid, which was purified by column chromatography on silica gel (100% MeOH) to provide ((2S,4R)-2-(aminomethyl)-4-hydroxypyrrolidin-1-yl)(biphenyl-2-yl)methanone as a white solid (1.1 g, 66% yield over two steps. MS (ESI) 297.05 (M+H).

N-(((2S,4R)-1-(Biphenylcarbonyl)-4-hydroxypyrrolidin-2-yl)methyl)quinoline-8-carboxamide N-(((2S,4R)-1-(biphenylcarbonyl)-4-hydroxypyrrolidin-2-yl)methyl)quinoline-8-carboxamide was obtained as a 3:1 rotamer mixture by following the general procedure A using ((2S,4R)-2-(aminomethyl)-4-hydroxypyrrolidin-1-yl)(biphenyl-2-yl)methanone and quinoline-8-carboxylic acid. $^1$H NMR (CDCl$_3$, 400 MHz) δ 11.28-11.01 (m, 1H), 8.84-8.70 (m, 1H), 8.60-8.40 (m, 1H), 8.13-8.08 (m, 1H), 7.80-7.77 (m, 1H), 7.50-7.03 (m, 11H), 4.41-4.30 (m 1H), 3.99-3.91 (m, 1H), 3.54-3.28 (m, 2H), 2.86-2.56 (m, 3H), 1.99-1.70 (m, 2H). MS (ESI) 452.16 (M+H).

Example 5

N-(((2S,4S)-1-(Biphenylcarbonyl)-4-fluoropyrrolidin-2-yl)methyl)quinoline-8-carboxamide

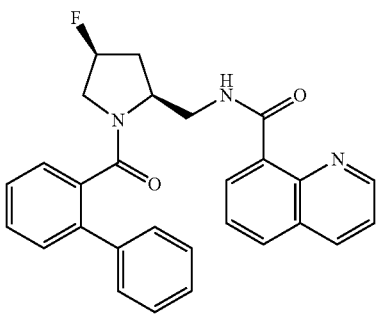 [SMILES: O=C(NC[C@@H]1C[C@H](F)CN1C(=O)c1ccccc1-c1ccccc1)c1cccc2cccnc12]

General Procedure D: Fluorination of Hydroxyl Group

A mixture of N-(((2S,4R)-1-(biphenylcarbonyl)-4-hydroxypyrrolidin-2-yl)methyl)quinoline-8-carboxamide (0.045 g, 0.10 mmol) in DCM was cooled to −78 C., added with bis(2-methoxyethyl)aminosulfur trifluoride (Aldrich) (41 μL, 0.22 mmol) dropwise. The resulting solution was stirred at −78° C. for 0.5 hr, allowed to warm to r.t. gradually over 1.5 hrs and stirred at r.t. for 0.5 hr, which was quenched by slow addition of MeOH and purified by preparative HPLC using acetonitrile and water (0.1% TFA) as eluent to provide N-(((2S,4S)-1-(biphenylcarbonyl)-4-fluoropyrrolidin-2-yl)methyl)quinoline-8-carboxamide as a white solid. MS (ESI) 454.14 (M+H).

Example 6

(S)—N-((1-(Biphenylcarbonyl)-4-oxopyrrolidin-2-yl)methyl)quinoline-8-carboxamide

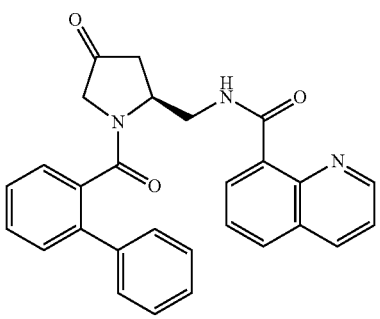 [SMILES: O=C1C[C@@H](CNC(=O)c2cccc3cccnc23)N(C(=O)c2ccccc2-c2ccccc2)C1]

General Procedure E: Swern Oxidation of Alcohols to Ketones

To a solution of oxalyl chloride (39 μL, 0.45 mmol) in DCM (7 mL) at −78° C., was added a solution of DMSO (64

μL, 0.90 mmol) in DCM (4 mL). After stirring at −78° C. for 15 min, a solution of N-(((2S,4R)-1-(biphenylcarbonyl)-4-hydroxypyrrolidin-2-yl)methyl)quinoline-8-carboxamide (0.135 g, 0.30 mmol) in DCM (4 mL) was added. The resulting mixture was stirred at −78° C. for 1 hr, treated with Et₃N (0.25 mL, 1.8 mmol) dropwise and then allowed to warm to r.t. gradually over 1.5 hr. The mixture was then concentrated in vacuo to a beige solid and purified by column chromatography on silica gel (70% MeOH in EtOAc) to provide (S)—N-((1-(biphenylcarbonyl)-4-oxopyrrolidin-2-yl)methyl)quinoline-8-carboxamide as a white solid (0.071 g, 53% yield). MS (ESI) 450.12 (M+H).

Example 7

(S)—N-((1-(Biphenylcarbonyl)-4,4-difluoropyrrolidin-2-yl)methyl)quinoline-8-carboxamide

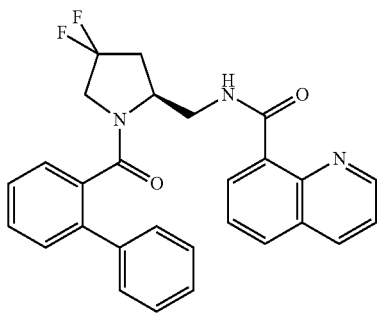 [SMILES: O=C(NC[C@@H]1CC(F)(F)CN1C(=O)c1ccccc1-c1ccccc1)c1cccc2cccnc12]

General Procedure F: Fluorination of Carbonyl Group

Bis(2-methoxyethyl)aminosulfur trifluoride (32 μL, 0.18 mmol) was added dropwise to a solution of (S)—N-((1-(biphenylcarbonyl)-4-oxopyrrolidin-2-yl)methyl)quinoline-8-carboxamide (0.036 g, 0.080 mmol) in DCM (80 μL), followed by addition of EtOH (1 μL) and stirred at r.t. overnight. The mixture was quenched with MeOH and purified by preparative HPLC using acetonitrile and water (0.1% TFA) as eluent to provide (S)—N-((1-(biphenylcarbonyl)-4,4-difluoropyrrolidin-2-yl)methyl)quinoline-8-carboxamide as a white solid. MS (ESI) 472.14 (M+H).

Example 8 rac-N-((2S,3R)-3-Methyl-1-(2-methyl-5-phenylthiazole-4-carbonyl)piperidin-2-yl)methyl)quinoline-8-carboxamide

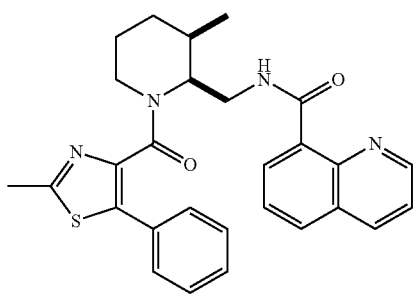 [SMILES: Cc1nc(C(=O)N2CCC[C@@H](C)[C@H]2CNC(=O)c2cccc3cccnc23)c(-c2ccccc2)s1]

3-Methylpicolinamide

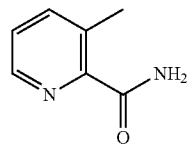

A mixture of 3-methylpicolinonitrile (2.36 g, 20 mmol) and conc. sulfuric acid (12.5 mL) was stirred at 80° C. for 25 min. The solution was cooled to r.t., poured into water (80 mL), followed by addition of sat. Na₂CO₃ (aq.) until pH ~7. The resulting mixture was extracted with DCM (3x) and the combined organic layer was dried over MgSO₄ and concentrated in vacuo to provide 3-methylpicolinamide as a white solid (2.65 g, 97%). ¹H NMR (CDCl₃, 400 MHz) δ 8.43 (dd, 1H), 7.93 (brs, 1H), 7.62 (dd, 1H), 7.35 (dd, 1H), 5.44 (brs, 1H), 2.76 (s, 3H).

rac-(2S,3R)-3-Methylpiperidine-2-carboxamide

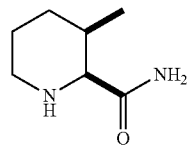

A mixture of 3-methylpicolinamide (2.23 g, 16.4 mmol) and PtO₂ (0.18 g, 0.8 mmol) in acetic acid (55 mL) was placed in a Parr shaker type hydrogenation apparatus, pressurized to 4.70 bar with H₂ and maintained at r.t. for 7 hrs. The mixture was filtered through Celite and the filtrate was concentrated in vacuo to a solid. A mixture of this crude solid and DCM and solid Na₂CO₃, were stirred at r.t. overnight. The resulting suspension was filtered and the filtrate was concentrated in vacuo to provide rac-(2S,3R)-3-methylpiperidine-2-carboxamide as a white solid (2.0 g, 86% yield). ¹H NMR (CDCl₃, 400 MHz) δ 6.51 (brs, 1H), 5.32 (brs, 1H), 3.37 (d, 1H), 3.14-3.10 (m, 1H), 2.70-2.63 (m, 1H), 2.33-2.28 (m, 1H), 1.73-1.58 (m, 4H), 1.42-1.39 (m, 1H), 1.00 (d, 3H).

rac-(2S,3R)-1-(4-Methoxybenzyl)-3-methylpiperidine-2-carboxamide

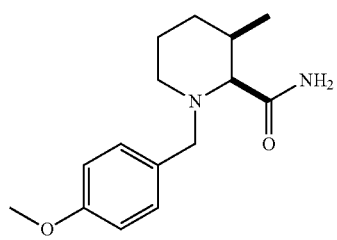 [SMILES: COc1ccc(CN2CCC[C@@H](C)[C@H]2C(N)=O)cc1]

1-(Chloromethyl)-4-methoxybenzene (1.0 mL, 7.5 mmol) was added to a mixture of rac-(2S,3R)-3-methylpiperidine-2-carboxamide (0.71 g, 5.0 mmol) in sat. Na₂CO₃ (aq.)/DCM (15 mL, 1:2 v/v) and stirred vigorously at r.t. overnight. The resulting suspension was diluted with water and extracted with EtOAc (2x). The combined organic layers were washed with brine, dried over MgSO₄ and concentrated in vacuo to a white residue, which was purified by column chromatography on silica gel (100% EtOAc) to provide rac-(2S,3R)-1-(4-methoxybenzyl)-3-methylpiperidine-2-carboxamide as a white solid (0.61 g, 41% yield. MS (ESI) 262.98 (M+H).

rac-((2S,3R)-1-(4-Methoxybenzyl)-3-methylpiperidin-2-yl)methanamine

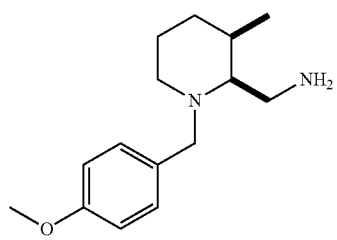 [SMILES: COc1ccc(CN2CCC[C@@H](C)[C@H]2CN)cc1]

Rac-(2S,3R)-1-(4-methoxybenzyl)-3-methylpiperidine-2-carboxamide (0.61 g, 2.33 mmol) was added portionwise to a suspension of LiAlH₄ (0.30 g, 7.50 mmol) and THF (12 mL) and heated to reflux for 14 hrs. The reaction mixture was then cooled to 0° C. and quenched with water and NaOH (aq.). The resulting mixture was stirred at r.t. for 1 hr, filtered and the filtrated was concentrated in vacuo to provide rac-((2S,3R)-1-(4-methoxybenzyl)-3-methylpiperidin-2-yl)methanamine as a colorless oil, used as-is without further purification.

rac-N-(((2S,3R)-1-(4-Methoxybenzyl)-3-methylpiperidin-2-yl)methyl)quinoline-8-carboxamide

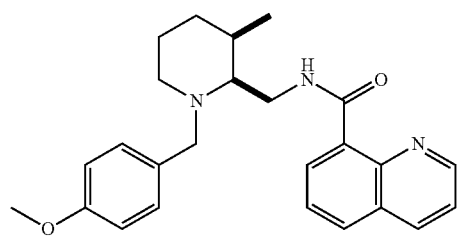 [SMILES: COc1ccc(CN2CCC[C@@H](C)[C@H]2CNC(=O)c2cccc3cccnc23)cc1]

Rac-N-(((2S,3R)-1-(4-methoxybenzyl)-3-methylpiperidin-2-yl)methyl)quinoline-8-carboxamide was obtained by following the general procedure A using the fore-mentioned crude rac-((2S,3R)-1-(4-methoxybenzyl)-3-methylpiperidin-2-yl)methanamine and quinoline-8-carboxylic acid. MS (ESI) 404.24 (M+H).

rac-N-(((2S,3R)-3-Methylpiperidin-2-yl)methyl)quinoline-8-carboxamide

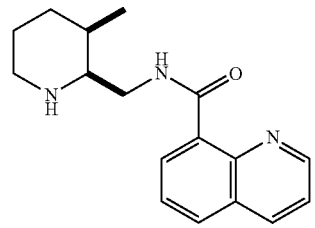

Cerium ammonium nitrate (1.25 g, 2.28 mmol) was added portionwise to a mixture of rac-N-(((2S,3R)-1-(4-methoxybenzyl)-3-methylpiperidin-2-yl)methyl)quinoline-8-carboxamide (0.23 g, 0.57 mmol) in acetone/water (10 mL, 9:1 v/v) at 0° C. and allowed to stir at r.t. for 5 hrs. Sat. NaHCO₃ (aq.) was added and the resulting suspension was stirred at r.t for 10 min, concentrated in vacuo to remove the acetone, then filtered through Celite and rinsed with EtOAc. The bi-layer filtrate was extracted with EtOAc and the combined organic layer was washed with brine, dried over MgSO₄ and concentrated in vacuo to provide a brown oil as a 1:1 mixture of rac-N-(((2S,3R)-3-methylpiperidin-2-yl)methyl)quinoline-8-carboxamide/4-methoxybenzaldehyde, which was used as-is without further purification. MS (ESI) 284.13 (M+H).

rac-N-(((2S,3R)-3-Methyl-1-(2-methyl-5-phenylthiazole-4-carbonyl)piperidin-2-yl)methyl)quinoline-8-carboxamide Rac-N-(((2S,3R)-3-methyl-1-(2-methyl-5-phenylthiazole-4-carbonyl)piperidin-2-yl)methyl)quinoline-8-carboxamide was obtained as a 1:1 rotamer mixture by following the general procedure A using the fore-mentioned crude rac-N-(((2S,3R)-3-methylpiperidin-2-yl)methyl)quinoline-8-carboxamide and 2-methyl-5-phenylthiazole-4-carboxylic acid. MS (ESI) 485.12 (M+H).

Example 9 rac-N-(((2S,3R)-3-Methyl-1-(2-methyl-4-phenylthiazole-5-carbonyl)piperidin-2-yl)methyl)quinoline-8-carboxamide

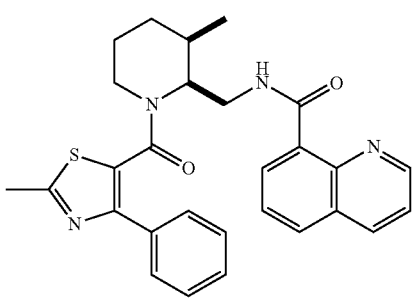

Rac-N-(((2S,3R)-3-methyl-1-(2-methyl-4-phenylthiazole-5-carbonyl)piperidin-2-yl)methyl)quinoline-8-carboxamide was obtained by following the general procedure A using the fore-mentioned crude rac-N-(((2S,3R)-3-methylpiperidin-2-yl)methyl)quinoline-8-carboxamide and 2-methyl-4-phenylthiazole-5-carboxylic acid. MS (ESI) 485.15 (M+H).

Example 10 rac-N-(((2S,3R)-1-(3-Fluoro-2-methoxybenzoyl)-3-methylpiperidin-2-yl)methyl)quinoline-8-carboxamide

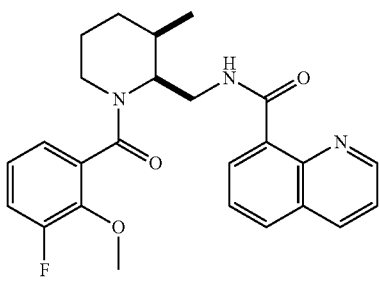

Rac-N-(((2S,3R)-1-(3-fluoro-2-methoxybenzoyl)-3-methylpiperidin-2-yl)methyl)quinoline-8-carboxamide was obtained by following the general procedure A using the fore-mentioned crude rac-N-(((2S,3R)-3-methylpiperidin-2-yl)methyl)quinoline-8-carboxamide and 3-fluoro-2-methoxybenzoic acid. MS (ESI) 436.14 (M+H).

Example 11 rac-(5-(4-fluorophenyl)-2-methylthiazol-4-yl)((2S,3R)-3-methyl-2-(((5-(trifluoromethyl)pyridin-2-yl)amino)methyl)piperidin-1-yl)methanone

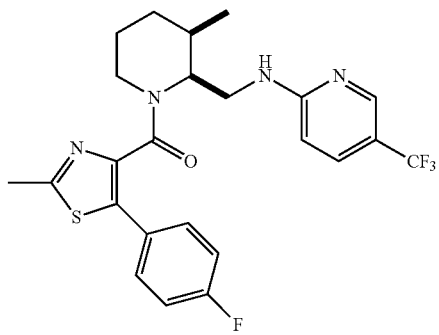

rac-tert-butyl (((2S,3R)-3-methylpiperidin-2-yl)methyl)carbamate

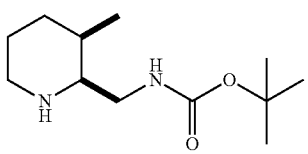

To a solution of 3-methyl-2-cyanopyridine (5 g) in acetic acid was added 10% Pd/C. The parr shaker bottle was evacuated/H2 purged 3x, and then shaken at 50 psi until starting material was consumed (typically <1 h). The reaction was filtered through celite and concentrated to yield (3-methylpyridin-2-yl)methanamine acetic acid salt which was used without further purification.

To the crude salt in THF was added aq 1M NaOH, followed by BOC2O (2 eq). The reaction was allowed to stir at room temperature overnight. After ~16 h, the reaction mixture was transferred to a seperatory funnel, diluted with EtOAc, and water, and the layers were separated. The organic layer was washed with brine, dried (MgSO4), and concentrated in vacuo to give a crude residue which was purified by chromatography on silica gel (EtOAc/hex) to afford tert-butyl ((3-methylpyridin-2-yl)methyl)carbamate.

To a solution of the BOC-protected pyridylamine in MeOH was added Nishimura's catalyst. The parr shaker bottle was evacuated/purged with H2 (3x) and then shaken at 50 psi for 24 h. The reaction was filtered through celite, and concentrated in vacuo to give the title compound as a near colorless oil, and was used without further purification. 1H NMR (D6-DMSO, 400 MHz) δ 6.7 (br s, NH), 4.0 (br s, 1H), 2.9-2.7 (m, 3H), 2.6-2.5 (m, 1H), 2.5-2.4 (m, 1H), 1.7-1.6 (br s, 1H), 1.6-1.45 (m, 3H), 1.4 (s, 9H), 1.3-1.2 (m, 1H), 0.8 (d, 3H).

rac-((2S,3R)-2-(aminomethyl)-3-methylpiperidin-1-yl)(5-(4-fluorophenyl)-2-methylthiazol-4-yl)methanone

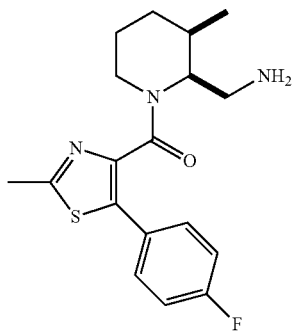

To a solution of tert-butyl (((2S,3R)-3-methylpiperidin-2-yl)methyl)carbamate (1.5 g) from the previous step in CH2Cl2 was added DIEA (2 eq) followed by 2-methyl-5-(4-fluorophenylthiazole)-4-carboxylic acid (2 g) and HATU (3.3 g). The reaction was allowed to stir at room temperature for 15 h, and was then concentrated in vacuo to remove the CH2Cl2. The crude residue was taken up in EtOAc and washed with 1M HCl, sat aq. NaHCO3, brine, dried (MgSO4), and concentrated. The crude residue was purified by chromatography on silica gel (EtOAc/hex) to give tert-butyl (((2S,3R)-1-(5-(4-fluorophenyl)-2-methylthiazole-4-carbonyl)-3-methylpiperidin-2-yl)methyl)carbamate as a light yellow oil which crystallized (2 g).

To a solution of this carbamate in CH2Cl2 was added TFA (1:1 v/v). The reaction was aged at room temperature and monitored for disappearance of starting material by analytical reverse-phase HPLC. When starting material was consumed, the reaction was concentrated in vacuo. The crude residue was taken up in EtOAc, and washed with sat aqueous NaHCO3, brine, dried (MgSO4), and concentrated to afford the title compound as a pale yellow oil which crystallized. MS (ESI) 348.06 (M+H).

rac-(5-(4-fluorophenyl)-2-methylthiazol-4-yl)((2S, 3R)-3-methyl-2-(((5-(trifluoromethyl)pyridin-2-yl) amino)methyl)piperidin-1-yl)methanone A mixture of ((2S,3R)-2-(aminomethyl)-3-methylpiperidin-1-yl)(5-(4-fluorophenyl)-2-methylthiazol-4-yl)methanone, 2-chloro-5-(trifluoromethyl)pyridine, and $K_2CO_3$ in DMAC was stirred at 120° C. overnight. The reaction mixture was diluted with EtOAc and washed with brine. The organic layer was separated, dried with $MgSO_4$ and concentrated in vacuo. The crude residue was purified by chromatography on silica gel (EtOAc/hex) to give the title compound as a pale yellow oil which solidified. MS (ESI) 493.01 (M+H).

Example 12 rac-((2S,3R)-2-((benzo[d]oxazol-2-ylamino)methyl)-3-methylpiperidin-1-yl)(2-methyl-5-phenylthiazol-4-yl)methanone

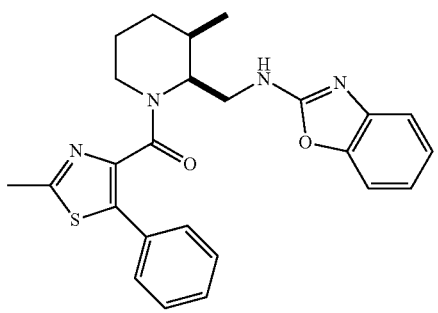

rac-((2S,3R)-2-(aminomethyl)-3-methylpiperidin-1-yl)(2-methyl-5-phenylthiazol-4-yl)methanone

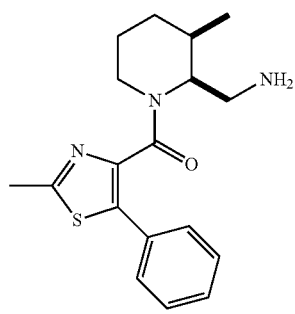

The title compound was synthesized following the same general protocol as described in Example 11 using tert-butyl (((2S,3R)-3-methylpiperidin-2-yl)methyl)carbamate and 2-methyl-5-phenylthiazole-4-carboxylic acid. MS (ESI) 330.08 (M+H).

rac-((2S,3R)-2-((benzo[d]oxazol-2-ylamino)methyl)-3-methylpiperidin-1-yl)(2-methyl-5-phenylthiazol-4-yl)methanone A mixture of ((2S,3R)-2-(aminomethyl)-3-methylpiperidin-1-yl)(2-methyl-5-phenylthiazol-4-yl)methanone, 2-chlorobenzoxazole, and DIEA in $CH_2Cl_2$ was stirred at 60° C. overnight. The reaction mixture was concentrated in vacuo to leave a near colorless solid. This solid was triturated with $Et_2O$/hexanes to leave the title compound as a colorless solid homogeneous by HPLC analysis. MS (ESI) 447.03 (M+H).

Example 13 rac-((2S,3R)-2-((benzo[d]oxazol-2-ylamino)methyl)-3-(trifluoromethyl)piperidin-1-yl)(2-methyl-5-phenylthiazol-4-yl)methanone

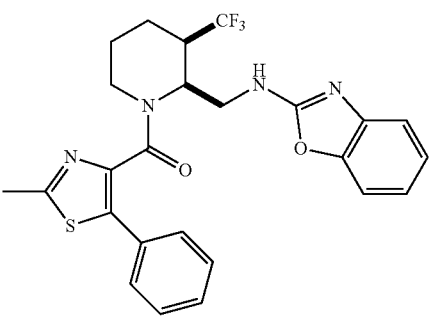

rac-tert-butyl (((2S,3R)-3-(trifluoromethyl)piperidin-2-yl)methyl)carbamate

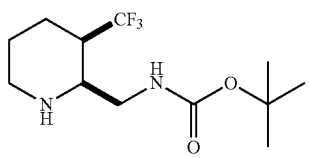

The title compound was synthesized following the same general protocol as described for rac-tert-butyl (((2S,3R)-3-methylpiperidin-2-yl)methyl)carbamate starting with 3-(trifluoromethyl)picolinonitrile. $^1$H NMR ($D_6$-DMSO, 400 MHz) δ 5.1 (br s, NH), 3.25 (br s, 2H), 3.1 (br s, 1H), 2.8 (br, 2H), 2.7 (br, 2H), 2.4 (br, 1H), 1.8-1.6 (m, 3H), 1.4 (s, 9H); MS (ESI) 283.2 (M+H).

rac-((2S,3R)-2-((benzo[d]oxazol-2-ylamino)methyl)-3-(trifluoromethyl)piperidin-1-yl)(2-methyl-5-phenylthiazol-4-yl)methanone The title compound was prepared following the same general protocol as described for Example's 11 and 12. MS (ESI) 501.05 (M+H).

Example 14 rac-(2-methyl-5-phenylthiazol-4-yl)((2S,3R)-3-(trifluoromethyl)-2-(((5-(trifluoromethyl)pyridin-2-yl)amino)methyl)piperidin-1-yl)methanone

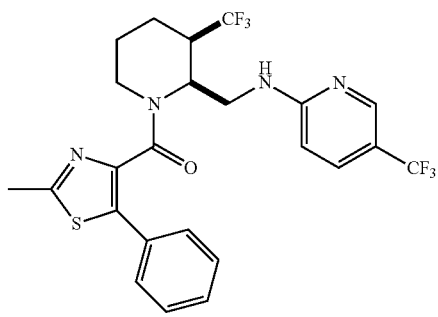

The title compound was prepared following the same general protocol as described for Example's 11 and 12 starting with 3-(trifluoromethyl)picolinonitrile. MS (ESI) 528.98 (M+H).

Example 15 rac-((2S,3R)-2-(((5-bromopyrimidin-2-yl)amino)methyl)-3-methylpiperidin-1-yl)(5-(4-fluorophenyl)-2-methylthiazol-4-yl)methanone

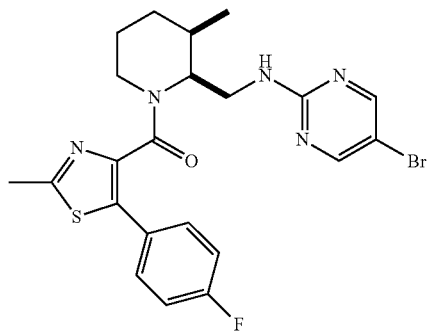

A mixture of ((2S,3R)-2-(aminomethyl)-3-methylpiperidin-1-yl)(5-(4-fluorophenyl)-2-methylthiazol-4-yl)methanone, 5-bromo-2-chloropyrimidine, and DIEA in isopropanol was stirred at 120° C. for 1 h in a microwave reactor. The reaction was complete as judged by reverse-phase analytical HPLC. The crude reaction mixture was purified by reverse-phase preparative HPLC to afford the title compound. MS (ESI) 505.88 (M+H).

Example 16 rac-((2S,3R)-2-(((5-ethylpyrimidin-2-yl)amino)methyl)-3-methylpiperidin-1-yl)(5-(4-fluorophenyl)-2-methylthiazol-4-yl)methanone

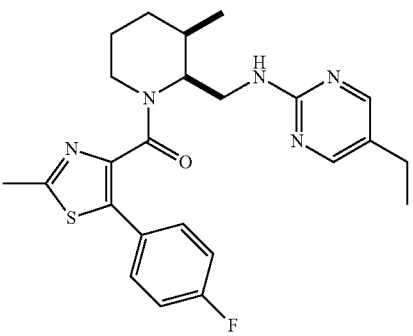

A mixture of ((2S,3R)-2-(aminomethyl)-3-methylpiperidin-1-yl)(5-(4-fluorophenyl)-2-methylthiazol-4-yl)methanone, 5-ethyl-2-chloropyrimidine, and DIEA in isopropanol was stirred at 110° C. for 18 h. The reaction was cooled and concentrated in vacuo. The crude reaction mixture was purified by reverse-phase preparative HPLC to afford the title compound. MS (ESI) 454.02 (M+H).

Example 17 rac-(5-(4-fluorophenyl)-2-methylthiazol-4-yl)((2S,3R)-2-(((4-methoxypyrimidin-2-yl)amino)methyl)-3-methylpiperidin-1-yl)methanone

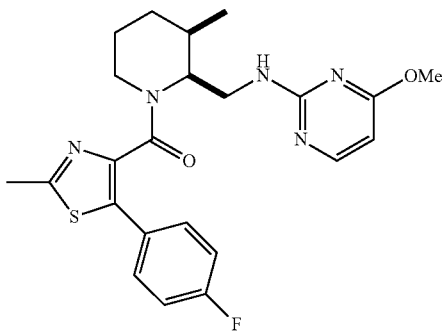

A mixture of ((2S,3R)-2-(aminomethyl)-3-methylpiperidin-1-yl)(5-(4-fluorophenyl)-2-methylthiazol-4-yl)methanone, 4-methoxy-2-chloropyrimidine, and DIEA in isopropanol was stirred at 110° C. for 18 h. The reaction was cooled and concentrated in vacuo. The crude reaction mixture was purified by reverse-phase preparative HPLC to afford the title compound. MS (ESI) 456.02 (M+H).

Example 18 rac-((2S,3R)-2-(((5-chloropyridin-2-yl)amino)methyl)-3-methylpiperidin-1-yl)(5-(4-fluorophenyl)-2-methylthiazol-4-yl)methanone

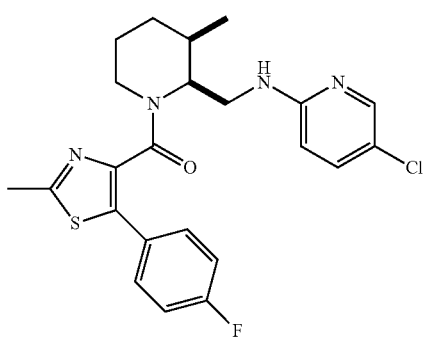

A mixture of ((2S,3R)-2-(aminomethyl)-3-methylpiperidin-1-yl)(5-(4-fluorophenyl)-2-methylthiazol-4-yl)methanone, 2-fluoro-5-chloropyridine, and $K_2CO_3$ in DMAC was stirred at 120° C. for 16 h. The reaction was cooled and concentrated in vacuo. The crude reaction mixture was purified by reverse-phase preparative HPLC to afford the title compound. MS (ESI) 458.95 (M+H).

Example 19 rac-((2S,3R)-2-(((2-chloropyrimidin-4-yl)amino)methyl)-3-methylpiperidin-1-yl)(5-(4-fluorophenyl)-2-methylthiazol-4-yl)methanone

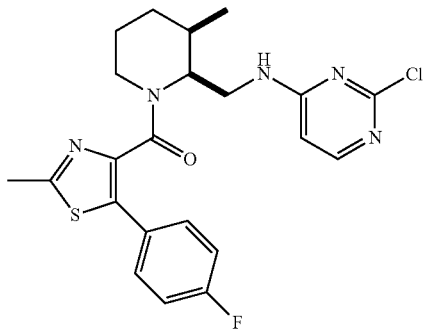 [SMILES: Cc1nc(C(=O)N2CCC[C@@H](C)[C@H]2CNc2ccnc(Cl)n2)c(-c2ccc(F)cc2)s1]

A mixture of ((2S,3R)-2-(aminomethyl)-3-methylpiperidin-1-yl)(5-(4-fluorophenyl)-2-methylthiazol-4-yl)methanone, 2,4-dichloropyrimidine, and $K_2CO_3$ in DMAC was stirred at 120° C. for 18 h. The reaction was cooled and concentrated in vacuo. The crude reaction mixture was purified by reverse-phase preparative HPLC to afford the title compound as the major isomer. MS (ESI) 459.94 (M+H).

Example 20 rac-((2S,3R)-2-(((4-chloropyrimidin-2-yl)amino)methyl)-3-methylpiperidin-1-yl)(5-(4-fluorophenyl)-2-methylthiazol-4-yl)methanone

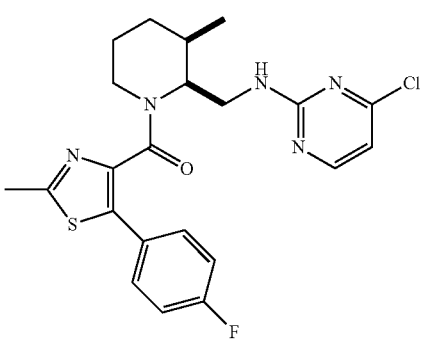 [SMILES: Cc1nc(C(=O)N2CCC[C@@H](C)[C@H]2CNc2nccc(Cl)n2)c(-c2ccc(F)cc2)s1]

The title compound was isolated as the minor isomer in the reaction described for Example 19. MS (ESI) 459.94 (M+H).

Example 21 rac-(5-(4-fluorophenyl)-2-methylthiazol-4-yl)((2S,3R)-3-methyl-2-(((4-(trifluoromethyl)pyridin-2-yl)amino)methyl)piperidin-1-yl)methanone

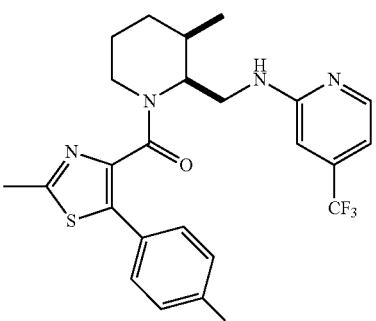

A mixture of ((2S,3R)-2-(aminomethyl)-3-methylpiperidin-1-yl)(5-(4-fluorophenyl)-2-methylthiazol-4-yl)methanone, 2-bromo-4-(trifluoromethyl)pyridine, $Pd_2$ $dba_3$, BINAP, and NaOtBu in toluene was purged with argon, and then stirred at 70° C. for 12 h. The reaction was cooled, filtered through a pad of silica gel and concentrated in vacuo. The crude reaction mixture was purified by reverse-phase preparative HPLC to afford the title compound. MS (ESI) 492.97 (M+H).

Example 22 rac-(5-(4-fluorophenyl)-2-methylthiazol-4-yl)((2S,3R)-3-methyl-2-(((3-(trifluoromethyl)pyridin-2-yl)amino)methyl)piperidin-1-yl)methanone

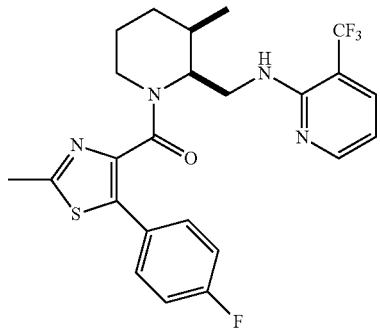 [SMILES: Cc1nc(C(=O)N2CCC[C@@H](C)[C@H]2CNc2ncccc2C(F)(F)F)c(-c2ccc(F)cc2)s1]

The title compound was prepared following the same general protocol as described for Example 21 using 2-bromo-3-(trifluoromethyl)pyridine. MS (ESI) 493.01 (M+H).

Example 23 rac-(5-(4-fluorophenyl)-2-methylthiazol-4-yl)((2S,3R)-3-methyl-2-(((6-methylpyridin-2-yl)amino)methyl)piperidin-1-yl)methanone

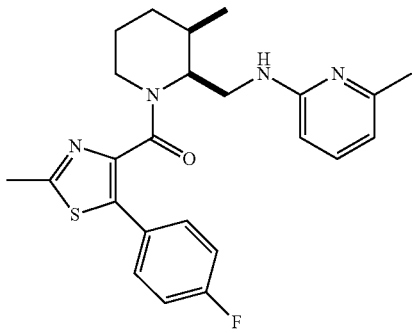

The title compound was prepared following the same general protocol as described for Example 21 using 2-bromo-6-(methyl)pyridine. MS (ESI) 439.04 (M+H).

Example 24 rac-((2S,3R)-2-((benzo[d]oxazol-2-ylamino)methyl)-3-methylpiperidin-1-yl)(5-(4-fluorophenyl)-2-methylthiazol-4-yl)methanone

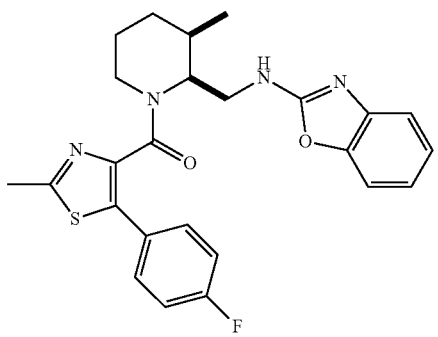 [SMILES: Cc1nc(C(=O)N2CCC[C@@H](C)[C@H]2CNc2nc3ccccc3o2)c(-c2ccc(F)cc2)s1]

A mixture of ((2S,3R)-2-(aminomethyl)-3-methylpiperidin-1-yl)(5-(4-fluorophenyl)-2-methylthiazol-4-yl)methanone, 2-chlorobenzoxazole, and DIEA in CH$_2$Cl$_2$ was stirred at 60° C. overnight. The reaction mixture was concentrated in vacuo to leave a near colorless solid. This solid was triturated with Et$_2$O/hex to leave the title compound as a colorless solid homogeneous by HPLC analysis. MS (ESI) 465.03 (M+H).

Example 25 rac-(2-((benzo[d]oxazol-2-ylamino)methyl)-6-methylpiperidin-1-yl)(5-(4-fluorophenyl)-2-methylthiazol-4-yl)methanone

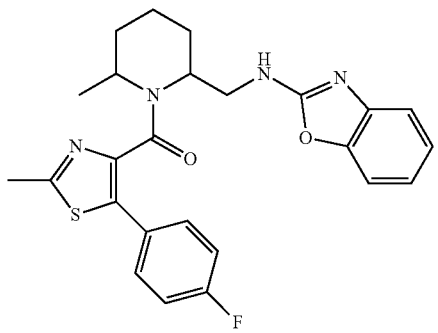 [SMILES: Cc1nc(C(=O)N2C(C)CCCC2CNc2nc3ccccc3o2)c(-c2ccc(F)cc2)s1]

tert-butyl ((6-methylpyridin-2-yl)methyl)carbamate

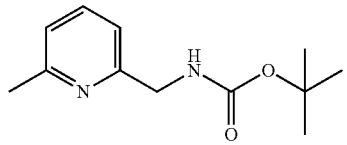 [SMILES: Cc1cccc(CNC(=O)OC(C)(C)C)n1]

To a solution of 6-methyl-2-cyanopyridine (5 g) and BOC$_2$O in EtOAc was added 10% Pd/C. The reaction mixture was stirred under a balloon of H$_2$ for 24 h, and then filtered through celite and concentrated in vacuo. The crude residue was purified by chromatography on silica gel (EtOAc/hex) to give the title compound as a colorless oil. $^1$H NMR (D$_6$-DMSO, 400 MHz) δ 7.6 (t, 1H), 7.4 (br s, NH), 7.2 (d, 1H), 7.1 (d, 1H), 4.2 (d, 2H), 2.4 (s, 3H), 1.4 (s, 9H).

rac-tert-butyl ((6-methylpiperidin-2-yl)methyl)carbamate

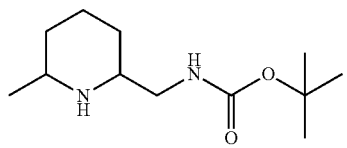 [SMILES: CC1CCCC(CNC(=O)OC(C)(C)C)N1]

To a solution of the product from the previous step in MeOH was added Nishimura's catalyst. The parr shaker bottle was evacuated/purged with H$_2$ (3x) and then shaken at 50 psi for 24 h. The reaction was filtered through celite, and concentrated in vacuo to give the title compound as a near colorless oil, and was used without further purification. ¹H NMR (D$_6$-DMSO, 400 MHz) δ 6.75 (br s, NH), 3.3 (br s, 1H), 2.9-2.8 (m, 1H), 2.8-2.7 (m, 1H), 2.5-2.4 (m, 1H), 2.0-1.8 (br s, 1H), 1.75-1.65 (m, 1H), 1.55-1.45 (m, 2H), 1.4 (s, 9H), 1.3-1.2 (m, 1H), 0.95 (d, 3H), 0.9-0.8 (m, 2H).

rac-(2-(aminomethyl)-6-methylpiperidin-1-yl)(5-(4-fluorophenyl)-2-methylthiazol-4-yl)methanone

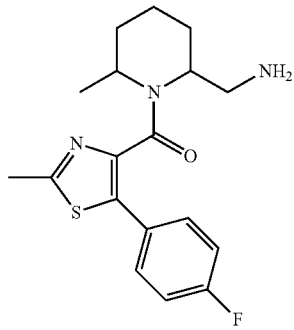 [SMILES: Cc1nc(C(=O)N2C(C)CCCC2CN)c(-c2ccc(F)cc2)s1]

The title compound was made following the same general protocol as described for Example 11. MS (ESI) 348.11 (M+H).

rac-(2-((benzo[d]oxazol-2-ylamino)methyl)-6-methylpiperidin-1-yl)(5-(4-fluorophenyl)-2-methylthiazol-4-yl)methanone The title compound was made following the same general protocol as described for Example 12. MS (ESI) 465.08 (M+H).

Example 26 rac-(5-(4-fluorophenyl)-2-methylthiazol-4-yl)(2-methyl-6-(((5-(trifluoromethyl)pyridin-2-yl)amino)methyl)piperidin-1-yl)methanone

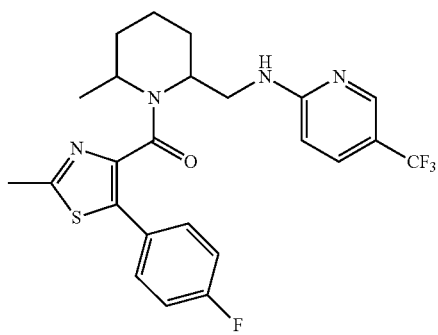 [SMILES: Cc1nc(C(=O)N2C(C)CCCC2CNc2ccc(C(F)(F)F)cn2)c(-c2ccc(F)cc2)s1]

The title compound was made following the same general protocol as described for Example 11. MS (ESI) 493.04 (M+H).

Example 27 rac-(5-(4-fluorophenyl)-2-methylthiazol-4-yl)(2-methyl-6-(((5-(trifluoromethyl)pyrimidin-2-yl)amino)methyl)piperidin-1-yl)methanone

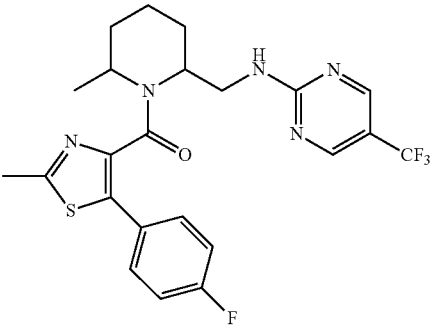

The title compound was made following the same general protocol as described for Example 11. MS (ESI) 494.04 (M+H).

Example 28 rac-(2-(((5-chloropyrimidin-2-yl)amino)methyl)-6-methylpiperidin-1-yl)(5-(4-fluorophenyl)-2-methylthiazol-4-yl)methanone

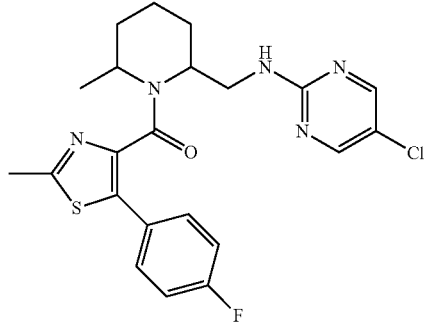 [SMILES: Cc1nc(C(=O)N2C(C)CCCC2CNc2ncc(Cl)cn2)c(-c2ccc(F)cc2)s1]

The title compound was made following the same general protocol as described for Example 11. MS (ESI) 460.04 (M+H).

Example 29 rac-N-((6-Methyl-1-(2-methyl-4-phenylthiazole-5-carbonyl)piperidin-2-yl)methyl)quinoline-8-carboxamide

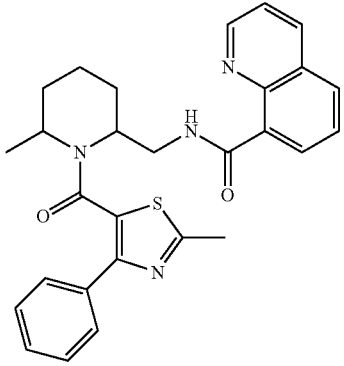 [SMILES: Cc1nc(-c2ccccc2)c(C(=O)N2C(C)CCCC2CNC(=O)c2cccc3cccnc23)s1]

Part I: rac-(2-(Aminomethyl)-6-methylpiperidin-1-yl)(2-methyl-4-phenylthiazol-5-yl)methanone

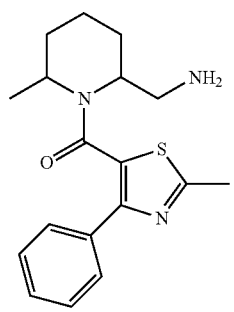

General Procedure G: Curtius Rearrangement of Carboxylic Acid

Ethyl chloroformate (0.28 mmol, 0.027 mL) and triethyl amine (0.28 mmol, 0.04 mL) were added to a solution of 2-(6-methyl-1-(2-methyl-4-phenylthiazole-5-carbonyl)piperidin-2-yl)acetic acid (0.14 mmol, 0.05 g) sequentially at 0° C. The resulting mixture was stirred at room temperature for 1 hr. Then, an aqueous solution of $NaN_3$ (1.40 mmol, 0.045 g) in water (1 mL) was added at 0° C. with vigorously stirring. The reaction was tracked by analytical HPLC. The reaction mixture was diluted with EtOAc and washed with brine. The organic layer was separated, dried with $MgSO_4$ and concentrated in vacuo. The resulting residue was mixed with toluene/tBuOH (5 mL/5 mL) and refluxed at 110° C. overnight. The solvent was removed in vacuo to give tert-butyl (6-methyl-1-(2-methyl-4-phenylthiazole-5-carbonyl)piperidin-2-yl)methylcarbamate which was deprotected of Boc in $TFA/CH_2Cl_2$ (volume: 1/1) to give desired (2-(aminomethyl)-6-methylpiperidin-1-yl)(2-methyl-4-phenylthiazol-5-yl)methanone.

rac-N-((6-Methyl-1-(2-methyl-4-phenylthiazole-5-carbonyl)piperidin-2-yl)methyl)quinoline-8-carboxamide The title compound was prepared by following the general procedure A using (2-(aminomethyl)-6-methylpiperidin-1-yl)(2-methyl-4-phenylthiazol-5-yl)methanone and quinoline-8-carboxylic acid. MS (ESI) 485 (M+H).

Example 30 rac-(2-Methyl-4-phenylthiazol-5-yl)(2-methyl-6-(2-phenoxyethyl)piperidin-1-yl)methanone

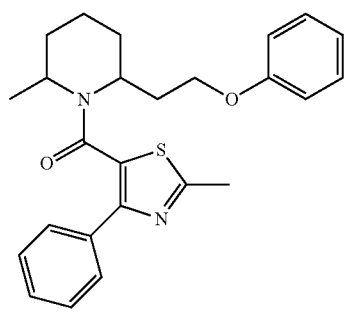

Part I: 2-Methyl-6-(2-phenoxyethyl)pyridine

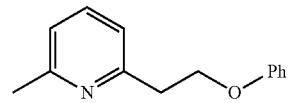 [SMILES: Cc1cccc(CCOc2ccccc2)n1]

MsCl (6.7 mmol, 0.52 mL) was added to a solution of 6-methyl-2-pyridineethanol (6.7 mmol, 0.92 g) and triethyl amine (13.4 mmol, 1.88 mL) in toluene (6 mL) at 0° C. dropwise. The resulting mixture was stirred at 0° C. for 30 min. The precipitate generated from reaction was filtered off. The filtrate was concentrated in vacuo to give crude 2-(6-methylpyridin-2-yl)ethyl methanesulfonate which was used for next step without further purification.

A mixture of above described 2-(6-methylpyridin-2-yl)ethyl methanesulfonate, PhOH (13.4 mmol, 1.26 g) and NaOH (13.4 mmol, 0.54 g) in isopropanol (20 mL) was refluxed at 90° C. for 3 hr. The reaction mixture was concentrated in vacuo and dissolved in EtOAc which was washed with water. The organic layer was separated, dried with $MgSO_4$ and concentrated in vacuo. The crude product was purified by chromatography to give desired 2-methyl-6-(2-phenoxyethyl)pyridine as a colorless oil in 26% yield.

Part II: rac-2-Methyl-6-(2-phenoxyethyl)piperidine

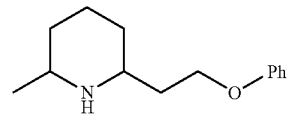 [SMILES: CC1CCCC(CCOc2ccccc2)N1]

General Procedure H: Hydrogenation of pyridine to piperidine using Adam Catalyst 2-Methyl-6-(2-phenoxyethyl)pyridine (0.19 mmol, 0.04 g) and Adam Catalyst (0.09 mmol, 0.02 g) in MeOH was stirred at room temperature under a hydrogen balloon overnight. The reaction mixture was filtered through Celite and concentrated in vacuo to provide the desired product 2-methyl-6-(2-phenoxyethyl)piperidine in 30% conversion. This crude residue was used in the next step without further purification.

(2-Methyl-4-phenylthiazol-5-yl)(2-methyl-6-(2-phenoxyethyl)piperidin-1-yl)methanone was prepared according to general procedure A using 2-methyl-6-(2-phenoxyethyl)piperidine and 2-methyl-5-phenyl-1,3-thiazole-4-carboxylic acid. $^1$H NMR (CDCl$_3$, 400 MHz) δ 7.64-7.60 (m, 2H), 7.37-7.29 (m, 3H), 7.24-7.14 (m, 2H), 6.93-6.85 (m, 2H), 6.64-6.62 (m, 1H), 4.87-4.78 (m, 1H), 4.07-4.01 (m, 1H), 3.93-3.78 (m, 1H), 3.62-3.50 (m, 1H), 3.13-3.07 (m, 1H), 2.69 (s, 1H), 2.55 (s, 2H), 2.01-2.00 (m, 1H), 1.48-1.21 (m, 9H). MS (ESI) 421 (M+H).

Example 31 rac-Biphenyl-2-yl(2-methyl-6-(2-phenoxyethyl)piperidin-1-yl)methanone

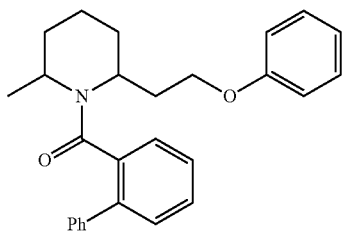 [SMILES: CC1CCCC(CCOc2ccccc2)N1C(=O)c1ccccc1-c1ccccc1]

Biphenyl-2-yl(2-methyl-6-(2-phenoxyethyl)piperidin-1-yl)methanone was prepared according to general procedure A using 2-methyl-6-(2-phenoxyethyl)piperidine and biphenyl-2-carboxylic acid. MS (ESI) 400 (M+H).

Example 32 rac-N-((1-(biphenylcarbonyl)-5-hydroxypiperidin-2-yl)methyl)quinoline-8-carboxamide

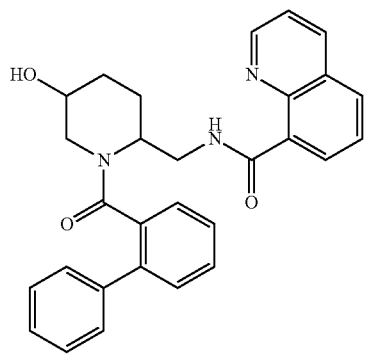 [SMILES: O=C(NCC1CCC(O)CN1C(=O)c1ccccc1-c1ccccc1)c1cccc2cccnc12]

Part I: rac-Methyl 5,5-dimethoxypiperidine-2-carboxylate

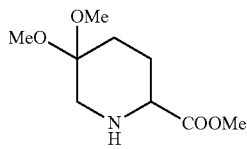 [SMILES: COC(=O)C1CCC(OC)(OC)CN1]

5-Oxopiperidine-2-carboxylic acid hydrochloride salt (41.1 mmol, 7.36 g) in MeOH was added thionyl chloride (206.7 mmol, 15 mL) dropwise by an additional funnel at −10° C. The resulting mixture was refluxed at 60° C. overnight. The reaction mixture was concentrated in vacuo to give desired product methyl 5,5-dimethoxypiperidine-2-carboxylate as the HCl salt. $^1$H NMR (CDCl$_3$, 400 MHz) δ 4.28-4.20 (m, 1H), 3.78 (s, 3H), 3.35-3.32 (m, 1H), 3.16 (s, 3H), 3.14 (s, 3H), 3.31-1.98 (m, 2H), 1.82-1.69 (m, 2H).

Part II: rac-Methyl 5-oxopiperidine-2-carboxylate

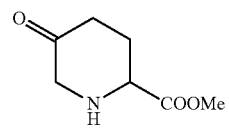 [SMILES: COC(=O)C1CCC(=O)CN1]

The above described ketal was stirred in TFA at room temperature for 4 hr. An aliquot was taken for NMR which confirmed 100% conversion of starting material. The reaction mixture was diluted with water and extracted with DCM. The DCM layer was discarded and the water layer was concentrated in vacuo to give desired methyl 5-oxopiperidine-2-carboxylate as the TFA salt in quantitative yield.

Part III: rac-Methyl 1-(biphenylcarbonyl)-5-oxopiperidine-2-carboxylate

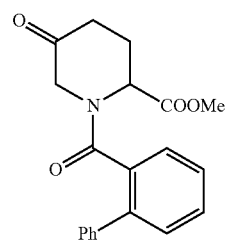 [SMILES: COC(=O)C1CCC(=O)CN1C(=O)c1ccccc1-c1ccccc1]

Methyl 1-(biphenylcarbonyl)-5-oxopiperidine-2-carboxylate was prepared according to general procedure A using methyl 5-oxopiperidine-2-carboxylate and biphenyl-2-carboxylic acid. MS (ESI) 338 (M+H).

Part IV: rac-Biphenyl-2-yl(2-(hydroxymethyl)-5,5-dimethoxypiperidin-1-yl)methanone

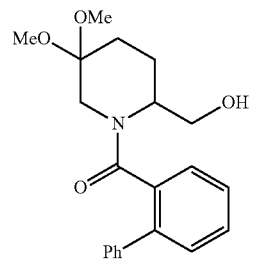 [SMILES: COC1(OC)CCC(CO)N(C(=O)c2ccccc2-c2ccccc2)C1]

Methyl 1-(biphenylcarbonyl)-5-oxopiperidine-2-carboxylate was converted to methyl 1-(biphenylcarbonyl)-5,5-dimethoxypiperidine-2-carboxylate (4.3 mmol, 1.65 g) following the general protocol described in Part I above. To a solution of this ketal in anhydrous THF was added LiBH$_4$ (2M in THF) (9.4 mmol, 4.7 mL) at 0° C. under argon. The resulting mixture was stirred at room temperature and the reaction was tracked by analytical HPLC. The reaction was carefully quenched with saturated NH$_4$Cl and extracted with EtOAc. The organic layer was separated, dried with MgSO$_4$, and concentrated in vacuo to give desired biphenyl-2-yl(2-

(hydroxymethyl)-5,5-dimethoxypiperidin-1-yl)methanone in quantitative yield which was used for next step without further purification.

Part V: rac-2-((1-(Biphenylcarbonyl)-5,5-dimethoxypiperidin-2-yl)methyl)isoindoline-1,3-dione

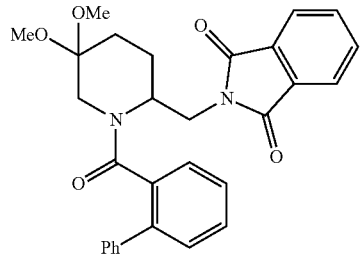 [SMILES: COC1(OC)CCC(CN2C(=O)c3ccccc3C2=O)N(C(=O)c2ccccc2-c2ccccc2)C1]

General Procedure I: Mitsunobu Reaction of Alcohol with Phthalimide

DIAD (15.15 mmol, 2.93 mL) was added to a mixture of (biphenyl-2-yl(2-(hydroxymethyl)-5-methoxy-3,4-dihydropyridin-1(2H)-yl)methanone (4.5 mmol, 1.63 g), phthalimide (15.15 mmol, 2.23 g) and PPh₃ (15.15 mmol, 3.97 g) in anhydrous THF dropwise at 0° C. under argon. The resulting mixture was stirred at room temperature for overnight and concentrated in vacuo to give a crude residue which was purified by chromatography to give the desired 2-((1-(biphenylcarbonyl)-5,5-dimethoxypiperidin-2-yl)methyl)isoindoline-1,3-dione with slight contamination of triphenylphosphine oxide. This contaminated product was used for next step without further purification.

Part VI: rac-(2-(Aminomethyl)-5,5-dimethoxypiperidin-1-yl)(biphenyl-2-yl)methanone

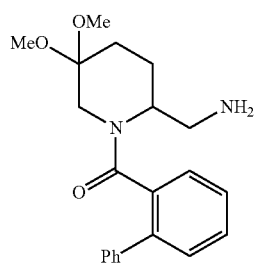 [SMILES: COC1(OC)CCC(CN)N(C(=O)c2ccccc2-c2ccccc2)C1]

General Procedure J. Conversion of Phthalimide to Primary Amine Using Hydrazine

A mixture of the above described 2-((1-(biphenylcarbonyl)-5,5-dimethoxypiperidin-2-yl)methyl)isoindoline-1,3-dione (1.13 g, 2.3 mmol) and hydrazine monohydrate (10.0 mmol, 0.4 g) in MeOH (10 mL) was stirred at 60° C. The reaction was tracked by analytical HPLC. MeOH was removed in vacuo and the reaction mixture was diluted with water followed by extraction with EtOAc. The organic layer was separated, dried with MgSO₄, and concentrated in vacuo to give desired (2-(aminomethyl)-5,5-dimethoxypiperidin-1-yl)(biphenyl-2-yl)ethanone.

Part VII: rac-N-((1-(biphenylcarbonyl)-5-oxopiperidin-2-yl)methyl)quinoline-8-carboxamide N-((1-(biphenylcarbonyl)-5-oxopiperidin-2-yl)methyl)quinoline-8-carboxamide was prepared according general procedure A using quinoline-8-carboxylic acid and N-((1-(biphenylcarbonyl)-5-methoxy-1,2,3,4-tetrahydropyridin-2-yl)methyl)quinoline-8-carboxamide which was synthesized from the product from Part VI above, following ketal cleavage using TFA and CH₂Cl₂. MS (ESI) 464 (M+H).

General Procedure K. Reduction of Ketone to Alcohol

NaBH₄ (3.49 mmol, 0.13 g) was added to a solution of N-((1-(biphenylcarbonyl)-5-oxopiperidin-2-yl)methyl)quinoline-8-carboxamide TFA salt (0.46 mmol, 0.26 g) in MeOH (10 mL) at 0° C. in three portions. The resulting mixture was stirred at room temperature and the reaction was tracked by analytical HPLC. The reaction was quenched with water and extracted with EtOAc. The organic layer was separated, dried with MgSO₄, and concentrated in vacuo to give crude residue which was purified by preparative HPLC to give desired N-((1-(biphenylcarbonyl)-5-hydroxypiperidin-2-yl)methyl)quinoline-8-carboxamide with unidentified stereochemistry (Y:75%). MS (ESI) 466 (M+H).

Example 33 rac-N-((5-hydroxy-1-(2-methyl-4-phenylthiazole-5-carbonyl)piperidin-2-yl)methyl)quinoline-8-carboxamide

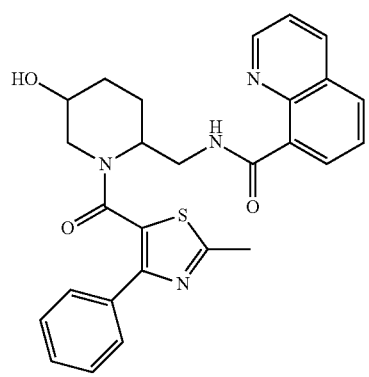 [SMILES: Cc1nc(-c2ccccc2)c(C(=O)N2CC(O)CCC2CNC(=O)c2cccc3cccnc23)s1]

Part I: rac-Methyl 5,5-dimethoxy-1-(2-methyl-4-phenylthiazole-5-carbonyl)piperidine-2-carboxylate

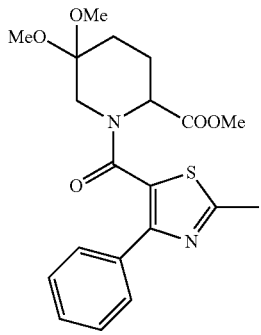 [SMILES: COC(=O)C1CCC(OC)(OC)CN1C(=O)c1sc(C)nc1-c1ccccc1]

Methyl 5,5-dimethoxy-1-(2-methyl-4-phenylthiazole-5-carbonyl)piperidine-2-carboxylate was prepared according to general procedure A using methyl 5,5-dimethoxypiperidine-2-carboxylate and 2-methyl-4-phenylthiazole-5-carboxylic acid.

Part II: rac-(2-(Hydroxymethyl)-5,5-dimethoxypiperidin-1-yl)(2-methyl-4-phenylthiazol-5-yl)methanone

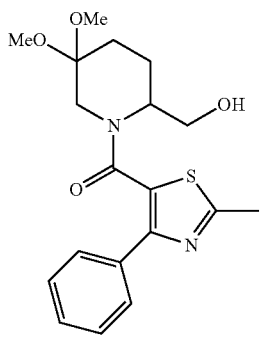 [SMILES: COC1(OC)CCC(CO)N(C(=O)c2sc(C)nc2-c2ccccc2)C1]

The title compound was prepared from the product of Part I following the same general protocol as described for Example 32 Part IV.

Part III: rac-N-((5,5-dimethoxy-1-(2-methyl-4-phenylthiazole-5-carbonyl)piperidin-2-yl)methyl)quinoline-8-carboxamide

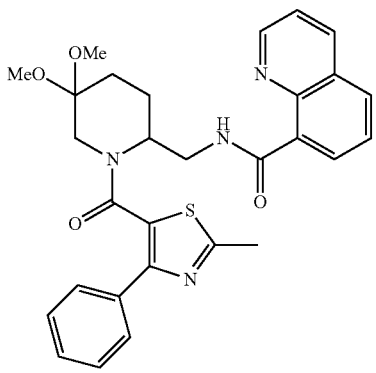 [SMILES: COC1(OC)CCC(CNC(=O)c2cccc3cccnc23)N(C(=O)c2sc(C)nc2-c2ccccc2)C1]

N-((5,5-dimethoxy-1-(2-methyl-4-phenylthiazole-5-carbonyl)piperidin-2-yl)methyl)quinoline-8-carboxamide was prepared according to general procedures I, J, and A using (2-(Hydroxymethyl)-5,5-dimethoxypiperidin-1-yl)(2-methyl-4-phenylthiazol-5-yl)methanone.

Part IV: rac-N-((1-(2-methyl-4-phenylthiazole-5-carbonyl)-5-oxopiperidin-2-yl)methyl)quinoline-8-carboxamide

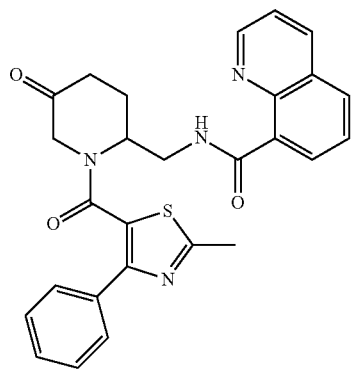 [SMILES: Cc1nc(-c2ccccc2)c(C(=O)N2CC(=O)CCC2CNC(=O)c2cccc3cccnc23)s1]

The title compound was prepared from the product of Part III above using TFA/CH$_2$Cl$_2$. MS (ESI) 485 (M+H).

N-((5-hydroxy-1-(2-methyl-4-phenylthiazole-5-carbonyl)piperidin-2-yl)methyl)quinoline-8-carboxamide was prepared according to general procedure K using N-((1-(2-methyl-4-phenylthiazole-5-carbonyl)-5-oxopiperidin-2-yl)methyl)quinoline-8-carboxamide. MS (ESI) 487 (M+H).

Example 34 rac-N-((5,5-difluoro-1-(2-methyl-4-phenylthiazole-5-carbonyl)piperidin-2-yl)methyl)quinoline-8-carboxamide

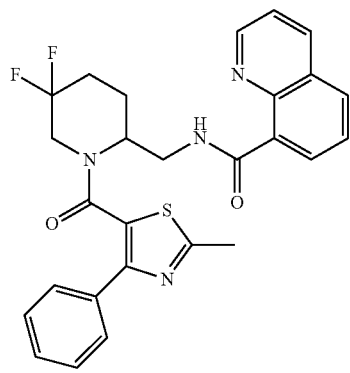 [SMILES: Cc1nc(-c2ccccc2)c(C(=O)N2CC(F)(F)CCC2CNC(=O)c2cccc3cccnc23)s1]

General Procedure L: Difluorination of Ketone with Deoxo-Fluo

Deoxo-fluo (0.17 mmol, 0.032 mL) in DCM (0.2 mL) was added to a solution of N-((1-(2-methyl-4-phenylthiazole-5-carbonyl)-5-oxopiperidin-2-yl)methyl)quinoline-8-carboxamide (0.10 mmol, 0.05 g) in DCM (0.2 mL) in a sealed tube at room temperature. Then EtOH (0.02 mmol, 0.0008 g) was added. The resulting mixture was stirred at room temperature overnight. The reaction mixture was diluted with DCM and quenched with saturated NaHCO$_3$. The organic layer was separated, dried with MgSO$_4$, and concentrated in vacuo to give crude residue which was purified by prep. HPLC to give desired N-((5,5-difluoro-1-(2-methyl-4-phenylthiazole-5-carbonyl)piperidin-2-yl)methyl)quinoline-8-carboxamide (Y:56%). MS (ESI) 507 (M+H).

Example 35 rac-N-((5-fluoro-1-(2-methyl-4-phenylthiazole-5-carbonyl)piperidin-2-yl)methyl)quinoline-8-carboxamide

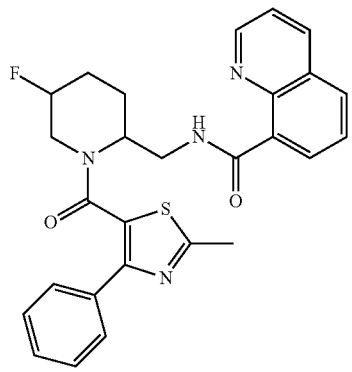 [SMILES: Cc1nc(-c2ccccc2)c(C(=O)N2CC(F)CCC2CNC(=O)c2cccc3cccnc23)s1]

General Procedure M: Fluorination of Alcohol with Deoxo-Fluo

A solution of N-((5-hydroxy-1-(2-methyl-4-phenylthiazole-5-carbonyl)piperidin-2-yl)methyl)quinoline-8-carboxamide (0.07 mmol, 0.036 g) in DCM (0.3 mL) was added to a mixture of Deoxo-fluoro (0.14 mmol, 0.027 mL) in DCM (0.2 mL) at −78° C. under argon. The resulting mixture was stirred at −78° C. for 1 hr and at room temperature for another 1.5 hr. The desired product was purified by preparative TLC to give N-((5-fluoro-1-(2-methyl-4-phenylthiazole-5-carbonyl)piperidin-2-yl)methyl)quinoline-8-carboxamide with unidentified stereochemistry (Y:16%). MS (ESI) 489 (M+H).

Example 36 rac-N-((1-(biphenylcarbonyl)-5,5-difluoropiperidin-2-yl)methyl)quinoline-8-carboxamide

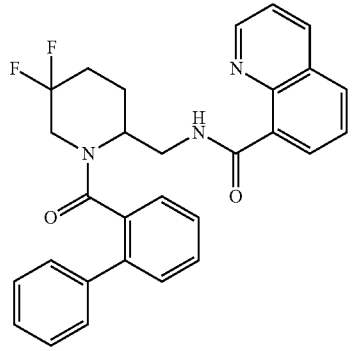 [SMILES: O=C(NCC1CCC(F)(F)CN1C(=O)c1ccccc1-c1ccccc1)c1cccc2cccnc12]

N-((1-(biphenylcarbonyl)-5,5-difluoropiperidin-2-yl)methyl)quinoline-8-carboxamide was prepared according to general procedure L using N-((1-(biphenylcarbonyl)-5-oxopiperidin-2-yl)methyl)quinoline-8-carboxamide. MS (ESI) 486 (M+H).

Example 37 rac-N-(((5S)-1-(biphenylcarbonyl)-5-fluoropiperidin-2-yl)methyl)quinoline-8-carboxamide

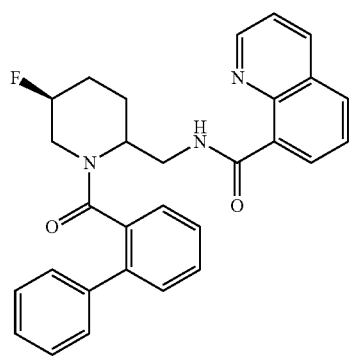 [SMILES: O=C(NCC1CC[C@H](F)CN1C(=O)c1ccccc1-c1ccccc1)c1cccc2cccnc12]

Example 38 rac-N-(((5R)-1-(biphenylcarbonyl)-5-fluoropiperidin-2-yl)methyl)quinoline-8-carboxamide

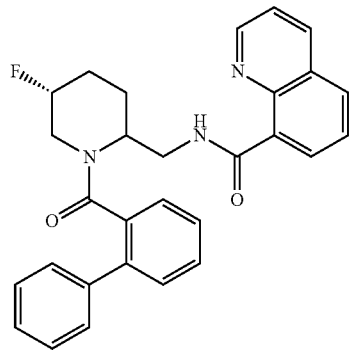 [SMILES: O=C(NCC1CC[C@@H](F)CN1C(=O)c1ccccc1-c1ccccc1)c1cccc2cccnc12]

Example 37 and Example 38 were two different fractions isolated from the fluorination of N-((1-(biphenylcarbonyl)-5-oxopiperidin-2-yl)methyl)quinoline-8-carboxamide by following general procedure M. However, the stereochemistry of isomers has not been verified. MS (ESI) 468 (M+H).

Example 39 rac-N-((5-amino-1-(biphenylcarbonyl)piperidin-2-yl)methyl)quinoline-8-carboxamide

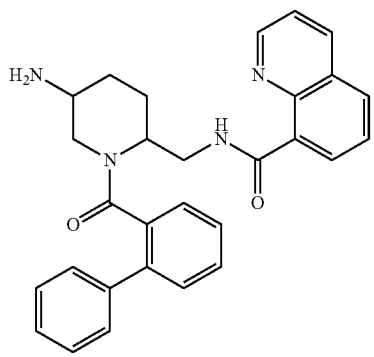 [SMILES: NC1CCC(CNC(=O)c2cccc3cccnc23)N(C(=O)c2ccccc2-c2ccccc2)C1]

General Procedure N: Reductive Amination of Ketone

NaBH$_3$CN (0.18 mmol, 0.011 g) was added to a solution of N-((1-(biphenylcarbonyl)-5-oxopiperidin-2-yl)methyl)quinoline-8-carboxamide (0.06 mmol, 0.027 g) and NH$_4$OAc (0.6 mmol, 0.011 g) in MeOH. The resulting mixture was stirred at room temperature for overnight and quenched with saturated NH$_4$Cl. The aqueous solution was extracted with EtOAc and the organic layer was separated, dried with MgSO$_4$, and concentrated in vacuo to give crude residue which was purified by preparative HPLC to give desired N-((5-amino-1-(biphenylcarbonyl)piperidin-2-yl)methyl)quinoline-8-carboxamide. (ESI) 465 (M+H).

Example 40 rac-N-((5-(benzylamino)-1-(biphenylcarbonyl)piperidin-2-yl)methyl)quinoline-8-carboxamide

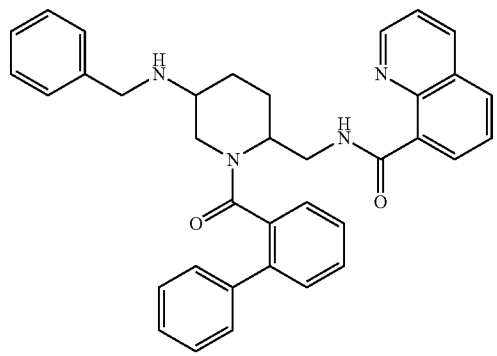 [SMILES: O=C(NCC1CCC(NCc2ccccc2)CN1C(=O)c1ccccc1-c1ccccc1)c1cccc2cccnc12]

N-((5-(benzylamino)-1-(biphenylcarbonyl)piperidin-2-yl)methyl)quinoline-8-carboxamide was prepared according general procedure N using N-((1-(biphenylcarbonyl)-5-oxopiperidin-2-yl)methyl)quinoline-8-carboxamide and benzyl amine. (ESI) 555 (M+H).

Example 41 rac-N-((1-(biphenylcarbonyl)-5-(dimethylamino)piperidin-2-yl)methyl)quinoline-8-carboxamide

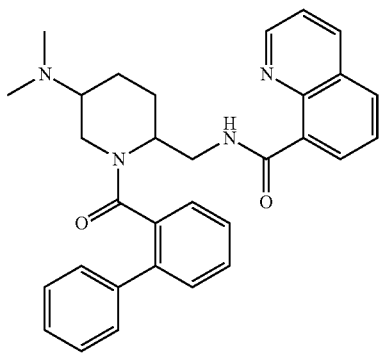 [SMILES: CN(C)C1CCC(CNC(=O)c2cccc3cccnc23)N(C(=O)c2ccccc2-c2ccccc2)C1]

N-((1-(biphenylcarbonyl)-5-(dimethylamino)piperidin-2-yl)methyl)quinoline-8-carboxamide was prepared according general procedure N using N-((1-(biphenylcarbonyl)-5-oxopiperidin-2-yl)methyl)quinoline-8-carboxamide and dimethyl amine. (ESI) 493 (M+H).

Example 42 rac-N-((1-(biphenylcarbonyl)-5-(2-hydroxyethylamino)piperidin-2-yl)methyl)quinoline-8-carboxamide

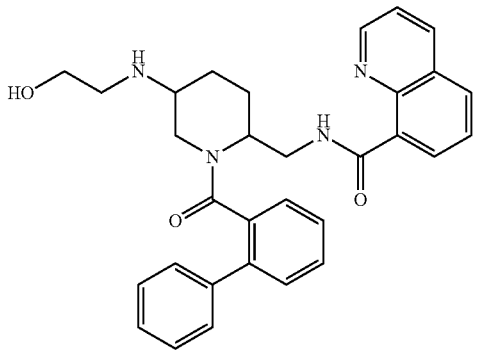 [SMILES: O=C(NCC1CCC(NCCO)CN1C(=O)c1ccccc1-c1ccccc1)c1cccc2cccnc12]

N-((1-(biphenylcarbonyl)-5-(2-hydroxyethylamino)piperidin-2-yl)methyl)quinoline-8-carboxamide was prepared according general procedure N using N-((1-(biphenylcarbonyl)-5-oxopiperidin-2-yl)methyl)quinoline-8-carboxamide and 2-aminoethanol. (ESI) 509 (M+H).

Example 43 rac-N-((5-acetamido-1-(biphenylcarbonyl)piperidin-2-yl)methyl)quinoline-8-carboxamide

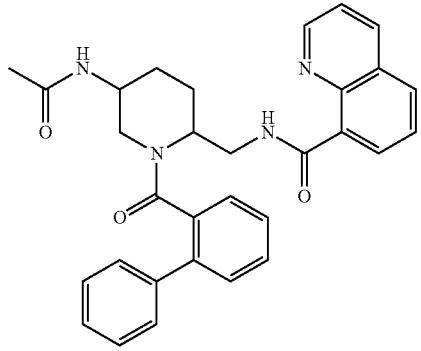 [SMILES: CC(=O)NC1CCC(CNC(=O)c2cccc3cccnc23)N(C(=O)c2ccccc2-c2ccccc2)C1]

Example 43 was isolated as a byproduct from the preparation of Example 39. (ESI) 507 (M+H).

Example 44 rac-N-((5-amino-1-(2-methyl-4-phenylthiazole-5-carbonyl)piperidin-2-yl)methyl)quinoline-8-carboxamide

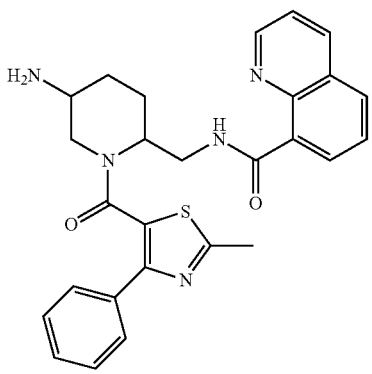

N-((5-amino-1-(2-methyl-4-phenylthiazole-5-carbonyl)piperidin-2-yl)methyl)quinoline-8-carboxamide was prepared according to general procedure N using N-((1-(2-methyl-4-phenylthiazole-5-carbonyl)-5-oxopiperidin-2-yl)methyl)quinoline-8-carboxamide. (ESI) 486 (M+H).

Example 45 rac-N-((1-(2-methyl-4-phenylthiazole-5-carbonyl)-5-(methylamino)piperidin-2-yl)methyl)quinoline-8-carboxamide

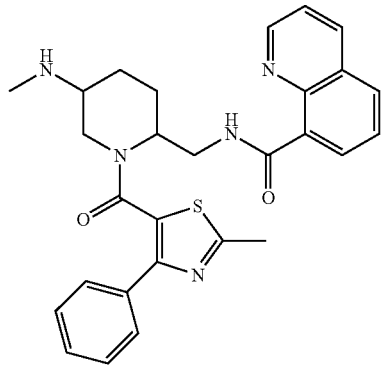 [SMILES: CNC1CCC(CNC(=O)c2cccc3cccnc23)N(C(=O)c2sc(C)nc2-c2ccccc2)C1]

N-((1-(2-methyl-4-phenylthiazole-5-carbonyl)-5-(methylamino)piperidin-2-yl)methyl)quinoline-8-carboxamide was prepared according to general procedure N using N-((1-(2-methyl-4-phenylthiazole-5-carbonyl)-5-oxopiperidin-2-yl)methyl)quinoline-8-carboxamide and methyl amine. (ESI) 500 (M+H).

Example 46 rac-N-((5-(ethylamino)-1-(2-methyl-4-phenylthiazole-5-carbonyl)piperidin-2-yl)methyl)quinoline-8-carboxamide

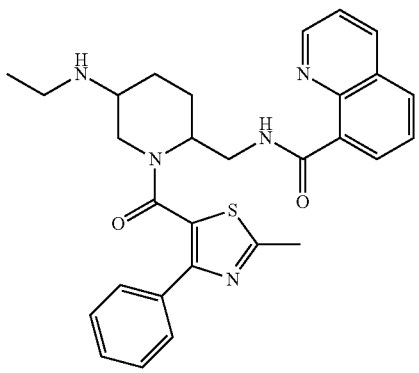 [SMILES: CCNC1CCC(CNC(=O)c2cccc3cccnc23)N(C(=O)c2sc(C)nc2-c2ccccc2)C1]

N-((5-(ethylamino)-1-(2-methyl-4-phenylthiazole-5-carbonyl)piperidin-2-yl)methyl)quinoline-8-carboxamide was prepared according to general procedure N using N-((1-(2-methyl-4-phenylthiazole-5-carbonyl)-5-oxopiperidin-2-yl)methyl)quinoline-8-carboxamide and ethyl amine. (ESI) 514 (M+H).

Example 47 rac-N-((5-(2-hydroxyethylamino)-1-(2-methyl-4-phenylthiazole-5-carbonyl)piperidin-2-yl)methyl)quinoline-8-carboxamide

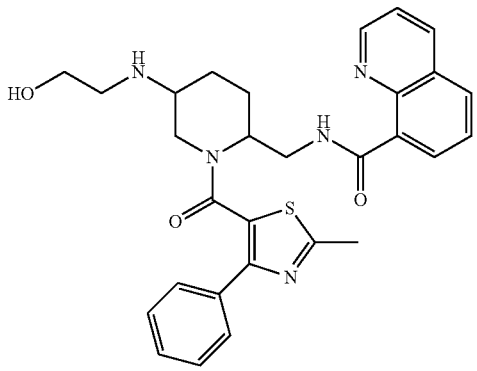 [SMILES: Cc1nc(-c2ccccc2)c(C(=O)N2CC(NCCO)CCC2CNC(=O)c2cccc3cccnc23)s1]

N-((5-(2-hydroxyethylamino)-1-(2-methyl-4-phenylthiazole-5-carbonyl)piperidin-2-yl)methyl)quinoline-8-carboxamide was prepared according to general procedure N using N-((1-(2-methyl-4-phenylthiazole-5-carbonyl)-5-oxopiperidin-2-yl)methyl)quinoline-8-carboxamide and 2-aminoethanol. (ESI) 530 (M+H).

Example 48 rac-N-((5-(isopropylamino)-1-(2-methyl-4-phenylthiazole-5-carbonyl)piperidin-2-yl)methyl)quinoline-8-carboxamide

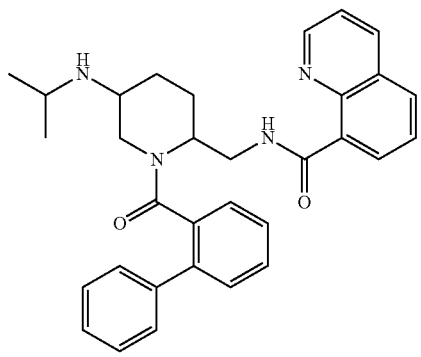 [SMILES: CC(C)NC1CCC(CNC(=O)c2cccc3cccnc23)N(C(=O)c2ccccc2-c2ccccc2)C1]

N-((5-(isopropylamino)-1-(2-methyl-4-phenylthiazole-5-carbonyl)piperidin-2-yl)methyl)quinoline-8-carboxamide was prepared according to general procedure N using N-((1-(2-methyl-4-phenylthiazole-5-carbonyl)-5-oxopiperidin-2-yl)methyl)quinoline-8-carboxamide and isopropyl amine. (ESI) 528 (M+H).

Example 49 rac-N-((1-(biphenylcarbonyl)-5-(methylamino)piperidin-2-yl)methyl)quinoline-8-carboxamide

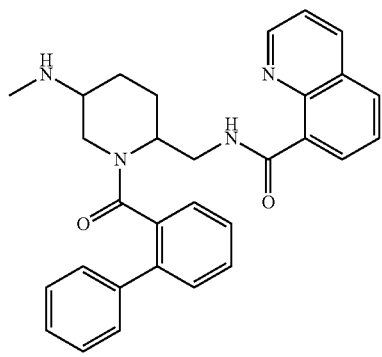

N-((1-(biphenylcarbonyl)-5-(methylamino)piperidin-2-yl)methyl)quinoline-8-carboxamide was prepared according to general procedure N using N-((1-(biphenylcarbonyl)-5-oxopiperidin-2-yl)methyl)quinoline-8-carboxamide and methyl amine. (ESI) 479 (M+H).

Example 50 rac-N-((1-(5-(3-fluorophenyl)-2-methylthiazole-4-carbonyl)-5-methoxypiperidin-2-yl)methyl)quinoline-8-carboxamide

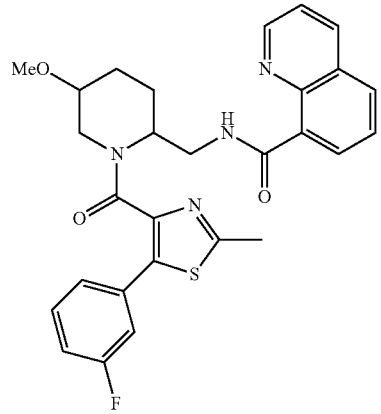 [SMILES: COC1CCC(CNC(=O)c2cccc3cccnc23)N(C(=O)c2nc(C)sc2-c2cccc(F)c2)C1]

Part I: rac-Methyl 1-(5-(3-fluorophenyl)-2-methylthiazole-4-carbonyl)-5,5-dimethoxypiperidine-2-carboxylate

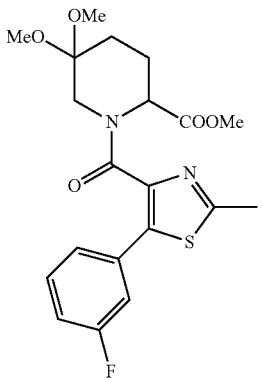 [SMILES: COC(=O)C1CCC(OC)(OC)CN1C(=O)c1nc(C)sc1-c1cccc(F)c1]

Methyl 1-(5-(3-fluorophenyl)-2-methylthiazole-4-carbonyl)-5,5-dimethoxypiperidine-2-carboxylate was prepared according to general procedure A using product methyl 5,5-dimethoxypiperidine-2-carboxylate and 5-(3-fluorophenyl)-2-methylthiazole-4-carboxylic acid.

Part II: rac-Methyl 1-(5-(3-fluorophenyl)-2-methylthiazole-4-carbonyl)-5-oxopiperidine-2-carboxylate

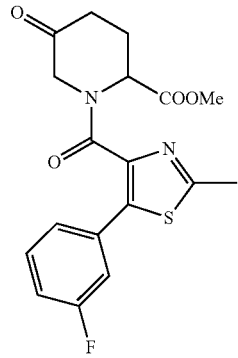 [SMILES: COC(=O)C1CCC(=O)CN1C(=O)c1nc(C)sc1-c1cccc(F)c1]

The title compound was prepared from the product of Part I above using TFA/CH$_2$Cl$_2$.

Part III: rac-Methyl 1-(5-(3-fluorophenyl)-2-methyl-thiazole-4-carbonyl)-5-hydroxypiperidine-2-carboxylate

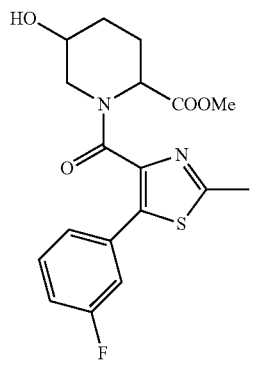 [SMILES: COC(=O)C1CCC(O)CN1C(=O)c1nc(C)sc1-c1cccc(F)c1]

Methyl 1-(5-(3-fluorophenyl)-2-methylthiazole-4-carbonyl)-5-hydroxypiperidine-2-carboxylate was prepared according to general procedure K using methyl 1-(5-(3-fluorophenyl)-2-methylthiazole-4-carbonyl)-5-oxopiperidine-2-carboxylate.

Part IV: rac-Methyl 1-(5-(3-fluorophenyl)-2-methyl-thiazole-4-carbonyl)-5-methoxypiperidine-2-carboxylate

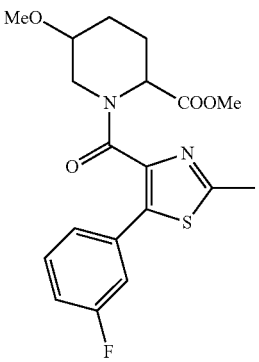 [SMILES: COC(=O)C1CCC(OC)CN1C(=O)c1nc(C)sc1-c1cccc(F)c1]

MeI (6.8 mmol, 0.43 mL) was added to a mixture of methyl 1-(5-(3-fluorophenyl)-2-methylthiazole-4-carbonyl)-5-hydroxypiperidine-2-carboxylate (0.68 mmol, 0.26 g) and Ag$_2$O (3.4 mmol, 0.8 g) in CH$_3$CN (3 mL) at room temperature. The resulting mixture was stirred at room temperature for two days. The reaction mixture was diluted with DCM and filtered through a pad of celite. The filtrate was concentrated in vacuo to give desired product methyl 1-(5-(3-fluorophenyl)-2-methylthiazole-4-carbonyl)-5-methoxypiperidine-2-carboxylate which was used for next step without further purification (Y: 96%).

Part V: rac-(5-(3-Fluorophenyl)-2-methylthiazol-4-yl)(2-(hydroxymethyl)-5-methoxypiperidin-1-yl)methanone

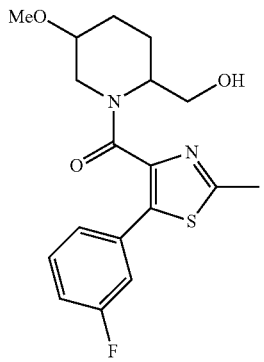 [SMILES: COC1CCC(CO)N(C(=O)c2nc(C)sc2-c2cccc(F)c2)C1]

The title compound was prepared from the product of Part IV following the same general protocol as described for Example 32 Part IV.

Part VI: rac-2-((1-(5-(3-Fluorophenyl)-2-methylthi-azole-4-carbonyl)-5-methoxypiperidin-2-yl)methyl)isoindoline-1,3-dione

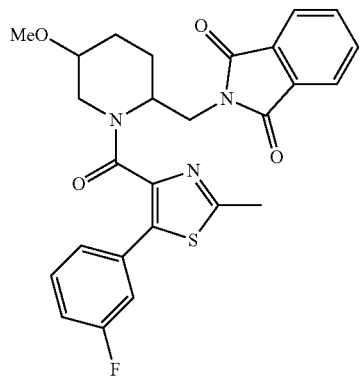 [SMILES: COC1CCC(CN2C(=O)c3ccccc3C2=O)N(C(=O)c2nc(C)sc2-c2cccc(F)c2)C1]

2-((1-(5-(3-Fluorophenyl)-2-methylthiazole-4-carbonyl)-5-methoxypiperidin-2-yl)methyl)isoindoline-1,3-dione was prepared according to general procedure I using (5-(3-fluorophenyl)-2-methylthiazol-4-yl)(2-(hydroxymethyl)-5-methoxypiperidin-1-yl)methanone and phthalimide.

Part VII: rac-(2-(Aminomethyl)-5-methoxypiperidin-1-yl)(5-(3-fluorophenyl)-2-methylthiazol-4-yl)methanone

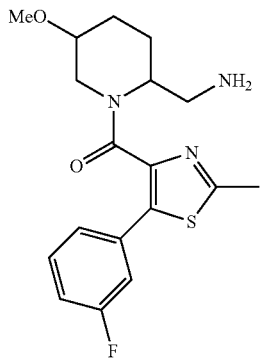 [SMILES: COC1CCC(CN)N(C(=O)c2nc(C)sc2-c2cccc(F)c2)C1]

(2-(Aminomethyl)-5-methoxypiperidin-1-yl)(5-(3-fluorophenyl)-2-methylthiazol-4-yl)methanone was prepared according to general procedure J using 2-((1-(5-(3-fluorophenyl)-2-methylthiazole-4-carbonyl)-5-methoxypiperidin-2-yl)methyl)isoindoline-1,3-dione. (ESI) 364 (M+H).

rac-N-((1-(5-(3-fluorophenyl)-2-methylthiazole-4-carbonyl)-5-methoxypiperidin-2-yl)methyl)quinoline-8-carboxamide The title compound was prepared according to general procedure A using (2-(aminomethyl)-5-methoxypiperidin-1-yl)(5-(3-fluorophenyl)-2-methylthiazol-4-yl)methanone and quinoline-8-carboxylic acid. (ESI) 519 (M+H).

Example 51 rac-N-((1-(5-(3-fluorophenyl)-2-methylthiazole-4-carbonyl)-5-hydroxypiperidin-2-yl)methyl)quinoline-8-carboxamide

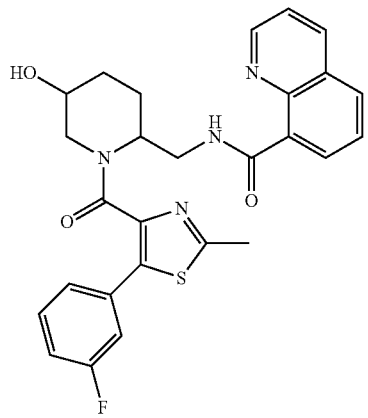 [SMILES: Cc1nc(C(=O)N2CC(O)CCC2CNC(=O)c2cccc3cccnc23)c(-c2cccc(F)c2)s1]

Part I: rac-N-((1-(5-(3-fluorophenyl)-2-methylthiazole-4-carbonyl)-5-oxopiperidin-2-yl)methyl)quinoline-8-carboxamide

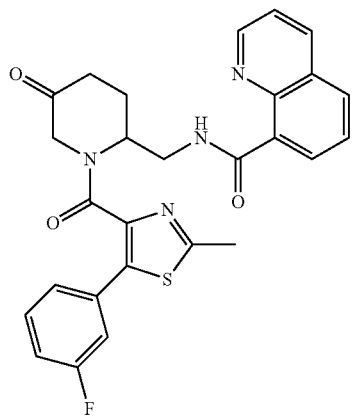 [SMILES: Cc1nc(C(=O)N2CC(=O)CCC2CNC(=O)c2cccc3cccnc23)c(-c2cccc(F)c2)s1]

N-((1-(5-(3-fluorophenyl)-2-methylthiazole-4-carbonyl)-5-oxopiperidin-2-yl)methyl)quinoline-8-carboxamide was prepared in a similar fashion as N-((1-(2-methyl-4-phenylthiazole-5-carbonyl)-5-oxopiperidin-2-yl)methyl)quinoline-8-carboxamide.

rac-N-((1-(5-(3-fluorophenyl)-2-methylthiazole-4-carbonyl)-5-hydroxypiperidin-2-yl)methyl)quinoline-8-carboxamide The title compound was prepared according to general procedure K using N-((1-(5-(3-fluorophenyl)-2-methylthiazole-4-carbonyl)-5-oxopiperidin-2-yl)methyl)quinoline-8-carboxamide. (ESI) 505 (M+H).

Example 52 rac-N-((5,5-difluoro-1-(5-(3-fluorophenyl)-2-methylthiazole-4-carbonyl)piperidin-2-yl)methyl)quinoline-8-carboxamide

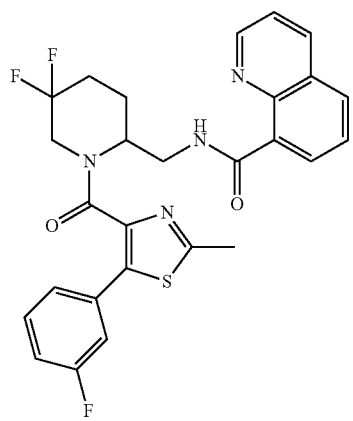 [SMILES: Cc1nc(C(=O)N2CC(F)(F)CCC2CNC(=O)c2cccc3cccnc23)c(-c2cccc(F)c2)s1]

N-((5,5-difluoro-1-(5-(3-fluorophenyl)-2-methylthiazole-4-carbonyl)piperidin-2-yl)methyl)quinoline-8-carboxamide was prepared according to general procedure L using N-((1-(5-(3-fluorophenyl)-2-methylthiazole-4-carbonyl)-5-oxopiperidin-2-yl)methyl)quinoline-8-carboxamide. (ESI) 525 (M+H).

Example 53 rac-N-((5-amino-1-(5-(3-fluorophenyl)-2-methylthiazole-4-carbonyl)piperidin-2-yl)methyl)quinoline-8-carboxamide

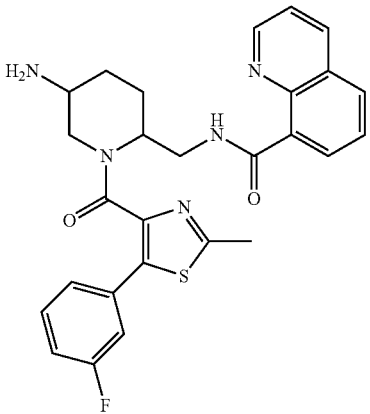 [SMILES: Cc1nc(C(=O)N2CC(N)CCC2CNC(=O)c2cccc3cccnc23)c(-c2cccc(F)c2)s1]

N-((5-amino-1-(5-(3-fluorophenyl)-2-methylthiazole-4-carbonyl)piperidin-2-yl)methyl)quinoline-8-carboxamide was prepared according to general procedure N using N-((1-(5-(3-fluorophenyl)-2-methylthiazole-4-carbonyl)-5-oxopiperidin-2-yl)methyl)quinoline-8-carboxamide. (ESI) 504 (M+H).

Example 54 rac-N-((1-(5-(3-fluorophenyl)-2-methylthiazole-4-carbonyl)-5-(2-hydroxyethylamino)piperidin-2-yl)methyl)quinoline-8-carboxamide

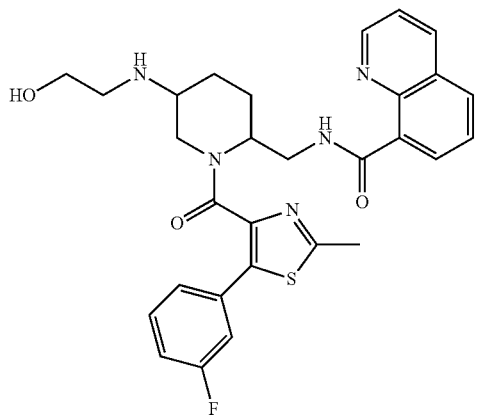

N-((1-(5-(3-fluorophenyl)-2-methylthiazole-4-carbonyl)-5-(2-hydroxyethylamino)piperidin-2-yl)methyl)quinoline-8-carboxamide was prepared according to general procedure N using N-((1-(5-(3-fluorophenyl)-2-methylthiazole-4-carbonyl)-5-oxopiperidin-2-yl)methyl)quinoline-8-carboxamide. (ESI) 548 (M+H).

Example 55 rac-N-((5-amino-1-(2-methyl-5-phenylthiazole-4-carbonyl)piperidin-2-yl)methyl)quinoline-8-carboxamide

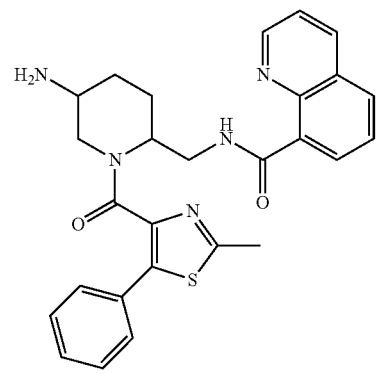 [SMILES: Cc1nc(C(=O)N2CC(N)CCC2CNC(=O)c2cccc3cccnc23)c(-c2ccccc2)s1]

N-((5-amino-1-(2-methyl-5-phenylthiazole-4-carbonyl)piperidin-2-yl)methyl)quinoline-8-carboxamide was prepared according to general procedure N using N-((1-(2-methyl-5-phenylthiazole-4-carbonyl)-5-oxopiperidin-2-yl)methyl)quinoline-8-carboxamide which was obtained in a similar fashion as N-((1-(2-methyl-4-phenylthiazole-5-carbonyl)-5-oxopiperidin-2-yl)methyl)quinoline-8-carboxamide and NH$_4$OAC. (ESI) 486 (M+H).

Example 56 rac-N-((5,5-difluoro-1-(2-methyl-5-phenylthiazole-4-carbonyl)piperidin-2-yl)methyl)quinoline-8-carboxamide

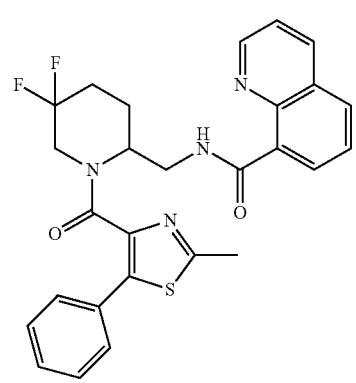 [SMILES: Cc1nc(C(=O)N2CC(F)(F)CCC2CNC(=O)c2cccc3cccnc23)c(-c2ccccc2)s1]

N-((5,5-difluoro-1-(2-methyl-5-phenylthiazole-4-carbonyl)piperidin-2-yl)methyl)quinoline-8-carboxamide was prepared according to general procedure L using N-((1-(2-methyl-5-phenylthiazole-4-carbonyl)-5-oxopiperidin-2-yl)methyl)quinoline-8-carboxamide. (ESI) 507 (M+H).

Example 57 rac-N-((5,5-difluoro-1-(5-(4-fluorophenyl)-2-methylthiazole-4-carbonyl)piperidin-2-yl)methyl)-2-methylbenzofuran-4-carboxamide

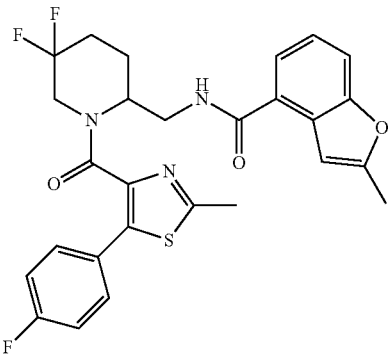 [SMILES: Cc1cc2c(C(=O)NCC3CCC(F)(F)CN3C(=O)c3nc(C)sc3-c3ccc(F)cc3)cccc2o1]

Part I: rac-Ethyl 5,5-diethoxypiperidine-2-carboxylate

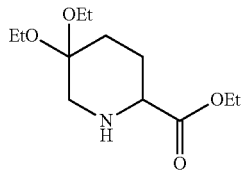 [SMILES: CCOC(=O)C1CCC(OCC)(OCC)CN1]

Ethyl 5,5-diethoxypiperidine-2-carboxylate was prepared according following the same general protocol as described in Example 32 Part I using 5-oxopiperidine-2-carboxylic acid and EtOH. $^1$H NMR (CDCl$_3$, 400 MHz) δ 4.22-4.17 (m, 2H), 3.74-3.42 (m, 4H), 3.82-3.35 (m, 1H), 3.23-3.13 (m, 1H), 2.62 (d, 1H), 2.10-2.05 (m, 1H), 1.98-1.93 (m, 1H), 1.92 (brs, 1H), 1.69-1.56 (m, 2H), 1.30-1.27 (m, 3H), 1.23-1.16 (m, 6H).

Part II: rac-(5,5-Diethoxypiperidin-2-yl)methanol

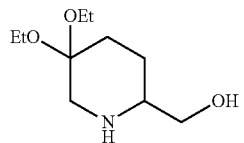 [SMILES: CCOC1(OCC)CCC(CO)NC1]

General Procedure O: LAH Reduction of Amino Ester to Amino Alcohol

A suspension of LAH (0.47 g, 12.25 mmol) in anhydrous THF (5 mL) was added a solution of ethyl 5,5-diethoxypiperidine-2-carboxylate (0.6 g, 2.45 mmol) in anhydrous THF (5 mL) dropwise at room temperature. The resulting mixture was refluxed at 70° C. for overnight. The reaction mixture was cooled down to 0° C. and quenched sequentially with water (0.47 g), 15% NaOH (0.47 g) and water (1.41 g). The resulting suspension was stirred at room temperature for 1 hr and filtered. The filtrate was concentrated in vacuo to give desired (5,5-diethoxypiperidin-2-yl)methanol in 95% yield as colorless oil. $^1$H NMR (CDCl$_3$, 400 MHz) δ 3.54-3.32 (m, 6H), 3.11-3.04 (m, 1H), 2.56-2.46 (m, 2H), 2.05-2.00 (m, 1H), 1.52-1.23 (m, 3H), 1.15-1.07 (m, 6H).

Part III: rac-(5,5-Diethoxy-2-(hydroxymethyl)piperidin-1-yl)(5-(4-fluorophenyl)-2-methylthiazol-4-yl)methanone

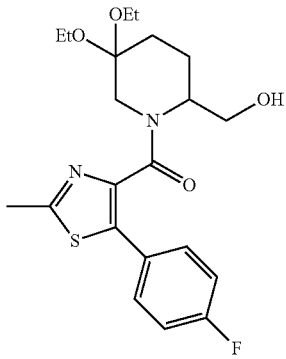 [SMILES: CCOC1(OCC)CCC(CO)N(C(=O)c2nc(C)sc2-c2ccc(F)cc2)C1]

(5,5-Diethoxy-2-(hydroxymethyl)piperidin-1-yl)(5-(4-fluorophenyl)-2-methylthiazol-4-yl)methanone was prepared according to general procedure A using 5-(4-fluorophenyl)-2-methylthiazole-4-carboxylic acid and (5,5-diethoxypiperidin-2-yl)methanol.

Part IV: rac-2-((5,5-Diethoxy-1-(5-(4-fluorophenyl)-2-methylthiazole-4-carbonyl)piperidin-2-yl)methyl)isoindoline-1,3-dione

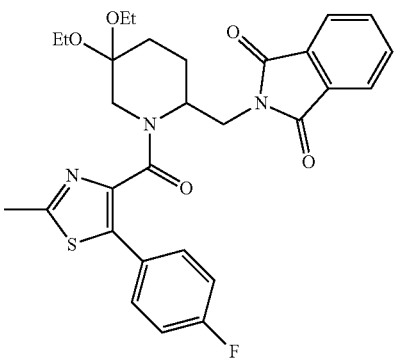 [SMILES: CCOC1(OCC)CCC(CN2C(=O)c3ccccc3C2=O)N(C(=O)c2nc(C)sc2-c2ccc(F)cc2)C1]

2-((5,5-Diethoxy-1-(5-(4-fluorophenyl)-2-methylthiazole-4-carbonyl)piperidin-2-yl)methyl)isoindoline-1,3-dione was prepared according to general procedure I using (5,5-diethoxy-2-(hydroxymethyl)piperidin-1-yl)(5-(4-fluorophenyl)-2-methylthiazol-4-yl)methanone. $^1$H NMR (CDCl$_3$, 400 MHz) δ 7.73-7.71 (m, 2H), 7.63-7.62 (m, 2H), 7.38-7.35 (m, 2H), 7.21-6.91 (m, 2H), 4.86-4.81 (m, 1H), 4.10-4.03 (m, 2H), 3.10 (d, 1H), 2.27 (s, 3H), 1.89-1.83 (m, 1H), 1.70-1.61 (m, 1H), 1.32-1.28 (m, 2H), 1.19-1.03 (m, 6H). MS (ESI) 506 (M+H): desired product lost EtOH in LC/MS.

Part V: rac-2-((1-(5-(4-fluorophenyl)-2-methylthiazole-4-carbonyl)-5-oxopiperidin-2-yl)methyl)isoindoline-1,3-dione

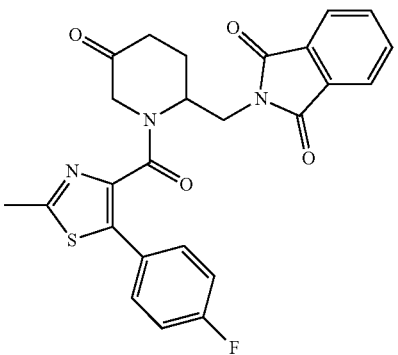 [SMILES: Cc1nc(C(=O)N2CC(=O)CCC2CN2C(=O)c3ccccc3C2=O)c(-c2ccc(F)cc2)s1]

The title compound was prepared from the product of Part IV above using TFA/CH$_2$Cl$_2$. NMR reported as a mixture of two possible rotamers. $^1$H NMR (CDCl$_3$, 400 MHz) δ 7.83-7.80 (m, 2H), 7.79-7.74 (m, 2H), 7.43-7.40 (m, 1H), 7.37-7.28 (m, 1H), 7.01-6.97 (m, 1H), 6.88-6.84 (m, 1H), 5.25-5.07 (m, 1H), 4.31-3.53 (m, 4H), 2.64 (s, 1.3H), 2.47 (s, 1.7H), 2.45-2.31 (m, 2H), 2.19-1.63 (m, 2H). MS (ESI) 478 (M+H).

215

Part VI: rac-2-((5,5-Difluoro-1-(5-(4-fluorophenyl)-2-methylthiazole-4-carbonyl)piperidin-2-yl)methyl)isoindoline-1,3-dione

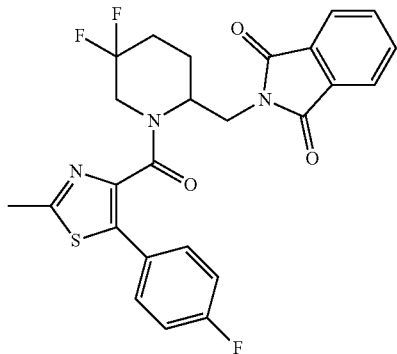 [SMILES: Cc1nc(C(=O)N2CC(F)(F)CCC2CN2C(=O)c3ccccc3C2=O)c(-c2ccc(F)cc2)s1]

2-((5,5-Difluoro-1-(5-(4-fluorophenyl)-2-methylthiazole-4-carbonyl)piperidin-2-yl)methyl)isoindoline-1,3-dione was prepared according to general procedure L using 2-((1-(5-(4-fluorophenyl)-2-methylthiazole-4-carbonyl)-5-oxopiperidin-2-yl)methyl)isoindoline-1,3-dione. MS (ESI) 500 (M+H).

Part VII: rac-(2-(aminomethyl)-5,5-difluoropiperidin-1-yl)(5-(4-fluorophenyl)-2-methylthiazol-4-yl)methanone

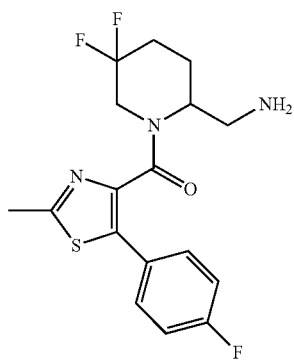 [SMILES: Cc1nc(C(=O)N2CC(F)(F)CCC2CN)c(-c2ccc(F)cc2)s1]

N-((5,5-difluoro-1-(2-methyl-5-phenylthiazole-4-carbonyl)piperidin-2-yl)methyl)-2-methylbenzofuran-4-carboxamide was prepared according to general procedure J using 2-((5,5-Difluoro-1-(5-(4-fluorophenyl)-2-methylthiazole-4-carbonyl)piperidin-2-yl)methyl)isoindoline-1,3-dione. MS (ESI) 370 (M+H).

N-((5,5-difluoro-1-(5-(4-fluorophenyl)-2-methylthiazole-4-carbonyl)piperidin-2-yl)methyl)-2-methylbenzofuran-4-carboxamide was prepared according to general procedure A using N-((5,5-difluoro-1-(2-methyl-5-phenylthiazole-4-carbonyl)piperidin-2-yl)methyl)-2-methylbenzofuran-4-carboxamide and 2-methylbenzofuran-4-carboxylic acid. The NMR was reported as a mixture of possible rotamers. $^1$H NMR (MeOH-d4, 400 MHz) δ 7.61-7.54 (m, 2H), 7.49-7.29 (m, 2H), 7.29-7.25 (m, 1H), 7.05-7.01 (m, 2H), 6.88-6.83 (m, 1H), 4.19-4.17 (m, 1H), 3.86-3.70 (m, 2H), 3.50-3.35 (m, 2H), 2.50-2.48 (m, 3H), 2.25 (s, 3H), 2.10-1.99 (m, 2H), 1.69-1.65 (m, 1H), 1.33-1.25 (m, 1H). MS (ESI) 528 (M+H).

216

Example 58 rac-N-((1-(5-(4-fluorophenyl)-2-methylthiazole-4-carbonyl)-6-methylpiperidin-2-yl)methyl)benzofuran-4-carboxamide

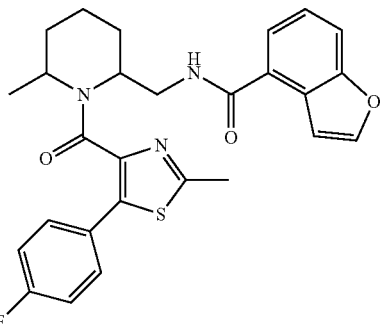

Part I: rac-tert-Butyl (6-methylpiperidin-2-yl)methylcarbamate

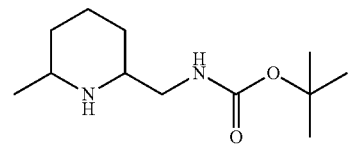 [SMILES: CC1CCCC(CNC(=O)OC(C)(C)C)N1]

Nishimura catalyst (0.53 g) was added to a solution of tert-butyl (6-methylpyridin-2-yl)methylcarbamate (4.4 g, 0.02 mmol) in MeOH (60 mL) in a Parr Shaker high pressure vessel which was installed on Parr Shaker. The vessel was shaken under constant 5 bar hydrogen pressure for 30 min. The reaction mixture was filtered through a pad of celite and the filtrate was concentrated in vacuo to give desired product tert-butyl (6-methylpiperidin-2-yl)methylcarbamate which was used for next step without further purification. $^1$H NMR (CDCl$_3$, 400 MHz) δ 3.20-3.17 (m, 1H), 3.01-2.96 (m, 1H), 2.72-2.64 (m, 2H), 1.82-1.77 (m, 1H), 1.63-1.54 (m, 2H), 1.49 (s, 9H), 1.39-1.35 (m, 2H), 1.12-0.99 (m, 5H).

Part II: rac-tert-Butyl (1-(5-(4-fluorophenyl)-2-methylthiazole-4-carbonyl)-6-methylpiperidin-2-yl)methylcarbamate

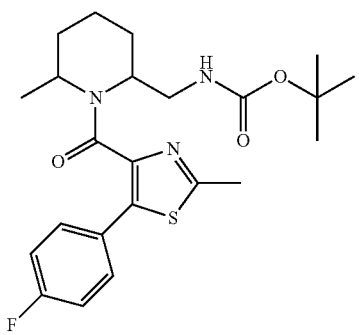 [SMILES: Cc1nc(C(=O)N2C(C)CCCC2CNC(=O)OC(C)(C)C)c(-c2ccc(F)cc2)s1]

tert-Butyl (1-(5-(4-fluorophenyl)-2-methylthiazole-4-carbonyl)-6-methylpiperidin-2-yl)methylcarbamate was prepared according to general procedure A using tert-butyl (6-methylpiperidin-2-yl)methylcarbamate and 5-(4-fluorophenyl)-2-methylthiazole-4-carboxylic acid.

Part III: rac-(2-(Aminomethyl)-6-methylpiperidin-1-yl)(5-(4-fluorophenyl)-2-methylthiazol-4-yl)methanone

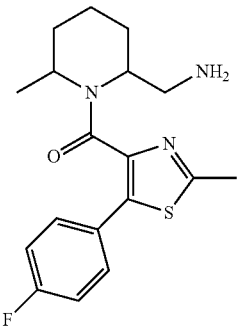 [SMILES: Cc1nc(C(=O)N2C(C)CCCC2CN)c(-c2ccc(F)cc2)s1]

To a solution of tert-Butyl (1-(5-(4-fluorophenyl)-2-methylthiazole-4-carbonyl)-6-methylpiperidin-2-yl)methylcarbamate in DCM was added TFA. The solution was aged at room temperature until starting material was consumed as judged by reverse phase analytical HPLC analysis. The solution was then concentrated in vacuo to give the TFA salt of the title compound as an oil which was used without further purification. MS (ESI) 348 (M+H).

rac-N-((1-(5-(4-fluorophenyl)-2-methylthiazole-4-carbonyl)-6-methylpiperidin-2-yl)methyl)benzofuran-4-carboxamide The title compound was prepared by following the general procedure A using 2-(aminomethyl)-6-methylpiperidin-1-yl)(5-(4-fluorophenyl)-2-methylthiazol-4-yl)methanone and benzofuran-4-carboxylic acid. MS (ESI) 492 (M+H).

Example 59 rac-N-((1-(5-(4-fluorophenyl)-2-methylthiazole-4-carbonyl)-6-methylpiperidin-2-yl)methyl)quinoline-8-carboxamide

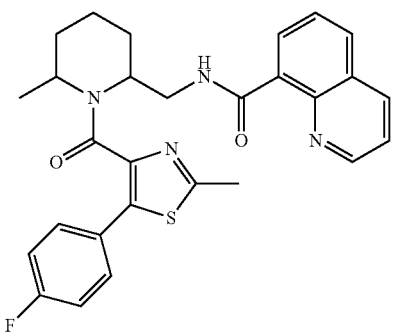 [SMILES: Cc1nc(C(=O)N2C(C)CCCC2CNC(=O)c2cccc3cccnc23)c(-c2ccc(F)cc2)s1]

N-((1-(5-(4-fluorophenyl)-2-methylthiazole-4-carbonyl)-6-methylpiperidin-2-yl)methyl)quinoline-8-carboxamide was prepared according to general procedure A using 2-(aminomethyl)-6-methylpiperidin-1-yl)(5-(4-fluorophenyl)-2-methylthiazol-4-yl)methanone and quinoline-8-carboxylic acid. MS (ESI) 503 (M+H).

Example 60 rac-3-Fluoro-N-((1-(5-(4-fluorophenyl)-2-methylthiazole-4-carbonyl)-6-methylpiperidin-2-yl)methyl)-2-methoxybenz amide

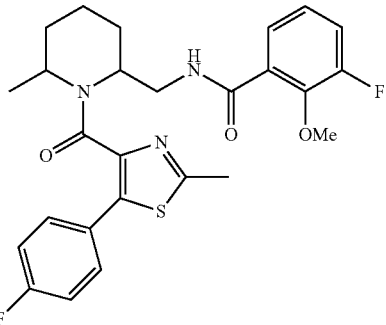

3-Fluoro-N-((1-(5-(4-fluorophenyl)-2-methylthiazole-4-carbonyl)-6-methylpiperidin-2-yl)methyl)-2-methoxybenzamide was prepared according to general procedure A using 2-(aminomethyl)-6-methylpiperidin-1-yl)(5-(4-fluorophenyl)-2-methylthiazol-4-yl)methanone and 3-fluoro-2-methoxybenzoic acid. MS (ESI) 500 (M+H).

Example 61 rac-N-((1-(5-(4-fluorophenyl)-2-methylthiazole-4-carbonyl)-6-methylpiperidin-2-yl)methyl)-2-methylbenzofuran-4-carboxamide

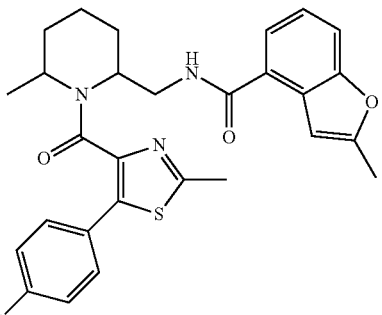

N-((1-(5-(4-fluorophenyl)-2-methylthiazole-4-carbonyl)-6-methylpiperidin-2-yl)methyl)-2-methylbenzofuran-4-carboxamide was prepared according to general procedure A using 2-methylbenzofuran-4-carboxylic acid and (2-(aminomethyl)-6-methylpiperidin-1-yl)(5-(4-fluorophenyl)-2-methylthiazol-4-yl)methanone which was obtained by removal of the BOC protecting group from tert-butyl (1-(5-(4-fluorophenyl)-2-methylthiazole-4-carbonyl)-6-methylpiperidin-2-yl)methylcarbamate following general procedure as described for Example 58. MS (ESI) 506 (M+H).

Example 62 rac-N-(((2S,3R)-3-methyl-1-(2-methyl-5-phenylthiazole-4-carbonyl)piperidin-2-yl)methyl)benzofuran-4-carboxamide

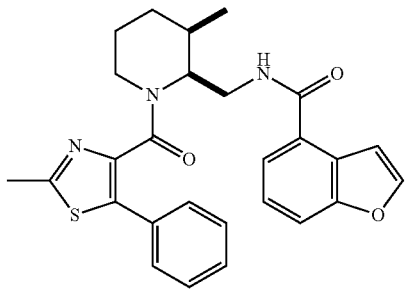 [SMILES: Cc1nc(C(=O)N2CCC[C@@H](C)[C@H]2CNC(=O)c2cccc3occc23)c(-c2ccccc2)s1]

The title compound was obtained following the general protocol as described for the synthesis of Example 8 using benzofuran-4-carboxylic acid. MS (ESI) 474.1 (M+H).

Example 63 rac-N-(((2S,3R)-1-(5-(4-fluorophenyl)-2-methylthiazole-4-carbonyl)-3-methylpiperidin-2-yl)methyl)benzofuran-4-carboxamide

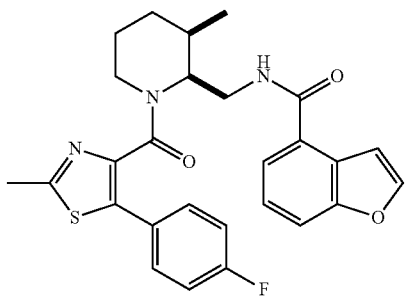 [SMILES: Cc1nc(C(=O)N2CCC[C@@H](C)[C@H]2CNC(=O)c2cccc3occc23)c(-c2ccc(F)cc2)s1]

The title compound was obtained following the general protocol as described for the synthesis of Example 8 using benzofuran-4-carboxylic acid and 5-(4-fluorophenyl)-2-methylthiazole-4-carboxylic acid. MS (ESI) 492.1 (M+H).

Example 64 and Example 65

Example 64 rac-N-(((1S,3aR,7aS)-2-(2-methyl-4-phenylthiazole-5-carbonyl)octahydro-1H-isoindol-1-yl)methyl)quinoline-8-carboxamide

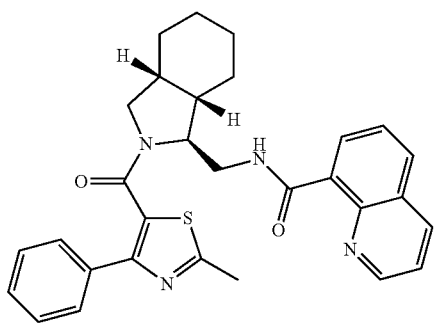 [SMILES: Cc1nc(-c2ccccc2)c(C(=O)N2C[C@@H]3CCCC[C@@H]3[C@H]2CNC(=O)c2cccc3cccnc23)s1]

Example 65 rac-N-(((1S,3aS,7aS)-2-(2-methyl-4-phenylthiazole-5-carbonyl)octahydro-1H-isoindol-1-yl)methyl)quinoline-8-carboxamide

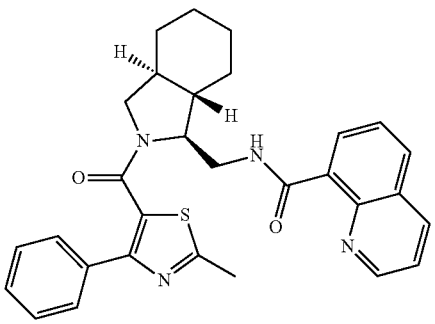 [SMILES: Cc1nc(-c2ccccc2)c(C(=O)N2C[C@H]3CCCC[C@@H]3[C@H]2CNC(=O)c2cccc3cccnc23)s1]

Part I: rac-(E)-ethyl 3-(2-(hydroxymethyl)cyclohexyl)acrylate

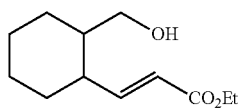

DIBAL-H (1M in toluene) (35.2 mmol, 35.2 mL) was added dropwise to a solution of hexahydroisobenzofuran-1(3H)-one (33.5 mol, 4.7 g) in anhydrous ether (100 mL) at −10° C. under argon. The resulting mixture was stirred at −10° C. for 30 min under argon and quenched with MeOH (30 mL). The mixture was stirred at room temperature for overnight and the resulting suspension was added saturated Rochelle's salt aqueous solution and stirred for additional 30 min at room temperature. The organic layer was separated and washed with saturated Rochelle's salt aqueous solution. The combined aqueous layer was extracted with ether (3x). The organic layer were combined, dried with dried with MgSO$_4$ and concentrated in vacuo to give lactol octahydroisobenzofuran-1-ol which was used for next step without further purification.

(Carbethoxymethylene)triphenylphosphorane (17.7 g, 50.7 mmol) was added to a solution of the above described octahydroisobenzofuran-1-ol in acetonitrile (100 mL) and the resulting mixture was refluxed at 85° C. overnight. Acetonitrile was removed in vacuo and the resulting residue was diluted with ether which was stirred at room temperature for 2 hr. The white precipitate was filtered off and washed with cold ether. All ether portion was combined and concentrated in vacuo to give crude product which was purified by chromatograph to afford desired (E)-ethyl 3-(2-(hydroxymethyl)cyclohexyl)acrylate as colorless oil (Y: 78.9% over two steps). $^1$H NMR (CDCl$_3$, 400 MHz) δ 7.12-7.05 (m, 1H), 5.80 (d, 1H), 4.15-4.09 (m, 2H), 3.40-3.37 (m, 2H), 2.63-2.59 (m, 1H), 1.80-1.29 (m, 9H), 1.25-1.19 (m, 3H).

Part II: rac-(E)-ethyl 3-(2-formylcyclohexyl)acrylate

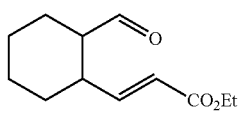

General Procedure P: Oxidation of Alcohol to Aldehyde Using PCC

A solution of (E)-ethyl 3-(2-(hydroxymethyl)cyclohexyl)acrylate (3.84 g, 18.1 mmol) in DCM (20 mL) was added to a suspension of PCC (5.86 g, 27.2 mmol) and celite (4.2 g) in DCM (40 mL). The resulting mixture was stirred under argon for 2 hr and filtered through a pad of silica which was rinsed with ether. The organic solvent was removed in vacuo to give desired product which was used for next step without further purification (Y: 85%). $^1$H NMR (CDCl$_3$, 400 MHz) δ 9.67 (s, 1H), 7.16-7.09 (m, 1H), 5.88 (d, 1H), 4.22-4.17 (m, 2H), 2.83-2.81 (m, 1H), 2.60-2.57 (m, 1H), 1.96-1.90 (m, 1H), 1.80-1.55 (m, 8H), 1.33-1.26 (m, 3H).

Part III: rac-Ethyl 2-(2-benzyloctahydro-1H-isoindol-1-yl)acetate

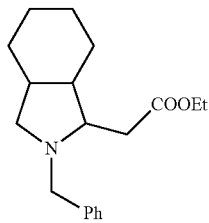 [SMILES: CCOC(=O)CC1C2CCCCC2CN1Cc1ccccc1]

A mixture of (E)-ethyl 3-(2-formylcyclohexyl)acrylate, benzyl amine and NaBH(OAc)$_3$ in DCM was stirred at room temperature for 3 hr. The reaction mixture was quenched with saturated NaHCO$_3$. The organic layer was separated and the aqueous layer was extracted with DCM (2 X). All organic layers were combined, dried with dried with MgSO$_4$ and concentrated in vacuo to give the crude product which was purified by chromatography to afford desired ethyl 2-(2-benzyloctahydro-1H-isoindol-1-yl)acetate. MS (ESI) 302 (M+H).

Part IV: rac-Ethyl 2-(octahydro-1H-isoindol-1-yl)acetate

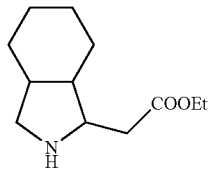 [SMILES: CCOC(=O)CC1NCC2CCCCC21]

Ethyl 2-(octahydro-1H-isoindol-1-yl)acetate was prepared following the same general protocol as described in Example 1 for debenzylation from ethyl 2-(2-benzyloctahydro-1H-isoindol-1-yl)acetate.

Part V: rac-Ethyl 2-(2-(2-methyl-4-phenylthiazole-5-carbonyl)octahydro-1H-isoindol-1-yl)acetate

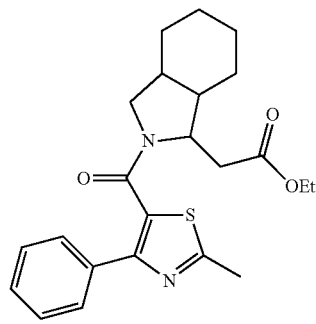 [SMILES: CCOC(=O)CC1C2CCCCC2CN1C(=O)c1sc(C)nc1-c1ccccc1]

Ethyl 2-(2-(2-methyl-4-phenylthiazole-5-carbonyl)octahydro-1H-isoindol-1-yl)acetate was prepared according general procedure A from ethyl 2-(octahydro-1H-isoindol-1-yl)acetate and 2-methyl-4-phenylthiazole-5-carboxylic acid.

Part VI: rac-2-(2-(2-methyl-4-phenylthiazole-5-carbonyl)octahydro-1H-isoindol-1-yl)acetic acid

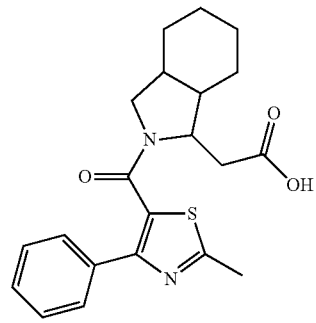 [SMILES: Cc1nc(-c2ccccc2)c(C(=O)N2CC3CCCCC3C2CC(=O)O)s1]

2-(2-(2-methyl-4-phenylthiazole-5-carbonyl)octahydro-1H-isoindol-1-yl)acetic acid was prepared according general procedure B from ethyl 2-(2-(2-methyl-4-phenylthiazole-5-carbonyl)octahydro-1H-isoindol-1-yl)acetate.

Part VII: rac-(1-(Aminomethyl)-1H-isoindol-2(3H,3aH,4H,5H,6H,7H,7aH)-yl)(2-methyl-4-phenylthiazol-5-yl)methanone

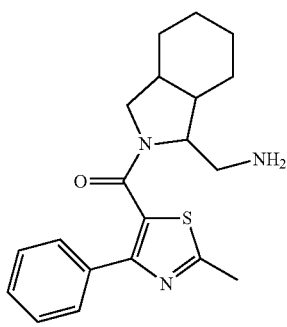 [SMILES: Cc1nc(-c2ccccc2)c(C(=O)N2CC3CCCCC3C2CN)s1]

(1-(aminomethyl)-1H-isoindol-2(3H,3aH,4H,5H,6H,7H,7aH)-yl)(2-methyl-4-phenylthiazol-5-yl)methanone was prepared according to general procedure G using 2-(2-(2-methyl-4-phenylthiazole-5-carbonyl)octahydro-1H-isoindol-1-yl)acetic acid.

The pair of stereo isomers Examples 64 and 65 were isolated by prep HPLC from the coupling reaction according general procedure A using (1-(aminomethyl)-1H-isoindol-2(3H,3aH,4H,5H,6H,7H,7aH)-yl)(2-methyl-4-phenylthiazol-5-yl)methanone and quinoline-8-carboxylic acid. The assignment of stereochemistry is not verified. MS (ESI) 511 (M+H).

Example 66 and Example 67

Example 66 rac-N-(((1S,3aR,7aS)-2-(biphenylcarbonyl)octahydro-1H-isoindol-1-yl)methyl)quinoline-8-carboxamide

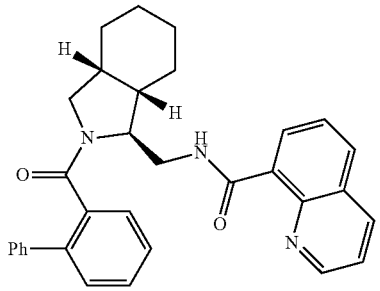 [SMILES: O=C(NC[C@@H]1[C@H]2CCCC[C@H]2CN1C(=O)c1ccccc1-c1ccccc1)c1cccc2cccnc12]

Example 67 rac-N-(((1S,3aS,7aS)-2-(biphenylcarbonyl)octahydro-1H-isoindol-1-yl)methyl)quinoline-8-carboxamide

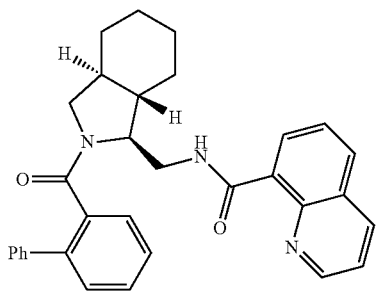 [SMILES: O=C(NC[C@@H]1[C@H]2CCCC[C@@H]2CN1C(=O)c1ccccc1-c1ccccc1)c1cccc2cccnc12]

Part I: rac-Ethyl 2-(2-(biphenylcarbonyl)octahydro-1H-isoindol-1-yl)acetate

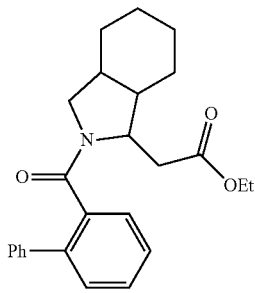 [SMILES: CCOC(=O)CC1C2CCCCC2CN1C(=O)c1ccccc1-c1ccccc1]

Ethyl 2-(2-(biphenylcarbonyl)octahydro-1H-isoindol-1-yl)acetate was prepared according to general procedure A using ethyl 2-(octahydro-1H-isoindol-1-yl)acetate and biphenyl-2-carboxylic acid.

Part II: rac-2-(2-(Biphenylcarbonyl)octahydro-1H-isoindol-1-yl)acetic acid

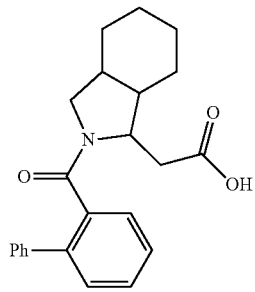

2-(2-(Biphenylcarbonyl)octahydro-1H-isoindol-1-yl)acetic acid was prepared by hydrolysis of ethyl 2-(2-(biphenylcarbonyl)octahydro-1H-isoindol-1-yl)acetate according to general procedure B.

Part III: rac-(1-(Aminomethyl)-1H-isoindol-2(3H,3aH,4H,5H,6H,7H,7aH)-yl)(biphenyl-2-yl)methanone

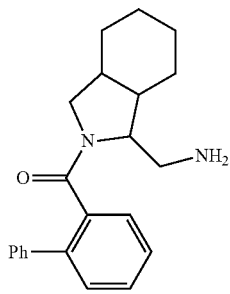 [SMILES: NCC1C2CCCCC2CN1C(=O)c1ccccc1-c1ccccc1]

(1-(Aminomethyl)-1H-isoindol-2(3H,3aH,4H,5H,6H,7H,7aH)-yl)(biphenyl-2-yl)methanone was prepared by following general procedure G using 2-(2-(biphenylcarbonyl)octahydro-1H-isoindol-1-yl)acetic acid.

The pair of stereo isomers Examples 66 and 67 were isolated by prep HPLC from the coupling reaction according general procedure A using (1-(aminomethyl)-1H-isoindol-2(3H,3aH,4H,5H,6H,7H,7aH)-yl)(biphenyl-2-yl)methanone and quinoline-8-carboxylic acid. The assignment of stereochemistry is not verified. MS (ESI) 335 (M+H).

Example 68 and Example 69

Example 68 rac-N-(((1S,3aR,7aS)-2-(2-methyl-5-phenylthiazole-4-carbonyl)octahydro-1H-isoindol-1-yl)methyl)quinoline-8-carboxamide

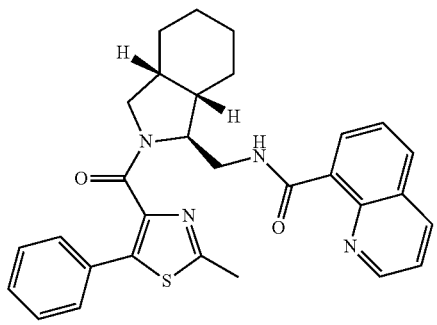 [SMILES: Cc1nc(C(=O)N2C[C@@H]3CCCC[C@@H]3[C@H]2CNC(=O)c2cccc3cccnc23)c(-c2ccccc2)s1]

Example 69 rac-N-(((1S,3aS,7aS)-2-(2-methyl-5-phenylthiazole-4-carbonyl)octahydro-1H-isoindol-1-yl)methyl)quinoline-8-carboxamide

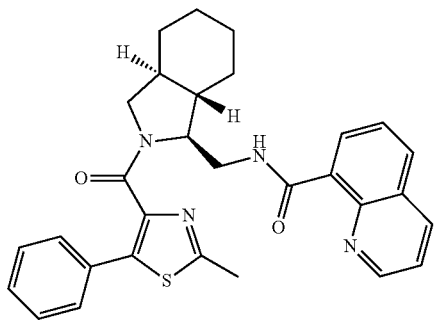 [SMILES: Cc1nc(C(=O)N2C[C@H]3CCCC[C@@H]3[C@H]2CNC(=O)c2cccc3cccnc23)c(-c2ccccc2)s1]

Part I: rac-Ethyl 2-(2-(2-methyl-5-phenylthiazole-4-carbonyl)octahydro-1H-isoindol-1-yl)acetate

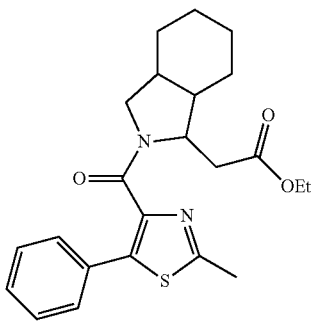 [SMILES: CCOC(=O)CC1C2CCCCC2CN1C(=O)c1nc(C)sc1-c1ccccc1]

Ethyl 2-(2-(2-methyl-5-phenylthiazole-4-carbonyl)octahydro-1H-isoindol-1-yl)acetate was prepared according to general procedure A using ethyl 2-(octahydro-1H-isoindol-1-yl)acetate and 2-methyl-5-phenylthiazole-4-carboxylic acid.

Part II: rac-2-(2-(2-Methyl-5-phenylthiazole-4-carbonyl)octahydro-1H-isoindol-1-yl)acetic acid

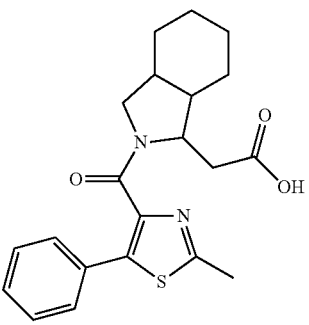 [SMILES: Cc1nc(C(=O)N2CC3CCCCC3C2CC(=O)O)c(-c2ccccc2)s1]

2-(2-(2-Methyl-5-phenylthiazole-4-carbonyl)octahydro-1H-isoindol-1-yl)acetic acid was prepared according to general procedure B using ethyl 2-(2-(2-methyl-5-phenylthiazole-4-carbonyl)octahydro-1H-isoindol-1-yl)acetate Part III: rac-(1-(Aminomethyl)-1H-isoindol-2(3H,3aH,4H,5H,6H,7H,7aH)-yl)(2-methyl-5-phenylthiazol-4-yl)methanone

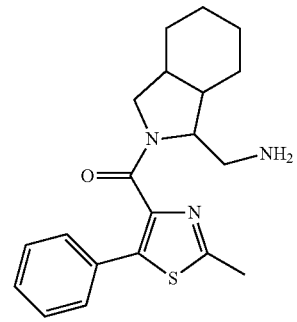 [SMILES: Cc1nc(C(=O)N2CC3CCCCC3C2CN)c(-c2ccccc2)s1]

(1-(Aminomethyl)-1H-isoindol-2(3H,3aH,4H,5H,6H,7H,7aH)-yl)(2-methyl-5-phenylthiazol-4-yl)methanone was prepared according to general procedure G using 2-(2-(2-methyl-5-phenylthiazole-4-carbonyl)octahydro-1H-isoindol-1-yl)acetic acid.

The pair of stereo isomers Examples 68 and 69 were isolated by prep HPLC from the coupling reaction according general procedure A (1-(aminomethyl)-1H-isoindol-2(3H,3aH,4H,5H,6H,7H,7aH)-yl)(2-methyl-5-phenylthiazol-4-yl)methanone and quinoline-8-carboxylic acid. The assignment of stereochemistry is not verified. MS (ESI) 511 (M+H).

Example 70 and Example 71

Example 70 rac-N-(((1S,3aR,7aS)-2-(2-methyl-5-phenylthiazole-4-carbonyl)octahydro-1H-isoindol-1-yl)methyl)benzofuran-4-carboxamide

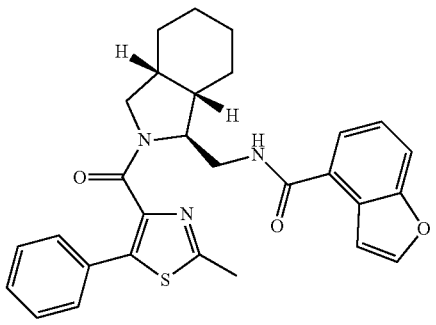 [SMILES: Cc1nc(C(=O)N2C[C@@H]3CCCC[C@@H]3[C@H]2CNC(=O)c2cccc3occc23)c(-c2ccccc2)s1]

Example 71 rac-N-(((1S,3aS,7aS)-2-(2-methyl-5-phenylthiazole-4-carbonyl)octahydro-1H-isoindol-1-yl)methyl)benzofuran-4-carboxamide

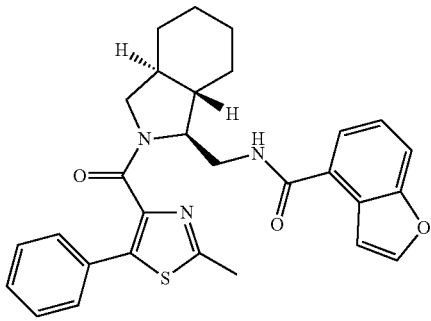 [SMILES: Cc1nc(C(=O)N2C[C@H]3CCCC[C@@H]3[C@H]2CNC(=O)c2cccc3occc23)c(-c2ccccc2)s1]

The pair of stereo isomers Examples 70 and 71 were isolated by prep HPLC from the coupling reaction according general procedure A (1-(aminomethyl)-1H-isoindol-2(3H,3aH,4H,5H,6H,7H,7aH)-yl)(2-methyl-5-phenylthiazol-4-yl)methanone and benzofuran-4-carboxylic acid. The assignment of stereochemistry is not verified. MS (ESI) 500 (M+H).

Example 72 rac-((2S,3R)-2-((benzo[d]thiazol-2-ylamino)methyl)-3-methylpiperidin-1-yl)(5-(4-fluorophenyl)-2-methylthiazol-4-yl)methanone

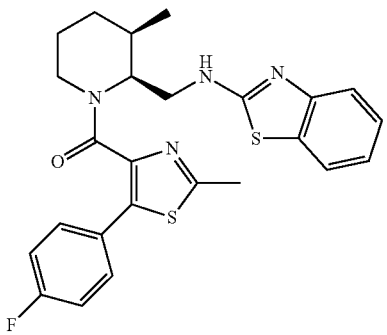

The title compound was prepared following the same general protocol as described for Example 12 using 2-chlorobenzothiazole. MS (ESI) 481.3 (M+H)

Example 73 rac-((2S,3R)-3-methyl-2-(((5-(trifluoromethyl)pyridin-2-yl)amino)methyl)piperidin-1-yl)(2-methyl-5-phenylthiazol-4-yl)methanone

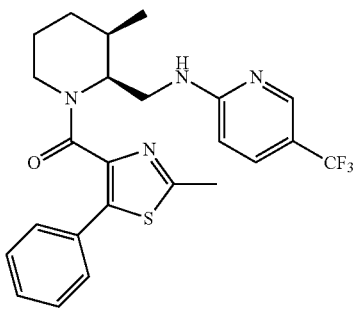 [SMILES: Cc1nc(C(=O)N2CCC[C@@H](C)[C@H]2CNc2ccc(C(F)(F)F)cn2)c(-c2ccccc2)s1]

The title compound was prepared following the same general protocol as described for Example 11 using 2-methyl-5-phenylthiazole-4-carboxylic acid and tert-butyl (((2S,3R)-3-methylpiperidin-2-yl)methyl)carbamate. MS (ESI) 475.2 (M+H)

Example 74 rac-((2S,3R)-3-methyl-2-((quinolin-8-ylamino)methyl)piperidin-1-yl)(5-(4-fluorophenyl)-2-methylthiazol-4-yl)methanone

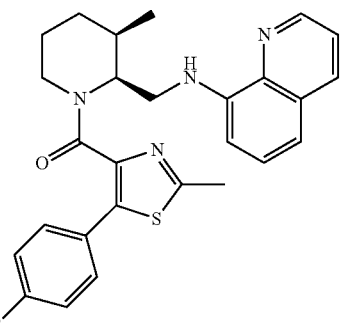

The title compound was prepared following the same general protocol as described for Example 21 using 8-bromoquinoline. MS (ESI) 475.2 (M+H)

Example 75 rac-((2S,3R)-3-methyl-2-(((5-(trifluoromethyl)pyrimidin-2-yl)amino)methyl)piperidin-1-yl)(5-(4-fluorophenyl)-2-methylthiazol-4-yl)methanone

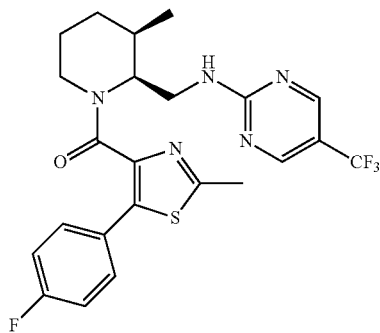 [SMILES: Cc1nc(C(=O)N2CCC[C@@H](C)[C@H]2CNc2ncc(C(F)(F)F)cn2)c(-c2ccc(F)cc2)s1]

The title compound was prepared following the same general protocol as described for Example 18 using 2-chloro-5-(trifluoromethyl)pyrimidine. MS (ESI) 494.2 (M+H)

Example 76 rac-((2S,3R)-3-ethyl-2-(((5-(trifluoromethyl)pyridin-2-yl)amino)methyl)piperidin-1-yl)(5-(4-fluorophenyl)-2-methylthiazol-4-yl)methanone

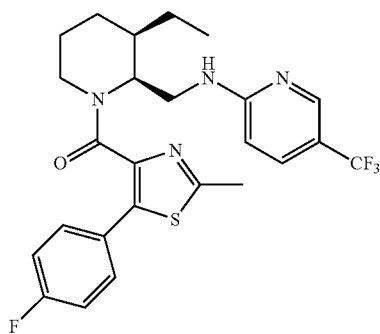 [SMILES: CC[C@@H]1CCCN(C(=O)c2nc(C)sc2-c2ccc(F)cc2)[C@@H]1CNc1ccc(C(F)(F)F)cn1]

rac-((2S,3R)-2-(aminomethyl)-3-ethylpiperidin-1-yl)(5-(4-fluorophenyl)-2-methylthiazol-4-yl)methanone

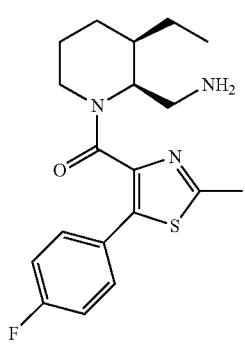 [SMILES: CC[C@@H]1CCCN(C(=O)c2nc(C)sc2-c2ccc(F)cc2)[C@@H]1CN]

The title compound was synthesized following the same general protocol as described in Example 11 using 3-ethyl-picolinonitrile and 5-(4-fluorophenyl)-2-methylthiazole-4-carboxylic acid. MS (ESI) 361.1 (M+H)

rac-((2S,3R)-3-ethyl-2-(((5-(trifluoromethyl)pyridin-2-yl)amino)methyl)piperidin-1-yl)(5-(4-fluorophenyl)-2-methylthiazol-4-yl)methanone The title compound was prepared following the same general protocol as described for Example 11 using rac-((2S,3R)-2-(aminomethyl)-3-ethylpiperidin-1-yl)(5-(4-fluorophenyl)-2-methylthiazol-4-yl)methanone. MS (ESI) 507.2 (M+H)

Example 77 rac-((2S,3R)-2-((benzo[d]oxazol-2-ylamino)methyl)-3-ethylpiperidin-1-yl)(5-(4-fluorophenyl)-2-methylthiazol-4-yl)methanone

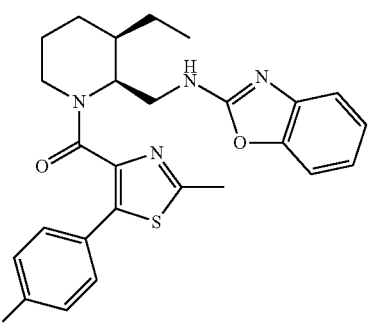

The title compound was prepared following the same general protocol as described for Example 12 using rac-((2S,3R)-2-(aminomethyl)-3-ethylpiperidin-1-yl)(5-(4-fluorophenyl)-2-methylthiazol-4-yl)methanone. MS (ESI) 479.3 (M+H)

Example 78 rac-((2S,3R)-3-ethyl-2-(((5-ethylpyrimidin-2-yl)amino)methyl)piperidin-1-yl)(5-(4-fluorophenyl)-2-methylthiazol-4-yl)methanone

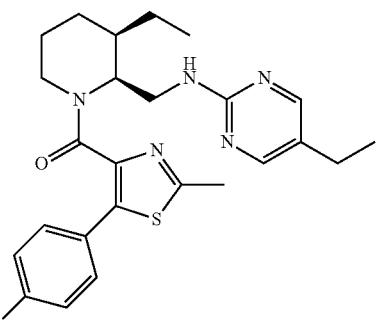

The title compound was prepared following the same general protocol as described for Example 16 using rac- ((2S,3R)-2-(aminomethyl)-3-ethylpiperidin-1-yl)(5-(4-fluorophenyl)-2-methylthiazol-4-yl)methanone. MS (ESI) 468.4 (M+H)

Example 79 rac-((2S,3R)-3-methyl-2-(((5-(trifluoromethyl)pyridin-2-yl)oxy)methyl)piperidin-1-yl)(5-(4-fluorophenyl)-2-methylthiazol-4-yl)methanone

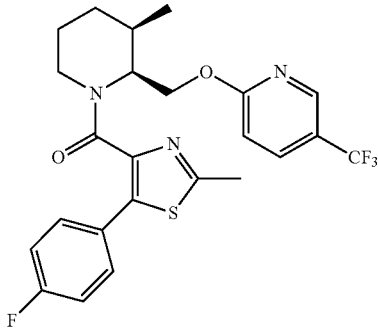

rac-((2S,3R)-3-methylpiperidin-2-yl)methanol

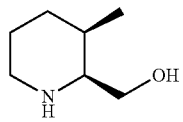

To a solution of methyl 3-methylpicolinate (5 g) and 36% HCl (2 eq) in methanol was added 10% Pd/C. The parr shaker bottle was evacuated/H$_2$ purged 3x, and then shaken at 50 psi until starting material was consumed (typically <1 h). The reaction was filtered through celite and concentrated to yield (2S,3R)-methyl 3-methylpiperidine-2-carboxylate hydrochloride salt without further purification.

To a suspension of LiAlH$_4$ (4 eq) in THF (40 ml) was added in portions the above crude salt at 0° C. The reaction was allowed to stir to room temperature overnight and then refluxed for 2 h. The reaction mixture was then quenched with saturated Na$_2$SO$_4$ at 0° C. and stirred for 1 h. The reaction mixture was filtered and concentrated in vacuo to give the title compound as a white solid.

$^1$H NMR (CDCl$_3$, 400 MHz) δ 3.4 (m, 2H), 2.9 (m, 1H), 2.8 (m, 1H), 2.6 (m, 1H), 1.7 (m, 1H), 1.6-1.4 (m, 4H), 0.8 (d, 3H).

rac-((2S,3R)-2-(hydroxymethyl)-3-methylpiperidin-1-yl)(5-(4-fluorophenyl)-2-methylthiazol-4-yl)methanone

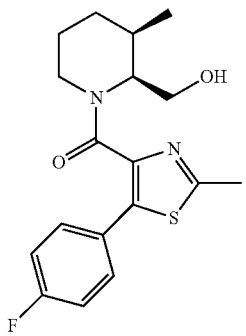 [SMILES: Cc1nc(C(=O)N2CCC[C@@H](C)[C@H]2CO)c(-c2ccc(F)cc2)s1]

To a solution of the product from the previous step (1.4 g) in DMAC was added DIEA (2 eq) followed by 5-(4-fluorophenyl)-2-methylthiazole-4-carboxylic acid (2.3 g) and HATU (1.1 eq). The reaction was allowed to stir at room temperature for 15 h, and was then concentrated in vacuo to remove the DMAC. The crude residue was taken up in EtOAc and washed with 1M HCl, sat aq. NaHCO$_3$, brine, dried (MgSO$_4$), and concentrated. The crude residue was purified by chromatography on silica gel (EtOAc/hex) to give the title compound as a brown oil which crystallized (2.6 g). MS (ESI) 349.4 (M+H).

rac-((2S,3R)-3-methyl-2-(((5-(trifluoromethyl)pyridin-2-yl)oxy)methyl)piperidin-1-yl)(5-(4-fluorophenyl)-2-methylthiazol-4-yl)methanone To a stirred solution of rac-((2S,3R)-2-(hydroxymethyl)-3-methylpiperidin-1-yl)(5-(4-fluorophenyl)-2-methylthiazol-4-yl)methanone in THF was added NaH (4 eq) at 0° C. and stirred for 30 min at RT. 2-chloro-5-(trifluoromethyl)pyridine (2 eq) was then added and solution refluxed for 2 h. The reaction was cooled and quenched with saturated NH$_4$Cl and concentrated in vacuo. The crude reaction mixture was purified by reverse-phase preparative HPLC to afford the title compound. MS (ESI) 493.7 (M+H).

Example 80 rac-((2S,3R)-2-((benzo[d]oxazol-2-yloxy)methyl)-3-methylpiperidin-1-yl)(5-(4-fluorophenyl)-2-methylthiazol-4-yl)methanone

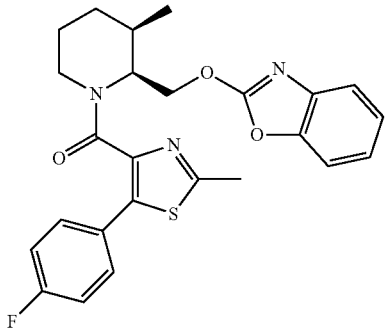 [SMILES: Cc1nc(C(=O)N2CCC[C@@H](C)[C@H]2COc2nc3ccccc3o2)c(-c2ccc(F)cc2)s1]

The title compound was prepared following the same general protocol as described for Example 79 using 2-chlorobenzoxazole. MS (ESI) 466.1 (M+H).

Example 81 rac-((2S,3R)-2-(((5-ethylpyrimidin-2-yl)oxy)methyl)-3-methylpiperidin-1-yl)(5-(4-fluorophenyl)-2-methylthiazol-4-yl)methanone

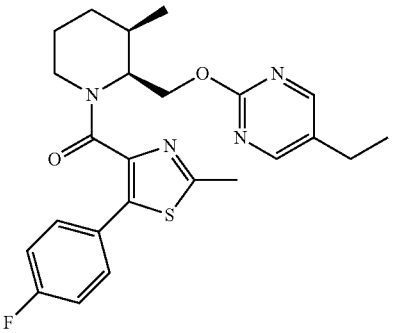

The title compound was prepared following the same general protocol as described for Example 79 using 2-chloro-5-ethylpyrimidine. MS (ESI) 454.8 (M+H).

Example 82 rac-((2S,3R)-2-(((5-chloropyrimidin-2-yl)amino)methyl)-3-methylpiperidin-1-yl)(5-(4-fluorophenyl)-2-methylthiazol-4-yl)methanone

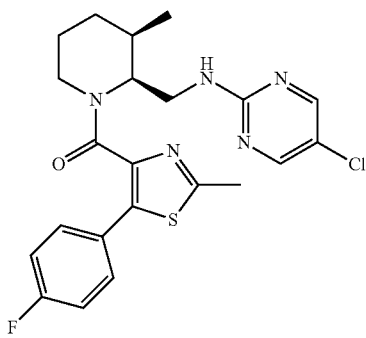 [SMILES: Cc1nc(C(=O)N2CCC[C@@H](C)[C@H]2CNc2ncc(Cl)cn2)c(-c2ccc(F)cc2)s1]

The title compound was prepared following the same general protocol as described for Example 16 using 2,5-dichloropyrimidine. MS (ESI) 460.0 (M+H).

Example 83 rac-((2S,3R)-3-methyl-2-(((5-methylpyrimidin-2-yl)amino)methyl)piperidin-1-yl)(5-(4-fluorophenyl)-2-methylthiazol-4-yl)methanone

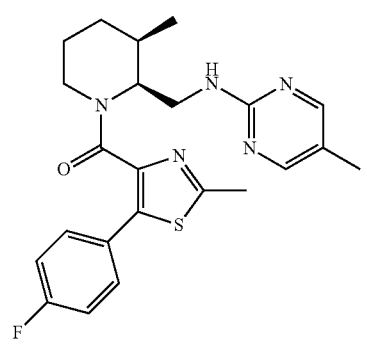

The title compound was prepared following the same general protocol as described for Example 16 using 2-chloro-5-methylpyrimidine. MS (ESI) 440.0 (M+H).

Example 84 rac-((2S,3S)-2-((benzo[d]oxazol-2-ylamino)methyl)-3-isopropylpiperidin-1-yl)(5-(4-fluorophenyl)-2-methylthiazol-4-yl)methanone

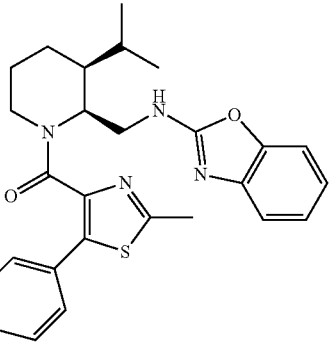

3-(prop-1-en-2-yl)picolinonitrile

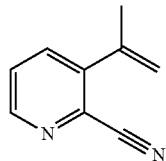

A mixture of 3-bromopicolnonitrile, Isopropenylboronic acid pinacol ester, Pd(PPh$_3$)$_4$, and K$_2$CO$_3$ in dioxane/water (4:1) was stirred at 100° C. for 1 h in a microwave reactor. The reaction mixture was transferred to a seperatory funnel, diluted with EtOAc, and water, and the layers were separated. The organic layer was washed with brine, dried (MgSO$_4$), and concentrated in vacuo to give a crude residue which was purified by chromatography on silica gel (EtOAc/hex) to afford the title compound. $^1$H NMR (CDCl$_3$, 400 MHz) δ 8.6 (m, 1H), 7.6 (m, 1H), 7.4 (m, 1H), 5.5 (s, 1H), 5.4 (s, 1H), 2.2 (s, 3H).

tert-butyl ((3-isopropylpyridine-2-yl)methyl)carbamate

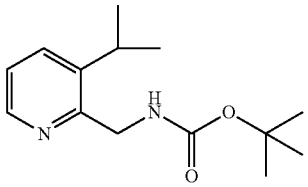 [SMILES: CC(C)c1cccnc1CNC(=O)OC(C)(C)C]

To a solution of 3-(prop-1-en-2-yl)picolinonitrile in acetic acid was added 10% Pd/C. The parr shaker bottle was evacuated/H2 purged 3x, and then shaken at 50 psi until starting material was consumed (typically <1 h). The reaction was filtered through celite and concentrated to yield (3-isopropylpyridine-2-yl)methanamine acetic acid salt which was used without further purification.

To the crude salt in THF was added aq 1M NaOH, followed by BOC$_2$O (2 eq). The reaction was allowed to stir at room temperature overnight. After ~16 h, the reaction mixture was transferred to a seperatory funnel, diluted with EtOAc, and water, and the layers were separated. The organic layer was washed with brine, dried (MgSO$_4$), and concentrated in vacuo to give a crude residue which was purified by chromatography on silica gel (EtOAc/hex) to afford the title compound as a clear oil.

$^1$H NMR (CDCl$_3$, 400 MHz) δ 8.4 (m, 1H), 7.5 (m, 1H), 7.2 (m, 1H), 4.5 (s, 2H), 3.1 (s, 1H), 1.4 (s, 9H), 1.2 (d, J=3.5 Hz, 6H)

rac-tert-butyl (((2S,3S)-3-isopropylpiperidin-2-yl)methyl)carbamate

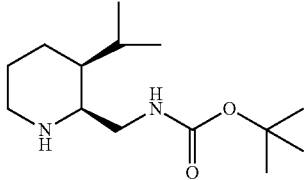 [SMILES: CC(C)[C@@H]1CCCN[C@@H]1CNC(=O)OC(C)(C)C]

To a solution of the BOC-protected pyridylamine prepared above in MeOH was added Nishimura's catalyst. The parr shaker bottle was evacuated/purged with H$_2$ (3x) and then shaken at 50 psi for 24 h. The reaction was filtered through celite, and concentrated in vacuo to give the title compound as a near colorless oil, and was used without further purification. MS (ESI) 251.3 (M+H)

rac-((2S,3S)-2-((benzo[d]oxazol-2-ylamino)methyl)-3-isopropylpiperidin-1-yl)(5-(4-fluorophenyl)-2-methylthiazol-4-yl)methanone The title compound was prepared following the same general protocol as described for Example's 11 and 12 using rac-((2S,3S)-2-((benzo[d]oxazol-2-ylamino)methyl)-3-isopropylpiperidin-1-yl)(5-(4-fluorophenyl)-2-methylthiazol-4-yl)methanone. MS (ESI) 493.3 (M+H).

Example 85 rac-((2S,3R)-2-(((5-fluoropyridin-2-yl)amino)methyl)-3-methylpiperidin-1-yl)(5-(4-fluorophenyl)-2-methylthiazol-4-yl)methanone

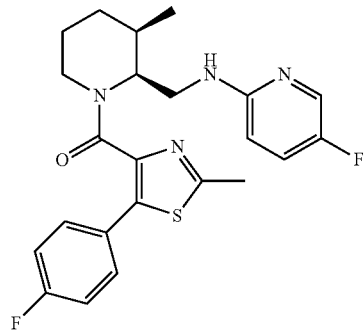 [SMILES: Cc1nc(C(=O)N2CCC[C@@H](C)[C@H]2CNc2ccc(F)cn2)c(-c2ccc(F)cc2)s1]

rac-(2S,3R)-1-(5-(4-fluorophenyl)-2-methylthiazole-4-carbonyl)-3-methylpiperidine-2-carbaldehyde

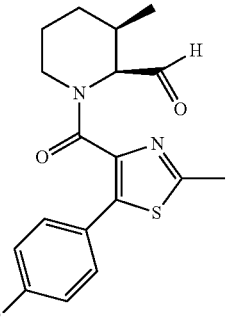

To a stirred solution of rac-((2S,3R)-2-(hydroxymethyl)-3-methylpiperidin-1-yl)(5-(4-fluorophenyl)-2-methylthiazol-4-yl)methanone in DCM was added Dess-Martin periodinane (1.5 eq) and stirred at room temperature for 4 h. The reaction mixture was transferred to a seperatory funnel, diluted with more DCM, water and the layers were separated. The organic layer was washed with brine, dried (MgSO$_4$), and concentrated in vacuo to give a crude residue which was purified by chromatography on silica gel (EtOAc/hex) to afford the title compound. MS (ESI) 347.1 (M+H).

rac-((2S,3R)-2-(((5-fluoropyridin-2-yl)amino)methyl)-3-methylpiperidin-1-yl)(5-(4-fluorophenyl)-2-methylthiazol-4-yl)methanone To a stirred solution of rac-(2S,3R)-1-(5-(4-fluorophenyl)-2-methylthiazole-4-carbonyl)-3-methylpiperidine-2-carbaldehyde and 5-fluoropyridin-2-amine in methanol/acetic acid (50:1) was added sodium cyanoborohydride at 0° C. The reaction was then stirred at room temperature overnight. After ~16 h, the reaction mixture was transferred to a seperatory funnel, diluted with EtOAc, saturated NaHCO$_3$ and the layers separated. The organic layer was washed with water, brine, dried (MgSO$_4$), and concentrated in vacuo. The crude reaction mixture was purified by reverse-phase preparative HPLC to afford the title compound. MS (ESI) 443.2 (M+H)

Example 86 rac-((2S,3R)-3-methyl-2-(((5-methylpyridin-2-yl)amino)methyl)piperidin-1-yl)(5-(4-fluorophenyl)-2-methylthiazol-4-yl)methanone

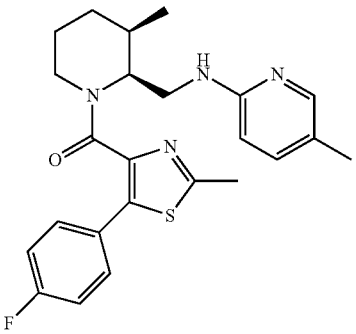 [SMILES: Cc1ccc(NC[C@@H]2[C@H](C)CCCN2C(=O)c2nc(C)sc2-c2ccc(F)cc2)nc1]

The title compound was prepared following the same general protocol as described for Example 85 using 5-methylpyridin-2-amine. MS (ESI) 439.2 (M+H)

Example 87 rac-((2S,3R)-3-methyl-2-(((6-(trifluoromethyl)pyridin-2-yl)amino)methyl)piperidin-1-yl)(5-(4-fluorophenyl)-2-methylthiazol-4-yl)methanone

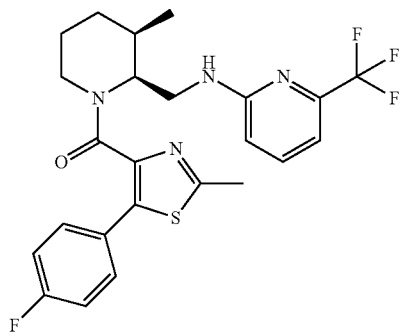 [SMILES: Cc1nc(C(=O)N2CCC[C@@H](C)[C@H]2CNc2cccc(C(F)(F)F)n2)c(-c2ccc(F)cc2)s1]

The title compound was prepared following the same general protocol as described for Example 85 using 6-(trifluoromethyl)pyridin-2-amine. MS (ESI) 493.2 (M+H)

Example 88 rac-((2S,3R)-2-(((5-methoxypyrimidin-2-yl)amino)methyl)-3-methylpiperidin-1-yl)(5-(4-fluorophenyl)-2-methylthiazol-4-yl)methanone

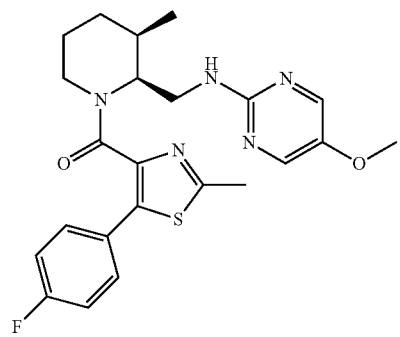 [SMILES: COc1cnc(NC[C@@H]2[C@H](C)CCCN2C(=O)c2nc(C)sc2-c2ccc(F)cc2)nc1]

A mixture of rac-((2S,3R)-2-(aminomethyl)-3-methylpiperidin-1-yl)(5-(4-fluorophenyl)-2-methylthiazol-4-yl)methanone, 2-chloro-5-methoxypyrimidine, Pd$_2$ dba$_3$, BINAP, and NaOtBu in toluene was purged with argon, and then stirred at 70° C. for 72 h. The reaction was cooled, filtered through a pad of silica gel and concentrated in vacuo. The crude reaction mixture was purified by reverse-phase preparative HPLC to afford the title compound. MS (ESI) 456.2 (M+H).

Example 89 rac-((2S,3R)-2-(((5-methoxypyrimidin-2-yl)oxy)methyl)-3-methylpiperidin-1-yl)(5-(4-fluorophenyl)-2-methylthiazol-4-yl)methanone

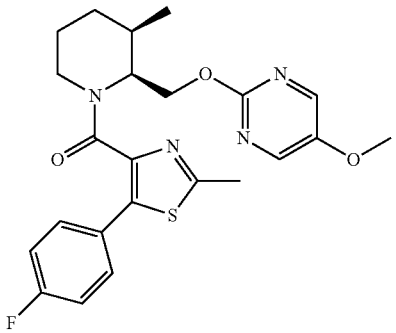 [SMILES: COc1cnc(OC[C@@H]2[C@H](C)CCCN2C(=O)c2nc(C)sc2-c2ccc(F)cc2)nc1]

The title compound was prepared following the same general protocol as described for Example 81 using 2-chloro-5-methoxypyrimidine. MS (ESI) 457.2 (M+H).

Example 90 rac-((2S,3R)-2-(((5-chloropyrimidin-2-yl)oxy)methyl)-3-methylpiperidin-1-yl)(5-(4-fluorophenyl)-2-methylthiazol-4-yl)methanone

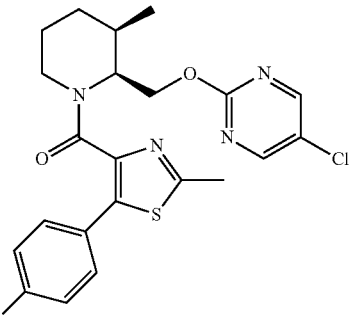

The title compound was prepared following the same general protocol as described for Example 81 using 2,5-dichloropyrimidine. MS (ESI) 461.1 (M+H).

Example 91 rac-6-((((2S,3R)-1-(5-(4-fluorophenyl)-2-methylthiazole-4-carbonyl)-3-methylpiperidin-2-yl)methyl)amino)nicotinonitrile

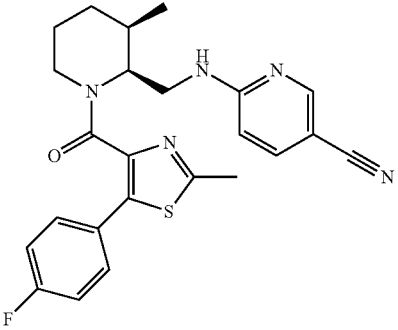 [SMILES: Cc1nc(C(=O)N2CCC[C@@H](C)[C@H]2CNc2ccc(C#N)cn2)c(-c2ccc(F)cc2)s1]

The title compound was prepared following the same general protocol as described for Example 18 using 6-chloronicotinonitrile. MS (ESI) 450.2 (M+H).

Example 92 rac-((2R,3R)-3-methoxy-2-(((5-(trifluoromethyl)pyridin-2-yl)amino)methyl)piperidin-1-yl)(5-(4-fluorophenyl)-2-methylthiazol-4-yl)methanone

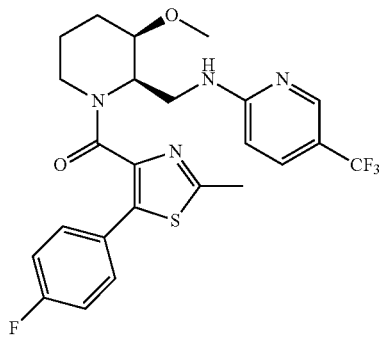 [SMILES: CO[C@@H]1CCCN(C(=O)c2nc(C)sc2-c2ccc(F)cc2)[C@@H]1CNc1ccc(C(F)(F)F)cn1]

rac-((2R,3R)-2-(aminomethyl)-3-methoxypiperidin-1-yl)(5-(4-fluorophenyl)-2-methylthiazol-4-yl)methanone

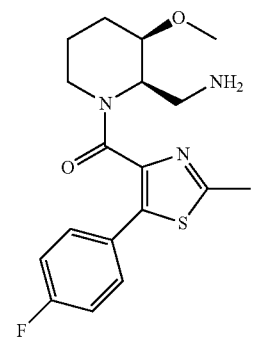 [SMILES: CO[C@@H]1CCCN(C(=O)c2nc(C)sc2-c2ccc(F)cc2)[C@@H]1CN]

The title compound was synthesized following the same general protocol as described in Example 11 using 3-methoxypicolinonitrile and 5-(4-fluorophenyl)-2-methylthiazole-4-carboxylic acid. MS (ESI) 464.4 (M+H)

rac-((2R,3R)-3-methoxy-2-(((5-(trifluoromethyl)pyridin-2-yl)amino)methyl)piperidin-1-yl)(5-(4-fluorophenyl)-2-methylthiazol-4-yl)methanone The title compound was prepared following the same general protocol as described for Example 11 using rac-((2R,3R)-2-(aminomethyl)-3-methoxypiperidin-1-yl)(5-(4-fluorophenyl)-2-methylthiazol-4-yl)methanone. MS (ESI) 509.4 (M+H).

Example 93 rac-((2R,3R)-2-(((5-chloropyrimidin-2-yl)amino)methyl)-3-methoxypiperidin-1-yl)(5-(4-fluorophenyl)-2-methylthiazol-4-yl)methanone

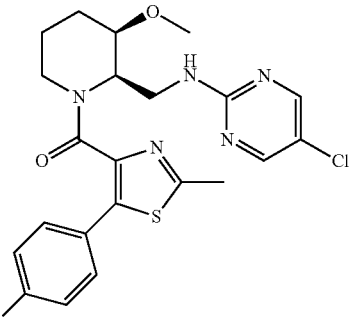

The title compound was prepared following the same general protocol as described for Example 16 using 2,5-dichloropyrimidine and rac-((2R,3R)-2-(aminomethyl)-3-methoxypiperidin-1-yl)(5-(4-fluorophenyl)-2-methylthiazol-4-yl)methanone. MS (ESI) 476.0 (M+H)

Example 94 rac-((2R,3R)-2-((benzo[d]thiazol-2-ylamino)methyl)-3-methoxypiperidin-1-yl)(5-(4-fluorophenyl)-2-methylthiazol-4-yl)methanone

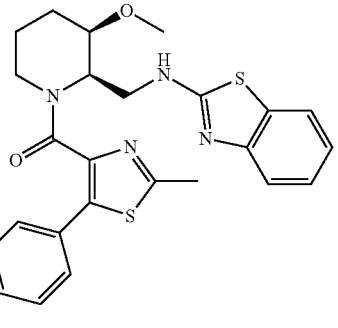

The title compound was prepared following the same general protocol as described for Example 12 using 2-chlorobenzothiazole and rac-((2R,3R)-2-(aminomethyl)-3-methoxypiperidin-1-yl)(5-(4-fluorophenyl)-2-methylthiazol-4-yl)methanone. MS (ESI) 497.0 (M+H)

Example 95 rac-((2R,3R)-2-((benzo[d]oxazol-2-ylamino)methyl)-3-methylpiperidin-1-yl)(5-(4-fluorophenyl)-2-methylthiazol-4-yl)methanone

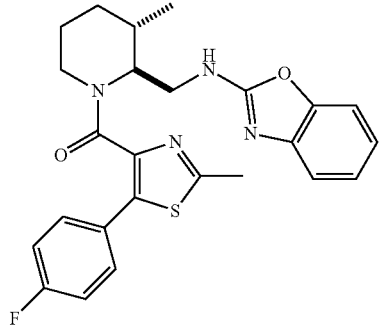 [SMILES: Cc1nc(C(=O)N2CCC[C@H](C)[C@H]2CNc2nc3ccccc3o2)c(-c2ccc(F)cc2)s1]

1-benzyl-2-(((tert-butoxycarbonyl)amino)methyl)-3-methylpyridin-1-ium bromide

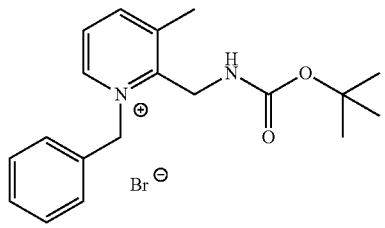 [SMILES: Cc1ccc[n+](Cc2ccccc2)c1CNC(=O)OC(C)(C)C ; [Br-]]

Tert-butyl ((3-methylpyridin-2-yl)methyl)carbamate (4.5 g) and Benzylbromide (2 eq) in 80 ml of acetonitrile was heated in a sealed tube at reflux overnight and then concentrated in vacuo to give the title compound and was used without further purification. MS (ESI) 313 (M+H)

rac-tert-butyl ((1-benzyl-3-methyl-1,2,5,6-tetrahydropyridin-2-yl)methyl)carbamate

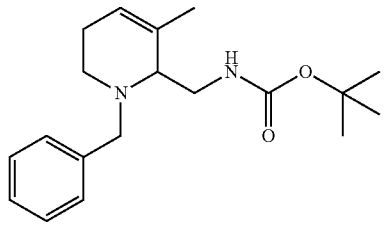 [SMILES: CC1=CCCN(Cc2ccccc2)C1CNC(=O)OC(C)(C)C]

To a solution of 1-benzyl-2-(((tert-butoxycarbonyl)amino)methyl)-3-methylpyridin-1-ium bromide (1.5 g) in MeOH (100 ml) was added NaBH$_4$ (3 eq) in three portions at 0° C. The solution was then stirred for 3 h at room temperature and then concentrated in vacuo. The crude residue was taken up in EtOAc and washed with sat aq. NaHCO$_3$, dried (MgSO$_4$), and concentrated. The crude residue was purified by chromatography on silica gel (EtOAc/hex) to give the title compound as a pale yellow oil in 63% yield. MS (ESI) 317 (M+H)

rac-tert-butyl (((2R,3R)-3-methylpiperidin-2-yl)methyl)carbamate

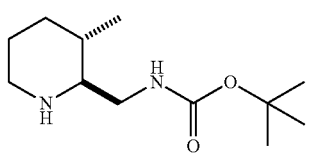 [SMILES: C[C@H]1CCCN[C@@H]1CNC(=O)OC(C)(C)C]

A mixture of rac-tert-butyl ((1-benzyl-3-methyl-1,2,5,6-tetrahydropyridin-2-yl)methyl)carbamate and Pd(OH)$_2$/C (20% wt, 0.1 eq) was pressurized to 4 bar with H$_2$ and maintained at room temperature for 5 h. The mixture was filtered through Celite and the filtrate was concentrated in vacuo to yield the title compound as a colorless oil. MS (ESI) 229.2 (M+H)

rac-((2S,3R)-2-(aminomethyl)-3-methylpiperidin-1-yl)(5-(4-fluorophenyl)-2-methylthiazol-4-yl)methanone

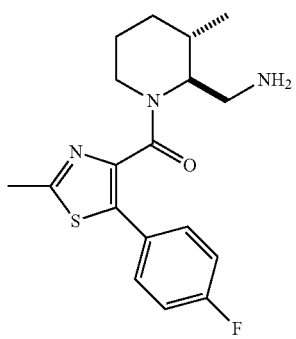 [SMILES: Cc1nc(C(=O)N2CCC[C@H](C)[C@H]2CN)c(-c2ccc(F)cc2)s1]

To a solution of rac-tert-butyl (((2R,3R)-3-methylpiperidin-2-yl)methyl)carbamate (1 eq) from the previous step in DMF was added DIEA (2 eq) followed by 5-(4-fluorophenyl)-2-methylthiazole-4-carboxylic acid (1.5 eq) and HATU (2 eq). The reaction was allowed to stir at room temperature for 15 h, and was then concentrated in vacuo to remove the DMF. The crude residue was taken up in EtOAc and washed with 1M HCl, sat aq. NaHCO$_3$, brine, dried (MgSO$_4$), and concentrated. The crude residue was purified by chromatography on silica gel (EtOAc/hex) to give tert-butyl (((2R,3R)-1-(5-(4-fluorophenyl)-2-methylthiazole-4-carbonyl)-3-methylpiperidin-2-yl)methyl)carbamate as a light yellow oil.

To a solution of this carbamate in CH$_2$Cl$_2$ was added TFA (1:1 v/v). The reaction was aged at room temperature and monitored for disappearance of starting material by analytical reverse-phase HPLC. When starting material was consumed, the reaction was concentrated in vacuo. The crude residue was taken up in EtOAc, and washed with sat aqueous NaHCO$_3$, brine, dried (MgSO$_4$), and concentrated to afford the title compound as a pale yellow oil which crystallized. MS (ESI) 348.2 (M+H).

rac-((2R,3R)-2-((benzo[d]oxazol-2-ylamino)methyl)-3-methylpiperidin-1-yl)(5-(4-fluorophenyl)-2-methylthiazol-4-yl)methanone A mixture of ((2R,3R)-2-(aminomethyl)-3-methylpiperidin-1-yl)(2-methyl-5-phenylthiazol-4-yl)methanone, 2-chlorobenzoxazole, and DIEA in ACN was stirred at 60° C. overnight. The reaction mixture was concentrated in vacuo. The crude reaction mixture was purified by reverse-phase preparative HPLC to afford the title compound. MS (ESI) 465.1 (M+H).

Example 96 rac-((2R,3R)-2-(((5-chloropyrimidin-2-yl)amino)methyl)-3-methylpiperidin-1-yl)(5-(4-fluorophenyl)-2-methylthiazol-4-yl)methanone

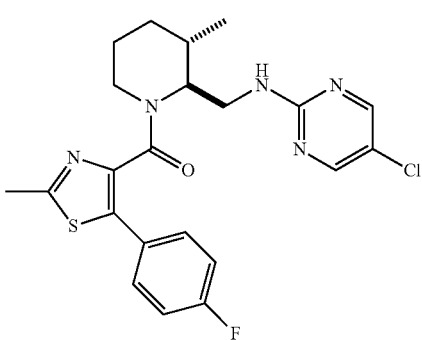 [SMILES: Cc1nc(C(=O)N2CCC[C@H](C)[C@H]2CNc2ncc(Cl)cn2)c(-c2ccc(F)cc2)s1]

The title compound was prepared following the same general protocol as described for Example 16 using 2,5-dichloropyrimidine and rac-((2S,3R)-2-(aminomethyl)-3-methylpiperidin-1-yl)(5-(4-fluorophenyl)-2-methylthiazol-4-yl)methanone. MS (ESI) 460.4 (M+H).

Example 97 rac-((2S,3R)-3-methyl-2-(((5-(trifluoromethyl)pyrimidin-2-yl)amino)methyl)piperidin-1-yl)(5-methyl-2-(2H-1,2,3-triazol-2-yl)phenyl)methanone

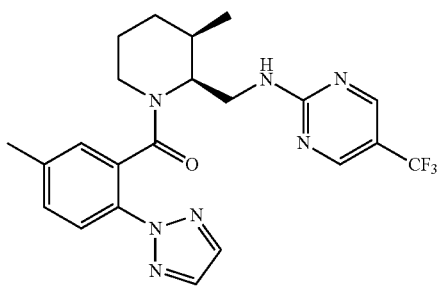 [SMILES: Cc1ccc(-n2nccn2)c(C(=O)N2CCC[C@@H](C)[C@H]2CNc2ncc(C(F)(F)F)cn2)c1]

rac-((2S,3R)-2-(aminomethyl)-3-methylpiperidin-1-yl)(5-methyl-2-(2H-1,2,3-triazol-2-yl)phenyl)methanone

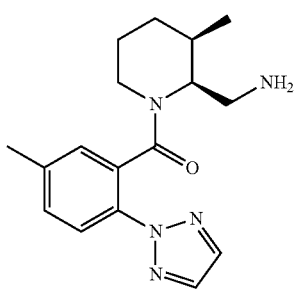 [SMILES: Cc1ccc(-n2nccn2)c(C(=O)N2CCC[C@@H](C)[C@H]2CN)c1]

To a solution of rac-tert-butyl (((2S,3R)-3-methylpiperidin-2-yl)methyl)carbamate (1 eq) from Example 11 in DMF was added DIEA (2 eq) followed by 5-methyl-2-(2H-1,2,3-triazol-2-yl)benzoic acid (1.5 eq) and HATU (2 eq). The reaction was allowed to stir at room temperature for 15 h, and was then concentrated in vacuo to remove the DMF. The crude residue was taken up in EtOAc and washed with 1M HCl, sat aq. NaHCO₃, brine, dried (MgSO₄), and concentrated. The crude residue was purified by chromatography on silica gel (EtOAc/hex) to give rac-tert-butyl (((2S,3R)-3-methyl-1-(5-methyl-2-(2H-1,2,3-triazol-2-yl)benzoyl)piperidin-2-yl)methyl)carbamates a light yellow oil.

To a solution of this carbamate in CH₂Cl₂ was added TFA (1:1 v/v). The reaction was aged at room temperature and monitored for disappearance of starting material by analytical reverse-phase HPLC. When starting material was consumed, the reaction was concentrated in vacuo. The crude residue was taken up in EtOAc, and washed with sat aqueous NaHCO₃, brine, dried (MgSO₄), and concentrated to afford the title compound as a pale yellow oil which crystallized. MS (ESI) 314.1 (M+H).

rac-((2S,3R)-3-methyl-2-(((5-(trifluoromethyl)pyrimidin-2-yl)amino)methyl)piperidin-1-yl)(5-methyl-2-(2H-1,2,3-triazol-2-yl)phenyl)methanone The title compound was prepared following the same general protocol as described for Example 18 using ((2S,3R)-2-(aminomethyl)-3-methylpiperidin-1-yl)(5-methyl-2-(2H-1,2,3-triazol-2-yl)phenyl)methanone and 2-chloro-5-(trifluoromethyl)pyrimidine. MS (ESI) 460.0 (M+H).

Example 98 rac-((2S,3R)-2-(((5-chloropyrimidin-2-yl)amino)methyl)-3-methylpiperidin-1-yl)(5-methyl-2-(2H-1,2,3-triazol-2-yl)phenyl)methanone

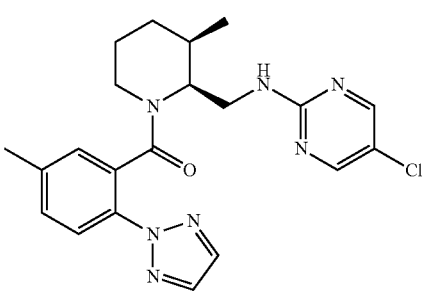 [SMILES: Cc1ccc(-n2nccn2)c(C(=O)N2CCC[C@@H](C)[C@H]2CNc2ncc(Cl)cn2)c1]

The title compound was prepared following the same general protocol as described for Example 16 starting with rac-((2S,3R)-2-(aminomethyl)-3-methylpiperidin-1-yl)(5-methyl-2-(2H-1,2,3-triazol-2-yl)phenyl)methanone and 2,5-dichloropyrimidine. MS (ESI) 426.4 (M+H).

Example 99 rac-(5-(4-fluorophenyl)-2-methylthiazol-4-yl)(1-(hydroxymethyl)hexahydrocyclopenta[c]pyrrol-2(1H)-yl)methanone

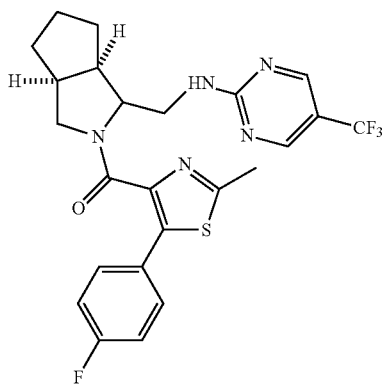 [SMILES: Cc1nc(C(=O)N2C[C@H]3CCC[C@H]3C2CNc2ncc(C(F)(F)F)cn2)c(-c2ccc(F)cc2)s1]

rac-diethyl 2-acetylhexahydrocyclopenta[c]pyrrole-1,1(2H)-dicarboxylate

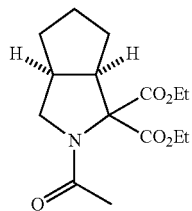 [SMILES: CCOC(=O)C1(C(=O)OCC)[C@@H]2CCC[C@@H]2CN1C(C)=O]

The title compound was prepared from cyclopenten-1-aldehyde (1 eq) and diethyl acetamidomalonate (1 eq) using the procedure by Chung et al (J. Org. Chem. 1990, 55, 270). MS (ESI) 298 (M+H)

rac-octahydrocyclopenta[c]pyrrole-1-carboxylic acid hydrobromide

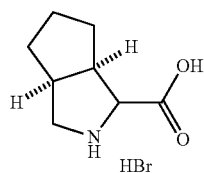

A solution of the diethyl 2-acetylhexahydrocyclopenta[c]pyrrole-1,1(2H)-dicarboxylate prepared above in 48% aqueous HBr 48% and AcOH (4:1) was heated at 120° C. overnight for 16 h. The reaction mixture was cooled, concentrated in vacuo and lyophilized to yield the title compound. MS (ESI) 156 (M+H).

rac-2-(tert-butoxycarbonyl)octahydrocyclopenta[c]pyrrole-1-carboxylic acid

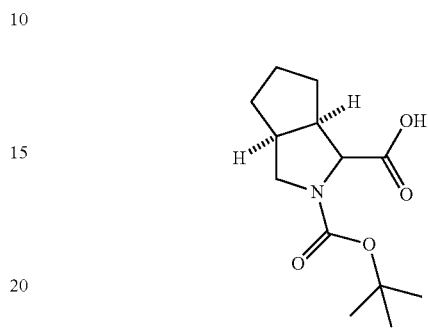

The amino acid prepared above and NaHCO$_3$ (2 eq.) were dissolved in water/dioxane (1:1, v/v) and Boc$_2$O (1.5 eq.) was added. After stirring overnight at room temperature, water was added and the resulting solution was washed with EtOAc (4 times). The aqueous solution was then acidified with 1N HCl to pH 1-2 and extracted with EtOAc (4 times), dried (MgSO$_4$), and concentrated. The crude residue was purified by chromatography on silica gel (EtOAc:CH$_2$Cl$_2$=1:3) to give the title compound as a creamy white solid. MS (ESI) 256 (M+H)

rac-tert-butyl (((2S,3R)-3-tert-butyl 1-(hydroxymethyl)hexahydrocyclopenta[c]pyrrole-2(1H)-carboxylate

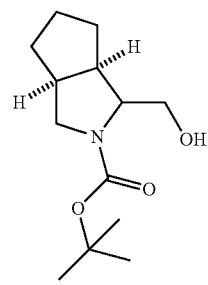 [SMILES: CC(C)(C)OC(=O)N1C[C@H]2CCC[C@H]2C1CO]

To a stirred solution of 2-(tert-butoxycarbonyl)octahydrocyclopenta[c]pyrrole-1-carboxylic acid (1 eq) in THF was added BH$_3$SMe$_2$ (10M, 2 eq) dropwise over 5 mins at 0° C. The reaction was then allowed to stir overnight at room temperature and then quenched with cooled water at 0° C. The reaction mixture was diluted with EtOAc and washed with water, brine, dried (MgSO$_4$), and concentrated. The crude residue was concentrated in vacuo to give the title compound as a clear oil. MS (ESI) 242.2 (M+H)

rac-(5-(4-fluorophenyl)-2-methylthiazol-4-yl)(1-(hydroxymethyl)hexahydrocyclopenta[c]pyrrol-2(1H)-yl)methanone

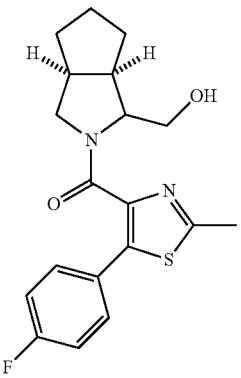 [SMILES: Cc1nc(C(=O)N2C[C@H]3CCC[C@H]3C2CO)c(-c2ccc(F)cc2)s1]

To a solution of the carbamate above in CH$_2$Cl$_2$ was added TFA (1:1 v/v). The reaction was stirred at room temperature for 30 minutes before being concentrated in vacuo. The crude residue was taken up in EtOAc, and washed with sat aqueous NaHCO$_3$, brine, dried (MgSO$_4$), and concentrated to afford (octahydrocyclopenta[c]pyrrol-1-yl)methanol as a pale yellow oil.

To a solution of (octahydrocyclopenta[c]pyrrol-1-yl)methanol (1 eq) in DMF was added DIEA (2 eq) followed by 5-(4-fluorophenyl)-2-methylthiazole-4-carboxylic acid (1.5 eq) and HATU (2 eq). The reaction was allowed to stir at room temperature for 15 h, and was then concentrated in vacuo to remove the DMF. The crude residue was taken up in EtOAc and washed with 1M HCl, sat aq. NaHCO$_3$, brine, dried (MgSO$_4$), and concentrated. The crude residue was purified by chromatography on silica gel (EtOAc/hex) to give the title compound as a clear oil. MS (ESI) 361.1 (M+H)

rac-2-((2-(5-(4-fluorophenyl)-2-methylthiazole-4-carbonyl)octahydrocyclopenta[c]pyrrol-1-yl)methyl)isoindoline-1,3-dione

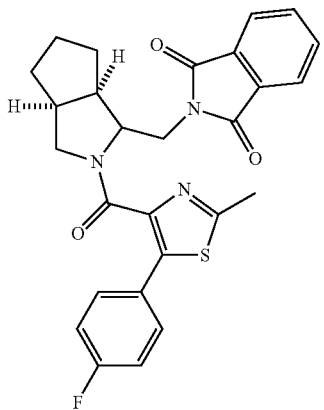 [SMILES: Cc1nc(C(=O)N2C[C@H]3CCC[C@H]3C2CN2C(=O)c3ccccc3C2=O)c(-c2ccc(F)cc2)s1]

A solution of (5-(4-fluorophenyl)-2-methylthiazol-4-yl)(1-(hydroxymethyl)hexahydrocyclopenta[c]pyrrol-2(1H)-yl)methanone (1 eq), phthalimide (2 eq) and triphenylphosphine (3 eq) in THF (56 mL) was cooled to 0° C. and added with DIAD (5 eq) dropwise. The resulting suspension was allowed to warm to r.t. gradually and stirred overnight, concentrated in vacuo to a brown oil. The reaction mixture was diluted with EtOAc and washed with water, brine, dried (MgSO$_4$), and concentrated. The crude residue was purified by chromatography on silica gel (EtOAc/hex) to give the title compound as a clear oil. MS (ESI) 490.4 (M+H).

rac-(1-(aminomethyl)hexahydrocyclopenta[c]pyrrol-2(1H)-yl)(5-(4-fluorophenyl)-2-methylthiazol-4-yl)methanone

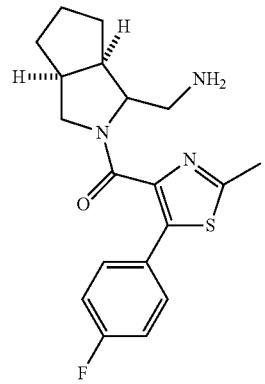 [SMILES: Cc1nc(C(=O)N2C[C@H]3CCC[C@H]3C2CN)c(-c2ccc(F)cc2)s1]

2-((-2-(5-(4-fluorophenyl)-2-methylthiazole-4-carbonyl)octahydrocyclopenta[c]pyrrol-1-yl)methyl)isoindoline-1,3-dione (1 eq) and hydrazine monohydrate (4 eq) in MeOH was stirred at 70° C. for 3 hrs and then concentrated in vacuo to a yellow oil. The reaction mixture was diluted with EtOAc and washed with water, brine, dried (MgSO$_4$), and concentrated. The crude residue was purified by chromatography on silica gel (20% MeOH in EtOAc) to firstly remove the impurities and then (2:8:1 MeOH/EtOAc/TEA) to elute the title compound which was concentrated to yield a yellow oil. MS (ESI) 360.3 (M+H).

rac-(5-(4-fluorophenyl)-2-methylthiazol-4-yl)(1-(hydroxymethyl)hexahydrocyclopenta[c]pyrrol-2(1H)-yl)methanone The title compound was prepared following the same general protocol as described for Example 18 using (1-(aminomethyl)hexahydrocyclopenta[c]pyrrol-2(1H)-yl)(5-(4-fluorophenyl)-2-methylthiazol-4-yl)methanone and 2-chloro-5-(trifluoromethyl)pyrimidine. MS (ESI) 506.4 (M+H).

Example 100 rac-(1-((benzo[d]oxazol-2-ylamino)methyl)hexahydrocyclopenta[c]pyrrol-2(1H)-yl)(5-(4-fluorophenyl)-2-methylthiazol-4-yl)methanone

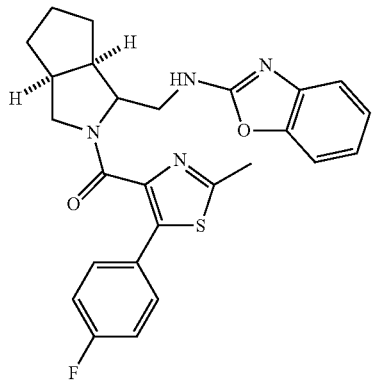 [SMILES: Cc1nc(C(=O)N2C[C@H]3CCC[C@H]3C2CNc2nc3ccccc3o2)c(-c2ccc(F)cc2)s1]

A mixture of (1-(aminomethyl)hexahydrocyclopenta[c]pyrrol-2(1H)-yl)(5-(4-fluorophenyl)-2-methylthiazol-4-yl)methanone, 2-chlorobenzoxazole, and DIEA in ACN was stirred at 60° C. overnight. The reaction mixture was concentrated in vacuo. The crude reaction mixture was purified by reverse-phase preparative HPLC to afford the title compound. MS (ESI) 477.4 (M+H).

Example 101 rac-(5-(4-fluorophenyl)-2-methylthiazol-4-yl)(1-(((5-(trifluoromethyl)pyridin-2-yl)oxy)methyl)hexahydrocyclopenta[c]pyrrol-2(1H)-yl)methanone

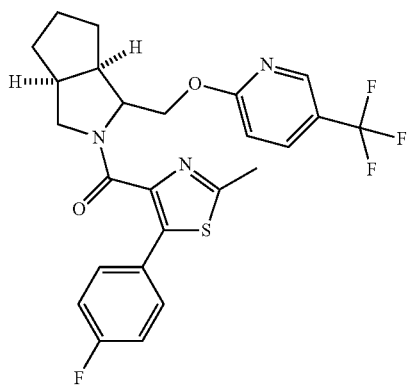 [SMILES: Cc1nc(C(=O)N2C[C@H]3CCC[C@H]3C2COc2ccc(C(F)(F)F)cn2)c(-c2ccc(F)cc2)s1]

The title compound was prepared following the same general protocol as described for Example 79 using (5-(4-fluorophenyl)-2-methylthiazol-4-yl)(1-(hydroxymethyl)hexahydrocyclopenta[c]pyrrol-2(1H)-yl)methanone. MS (ESI) 506.2 (M+H).

Example 102 rac-(1-((benzo[d]oxazol-2-yloxy)methyl)hexahydrocyclopenta[c]pyrrol-2(1H)-yl)(5-(4-fluorophenyl)-2-methylthiazol-4-yl)methanone

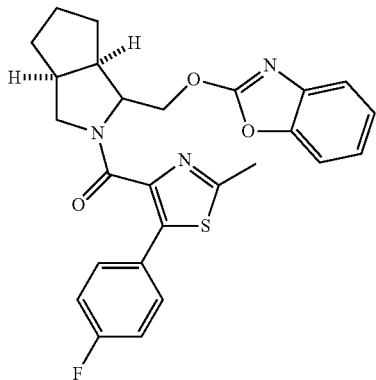 [SMILES: Cc1nc(C(=O)N2C[C@H]3CCC[C@H]3C2COc2nc3ccccc3o2)c(-c2ccc(F)cc2)s1]

The title compound was prepared following the same general protocol as described for Example 80 using (5-(4-fluorophenyl)-2-methylthiazol-4-yl)(1-(hydroxymethyl)hexahydrocyclopenta[c]pyrrol-2(1H)-yl)methanone and 2-chlorobenzoxazole. MS (ESI) 478.2 (M+H)

Example 103 rac-((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone

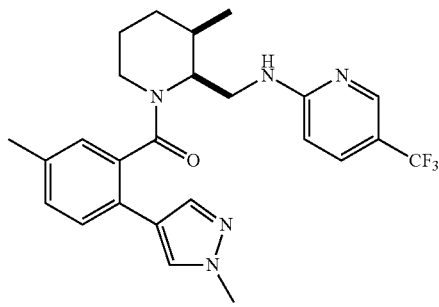 [SMILES: Cc1ccc(-c2cnn(C)c2)c(C(=O)N2CCC[C@@H](C)[C@H]2CNc2ccc(C(F)(F)F)cn2)c1]

rac-((2S,3R)-2-(aminomethyl)-3-methylpiperidin-1-yl)(2-bromo-5-methylphenyl)methanone

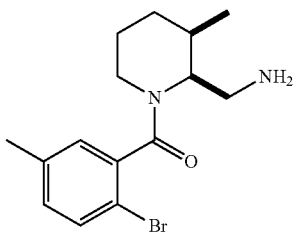 [SMILES: Cc1ccc(Br)c(C(=O)N2CCC[C@@H](C)[C@H]2CN)c1]

The title compound was synthesized following the same general protocol as described in Example 11 using tert-butyl (((2S,3R)-3-methylpiperidin-2-yl)methyl)carbamate and 2-bromo-5-methylbenzoic acid. ESI-MS (m/z): 325, 327, [M]⁺, [M+2]⁺.

rac-(2-bromo-5-methylphenyl)((2S,3R)-3-methyl-2-(((5-(trifluoromethyl)pyridin-2-yl)amino)methyl)piperidin-1-yl)methanone

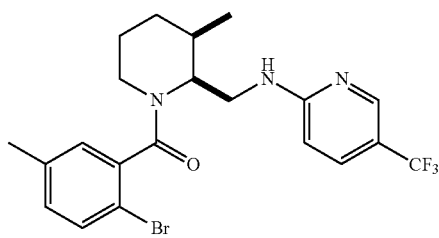 [SMILES: Cc1ccc(Br)c(C(=O)N2CCC[C@@H](C)[C@H]2CNc2ccc(C(F)(F)F)cn2)c1]

The title compound was prepared following the same general protocol as described for Example 11 starting with rac-((2S,3R)-2-(aminomethyl)-3-methylpiperidin-1-yl)(2-bromo-5-methylphenyl)methanone and 2-chloro-5-(trifluoromethyl)pyridine. ESI-MS (m/z): 470, 472, [M]⁺, [M+2]⁺.

rac-((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone The mixture of rac-(2-bromo-5-methylphenyl)((2S,3R)-3-methyl-2-(((5-(trifluoromethyl)pyridin-2-yl)amino)methyl)piperidin-1-yl)methanone (0.045 g, 0.097 mmol), 1-methyl-4-(4,4,5,5-tetramethyl-1,3,2-dioxaborolan-2-yl)-1H-pyrazole (0.024 g, 0.116 mmol), P(PPh₃)₄ (0.017 g, 0.015 mmol), K₂CO₃ (0.4 g, 0.291 mmol) and dioxane/H₂O (4:1, 3 mL) was degassed for 5 min and heated overnight at 100° C. oil bath. The completion of reaction was monitored by analytical HPLC. The mixture was cooled and extracted with EtOAc. The combined organic layers were washed with saturated NaHCO₃ and dried over Na₂SO₄. The solvent was removed in vacuo to obtain a crude residue, which was purified by preparative-HPLC to obtain the title compound as TFA salt. ESI-MS (m/z): 472, [M+1]⁺.

Example 104 rac-((2S,3R)-3-methyl-2-(((5-(trifluoromethyl)pyridin-2-yl)amino)methyl)piperidin-1-yl)(5-methyl-2-(pyridin-3-yl)phenyl)methanone

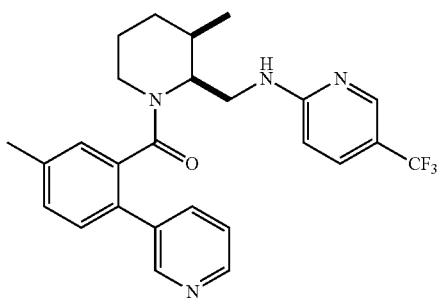

The title compound as TFA salt was prepared following the same general protocol as described for Example 103 starting with pyridin-3-ylboronic acid. ESI-MS (m/z): 469, [M+1]⁺.

Example 105 rac-((2S,3R)-3-methyl-2-(((5-(trifluoromethyl)pyridin-2-yl)amino)methyl)piperidin-1-yl)(5-methyl-2-(6-methylpyridin-3-yl)phenyl)methanone

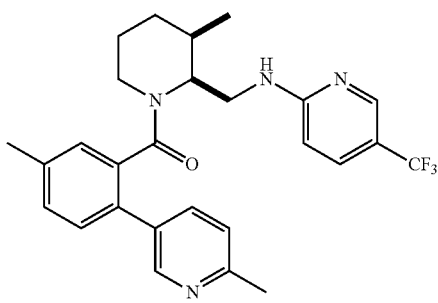

The title compound as TFA salt was prepared following the same general protocol as described for Example 103 starting with (6-methylpyridin-3-yl)boronic acid. ESI-MS (m/z): 483, [M+1]⁺.

Example 106 rac-((2S,3R)-3-methyl-2-(((5-(trifluoromethyl)pyridin-2-yl)amino)methyl)piperidin-1-yl)(5-methyl-2-(pyridin-4-yl)phenyl)methanone

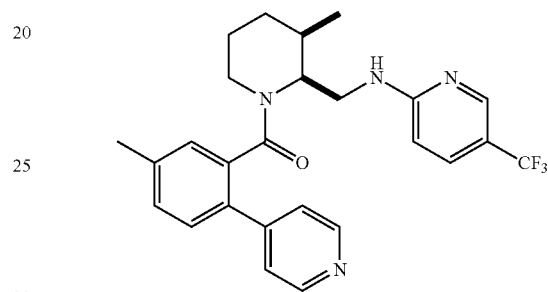

The title compound as TFA salt was prepared following the same general protocol as described for Example 103 starting with pyridin-4-ylboronic acid. ESI-MS (m/z): 469, [M+1]⁺.

Example 107 rac-((2S,3R)-3-methyl-2-(((5-(trifluoromethyl)pyridin-2-yl)amino)methyl)piperidin-1-yl)(5-methyl-2-(pyrimidin-5-yl)phenyl)methanone

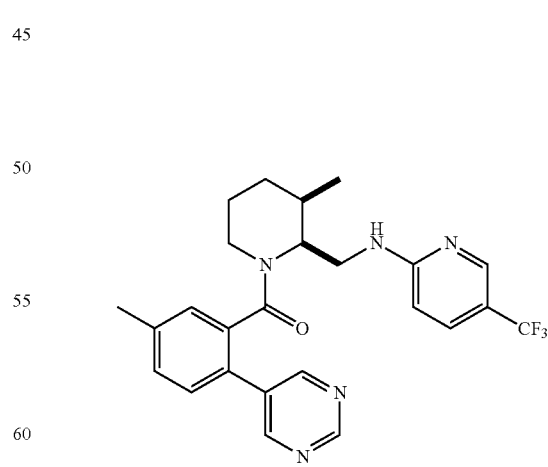

The title compound as TFA salt was prepared following the same general protocol as described for Example 103 starting with pyrimidin-5-ylboronic acid. ESI-MS (m/z): 470, [M+1]⁺.

Example 108 rac-((2S,3R)-3-methyl-2-(((5-(trifluoromethyl)pyridin-2-yl)amino)methyl)piperidin-1-yl)(5-methyl-2-(1-methyl-1H-pyrazol-5-yl)phenyl)methanone

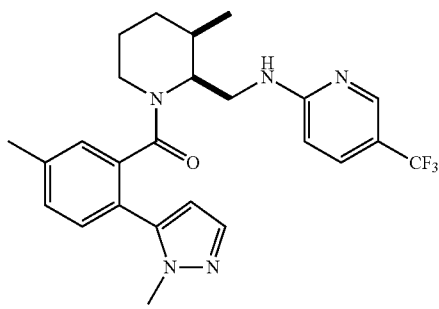 [SMILES: Cc1ccc(-c2ccnn2C)c(C(=O)N2CCC[C@@H](C)[C@H]2CNc2ccc(C(F)(F)F)cn2)c1]

The title compound as TFA salt was prepared following the same general protocol as described for Example 103 starting with 1-methyl-5-(4,4,5,5-tetramethyl-1,3,2-dioxaborolan-2-yl)-1H-pyrazole. ESI-MS (m/z): 472, [M+1]$^+$.

Example 109 rac-((2S,3R)-3-methyl-2-(((5-(trifluoromethyl)pyridin-2-yl)amino)methyl)piperidin-1-yl)(5-methyl-2-(2-(4-methylpiperazin-1-yl)pyrimidin-5-yl)phenyl)methanone

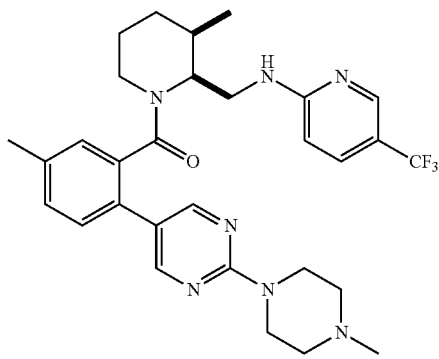 [SMILES: Cc1ccc(-c2cnc(N3CCN(C)CC3)nc2)c(C(=O)N2CCC[C@@H](C)[C@H]2CNc2ccc(C(F)(F)F)cn2)c1]

The title compound as TFA salt was prepared following the same general protocol as described for Example 103 starting with 2-(4-methylpiperazin-1-yl)-5-(4,4,5,5-tetramethyl-1,3,2-dioxaborolan-2-yl)pyrimidine. ESI-MS (m/z): 568, [M+1]$^+$.

Example 110 rac-((2S,3R)-3-methyl-2-(((5-(trifluoromethyl)pyridin-2-yl)amino)methyl)piperidin-1-yl)(5-methyl-2-(6-(4-methylpiperazin-1-yl)pyridin-3-yl)phenyl)methanone

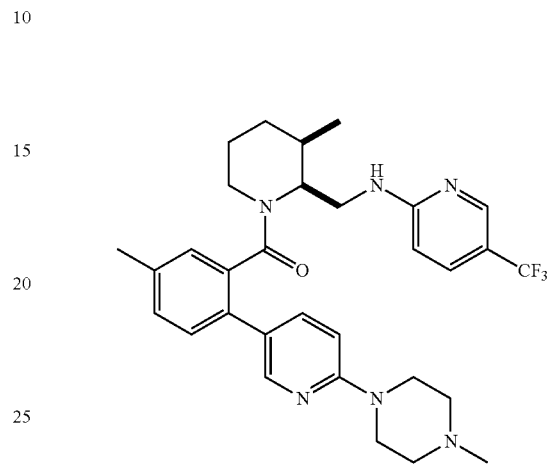

The title compound as TFA salt was prepared following the same general protocol as described for Example 103 starting with 1-methyl-4-(5-(4,4,5,5-tetramethyl-1,3,2-dioxaborolan-2-yl)pyridin-2-yl)piperazine. ESI-MS (m/z): 567, [M+1]$^+$.

Example 111 rac-((2S,3R)-3-methyl-2-(((5-(trifluoromethyl)pyridin-2-yl)amino)methyl)piperidin-1-yl)(5-methyl-2-(1-(2-morpholinoethyl)-1H-pyrazol-4-yl)phenyl)methanone

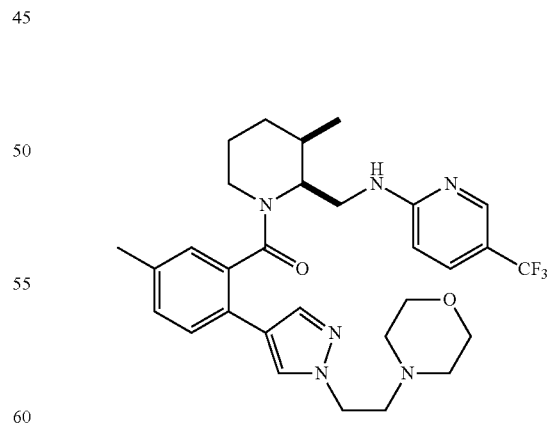

The title compound as TFA salt was prepared following the same general protocol as described for Example 103 starting with 4-(2-(4-(4,4,5,5-tetramethyl-1,3,2-dioxaborolan-2-yl)-1H-pyrazol-1-yl)ethyl)morpholine. ESI-MS (m/z): 571, [M+1]$^+$.

Example 112 rac-((2S,3R)-3-methyl-2-(((5-(trifluoromethyl)pyridin-2-yl)amino)methyl)piperidin-1-yl)(5-methyl-2-(pyrimidin-2-yl)phenyl)methanone

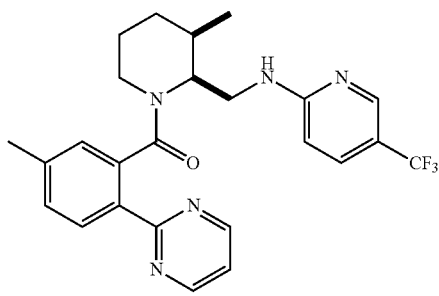

The mixture of rac-(2-bromo-5-methylphenyl)((2S,3R)-3-methyl-2-(((5-(trifluoromethyl)pyridin-2-yl)amino)methyl)piperidin-1-yl)methanone (0.03 g, 0.0638 mmol), 2-(tributylstannyl)pyrimidine (0.028 g, 0.0766 mmol), P(PPh$_3$)$_4$ (0.011 g, 0.01 mmol), Cs$_2$CO$_3$ (0.42 g, 0.13 mmol) and dioxane (1 mL) was degassed for 5 min and heated overnight at 140° C. oil bath. The completion of reaction was monitored by analytical HPLC. The mixture was cooled and extracted with EtOAc. The combine organic layers were washed with saturated NaHCO$_3$ and dried over Na$_2$SO$_4$. The solvent was removed in vacuo to obtain the crude, which was purified by preparative-HPLC to obtain the title compound as TFA salt. ESI-MS (m/z): 470, [M+1]$^+$.

Example 113 rac-((2S,3R)-3-methyl-2-(((5-(trifluoromethyl)pyridin-2-yl)amino)methyl)piperidin-1-yl)(5-methyl-2-(oxazol-2-yl)phenyl)methanone

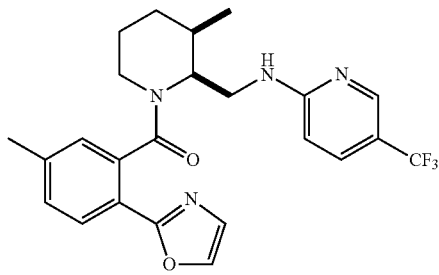 [SMILES: Cc1ccc(-c2ncco2)c(C(=O)N2CCC[C@@H](C)[C@H]2CNc2ccc(C(F)(F)F)cn2)c1]

The title compound as TFA salt was prepared following the same general protocol as described for Example 112 starting with 2-(tributylstannyl)oxazole. ESI-MS (m/z): 459, [M+1]$^+$.

Example 114 rac-((2S,3R)-3-methyl-2-(((5-(trifluoromethyl)pyridin-2-yl)amino)methyl)piperidin-1-yl)(5-methyl-2-(2H-1,2,3-triazol-2-yl)phenyl)methanone

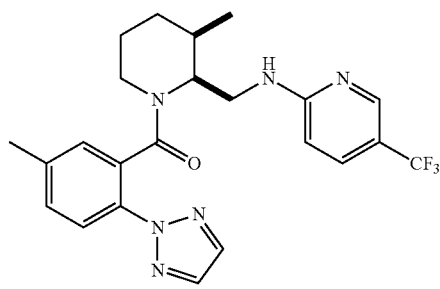 [SMILES: Cc1ccc(-n2nccn2)c(C(=O)N2CCC[C@@H](C)[C@H]2CNc2ccc(C(F)(F)F)cn2)c1]

rac-(2S,3R)-allyl 2-(((tert-butoxycarbonyl)amino)methyl)-3-methylpiperidine-1-carboxylate

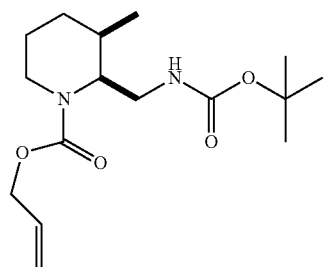 [SMILES: C=CCOC(=O)N1CCC[C@@H](C)[C@H]1CNC(=O)OC(C)(C)C]

To the mixture of rac-tert-butyl (((2S,3R)-3-methylpiperidin-2-yl)methyl)carbamate (9.48 g, 41.53 mmol) in THF (25 mL) was added NaOH (2 M, 25 mL), followed by allyl chloroformate (6.65 mL, 62.3 mmol). The mixture was stirred at RT overnight. The mixture was diluted with EtOAc, washed with H$_2$O and Brine. The solvent was removed in vacuo and the resulting crude residue was purified by chromatography on silica gel (0~100% DCM/EtOAc) to obtain the title compound as a colorless oil.

rac-(2S,3R)-allyl 2-(aminomethyl)-3-methylpiperidine-1-carboxylate

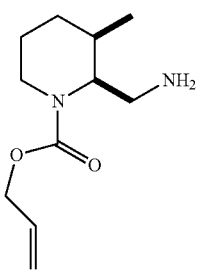

To a solution of this carbamate in CH$_2$Cl$_2$ was added TFA (1:1 v/v). The reaction was aged at room temperature and monitored for disappearance of starting material thin layer chromatography (tlc). When starting material was consumed, the reaction was concentrated in vacuo. The crude residue was taken up in EtOAc, and washed with sat aqueous NaHCO₃, brine, dried (MgSO₄), and concentrated to afford the title compound.

rac-(2S,3R)-allyl 3-methyl-2-(((5-(trifluoromethyl)pyridin-2-yl)amino)methyl)piperidine-1-carboxylate

A mixture of rac-(2S,3R)-allyl 2-(aminomethyl)-3-methylpiperidine-1-carboxylate (1.36 g, 6.43 mmol), 2-chloro-5-(trifluoromethyl)pyridine (1.75 g, 9.645 mmol), and Cs₂CO₃ (4.2 g, 12.86 mmol) in DMF (20 mL) was stirred at 80° C. for 2 days. The reaction mixture was diluted with EtOAc and washed with brine. The organic layer was separated, dried with MgSO₄ and concentrated in vacuo. The crude residue was purified by chromatography on silica gel (EtOAc/hex) to give the title compound. ESI-MS (m/z): 358, [M+1]⁺.

rac-N-(((2S,3R)-3-methylpiperidin-2-yl)methyl)-5-(trifluoromethyl)pyridin-2-amine

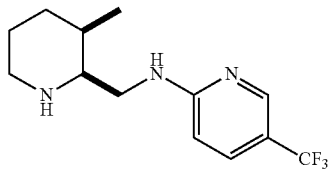 [SMILES: C[C@@H]1CCCN[C@@H]1CNc1ccc(C(F)(F)F)cn1]

To a mixture of rac-(2S,3R)-allyl 3-methyl-2-(((5-(trifluoromethyl)pyridin-2-yl)amino)methyl)piperidine-1-carboxylate (1.18 g, 3.32 mmol), Pd(PPh₃)₄ (0.384 g, 0.003 mmol) and THF (20 mL) was added morpholine (3.0 mL, 33.2 mmol). The mixture was degassed for 5 min and stirred at room temperature. The reaction was monitored for disappearance of starting material by analytical reverse-phase HPLC. After ~1 h, the reaction was concentrated in vacuo. The crude residue was taken up in EtOAc, and washed with sat aqueous NaHCO₃, brine, dried (MgSO₄), and concentrated and the resulting crude residue was purified by silica gel chromatography (0~100% DCM/EtOAc) to afford the title compound ESI-MS (m/z): 472, [M+1]⁺.

5-methyl-2-(2H-1,2,3-triazol-2-yl)benzoic acid and 5-methyl-2-(1H-1,2,3-triazol-1-yl)benzoic acid

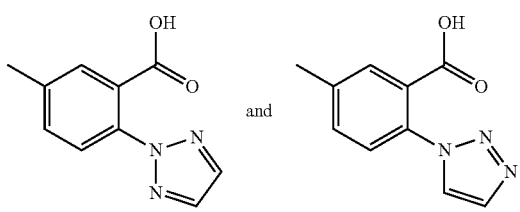

The mixture of 2-bromo-5-methylbenzoic acid (1 g, 4.65 mmol), 1,2,3-triazole (0.58 g, 8.37 mmol), (1S,2S)—N1,N2-dimethylcyclohexane-1,2-diamine (0.265 g, 1.86 mmol), Cs₂CO₃ (3.0 g, 9.3 mmol) and CuI (0.089 g, 0.465 mmol) in DMF (15 mL) was degassed and heated at 120° C. for 1 h in a microwave reactor. The reaction was cooled to RT, diluted with MeOH, and acidified with AcOH to pH4~5. The solvent was removed in vacuo to obtain the crude which was purified by silica gel chromatography (0~100% DCM/EtOAc) to obtain the faster eluting acid 5-methyl-2-(2H-1,2,3-triazol-2-yl)benzoic acid as the major product and the second eluting 5-methyl-2-(1H-1,2,3-triazol-1-yl)benzoic acid as the minor product. ESI-MS (m/z): 204, [M+1]⁺.

rac-((2S,3R)-3-methyl-2-(((5-(trifluoromethyl)pyridin-2-yl)amino)methyl)piperidin-1-yl)(5-methyl-2-(2H-1,2,3-triazol-2-yl)phenyl)methanone The title compound was synthesized following the same general protocol as described in Example 11 using 5-methyl-2-(2H-1,2,3-triazol-2-yl)benzoic acid and rac-N-(((2S,3R)-3-methylpiperidin-2-yl)methyl)-5-(trifluoromethyl)pyridin-2-amine. ESI-MS (m/z): 459, [M+1]⁺.

Example 115 rac-((2S,3R)-3-methyl-2-(((5-(trifluoromethyl)pyridin-2-yl)amino)methyl)piperidin-1-yl)(5-methyl-2-(1H-1,2,3-triazol-1-yl)phenyl)methanone

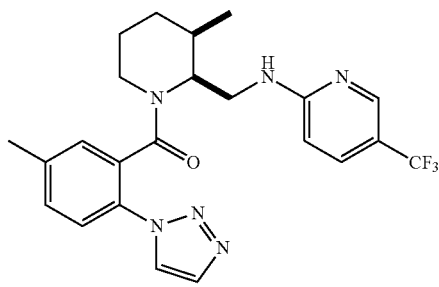

The title compound was synthesized following the same general protocol as described in Example 11 using 5-methyl-2-(1H-1,2,3-triazol-1-yl)benzoic acid and rac-N-(((2S,3R)-3-methylpiperidin-2-yl)methyl)-5-(trifluoromethyl)pyridin-2-amine. ESI-MS (m/z): 459, [M+1]⁺.

Example 116 rac-(2-(1H-imidazol-1-yl)-5-methylphenyl)((2S,3R)-3-methyl-2-(((5-(trifluoromethyl)pyridin-2-yl)amino)methyl)piperidin-1-yl)methanone

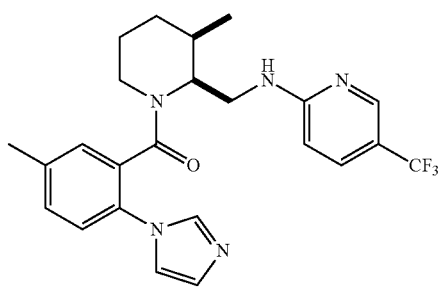 [SMILES: Cc1ccc(-n2ccnc2)c(C(=O)N2CCC[C@@H](C)[C@H]2CNc2ccc(C(F)(F)F)cn2)c1]

2-(1H-imidazol-1-yl)-5-methylbenzoic acid

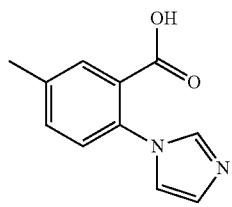

The title compound was synthesized following the same general protocol as described in Example 114 using imidazole instead of 1,2,3-triazole. ESI-MS (m/z): 203, [M+1]$^+$.

rac-(2-(1H-imidazol-1-yl)-5-methylphenyl)((2S,3R)-3-methyl-2-(((5-(trifluoromethyl)pyridin-2-yl)amino)methyl)piperidin-1-yl)methanone The title compound was synthesized following the same general protocol as described in Example 11 using 2-(1H-imidazol-1-yl)-5-methylbenzoic acid and rac-N-(((2S,3R)-3-methylpiperidin-2-yl)methyl)-5-(trifluoromethyl)pyridin-2-amine. ESI-MS (m/z): 458, [M+1]$^+$.

Example 117 rac-((2S,3R)-3-methyl-2-(((5-(trifluoromethyl)pyridin-2-yl)amino)methyl)piperidin-1-yl)(5-methyl-2-(1H-1,2,4-triazol-1-yl)phenyl)methanone

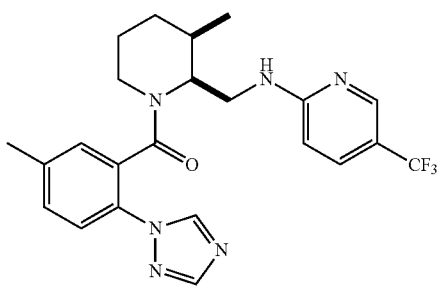 [SMILES: Cc1ccc(-n2cncn2)c(C(=O)N2CCC[C@@H](C)[C@H]2CNc2ccc(C(F)(F)F)cn2)c1]

5-methyl-2-(1H-1,2,4-triazol-1-yl)benzoic acid

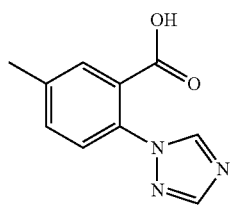

The title compound was synthesized following the same general protocol as described in Example 114 using 1H-1,2,4-triazole instead of 1,2,3-triazole. ESI-MS (m/z): 204, [M+1]$^+$.

rac-(2-(1H-imidazol-1-yl)-5-methylphenyl)((2S,3R)-3-methyl-2-(((5-(trifluoromethyl)pyridin-2-yl)amino)methyl)piperidin-1-yl)methanone The title compound was synthesized following the same general protocol as described in Example 11 using 5-methyl-2-(1H-1,2,4-triazol-1-yl)benzoic acid and rac-N-(((2S,3R)-3-methylpiperidin-2-yl)methyl)-5-(trifluoromethyl)pyridin-2-amine. ESI-MS (m/z): 459, [M+1]$^+$.

Example 118 rac-((2S,3R)-3-methyl-2-(((5-(trifluoromethyl)pyridin-2-yl)amino)methyl)piperidin-1-yl)(2-phenoxyphenyl)methanone

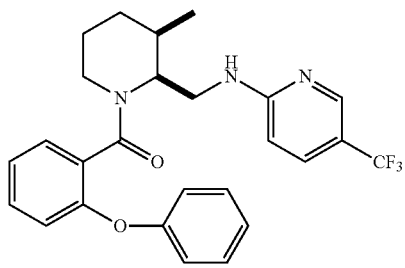 [SMILES: C[C@@H]1CCCN(C(=O)c2ccccc2Oc2ccccc2)[C@@H]1CNc1ccc(C(F)(F)F)cn1]

The title compound was synthesized following the same general protocol as described in Example 11 using 2-phenoxybenzoic acid and rac-N-(((2S,3R)-3-methylpiperidin-2-yl)methyl)-5-(trifluoromethyl)pyridin-2-amine. ESI-MS (m/z): 470, [M+1]$^+$.

Example 119 rac-((2S,3R)-3-methyl-2-(((5-(trifluoromethyl)pyridin-2-yl)amino)methyl)piperidin-1-yl)(1-phenyl-1H-pyrazol-5-yl)methanone

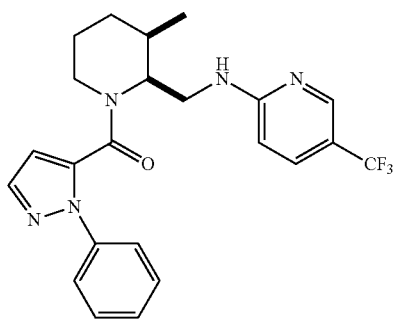 [SMILES: C[C@@H]1CCCN(C(=O)c2ccnn2-c2ccccc2)[C@@H]1CNc1ccc(C(F)(F)F)cn1]

The title compound was synthesized following the same general protocol as described in Example 11 using 1-phenyl-1H-pyrazole-5-carboxylic acid and rac-N-(((2S,3R)-3-methylpiperidin-2-yl)methyl)-5-(trifluoromethyl)pyridin-2-amine. ESI-MS (m/z): 444, [M+1]$^+$.

Example 120 rac-((2S,3R)-3-methyl-2-(((5-(trifluoromethyl)pyridin-2-yl)amino)methyl)piperidin-1-yl)(5-methyl-2-(1H-pyrazol-1-yl)phenyl)methanone

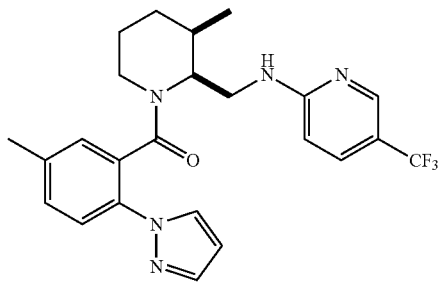

A mixture of rac-(2-bromo-5-methylphenyl)((2S,3R)-3-methyl-2-(((5-(trifluoromethyl)pyridin-2-yl)amino)methyl)piperidin-1-yl)methanone (0.0326 g, 0.0693 mmol), pyrazole (0.0094 g, 0.139 mmol), (1S,2S)—N1,N2-dimethylcyclohexane-1,2-diamine (0.004 g, 0.0277 mmol), Cs$_2$CO$_3$ (0.045 g, 0.139 mmol) and CuI (0.003 g, 0.0139 mmol) and dioxane (1.0 mL) was degassed and heated overnight at 140° C. The reaction was cooled to RT, and acidified with TFA to pH4~5. The solvent was removed in vacuo to obtain the crude which as purified by preparative-HPLC to obtain the title compound as a TFA salt. ESI-MS (m/z): 458, [M+1]$^+$.

Example 121 rac-((2S,3R)-2-(((3-chloropyrazin-2-yl)amino)methyl)-3-methylpiperidin-1-yl)(5-(4-fluorophenyl)-2-methylthiazol-4-yl)methanone

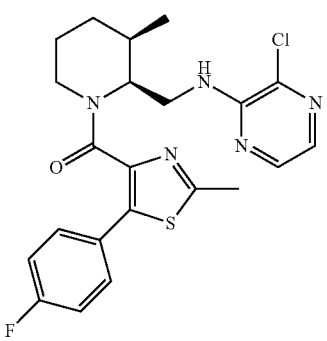 [SMILES: Cc1nc(C(=O)N2CCC[C@@H](C)[C@H]2CNc2nccnc2Cl)c(-c2ccc(F)cc2)s1]

The title compound was prepared following the same general protocol as described for Example 18 using 2,3-dichloropyrazine. MS (ESI) 460.2 (M+H)

Example 122 rac-((2S,3R)-2-(((5-chloropyrimidin-2-yl)amino)methyl)-3-methylpiperidin-1-yl)(2-(trifluoromethoxy)phenyl)methanone

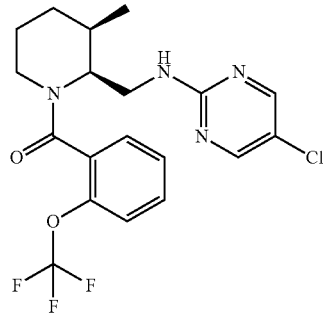 [SMILES: C[C@@H]1CCCN(C(=O)c2ccccc2OC(F)(F)F)[C@@H]1CNc1ncc(Cl)cn1]

rac-(2S,3R)-allyl 2-(((5-chloropyrimidin-2-yl)amino)methyl)-3-methylpiperidine-1-carboxylate

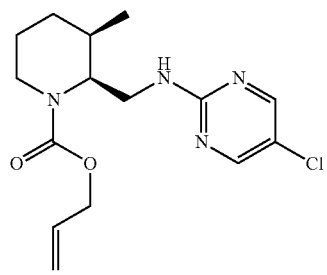 [SMILES: C=CCOC(=O)N1CCC[C@@H](C)[C@H]1CNc1ncc(Cl)cn1]

The title compound was prepared following the same general protocol as described for Example 16 using 2,5-dichloropyrimidine and rac-(2S,3R)-allyl 2-(aminomethyl)-3-methylpiperidine-1-carboxylate. MS (ESI) 325.2 (M+H)

rac-5-chloro-N-(((2S,3R)-3-methylpiperidin-2-yl)methyl)pyrimidin-2-amine

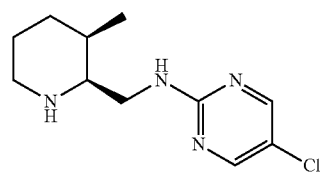 [SMILES: C[C@@H]1CCCN[C@@H]1CNc1ncc(Cl)cn1]

The title compound was prepared following the same general protocol as described for Example 114 using rac-(2S,3R)-allyl 2-(((5-chloropyrimidin-2-yl)amino)methyl)-3-methylpiperidine-1-carboxylate from the previous step. (ESI) 241.4 (M+H)

rac-((2S,3R)-2-(((5-chloropyrimidin-2-yl)amino)
methyl)-3-methylpiperidin-1-yl)(2-(trifluoromethoxy)phenyl)methanone To a solution of the aforementioned rac-5-chloro-N-(((2S,3R)-3-methylpiperidin-2-yl)methyl)pyrimidin-2-amine and diisopropylamine (3 eq) in DCM was added 2-(trifluoromethoxy)benzoyl chloride (1.2 eq) dropwise. The reaction was stirred at reflux for 3 h and concentrated in vacuo. The crude reaction mixture was purified by reverse-phase preparative HPLC to afford the title compound. (ESI) 429.1 (M+H)

Example 123 rac-((2S,3R)-2-(6-chloropyrazin-2-yl)amino)
methyl)-3-methylpiperidin-1-yl)(5-(4-fluorophenyl)-2-methylthiazol-4-yl)methanone

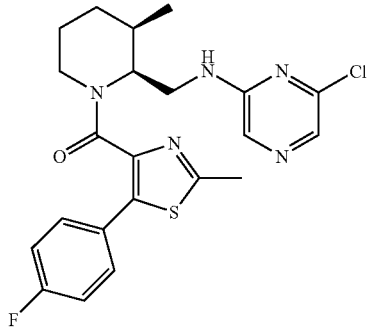 [SMILES: Cc1nc(C(=O)N2CCC[C@@H](C)[C@H]2CNc2cncc(Cl)n2)c(-c2ccc(F)cc2)s1]

The title compound was prepared following the same general protocol as described for Example 18 using 2,6-dichloropyrazine. MS (ESI) 460.2 (M+H)

Example 124 rac-2-methyl-N-(((2S,3R)-3-methyl-1-(2-methyl-5-phenylthiazole-4-carbonyl)piperidin-2-yl)methyl)
benzofuran-4-carboxamide

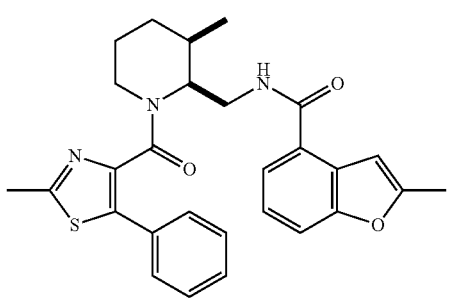

The title compound was obtained following the general protocol as described for the synthesis of Example 8 using 2-methylbenzofuran-4-carboxylic acid. MS (ESI) 488.1 (M+H).

Example 125 rac-N-(((2S,3R)-1-(5-(4-fluorophenyl)-2-methylthiazole-4-carbonyl)-3-methylpiperidin-2-yl)methyl)
quinoline-8-carboxamide

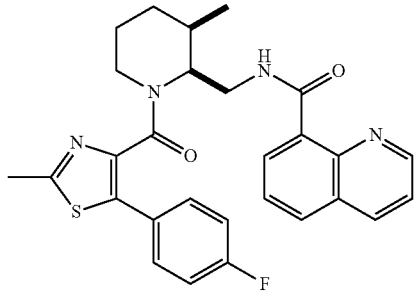 [SMILES: Cc1nc(C(=O)N2CCC[C@@H](C)[C@H]2CNC(=O)c2cccc3cccnc23)c(-c2ccc(F)cc2)s1]

The title compound was obtained following the general protocol as described for the synthesis of Example 8 using 5-(4-fluorophenyl)-2-methylthiazole-4-carboxylic acid. MS (ESI) 503.1 (M+H).

Example 126

N-(((2S,4S)-1-([1,1'-biphenyl]-2-carbonyl)-4-hydroxypyrrolidin-2-yl)methyl)quinoline-8-carboxamide

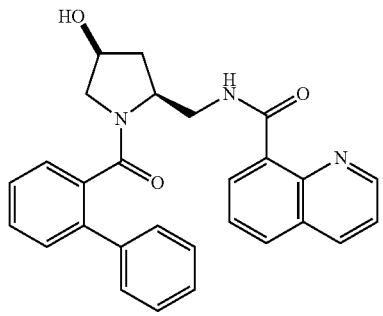 [SMILES: O=C(NC[C@@H]1C[C@H](O)CN1C(=O)c1ccccc1-c1ccccc1)c1cccc2cccnc12]

The title compound was synthesized following the same standard protocol as described in Examples 4 starting with (2S,4S)-tert-butyl 4-hydroxy-2-(hydroxymethyl)pyrrolidine-1-carboxylate. MS (ESI) 452.2 (M+H).

Example 127

N-(((2S,4S)-1-([1,1'-biphenyl]-2-carbonyl)-4-methoxypyrrolidin-2-yl)methyl)quinoline-8-carboxamide

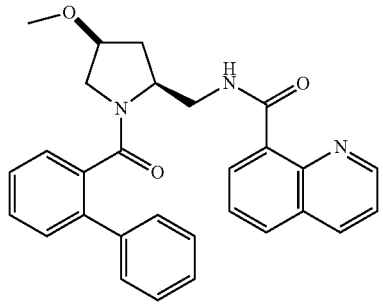 [SMILES: CO[C@H]1C[C@@H](CNC(=O)c2cccc3cccnc23)N(C(=O)c2ccccc2-c2ccccc2)C1]

To a vigorously stirred suspension of the product from the previous example in $CH_2Cl_2$ and 45% $HBF_4$(aq) at 0° C. was added in three portions 0.1 mL 2M TMS-CH$_2$N$_2$ hexane solution dropwise over 10 minutes. The reaction was allowed to stir at room temperature overnight. The crude mixture was loaded directly onto a reverse-phase prep-HPLC and two peaks were collected, the first being the desired product, the second being recovered starting material. MS (ESI) 466.2 (M+H).

Example 128

N-((2S,4R)-1-(Biphenylcarbonyl)-4-fluoropyrrolidin-2-yl)methyl)quinoline-8-carboxamide

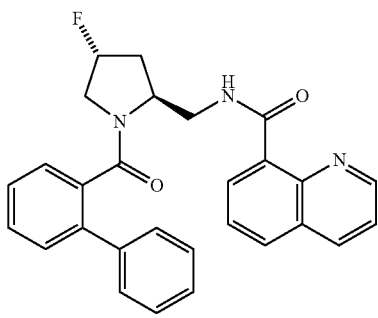 [SMILES: O=C(NC[C@@H]1C[C@@H](F)CN1C(=O)c1ccccc1-c1ccccc1)c1cccc2cccnc12]

The title compound was synthesized following the same standard protocol as described in Examples 5 starting with N-(((2S,4S)-1-([1,1'-biphenyl]-2-carbonyl)-4-hydroxypyrrolidin-2-yl)methyl)quinoline-8-carboxamide. MS (ESI) 454.1 (M+H).

Example 129

N-(((2S,4R)-1-([1,1'-biphenyl]-2-carbonyl)-4-methoxypyrrolidin-2-yl)methyl)quinoline-8-carboxamide

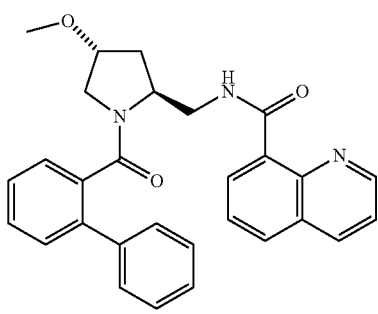 [SMILES: CO[C@@H]1C[C@@H](CNC(=O)c2cccc3cccnc23)N(C(=O)c2ccccc2-c2ccccc2)C1]

The title compound was made following the same general protocol as described for Example 127 using the product from Example 4. MS (ESI) 466.2 (M+H).

Example 130

N-(((2R,3S)-3-hydroxy-1-(2-methyl-4-phenylthiazole-5-carbonyl)pyrrolidin-2-yl)methyl)quinoline-8-carboxamide

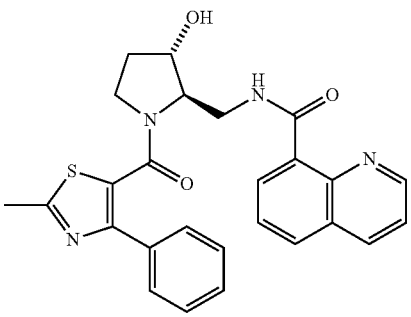 [SMILES: Cc1nc(-c2ccccc2)c(C(=O)N2CC[C@H](O)[C@H]2CNC(=O)c2cccc3cccnc23)s1]

(2R,3S)-tert-butyl 2-(aminomethyl)-3-hydroxypyrrolidine-1-carboxylate

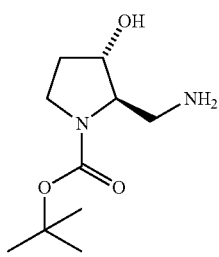

To a solution of (2S,3S)-1-(tert-butoxycarbonyl)-3-hydroxypyrrolidine-2-carboxylic acid in THF at 0° C. was added BH$_3$-DMS. The reaction was allowed to warm to room temperature overnight, and then quenched by the careful addition of MeOH. The reaction was concentrated in vacuo to give (2R,3S)-tert-butyl 3-hydroxy-2-(hydroxymethyl)pyrrolidine-1-carboxylate as a near colorless oil which was used without further purification.

(2R,3S)-tert-butyl 3-hydroxy-2-(hydroxymethyl)pyrrolidine-1-carboxylate was converted to the title compound following the same general protocol for Mitsunobu reaction with phthalimide followed by hydrazine cleavage as described for Example 32 Part V and Part VI.

(2R,3S)-tert-butyl 3-hydroxy-2-((quinoline-8-carboxamido)methyl)pyrrolidine-1-carboxylate

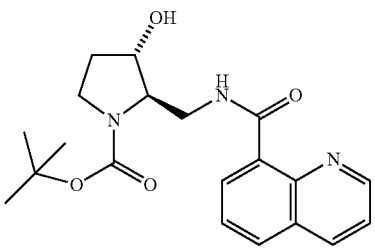 [SMILES: CC(C)(C)OC(=O)N1CC[C@H](O)[C@H]1CNC(=O)c1cccc2cccnc12]

The title compound was prepared according general procedure A using quinoline-8-carboxylic acid and the product from the previous step. MS (ESI) 371.93 (M+H).

N-(((2R,3S)-3-hydroxy-1-(2-methyl-4-phenylthiazole-5-carbonyl)pyrrolidin-2-yl)methyl)quinoline-8-carboxamide To a solution of the product from the previous step in CH$_2$Cl$_2$ was added TFA. The reaction was aged at room temperature for 1 h, and then concentrated in vacuo to give the crude amine as a TFA salt. This crude amine was coupled with 2-methyl-4-phenylthiazole-5-carboxylic acid according to general procedure A to give the title compound as a pale yellow solid. MS (ESI) 473.1 (M+H).

Example 131

(3S,5S)-1-([1,1'-biphenyl]-2-carbonyl)-5-((quinoline-8-carboxamido)methyl)pyrrolidin-3-yl acetate

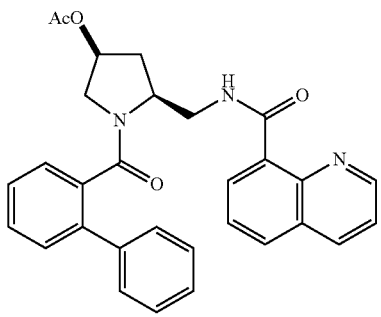 [SMILES: CC(=O)O[C@H]1C[C@@H](CNC(=O)c2cccc3cccnc23)N(C(=O)c2ccccc2-c2ccccc2)C1]

To a 0° C. solution of the product from Example 4 in THF was added Ph$_3$P, acetic acid, followed by diisopropylazodicarboxylate (DIAD). The reaction was allowed to warm to room temperature overnight. After 18 h, the reaction mixture was directly loaded onto a reverse-phase preparative HPLC, and the desired product was isolated as a colorless solid. MS (ESI) 494.1 (M+H).

Example 132

(R)—N-((1-(2-methyl-4-phenylthiazole-5-carbonyl)-3-oxopyrrolidin-2-yl)methyl)quinoline-8-carboxamide

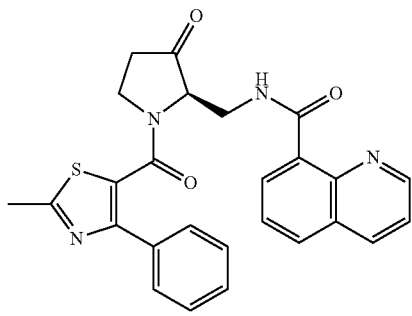 [SMILES: Cc1nc(-c2ccccc2)c(C(=O)N2CCC(=O)[C@H]2CNC(=O)c2cccc3cccnc23)s1]

To a −78° C. solution of (COCl)$_2$ in CH$_2$Cl$_2$ was added a solution of DMSO in CH$_2$Cl$_2$. After 20 min, a solution of the product from Example 130 in CH$_2$Cl$_2$ was added dropwise. The reaction was aged at −78° C. for 3 h, and then allowed to warm to room temperature over 1 h. The reaction mixture was concentrated in vacuo to give a beige solid which was purified by chromatography on silica gel to give the title compound as a colorless solid. MS (ESI) 471.1 (M+H).

Example 133

(R)—N-((3,3-difluoro-1-(2-methyl-4-phenylthiazole-5-carbonyl)pyrrolidin-2-yl)methyl)quinoline-8-carboxamide

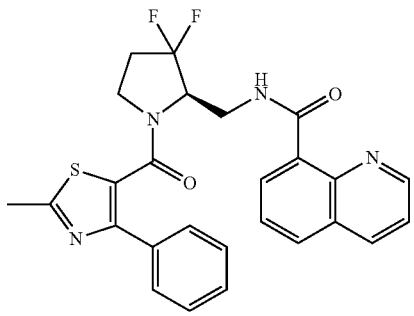 [SMILES: Cc1nc(-c2ccccc2)c(C(=O)N2CCC(F)(F)[C@H]2CNC(=O)c2cccc3cccnc23)s1]

The title compound was prepared following the same general protocol as described for Example 7. MS (ESI) 493.1 (M+H).

Example 134

N-(((2S,4R)-4-hydroxy-1-(2-methyl-4-phenylthiazole-5-carbonyl)piperidin-2-yl)methyl)quinoline-8-carboxamide

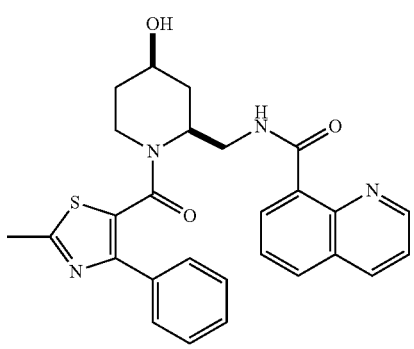 [SMILES: Cc1nc(-c2ccccc2)c(C(=O)N2CC[C@@H](O)C[C@H]2CNC(=O)c2cccc3cccnc23)s1]

The title compound was prepared following the same standard protocols as described for Example 130 starting with (2S,4R)-1-(tert-butoxycarbonyl)-4-hydroxypiperidine-2-carboxylic acid. MS (ESI) 487.1 (M+H).

Example 135

(S)—N-((1-(2-methyl-4-phenylthiazole-5-carbonyl)-4-oxopiperidin-2-yl)methyl)quinoline-8-carboxamide

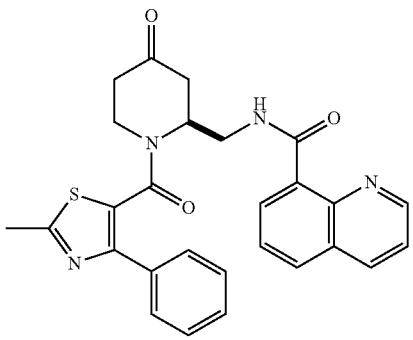 [SMILES: Cc1nc(-c2ccccc2)c(C(=O)N2CCC(=O)C[C@H]2CNC(=O)c2cccc3cccnc23)s1]

The title compound was prepared following the same standard protocol as described for Example 132 starting with the product from Example 134. MS (ESI) 485.1 (M+H).

Example 136

(S)—N-((4,4-difluoro-1-(2-methyl-4-phenylthiazole-5-carbonyl)piperidin-2-yl)methyl)quinoline-8-carboxamide

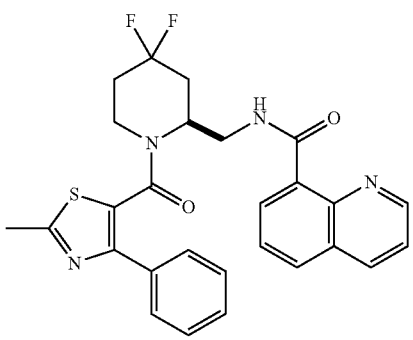 [SMILES: Cc1nc(-c2ccccc2)c(C(=O)N2CCC(F)(F)C[C@H]2CNC(=O)c2cccc3cccnc23)s1]

The title compound was prepared following the same standard protocol as described for Example 133 starting with the product from Example 135. MS (ESI) 507.1 (M+H).

Example 137 rac-N-(((2S,3S)-3-methyl-1-(2-methyl-5-phenylthiazole-4-carbonyl)piperidin-2-yl)methyl)quinoline-8-carboxamide

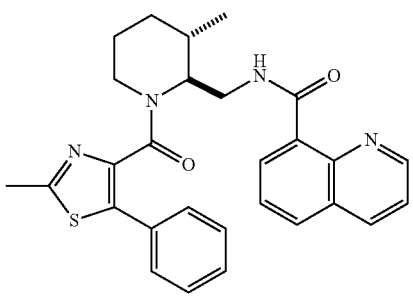 [SMILES: Cc1nc(C(=O)N2CCC[C@H](C)[C@H]2CNC(=O)c2cccc3cccnc23)c(-c2ccccc2)s1]

rac-tert-butyl (((2S,3S)-3-methyl-1-(2-methyl-5-phenylthiazole-4-carbonyl)piperidin-2-yl)methyl)carbamate

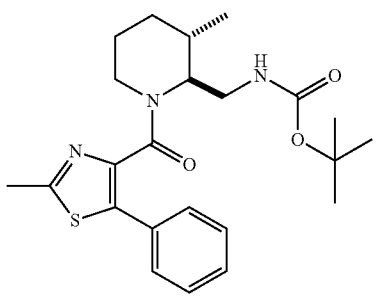 [SMILES: Cc1nc(C(=O)N2CCC[C@H](C)[C@H]2CNC(=O)OC(C)(C)C)c(-c2ccccc2)s1]

The title compound was made following General Procedure A using tert-butyl (((2S,3S)-3-methylpiperidin-2-yl)methyl)carbamate from Example 95 and 2-methyl-5-phenylthiazole-4-carboxylic acid. MS (ESI) 429.83 (M+H).

rac-N-(((2S,3S)-3-methyl-1-(2-methyl-5-phenylthiazole-4-carbonyl)piperidin-2-yl)methyl)quinoline-8-carboxamide The title compound was made following BOC-deprotection of the compound from the previous step using TFA/CH$_2$Cl$_2$, followed by coupling to quinoline-8-carboxylic acid using the standard protocol as describe in General Procedure A. The product was isolated as a beige solid. MS (ESI) 485.1 (M+H).

Example 138 rac-N-(((2S,3R)-1-(2-methyl-5-phenylthiazole-4-carbonyl)-3-(trifluoromethyl)piperidin-2-yl)methyl)quinoline-8-carboxamide

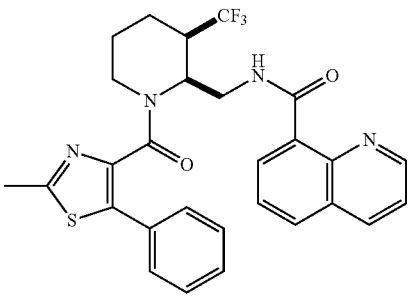 [SMILES: Cc1nc(C(=O)N2CCC[C@@H](C(F)(F)F)[C@H]2CNC(=O)c2cccc3cccnc23)c(-c2ccccc2)s1]

271 rac-tert-butyl (((2S,3R)-1-(2-methyl-5-phenylthiaz-
ole-4-carbonyl)-3-(trifluoromethyl)piperidin-2-yl)
methyl)carbamate

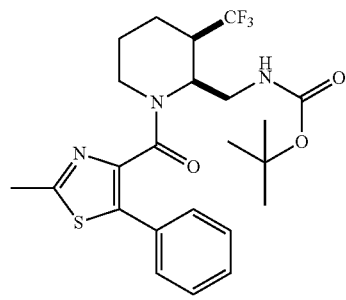 [SMILES: Cc1nc(C(=O)N2CCC[C@@H](C(F)(F)F)[C@H]2CNC(=O)OC(C)(C)C)c(-c2ccccc2)s1]

The title compound was made following General Procedure A using tert-butyl (((2S,3R)-3-(trifluoromethyl)piperidin-2-yl)methyl)carbamate from Example 13 and 2-methyl-5-phenylthiazole-4-carboxylic acid. MS (ESI) 483.8 (M+H).

rac-N-(((2S,3R)-1-(2-methyl-5-phenylthiazole-4-
carbonyl)-3-(trifluoromethyl)piperidin-2-yl)methyl)
quinoline-8-carboxamide The title compound was made following BOC-deprotection of the compound from the previous step using TFA/CH₂Cl₂, followed by coupling to quinoline-8-carboxylic acid using the standard protocol as describe in General Procedure A. The product was isolated as a near colorless solid. MS (ESI) 539.14 (M+H).

Example 139 rac-N-(((2S,3R)-1-(2-methyl-5-phenylthiazole-4-
carbonyl)-3-(trifluoromethyl)piperidin-2-yl)methyl)
benzofuran-4-carboxamide

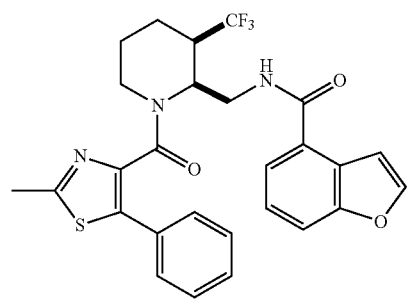 [SMILES: Cc1nc(C(=O)N2CCC[C@@H](C(F)(F)F)[C@H]2CNC(=O)c2cccc3occc23)c(-c2ccccc2)s1]

The title compound was made following the same general protocol as described for Example 138 using benzofuran-4-carboxylic acid. MS (ESI) 528.1 (M+H).

272

Example 140 rac-N-(((1s,4s)-2-([1,1'-biphenyl]-2-carbonyl)-2-
azabicyclo[2.2.2]octan-3-yl)methyl)quinoline-8-
carboxamide

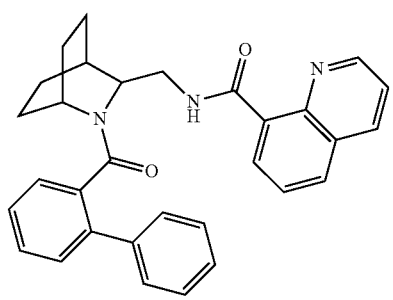 [SMILES: O=C(NCC1C2CCC(CC2)N1C(=O)c1ccccc1-c1ccccc1)c1cccc2cccnc12]

rac-(1s,4s)-2-azabicyclo[2.2.2]octan-3-ylmethanol

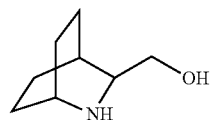

The title compound was prepared following General Procedure O starting with commercially available (1s,4s)-ethyl 2-azabicyclo[2.2.2]octane-3-carboxylate. ¹H NMR (CDCl₃, 400 MHz) δ 3.7-3.6 (m, 1H), 3.6-3.48 (m, 2H), 3.2 (t, 1H), 2.6-2.35 (m, 2H), 1.8-1.4 (m, 5H), 1.3-1.1 (m, 2H), 1.1-0.9 (m, 1H).

[1,1'-biphenyl]-2-yl((1s,4s)-3-(hydroxymethyl)-2-
azabicyclo[2.2.2]octan-2-yl)methanone

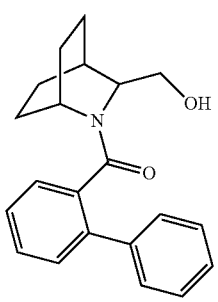 [SMILES: O=C(c1ccccc1-c1ccccc1)N1C2CCC(CC2)C1CO]

The title compound was prepared following General Procedure A starting with the product from the previous step and [1,1'-biphenyl]-2-carboxylic acid.

273 rac-[1,1'-biphenyl]-2-yl((1s,4s)-3-(aminomethyl)-2-azabicyclo[2.2.2]octan-2-yl)methanone

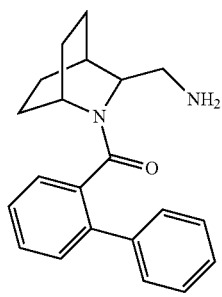 [SMILES: NCC1C2CCC(CC2)N1C(=O)c1ccccc1-c1ccccc1]

The title compound was prepared following General Procedure C starting with the product from the previous step. MS (ESI) 321.1 (M+H).

rac-N-(((1s,4s)-2-([1,1'-biphenyl]-2-carbonyl)-2-azabicyclo[2.2.2]octan-3-yl)methyl)quinoline-8-carboxamide The title compound was prepared following General Procedure A starting with the product from the previous step and quinoline-8-carboxylic acid. MS (ESI) 476.2 (M+H).

Example 141 rac-N-(((1s,4s)-2-(2-methyl-5-phenylthiazole-4-carbonyl)-2-azabicyclo[2.2.2]octan-3-yl)methyl)quinoline-8-carboxamide

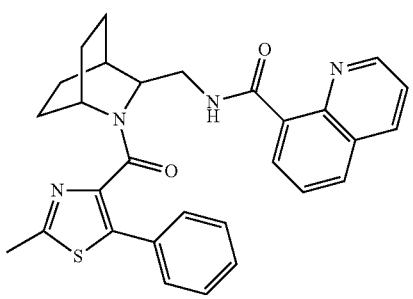 [SMILES: Cc1nc(C(=O)N2C3CCC(CC3)C2CNC(=O)c2cccc3cccnc23)c(-c2ccccc2)s1]

The title compound was prepared following same general protocol as described for Example 140, but using 2-methyl-5-phenylthiazole-4-carboxylic acid. MS (ESI) 497.2 (M+H).

Additional synthetic examples are described in the following procedures for Examples A1 to A389 P.

274

Example A1

(2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone

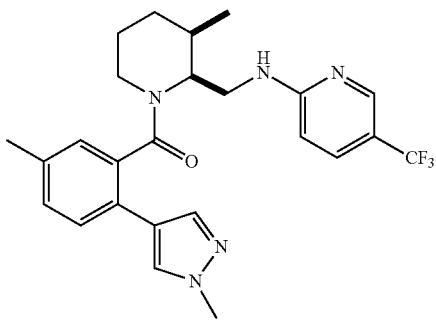 [SMILES: Cc1ccc(-c2cnn(C)c2)c(C(=O)N2CCC[C@@H](C)[C@H]2CNc2ccc(C(F)(F)F)cn2)c1]

Step 1. rac-3-Methylpiperidine-2-carboxylic acid hydrochloride

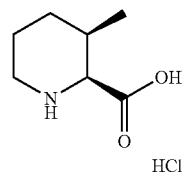

3-Methylpicolinic acid (50 g, 365 mmol) was dissolved in 400 ml of EtOH:H$_2$O (1:1) with 60 ml of aq. HCl (32%). PtO$_2$ (5 g) was then added and the reaction stirred at room temperature under a hydrogen balloon until NMR indicated completion. The reaction was filtered through diatomaceous earth and concentrated to yield the title compound as a white solid which was used without further purification (60.5 g, 92%). $^1$H NMR (MeOD, 400 MHz) δ 4.13-4.11 (m, 1H), 3.40-3.33 (m, 1H), 3.05-2.99 (m, 1H), 2.61-2.58 (m, 1H), 1.92-1.72 (m, 4H), 1.09 (d, J=7.0 Hz, 3H). MS (ESI) 452.16 (M+H).

Step 2. rac-1-((Benzyloxy)carbonyl)-3-methylpiperidine-2-carboxylic acid

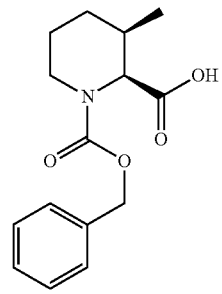 [SMILES: C[C@@H]1CCCN(C(=O)OCc2ccccc2)[C@@H]1C(=O)O]

3-Methylpiperidine-2-carboxylic acid hydrochloride (28.5 g, 31.6 mmol) was dissolved in (1:1) 2 M NaOH/THF (600 ml) and cooled to 0° C. Benzyl chloroformate (31.57 ml, 222 mmol) was then added dropwise and the reaction was stirred overnight. Toluene was then added and organic layer discarded to remove unreacted chloroformate. The aqueous layer was made acidic (pH=2) with conc. HCl and the product was extracted with EtOAc, dried (MgSO₄), and concentrated in vacuo to give a crude residue which was used without further purification (41.6 g, 94.5%). ¹H NMR (CDCl₃, 400 MHz) δ 7.40-7.37 (m, 5H), 5.19 (m, 2H), 4.95-4.72 (m, 1H), 4.14-4.03 (m, 1H), 3.36-3.25 (m, 1H), 1.93-1.53 (m, 5H), 1.20-1.05 (m, 3H).

Step 3. D-Tyrosine Hydrazide

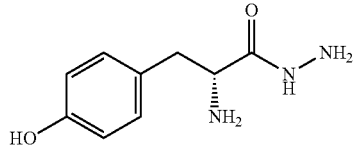 [SMILES: NNC(=O)[C@H](N)Cc1ccc(O)cc1]

D-Tyrosine methyl ester (30 g, 129 mmol, 99% ee) was dissolved in 150 ml of methanol and stirred until dissolved. Hydrazine hydrate (23 ml, 453 mmol) was then added and solution stirred overnight. Methanol was removed at reduced pressure and saturated NaHCO₃ was added (150 ml). The product was precipitated, filtered and dried to yield the title compound as a white powder (23.5 g, 93%).

¹H NMR (CD₃OD, 400 MHz) δ 7.03 (ad, J=8.8 Hz, 2H), 6.72 (ad, J=8.8 Hz, 2H), 3.44 (t, J=6.8 Hz, 1H), 2.91-2.86 (m, 1H), 2.76-2.71 (m, 1H). ESI-MS (m/z): 196.1 [M+1]⁺.

Step 4A. (2S,3R)-1-((Benzyloxy)carbonyl)-3-methylpiperidine-2-carboxylate D-tyrosine hydrazide salt

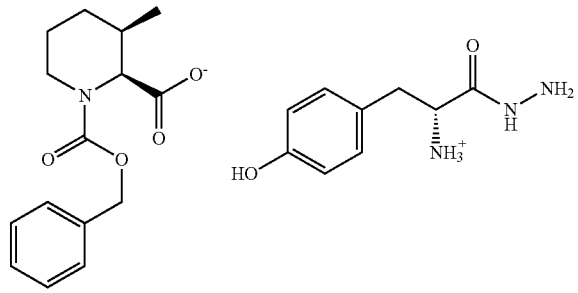 [SMILES: C[C@@H]1CCCN(C(=O)OCc2ccccc2)[C@@H]1C(=O)[O-] ; NNC(=O)[C@H](N)Cc1ccc(O)cc1]

rac-1-(Benzyloxy)carbonyl)-3-methylpiperidine-2-carboxylic acid (41.6 g, 150 mmol) was dissolved in 100 ml of methanol and 300 ml of isopropanol. D-Tyrosine Hydrazide (11.71 g, 60 mmol) was added to give a heterogenous mixture which was heated to reflux. Methanol was added in 100 ml portions until a homogenous solution was formed. The reaction was stirred for 1 h and then allowed to cool to room temperature overnight to yield thick slurry. The reaction mixture was filtered and washed with isopropanol to yield the title compound as a white solid with 92.0% ee (23 g, 81%). The white solid was again dissolved in isopropanol (1.2 L) and heated at reflux until homogenous. Reaction was stirred overnight to yield a slurry which was filtered and washed with isopropanol to yield the title compound as a white solid with 98.9% ee (21 g, 73%).

Step 4B. (2R,3S)-1-((Benzyloxy)carbonyl)-3-methylpiperidine-2-carboxylate D-tyrosine hydrazide salt

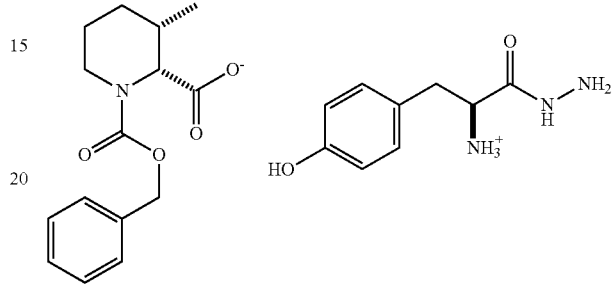

The 2R,3S enantiomer was prepared in the same fashion as described above in >98% ee using L-tyrosine hydrazide.

Step 5. (2S,3R)-Benzyl 2-(hydroxymethyl)-3-methylpiperidine-1-carboxylate

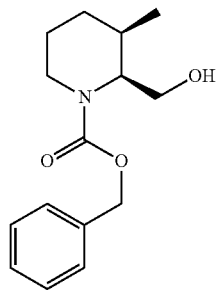 [SMILES: C[C@@H]1CCCN(C(=O)OCc2ccccc2)[C@@H]1CO]

(2S,3R)-1-((Benzyloxy)carbonyl)-3-methylpiperidine-2-carboxylate D-tyrosine hydrazide salt (17 g, 37.3 mmol) was dissolved in ethyl acetate and washed with 1 M HCl (150 ml×3), brine (100 ml) dried (MgSO₄), and concentrated to yield a clear oil (10.2 g, 98%). The clear oil was then dissolved in 150 ml of THF and cooled to 0° C. 1 M Borane THF complex solution (40.4 ml, 40.4 mmol) was then added dropwise over 15 min. The reaction was then allowed to warm to room temperature overnight and then quenched with water at 0° C. The reaction mixture was diluted with EtOAc and washed with water, brine, dried (MgSO₄), and concentrated. The crude residue was concentrated in vacuo to give the title compound as a clear oil which was used without further purification (8.7 g, 89%). ESI-MS (m/z): 263.93 [M+1]⁺.

Step 6. (2S,3R)-Benzyl 2-((1,3-dioxoisoindolin-2-yl)methyl)-3-methylpiperidine-1-carboxylate

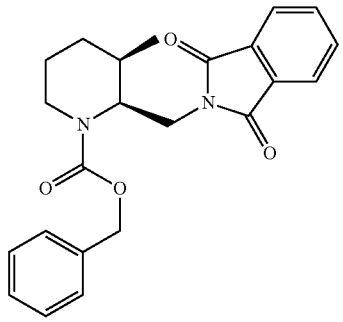 [SMILES: C[C@@H]1CCCN(C(=O)OCc2ccccc2)[C@@H]1CN1C(=O)c2ccccc2C1=O]

A solution of triphenylphosphine (21.5 g, 82 mmol) in 30 ml of THF was cooled to 0° C. DIAD (16.1 ml, 82 mmol) was then added dropwise and reaction stirred for 20 minutes. A solution of (2S,3R)-benzyl 2-(hydroxymethyl)-3-methyl-piperidine-1-carboxylate (8.7 g, 32.9 mmol) in 15 ml THF was then added dropwise and stirred at 0° C. for 30 minutes. Phthalimide (6.3 g, 42.7 mmol) was then added and the reaction was warmed to room temperature overnight. The resulting suspension was concentrated in vacuo, diluted with EtOAc and washed with water, brine, dried (MgSO$_4$), and concentrated. The crude residue was purified by chromatography on silica gel (EtOAc/hexanes) to give the title compound (14.2 g, 110%, DIAD contamination), which was used without further purification. $^1$H NMR (CDCl$_3$, 400 MHz) δ 7.72-7.71 (m, 1H), 7.62-7.60 (m, 3H), 7.17-7.13 (m, 3H), 7.05-7.04 (m, 1H), 6.98-6.96 (m, 1H), 4.76-4.69 (m, 1H), 4.54-4.39 (m, 1H), 4.03-3.98 (m, 2H), 3.63-3.54 (m, 1H), 3.25-3.07 (m, 1H), 1.91-1.80 (m, 1H), 1.73-1.54 (m, 2H), 1.47-1.25 (m, 2H), 1.07-1.04 (m, 3H). ESI-MS (m/z): 263.93 [M+1]$^+$.

Step 7. 2-(((2S,3R)-3-methylpiperidin-2-yl)methyl)isoindoline-1,3-dione

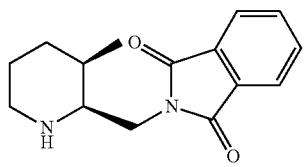 [SMILES: C[C@@H]1CCCN[C@@H]1CN1C(=O)c2ccccc2C1=O]

To a solution of (2S,3R)-benzyl 2-((1,3-dioxoisoindolin-2-yl)methyl)-3-methylpiperidine-1-carboxylate (14.2 g, 36.1 mmol) in acetic acid (40 ml) was added 10% Pd/C (1.5 g). The reaction was then stirred under H$_2$ until HPLC indicated complete removal of the Cbz group. The reaction was the filtered through diatomaceous earth and concentrated. The crude residue was then dissolved in EtOAc and washed with saturated NaHCO$_3$, brine, dried (MgSO$_4$), and concentrated to yield the title compound as a yellow solid (8.2 g, 88%). $^1$H NMR (CDCl$_3$, 400 MHz) δ 7.82-7.81 (m, 2H), 7.71-7.70 (m, 2H), 4.19-4.15 (m, 1H), 3.81-3.78 (m, 2H), 3.44 (m, 2H), 2.96 (m, 1H), 2.31 (m, 1H), 1.79-1.67 (m, 2H), 1.27 (d, J=4.0 Hz, 3H). ESI-MS (m/z): 259.2 [M+1]$^+$.

Step 8. Methyl 2-bromo-5-methylbenzoate

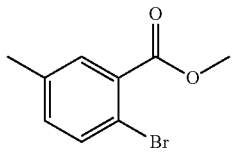

2-Bromo-5-methylbenzoic acid (9.3 g, 43.4 mmol) was dissolved in MeOH (100 mL) and then cat. conc. H$_2$SO$_4$ was added. The mixture was refluxed at 100° C. overnight. The mixture was cooled to RT and the solvent was removed at reduced pressure. The crude residue was dissolved with EtOAc, and washed with water twice, followed by saturated NaHCO$_3$ and brine, dried over anhydrous Na$_2$SO$_4$. The solvent was removed in vacuo to obtain the title compound with no further purification.

Step 9. Methyl 5-methyl-2-(1-methyl-1H-pyrazol-4-yl)benzoate

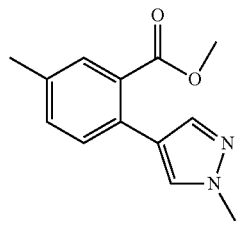

A mixture of methyl 2-bromo-5-methylbenzoate (1.01 g, 4.41 mmol), 1-methyl-4-(4,4,5,5-tetramethyl-1,3,2-dioxaborolan-2-yl)-1H-pyrazole (1.1 g, 5.28 mmol), Pd(PPh$_3$)$_4$ (0.764 g, 0.66 mmol), K$_2$CO$_3$ (1.83 g, 13.23 mmol) and dioxane/H$_2$O (4:1, 15 mL) was degassed for 10 min and then heated overnight at 100° C. The mixture was cooled, diluted with brine and extracted with EtOAc. The combined organic layers were washed with saturated NaHCO$_3$ and dried over Na$_2$SO$_4$. The solvent was removed in vacuo to obtain the crude material, which was purified by silica gel chromatography to obtain the title compound. ESI-MS (m/z): 231 [M+1]$^+$.

Step 10. 5-Methyl-2-(1-methyl-1H-pyrazol-4-yl)benzoic acid

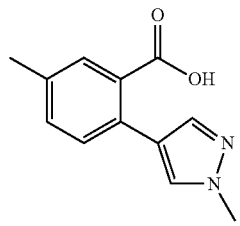

Methyl 5-methyl-2-(1-methyl-1H-pyrazol-4-yl)benzoate (~1 g, ~4.41 mmol) was dissolved in MeOH/H$_2$O (4:1, 50 mL) and then LiOH (0.36 g, 15 mmol) was added. The mixture was refluxed for 2 h at 100° C. The reaction was monitored by anal. HPLC. When starting material was consumed, the mixture was cooled to 0° C. and 2M HCl solution was added bring the pH ~4. MeOH was removed in vacuo and the acid was precipitated. The acid was collected by filtration and dried in vacuo and used without further purification. ESI-MS (m/z): 217 [M+1]⁺.

Step 11. 2-(((2S,3R)-3-Methyl-1-(5-methyl-2-(1-methyl-1H-pyrazol-4-yl)benzoyl)piperidin-2-yl)methyl)isoindoline-1,3-dione

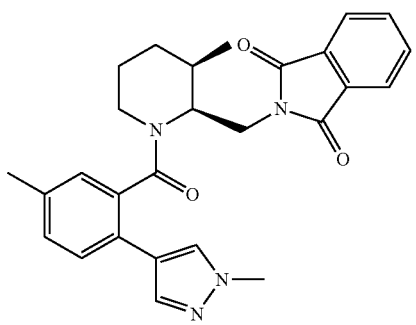 [SMILES: Cc1ccc(-c2cnn(C)c2)c(C(=O)N2CCC[C@@H](C)[C@H]2CN2C(=O)c3ccccc3C2=O)c1]

A mixture of 2-(((2S,3R)-3-methylpiperidin-2-yl)methyl) isoindoline-1,3-dione (0.66 g, 2.55 mmol), 5-methyl-2-(1-methyl-1H-pyrazol-4-yl)benzoic acid (0.5 g, 2.318 mmol), diisopropyl ethyl amine (0.7 mL, 6.954 mmol) and HATU (0.881 g, 2.318 mmol) in DCM was stirred at room temperature for 1 h. The reaction mixture was diluted with DCM and washed with sat'd NaHCO₃ and brine successively. The organic layer was separated, dried with MgSO₄ and concentrated in vacuo. The crude product was purified by chromatography on silica gel (EtOAc/hex) to afford the title compound. ESI-MS (m/z): 457 [M+1]⁺.

Step 12. ((2S,3R)-2-(Aminomethyl)-3-methylpiperidin-1-yl)(5-methyl-2-(1-methyl-1H-pyrazol-4-yl)phenyl)methanone

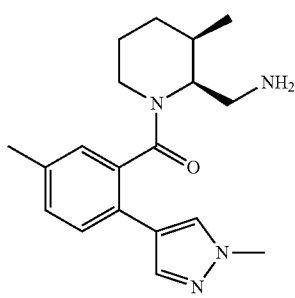 [SMILES: Cc1ccc(-c2cnn(C)c2)c(C(=O)N2CCC[C@@H](C)[C@H]2CN)c1]

A mixture of 2-(((2S,3R)-3-methyl-1-(5-methyl-2-(1-methyl-1H-pyrazol-4-yl)benzoyl)piperidin-2-yl)methyl) isoindoline-1,3-dione (0.67 g, 1.5 mmol) and hydrazine hydrate (0.46 g, 9.27 mmol) in MeOH (10 mL) was heated at 60° C. for 2 h. When the reaction was judged complete by analytical HPLC, the mixture was cooled to room temperature and the solvent was removed in vacuo. The crude was dissolved in EtOAc and washed with 2 N NaOH (2x), brine, and then dried (Na₂SO₄). The solvent was removed in vacuo to obtain the title compound which was used without further purification. ESI-MS (m/z): 327 [M+1]⁺.

Step 13. ((2S,3R)-3-Methyl-2-(((5-(trifluoromethyl) pyridin-2-yl)amino)methyl)piperidin-1-yl)(5-methyl-2-(1-methyl-1H-pyrazol-4-yl)phenyl)methanone A mixture of ((2S,3R)-2-(aminomethyl)-3-methylpiperidin-1-yl)(5-methyl-2-(1-methyl-1H-pyrazol-4-yl)phenyl) methanone (0.282 g, 0.864 mmol) and 2-fluoro-5-(trifluoromethyl)pyridine (0.29 g, 1.728 mmol) and anhydrous K₂CO₃ (0.24 g, 1.73 mmol) in DMF (10 mL) was heated at 100° C. overnight. The mixture was cooled to room temperature and the solvent was removed in vacuo. The crude was dissolved in EtOAc and washed with sat'd NaHCO₃, brine, and dried (MgSO₄). The solvent was removed and the crude was purified by chromatography on silica gel (EtOAc/ hexanes) to afford the title compound. ¹H NMR (CDCl₃, 400 MHz) δ 8.31-8.32 (m, 1H), 7.63-7.53 (m, 4H), 7.26-7.14 (m, 2H), 6.53-6.50 (m, 1H), 4.20-4.11 (m, 1H), 3.92 (s, 3H), 3.60-3.25 (m, 2H), 3.01-2.94 (m, 1H), 2.38 (s, 1H), 2.22 (s, 2H), 1.45-1.22 (m, 4H), 1.04 (d, T=7.0 Hz, 3H), 0.73-0.44 (m, 1H); ESI-MS (m/z): 472 [M+1]⁺. $[\alpha]^{25}_D$=−8.9° (c=0.1, MeOH).

Example A2

((2S,3R)-2-((Benzo[d]oxazol-2-ylamino)methyl)-3-methylpiperidin-1-yl)(5-methyl-2-(1-methyl-1H-pyrazol-4-yl)phenyl)methanone

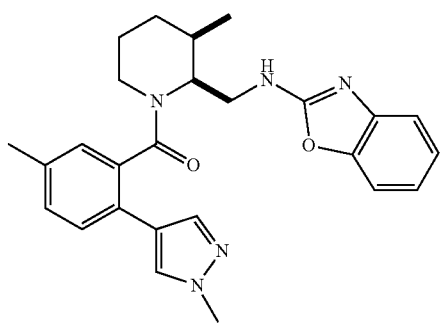 [SMILES: Cc1ccc(-c2cnn(C)c2)c(C(=O)N2CCC[C@@H](C)[C@H]2CNc2nc3ccccc3o2)c1]

A mixture of ((2S,3R)-2-(aminomethyl)-3-methylpiperidin-1-yl)(5-methyl-2-(1-methyl-1H-pyrazol-4-yl)phenyl) methanone (40 mg, 122 µmol), 2-chlorobenzoxazole (38 mg, 245 µmol) and DIPEA (43 µl, 245 µmol) in CH₃CN (2 mL) was heated at reflux overnight. The mixture was cooled to room temperature and the solvent was removed in vacuo. The crude was dissolved in EtOAc and washed with sat'd NaHCO₃, brine, and dried (MgSO₄). The solvent was removed and the crude was purified by reverse-phase preparative HPLC to afford the title compound. MS (ESI) 442 (M+H).

Example A3

((2S,3R)-3-Methyl-2-(((5-(trifluoromethyl)pyridin-2-yl)amino)methyl)piperidin-1-yl)(5-methyl-2-(1H-pyrazol-4-yl)phenyl)methanone

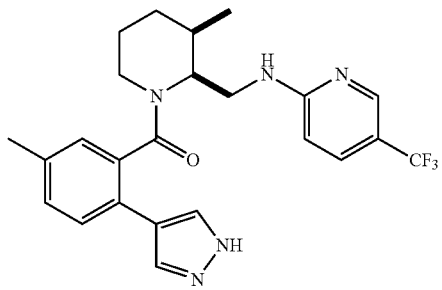 [SMILES: Cc1ccc(-c2cn[nH]c2)c(C(=O)N2CCC[C@@H](C)[C@H]2CNc2ccc(C(F)(F)F)cn2)c1]

Step 1. ((2S,3R)-2-(Aminomethyl)-3-methylpiperidin-1-yl)(2-bromo-5-methylphenyl)methanone

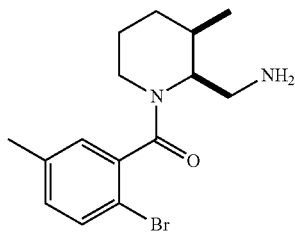 [SMILES: Cc1ccc(Br)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, starting with 2-(((2S,3R)-3-methylpiperidin-2-yl)methyl)isoindoline-1,3-dione and 2-bromo-5-methylbenzoic acid. ESI-MS (m/z): 325, 327 [M]$^+$, [M+2]$^+$.

Step 2. (2-Bromo-5-methylphenyl)((2S,3R)-3-methyl-2-(((5-(trifluoromethyl)pyridin-2-yl)amino)methyl)piperidin-1-yl)methanone

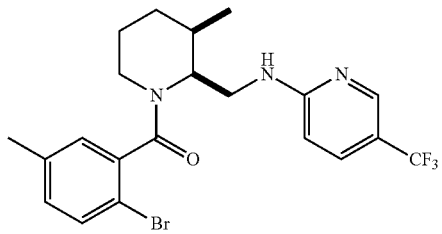

The title compound was prepared following the same general protocol as described for Example A1, using ((2S,3R)-2-(aminomethyl)-3-methylpiperidin-1-yl)(2-bromo-5-methylphenyl)methanone and 2-fluoro-5-(trifluoromethyl)pyridine. ESI-MS (m/z): 470, 472 [M]$^+$, [M+2]$^+$.

Step 3. ((2S,3R)-3-Methyl-2-(((5-(trifluoromethyl)pyridin-2-yl)amino)methyl)piperidin-1-yl)(5-methyl-2-(1H-pyrazol-4-yl)phenyl)methanone A mixture of (2-bromo-5-methylphenyl)((2S,3R)-3-methyl-2-(((5-(trifluoromethyl)pyridin-2-yl)amino)methyl)piperidin-1-yl)methanone (0.045 g, 0.097 mmol), tert-butyl 4-(4,4,5,5-tetramethyl-1,3,2-dioxaborolan-2-yl)-1H-pyrazole-1-carboxylate (0.034 g, 0.116 mmol), Pd(PPh$_3$)$_4$ (0.017 g, 0.015 mmol), K$_2$CO$_3$ (0.4 g, 0.291 mmol) and dioxane/H$_2$O (4:1, 3 mL) was degassed for 5 min and heated overnight at 100° C. The completion of the reaction was monitored by anal. HPLC. The mixture was cooled and extracted with EtOAc. The combined organic layers were washed with saturated NaHCO$_3$ and dried over Na$_2$SO$_4$. The solvent was removed in vacuo to obtain the crude, which was purified by preparative-HPLC to obtain the title compound as TFA salt. ESI-MS (m/z): 458 [M+1]$^+$.

Example A4

(2-(2-Methoxypyrimidin-5-yl)-5-methylphenyl)((2S,3R)-3-methyl-2-(((5-(trifluoromethyl)pyridin-2-yl)amino)methyl)piperidin-1-yl)methanone

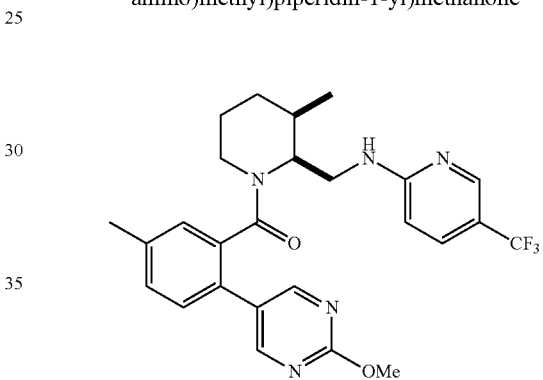

The title compound was prepared following the same general protocol as described for Example A3, using (2-methoxypyrimidin-5-yl)boronic acid. ESI-MS (m/z): 500 [M+1]$^+$.

Example A5

((2S,3R)-3-methyl-2-(((5-(trifluoromethyl)pyridin-2-yl)amino)methyl)piperidin-1-yl)(5-methyl-2-(5-methylpyridin-3-yl)phenyl)methanone

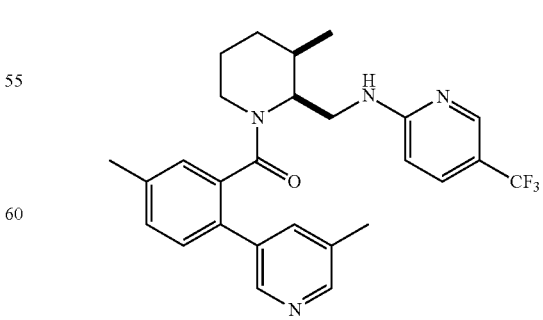

The title compound was prepared following the same general protocol as described for Example A3, using (3-methyl-5-(4,4,5,5-tetramethyl-1,3,2-dioxaborolan-2-yl)pyridine. ESI-MS (m/z): 483 [M+1]$^+$.

Example A6

((2S,3R)-3-Methyl-2-(((5-(trifluoromethyl)pyridin-2-yl)amino)methyl)piperidin-1-yl)(5-methyl-2-(1-methyl-1H-pyrrol-3-yl)phenyl)methanone

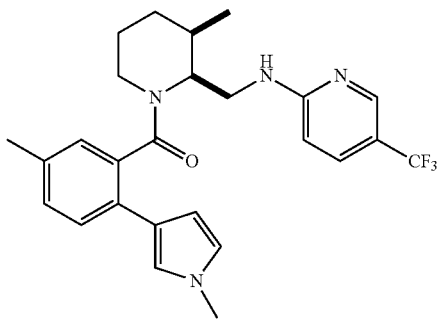 [SMILES: Cc1ccc(-c2ccn(C)c2)c(C(=O)N2CCC[C@@H](C)[C@H]2CNc2ccc(C(F)(F)F)cn2)c1]

The title compound was prepared following the same general protocol as described for Example A3, using 1-methyl-3-(4,4,5,5-tetramethyl-1,3,2-dioxaborolan-2-yl)-1H-pyrrole. ESI-MS (m/z): 471 [M+1]$^+$.

Example A7

(2-(3,5-Dimethylisoxazol-4-yl)-5-methylphenyl)((2S,3R)-3-methyl-2-(((5-(trifluoromethyl)pyridin-2-yl)amino)methyl)piperidin-1-yl)methanone

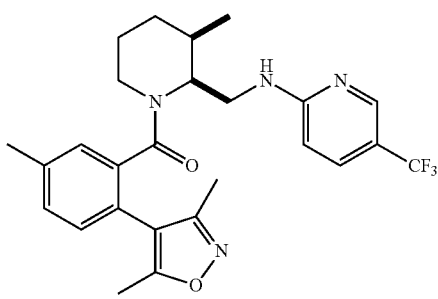 [SMILES: Cc1ccc(-c2c(C)noc2C)c(C(=O)N2CCC[C@@H](C)[C@H]2CNc2ccc(C(F)(F)F)cn2)c1]

Step 1. (2S,3R)-Allyl 2-(aminomethyl)-3-methylpiperidine-1-carboxylate

To a solution of 2-(((2S,3R)-3-methylpiperidin-2-yl)methyl)isoindoline-1,3-dione (5 g, 19.4 mmol) in $CH_2Cl_2$ at 0° C. was added diethylisopropylamine (3.8 mL), followed by allylchloroformate (2.6 mL). The reaction was allowed to warm to room temperature overnight. After 16 h, the reaction was concentrated to remove the $CH_2Cl_2$, and then re-suspended in EtOAc and washed with 1 M HCl (2x), brine (2x), dried ($MgSO_4$) and concentrated to give the crude carbamate which was used without further purification.

A mixture of the crude carbamate and hydrazine hydrate (2 g, 39 mmol) in MeOH (100 mL) was heated at 60° C. for 2 h. When the reaction was judged complete by anal. HPLC, the mixture was cooled to room temperature and the solvent was removed in vacuo. The crude was dissolved in EtOAc and washed with 2 N NaOH (2x), brine, and then dried ($Na_2SO_4$). The solvent was removed in vacuo to obtain the title compound which was used without further purification. ESI-MS (m/z): 213 [M+1]$^+$.

Step 2. (2S,3R)-allyl 3-methyl-2-(((5-(trifluoromethyl)pyridin-2-yl)amino)methyl)piperidine-1-carboxylate

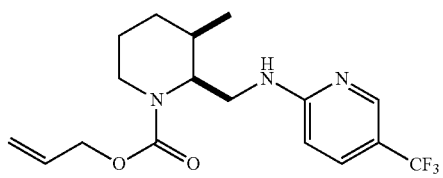 [SMILES: C=CCOC(=O)N1CCC[C@@H](C)[C@H]1CNc1ccc(C(F)(F)F)cn1]

A mixture of (2S,3R)-allyl 2-(aminomethyl)-3-methylpiperidine-1-carboxylate (1.36 g, 6.43 mmol), 2-chloro-5-(trifluoromethyl)pyridine (1.75 g, 9.645 mmol), and $Cs_2CO_3$ (4.2 g, 12.86 mmol) in DMF (20 mL) was stirred at 80° C. for 2 days. The reaction mixture was diluted with EtOAc and washed with brine. The organic layer was separated, dried with $MgSO_4$ and concentrated in vacuo. The crude residue was purified by chromatography on silica gel (EtOAc/hex) to give the title compound. ESI-MS (m/z): 358 [M+1]$^+$.

Step 3. N-(((2S,3R)-3-Methylpiperidin-2-yl)methyl)-5-(trifluoromethyl)pyridin-2-amine

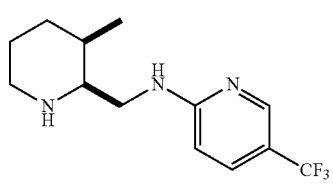 [SMILES: C[C@@H]1CCCN[C@@H]1CNc1ccc(C(F)(F)F)cn1]

A mixture of (2S,3R)-allyl 3-methyl-2-(((5-(trifluoromethyl)pyridin-2-yl)amino)methyl)piperidine-1-carboxylate (0.528 g, 1.48 mmol), $Pd(PPh_3)_4$ (0.086 g, 0.0074 mmol) and 1,3-dimethylpyrimidine-2,4,6(1H,3H,5H)-trione (0.14 g, 0.89 mmol) in DCM (20 mL) was stirred at RT. When the starting material was consumed as judged by reverse-phase HPLC analysis, the reaction was concentrated in vacuo. The crude residue was taken up in EtOAc, and washed with sat aqueous $NaHCO_3$, brine, dried ($MgSO_4$), and concentrated to obtain the crude which was purified by silica gel (0~100% DCM/EtOAc) to afford the title compound ESI-MS (m/z): 274 [M+1]⁺.

Step 4.
2-(3,5-Dimethylisoxazol-4-yl)-5-methylbenzoic acid

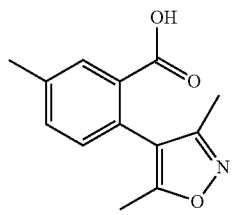 [SMILES: Cc1ccc(-c2c(C)noc2C)c(C(=O)O)c1]

The title compound was synthesized following the same general protocol as described for 5-methyl-2-(1-methyl-1H-pyrazol-4-yl)benzoic acid in Example A1, using 3,5-dimethyl-4-(4,4,5,5-tetramethyl-1,3,2-dioxaborolan-2-yl)isoxazole. ESI-MS (m/z): 232 [M+1]⁺.

Step 5. (2-(3,5-dimethylisoxazol-4-yl)-5-methylphenyl)((2S,3R)-3-methyl-2-(((5-(trifluoromethyl)pyridin-2-yl)amino)methyl)piperidin-1-yl)methanone The title compound was prepared following the same general protocol as described for Example A1, using 2-(3,5-dimethylisoxazol-4-yl)-5-methylbenzoic acid and N-(((2S,3R)-3-methylpiperidin-2-yl)methyl)-5-(trifluoromethyl)pyridin-2-amine. ESI-MS (m/z): 487 [M+1]⁺.

Example A8

((2S,3R)-3-Methyl-2-(((5-(trifluoromethyl)pyridin-2-yl)amino)methyl)piperidin-1-yl)(5-methyl-2-(4-methylpyridin-3-yl)phenyl)methanone

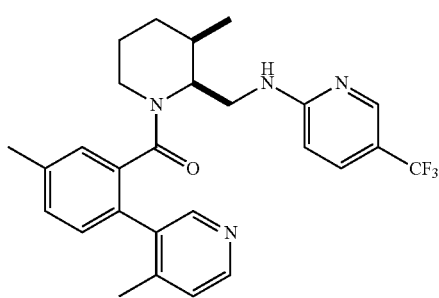 [SMILES: Cc1ccc(-c2cnccc2C)c(C(=O)N2CCC[C@@H](C)[C@H]2CNc2ccc(C(F)(F)F)cn2)c1]

Step 1. 5-Methyl-2-(4-methylpyridin-3-yl)benzoic acid

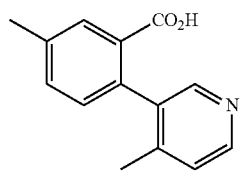 [SMILES: Cc1ccc(-c2cnccc2C)c(C(=O)O)c1]

The title compound was synthesized following the same general protocol as described for 5-methyl-2-(1-methyl-1H-pyrazol-4-yl)benzoic acid in Example A1, using (4-methylpyridin-3-yl)boronic acid. ESI-MS (m/z): 228 [M+1]⁺.

Step 2. ((2S,3R)-3-methyl-2-(((5-(trifluoromethyl)pyridin-2-yl)amino)methyl)piperidin-1-yl)(5-methyl-2-(4-methylpyridin-3-yl)phenyl)methanone The title compound was prepared following the same general protocol as described for Example A1, using 5-methyl-2-(4-methylpyridin-3-yl)benzoic acid and N-(((2S,3R)-3-methylpiperidin-2-yl)methyl)-5-(trifluoromethyl)pyridin-2-amine. ESI-MS (m/z): 483 [M+1]⁺.

Example A9

((2S,3R)-3-methyl-2-(((5-(trifluoromethyl)pyridin-2-yl)amino)methyl)piperidin-1-yl)(5-methyl-2-(pyridin-2-yl)phenyl)methanone

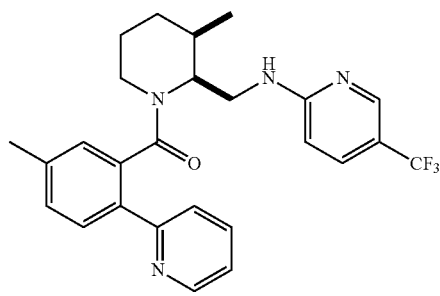 [SMILES: Cc1ccc(-c2ccccn2)c(C(=O)N2CCC[C@@H](C)[C@H]2CNc2ccc(C(F)(F)F)cn2)c1]

Step 1. Methyl 5-methyl-2-(pyridin-2-yl)benzoate

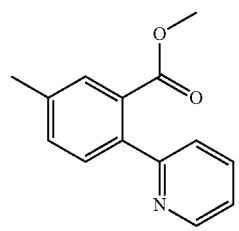 [SMILES: COC(=O)c1cc(C)ccc1-c1ccccn1]

A mixture of methyl 2-bromo-5-methylbenzoate (0.629 g, 2.747 mmol), 2-(tributylstannyl)pyridine (1.32 g, 3.585 mmol), CsF (0.834 g, 5.494 mmol), Pd(PPh₃)₄ (0.4 g, 0.27 mmol), and CuI (0.105 g, 0.549 mmol) in DMF (20 mL) was degassed for 10 min and then heated in the microwave reactor for 30 min at 130° C. The completion of reaction was monitored by anal. HPLC. The mixture was cooled and the solvent was removed in vacuo. The crude was dissolved with EtOAc and then washed with saturated NaHCO₃ and dried over Na₂SO₄. The solvent was removed in vacuo to obtain the crude, which was purified by silica gel to obtain the title compound. ESI-MS (m/z): 228 [M+1]⁺.

Step 2. 5-Methyl-2-(pyridin-2-yl)benzoic acid

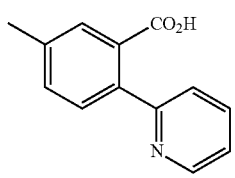 [SMILES: Cc1ccc(-c2ccccn2)c(C(=O)O)c1]

The title compound was synthesized following the same general protocol as described for 5-methyl-2-(1-methyl-1H-pyrazol-4-yl)benzoic acid in Example A1, using methyl 5-methyl-2-(pyridin-2-yl)benzoate. ESI-MS (m/z): 214 [M+1]$^+$.

Step 3. ((2S,3R)-3-Methyl-2-(((5-(trifluoromethyl)pyridin-2-yl)amino)methyl)piperidin-1-yl)(5-methyl-2-(pyridin-2-yl)phenyl)methanone The title compound was prepared following the same general protocol as described in Example A1, starting from 5-methyl-2-(pyridin-2-yl)benzoic acid and 2-(((2S,3R)-3-methylpiperidin-2-yl)methyl)isoindoline-1,3-dione. ESI-MS (m/z): 469 [M+1]$^+$.

Example A10

((2S,3R)-2-(((6-Chlorobenzo[d]oxazol-2-yl)amino)methyl)-3-methylpiperidin-1-yl)(5-methyl-2-(1-methyl-1H-pyrazol-4-yl)phenyl)methanone

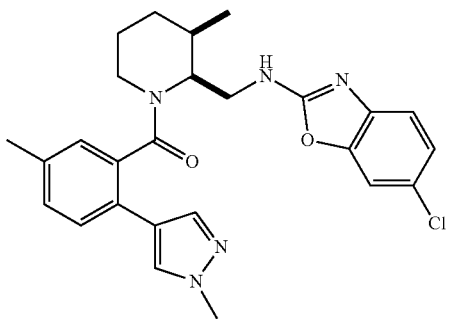 [SMILES: Cc1ccc(-c2cnn(C)c2)c(C(=O)N2CCC[C@@H](C)[C@H]2CNc2nc3ccc(Cl)cc3o2)c1]

The title compound was prepared following the same general protocol as described for Example A1 using 2,6-dichlorobenzoxazole. MS (ESI) 478 (M+H).

Example A11

((2S,3R)-2-(((5-Chlorobenzo[d]oxazol-2-yl)amino)methyl)-3-methylpiperidin-1-yl)(5-methyl-2-(2H-1,2,3-triazol-2-yl)phenyl)methanone

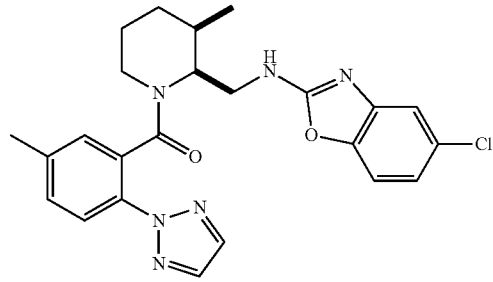 [SMILES: Cc1ccc(-n2nccn2)c(C(=O)N2CCC[C@@H](C)[C@H]2CNc2nc3cc(Cl)ccc3o2)c1]

Step 1. 5-Methyl-2-(2H-1,2,3-triazol-2-yl)benzoic acid

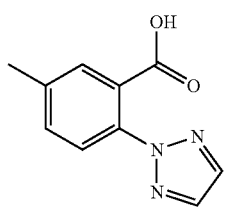

A mixture of 2-bromo-5-methylbenzoic acid (2.0 g, 9.30 mmol), 1,2,3-triazole (1.08 ml, 18.6 mmol), (1S,2S)—N1,N2-dimethylcyclohexane-1,2-diamine (2.23 ml, 13.95 mmol), Cs$_2$CO$_3$ (4.55 g, 13.95 mmol) and CuI (124 mg, 0.65 mmol) in DMF (12 mL) was degassed and heated at 120° C. for 1 h in a microwave reactor. The reaction was cooled to RT, diluted with MeOH, and acidified with AcOH to pH4~5. The solvent was removed in vacuo to obtain the crude which was purified by silica gel chromatography (0~100% DCM/EtOAc) to yield the title compound as a yellow oil (1.5 g, 61%). MS (ESI) 204 (M+H).

Step 2. ((2S,3R)-2-(Aminomethyl)-3-methylpiperidin-1-yl)(5-methyl-2-(2H-1,2,3-triazol-2-yl)phenyl)methanone

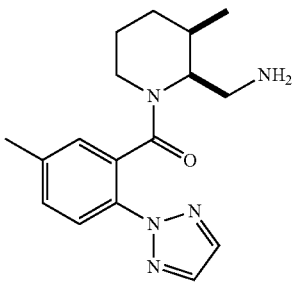 [SMILES: Cc1ccc(-n2nccn2)c(C(=O)N2CCC[C@@H](C)[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-methyl-2-(2H-1,2,3-triazol-2-yl)benzoic acid. MS (ESI) 314 (M+H).

Step 3. ((2S,3R)-2-(((5-Chlorobenzo[d]oxazol-2-yl)amino)methyl)-3-methylpiperidin-1-yl)(5-methyl-2-(2H-1,2,3-triazol-2-yl)phenyl)methanone The title compound was prepared following the same general protocol as described for Example A2 using 2,5-dichlorobenzoxazole. MS (ESI) 465 (M+H).

Example A12

((2S,3R)-2-(((5-chlorobenzo[d]oxazol-2-yl)amino)
methyl)-3-methylpiperidin-1-yl)(5-methyl-2-(1-
methyl-1H-pyrazol-4-yl)phenyl)methanone

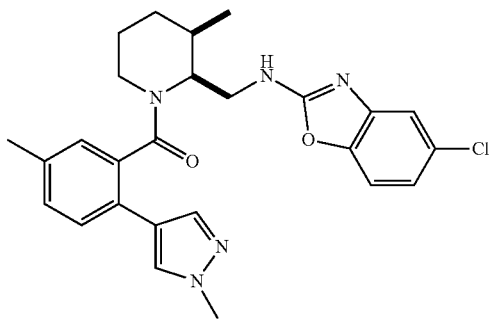 [SMILES: Cc1ccc(-c2cnn(C)c2)c(C(=O)N2CCC[C@@H](C)[C@H]2CNc2nc3cc(Cl)ccc3o2)c1]

The title compound was prepared following the same general protocol as described for Example A2 using 2,5-dichlorobenzoxazole. MS (ESI) 478 (M+H).

Example A13

((2S,3R)-2-(((5-Chlorobenzo[d]oxazol-2-yl)amino)
methyl)-3-methylpiperidin-1-yl)(5-(4-fluorophenyl)-
2-methylthiazol-4-yl)methanone

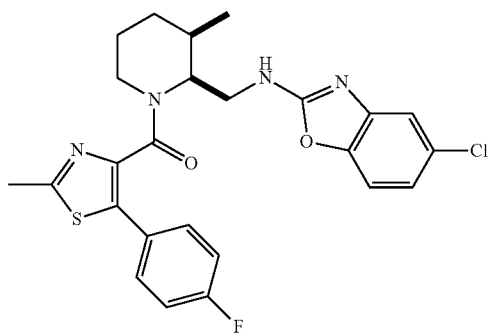 [SMILES: Cc1nc(C(=O)N2CCC[C@@H](C)[C@H]2CNc2nc3cc(Cl)ccc3o2)c(-c2ccc(F)cc2)s1]

Step 1. 2-(((2S,3R)-1-(5-(4-Fluorophenyl)-2-methyl-
thiazole-4-carbonyl)-3-methylpiperidin-2-yl)methyl)
isoindoline-1,3-dione

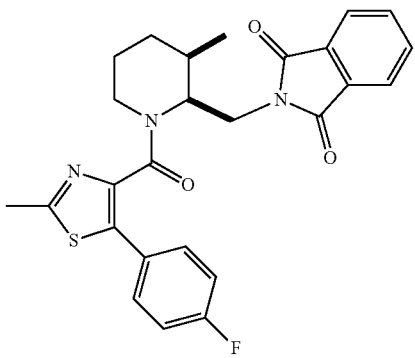 [SMILES: Cc1nc(C(=O)N2CCC[C@@H](C)[C@H]2CN2C(=O)c3ccccc3C2=O)c(-c2ccc(F)cc2)s1]

To a solution of ((2S,3R)-3-methyl-2-(((5-(trifluorom-ethyl)pyridin-2-yl)amino)methyl)piperidin-1-yl)(5-methyl-2-(1-methyl-1H-pyrazol-4-yl)phenyl)methanone (100 mg, 387 µmol) in DMF was added DIPEA (202 µl, 1.16 mmol) followed by 5-(4-fluorophenyl)-2-methylthiazole-4-carboxylic acid (137 mg, 580 µmol) and HATU (176 mg, 465 µmol). The reaction was allowed to stir at room temperature for 15 h, and was then concentrated in vacuo to remove the DMF. The crude residue was taken up in EtOAc and washed with 1 M HCl, sat aq. NaHCO₃, brine, dried (MgSO₄), and concentrated. The crude residue was purified by chromatography on silica gel (EtOAc/hexanes) to give 2-(((2S,3R)-1-(5-(4-fluorophenyl)-2-methylthiazole-4-carbonyl)-3-methylpiperidin-2-yl)methyl)isoindoline-1,3-dione as a light yellow oil (130 mg, 71%). MS (ESI) 478 (M+H).

Step 2. ((2S,3R)-2-(Aminomethyl)-3-methylpiperi-
din-1-yl)(5-(4-fluorophenyl)-2-methylthiazol-4-yl)
methanone

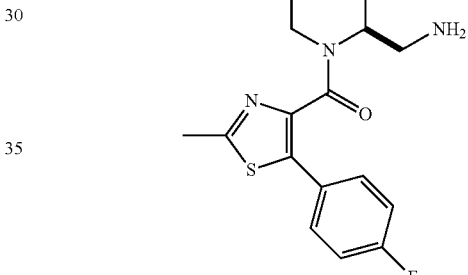

A mixture of 2-(((2S,3R)-1-(5-(4-fluorophenyl)-2-methylthiazole-4-carbonyl)-3-methylpiperidin-2-yl)methyl)isoindoline-1,3-dione (130 mg, 272 µmol) and hydrazine hydrate (67 µl, 1.36 mmol) in MeOH (3 mL) was heated at reflux for 2 h. The reaction was monitored by anal. HPLC until starting material was consumed. The mixture was cooled and the solvent was removed in vacuo. The crude was dissolved in EtOAc and washed with 2N NaOH (2x) and brine. The organic solution was dried over anhydrous Na₂SO₄. The solvent was removed to obtain the title compound which was used without further purification. MS (ESI) 348 (M+H).

Step 3. ((2S,3R)-2-(((5-Chlorobenzo[d]oxazol-2-yl)
amino)methyl)-3-methylpiperidin-1-yl)(5-(4-fluoro-
phenyl)-2-methylthiazol-4-yl)methanone The title compound was prepared following the same general protocol as described for Example A2 using ((2S,3R)-2-(aminomethyl)-3-methylpiperidin-1-yl)(5-(4-fluorophenyl)-2-methylthiazol-4-yl)methanone and 2,5-dichlorobenzoxazole. MS (ESI) 499 (M+H).

Example A14

((2S,3R)-2-(((6-Chlorobenzo[d]oxazol-2-yl)amino)methyl)-3-methylpiperidin-1-yl)(5-methyl-2-(2H-1,2,3-triazol-2-yl)phenyl)methanone

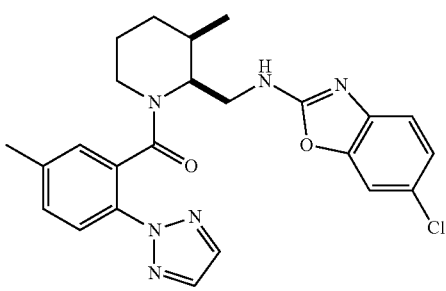 [SMILES: Cc1ccc(-n2nccn2)c(C(=O)N2CCC[C@@H](C)[C@H]2CNc2nc3ccc(Cl)cc3o2)c1]

The title compound was prepared following the same general protocol as described for Example A11 using 2,6-dichlorobenzoxazole. MS (ESI) 465 (M+H).

Example A15

((2S,3R)-2-(((5-Fluorobenzo[d]oxazol-2-yl)amino)methyl)-3-methylpiperidin-1-yl)(5-(4-fluorophenyl)-2-methylthiazol-4-yl)methanone

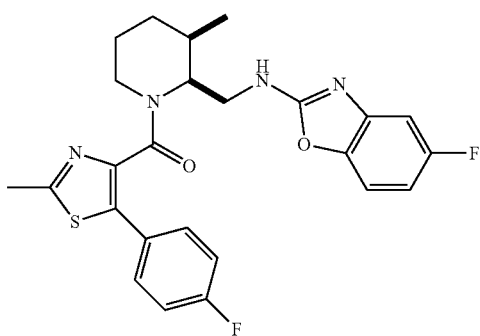 [SMILES: Cc1nc(C(=O)N2CCC[C@@H](C)[C@H]2CNc2nc3cc(F)ccc3o2)c(-c2ccc(F)cc2)s1]

A mixture of ((2S,3R)-2-(aminomethyl)-3-methylpiperidin-1-yl)(5-(4-fluorophenyl)-2-methylthiazol-4-yl)methanone (40 mg, 115 µmol), 2-chloro-5-fluorobenzoxazole (24 mg, 138 µmol) and DIPEA (60 µl, 345 µmol) in CH$_3$CN (2 mL) was heated at reflux overnight. The mixture was cooled to room temperature and the solvent was removed in vacuo. The crude was dissolved in EtOAc and washed with sat'd NaHCO$_3$ and brine. The solvent was removed and the crude was purified by reverse-phase preparative HPLC to afford the title compound. MS (ESI) 483 (M+H).

Example A16

((2S,3R)-3-Methyl-2-(((5-(trifluoromethyl)pyridin-2-yl)amino)methyl)piperidin-1-yl)(5-methyl-2-(5-methyl-1H-1,2,4-triazol-1-yl)phenyl)methanone

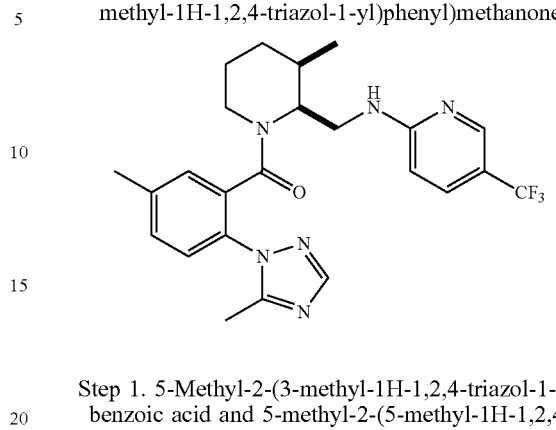

Step 1. 5-Methyl-2-(3-methyl-1H-1,2,4-triazol-1-yl)benzoic acid and 5-methyl-2-(5-methyl-1H-1,2,4-triazol-1-yl)benzoic acid

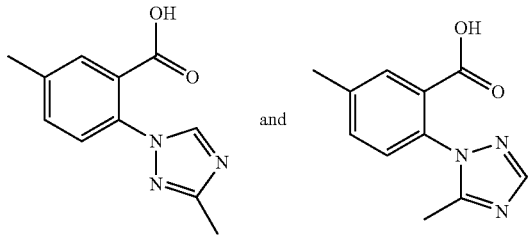 [SMILES: Cc1ccc(-n2cnc(C)n2)c(C(=O)O)c1 ; Cc1ccc(-n2ncnc2C)c(C(=O)O)c1]

The title compound was synthesized following the same general protocol as described in Example A11 using 3-methyl-1H-1,2,4-triazole—the faster eluting 5-methyl-2-(3-methyl-1H-1,2,4-triazol-1-yl)benzoic acid was the major product and the slower eluting 5-methyl-2-(5-methyl-1H-1,2,4-triazol-1-yl)benzoic acid was the minor product ESI-MS (m/z): 218 [M+1]$^+$.

Step 2. ((2S,3R)-3-Methyl-2-(((5-(trifluoromethyl)pyridin-2-yl)amino)methyl)piperidin-1-yl)(5-methyl-2-(5-methyl-1H-1,2,4-triazol-1-yl)phenyl)methanone The title compound was prepared following the same general protocol as described for Example A1, using 5-methyl-2-(5-methyl-1H-1,2,4-triazol-1-yl)benzoic acid and N-(((2S,3R)-3-methylpiperidin-2-yl)methyl)-5-(trifluoromethyl)pyridin-2-amine. ESI-MS (m/z): 473 [M+1]$^+$.

Example A17

((2S,3R)-3-methyl-2-(((5-(trifluoromethyl)pyridin-2-yl)amino)methyl)piperidin-1-yl)(5-methyl-2-(3-methyl-1H-1,2,4-triazol-1-yl)phenyl)methanone

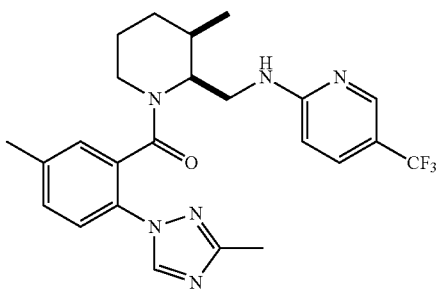 [SMILES: Cc1ccc(-n2cnc(C)n2)c(C(=O)N2CCC[C@@H](C)[C@H]2CNc2ccc(C(F)(F)F)cn2)c1]

The title compound was prepared following the same general protocol as described for Example A16, using 5-methyl-2-(3-methyl-1H-1,2,4-triazol-1-yl)benzoic acid. ESI-MS (m/z): 473 [M+1]⁺.

Example A18

((2S,3R)-3-Methyl-2-(((5-(trifluoromethyl)pyridin-2-yl)amino)methyl)piperidin-1-yl)(5-methyl-2-(1-methyl-1H-pyrazol-3-yl)phenyl)methanone

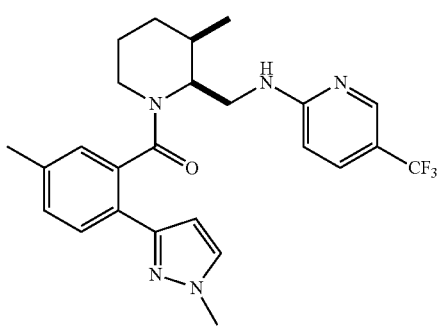 [SMILES: Cc1ccc(-c2ccn(C)n2)c(C(=O)N2CCC[C@@H](C)[C@H]2CNc2ccc(C(F)(F)F)cn2)c1]

Step 1. Methyl 5-methyl-2-(1H-pyrazol-5-yl)benzoate

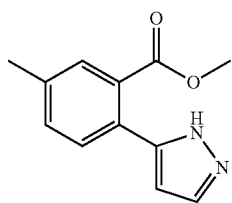

The title compound was synthesized following the same general protocol as described for methyl 5-methyl-2-(1-methyl-1H-pyrazol-4-yl)benzoate in Example A1, using (1H-pyrazol-5-yl)boronic acid. ESI-MS (m/z): 217 [M+1]⁺.

Step 2. Methyl 5-methyl-2-(1-methyl-1H-pyrazol-3-yl)benzoate

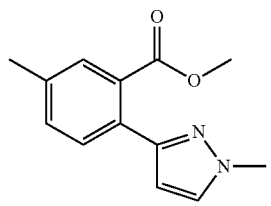

To a solution of methyl 5-methyl-2-(1H-pyrazol-3-yl)benzoate (0.16 g, 0.744 mmol) in DMF (3 mL) at room temperature was added NaH (60%, 0.081 g, 2.02 mmol) under argon protection. The mixture was stirred at room temperature for 1 h, and then MeI (0.07 mL, 1.116 mmol) was added. The resulting mixture was stirred for another 1 h. The solvent was removed in vacuo. The crude was dissolved with EtOAc and washed with sat'd NaHCO₃, brine, and dried (MgSO₄). The solvent was removed and the crude was purified by silica gel chromatography to obtain the faster eluting methyl 5-methyl-2-(1-methyl-1H-pyrazol-5-yl)benzoate as the minor product and the slower eluting methyl 5-methyl-2-(1-methyl-1H-pyrazol-3-yl)benzoate as the title compound and major product. ESI-MS (m/z): 231 [M+1]⁺.

Step 3.
5-Methyl-2-(1-methyl-1H-pyrazol-3-yl)benzoic acid

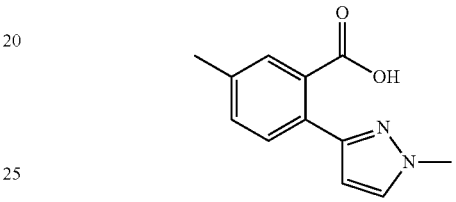

The title compound was synthesized following the same general protocol as described for 5-methyl-2-(1-methyl-1H-pyrazol-4-yl)benzoic acid in Example A1, using methyl 5-methyl-2-(1-methyl-1H-pyrazol-3-yl)benzoate. ESI-MS (m/z): 217 [M+1]⁺.

Step 4. ((2S,3R)-3-Methyl-2-(((5-(trifluoromethyl)pyridin-2-yl)amino)methyl)piperidin-1-yl)(5-methyl-2-(1-methyl-1H-pyrazol-3-yl)phenyl)methanone The title compound was prepared following the same general protocol as described for Example A1, using 5-methyl-2-(1-methyl-1H-pyrazol-3-yl)benzoic acid and N-(((2S,3R)-3-methylpiperidin-2-yl)methyl)-5-(trifluoromethyl)pyridin-2-amine. ESI-MS (m/z): 472 [M+1]⁺.

Example A19

((2S,3R)-3-methyl-2-(((5-(trifluoromethyl)pyridin-2-yl)amino)methyl)piperidin-1-yl)(5-methyl-2-(pyrazin-2-yl)phenyl)methanone

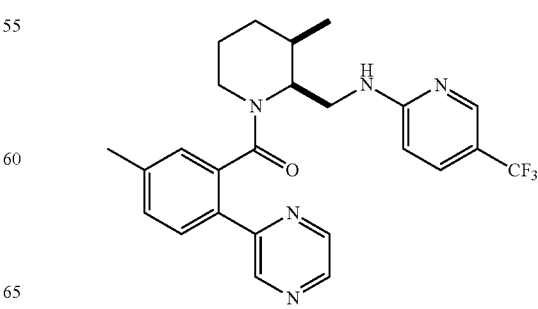

Step 1. Methyl 5-methyl-2-(4,4,5,5-tetramethyl-1,3,2-dioxaborolan-2-yl)benzoate

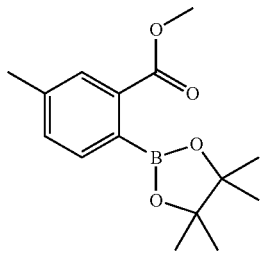

A mixture of methyl 2-bromo-5-methylbenzoate (1.153 g, 5.03 mmol), 4,4,4',4',5,5,5',5'-octamethyl-2,2'-bi(1,3,2-dioxaborolane) (1.9 g, 5.533 mmol), $PdCl_2(PPh_3)_2$ (0.35 g, 0.5 mmol) and AcOK (0.98 g, 10.06 mmol) in dioxane (10 mL) was degassed and heated for 16 h at 100° C. The mixture was cooled to room temperature and filtered through a pad of diatomaceous earth, washing with EtOAc. The organic phase was washed with sat'd $NaHCO_3$, brine, and dried ($MgSO_4$). The solvent was removed in vacuo and the resulting crude residue was purified by silica gel chromatography (EtOAc/hex) to give the title compound.

Step 2. Methyl 5-methyl-2-(pyrazin-2-yl)benzoate

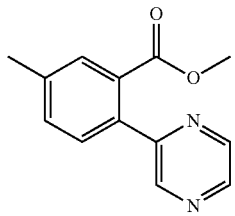 [SMILES: COC(=O)c1cc(C)ccc1-c1cnccn1]

The title compound was synthesized following the same general protocol as described for methyl 5-methyl-2-(1-methyl-1H-pyrazol-4-yl)benzoate in Example A1, using methyl 5-methyl-2-(4,4,5,5-tetramethyl-1,3,2-dioxaborolan-2-yl)benzoate and using 2-iodopyrazine. ESI-MS (m/z): 229 $[M+1]^+$.

Step 3. 5-Methyl-2-(pyrazin-2-yl)benzoic acid

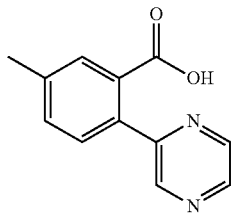 [SMILES: Cc1ccc(-c2cnccn2)c(C(=O)O)c1]

The title compound was synthesized following the same general protocol as described for 5-methyl-2-(1-methyl-1H-pyrazol-4-yl)benzoic acid in Example A1, using methyl 5-methyl-2-(pyrazin-2-yl)benzoate. ESI-MS (m/z): 215 $[M+1]^+$.

Step 4. ((2S,3R)-3-Methyl-2-(((5-(trifluoromethyl)pyridin-2-yl)amino)methyl)piperidin-1-yl)(5-methyl-2-(pyrazin-2-yl)phenyl)methanone The title compound was prepared following the same general protocol as described for Example A1, using 5-methyl-2-(pyrazin-2-yl)benzoic acid and N-(((2S,3R)-3-methylpiperidin-2-yl)methyl)-5-(trifluoromethyl)pyridin-2-amine. ESI-MS (m/z): 470 $[M+1]^+$.

Example A20

((2S,3R)-3-Methyl-2-(((5-(trifluoromethyl)pyridin-2-yl)amino)methyl)piperidin-1-yl)(5-methyl-2-(1-methyl-1H-imidazol-2-yl)phenyl)methanone

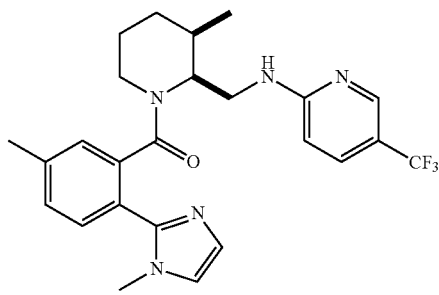 [SMILES: Cc1ccc(-c2nccn2C)c(C(=O)N2CCC[C@@H](C)[C@H]2CNc2ccc(C(F)(F)F)cn2)c1]

Step 1. 5-Methyl-2-(1-methyl-1H-imidazol-2-yl)benzoic acid

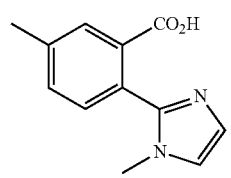 [SMILES: Cc1ccc(-c2nccn2C)c(C(=O)O)c1]

The title compound was prepared following the same general protocol as described for 5-methyl-2-(pyrazin-2-yl)benzoic acid in Example A19, starting from 2-bromo-1-methyl-1H-imidazole. ESI-MS (m/z): 217 $[M+1]^+$.

Step 2. ((2S,3R)-3-Methyl-2-(((5-(trifluoromethyl)pyridin-2-yl)amino)methyl)piperidin-1-yl)(5-methyl-2-(1-methyl-1H-imidazol-2-yl)phenyl)methanone The title compound was prepared following the same general protocol as described in Example A1, using 5-methyl-2-(1-methyl-1H-imidazol-2-yl)benzoic acid and N-(((2S,3R)-3-methylpiperidin-2-yl)methyl)-5-(trifluoromethyl)pyridin-2-amine. ESI-MS (m/z): 472 $[M+1]^+$.

Example A21

(2-(4-Methoxypyrimidin-2-yl)-5-methylphenyl)((2S,3R)-3-methyl-2-(((5-(trifluoromethyl)pyridin-2-yl)amino)methyl)piperidin-1-yl)methanone

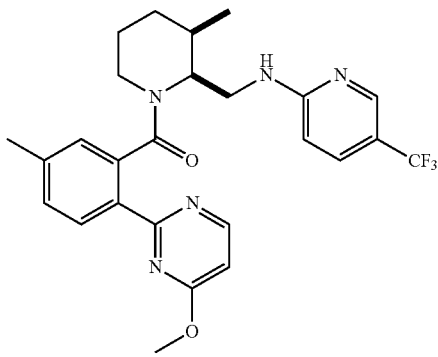 [SMILES: COc1ccnc(-c2ccc(C)cc2C(=O)N2CCC[C@@H](C)[C@H]2CNc2ccc(C(F)(F)F)cn2)n1]

Step 1.
2-(4-Methoxypyrimidin-2-yl)-5-methylbenzoic acid

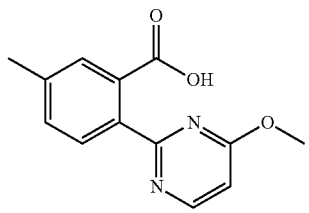

The title compound was prepared following the same general protocol as described for 5-methyl-2-(pyrazin-2-yl)benzoic acid in Example A19, starting from 2-chloro-4-methoxypyrimidine. ESI-MS (m/z): 245 [M+1]+.

Step 2. (2-(4-Methoxypyrimidin-2-yl)-5-methylphenyl)((2S,3R)-3-methyl-2-(((5-(trifluoromethyl)pyridin-2-yl)amino)methyl)piperidin-1-yl)methanone The title compound was prepared following the same general protocol as described in Example A1, using 2-(4-methoxypyrimidin-2-yl)-5-methylbenzoic acid and N-(((2S,3R)-3-methylpiperidin-2-yl)methyl)-5-(trifluoromethyl)pyridin-2-amine. ESI-MS (m/z): 500 [M+1]+.

Example A22

4-Methyl-2-((2S,3R)-3-methyl-2-(((5-(trifluoromethyl)pyridin-2-yl)amino)methyl)piperidine-1-carbonyl)benzonitrile

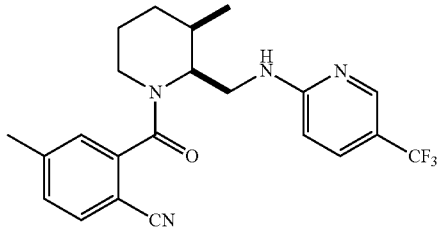

A mixture of (2-bromo-5-methylphenyl)((2S,3R)-3-methyl-2-(((5-(trifluoromethyl)pyridin-2-yl)amino)methyl)piperidin-1-yl)methanone (synthesized from Example A3, 0.35 g, 0.744 mmol), $Zn(CN)_2$ (0.105 g, 0.818 mmol), $Pd_2(dba)_3$ (0.068 g, 0.074 mmol) and S-Phos (0.076 g, 0.186 mmol) in wet DMF (DMF:$H_2O$ 10:1, 20 mL) was degassed and sealed and heated in a microwave reactor for 1 h at 150° C. The reaction was cooled to room temperature and the solvent was removed in vacuo. The crude was dissolved with EtOAc, washed with sat's $NaHCO_3$ and brine and dried over $Na_2SO_4$. The solvent was removed and the crude was purified in silica gel with 0~100% EtOAc/Hex to obtain the title compound. ESI-MS (m/z): 417 [M+1]+.

Example A23

((2S,3R)-3-Methyl-2-(((5-(trifluoromethyl)pyridin-2-yl)amino)methyl)piperidin-1-yl)(5-methyl-2-(2H-tetrazol-5-yl)phenyl)methanone

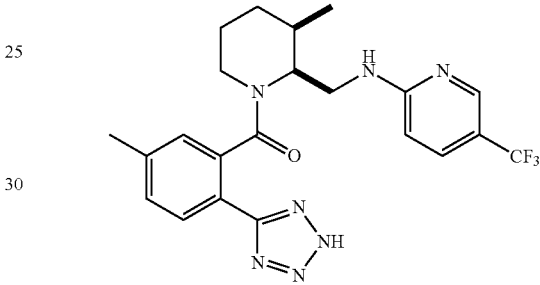

A mixture of 4-methyl-2-((2S,3R)-3-methyl-2-(((5-(trifluoromethyl)pyridin-2-yl)amino)methyl)piperidine-1-carbonyl)benzonitrile (obtained from Example A22, 0.098 g, 0.235 mmol), $TMSN_3$ (0.06 mL, 0.47 mmol) and SnO(n-Bu)$_2$ (0.006 g, 0.024 mmol) in toluene (2 mL) was heated at 110° C. overnight. The mixture was cooled to room temperature and filtered through a pad of diatomaceous earth, washing with methanol. The solvent was removed in vacuo and the resulting crude residue was purified by reverse-phase preparative HPLC to obtain the title compound. ESI-MS (m/z): 460 [M+1]+.

Example A24

((2S,3R)-3-Methyl-2-(((5-(trifluoromethyl)pyridin-2-yl)amino)methyl)piperidin-1-yl)(5-methyl-2-(thiazol-2-yl)phenyl)methanone

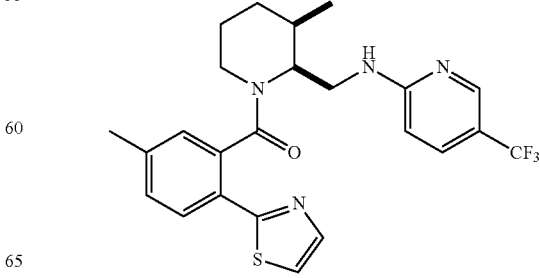

Step 1. 5-Methyl-2-(thiazol-2-yl)benzoic acid

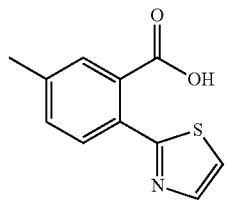

The title compound was prepared following the same general protocol as described for 5-methyl-2-(pyrazin-2-yl)benzoic acid in Example A19, starting from 2-bromothiazole. ESI-MS (m/z): 220 [M+1]$^+$.

Step 2. ((2S,3R)-3-Methyl-2-(((5-(trifluoromethyl)pyridin-2-yl)amino)methyl)piperidin-1-yl)(5-methyl-2-(thiazol-2-yl)phenyl)methanone The title compound was prepared following the same general protocol as described in Example A1, using 5-methyl-2-(thiazol-2-yl)benzoic acid and N-(((2S,3R)-3-methylpiperidin-2-yl)methyl)-5-(trifluoromethyl)pyridin-2-amine. ESI-MS (m/z): 475 [M+1]$^+$.

Example A25

((2S,3R)-3-Methyl-2-(((5-(trifluoromethyl)pyridin-2-yl)amino)methyl)piperidin-1-yl)(5-methyl-2-(thiazol-5-yl)phenyl)methanone

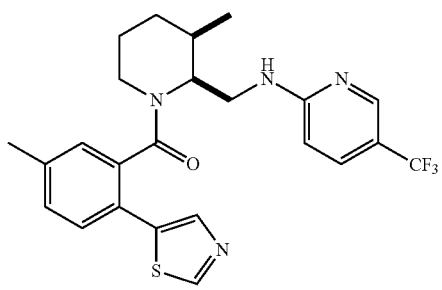

Step 1. 5-Methyl-2-(thiazol-5-yl)benzoic acid

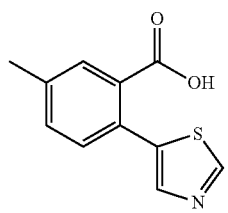

The title compound was prepared following the same general protocol as described for 5-methyl-2-(pyrazin-2-yl)benzoic acid in Example A19, starting from 5-bromothiazole. ESI-MS (m/z): 220 [M+1]$^+$.

Step 2. ((2S,3R)-3-Methyl-2-(((5-(trifluoromethyl)pyridin-2-yl)amino)methyl)piperidin-1-yl)(5-methyl-2-(thiazol-5-yl)phenyl)methanone The title compound was prepared following the same general protocol as described in Example A1, using 5-methyl-2-(thiazol-5-yl)benzoic acid and N-(((2S,3R)-3-methylpiperidin-2-yl)methyl)-5-(trifluoromethyl)pyridin-2-amine. ESI-MS (m/z): 475 [M+1]$^+$.

Example A26

((2S,3R)-3-Methyl-2-(((5-(trifluoromethyl)pyridin-2-yl)amino)methyl)piperidin-1-yl)(5-methyl-2-(1-methyl-1H-imidazol-5-yl)phenyl)methanone

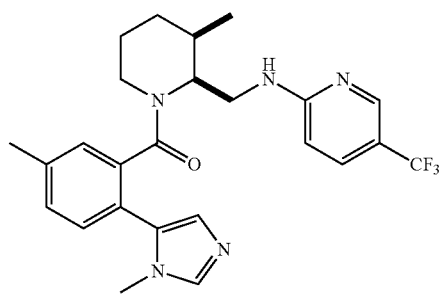 [SMILES: Cc1ccc(-c2cncn2C)c(C(=O)N2CCC[C@@H](C)[C@H]2CNc2ccc(C(F)(F)F)cn2)c1]

Step 1. 5-Methyl-2-(1-methyl-1H-imidazol-5-yl)benzoic acid

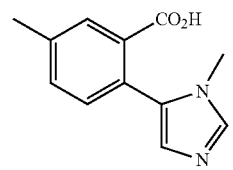 [SMILES: Cc1ccc(-c2cncn2C)c(C(=O)O)c1]

The title compound was prepared following the same general protocol as described for 5-methyl-2-(pyrazin-2-yl)benzoic acid in Example A19, starting from 5-bromo-1-methyl-1H-imidazole. ESI-MS (m/z): 217 [M+1]$^+$.

Step 2. ((2S,3R)-3-Methyl-2-(((5-(trifluoromethyl)pyridin-2-yl)amino)methyl)piperidin-1-yl)(5-methyl-2-(1-methyl-1H-imidazol-5-yl)phenyl)methanone The title compound was prepared following the same general protocol as described in Example A1, using 5-methyl-2-(1-methyl-1H-imidazol-5-yl)benzoic acid and N-(((2S,3R)-3-methylpiperidin-2-yl)methyl)-5-(trifluoromethyl)pyridin-2-amine. ESI-MS (m/z): 472 [M+1]$^+$.

Example A27

((2S,3R)-2-(((5-Chlorobenzo[d]oxazol-2-yl)amino)methyl)-3-methylpiperidin-1-yl)(5-methyl-2-(2-methylpyrimidin-4-yl)phenyl)methanone

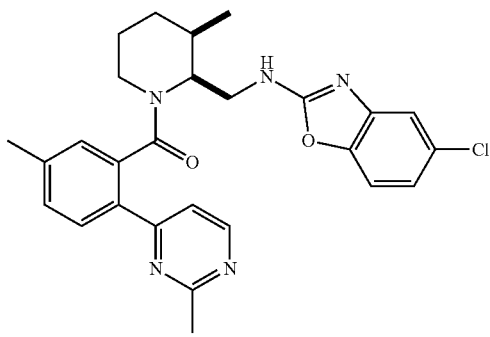 [SMILES: Cc1ccc(-c2ccnc(C)n2)c(C(=O)N2CCC[C@@H](C)[C@H]2CNc2nc3cc(Cl)ccc3o2)c1]

Step 1. Methyl 2-(2-chloropyrimidin-4-yl)-5-methylbenzoate

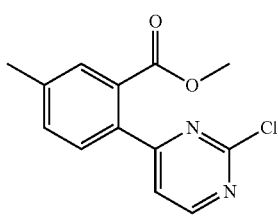 [SMILES: COC(=O)c1cc(C)ccc1-c1ccnc(Cl)n1]

The title compound was synthesized following the same general protocol as described for methyl 5-methyl-2-(1-methyl-1H-pyrazol-4-yl)benzoate in Example A1, using methyl 5-methyl-2-(4,4,5,5-tetramethyl-1,3,2-dioxaborolan-2-yl)benzoate and 2,4-dichloropyrimidine. ESI-MS (m/z): 263 [M+1]$^+$.

Step 2. Methyl 5-methyl-2-(2-methylpyrimidin-4-yl)benzoate

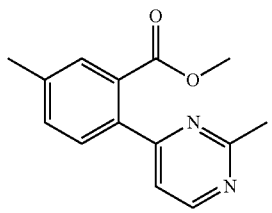

The title compound was synthesized following the same general protocol as described for methyl 5-methyl-2-(1-methyl-1H-pyrazol-4-yl)benzoate in Example A1, using methyl 2-(2-chloropyrimidin-4-yl)-5-methylbenzoate and 2,4,6-trimethyl-1,3,5,2,4,6-trioxatriborinane. ESI-MS (m/z): 243 [M+1]$^+$.

Step 3. 5-Methyl-2-(2-methylpyrimidin-4-yl)benzoic acid

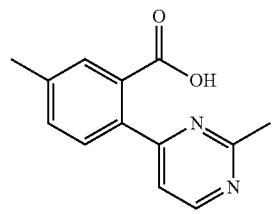

The title compound was synthesized following the same general protocol as described for 5-methyl-2-(1-methyl-1H-pyrazol-4-yl)benzoic acid in Example A1, using methyl 5-methyl-2-(2-methylpyrimidin-4-yl)benzoate. ESI-MS (m/z): 229 [M+1]$^+$.

Step 4. (2S,3R)-Allyl 2-(((5-chlorobenzo[d]oxazol-2-yl)amino)methyl)-3-methylpiperidine-1-carboxylate

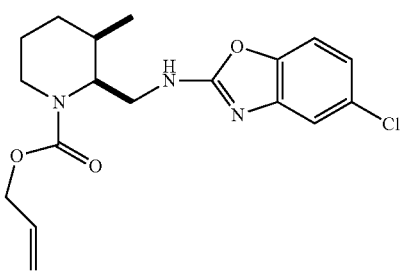 [SMILES: C=CCOC(=O)N1CCC[C@@H](C)[C@H]1CNc1nc2cc(Cl)ccc2o1]

A mixture of (2S,3R)-allyl 2-(aminomethyl)-3-methylpiperidine-1-carboxylate (0.804 g, 3.787 mmol), 2,5-dichlorobenzo[d]oxazole (0.712 g, 3.787 mmol) and DIEA (1 mL, 5.68 mmol) in acetonitrile (15 mL) was heated at 40° C. overnight. The solvent was removed in vacuo and the crude was purified via silica gel with 0-100% EtOAc/Hexanes to obtain the title compound. ESI-MS (m/z): 364 [M+1]$^+$.

Step 5. 5-Chloro-N-(((2S,3R)-3-methylpiperidin-2-yl)methyl)benzo[d]oxazol-2-amine

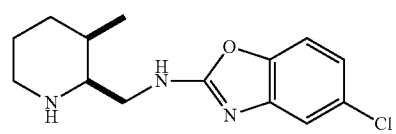 [SMILES: C[C@@H]1CCCN[C@@H]1CNc1nc2cc(Cl)ccc2o1]

To a solution of (2S,3R)-allyl 2-(((5-chlorobenzo[d]oxazol-2-yl)amino)methyl)-3-methylpiperidine-1-carboxylate (1.18 g, 3.248 mmol) and morpholine (2.8 mL, 32.48 mmol) in THF (30 mL) was added Pd (PPh$_3$)$_4$ (0.375 g, 0.32 mmol). The mixture was stirred at room temperature for 2 h wherein starting material was judged consumed by HPLC analysis. The solvent was removed in vacuo. The crude was purified via silica gel with 0→100% EtOAc/DCM to obtain the title compound. ESI-MS (m/z): 280 [M+1]$^+$.

Step 6. ((2S,3R)-2-(((5-Chlorobenzo[d]oxazol-2-yl) amino)methyl)-3-methylpiperidin-1-yl)(5-methyl-2-(2-methylpyrimidin-4-yl)phenyl)methanone The title compound was prepared following the same general protocol as described in Example A1, using 5-methyl-2-(2-methylpyrimidin-4-yl)benzoic acid and 5-chloro-N-(((2S,3R)-3-methylpiperidin-2-yl)methyl)benzo[d]oxazol-2-amine. ESI-MS (m/z): 490 [M+1]$^+$.

Example A28

((2S,3R)-2-(((5-Chlorobenzo[d]oxazol-2-yl)amino) methyl)-3-methylpiperidin-1-yl)(5-methyl-2-(1H-1,2,4-triazol-1-yl)phenyl)methanone

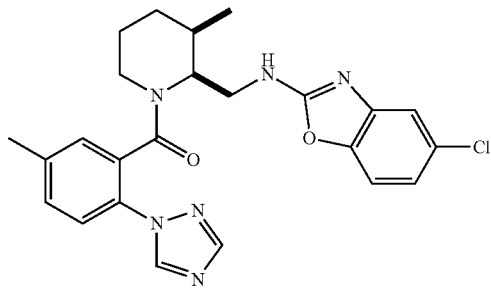 [SMILES: Cc1ccc(-n2cncn2)c(C(=O)N2CCC[C@@H](C)[C@H]2CNc2nc3cc(Cl)ccc3o2)c1]

Step 1. 5-Methyl-2-(1H-1,2,4-triazol-1-yl)benzoic acid

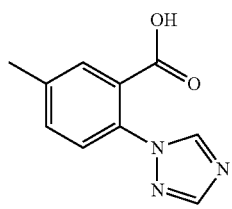

The title compound was synthesized following the same general protocol as described for 5-methyl-2-(2H-1,2,3-triazol-2-yl)benzoic acid in Example A11 using 1H-1,2,4-triazole. ESI-MS (m/z): 204 [M+1]$^+$.

Step 2. ((2S,3R)-2-(((5-Chlorobenzo[d]oxazol-2-yl) amino)methyl)-3-methylpiperidin-1-yl)(5-methyl-2-(1H-1,2,4-triazol-1-yl)phenyl)methanone The title compound was prepared following the same general protocol as described in Example A1, using 5-methyl-2-(1H-1,2,4-triazol-1-yl)benzoic acid and 5-chloro-N-(((2S,3R)-3-methylpiperidin-2-yl)methyl)benzo[d]oxazol-2-amine. ESI-MS (m/z): 465 [M+1]$^+$.

Example A29

((2S,3R)-2-(((5-Chlorobenzo[d]oxazol-2-yl)amino) methyl)-3-methylpiperidin-1-yl)(5-methyl-2-(3-methyl-1H-1,2,4-triazol-1-yl)phenyl)methanone

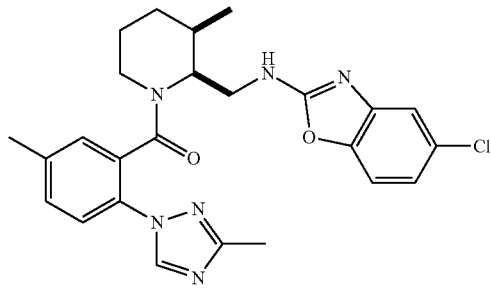 [SMILES: Cc1ccc(-n2cnc(C)n2)c(C(=O)N2CCC[C@@H](C)[C@H]2CNc2nc3cc(Cl)ccc3o2)c1]

The title compound was prepared following the same general protocol as described in Example A1, using 5-methyl-2-(3-methyl-1H-1,2,4-triazol-1-yl)benzoic acid and 5-chloro-N-(((2S,3R)-3-methylpiperidin-2-yl)methyl)benzo[d]oxazol-2-amine. ESI-MS (m/z): 479 [M+1]$^+$.

Example A30

((2S,3R)-2-(((5-Chlorobenzo[d]oxazol-2-yl)amino) methyl)-3-methylpiperidin-1-yl)(5-methyl-2-(thiazol-2-yl)phenyl)methanone

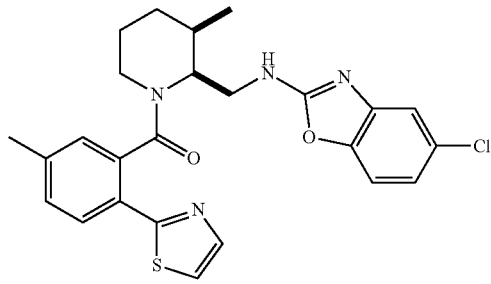

The title compound was prepared following the same general protocol as described in Example A1, using 5-methyl-2-(thiazol-2-yl)benzoic acid and 5-chloro-N-(((2S,3R)-3-methylpiperidin-2-yl)methyl)benzo[d]oxazol-2-amine. ESI-MS (m/z): 481 [M+1]$^+$.

Example A31

((2S,3R)-2-(((5-Chlorobenzo[d]oxazol-2-yl)amino) methyl)-3-methylpiperidin-1-yl)(5-methyl-2-(pyridin-3-yl)phenyl)methanone

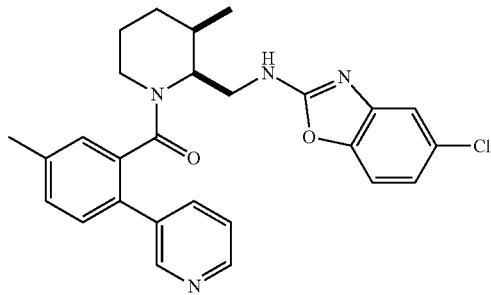

Step 1. 5-Methyl-2-(pyridin-3-yl)benzoic acid

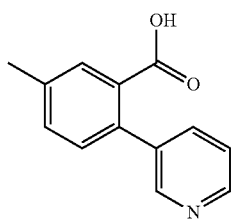 [SMILES: Cc1ccc(-c2cccnc2)c(C(=O)O)c1]

The title compound was synthesized following the same general protocol as described for 5-methyl-2-(1-methyl-1H-pyrazol-4-yl)benzoic acid in Example A1, using pyridin-3-ylboronic acid. ESI-MS (m/z): 214 [M+1]$^+$.

Step 2. ((2S,3R)-2-(((5-Chlorobenzo[d]oxazol-2-yl)amino)methyl)-3-methylpiperidin-1-yl)(5-methyl-2-(pyridin-3-yl)phenyl)methanone The title compound was prepared following the same general protocol as described in Example A1, using 5-methyl-2-(pyridin-3-yl)benzoic acid and 5-chloro-N-(((2S,3R)-3-methylpiperidin-2-yl)methyl)benzo[d]oxazol-2-amine. ESI-MS (m/z): 475 [M+1]$^+$.

Example A32

((2S,3R)-2-(((5-Chlorobenzo[d]oxazol-2-yl)amino)methyl)-3-methylpiperidin-1-yl)(5-methyl-2-(pyridin-2-yl)phenyl)methanone

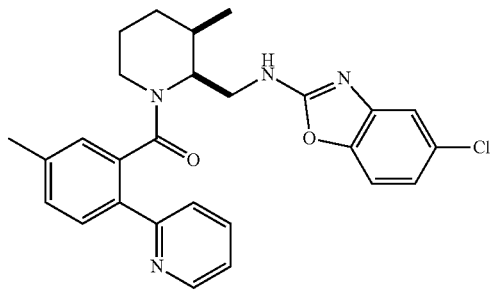 [SMILES: Cc1ccc(-c2ccccn2)c(C(=O)N2CCC[C@@H](C)[C@H]2CNc2nc3cc(Cl)ccc3o2)c1]

The title compound was prepared following the same general protocol as described in Example A1, using 5-methyl-2-(pyridin-2-yl)benzoic acid and 5-chloro-N-(((2S,3R)-3-methylpiperidin-2-yl)methyl)benzo[d]oxazol-2-amine. ESI-MS (m/z): 475 [M+1]$^+$.

Example A33

(2-(1H-Imidazol-1-yl)-5-methylphenyl)((2S,3R)-2-(((5-chlorobenzo[d]oxazol-2-yl)amino)methyl)-3-methylpiperidin-1-yl)methanone

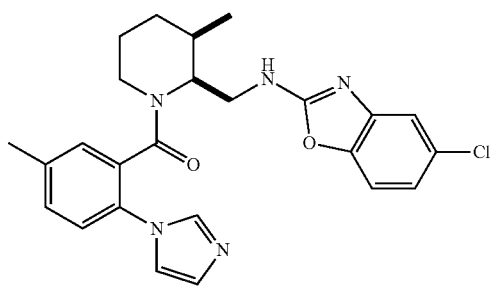

Step 1. 2-(1H-Imidazol-1-yl)-5-methylbenzoic acid

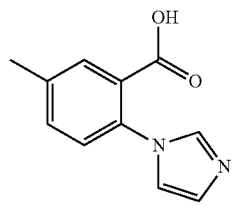

The title compound was synthesized following the same general protocol as described for 5-methyl-2-(2H-1,2,3-triazol-2-yl)benzoic acid in Example A11, using imidazole. ESI-MS (m/z): 203 [M+1]$^+$.

Step 2. (2-(1H-Imidazol-1-yl)-5-methylphenyl)((2S,3R)-2-(((5-chlorobenzo[d]oxazol-2-yl)amino)methyl)-3-methylpiperidin-1-yl)methanone The title compound was prepared following the same general protocol as described in Example A1, using 2-(1H-imidazol-1-yl)-5-methylbenzoic acid and 5-chloro-N-(((2S,3R)-3-methylpiperidin-2-yl)methyl)benzo[d]oxazol-2-amine. ESI-MS (m/z): 464 [M+1]$^+$.

Example A34

((2S,3R)-2-(((5-Chlorobenzo[d]oxazol-2-yl)amino)methyl)-3-methylpiperidin-1-yl)(5-methyl-2-(thiazol-5-yl)phenyl)methanone

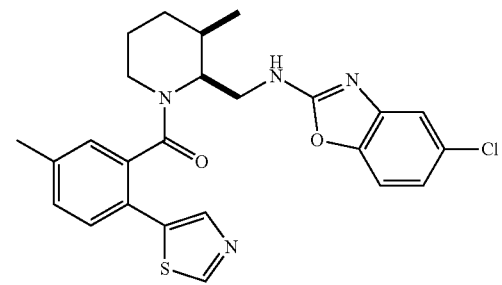 [SMILES: Cc1ccc(-c2cncs2)c(C(=O)N2CCC[C@@H](C)[C@H]2CNc2nc3cc(Cl)ccc3o2)c1]

The title compound was prepared following the same general protocol as described in Example A1, using 5-methyl-2-(thiazol-5-yl)benzoic acid and 5-chloro-N-(((2S,3R)-3-methylpiperidin-2-yl)methyl)benzo[d]oxazol-2-amine. ESI-MS (m/z): 481 [M+1]$^+$.

Example A35

((2S,3R)-2-(((5-Chlorobenzo[d]oxazol-2-yl)amino)methyl)-3-methylpiperidin-1-yl)(5-methyl-2-(4-methylpyrimidin-2-yl)phenyl)methanone

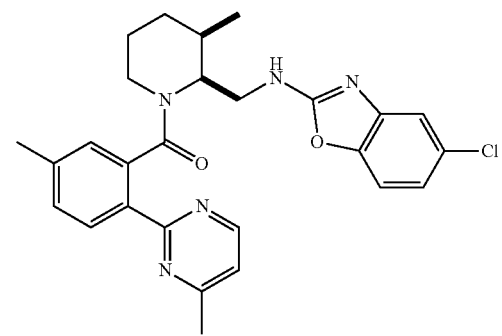 [SMILES: Cc1ccc(-c2nccc(C)n2)c(C(=O)N2CCC[C@@H](C)[C@H]2CNc2nc3cc(Cl)ccc3o2)c1]

Step 1.
5-Methyl-2-(4-methylpyrimidin-2-yl)benzoic acid

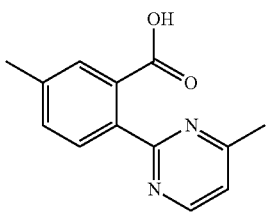

The title compound was prepared following the same general protocol as described for 5-methyl-2-(pyrazin-2-yl)benzoic acid in Example A19, starting from 2-chloro-4-methylpyrimidine. ESI-MS (m/z): 229 [M+1]$^+$.

Step 2. ((2S,3R)-2-(((5-Chlorobenzo[d]oxazol-2-yl)amino)methyl)-3-methylpiperidin-1-yl)(5-methyl-2-(4-methylpyrimidin-2-yl)phenyl)methanone The title compound was prepared following the same general protocol as described in Example A1, using 5-methyl-2-(4-methylpyrimidin-2-yl)benzoic acid and 5-chloro-N-(((2S,3R)-3-methylpiperidin-2-yl)methyl)benzo[d]oxazol-2-amine. ESI-MS (m/z): 490 [M+1]$^+$.

Example A36

((2S,3R)-2-(((5-Chlorobenzo[d]oxazol-2-yl)amino)methyl)-3-methylpiperidin-1-yl)(5-methyl-2-(1-methyl-1H-pyrazol-5-yl)phenyl)methanone

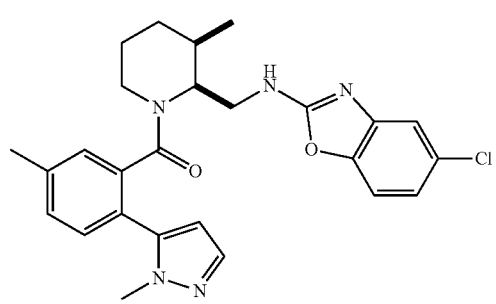 [SMILES: Cc1ccc(-c2ccnn2C)c(C(=O)N2CCC[C@@H](C)[C@H]2CNc2nc3cc(Cl)ccc3o2)c1]

Step 1.
5-Methyl-2-(1-methyl-1H-pyrazol-5-yl)benzoic acid

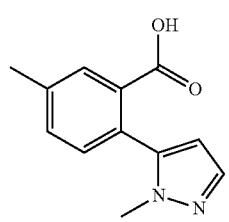 [SMILES: Cc1ccc(-c2ccnn2C)c(C(=O)O)c1]

The title compound was synthesized following the same general protocol as described for 5-methyl-2-(1-methyl-1H-pyrazol-4-yl)benzoic acid in Example A1, using 1-methyl-5-(4,4,5,5-tetramethyl-1,3,2-dioxaborolan-2-yl)-1H-pyrazole. ESI-MS (m/z): 217 [M+1]$^+$.

Step 2. ((2S,3R)-2-(((5-Chlorobenzo[d]oxazol-2-yl)amino)methyl)-3-methylpiperidin-1-yl)(5-methyl-2-(1-methyl-1H-pyrazol-5-yl)phenyl)methanone The title compound was prepared following the same general protocol as described in Example A1, using 5-methyl-2-(1-methyl-1H-pyrazol-5-yl)benzoic acid and 5-chloro-N-(((2S,3R)-3-methylpiperidin-2-yl)methyl)benzo[d]oxazol-2-amine. ESI-MS (m/z): 478 [M+1]$^+$.

Example A37

((2S,3R)-2-(((5-Chlorobenzo[d]oxazol-2-yl)amino)methyl)-3-methylpiperidin-1-yl)(5-methyl-2-(2-methylpyridin-4-yl)phenyl)methanone

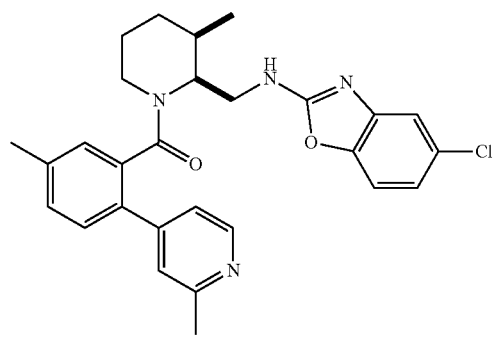

Step 1. 5-Methyl-2-(2-methylpyridin-4-yl)benzoic acid

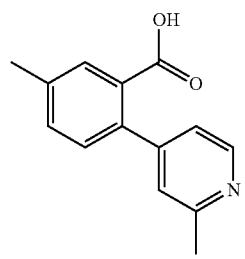 [SMILES: Cc1ccc(-c2ccnc(C)c2)c(C(=O)O)c1]

The title compound was synthesized following the same general protocol as described for 5-methyl-2-(1-methyl-1H-pyrazol-4-yl)benzoic acid in Example A1, using 2-methyl-4-(4,4,5,5-tetramethyl-1,3,2-dioxaborolan-2-yl)pyridine. ESI-MS (m/z): 228 [M+1]$^+$.

Step 2. ((2S,3R)-2-(((5-Chlorobenzo[d]oxazol-2-yl)amino)methyl)-3-methylpiperidin-1-yl)(5-methyl-2-(2-methylpyridin-4-yl)phenyl)methanone The title compound was prepared following the same general protocol as described in Example A1, using 5-methyl-2-(2-methylpyridin-4-yl)benzoic acid and 5-chloro-N-(((2S,3R)-3-methylpiperidin-2-yl)methyl)benzo[d]oxazol-2-amine. ESI-MS (m/z): 489 [M+1]$^+$.

Example A38

((2S,3R)-2-(((5-Chlorobenzo[d]oxazol-2-yl)amino)methyl)-3-methylpiperidin-1-yl)(5-methyl-2-(6-methylpyridin-3-yl)phenyl)methanone

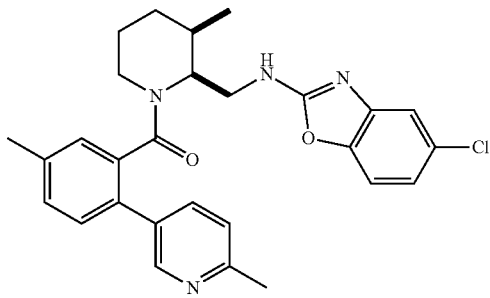 [SMILES: Cc1ccc(-c2ccc(C)nc2)c(C(=O)N2CCC[C@@H](C)[C@H]2CNc2nc3cc(Cl)ccc3o2)c1]

Step 1. 5-Methyl-2-(6-methylpyridin-3-yl)benzoic acid

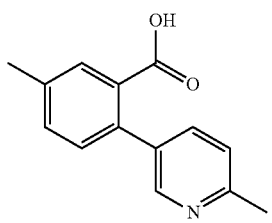

The title compound was synthesized following the same general protocol as described for 5-methyl-2-(1-methyl-1H-pyrazol-4-yl)benzoic acid in Example A1, using (6-methyl-pyridin-3-yl)boronic acid. ESI-MS (m/z): 228 [M+1]$^+$.

Step 2. ((2S,3R)-2-(((5-Chlorobenzo[d]oxazol-2-yl)amino)methyl)-3-methylpiperidin-1-yl)(5-methyl-2-(6-methylpyridin-3-yl)phenyl)methanone The title compound was prepared following the same general protocol as described in Example A1, using 5-methyl-2-(6-methylpyridin-3-yl)benzoic acid and 5-chloro-N-(((2S,3R)-3-methylpiperidin-2-yl)methyl)benzo[d]oxazol-2-amine. ESI-MS (m/z): 489 [M+1]$^+$.

Example A39

((2S,3R)-2-(((5-Chlorobenzo[d]oxazol-2-yl)amino)methyl)-3-methylpiperidin-1-yl)(2-(2-methoxypyrimidin-5-yl)-5-methylphenyl)methanone

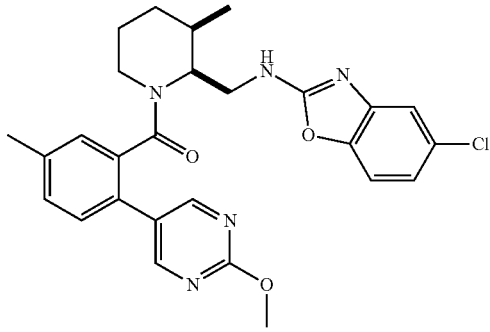 [SMILES: COc1ncc(-c2ccc(C)cc2C(=O)N2CCC[C@@H](C)[C@H]2CNc2nc3cc(Cl)ccc3o2)cn1]

Step 1. 2-(2-Methoxypyrimidin-5-yl)-5-methylbenzoic acid

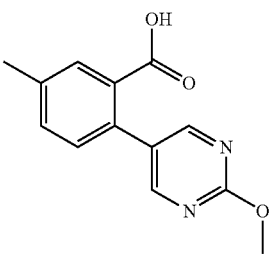

The title compound was synthesized following the same general protocol as described for 5-methyl-2-(1-methyl-1H-pyrazol-4-yl)benzoic acid in Example A1, using (2-methoxypyrimidin-5-yl)boronic acid. ESI-MS (m/z): 245 [M+1]$^+$.

Step 2. ((2S,3R)-2-(((5-Chlorobenzo[d]oxazol-2-yl)amino)methyl)-3-methylpiperidin-1-yl)(2-(2-methoxypyrimidin-5-yl)-5-methylphenyl)methanone The title compound was prepared following the same general protocol as described in Example A1, using 2-(2-methoxypyrimidin-5-yl)-5-methylbenzoic acid and 5-chloro-N-(((2S,3R)-3-methylpiperidin-2-yl)methyl)benzo[d]oxazol-2-amine. ESI-MS (m/z): 506 [M+1]$^+$.

Example A40

((2S,3R)-2-(((5-Chlorobenzo[d]oxazol-2-yl)amino)methyl)-3-methylpiperidin-1-yl)(5-methyl-2-(1-methyl-1H-pyrazol-4-yl)phenyl)methanone

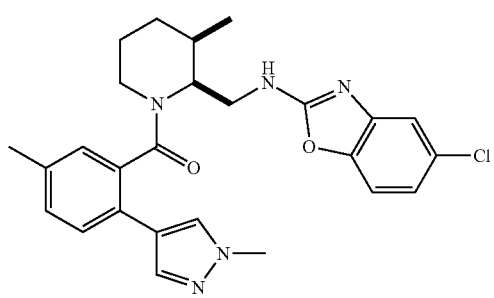 [SMILES: Cc1ccc(-c2cnn(C)c2)c(C(=O)N2CCC[C@@H](C)[C@H]2CNc2nc3cc(Cl)ccc3o2)c1]

The title compound was prepared following the same general protocol as described in Example A1, using 5-methyl-2-(1-methyl-1H-pyrazol-4-yl)benzoic acid and 5-chloro-N-(((2S,3R)-3-methylpiperidin-2-yl)methyl)benzo[d]oxazol-2-amine. ESI-MS (m/z): 478 [M+1]$^+$.

Example A41

((2S,3R)-2-(((5-Chloropyrimidin-2-yl)amino)methyl)-3-methylpiperidin-1-yl)(5-(4-fluorophenyl)-2-methylthiazol-4-yl)methanone

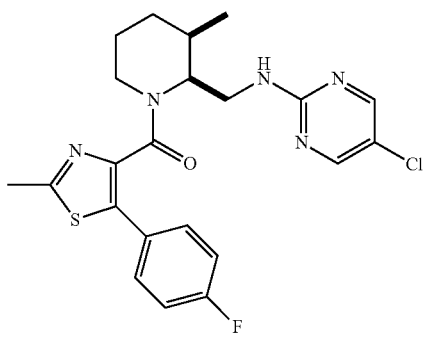

A mixture of ((2S,3R)-2-(aminomethyl)-3-methylpiperidin-1-yl)(5-(4-fluorophenyl)-2-methylthiazol-4-yl)methanone (50 mg, 145 μmol), 2,5-dichloropyrimidine (43 mg, 287 μmol), and DIEA (75 mg, 431 μmol) in isopropanol was stirred at 120° C. for 1 h in a microwave reactor. The crude reaction mixture was purified by reverse-phase preparative HPLC to afford the title compound. MS (ESI) 459 (M+H).

Example A42

((2R,3S)-2-((Benzo[d]oxazol-2-ylamino)methyl)-3-methylpiperidin-1-yl)(5-(4-fluorophenyl)-2-methylthiazol-4-yl)methanone

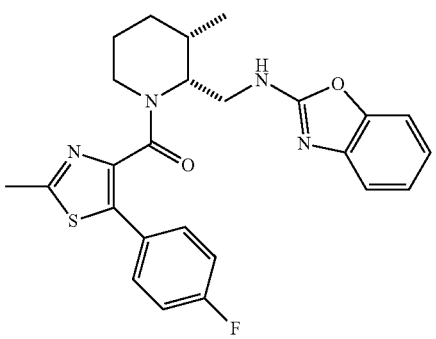 [SMILES: Cc1nc(C(=O)N2CCC[C@H](C)[C@@H]2CNc2nc3ccccc3o2)c(-c2ccc(F)cc2)s1]

Step 1. 2-(((2R,3S)-3-Methylpiperidin-2-yl)methyl)isoindoline-1,3-dione

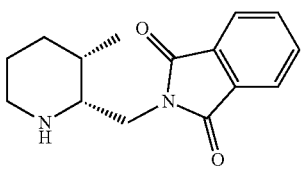 [SMILES: C[C@H]1CCCN[C@H]1CN1C(=O)c2ccccc2C1=O]

The title compound was prepared following the same general protocol as described for 2-(((2S,3R)-3-methylpiperidin-2-yl)methyl)isoindoline-1,3-dione in Example A1 instead using (2R,3S)-1-((benzyloxy)carbonyl)-3-methylpiperidine-2-carboxylic acid. MS (ESI) 259 (M+H).

Step 2. ((2R,3S)-2-(Aminomethyl)-3-methylpiperidin-1-yl)(5-(4-fluorophenyl)-2-methylthiazol-4-yl)methanone

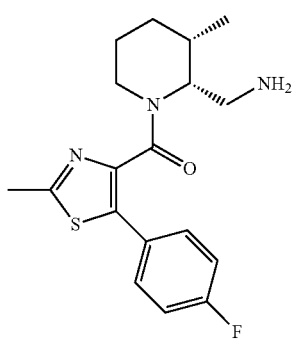 [SMILES: Cc1nc(C(=O)N2CCC[C@H](C)[C@@H]2CN)c(-c2ccc(F)cc2)s1]

The title compound was prepared following the same general protocol as described for ((2S,3R)-2-(aminomethyl)-3-methylpiperidin-1-yl)(5-(4-fluorophenyl)-2-methylthiazol-4-yl)methanone in Example A13 using 2-(((2R,3S)-3-methylpiperidin-2-yl)methyl)isoindoline-1,3-dione. MS (ESI) 348 (M+H).

Step 3. ((2R,3S)-2-((Benzo[d]oxazol-2-ylamino)methyl)-3-methylpiperidin-1-yl)(5-(4-fluorophenyl)-2-methylthiazol-4-yl)methanone The title compound was prepared following the same general protocol as described for Example A2 using ((2R,3S)-2-(aminomethyl)-3-methylpiperidin-1-yl)(5-(4-fluorophenyl)-2-methylthiazol-4-yl)methanone. MS (ESI) 459 (M+H).

Example A43

(5-(4-Fluorophenyl)-2-methylthiazol-4-yl)((2R,3S)-3-methyl-2-(((5-(trifluoromethyl)pyridin-2-yl)amino)methyl)piperidin-1-yl)methanone

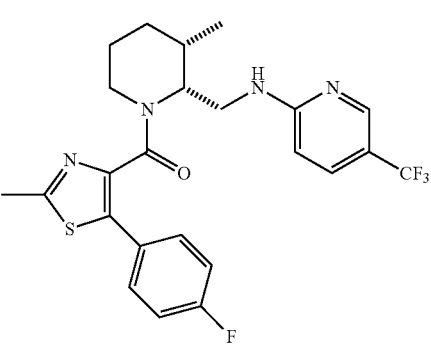 [SMILES: Cc1nc(C(=O)N2CCC[C@H](C)[C@@H]2CNc2ccc(C(F)(F)F)cn2)c(-c2ccc(F)cc2)s1]

The title compound was prepared following the same general protocol as described for Example A1 using ((2R, 3S)-2-(aminomethyl)-3-methylpiperidin-1-yl)(5-(4-fluorophenyl)-2-methylthiazol-4-yl)methanone. MS (ESI) 465 (M+H).

Example A44

((2S,3R)-2-(((5-Fluoropyridin-2-yl)amino)methyl)-3-methylpiperidin-1-yl)(5-methyl-2-(1-methyl-1H-pyrazol-4-yl)phenyl)methanone

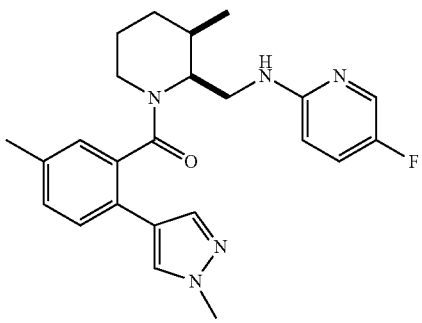 [SMILES: Cc1ccc(-c2cnn(C)c2)c(C(=O)N2CCC[C@@H](C)[C@H]2CNc2ccc(F)cn2)c1]

A mixture of ((2S,3R)-2-(aminomethyl)-3-methylpiperidin-1-yl) (5-methyl-2-(1-methyl-1H-pyrazol-4-yl)phenyl)methanone (80 mg, 245 μmol), 2-bromo-5-fluoropyridine (47 mg, 270 μmol), Pd$_2$dba$_3$ (5.0 mg, 4.9 μmol), xantphos (4.2 mg, 7 μmol), and NaOtBu (35 mg, 368 μmol) in dioxane (2 ml) was purged with argon, and then stirred at 100° C. overnight. The reaction was cooled, filtered through a pad of silica gel and concentrated in vacuo. The crude reaction mixture was purified by reverse-phase preparative HPLC to afford the title compound. MS (ESI) 422 (M+H).

Example A45

6-((((2S,3R)-3-Methyl-1-(5-methyl-2-(1-methyl-1H-pyrazol-4-yl)benzoyl)piperidin-2-yl)methyl)amino)nicotinonitrile

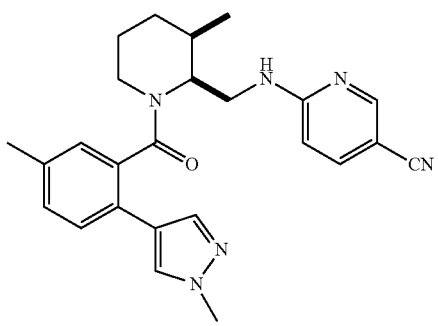 [SMILES: Cc1ccc(-c2cnn(C)c2)c(C(=O)N2CCC[C@@H](C)[C@H]2CNc2ccc(C#N)cn2)c1]

A mixture of ((2S,3R)-2-(aminomethyl)-3-methylpiperidin-1-yl)(5-methyl-2-(1-methyl-1H-pyrazol-4-yl)phenyl)methanone (80 mg, 245 μmol), 6-chloronicotinonitrile (50 mg, 368 μmol) and anhydrous K$_2$CO$_3$ (102 mg, 735 μmol) in DMF (2 mL) was heated at 100° C. overnight. The mixture was cooled to room temperature and the solvent was removed in vacuo. The crude was dissolved in EtOAc and washed with sat'd NaHCO$_3$, brine and then dried (MgSO$_4$). The solvent was removed and the crude was purified by reverse-phase preparative HPLC to afford the title compound. MS (ESI) 429 (M+H).

Example A46

6-((((2S,3R)-3-Methyl-1-(5-methyl-2-(2H-1,2,3-triazol-2-yl)benzoyl)piperidin-2-yl)methyl)amino)nicotinonitrile

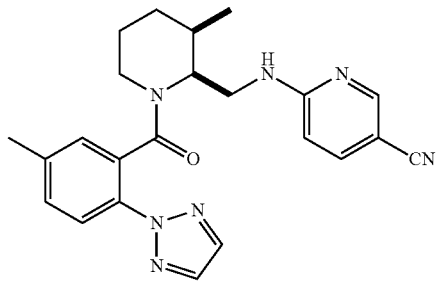

The title compound was prepared following the same general protocol as described for Example A45 using ((2S,3R)-2-(aminomethyl)-3-methylpiperidin-1-yl)(5-methyl-2-(2H-1,2,3-triazol-2-yl)phenyl)methanone. MS (ESI) 416 (M+H).

Example A47

((2S,3R)-2-(((5-Fluoropyridin-2-yl)amino)methyl)-3-methylpiperidin-1-yl)(5-methyl-2-(2H-1,2,3-triazol-2-yl)phenyl)methanone

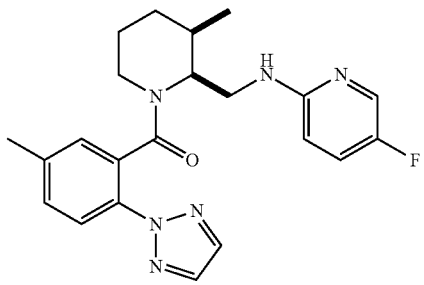

The title compound was prepared following the same general protocol as described for Example A44 using ((2S,3R)-2-(aminomethyl)-3-methylpiperidin-1-yl)(5-methyl-2-(2H-1,2,3-triazol-2-yl)phenyl)methanone. MS (ESI) 409.2 (M+H).

Example A48

((2S,3R)-3-Methyl-2-(((5-methylpyridin-2-yl)amino)methyl)piperidin-1-yl)(5-methyl-2-(2H-1,2,3-triazol-2-yl)phenyl)methanone

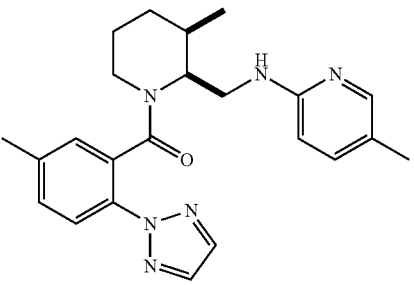

The title compound was prepared following the same general protocol as described for Example A44 using ((2S, 3R)-2-(aminomethyl)-3-methylpiperidin-1-yl)(5-methyl-2-(2H-1,2,3-triazol-2-yl)phenyl)methanone and 2-bromo-5-methylpyridine. MS (ESI) 409.2 (M+H).

Example A49

((2S,3R)-3-Methyl-2-(((5-methylpyridin-2-yl)amino)methyl)piperidin-1-yl)(5-methyl-2-(1-methyl-1H-pyrazol-4-yl)phenyl)methanone

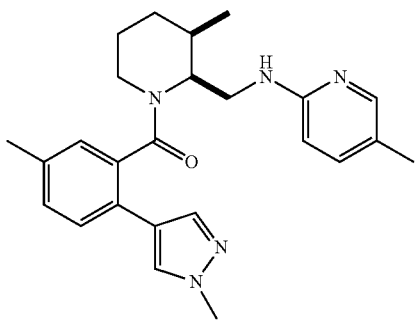

The title compound was prepared following the same general protocol as described for Example A44 using 2-bromo-5-methylpyridine. MS (ESI) 409.2 (M+H).

Example A50

((2S,3R)-2-(((5-Chlorobenzo[d]oxazol-2-yl)amino)methyl)-3-methylpiperidin-1-yl)(5-methyl-2-(1-methyl-1H-pyrazol-5-yl)phenyl)methanone

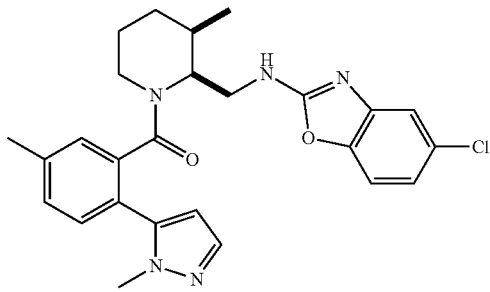 [SMILES: Cc1ccc(-c2ccnn2C)c(C(=O)N2CCC[C@@H](C)[C@H]2CNc2nc3cc(Cl)ccc3o2)c1]

The title compound was prepared following the same general protocol as described in Example A1, using 5-methyl-2-(1-methyl-1H-pyrazol-5-yl)benzoic acid and 5-chloro-N-(((2S,3R)-3-methylpiperidin-2-yl)methyl)benzo[d]oxazol-2-amine. ESI-MS (m/z): 478 [M+1]⁺.

Example A51

6-(((((2S,3R)-3-Methyl-1-(5-methyl-2-(3-(trifluoromethyl)-1H-1,2,4-triazol-1-yl)benzoyl)piperidin-2-yl)methyl)amino)nicotinonitrile

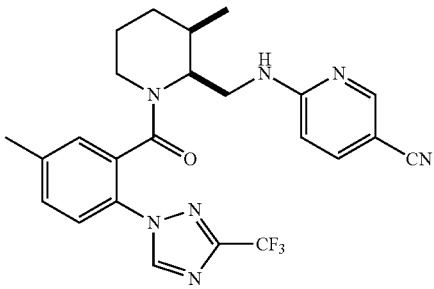 [SMILES: Cc1ccc(-n2cnc(C(F)(F)F)n2)c(C(=O)N2CCC[C@@H](C)[C@H]2CNc2ccc(C#N)cn2)c1]

Step 1. 5-Methyl-2-(3-(trifluoromethyl)-1H-1,2,4-triazol-1-yl)benzoic acid

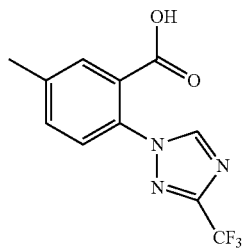 [SMILES: Cc1ccc(-n2cnc(C(F)(F)F)n2)c(C(=O)O)c1]

The title compound was synthesized following the same general protocol as described in Example A11 using 3-(trifluoromethyl)-1H-1,2,4-triazole. ESI-MS (m/z): 272 [M+1]⁺.

Step 2. tert-butyl (((2S,3R)-3-methyl-1-(5-methyl-2-(3-(trifluoromethyl)-1H-1,2,4-triazol-1-yl)benzoyl)piperidin-2-yl)methyl)carbamate

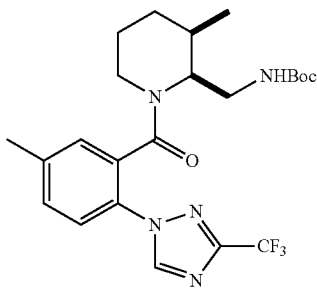 [SMILES: Cc1ccc(-n2cnc(C(F)(F)F)n2)c(C(=O)N2CCC[C@@H](C)[C@H]2CNC(=O)OC(C)(C)C)c1]

To a mixture of 5-methyl-2-(3-(trifluoromethyl)-1H-1,2,4-triazol-1-yl)benzoic acid (0.24 g, 0.869 mmol), tert-butyl (((2S,3R)-3-methylpiperidin-2-yl)methyl)carbamate (0.22 g, 0.96 mmol) and DIEA (0.3 mL, 1.738 mmol) in DCM (20 mL) was added HATU (0.33 g, 0.869 mmol). The mixture was stirred at rt for 1 h. The mixture was diluted with DCM and was washed with sat'd NaHCO₃ and brine and dried over Na$_2$SO$_4$. The solvent was removed in vacuo to obtain the title compound with no further purification for next step. ESI-MS (m/z): 482 [M+1]$^+$.

Step 3. ((2S,3R)-2-(Aminomethyl)-3-methylpiperidin-1-yl)(5-methyl-2-(3-(trifluoromethyl)-1H-1,2,4-triazol-1-yl)phenyl)methanone

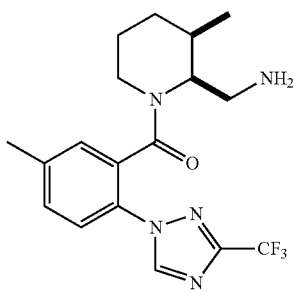 [SMILES: Cc1ccc(-n2cnc(C(F)(F)F)n2)c(C(=O)N2CCC[C@@H](C)[C@H]2CN)c1]

tert-Butyl(((2S,3R)-3-methyl-1-(5-methyl-2-(3-(trifluoromethyl)-1H-1,2,4-triazol-1-yl)benzoyl)piperidin-2-yl)methyl)carbamate obtained from the previous step was dissolved in DCM (20 mL) and then TFA (8 mL) was added. The mixture was stirred at rt for 2 h. The solvent was removed in vacuo to give the crude product as a TFA salt which was used without further purification. ESI-MS (m/z): 482 [M+1]$^+$.

Step 4. 6-((((2S,3R)-3-Methyl-1-(5-methyl-2-(3-(trifluoromethyl)-1H-1,2,4-triazol-1-yl)benzoyl)piperidin-2-yl)methyl)amino)nicotinonitrile The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(3-(trifluoromethyl)-1H-1,2,4-triazol-1-yl)phenyl)methanone and 6-chloronicotinonitrile. ESI-MS (m/z): 484 [M+1]$^+$.

Example A52

6-((((2S,3R)-3-methyl-1-(5-methyl-2-(3-methyl-1H-1,2,4-triazol-1-yl)benzoyl)piperidin-2-yl)methyl)amino)nicotinonitrile

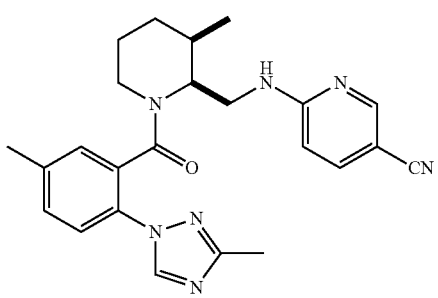 [SMILES: Cc1ccc(-n2cnc(C)n2)c(C(=O)N2CCC[C@@H](C)[C@H]2CNc2ccc(C#N)cn2)c1]

Step 1. ((2S,3R)-2-(aminomethyl)-3-methylpiperidin-1-yl)(5-methyl-2-(3-methyl-1H-1,2,4-triazol-1-yl)phenyl)methanone

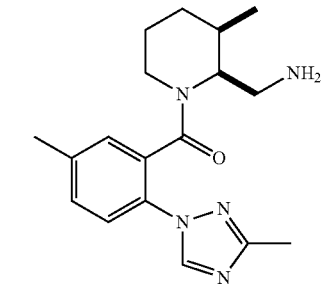 [SMILES: Cc1ccc(-n2cnc(C)n2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A51, starting from 5-methyl-2-(3-methyl-1H-1,2,4-triazol-1-yl)benzoic acid. ESI-MS (m/z): 328 [M+1]$^+$.

Step 2. 6-((((2S,3R)-3-methyl-1-(5-methyl-2-(3-methyl-1H-1,2,4-triazol-1-yl)benzoyl)piperidin-2-yl)methyl)amino)nicotinonitrile The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl) (5-methyl-2-(3-methyl-1H-1,2,4-triazol-1-yl)phenyl)methanone and 6-chloronicotinonitrile. ESI-MS (m/z): 430 [M+1]$^+$.

Example A53

((2S,3R)-2-(((5-Fluoropyridin-2-yl)amino)methyl)-3-methylpiperidin-1-yl)(5-methyl-2-(2-methylpyridin-4-yl)phenyl)methanone

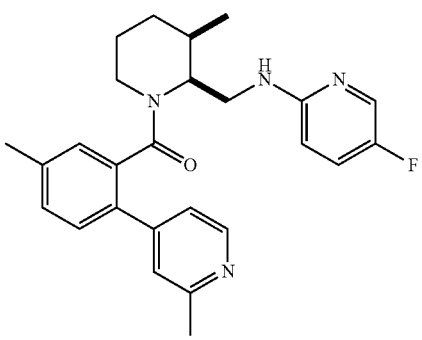 [SMILES: Cc1ccc(-c2ccnc(C)c2)c(C(=O)N2CCC[C@@H](C)[C@H]2CNc2ccc(F)cn2)c1]

Step 1. ((2S,3R)-2-(Aminomethyl)-3-methylpiperidin-1-yl)(5-methyl-2-(2-methylpyridin-4-yl)phenyl)methanone

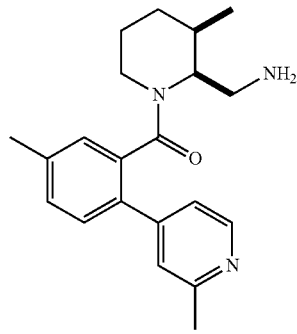 [SMILES: Cc1ccc(-c2ccnc(C)c2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A51, starting from 5-methyl-2-(2-methylpyridin-4-yl)benzoic acid. ESI-MS (m/z): 338 [M+1]$^+$.

Step 2. ((2S,3R)-2-(((5-Fluoropyridin-2-yl)amino)methyl)-3-methylpiperidin-1-yl)(5-methyl-2-(2-methylpyridin-4-yl)phenyl)methanone The title compound was synthesized following the same general protocol as described in Example A44, using ((2S,3R)-2-(aminomethyl)-3-methylpiperidin-1-yl)(5-methyl-2-(2-methylpyridin-4-yl)phenyl)methanone. ESI-MS (m/z): 433 [M+1]$^+$.

Example A54

((2S,3R)-3-Methyl-2-(((5-methylpyridin-2-yl)amino)methyl)piperidin-1-yl)(5-methyl-2-(3-methyl-1H-1,2,4-triazol-1-yl)phenyl)methanone

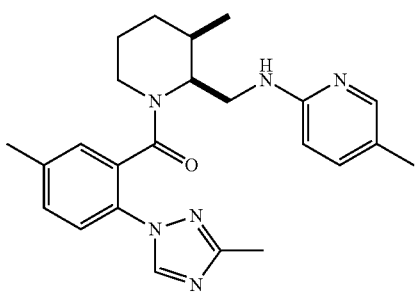

The title compound was synthesized following the same general protocol as described in Example A44, using ((2S,3R)-2-(aminomethyl)-3-methylpiperidin-1-yl)(5-methyl-2-(3-methyl-1H-1,2,4-triazol-1-yl)phenyl)methanone and 2-bromo-5-methylpyridine. ESI-MS (m/z): 419 [M+1]$^+$.

Example A55

((2S,3R)-2-(((5-fluoropyridin-2-yl)amino)methyl)-3-methylpiperidin-1-yl)(5-methyl-2-(3-methyl-1H-1,2,4-triazol-1-yl)phenyl)methanone

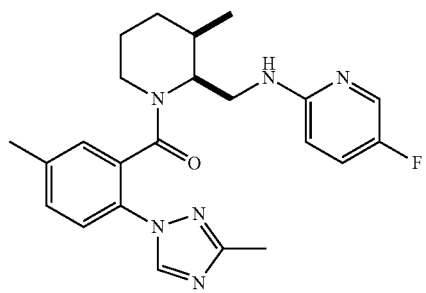 [SMILES: Cc1ccc(-n2cnc(C)n2)c(C(=O)N2CCC[C@@H](C)[C@H]2CNc2ccc(F)cn2)c1]

The title compound was synthesized following the same general protocol as described in Example A44, using ((2S,3R)-2-(aminomethyl)-3-methylpiperidin-1-yl)(5-methyl-2-(3-methyl-1H-1,2,4-triazol-1-yl)phenyl)methanone and 2-bromo-5-fluoropyridine. ESI-MS (m/z): 423 [M+1]$^+$.

Example A56

((2S,3R)-3-Methyl-2-(((5-methylpyridin-2-yl)amino)methyl)piperidin-1-yl)(5-methyl-2-(3-(trifluoromethyl)-1H-1,2,4-triazol-1-yl)phenyl)methanone

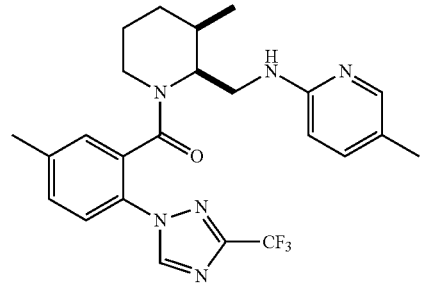

The title compound was synthesized following the same general protocol as described in Example A44, using ((2S,3R)-2-(aminomethyl)-3-methylpiperidin-1-yl)(5-methyl-2-(3-(trifluoromethyl)-1H-1,2,4-triazol-1-yl)phenyl)methanone and 2-bromo-5-methylpyridine. ESI-MS (m/z): 473 [M+1]$^+$.

Example A57

((2S,3R)-2-(((5-Fluoropyridin-2-yl)amino)methyl)-3-methylpiperidin-1-yl)(5-methyl-2-(3-(trifluoromethyl)-1H-1,2,4-triazol-1-yl)phenyl)methanone

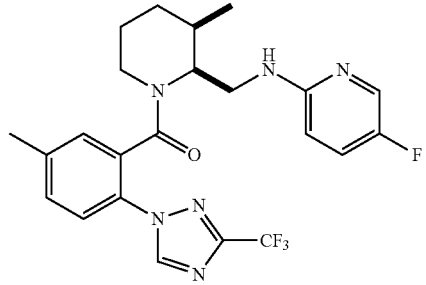

The title compound was synthesized following the same general protocol as described in Example A44, using ((2S,3R)-2-(aminomethyl)-3-methylpiperidin-1-yl)(5-methyl-2-(3-(trifluoromethyl)-1H-1,2,4-triazol-1-yl)phenyl)methanone and 2-bromo-5-fluoropyridine. ESI-MS (m/z): 477 [M+1]+.

Example A58

((2S,3R)-2-(((5-Fluoropyridin-2-yl)amino)methyl)-3-methylpiperidin-1-yl)(5-methyl-2-(pyridin-2-yl)phenyl)methanone

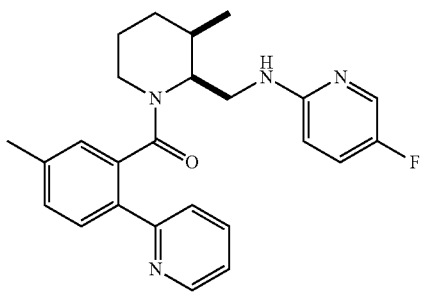 [SMILES: Cc1ccc(-c2ccccn2)c(C(=O)N2CCC[C@@H](C)[C@H]2CNc2ccc(F)cn2)c1]

Step 1. ((2S,3R)-2-(Aminomethyl)-3-methylpiperidin-1-yl)(5-methyl-2-(pyridin-2-yl)phenyl)methanone

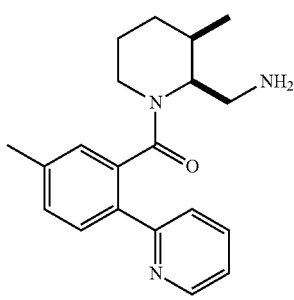 [SMILES: Cc1ccc(-c2ccccn2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A51, starting from 5-methyl-2-(pyridin-2-yl)benzoic acid. ESI-MS (m/z): 324 [M+1]+.

Step 2. ((2S,3R)-2-(((5-Fluoropyridin-2-yl)amino)methyl)-3-methylpiperidin-1-yl)(5-methyl-2-(pyridin-2-yl)phenyl)methanone The title compound was synthesized following the same general protocol as described in Example A44, using ((2S,3R)-2-(aminomethyl)-3-methylpiperidin-1-yl)(5-methyl-2-(pyridin-2-yl)phenyl)methanone and 2-bromo-5-fluoropyridine. ESI-MS (m/z): 419 [M+1]+.

Example A59

((2S,3R)-3-Methyl-2-(((5-methylpyridin-2-yl)amino)methyl)piperidin-1-yl)(5-methyl-2-(pyridin-2-yl)phenyl)methanone

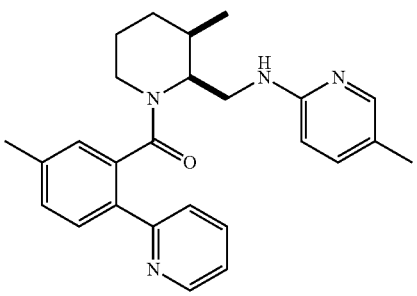

The title compound was synthesized following the same general protocol as described in Example A44, using ((2S,3R)-2-(aminomethyl)-3-methylpiperidin-1-yl)(5-methyl-2-(pyridin-2-yl)phenyl)methanone and 2-bromo-5-methylpyridine. ESI-MS (m/z): 415 [M+1]+.

Example A60

6-(((2S,3R)-3-Methyl-1-(5-methyl-2-(pyridin-2-yl)benzoyl)piperidin-2-yl)methyl)amino)nicotinonitrile

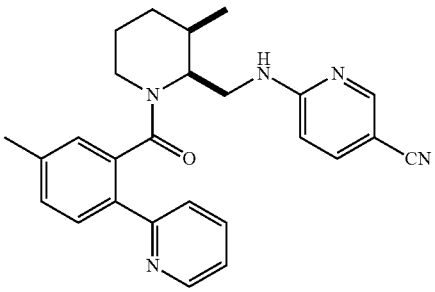

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(pyridin-2-yl)phenyl)methanone and 6-chloronicotinonitrile. ESI-MS (m/z): 426 [M+1]+.

Example A61

((2S,3R)-2-(((5-Fluoropyridin-2-yl)amino)methyl)-3-methylpiperidin-1-yl)(5-methyl-2-(1-methyl-1H-pyrazol-5-yl)phenyl)methanone

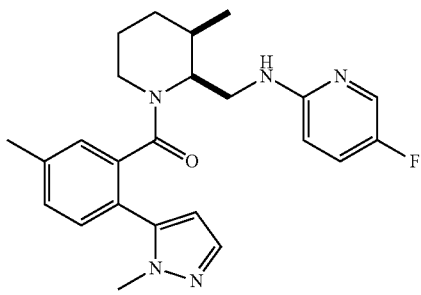 [SMILES: Cc1ccc(-c2ccnn2C)c(C(=O)N2CCC[C@@H](C)[C@H]2CNc2ccc(F)cn2)c1]

Step 1. ((2S,3R)-2-(Aminomethyl)-3-methylpiperidin-1-yl)(5-methyl-2-(1-methyl-1H-pyrazol-5-yl)phenyl)methanone

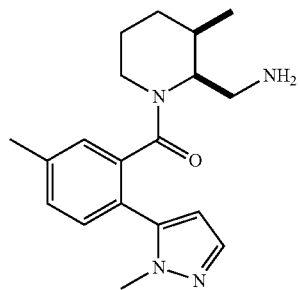 [SMILES: Cc1ccc(-c2ccnn2C)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A51, starting from 5-methyl-2-(1-methyl-1H-pyrazol-5-yl) benzoic acid. ESI-MS (m/z): 327 [M+1]+.

Step 2. ((2S,3R)-2-(((5-Fluoropyridin-2-yl)amino)methyl)-3-methylpiperidin-1-yl)(5-methyl-2-(1-methyl-1H-pyrazol-5-yl)phenyl)methanone The title compound was synthesized following the same general protocol as described in Example A44, using ((2S,3R)-2-(aminomethyl)-3-methylpiperidin-1-yl)(5-methyl-2-(1-methyl-1H-pyrazol-5-yl)phenyl)methanone and 2-bromo-5-fluoropyridine. ESI-MS (m/z): 422 [M+1]+.

Example A62

((2S,3R)-3-Methyl-2-(((5-methylpyridin-2-yl)amino) methyl)piperidin-1-yl)(5-methyl-2-(1-methyl-1H-pyrazol-5-yl)phenyl)methanone

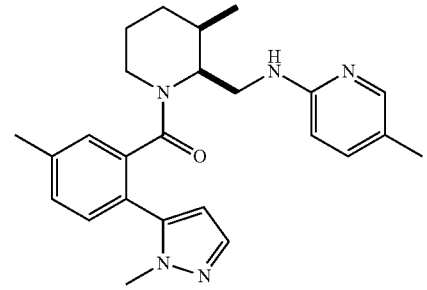

The title compound was synthesized following the same general protocol as described in Example A44, using ((2S,3R)-2-(aminomethyl)-3-methylpiperidin-1-yl)(5-methyl-2-(1-methyl-1H-pyrazol-5-yl)phenyl)methanone and 2-bromo-5-methylpyridine. ESI-MS (m/z): 418 [M+1]+.

Example A63

6-((((2S,3R)-3-Methyl-1-(5-methyl-2-(1-methyl-1H-pyrazol-5-yl)benzoyl)piperidin-2-yl)methyl)amino) nicotinonitrile

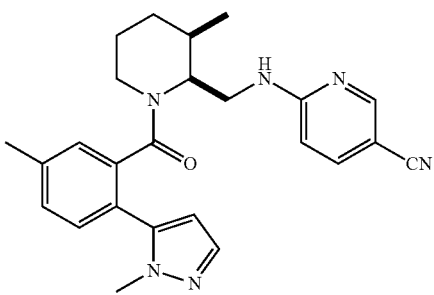 [SMILES: Cc1ccc(-c2ccnn2C)c(C(=O)N2CCC[C@@H](C)[C@H]2CNc2ccc(C#N)cn2)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(1-methyl-1H-pyrazol-5-yl)phenyl)methanone and 6-chloronicotinonitrile. ESI-MS (m/z): 429 [M+1]+.

Example A64

((2S,3R)-2-(((5-Chlorobenzo[d]oxazol-2-yl)amino)methyl)-3-methylpiperidin-1-yl)(5-methyl-2-(3-(trifluoromethyl)-1H-1,2,4-triazol-1-yl)phenyl)methanone

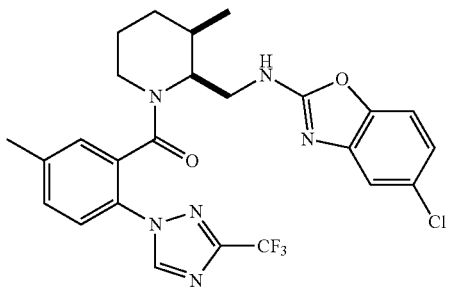 [SMILES: Cc1ccc(-n2cnc(C(F)(F)F)n2)c(C(=O)N2CCC[C@@H](C)[C@H]2CNc2nc3cc(Cl)ccc3o2)c1]

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(3-(trifluoromethyl)-1H-1,2,4-triazol-1-yl)phenyl)methanone. ESI-MS (m/z): 533 [M+1]⁺.

Example A65

(5-(4-Fluorophenyl)-2-methylthiazol-4-yl)((2S,3S)-3-methyl-2-(((5-(trifluoromethyl)pyridin-2-yl)amino)methyl)piperidin-1-yl)methanone

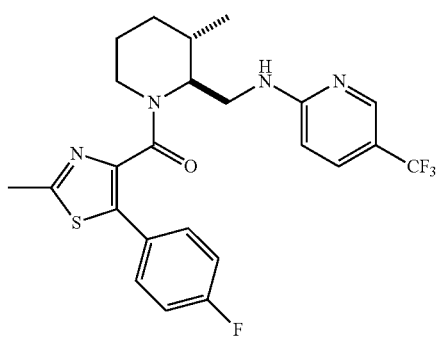

Step 1. 1-Benzyl-2-(((tert-butoxycarbonyl)amino)methyl)-3-methylpyridin-1-ium bromide

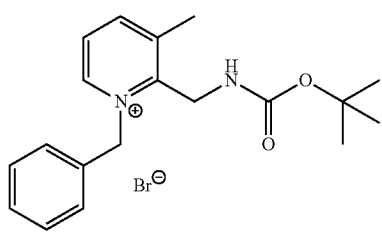 [SMILES: Cc1ccc[n+](Cc2ccccc2)c1CNC(=O)OC(C)(C)C ; [Br-]]

A solution of tert-butyl ((3-methylpyridin-2-yl)methyl)carbamate (9.2 g, 41 mmol) and benzylbromide (9.9 ml, 83 mmol) in 150 ml of acetonitrile was heated in a sealed vessel at reflux overnight and then concentrated in vacuo to give the title compound which was used without further purification. MS (ESI) 313 (M+H).

Step 2. rac-tert-Butyl ((1-benzyl-3-methyl-1,2,5,6-tetrahydropyridin-2-yl)methyl)carbamate

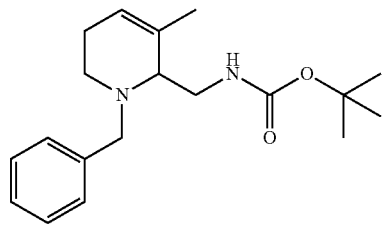 [SMILES: CC1=CCCN(Cc2ccccc2)C1CNC(=O)OC(C)(C)C]

To a solution of 1-benzyl-2-(((tert-butoxycarbonyl)amino)methyl)-3-methylpyridin-1-ium bromide (10.9 g, 35 mmol) in MeOH (500 ml) was added NaBH₄ (3.95 g, 104 mmol) in three portions at 0° C. The solution was then stirred for 3 h at room temperature and then concentrated in vacuo. The crude residue was taken up in EtOAc and washed with sat aq. NaHCO₃, dried (MgSO₄), and concentrated. The crude residue was purified by chromatography on silica gel (EtOAc/hexanes) to give the title compound as a pale yellow oil (6.67, 61%). MS (ESI) 317 (M+H).

Step 2. rac-tert-Butyl (((2S,3S)-3-methylpiperidin-2-yl)methyl)carbamate

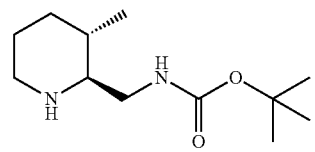 [SMILES: C[C@H]1CCCN[C@@H]1CNC(=O)OC(C)(C)C]

A mixture of rac-tert-butyl ((1-benzyl-3-methyl-1,2,5,6-tetrahydropyridin-2-yl)methyl)carbamate (2.5 g) and Pd(OH)₂/C (20% wt, 0.5 eq) was pressurized to 4 bar with H₂ and maintained at room temperature for 5 h. The mixture was filtered through diatomaceous earth and the filtrate was concentrated in vacuo. The mixture was then precipitated using hexane to yield the title compound as a white solid (404 mg, 29%). MS (ESI) 229.2 (M+H).

Step 3. rac-((2S,3S)-2-(Aminomethyl)-3-methylpiperidin-1-yl)(5-(4-fluorophenyl)-2-methylthiazol-4-yl)methanone

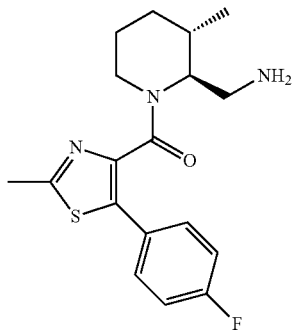 [SMILES: Cc1nc(C(=O)N2CCC[C@H](C)[C@H]2CN)c(-c2ccc(F)cc2)s1]

327

To a solution of rac-tert-butyl (((2R,3R)-3-methylpiperidin-2-yl)methyl)carbamate (37 mg, 162 mol) from the previous step in DMF was added DIPEA (85 μl, 486 μmol) followed by 5-(4-fluorophenyl)-2-methylthiazole-4-carboxylic acid (57 mg, 243 μmol) and HATU (123 mg, 324 μmol). The reaction was allowed to stir at room temperature for 15 h, and was then concentrated in vacuo to remove the DMF. The crude residue was taken up in EtOAc and washed with sat aq. NaHCO3, brine, dried (MgSO4), and concentrated. The crude residue was purified by chromatography on silica gel (EtOAc/hexanes) to give rac-tert-butyl (((2R,3R)-1-(5-(4-fluorophenyl)-2-methylthiazole-4-carbonyl)-3-methylpiperidin-2-yl)methyl)carbamate as a light yellow oil.

To a solution of this carbamate in DCM was added TFA (1:1 v/v). The reaction was aged at room temperature and monitored for disappearance of starting material by analytical reverse-phase HPLC. When starting material was consumed, the reaction was concentrated in vacuo. The crude residue was taken up in EtOAc, and washed with sat aqueous NaHCO3, brine, dried (MgSO4), and concentrated to afford the title compound as a pale yellow oil (34 mg, 60%). MS (ESI) 348.2 (M+H).

Step 4: (5-(4-Fluorophenyl)-2-methylthiazol-4-yl)((2S,3S)-3-methyl-2-(((5-(trifluoromethyl)pyridin-2-yl)amino)methyl)piperidin-1-yl)methanone The title compound was prepared following the same general protocol as described for Example A1 using ((2S,3S)-2-(aminomethyl)-3-methylpiperidin-1-yl) (5-methyl-2-(2H-1,2,3-triazol-2-yl)phenyl)methanone. MS (ESI) 416 (M+H).

Example A66

((2S,3S)-3-Methyl-2-(((5-(trifluoromethyl)pyridin-2-yl)amino)methyl)piperidin-1-yl)(5-methyl-2-(1-methyl-1H-pyrazol-4-yl)phenyl)methanone

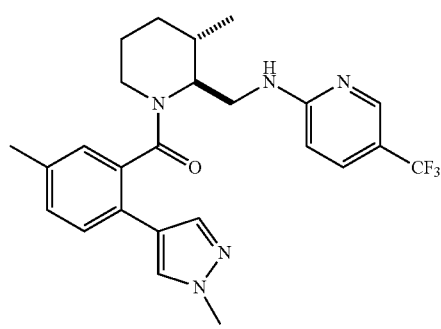 [SMILES: Cc1ccc(-c2cnn(C)c2)c(C(=O)N2CCC[C@H](C)[C@H]2CNc2ccc(C(F)(F)F)cn2)c1]

328

Step 1. ((2S,3S)-2-(Aminomethyl)-3-methylpiperidin-1-yl)(5-methyl-2-(1-methyl-1H-pyrazol-4-yl)phenyl)methanone

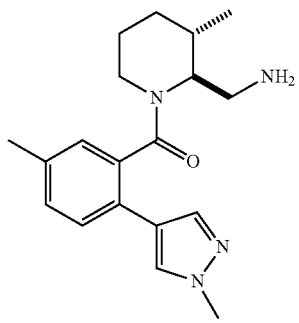 [SMILES: Cc1ccc(-c2cnn(C)c2)c(C(=O)N2CCC[C@H](C)[C@H]2CN)c1]

The title compound was prepared following the same general protocol as described for rac-((2S,3S)-2-(aminomethyl)-3-methylpiperidin-1-yl)(5-(4-fluorophenyl)-2-methylthiazol-4-yl)methanone in Example A65 using 5-methyl-2-(1-methyl-1H-pyrazol-4-yl)benzoic acid. MS (ESI) 327 (M+H).

Step 2. ((2S,3S)-3-Methyl-2-(((5-(trifluoromethyl)pyridin-2-yl)amino)methyl)piperidin-1-yl)(5-methyl-2-(1-methyl-1H-pyrazol-4-yl)phenyl)methanone The title compound was prepared following the same general protocol as described for Example A1 using ((2S,3S)-2-(aminomethyl)-3-methylpiperidin-1-yl)(5-methyl-2-(2H-1,2,3-triazol-2-yl)phenyl)methanone. MS (ESI) 472 (M+H).

Example A67

((2S,3S)-3-Methyl-2-(((5-(trifluoromethyl)pyridin-2-yl)amino)methyl)piperidin-1-yl)(5-methyl-2-(2H-1,2,3-triazol-2-yl)phenyl)methanone

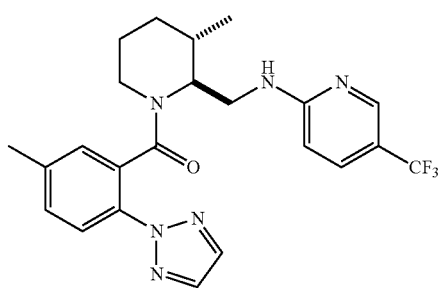 [SMILES: Cc1ccc(-n2nccn2)c(C(=O)N2CCC[C@H](C)[C@H]2CNc2ccc(C(F)(F)F)cn2)c1]

Step 1. ((2S,3S)-2-(Aminomethyl)-3-methylpiperidin-1-yl)(5-methyl-2-(2H-1,2,3-triazol-2-yl)phenyl)methanone

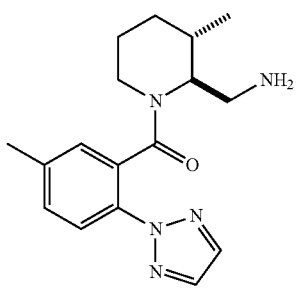 [SMILES: Cc1ccc(-n2nccn2)c(C(=O)N2CCC[C@H](C)[C@H]2CN)c1]

The title compound was prepared following the same general protocol as described for rac-((2S,3S)-2-(aminomethyl)-3-methylpiperidin-1-yl)(5-(4-fluorophenyl)-2-methylthiazol-4-yl)methanone in Example A65 using 5-methyl-2-(2H-1,2,3-triazol-2-yl)benzoic acid. MS (ESI) 314 (M+H).

Step 2. ((2S,3S)-3-Methyl-2-(((5-(trifluoromethyl)pyridin-2-yl)amino)methyl)piperidin-1-yl)(5-methyl-2-(2H-1,2,3-triazol-2-yl)phenyl)methanone The title compound was prepared following the same general protocol as described for Example A1 using ((2S,3S)-2-(aminomethyl)-3-methylpiperidin-1-yl)(5-methyl-2-(2H-1,2,3-triazol-2-yl)phenyl)methanone. MS (ESI) 459 (M+H).

Example A68

(1-(((5-Chlorobenzo[d]oxazol-2-yl)amino)methyl)hexahydrocyclopenta[d]pyrrol-2(1H)-yl)(5-methyl-2-(2H-1,2,3-triazol-2-yl)phenyl)methanone

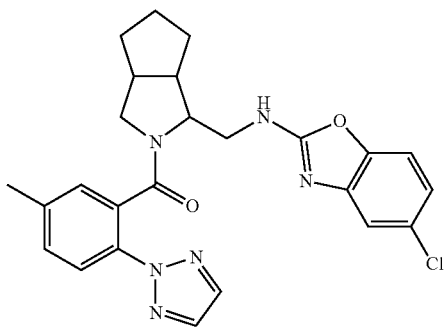 [SMILES: Cc1ccc(-n2nccn2)c(C(=O)N2CC3CCCC3C2CNc2nc3cc(Cl)ccc3o2)c1]

Step 1. Diethyl 2-acetylhexahydrocyclopenta[c]pyrrole-1,1(2H)-dicarboxylate

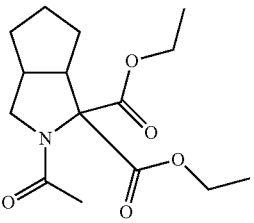 [SMILES: CCOC(=O)C1(C(=O)OCC)C2CCCC2CN1C(C)=O]

The title compound was prepared from cyclopenten-1-aldehyde (1 equiv.) and diethyl 2-acetamidomalonate using the procedure by Chung et al (*J. Org. Chem.* 1990, 55, 270). MS (ESI) 298 (M+H).

Step 2. Octahydrocyclopenta[c]pyrrole-1-carboxylic acid hydrobromide

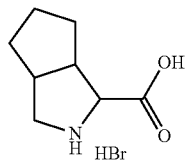 [SMILES: O=C(O)C1NCC2CCCC21 ; Br]

A solution of diethyl 2-acetylhexahydrocyclopenta[c]pyrrole-1,1(2H)-dicarboxylate prepared above in 48% aqueous HBr and AcOH (4:1) was heated at 120° C. for 16 h. The reaction mixture was cooled, concentrated in vacuo and lyophilized to yield the title compound. MS (ESI) 156 (M+H).

Step 3. 2-(tert-Butoxycarbonyl)octahydrocyclopenta[c]pyrrole-1-carboxylic acid

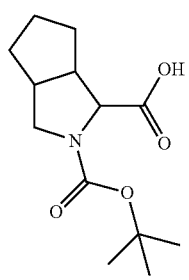 [SMILES: CC(C)(C)OC(=O)N1CC2CCCC2C1C(=O)O]

A mixture of the amino acid prepared above, NaHCO$_3$ (2 equiv.) and Boc$_2$O (1.5 equiv.) were dissolved in water/dioxane (1:1, 10 mL) and stirred at room temperature overnight. Water was added and the resulting solution was washed with EtOAc (4x). The aqueous solution was then acidified with 1 N HCl to pH 1-2 and extracted with EtOAc (4x), dried (MgSO$_4$), and concentrated. The crude residue was purified by chromatography on silica gel (1:3 EtOAc/CH$_2$Cl$_2$) to give the title compound as a creamy white solid. MS (ESI) 256 (M+H).

Step 4. tert-Butyl (((2S,3R)-3-tert-butyl 1-(hydroxymethyl)hexahydrocyclopenta[c]pyrrole-2(1H)-carboxylate

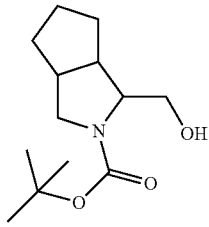 [SMILES: CC(C)(C)OC(=O)N1CC2CCCC2C1CO]

To a stirred solution of 2-(tert-butoxycarbonyl)octahydrocyclopenta[c]pyrrole-1-carboxylic acid (1 equiv.) in THF was added BH$_3$SMe$_2$ (10 M, 2 equiv.) dropwise over 5 min at 0° C. The reaction was then allowed to stir overnight at room temperature and then quenched with cooled water at 0° C. The reaction mixture was diluted with EtOAc and washed with water, brine, dried (MgSO$_4$), and concentrated. The crude residue was concentrated in vacuo to give the title compound as a clear oil. MS (ESI) 242.2 (M+H).

Step 5. (1-(Hydroxymethyl)hexahydrocyclopenta[c]pyrrol-2(1H)-yl)(5-methyl-2-(2H-1,2,3-triazol-2-yl)phenyl)methanone

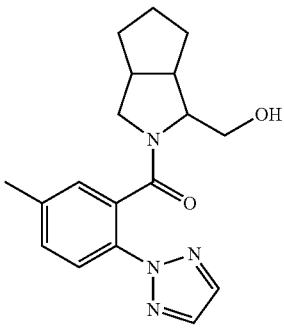 [SMILES: Cc1ccc(-n2nccn2)c(C(=O)N2CC3CCCC3C2CO)c1]

To a solution of the carbamate above in DCM was added TFA (1:1 v/v). The reaction was stirred at room temperature for 30 minutes before being concentrated in vacuo. The crude residue was taken up in EtOAc, and washed with sat aqueous NaHCO$_3$, brine, dried (MgSO$_4$), and concentrated to afford (octahydrocyclopenta[c]pyrrol-1-yl)methanol as a pale yellow oil.

To a solution of (octahydrocyclopenta[c]pyrrol-1-yl)methanol (1 equiv.) from the previous step in DMF was added DIEA (2 equiv.) followed by 5-methyl-2-(2H-1,2,3-triazol-2-yl)benzoic acid (1.5 equiv.) and HATU (2 equiv.). The reaction was allowed to stir at room temperature for 15 h, and was then concentrated in vacuo to remove the DMF. The crude residue was taken up in EtOAc and washed with 1 M HCl, sat aq. NaHCO$_3$, brine, dried (MgSO$_4$), and concentrated. The crude residue was purified by chromatography on silica gel (EtOAc/hexanes) to give the title compound as a clear oil. MS (ESI) 326 (M+H).

Step 6. 2-((2-(5-Methyl-2-(2H-1,2,3-triazol-2-yl)benzoyl)octahydrocyclopenta[c]pyrrol-1-yl)methyl)isoindoline-1,3-dione

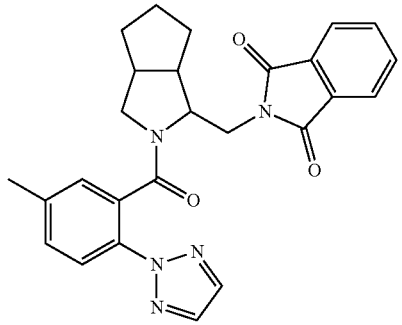 [SMILES: Cc1ccc(-n2nccn2)c(C(=O)N2CC3CCCC3C2CN2C(=O)c3ccccc3C2=O)c1]

To a 0° C. solution of (1-(hydroxymethyl)hexahydrocyclopenta[c]pyrrol-2(1H)-yl)(5-methyl-2-(2H-1,2,3-triazol-2-yl)phenyl)methanone (1 equiv.), phthalimide (2 equiv.) and triphenylphosphine (3 equiv.) in THF (0.5M in amine) was added with DIAD (5 equiv.) dropwise. The resulting suspension was allowed to warm to rt gradually, stirred overnight, and then concentrated in vacuo to a brown oil. The reaction mixture was diluted with EtOAc and washed with water, brine, dried (MgSO$_4$), and concentrated. The crude residue was purified by chromatography on silica gel (EtOAc/hex) to give the title compound as a clear oil. MS (ESI) 456 (M+H).

Step 7. (1-(Aminomethyl)hexahydrocyclopenta[c]pyrrol-2(1H)-yl)(5-methyl-2-(2H-1,2,3-triazol-2-yl)phenyl)methanone

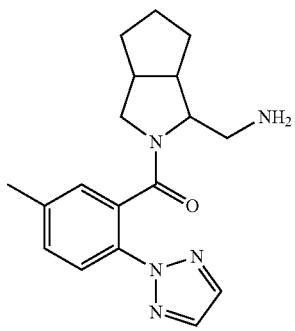 [SMILES: Cc1ccc(-n2nccn2)c(C(=O)N2CC3CCCC3C2CN)c1]

A solution of 2-((2-(5-methyl-2-(2H-1,2,3-triazol-2-yl)benzoyl)octahydrocyclopenta[c]pyrrol-1-yl)methyl)isoindoline-1,3-dione (1 equiv.) and hydrazine monohydrate (4 equiv.) in MeOH (0.5M) was stirred at 70° C. for 3 h and then concentrated in vacuo to a yellow oil. The reaction mixture was diluted with EtOAc and washed with water, brine, dried (MgSO$_4$), and concentrated. The crude residue was purified by chromatography on silica gel (20% MeOH in EtOAc) to firstly remove the impurities and then (2:8:1 MeOH/EtOAc/TEA) to elute the title compound which was concentrated to yield a yellow oil. MS (ESI) 326 (M+H).

Step 8. (1-(((5-Chlorobenzo[d]oxazol-2-yl)amino)methyl)hexahydrocyclopenta[c]pyrrol-2(1H)-yl)(5-methyl-2-(2H-1,2,3-triazol-2-yl)phenyl)methanone The title compound was prepared following the same general protocol as described for Example A2 using (1-(aminomethyl)hexahydrocyclopenta[c]pyrrol-2(1H)-yl)(5-methyl-2-(2H-1,2,3-triazol-2-yl)phenyl)methanone and 2,5-dichlorobenzoxazole. MS (ESI) 477 (M+H).

Example A69

(5-Methyl-2-(2H-1,2,3-triazol-2-yl)phenyl)(1-(((5-(trifluoromethyl)pyridin-2-yl)amino)methyl)hexahydrocyclopenta[c]pyrrol-2(1H)-yl)methanone

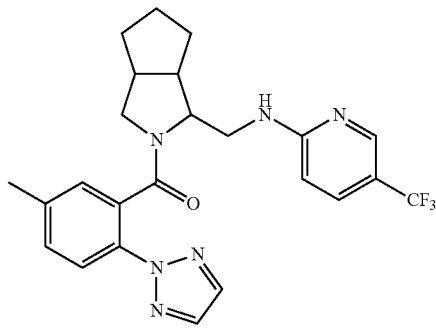 [SMILES: Cc1ccc(-n2nccn2)c(C(=O)N2CC3CCCC3C2CNc2ccc(C(F)(F)F)cn2)c1]

The title compound was prepared following the same general protocol as described for Example A1 using (1-(aminomethyl)hexahydrocyclopenta[c]pyrrol-2(1H)-yl)(5-methyl-2-(2H-1,2,3-triazol-2-yl)phenyl)methanone. MS (ESI) 471 (M+H).

Example A70

(1-(((5-Chlorobenzo[d]oxazol-2-yl)amino)methyl)hexahydrocyclopenta[c]pyrrol-2(1H)-yl)(5-methyl-2-(1-methyl-1H-pyrazol-4-yl)phenyl)methanone

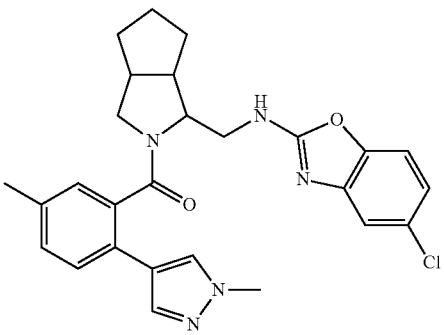 [SMILES: Cc1ccc(-c2cnn(C)c2)c(C(=O)N2CC3CCCC3C2CNc2nc3cc(Cl)ccc3o2)c1]

Step 1. (1-(Aminomethyl)hexahydrocyclopenta[c]pyrrol-2(1H)-yl)(5-methyl-2-(1-methyl-1H-pyrazol-4-yl)phenyl)methanone

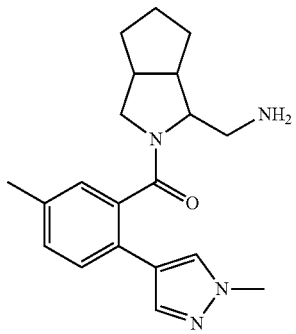 [SMILES: Cc1ccc(-c2cnn(C)c2)c(C(=O)N2CC3CCCC3C2CN)c1]

The title compound was prepared following the same general protocol as described for (1-(aminomethyl)hexahydrocyclopenta[c]pyrrol-2(1H)-yl)(5-methyl-2-(2H-1,2,3-triazol-2-yl)phenyl)methanone in Example A68 using 5-methyl-2-(1-methyl-1H-pyrazol-4-yl)benzoic acid. MS (ESI) 339 (M+H).

Step 2. (1-(((5-Chlorobenzo[d]oxazol-2-yl)amino)methyl)hexahydrocyclopenta[c]pyrrol-2(1H)-yl)(5-methyl-2-(1-methyl-1H-pyrazol-4-yl)phenyl)methanone The title compound was prepared following the same general protocol as described for Example A2 using (1-(aminomethyl)hexahydrocyclopenta[c]pyrrol-2(1H)-yl)(5-methyl-2-(1-methyl-1H-pyrazol-4-yl)phenyl)methanone. MS (ESI) 490 (M+H).

Example A71

(5-Methyl-2-(1-methyl-1H-pyrazol-4-yl)phenyl)(1-(((5-(trifluoromethyl)pyridin-2-yl)amino)methyl)hexahydrocyclopenta[c]pyrrol-2(1H)-yl)methanone

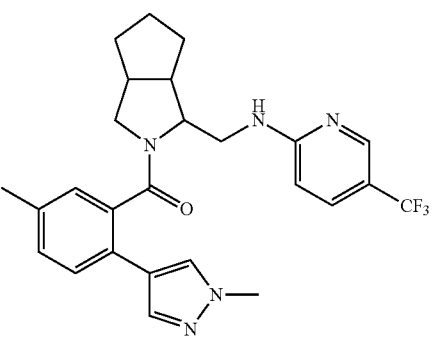 [SMILES: Cc1ccc(-c2cnn(C)c2)c(C(=O)N2CC3CCCC3C2CNc2ccc(C(F)(F)F)cn2)c1]

The title compound was prepared following the same general protocol as described for Example A1 using (1-(aminomethyl)hexahydrocyclopenta[c]pyrrol-2(1H)-yl)(5-methyl-2-(1-methyl-1H-pyrazol-4-yl)phenyl)methanone. MS (ESI) 484 (M+H).

Example A72

(1-(((5-Chlorobenzo[d]oxazol-2-yl)amino)methyl)hexahydrocyclopenta[c]pyrrol-2(1H)-yl)(5-methyl-2-(3-(trifluoromethyl)-1H-1,2,4-triazol-1-yl)phenyl)methanone

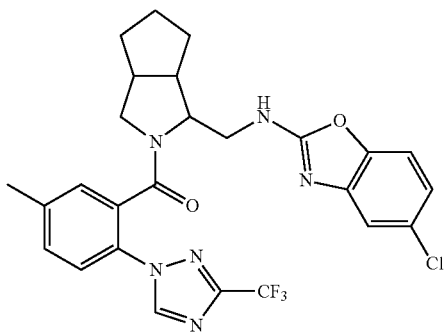 [SMILES: Cc1ccc(-n2cnc(C(F)(F)F)n2)c(C(=O)N2CC3CCCC3C2CNc2nc3cc(Cl)ccc3o2)c1]

Step 1. (1-(Aminomethyl)hexahydrocyclopenta[c]pyrrol-2(1H)-yl)(5-methyl-2-(3-(trifluoromethyl)-1H-1,2,4-triazol-1-yl)phenyl)methanone

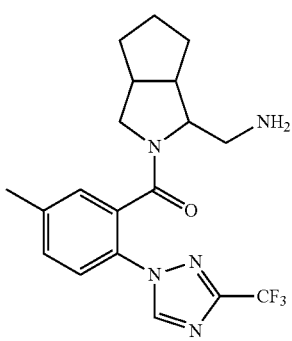 [SMILES: Cc1ccc(-n2cnc(C(F)(F)F)n2)c(C(=O)N2CC3CCCC3C2CN)c1]

The title compound was prepared following the same general protocol as described for (1-(aminomethyl)hexahydrocyclopenta[c]pyrrol-2(1H)-yl)(5-methyl-2-(2H-1,2,3-triazol-2-yl)phenyl)methanone in Example A68 using 5-methyl-2-(3-(trifluoromethyl)-1H-1,2,4-triazol-1-yl)benzoic acid. MS (ESI) 394 (M+H).

Step 2. (1-(((5-Chlorobenzo[d]oxazol-2-yl)amino)methyl)hexahydrocyclopenta[c]pyrrol-2(1H)-yl)(5-methyl-2-(3-(trifluoromethyl)-1H-1,2,4-triazol-1-yl)phenyl)methanone The title compound was prepared following the same general protocol as described for Example A2 using (1-(aminomethyl)hexahydrocyclopenta[c]pyrrol-2(1H)-yl)(5-methyl-2-(3-(trifluoromethyl)-1H-1,2,4-triazol-1-yl)phenyl)methanone. MS (ESI) 539 (M+H)

Example A73

(3-(4-Fluorophenyl)-6-methylpyridin-2-yl)((2S,3R)-3-methyl-2-(((5-(trifluoromethyl)pyridin-2-yl)amino)methyl)piperidin-1-yl)methanone

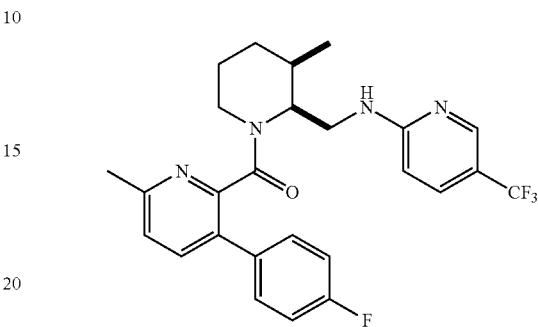

Step 1. 5-Bromo-2-methylpyridine 1-oxide

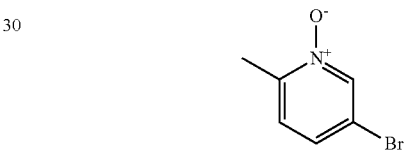

A solution of 5-bromo-2-methylpyridine (10 g, 58.13 mmol) and meta-chloroperbenzoic acid (mCPBA, 30 g, 174.39 mmol) in CHCl$_3$ (160 mL) was heated at 60° C. for 16 h. The mixture was cooled to room temperature and neutralized with sat'd NaHCO$_3$. The resulting mixture was extracted with DCM. The organic layers were combined and washed with brine and dried (MgSO$_4$). The solvent was removed in vacuo. The crude was purified by silica gel chromatography (EtOAc/Hex) to obtain the title compound.

Step 2. 3-Bromo-6-methylpicolinonitrile

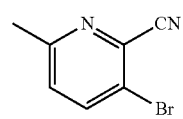

To the solution of 5-bromo-2-methylpyridine 1-oxide (8.935 g, 47.52 mmol) in acetonitrile (240 mL) was added trimethylsilyl cyanide (TMSCN) (25 mL, 190 mmol) and triethylamine (20 mL, 142.56 mmol). The reaction was heated at 100° C. for 16 h. The mixture was cooled to room temperature and concentrated in vacuo. The crude was purified by silica gel chromatography using 0-50% EtOAc in hexane to obtain the title compound.

Step 3. 3-(4-Fluorophenyl)-6-methylpicolinonitrile

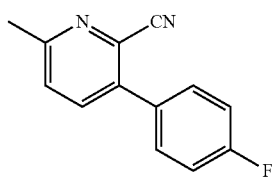 [SMILES: Cc1ccc(-c2ccc(F)cc2)c(C#N)n1]

The title compound was synthesized following the same general protocol as described for methyl 5-methyl-2-(1-methyl-1H-pyrazol-4-yl)benzoate in Example A1, using 2-(4-fluorophenyl)-4,4,5,5-tetramethyl-1,3,2-dioxaborolane and 3-bromo-6-methylpicolinonitrile. ESI-MS (m/z): 213 [M+1]+.

Step 4. 3-(4-Fluorophenyl)-6-methylpicolinic acid

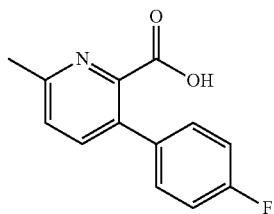 [SMILES: Cc1ccc(-c2ccc(F)cc2)c(C(=O)O)n1]

To the solution of 3-(4-fluorophenyl)-6-methylpicolinonitrile (0.555 g, 2.615 mmol) in MeOH (3 mL) was added NaOH (1.1 g, 27.5 mmol) and H$_2$O (1.8 mL). The mixture was heated at 100° C. for 8 h. The reaction was cooled to room temperature and acidified to pH ~5. The solvent was removed in vacuo. The crude was extracted with MeOH. The solvent was removed in vacuo and the obtained acid was dried in vacuum for next step with no further purification. ESI-MS (m/z): 233 [M+1]+.

Step 5. ((2S,3R)-2-(Aminomethyl)-3-methylpiperidin-1-yl)(3-(4-fluorophenyl)-6-methylpyridin-2-yl)methanone

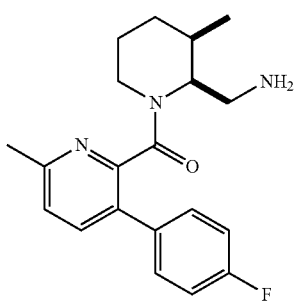

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A51, starting from 3-(4-fluorophenyl)-6-methylpicolinic acid. ESI-MS (m/z): 342 [M+1]+.

Step 6. (3-(4-Fluorophenyl)-6-methylpyridin-2-yl)((2S,3R)-3-methyl-2-(((5-(trifluoromethyl)pyridin-2-yl)amino)methyl)piperidin-1-yl)methanone The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(3-(4-fluorophenyl)-6-methylpyridin-2-yl)methanone. ESI-MS (m/z): 487 [M+1]+.

Example A74

((2S,3R)-3-Methyl-2-(((5-(trifluoromethyl)pyridin-2-yl)amino)methyl)piperidin-1-yl)(6-methyl-3-(1-methyl-1H-pyrazol-4-yl)pyridin-2-yl)methanone

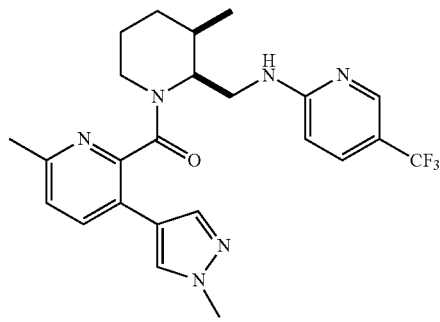 [SMILES: Cc1ccc(-c2cnn(C)c2)c(C(=O)N2CCC[C@@H](C)[C@H]2CNc2ccc(C(F)(F)F)cn2)n1]

The title compound was synthesized following the same general protocol as in Example A73, starting with 1-methyl-4-(4,4,5,5-tetramethyl-1,3,2-dioxaborolan-2-yl)-1H-pyrazole. ESI-MS (m/z): 473 [M+1]+.

Example A75

(3-Fluoro-2-methoxyphenyl)((2S,3R)-3-methyl-2-(((5-(trifluoromethyl)pyridin-2-yl)amino)methyl)piperidin-1-yl)methanone

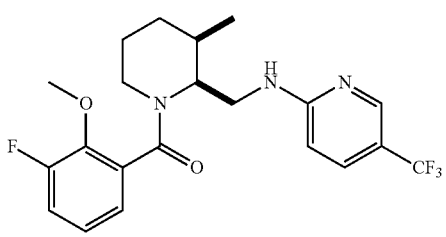 [SMILES: COc1c(F)cccc1C(=O)N1CCC[C@@H](C)[C@H]1CNc1ccc(C(F)(F)F)cn1]

Step 1. ((2S,3R)-2-(Aminomethyl)-3-methylpiperidin-1-yl)(3-fluoro-2-methoxyphenyl)methanone

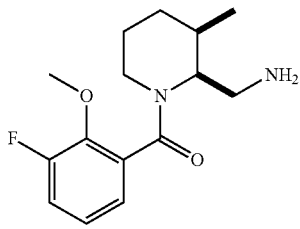 [SMILES: COc1c(F)cccc1C(=O)N1CCC[C@@H](C)[C@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 3-fluoro-2-methoxybenzoic acid. MS (ESI) 281 (M+H).

Step 2. (3-Fluoro-2-methoxyphenyl)((2S,3R)-3-methyl-2-(((5-(trifluoromethyl)pyridin-2-yl)amino)methyl)piperidin-1-yl)methanone The title compound was prepared following the same general protocol as described for Example A1 using ((2S,3R)-2-(aminomethyl)-3-methylpiperidin-1-yl) (3-fluoro-2-methoxyphenyl)methanone. MS (ESI) 426 (M+H).

Example A76

(6-(6-Chlorobenzo[d]oxazol-2-yl)octahydro-1H-pyrrolo[3,4-b]pyridin-1-yl)(5-(4-fluorophenyl)-2-methylthiazol-4-yl)methanone

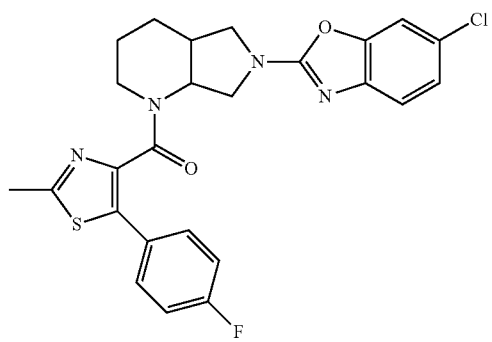 [SMILES: Cc1nc(C(=O)N2CCCC3CN(c4nc5ccc(Cl)cc5o4)CC32)c(-c2ccc(F)cc2)s1]

Step 1. (5-(4-Fluorophenyl)-2-methylthiazol-4-yl)(octahydro-1H-pyrrolo[3,4-b]pyridin-1-yl)methanone

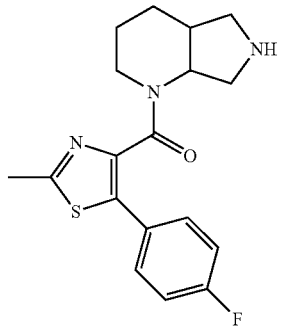 [SMILES: Cc1nc(C(=O)N2CCCC3CNCC32)c(-c2ccc(F)cc2)s1]

The title compound was prepared following the same general protocol as described for rac-((2S,3S)-2-(aminomethyl)-3-methylpiperidin-1-yl)(5-(4-fluorophenyl)-2-methylthiazol-4-yl)methanone in Example A65 using tert-butyl hexahydro-1H-pyrrolo[3,4-b]pyridine-6(2H)-carboxylate. MS (ESI) 346 (M+H).

Step 2. (6-(6-Chlorobenzo[d]oxazol-2-yl)octahydro-1H-pyrrolo[3,4-b]pyridin-1-yl)(5-(4-fluorophenyl)-2-methylthiazol-4-yl)methanone The title compound was prepared following the same general protocol as described for Example A2 using (5-(4-fluorophenyl)-2-methylthiazol-4-yl)(octahydro-1H-pyrrolo[3,4-b]pyridin-1-yl)methanone and 2,6-dichlorobenzoxazole. MS (ESI) 497 (M+H).

Example A77

(5-(4-Fluorophenyl)-2-methylthiazol-4-yl)(6-(5-(trifluoromethyl)pyridin-2-yl)octahydro-1H-pyrrolo[3,4-b]pyridin-1-yl)methanone

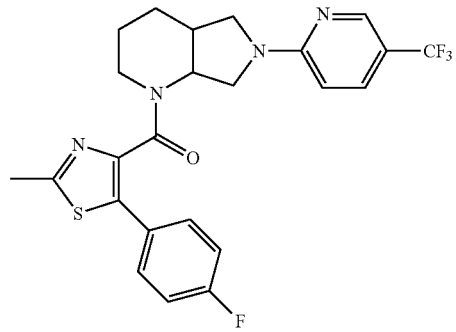 [SMILES: Cc1nc(C(=O)N2CCCC3CN(c4ccc(C(F)(F)F)cn4)CC32)c(-c2ccc(F)cc2)s1]

The title compound was prepared following the same general protocol as described for Example A1 using (5-(4-fluorophenyl)-2-methylthiazol-4-yl)(octahydro-1H-pyrrolo[3,4-b]pyridin-1-yl)methanone. MS (ESI) 491 (M+H).

Example A78

((2S,3R)-2-(((5-Chloropyridin-2-yl)amino)methyl)-3-methylpiperidin-1-yl)(5-methyl-2-(2H-1,2,3-triazol-2-yl)phenyl)methanone

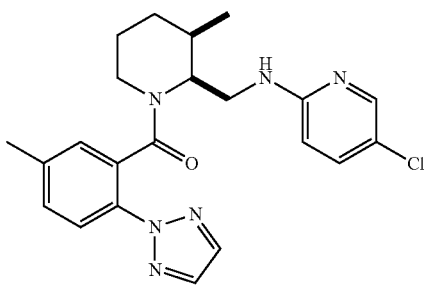 [SMILES: Cc1ccc(-n2nccn2)c(C(=O)N2CCC[C@@H](C)[C@H]2CNc2ccc(Cl)cn2)c1]

The title compound was prepared following the same general protocol as described for Example A44 using 2-bromo-5-chloropyridine. MS (ESI) 425 (M+H).

Example A79

((2S,3R)-3-Methyl-2-(((6-methylpyridin-2-yl)amino)methyl)piperidin-1-yl)(5-methyl-2-(2H-1,2,3-triazol-2-yl)phenyl)methanone

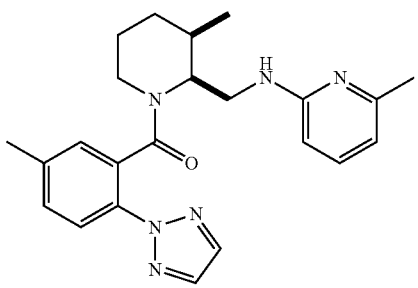

The title compound was prepared following the same general protocol as described for Example A44 using 2-bromo-6-methylpyridine. ESI-MS (m/z): 405 [M+1]$^+$.

Example A80

((2S,3R)-2-(((6-Methoxypyridin-2-yl)amino)methyl)-3-methylpiperidin-1-yl)(5-methyl-2-(2H-1,2,3-triazol-2-yl)phenyl)methanone

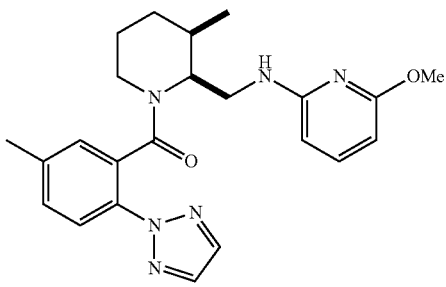 [SMILES: COc1cccc(NC[C@@H]2[C@H](C)CCCN2C(=O)c2cc(C)ccc2-n2nccn2)n1]

The title compound was prepared following the same general protocol as described for Example A44 using 2-bromo-6-methoxypyridine. ESI-MS (m/z): 421 [M+1]$^+$.

Example A81

6-((((2S,3R)-3-Methyl-1-(5-methyl-2-(2H-1,2,3-triazol-2-yl)benzoyl)piperidin-2-yl)methyl)amino)picolinonitrile

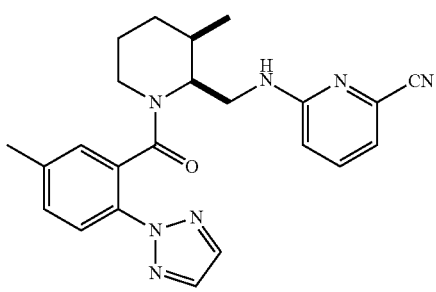 [SMILES: Cc1ccc(-n2nccn2)c(C(=O)N2CCC[C@@H](C)[C@H]2CNc2cccc(C#N)n2)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(2H-1,2,3-triazol-2-yl)phenyl)methanone and 6-chloropicolinonitrile. ESI-MS (m/z): 416 [M+1]$^+$.

Example A82

((2S,3R)-2-(((3-Fluoro-5-(trifluoromethyl)pyridin-2-yl)amino)methyl)-3-methylpiperidin-1-yl)(5-methyl-2-(2H-1,2,3-triazol-2-yl)phenyl)methanone

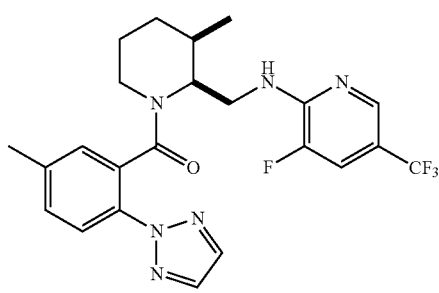 [SMILES: Cc1ccc(-n2nccn2)c(C(=O)N2CCC[C@@H](C)[C@H]2CNc2ncc(C(F)(F)F)cc2F)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(2H-1,2,3-triazol-2-yl)phenyl)methanone and 2-bromo-3-fluoro-5-(trifluoromethyl)pyridine. ESI-MS (m/z): 477 [M+1]$^+$.

Example A83

((2S,3R)-2-(((3-Fluoro-5-(trifluoromethyl)pyridin-2-yl)amino)methyl)-3-methylpiperidin-1-yl)(5-methyl-2-(1-methyl-1H-pyrazol-4-yl)phenyl)methanone

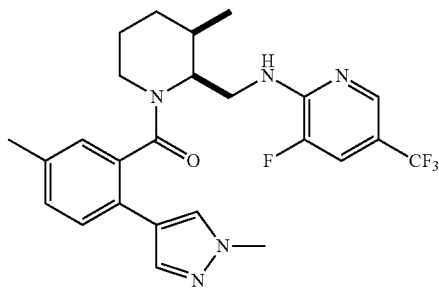 [SMILES: Cc1ccc(-c2cnn(C)c2)c(C(=O)N2CCC[C@@H](C)[C@H]2CNc2ncc(C(F)(F)F)cc2F)c1]

The title compound was synthesized following the same general protocol as described for ((2S,3R)-3-methyl-2-(((5-

(trifluoromethyl)pyridin-2-yl)amino)methyl)piperidin-1-yl) (5-methyl-2-(1-methyl-1H-pyrazol-4-yl)phenyl)methanone in Example A1, using 2-bromo-3-fluoro-5-(trifluoromethyl) pyridine. ESI-MS (m/z): 490 [M+1]$^+$.

Example A84

((2S,3R)-2-(((5-Chlorobenzo[d]oxazol-2-yl)amino) methyl)-3-methylpiperidin-1-yl)(5-(4-fluorophenyl)- 2-methylthiazol-4-yl)methanone

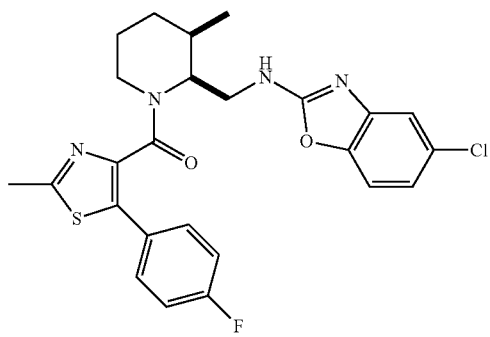 [SMILES: Cc1nc(C(=O)N2CCC[C@@H](C)[C@H]2CNc2nc3cc(Cl)ccc3o2)c(-c2ccc(F)cc2)s1]

The title compound was prepared following the same general protocol as described for Example A2 using ((2S, 3R)-2-(aminomethyl)-3-methylpiperidin-1-yl)(5-(4-fluorophenyl)-2-methylthiazol-4-yl)methanone and 2,5-dichlorobenzoxazole. MS (ESI) 499 (M+H).

Example A85

(5-(4-Fluorophenyl)-2-methylthiazol-4-yl)((2S,3R)- 3-methyl-2-(((5-(trifluoromethyl)pyridin-2-yl) amino)methyl)piperidin-1-yl)methanone

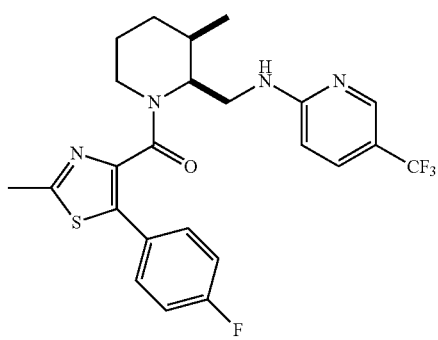

The title compound was prepared following the same general protocol as described for Example A1 using ((2S, 3R)-2-(aminomethyl)-3-methylpiperidin-1-yl)(5-(4-fluorophenyl)-2-methylthiazol-4-yl)methanone. MS (ESI) 499 (M+H).

Example A86

6-(((((2S,3R)-3-Methyl-1-(5-methyl-2-(1-methyl-1H-pyrazol-4-yl)benzoyl)piperidin-2-yl)methyl)amino) picolinonitrile

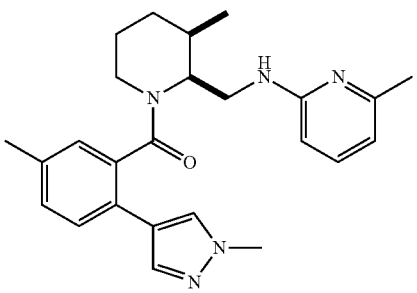

The title compound was prepared following the same general protocol as described for Example A1 using 6-chloropicolinonitrile. ESI-MS (m/z): 429 [M+1]$^+$.

Example A87

((2S,3R)-3-Methyl-2-(((6-methylpyridin-2-yl)amino) methyl)piperidin-1-yl)(5-methyl-2-(1-methyl-1H-pyrazol-4-yl)phenyl)methanone The title compound was synthesized following the same general protocol as described in Example A44, using ((2S, 3R)-2-(aminomethyl)-3-methylpiperidin-1-yl)(5-methyl-2-(1-methyl-1H-pyrazol-4-yl)phenyl)methanone and 2-bromo-6-methylpyridine. ESI-MS (m/z): 418 [M+1]$^+$.

Example A88

((2S,3R)-3-Methyl-2-(((3-(trifluoromethyl)pyridin-2-yl)amino)methyl)piperidin-1-yl)(5-methyl-2-(2H-1,2,3-triazol-2-yl)phenyl)methanone

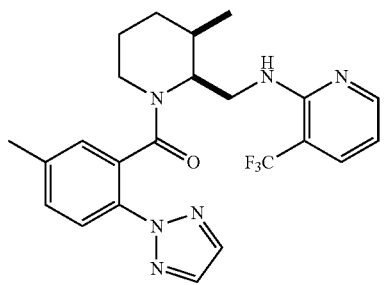 [SMILES: Cc1ccc(-n2nccn2)c(C(=O)N2CCC[C@@H](C)[C@H]2CNc2ncccc2C(F)(F)F)c1]

The title compound was synthesized following the same general protocol as described for ((2S,3R)-3-methyl-2-(((5-

(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(2H-1,2,3-triazol-2-yl)phenyl)methanone and 2-chloro-3-(trifluoromethyl)pyridine. ESI-MS (m/z): 459 [M+1]$^+$.

Example A89

((2S,3R)-3-Methyl-2-(((6-(trifluoromethyl)pyridin-2-yl)amino)methyl)piperidin-1-yl)(5-methyl-2-(2H-1,2,3-triazol-2-yl)phenyl)methanone

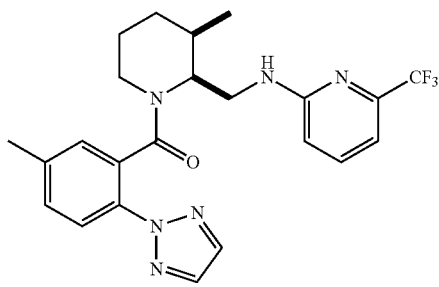

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(2H-1,2,3-triazol-2-yl)phenyl)methanone and 2-chloro-6-(trifluoromethyl)pyridine. ESI-MS (m/z): 459 [M+1]$^+$.

Example A90

2-(((2S,3R)-3-Methyl-1-(5-methyl-2-(2H-1,2,3-triazol-2-yl)benzoyl)piperidin-2-yl)methyl)amino)nicotinonitrile

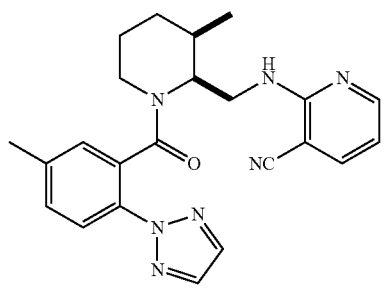

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(2H-1,2,3-triazol-2-yl)phenyl)methanone and 2-chloronicotinonitrile. ESI-MS (m/z): 416 [M+1]$^+$.

Example A91

((2S,3R)-2-(((3,5-Difluoropyridin-2-yl)amino)methyl)-3-methylpiperidin-1-yl)(5-methyl-2-(2H-1,2,3-triazol-2-yl)phenyl)methanone

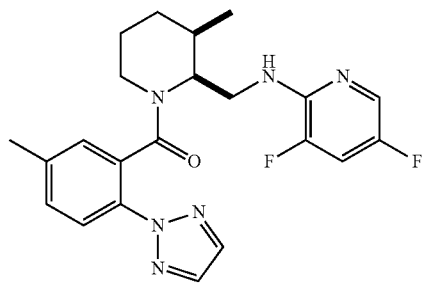 [SMILES: Cc1ccc(-n2nccn2)c(C(=O)N2CCC[C@@H](C)[C@H]2CNc2ncc(F)cc2F)c1]

The title compound was prepared following the same general protocol as described for Example A44 using 2-bromo-3,5-difluoropyridine. ESI-MS (m/z): 427 [M+1]$^+$.

Example A92

((2S,3R)-2-(((5-Chloro-3-fluoropyridin-2-yl)amino)methyl)-3-methylpiperidin-1-yl)(5-methyl-2-(2H-1,2,3-triazol-2-yl)phenyl)methanone

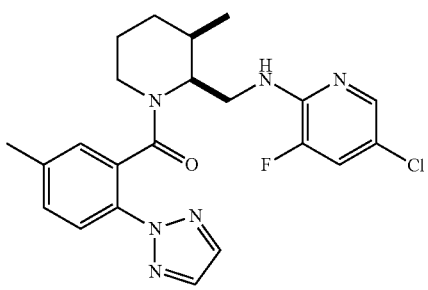 [SMILES: Cc1ccc(-n2nccn2)c(C(=O)N2CCC[C@@H](C)[C@H]2CNc2ncc(Cl)cc2F)c1]

The title compound was prepared following the same general protocol as described for Example A44 using 2-bromo-5-chloro-3-fluoropyridine. ESI-MS (m/z): 443 [M+1]$^+$.

Example A93

((2S,3R)-3-Methyl-2-(((3-(trifluoromethyl)pyridin-2-yl)amino)methyl)piperidin-1-yl)(5-methyl-2-(1-methyl-1H-pyrazol-4-yl)phenyl)methanone

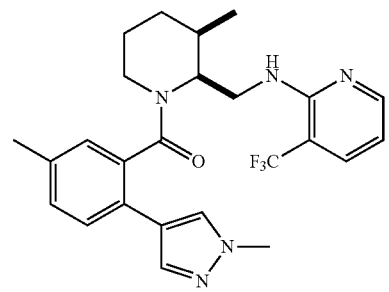 [SMILES: Cc1ccc(-c2cnn(C)c2)c(C(=O)N2CCC[C@@H](C)[C@H]2CNc2ncccc2C(F)(F)F)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using 2-chloro-3-(trifluoromethyl)pyridine. ESI-MS (m/z): 472 [M+1]$^+$.

Example A94

((2S,3R)-3-Methyl-2-(((6-(trifluoromethyl)pyridin-2-yl)amino)methyl)piperidin-1-yl)(5-methyl-2-(1-methyl-1H-pyrazol-4-yl)phenyl)methanone

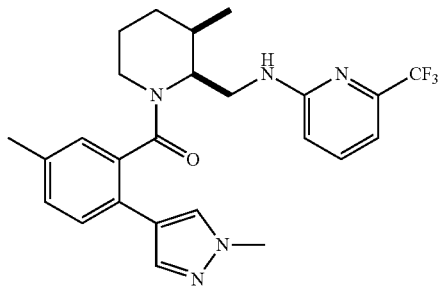 [SMILES: Cc1ccc(-c2cnn(C)c2)c(C(=O)N2CCC[C@@H](C)[C@H]2CNc2cccc(C(F)(F)F)n2)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using 2-chloro-6-(trifluoromethyl)pyridine. ESI-MS (m/z): 472 [M+1]$^+$.

Example A95

2-(((2S,3R)-3-Methyl-1-(5-methyl-2-(1-methyl-1H-pyrazol-4-yl)benzoyl)piperidin-2-yl)methyl)amino)nicotinonitrile

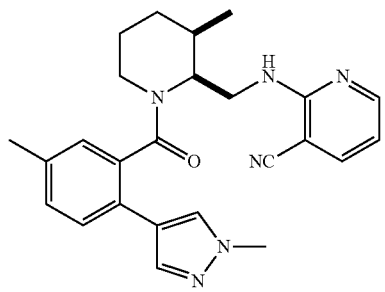 [SMILES: Cc1ccc(-c2cnn(C)c2)c(C(=O)N2CCC[C@@H](C)[C@H]2CNc2ncccc2C#N)c1]

The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using 2-chloronicotinonitrile. ESI-MS (m/z): 429 [M+1]$^+$.

Example A96

((2S,3R)-2-(((3,5-Difluoropyridin-2-yl)amino)methyl)-3-methylpiperidin-1-yl)(5-methyl-2-(1-methyl-1H-pyrazol-4-yl)phenyl)methanone

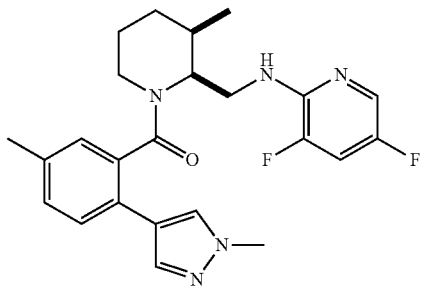 [SMILES: Cc1ccc(-c2cnn(C)c2)c(C(=O)N2CCC[C@@H](C)[C@H]2CNc2ncc(F)cc2F)c1]

The title compound was prepared following the same general protocol as described for Example A44 using ((2S,3R)-2-(aminomethyl)-3-methylpiperidin-1-yl)(5-methyl-2-(1-methyl-1H-pyrazol-4-yl)phenyl)methanone and 2-bromo-3,5-difluoropyridine. ESI-MS (m/z): 440 [M+1]$^+$.

Example A97

((2S,3R)-2-(((5-Chloro-3-fluoropyridin-2-yl)amino)methyl)-3-methylpiperidin-1-yl)(5-methyl-2-(1-methyl-1H-pyrazol-4-yl)phenyl)methanone

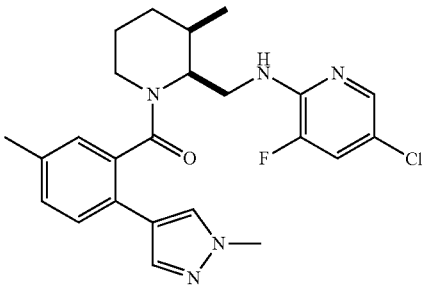 [SMILES: Cc1ccc(-c2cnn(C)c2)c(C(=O)N2CCC[C@@H](C)[C@H]2CNc2ncc(Cl)cc2F)c1]

The title compound was prepared following the same general protocol as described for Example A44 using ((2S,3R)-2-(aminomethyl)-3-methylpiperidin-1-yl)(5-methyl-2-(1-methyl-1H-pyrazol-4-yl)phenyl)methanone and 2-bromo-5-chloro-3-fluoropyridine. ESI-MS (m/z): 456 [M+1]$^+$.

Example A98

((2S,3R)-2-(((3-Methoxypyridin-2-yl)amino)methyl)-3-methylpiperidin-1-yl)(5-methyl-2-(2H-1,2,3-triazol-2-yl)phenyl)methanone

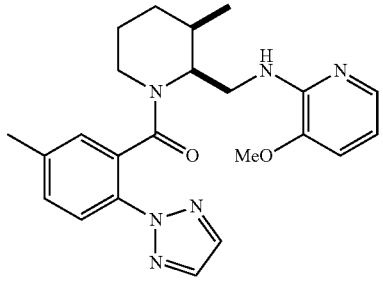 [SMILES: COc1cccnc1NC[C@@H]1[C@H](C)CCCN1C(=O)c1cc(C)ccc1-n1nccn1]

The title compound was prepared following the same general protocol as described for Example A44 using 2-bromo-3-methoxypyridine. ESI-MS (m/z): 421 [M+1]⁺.

Example A99

((2S,3R)-3-Methyl-2-(((3-methylpyridin-2-yl)amino)methyl)piperidin-1-yl)(5-methyl-2-(2H-1,2,3-triazol-2-yl)phenyl)methanone

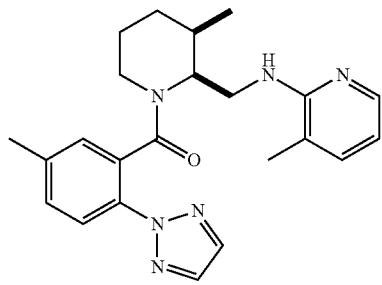 [SMILES: Cc1ccc(-n2nccn2)c(C(=O)N2CCC[C@@H](C)[C@H]2CNc2ncccc2C)c1]

The title compound was prepared following the same general protocol as described for Example A44 using 2-bromo-3-methylpyridine. ESI-MS (m/z): 405 [M+1]⁺.

Example A100

((2S,3R)-3-Methyl-2-(((3-methylpyridin-2-yl)amino)methyl)piperidin-1-yl)(5-methyl-2-(1-methyl-1H-pyrazol-4-yl)phenyl)methanone

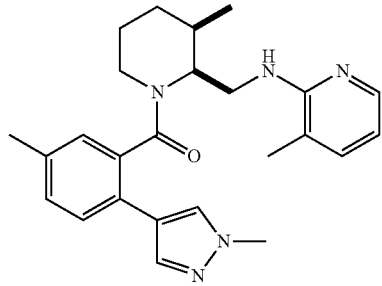 [SMILES: Cc1ccc(-c2cnn(C)c2)c(C(=O)N2CCC[C@@H](C)[C@H]2CNc2ncccc2C)c1]

The title compound was prepared following the same general protocol as described for Example A44 using ((2S,3R)-2-(aminomethyl)-3-methylpiperidin-1-yl)(5-methyl-2-(1-methyl-1H-pyrazol-4-yl)phenyl)methanone and 2-bromo-3-methylpyridine. ESI-MS (m/z): 418 [M+1]⁺.

Example A101

((2S,3R)-2-(((3-Methoxypyridin-2-yl)amino)methyl)-3-methylpiperidin-1-yl)(5-methyl-2-(1-methyl-1H-pyrazol-4-yl)phenyl)methanone

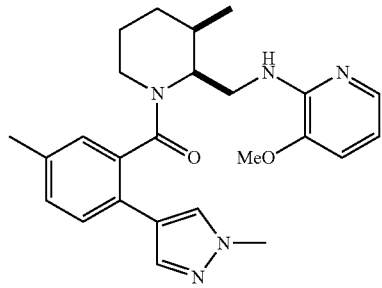 [SMILES: COc1cccnc1NC[C@@H]1[C@H](C)CCCN1C(=O)c1cc(C)ccc1-c1cnn(C)c1]

The title compound was prepared following the same general protocol as described for Example A44 using ((2S,3R)-2-(aminomethyl)-3-methylpiperidin-1-yl)(5-methyl-2-(1-methyl-1H-pyrazol-4-yl)phenyl)methanone and 2-bromo-3-methoxypyridine. ESI-MS (m/z): 434 [M+1]⁺.

Example A102

((2S,3R)-3-Methyl-2-(((5-(trifluoromethyl)-1,3,4-thiadiazol-2-yl)amino)methyl)piperidin-1-yl)(5-methyl-2-(2H-1,2,3-triazol-2-yl)phenyl)methanone

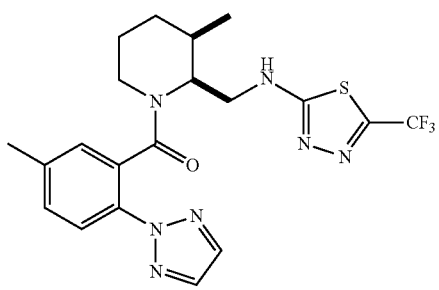 [SMILES: Cc1ccc(-n2nccn2)c(C(=O)N2CCC[C@@H](C)[C@H]2CNc2nnc(C(F)(F)F)s2)c1]

A mixture of ((2S,3R)-2-(aminomethyl)-3-methylpiperidin-1-yl)(5-methyl-2-(2H-1,2,3-triazol-2-yl)phenyl)methanone (0.032 g, 0.1 mmol), 2-chloro-5-(trifluoromethyl)-1,3,4-thiadiazole (0.019 g, 0.1 mmol) and K₂CO₃ (0.018 g, 0.13 mmol) in DMF was heated at 80° C. overnight. The mixture was purified via preparative-HPLC to obtain the title compound. ESI-MS (m/z): 466 [M+1]⁺.

Example A103

((2S,3R)-3-Methyl-2-(((5-(trifluoromethyl)-1,3,4-thiadiazol-2-yl)amino)methyl)piperidin-1-yl)(5-methyl-2-(1-methyl-1H-pyrazol-4-yl)phenyl)methanone

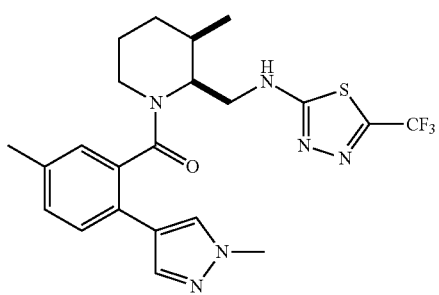 [SMILES: Cc1ccc(-c2cnn(C)c2)c(C(=O)N2CCC[C@@H](C)[C@H]2CNc2nnc(C(F)(F)F)s2)c1]

The title compound was prepared following the same general protocol as described for Example A102 using ((2S,3R)-2-(aminomethyl)-3-methylpiperidin-1-yl)(5-methyl-2-(1-methyl-1H-pyrazol-4-yl)phenyl)methanone. ESI-MS (m/z): 479 [M+1]⁺.

Example A104

((2S,3R)-3-Methyl-2-(((5-(trifluoromethyl)pyridin-2-yl)amino)methyl)piperidin-1-yl)(5-methyl-2-(6-methylpyridin-2-yl)phenyl)methanone

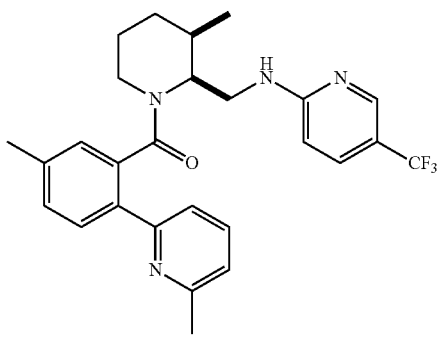 [SMILES: Cc1ccc(-c2cccc(C)n2)c(C(=O)N2CCC[C@@H](C)[C@H]2CNc2ccc(C(F)(F)F)cn2)c1]

Step 1.
2-(4-Methoxypyrimidin-2-yl)-5-methylbenzoic acid

The title compound was synthesized following the same general protocol as described for 5-methyl-2-(pyrazin-2-yl)benzoic acid in Example A19, using 2-bromo-6-methylpyridine. ESI-MS (m/z): 228 [M+1]$^+$.

Step 2. tert-Butyl (((2S,3R)-3-methyl-1-(5-methyl-2-(6-methylpyridin-2-yl)benzoyl)piperidin-2-yl)methyl)carbamate

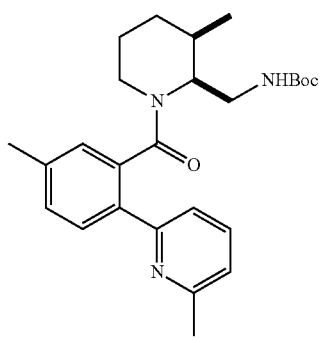 [SMILES: Cc1ccc(-c2cccc(C)n2)c(C(=O)N2CCC[C@@H](C)[C@H]2CNC(=O)OC(C)(C)C)c1]

To the mixture of 5-methyl-2-(6-methylpyridin-2-yl)benzoic acid (0.229 g, 0.868 mmol), tert-butyl (((2S,3R)-3-methylpiperidin-2-yl)methyl)carbamate (0.24 g, 1.04 mmol) and DIEA (0.3 mL, 1.738 mmol) in DCM (20 mL) was slowly added TBTU (0.278 g, 0.869 mmol). The mixture was stirred at rt for 1 h. The mixture was diluted with DCM and was washed with sat'd NaHCO$_3$ and brine and dried over Na$_2$SO$_4$. The solvent was removed in vacuo to obtain the title compound which was used without further purification. ESI-MS (m/z): 438 [M+1]$^+$.

Step 3. ((2S,3R)-2-(Aminomethyl)-3-methylpiperidin-1-yl)(5-methyl-2-(6-methylpyridin-2-yl)phenyl)methanone

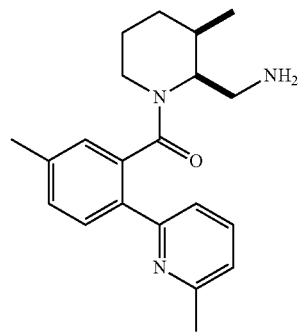 [SMILES: Cc1ccc(-c2cccc(C)n2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(3-(trifluoromethyl)-1H-1,2,4-triazol-1-yl)phenyl)methanone in Example A52, using 2-bromo-6-methylpyridine. ESI-MS (m/z): 338 [M+1]$^+$.

Step 4. ((2S,3R)-3-Methyl-2-(((5-(trifluoromethyl)pyridin-2-yl)amino)methyl)piperidin-1-yl)(5-methyl-2-(6-methylpyridin-2-yl)phenyl)methanone The title compound was synthesized following the same general protocol as described for ((2S,3R)-3-methyl-2-(((5-(trifluoromethyl)pyridin-2-yl)amino)methyl)piperidin-1-yl)(5-methyl-2-(1-methyl-1H-pyrazol-4-yl)phenyl)methanone in Example A1, using ((2S,3R)-2-(aminomethyl)-3-methylpiperidin-1-yl)(5-methyl-2-(6-methylpyridin-2-yl)phenyl)methanone. ESI-MS (m/z): 483 [M+1]$^+$.

Example A105

((2S,3R)-2-(((5-Chloropyridin-2-yl)amino)methyl)-3-methylpiperidin-1-yl)(5-methyl-2-(1-methyl-1H-pyrazol-4-yl)phenyl)methanone

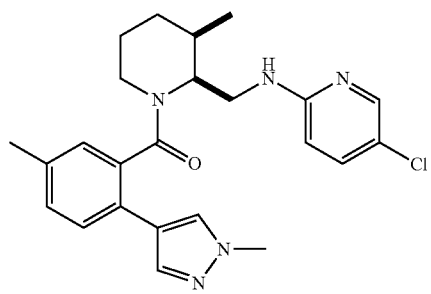 [SMILES: Cc1ccc(-c2cnn(C)c2)c(C(=O)N2CCC[C@@H](C)[C@H]2CNc2ccc(Cl)cn2)c1]

The title compound was prepared following the same general protocol as described for Example A44 using 2-bromo-5-chloropyridine. MS (ESI) 438 (M+H).

Example A106

((2S,3R)-3-Methyl-2-(((5-(trifluoromethyl)pyridin-2-yl)oxy)methyl)piperidin-1-yl)(5-methyl-2-(2H-1,2,3-triazol-2-yl)phenyl)methanone

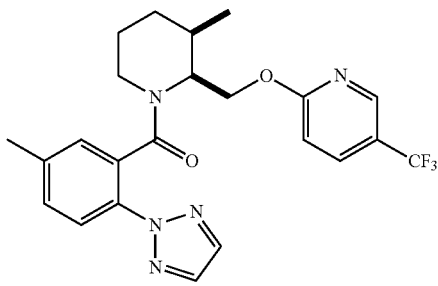 [SMILES: Cc1ccc(-n2nccn2)c(C(=O)N2CCC[C@@H](C)[C@H]2COc2ccc(C(F)(F)F)cn2)c1]

Step 1. ((2S,3R)-3-Methylpiperidin-2-yl)methanol

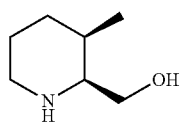

To a solution of (2S,3R)-benzyl 2-(hydroxymethyl)-3-methylpiperidine-1-carboxylate (5 g) in methanol was added 10% Pd/C (0.5 g). The flask was evacuated/H$_2$ purged (3x), and then stirred under a balloon of H$_2$ until starting material was consumed as judged by t.l.c. analysis. The reaction was filtered through diatomaceous earth and concentrated to yield (2S,3R)-methyl 3-methylpiperidine-2-carboxylate as a white solid which was used without further purification. $^1$H NMR (CDCl$_3$, 400 MHz) δ 3.4 (m, 2H), 2.9 (m, 1H), 2.8 (m, 1H), 2.6 (m, 1H), 1.7 (m, 1H), 1.6-1.4 (m, 4H), 0.8 (d, 3H).

Step 2. ((2S,3R)-2-(Hydroxymethyl)-3-methylpiperidin-1-yl)(5-methyl-2-(2H-1,2,3-triazol-2-yl)phenyl)methanone

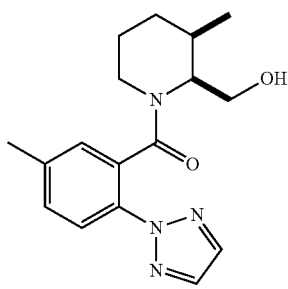 [SMILES: Cc1ccc(-n2nccn2)c(C(=O)N2CCC[C@@H](C)[C@H]2CO)c1]

((2S,3R)-3-Methylpiperidin-2-yl)methanol from the previous step in DMAC (0.2M) was added DIEA (2 equiv.) followed by 5-methyl-2-(2H-1,2,3-triazol-2-yl)benzoic acid (1.2 eq) and HATU (1.1 equiv.). The reaction was allowed to stir at room temperature for 15 h, and was then concentrated in vacuo to remove the DMAC. The crude residue was taken up in EtOAc and washed with 1M HCl, sat aq. NaHCO$_3$, brine, dried (MgSO$_4$), and concentrated. The crude residue was purified by chromatography on silica gel (EtOAc/hexanes) to give the title compound as a brown oil which crystallized (2.6 g). MS (ESI) 315 (M+H).

Step 3. ((2S,3R)-3-Methyl-2-(((5-(trifluoromethyl)pyridin-2-yl)oxy)methyl)piperidin-1-yl) (5-(4-fluorophenyl)-2-methylthiazol-4-yl)methanone To a stirred solution of ((2S,3R)-2-(hydroxymethyl)-3-methylpiperidin-1-yl)(5-(4-fluorophenyl)-2-methylthiazol-4-yl)methanone in THF was added NaH (4 equiv.) at 0° C. The reaction was allowed to warm to room temperature and stirred an additional 30 min. 2-chloro-5-(trifluoromethyl) pyridine (2 equiv.) was then added and the solution was warmed to reflux for 2 h. The reaction was cooled and quenched with saturated NH$_4$Cl and concentrated in vacuo. The crude reaction mixture was purified by reverse-phase preparative HPLC to afford the title compound. MS (ESI) 460 (M+H).

Example A107

((2S,3R)-3-Methyl-2-(((5-(trifluoromethyl)pyridin-2-yl)amino)methyl)piperidin-1-yl)(5-methyl-2-(4-methyl-1H-pyrazol-1-yl)phenyl)methanone

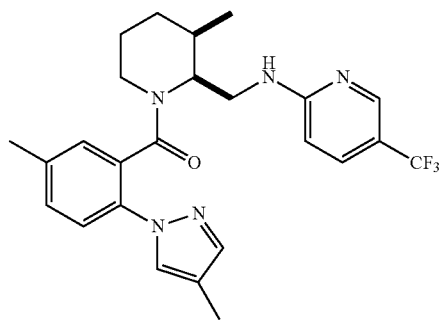 [SMILES: Cc1ccc(-n2cc(C)cn2)c(C(=O)N2CCC[C@@H](C)[C@H]2CNc2ccc(C(F)(F)F)cn2)c1]

Step 1.
5-Methyl-2-(4-methyl-1H-pyrazol-1-yl)benzoic acid

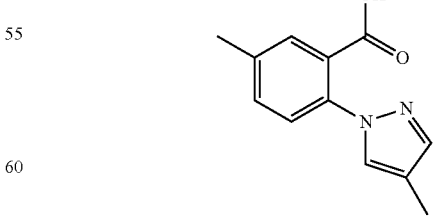

The title compound was prepared following the same general protocol as described for 5-methyl-2-(2H-1,2,3-triazol-2-yl)benzoic acid in Example A11 using 4-methyl-1H-pyrazole. MS (ESI) 217 (M+H).

Step 2. ((2S,3R)-2-(Aminomethyl)-3-methylpiperidin-1-yl)(5-methyl-2-(4-methyl-1H-pyrazol-1-yl)phenyl)methanone

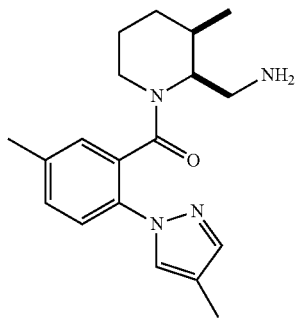

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-methyl-2-(4-methyl-1H-pyrazol-1-yl)benzoic acid. MS (ESI) 327 (M+H).

Step 3. ((2S,3R)-3-Methyl-2-(((5-(trifluoromethyl)pyridin-2-yl)amino)methyl)piperidin-1-yl)(5-methyl-2-(4-methyl-1H-pyrazol-1-yl)phenyl)methanone The title compound was prepared following the same general protocol as described for Example A1 using ((2S,3R)-2-(aminomethyl)-3-methylpiperidin-1-yl)(5-methyl-2-(4-methyl-1H-pyrazol-1-yl)phenyl)methanone. MS (ESI) 472 (M+H).

Example A108

((2S,3R)-3-Methyl-2-(((5-(trifluoromethyl)pyridin-2-yl)amino)methyl)piperidin-1-yl)(5-methyl-2-(3-methyl-1H-pyrazol-1-yl)phenyl)methanone

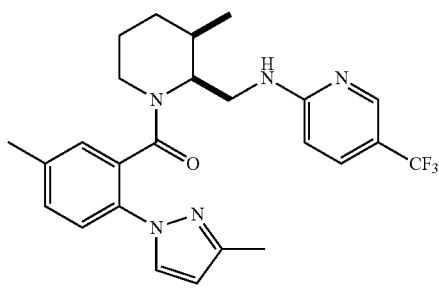

Step 1.
5-Methyl-2-(3-methyl-1H-pyrazol-1-yl)benzoic acid

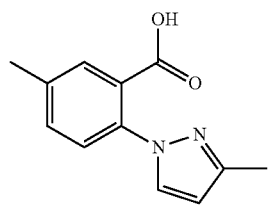

The title compound was prepared following the same general protocol as described for 5-methyl-2-(2H-1,2,3-triazol-2-yl)benzoic acid in Example A11 using 3-methyl-1H-pyrazole. MS (ESI) 217 (M+H).

Step 2. ((2S,3R)-2-(Aminomethyl)-3-methylpiperidin-1-yl)(5-methyl-2-(3-methyl-1H-pyrazol-1-yl)phenyl)methanone

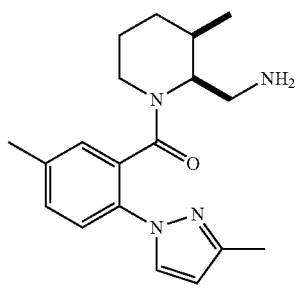

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-methyl-2-(3-methyl-1H-pyrazol-1-yl)benzoic acid. MS (ESI) 327 (M+H).

Step 3. ((2S,3R)-3-Methyl-2-(((5-(trifluoromethyl)pyridin-2-yl)amino)methyl)piperidin-1-yl)(5-methyl-2-(3-methyl-1H-pyrazol-1-yl)phenyl)methanone The title compound was prepared following the same general protocol as described for Example A1 using ((2S,3R)-2-(aminomethyl)-3-methylpiperidin-1-yl)(5-methyl-2-(3-methyl-1H-pyrazol-1-yl)phenyl)methanone. MS (ESI) 472 (M+H).

Example A109

(5-(3-Fluorophenyl)-2-methylthiazol-4-yl)((2S,3R)-3-methyl-2-(((5-(trifluoromethyl)pyridin-2-yl)amino)methyl)piperidin-1-yl)methanone

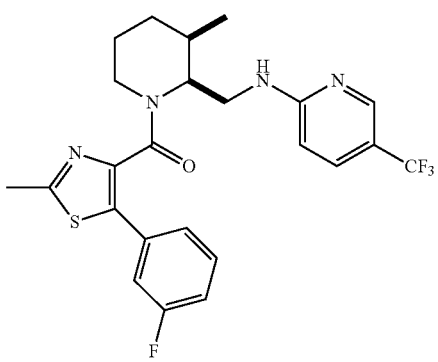 [SMILES: Cc1nc(C(=O)N2CCC[C@@H](C)[C@H]2CNc2ccc(C(F)(F)F)cn2)c(-c2cccc(F)c2)s1]

Step 1. ((2S,3R)-2-(Aminomethyl)-3-methylpiperi-
din-1-yl)(5-(3-fluorophenyl)-2-methylthiazol-4-yl)
methanone

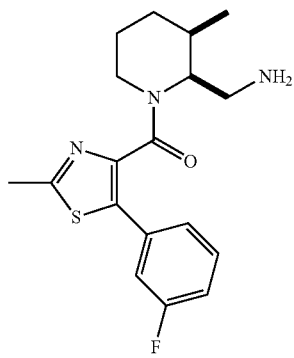 [SMILES: Cc1nc(C(=O)N2CCC[C@@H](C)[C@H]2CN)c(-c2cccc(F)c2)s1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-(3-fluorophenyl)-2-methylthiazole-4-carboxylic acid. MS (ESI) 348 (M+H).

Step 2. (5-(3-Fluorophenyl)-2-methylthiazol-4-yl)
((2S,3R)-3-methyl-2-(((5-(trifluoromethyl)pyridin-2-
yl)amino)methyl)piperidin-1-yl)methanone The title compound was prepared following the same general protocol as described for Example A1 using ((2S,3R)-2-(aminomethyl)-3-methylpiperidin-1-yl)(5-(3-fluorophenyl)-2-methylthiazol-4-yl)methanone. MS (ESI) 493 (M+H).

Example A110

(2-(1-Ethyl-1H-pyrazol-4-yl)-5-methylphenyl)((2S,3R)-3-methyl-2-(((5-(trifluoromethyl)pyridin-2-yl)amino)methyl)piperidin-1-yl)methanone

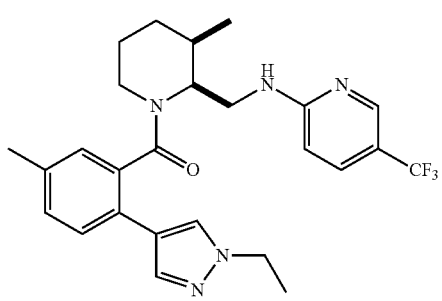 [SMILES: CCn1cc(-c2ccc(C)cc2C(=O)N2CCC[C@@H](C)[C@H]2CNc2ccc(C(F)(F)F)cn2)cn1]

The title compound was prepared following the same general protocol as described for Example A1 starting with 1-ethyl-4-(4,4,5,5-tetramethyl-1,3,2-dioxaborolan-2-yl)-1H-pyrazole. ESI-MS (m/z): 486 [M+1]$^+$.

Example A111

(2-(1-Isopropyl-1H-pyrazol-4-yl)-5-methylphenyl)
((2S,3R)-3-methyl-2-(((5-(trifluoromethyl)pyridin-2-
yl)amino)methyl)piperidin-1-yl)methanone

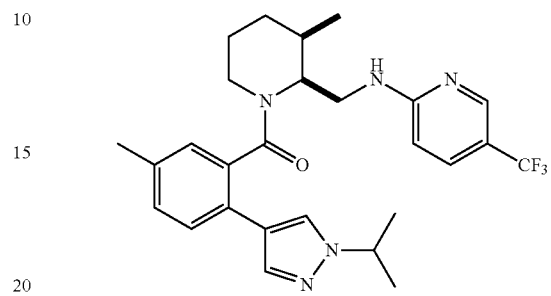

The title compound was prepared following the same general protocol as described for Example A1 starting with 1-isopropyl-4-(4,4,5,5-tetramethyl-1,3,2-dioxaborolan-2-yl)-1H-pyrazole. ESI-MS (m/z): 500 [M+1]$^+$.

Example A112

((2S,3R)-3-Methyl-2-(((5-(trifluoromethyl)pyridin-
2-yl)amino)methyl)piperidin-1-yl)(5-methyl-2-(4-
methyl-2H-1,2,3-triazol-2-yl)phenyl)methanone

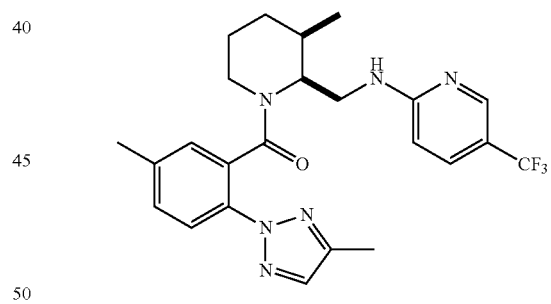

Step 1. 5-Methyl-2-(4-methyl-2H-1,2,3-triazol-2-yl)
benzoic acid and 5-methyl-2-(4-methyl-1H-1,2,3-
triazol-1-yl)benzoic acid

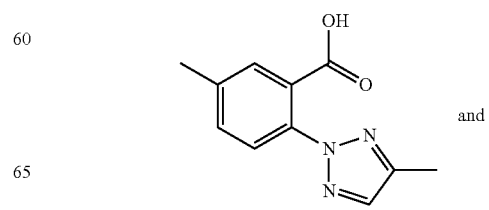

and

-continued

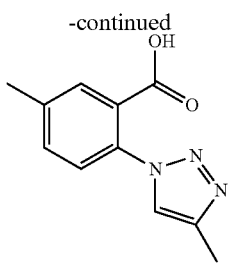

The title compound was synthesized following the same general protocol as described in Example A11 using 4-methyl-2H-1,2,3-triazole. The faster eluting 5-methyl-2-(4-methyl-2H-1,2,3-triazol-2-yl)benzoic acid was the major product and the slower eluting 5-methyl-2-(4-methyl-1H-1,2,3-triazol-1-yl)benzoic acid was the minor product. ESI-MS (m/z): 218 [M+1]⁺.

Step 2. ((2S,3R)-2-(Aminomethyl)-3-methylpiperidin-1-yl)(5-methyl-2-(4-methyl-2H-1,2,3-triazol-2-yl)phenyl)methanone

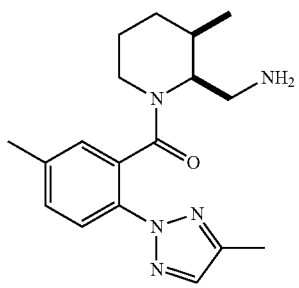 [SMILES: Cc1ccc(-n2ncc(C)n2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, starting with 5-methyl-2-(4-methyl-2H-1,2,3-triazol-2-yl)benzoic acid. ESI-MS (m/z): 328 [M+1]⁺.

Step 3. ((2S,3R)-3-Methyl-2-(((5-(trifluoromethyl)pyridin-2-yl)amino)methyl)piperidin-1-yl)(5-methyl-2-(4-methyl-2H-1,2,3-triazol-2-yl)phenyl)methanone The title compound was prepared following the same general protocol as described for Example A1 using ((2S,3R)-2-(aminomethyl)-3-methylpiperidin-1-yl)(5-methyl-2-(4-methyl-2H-1,2,3-triazol-2-yl)phenyl)methanone. ESI-MS (m/z): 473 [M+1]⁺.

Example A113

((2S,3R)-3-Methyl-2-(((5-(trifluoromethyl)pyridin-2-yl)amino)methyl)piperidin-1-yl)(5-methyl-2-(4-methyl-1H-1,2,3-triazol-1-yl)phenyl)methanone

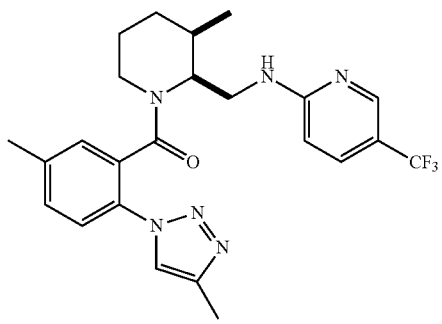

Step 1. ((2S,3R)-2-(Aminomethyl)-3-methylpiperidin-1-yl)(5-methyl-2-(4-methyl-1H-1,2,3-triazol-1-yl)phenyl)methanone

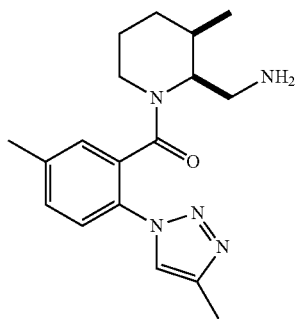 [SMILES: Cc1ccc(-n2cc(C)nn2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, starting 5-methyl-2-(4-methyl-1H-1,2,3-triazol-1-yl)benzoic acid. ESI-MS (m/z): 328 [M+1]⁺.

Step 2. ((2S,3R)-3-Methyl-2-(((5-(trifluoromethyl)pyridin-2-yl)amino)methyl)piperidin-1-yl)(5-methyl-2-(4-methyl-1H-1,2,3-triazol-1-yl)phenyl)methanone The title compound was prepared following the same general protocol as described for Example A1 using ((2S,3R)-2-(aminomethyl)-3-methylpiperidin-1-yl)(5-methyl-2-(4-methyl-1H-1,2,3-triazol-1-yl)phenyl)methanone. ESI-MS (m/z): 473 [M+1]⁺.

Example A114

((2S,3R)-3-Methyl-2-(((5-(trifluoromethyl)pyridin-2-yl)oxy)methyl)piperidin-1-yl)(5-methyl-2-(1-methyl-1H-pyrazol-4-yl)phenyl)methanone

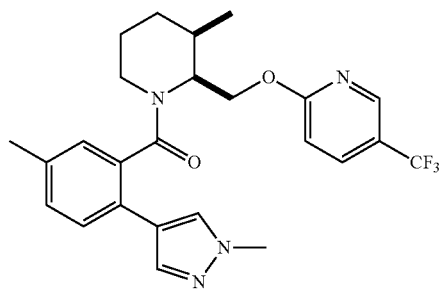

Step 1. ((2S,3R)-2-(Hydroxymethyl)-3-methylpiperidin-1-yl)(5-methyl-2-(1-methyl-1H-pyrazol-4-yl)phenyl)methanone

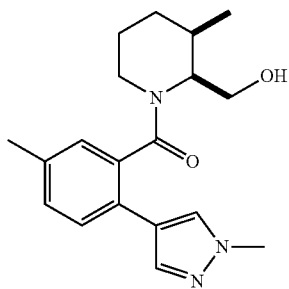 [SMILES: Cc1ccc(-c2cnn(C)c2)c(C(=O)N2CCC[C@@H](C)[C@H]2CO)c1]

The title compound was prepared following the same general protocol as described for ((2S,3R)-2-(hydroxymethyl)-3-methylpiperidin-1-yl)(5-methyl-2-(2H-1,2,3-triazol-2-yl)phenyl)methanone in Example A106 using 5-methyl-2-(3-methyl-1H-pyrazol-1-yl)benzoic acid. MS (ESI) 328 (M+H).

Step 2. ((2S,3R)-3-Methyl-2-(((5-(trifluoromethyl)pyridin-2-yl)oxy)methyl)piperidin-1-yl)(5-methyl-2-(1-methyl-1H-pyrazol-4-yl)phenyl)methanone The title compound was prepared following the same general protocol as described for Example A1 using ((2S,3R)-2-(hydroxymethyl)-3-methylpiperidin-1-yl)(5-methyl-2-(1-methyl-1H-pyrazol-4-yl)phenyl)methanone. MS (ESI) 473 (M+H).

Example A115

((2S,3R)-2-(((5-Chlorobenzo[d]oxazol-2-yl)amino)methyl)-3-methylpiperidin-1-yl)(5-methyl-2-(3-methyl-1H-pyrazol-1-yl)phenyl)methanone

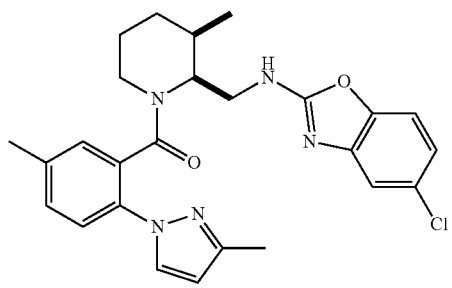 [SMILES: Cc1ccc(-n2ccc(C)n2)c(C(=O)N2CCC[C@@H](C)[C@H]2CNc2nc3cc(Cl)ccc3o2)c1]

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(3-methyl-1H-pyrazol-1-yl)phenyl)methanone. ESI-MS (m/z): 478 [M+1]$^+$.

Example A116

((2S,3R)-2-(((5-Chlorobenzo[d]oxazol-2-yl)amino)methyl)-3-methylpiperidin-1-yl)(5-methyl-2-(4-methyl-2H-1,2,3-triazol-2-yl)phenyl)methanone

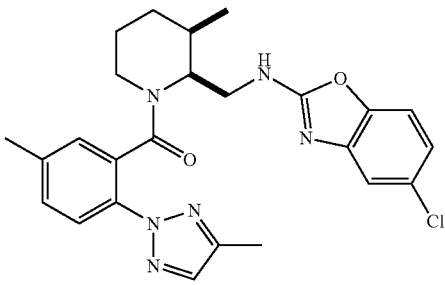

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(4-methyl-2H-1,2,3-triazol-2-yl)phenyl)methanone. ESI-MS (m/z): 479 [M+1]$^+$.

Example A117

((2S,3R)-2-(((5-chloropyridin-2-yl)amino)methyl)-3-methylpiperidin-1-yl)(5-methyl-2-(pyridin-2-yl)phenyl)methanone

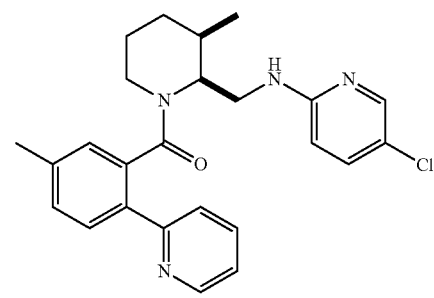

The title compound was prepared following the same general protocol as described for Example A44 using ((2S,3R)-2-(aminomethyl)-3-methylpiperidin-1-yl)(5-methyl-2-(pyridin-2-yl)phenyl)methanone and 2-bromo-5-chloropyridine. ESI-MS (m/z): 435 [M+1]$^+$.

Example A118

((2S,3R)-3-Methyl-2-(((5-(trifluoromethyl)pyridin-2-yl)amino)methyl)piperidin-1-yl)(5-methyl-2-(5-methylpyridin-2-yl)phenyl)methanone

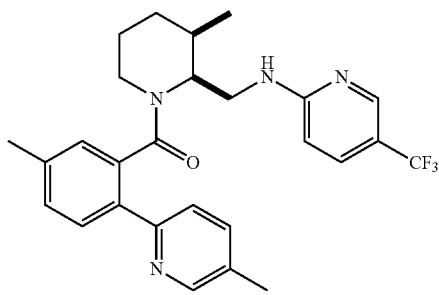

Step 1. 5-Methyl-2-(5-methylpyridin-2-yl)benzoic acid

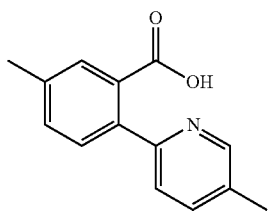

The title compound was synthesized following the same general protocol as described for 5-methyl-2-(pyrazin-2-yl)benzoic acid in Example A19, using 2-bromo-5-methylpyridine. ESI-MS (m/z): 228 [M+1]$^+$.

Step 2. ((2S,3R)-2-(Aminomethyl)-3-methylpiperidin-1-yl)(5-methyl-2-(5-methylpyridin-2-yl)phenyl)methanone

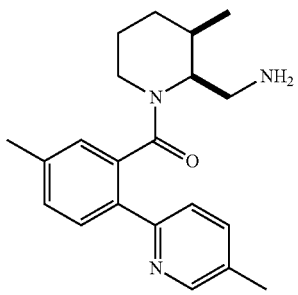

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, starting with 5-methyl-2-(5-methylpyridin-2-yl)benzoic acid. ESI-MS (m/z): 338 [M+1]$^+$.

Step 3. ((2S,3R)-3-Methyl-2-(((5-(trifluoromethyl)pyridin-2-yl)amino)methyl)piperidin-1-yl)(5-methyl-2-(5-methylpyridin-2-yl)phenyl)methanone The title compound was prepared following the same general protocol as described for Example A1 using ((2S,3R)-2-(aminomethyl)-3-methylpiperidin-1-yl)(5-methyl-2-(5-methylpyridin-2-yl)phenyl)methanone. ESI-MS (m/z): 483 [M+1]$^+$.

Example A119

((2S,3R)-3-Methyl-2-(((6-(trifluoromethyl)pyridazin-3-yl)amino)methyl)piperidin-1-yl)(5-methyl-2-(2H-1,2,3-triazol-2-yl)phenyl)methanone

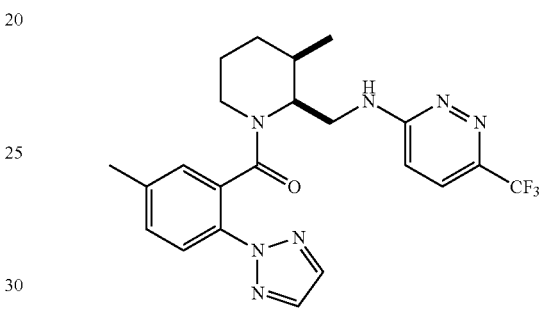

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 3-chloro-6-(trifluoromethyl)pyridazine. ESI-MS (m/z): 460 [M+1]$^+$.

Example A120

((2S,3R)-2-(((5-Chloropyridin-2-yl)amino)methyl)-3-methylpiperidin-1-yl)(5-methyl-2-(3-methyl-1H-pyrazol-1-yl)phenyl)methanone

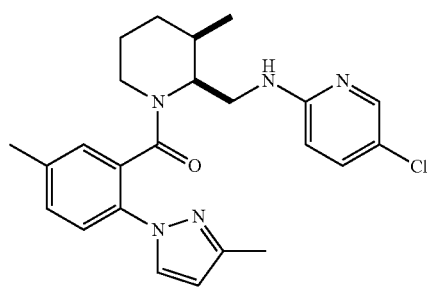

The title compound was prepared following the same general protocol as described for Example A44 using ((2S,3R)-2-(aminomethyl)-3-methylpiperidin-1-yl)(5-methyl-2-(3-methyl-1H-pyrazol-1-yl)phenyl)methanone and 2-bromo-5-chloropyridine. ESI-MS (m/z): 438 [M+1]$^+$.

Example A121

((2S,3R)-2-(((5-Chloropyridin-2-yl)amino)methyl)-3-methylpiperidin-1-yl)(5-methyl-2-(4-methyl-2H-1,2,3-triazol-2-yl)phenyl)methanone

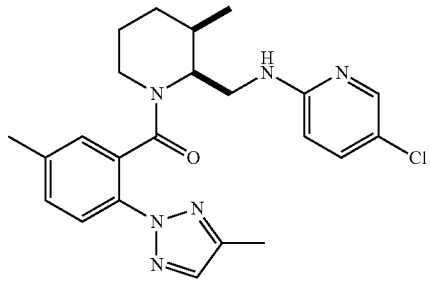

The title compound was prepared following the same general protocol as described for Example A44 using ((2S,3R)-2-(aminomethyl)-3-methylpiperidin-1-yl)(5-methyl-2-(4-methyl-2H-1,2,3-triazol-2-yl)phenyl)methanone and 2-bromo-5-chloropyridine. ESI-MS (m/z): 439 [M+1]+.

Example A122

((2S,3R)-2-(((6-Bromoquinazolin-2-yl)amino)methyl)-3-methylpiperidin-1-yl)(5-methyl-2-(2H-1,2,3-triazol-2-yl)phenyl)methanone

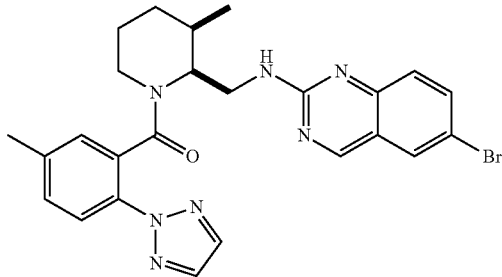

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 6-bromo-2-chloroquinazoline. ESI-MS (m/z): 520, 522 [M]+ [M+2]+.

Example A123

((2S,3R)-3-Methyl-2-(((4-(trifluoromethyl)thiazol-2-yl)amino)methyl)piperidin-1-yl)(5-methyl-2-(2H-1,2,3-triazol-2-yl)phenyl)methanone

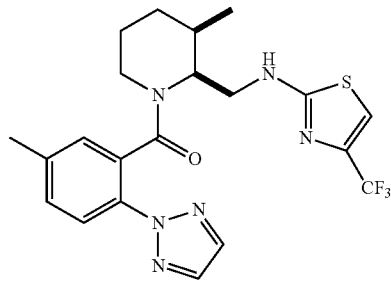

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 2-chloro-4-(trifluoromethyl)thiazole. ESI-MS (m/z): 465 [M+1]+.

Example A124

((2S,3R)-3-Methyl-2-(((4-methylthiazol-2-yl)amino)methyl)piperidin-1-yl)(5-methyl-2-(2H-1,2,3-triazol-2-yl)phenyl)methanone

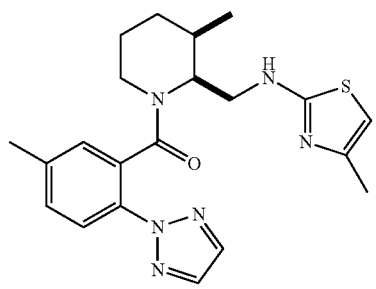

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 2-chloro-4-methylthiazole. ESI-MS (m/z): 411 [M+1]+.

Example A125

((2S,3R)-3-methyl-2-(((6-(trifluoromethyl)pyridazin-3-yl)amino)methyl)piperidin-1-yl)(5-methyl-2-(4-methyl-2H-1,2,3-triazol-2-yl)phenyl)methanone

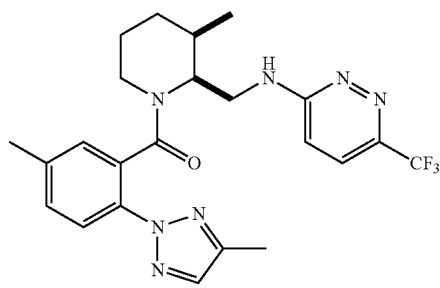

The title compound was prepared following the same general protocol as described for Example A1, using ((2S,3R)-2-(aminomethyl)-3-methylpiperidin-1-yl)(5-methyl-2-(4-methyl-2H-1,2,3-triazol-2-yl)phenyl)methanone and 3-chloro-6-(trifluoromethyl)pyridazine. ESI-MS (m/z): 474 [M+1]+.

Example A126

((2S,3R)-2-(((5-Methoxypyridin-2-yl)amino)methyl)-3-methylpiperidin-1-yl)(5-methyl-2-(2H-1,2,3-triazol-2-yl)phenyl)methanone

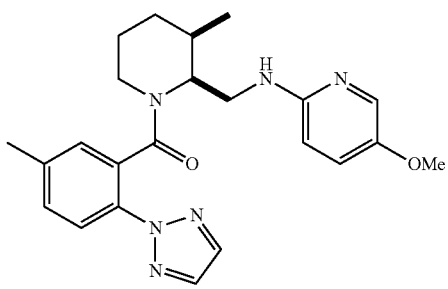

The title compound was prepared following the same general protocol as described for Example A44 using 2-bromo-5-methoxypyridine. ESI-MS (m/z): 421 [M+1]+.

Example A127

6-(((2S,3R)-3-Methyl-1-(5-methyl-2-(2H-1,2,3-triazol-2-yl)benzoyl)piperidin-2-yl)methyl)amino)nicotinonitrile

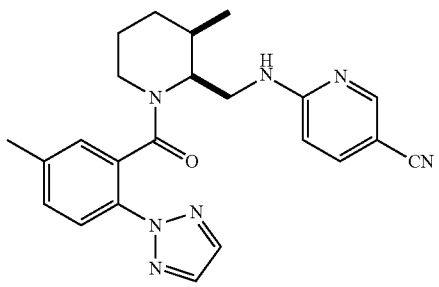

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 6-chloronicotinonitrile. ESI-MS (m/z): 416 [M+1]+.

Example A128

((2S,3R)-2-(((5-Fluorobenzo[d]oxazol-2-yl)amino)methyl)-3-methylpiperidin-1-yl)(5-methyl-2-(pyridin-2-yl)phenyl)methanone

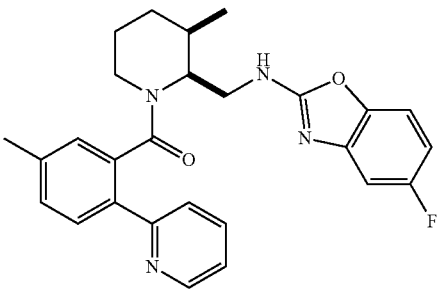

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(pyridin-2-yl)phenyl)methanone and 2-chloro-5-fluorobenzo[d]oxazole. ESI-MS (m/z): 459 [M+1]+.

Example A129

((2S,3R)-2-(((5-Fluorobenzo[d]oxazol-2-yl)amino)methyl)-3-methylpiperidin-1-yl)(5-methyl-2-(2H-1,2,3-triazol-2-yl)phenyl)methanone

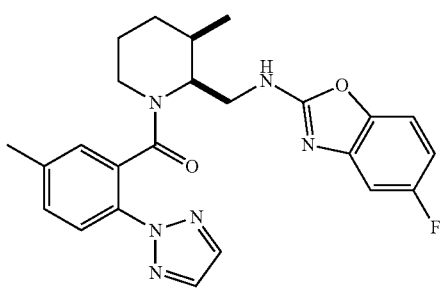 [SMILES: Cc1ccc(-n2nccn2)c(C(=O)N2CCC[C@@H](C)[C@H]2CNc2nc3cc(F)ccc3o2)c1]

The title compound was synthesized following the same general protocol as described for (2S,3R)-allyl 2-(((5-chlorobenzo[d]oxazol-2-yl)amino)methyl)-3-methylpiperidine-1-carboxylate in Example A27, ((2S,3R)-2-(aminomethyl)-3-methylpiperidin-1-yl)(5-methyl-2-(2H-1,2,3-triazol-2-yl)phenyl)methanone and 2-chloro-5-fluorobenzo[d]oxazole. ESI-MS (m/z): 449 [M+1]+.

Example A130

((2S,3R)-3-Methyl-2-(((6-(trifluoromethyl)pyridazin-3-yl)amino)methyl)piperidin-1-yl)(5-methyl-2-(3-methyl-1H-pyrazol-1-yl)phenyl)methanone

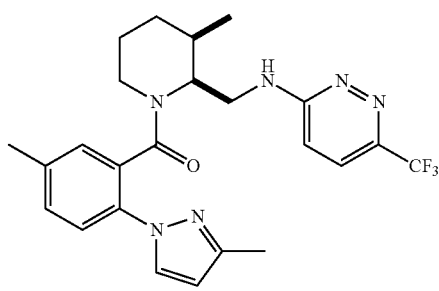

The title compound was prepared following the same general protocol as described for Example A1 using ((2S,3R)-2-(aminomethyl)-3-methylpiperidin-1-yl)(5-methyl-2-(3-methyl-1H-pyrazol-1-yl)phenyl)methanone and 3-chloro-6-(trifluoromethyl)pyridazine. ESI-MS (m/z): 473 [M+1]+.

Example A131

2-((((2S,3R)-3-Methyl-1-(5-methyl-2-(3-methyl-1H-pyrazol-1-yl)benzoyl)piperidin-2-yl)methyl)amino)pyrimidine-5-carbonitrile

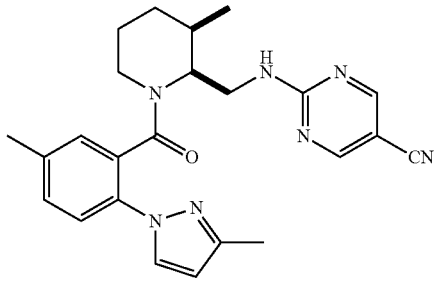 [SMILES: Cc1ccc(-n2ccc(C)n2)c(C(=O)N2CCC[C@@H](C)[C@H]2CNc2ncc(C#N)cn2)c1]

The title compound was prepared following the same general protocol as described for Example A1 using ((2S,3R)-2-(aminomethyl)-3-methylpiperidin-1-yl)(5-methyl-2-(3-methyl-1H-pyrazol-1-yl)phenyl)methanone and 2-chloropyrimidine-5-carbonitrile. ESI-MS (m/z): 430 [M+1]$^+$.

Example A132

((2S,3R)-3-Methyl-2-(((5-(trifluoromethyl)-1,3,4-thiadiazol-2-yl)amino)methyl)piperidin-1-yl)(5-methyl-2-(3-methyl-1H-pyrazol-1-yl)phenyl)methanone

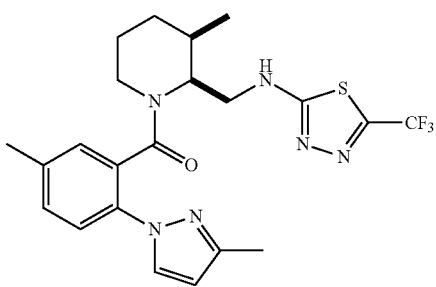

The title compound was prepared following the same general protocol as described for Example A102, using ((2S,3R)-2-(aminomethyl)-3-methylpiperidin-1-yl)(5-methyl-2-(3-methyl-1H-pyrazol-1-yl)phenyl)methanone. ESI-MS (m/z): 479 [M+1]$^+$.

Example A133

6-((((2S,3R)-3-Methyl-1-(5-methyl-2-(3-methyl-1H-pyrazol-1-yl)benzoyl)piperidin-2-yl)methyl)amino)nicotinonitrile

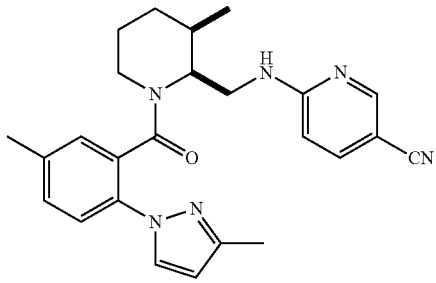 [SMILES: Cc1ccc(-n2ccc(C)n2)c(C(=O)N2CCC[C@@H](C)[C@H]2CNc2ccc(C#N)cn2)c1]

The title compound was prepared following the same general protocol as described for Example A1 using ((2S,3R)-2-(aminomethyl)-3-methylpiperidin-1-yl)(5-methyl-2-(3-methyl-1H-pyrazol-1-yl)phenyl)methanone and 6-chloronicotinonitrile. ESI-MS (m/z): 429 [M+1]$^+$.

Example A134

2-((((2S,3R)-3-Methyl-1-(5-methyl-2-(2H-1,2,3-triazol-2-yl)benzoyl)piperidin-2-yl)methyl)amino)pyrimidine-5-carbonitrile

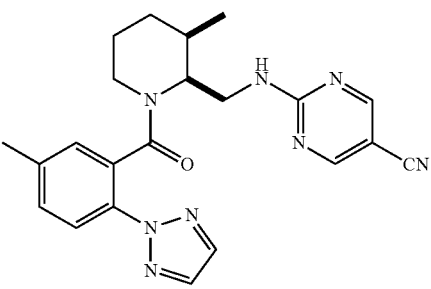

The title compound was prepared following the same general protocol as described for Example A1 using ((2S,3R)-2-(aminomethyl)-3-methylpiperidin-1-yl)(5-methyl-2-(2H-1,2,3-triazol-2-yl)phenyl)methanone and 2-chloropyrimidine-5-carbonitrile. ESI-MS (m/z): 417 [M+1]$^+$.

Example A135

((2S,3R)-3-Methyl-2-(((5-(trifluoromethyl)-1,3,4-thiadiazol-2-yl)amino)methyl)piperidin-1-yl)(5-methyl-2-(4-methyl-2H-1,2,3-triazol-2-yl)phenyl)methanone

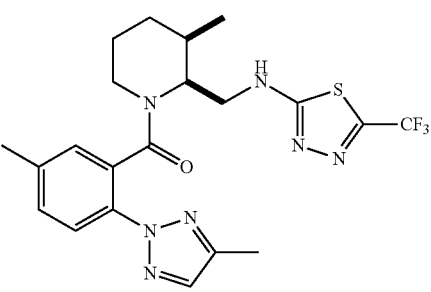 [SMILES: Cc1ccc(-n2ncc(C)n2)c(C(=O)N2CCC[C@@H](C)[C@H]2CNc2nnc(C(F)(F)F)s2)c1]

The title compound was prepared following the same general protocol as described for Example A102, using ((2S,3R)-2-(aminomethyl)-3-methylpiperidin-1-yl)(5-methyl-2-(4-methyl-2H-1,2,3-triazol-2-yl)phenyl)methanone. ESI-MS (m/z): 480 [M+1]$^+$.

Example A136

((2S,3R)-2-(((5-Cyclopropylpyridin-2-yl)amino)methyl)-3-methylpiperidin-1-yl)(5-methyl-2-(2H-1,2,3-triazol-2-yl)phenyl)methanone

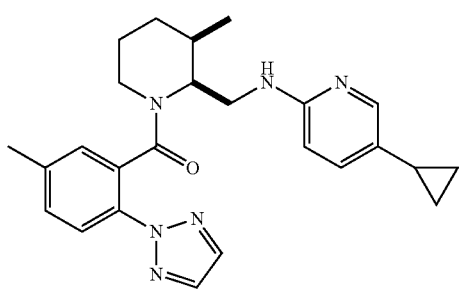 [SMILES: Cc1ccc(-n2nccn2)c(C(=O)N2CCC[C@@H](C)[C@H]2CNc2ccc(C3CC3)cn2)c1]

Step 1. ((2S,3R)-2-(((5-Bromopyridin-2-yl)amino)methyl)-3-methylpiperidin-1-yl)(5-methyl-2-(2H-1,2,3-triazol-2-yl)phenyl)methanone

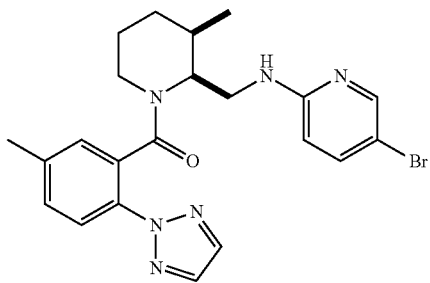 [SMILES: Cc1ccc(-n2nccn2)c(C(=O)N2CCC[C@@H](C)[C@H]2CNc2ccc(Br)cn2)c1]

The title compound was prepared following the same general protocol as described for Example A44 using 2,5-dibromopyridine. MS (ESI) 469, 471 [M]$^+$, [M+2]$^+$.

Step 2. ((2S,3R)-2-(((5-Cyclopropylpyridin-2-yl)amino)methyl)-3-methylpiperidin-1-yl)(5-methyl-2-(2H-1,2,3-triazol-2-yl)phenyl)methanone A mixture of ((2S,3R)-2-(((5-bromopyridin-2-yl)amino)methyl)-3-methylpiperidin-1-yl)(5-methyl-2-(2H-1,2,3-triazol-2-yl)phenyl)methanone (0.052 g, 0.089 mmol), cyclopropylboronic acid (0.011 g, 1 mmol), Pd(OAc)$_2$ (0.004 g, 0.018 mmol), tricyclohexylphosphine (0.01 g, 0.036 mmol) and K$_3$PO$_4$ (0.057 g, 0.267 mmol) in toluene (5 mL) and H$_2$O (0.5 mL) was degassed, sealed and heated overnight at 100° C. in a microwave reactor. The reaction was filtered through a pad of diatomaceous earth, washing with EtOAc. The solvent was removed in vacuo and the crude was purified by reverse-phase preparative-HPLC to obtain the title compound. ESI-MS (m/z): 431 [M+1]$^+$.

Example A137

((2S,3R)-3-Methyl-2-(((6-(trifluoromethyl)pyridazin-3-yl)amino)methyl)piperidin-1-yl)(5-methyl-2-(pyrimidin-2-yl)phenyl)methanone

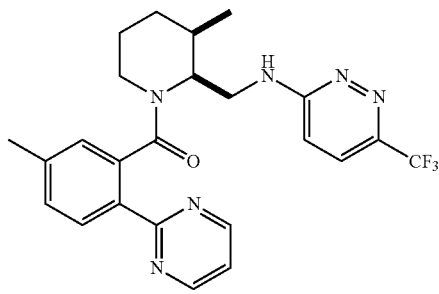

The title compound was prepared following the same general protocol as described for Example A1, using ((2S,3R)-2-(aminomethyl)-3-methylpiperidin-1-yl)(5-methyl-2-(pyrimidin-2-yl)phenyl)methanone and 3-chloro-6-(trifluoromethyl)pyridazine. ESI-MS (m/z): 471 [M+1]$^+$.

Example A138

((2S,3R)-2-(((5-Chloropyridin-2-yl)amino)methyl)-3-methylpiperidin-1-yl)(5-methyl-2-(pyrimidin-2-yl)phenyl)methanone

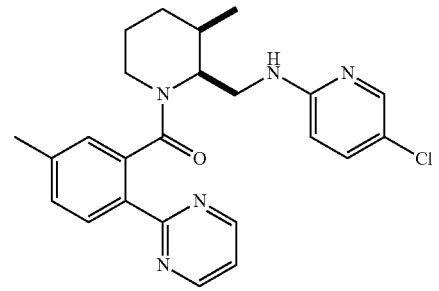 [SMILES: Cc1ccc(-c2ncccn2)c(C(=O)N2CCC[C@@H](C)[C@H]2CNc2ccc(Cl)cn2)c1]

Step 1. 2-(((2S,3R)-1-(2-Iodo-5-methylbenzoyl)-3-methylpiperidin-2-yl)methyl)isoindoline-1,3-dione

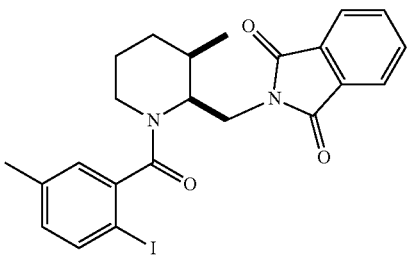 [SMILES: Cc1ccc(I)c(C(=O)N2CCC[C@@H](C)[C@H]2CN2C(=O)c3ccccc3C2=O)c1]

A mixture of 2-(((2S,3R)-3-methylpiperidin-2-yl)methyl)isoindoline-1,3-dione (0.70 g, 2.71 mmol), 2-iodo-5-methylbenzoic acid (0.64 g, 2.71 mmol), diisopropylethylamine (1.41 mL, 8.13 mmol) and HATU (1.24 g, 3.25 mmol) in DMF (4 ml) was stirred at room temperature for 1 h. The reaction mixture was diluted with ethyl acetate and washed with sat'd NaHCO$_3$ and brine successively. The organic layer was separated, dried with MgSO$_4$ and concentrated in vacuo. The crude product was purified by chromatography on silica gel (EtOAc/hexanes) to afford the title compound. MS (ESI) 503 (M+H).

Step 2. 2-(((2S,3R)-3-Methyl-1-(5-methyl-2-(pyrimidin-2-yl)benzoyl)piperidin-2-yl)methyl)isoindoline-1,3-dione

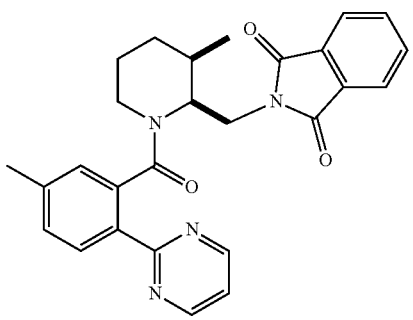 [SMILES: Cc1ccc(-c2ncccn2)c(C(=O)N2CCC[C@@H](C)[C@H]2CN2C(=O)c3ccccc3C2=O)c1]

A mixture of 2-(((2S,3R)-1-(2-iodo-5-methylbenzoyl)-3-methylpiperidin-2-yl)methyl)isoindoline-1,3-dione (0.20 g, 0.40 mmol), 2-(tributylstannyl)pyrimidine (0.15 ml, 0.48 mmol), cesium fluoride (121 mg, 0.80 mmol), CuI (15 mg, 0.08 mmol) and Pd(PPh$_3$)$_4$ (46 mg, 0.04 mmol) in DMF (10 mL) was degassed and heated at 120° C. for 1 h in a microwave reactor. The solvent was removed in vacuo to obtain the crude which was purified by silica gel chromatography (0~100% Hexane/EtOAc) to yield the title compound as a brown oil (0.11 g, 61%). MS (ESI) 455 (M+H).

Step 3. ((2S,3R)-2-(Aminomethyl)-3-methylpiperidin-1-yl)(5-methyl-2-(pyrimidin-2-yl)phenyl)methanone

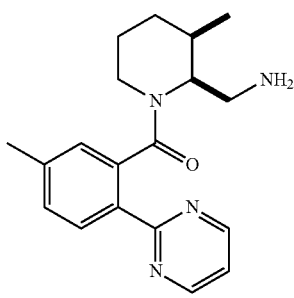 [SMILES: Cc1ccc(-c2ncccn2)c(C(=O)N2CCC[C@@H](C)[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1. MS (ESI) 325 (M+H).

Step 4. ((2S,3R)-2-(((5-Chloropyridin-2-yl)amino)methyl)-3-methylpiperidin-1-yl)(5-methyl-2-(pyrimidin-2-yl)phenyl)methanone The title compound was prepared following the same general protocol as described for Example A44 using ((2S,3R)-2-(aminomethyl)-3-methylpiperidin-1-yl)(5-methyl-2-(pyrimidin-2-yl)phenyl)methanone and 2-bromo-5-chloropyridine. MS (ESI) 436 (M+H).

Example A139

6-((((2S,3R)-3-Methyl-1-(5-methyl-2-(pyrimidin-2-yl)benzoyl)piperidin-2-yl)methyl)amino)nicotinonitrile

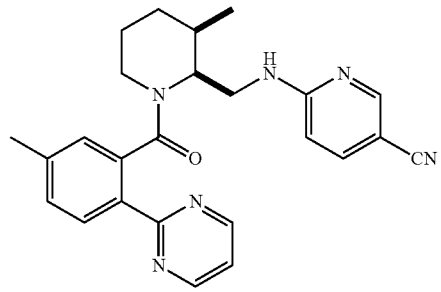 [SMILES: Cc1ccc(-c2ncccn2)c(C(=O)N2CCC[C@@H](C)[C@H]2CNc2ccc(C#N)cn2)c1]

The title compound was prepared following the same general protocol as described for Example A1, using ((2S,3R)-2-(aminomethyl)-3-methylpiperidin-1-yl)(5-methyl-2-(pyrimidin-2-yl)phenyl)methanone and 6-chloronicotinonitrile. ESI-MS (m/z): 427 [M+1]$^+$.

Example A140

1-(6-((((2S,3R)-3-Methyl-1-(5-methyl-2-(2H-1,2,3-triazol-2-yl)benzoyl)piperidin-2-yl)methyl)amino)pyridin-3-yl)cyclopropanecarbonitrile

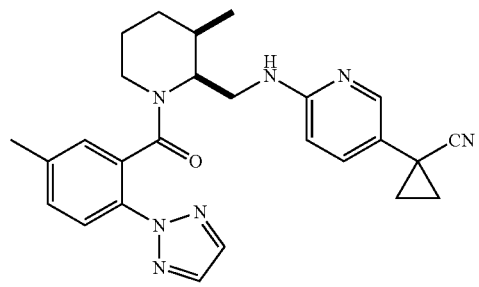 [SMILES: Cc1ccc(-n2nccn2)c(C(=O)N2CCC[C@@H](C)[C@H]2CNc2ccc(C3(C#N)CC3)cn2)c1]

The title compound was prepared following the same general protocol as described for Example A44 using 1-(6-bromopyridin-3-yl)cyclopropanecarbonitrile. ESI-MS (m/z): 456 [M+1]$^+$.

Example A141

((2S,3R)-2-(((5-Fluorobenzo[d]oxazol-2-yl)amino)methyl)-3-methylpiperidin-1-yl)(5-methyl-2-(4-methyl-2H-1,2,3-triazol-2-yl)phenyl)methanone

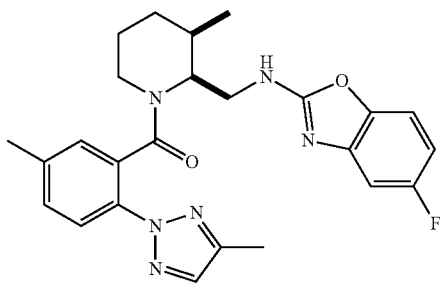 [SMILES: Cc1ccc(-n2ncc(C)n2)c(C(=O)N2CCC[C@@H](C)[C@H]2CNc2nc3cc(F)ccc3o2)c1]

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(4-methyl-2H-1,2,3-triazol-2-yl)phenyl)methanone and 2-chloro-5-fluorobenzo[d]oxazole. ESI-MS (m/z): 463 [M+1]+.

Example A142

((2S,3R)-2-(((5-Fluoropyridin-2-yl)amino)methyl)-3-methylpiperidin-1-yl)(5-methyl-2-(4-methyl-2H-1,2,3-triazol-2-yl)phenyl)methanone

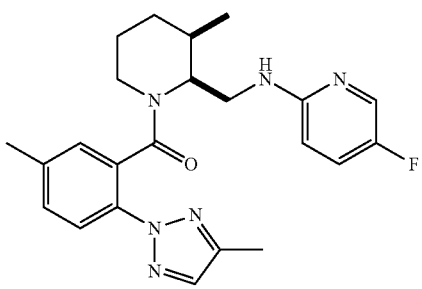 [SMILES: Cc1ccc(-n2ncc(C)n2)c(C(=O)N2CCC[C@@H](C)[C@H]2CNc2ccc(F)cn2)c1]

The title compound was prepared following the same general protocol as described for Example A44 using ((2S,3R)-2-(aminomethyl)-3-methylpiperidin-1-yl)(5-methyl-2-(4-methyl-2H-1,2,3-triazol-2-yl)phenyl)methanone and 2-bromo-5-fluoropyridine. ESI-MS (m/z): 423 [M+1]+.

Example A143

((2S,3R)-3-Methyl-2-(((5-methylpyridin-2-yl)amino)methyl)piperidin-1-yl)(5-methyl-2-(pyrimidin-2-yl)phenyl)methanone

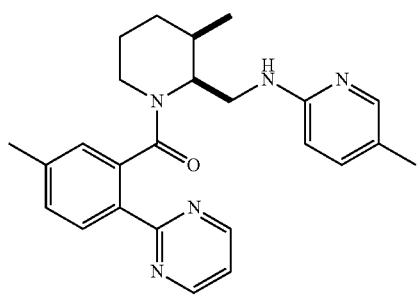

The title compound was prepared following the same general protocol as described for Example A44 using ((2S,3R)-2-(aminomethyl)-3-methylpiperidin-1-yl)(5-methyl-2-(pyrimidin-2-yl)phenyl)methanone and 2-bromo-5-methylpyridine. ESI-MS (m/z): 416 [M+1]+.

Example A144

((2S,3R)-2-(((5-Fluorobenzo[d]oxazol-2-yl)amino)methyl)-3-methylpiperidin-1-yl)(5-methyl-2-(pyridin-2-yl)phenyl)methanone

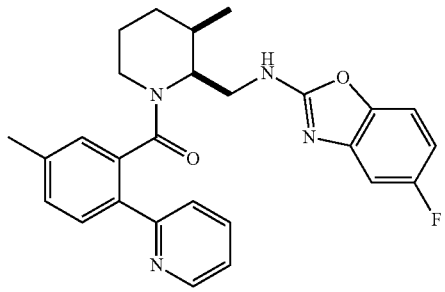

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(5-methyl-2-(pyridin-2-yl)phenyl)methanone and 2-chloro-5-fluorobenzo[d]oxazole. ESI-MS (m/z): 459 [M+1]+.

Example A145

6-((((2S,3R)-3-Methyl-1-(5-methyl-2-(2H-1,2,3-triazol-2-yl)benzoyl)piperidin-2-yl)methyl)amino)pyridazine-3-carbonitrile

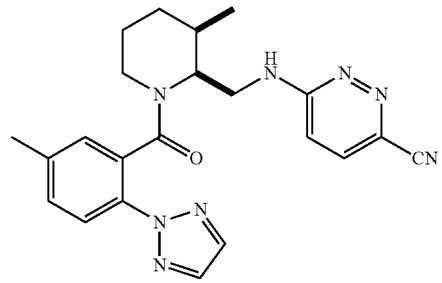 [SMILES: Cc1ccc(-n2nccn2)c(C(=O)N2CCC[C@@H](C)[C@H]2CNc2ccc(C#N)nn2)c1]

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 6-chloropyridazine-3-carbonitrile. ESI-MS (m/z): 417 [M+1]+.

Example A146

((2S,3R)-3-Methyl-2-(((6-methylpyridazin-3-yl)amino)methyl)piperidin-1-yl)(5-methyl-2-(2H-1,2,3-triazol-2-yl)phenyl)methanone

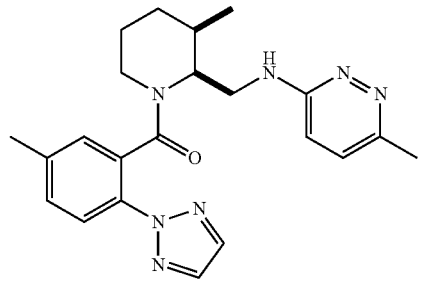

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 3-chloro-6-methylpyridazine. ESI-MS (m/z): 406 [M+1]⁺.

Example A147

((2S,3R)-2-(((5-Chloropyrimidin-2-yl)amino)methyl)-3-methylpiperidin-1-yl)(5-methyl-2-(2H-1,2,3-triazol-2-yl)phenyl)methanone

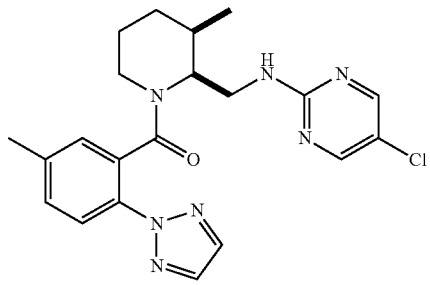 [SMILES: Cc1ccc(-n2nccn2)c(C(=O)N2CCC[C@@H](C)[C@H]2CNc2ncc(Cl)cn2)c1]

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 2,5-dichloropyrimidine. ESI-MS (m/z): 426 [M+1]⁺.

Example A148

5-Fluoro-6-((((2S,3R)-3-methyl-1-(5-methyl-2-(2H-1,2,3-triazol-2-yl)benzoyl)piperidin-2-yl)methyl)amino)nicotinonitrile

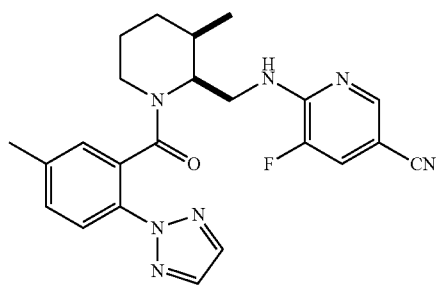 [SMILES: Cc1ccc(-n2nccn2)c(C(=O)N2CCC[C@@H](C)[C@H]2CNc2ncc(C#N)cc2F)c1]

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 6-chloro-5-fluoronicotinonitrile. ESI-MS (m/z): 434 [M+1]⁺.

Example A149

((2S,3R)-3-Methyl-2-(((5-(trifluoromethyl)pyrimidin-2-yl)amino)methyl)piperidin-1-yl)(5-methyl-2-(2H-1,2,3-triazol-2-yl)phenyl)methanone

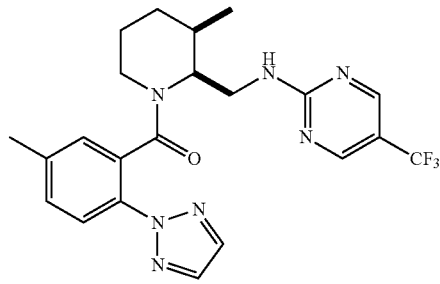

The title compound was prepared following the same general protocol as described for Example A1, using ((2S,3R)-2-(aminomethyl)-3-methylpiperidin-1-yl)(5-methyl-2-(2H-1,2,3-triazol-2-yl)phenyl)methanone and 2-chloro-5-(trifluoromethyl)pyrimidine. ESI-MS (m/z): 460 [M+1]⁺.

Example A150

((2S,3R)-3-Methyl-2-(((6-(trifluoromethyl)pyridazin-3-yl)amino)methyl)piperidin-1-yl)(5-methyl-2-(pyridin-2-yl)phenyl)methanone

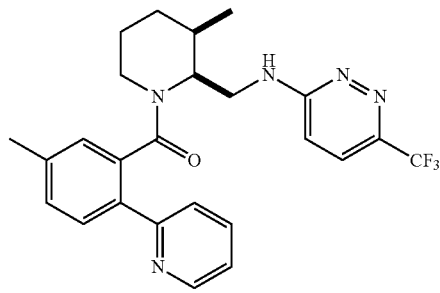 [SMILES: Cc1ccc(-c2ccccn2)c(C(=O)N2CCC[C@@H](C)[C@H]2CNc2ccc(C(F)(F)F)nn2)c1]

The title compound was prepared following the same general protocol as described for Example A1, using ((2S,3R)-2-(aminomethyl)-3-methylpiperidin-1-yl)(5-methyl-2-(pyridin-2-yl)phenyl)methanone and 3-chloro-6-trifluoromethylpyridazine. ESI-MS (m/z): 470 [M+1]⁺.

Example A151

((2S,3R)-3-Methyl-2-(((5-(trifluoromethyl)-1,3,4-thiadiazol-2-yl)amino)methyl)piperidin-1-yl)(5-methyl-2-(pyridin-2-yl)phenyl)methanone

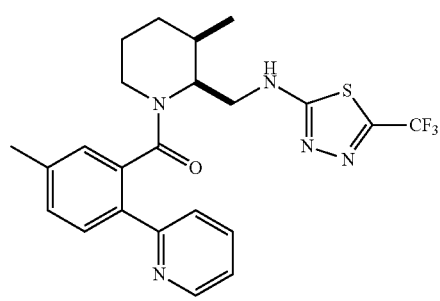 [SMILES: Cc1ccc(-c2ccccn2)c(C(=O)N2CCC[C@@H](C)[C@H]2CNc2nnc(C(F)(F)F)s2)c1]

The title compound was prepared following the same general protocol as described for Example A102 using ((2S,3R)-2-(aminomethyl)-3-methylpiperidin-1-yl)(5-methyl-2-(pyridin-2-yl)phenyl)methanone. ESI-MS (m/z): 476 [M+1]⁺.

Example A152

((2S,3R)-3-Methyl-2-(((5-(trifluoromethyl)pyrimidin-2-yl)amino)methyl)piperidin-1-yl)(5-methyl-2-(pyridin-2-yl)phenyl)methanone

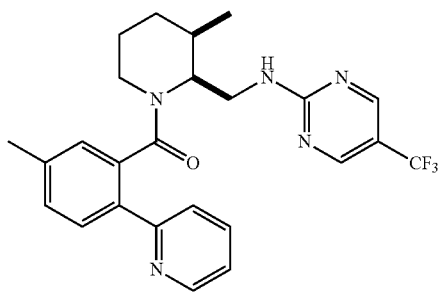 [SMILES: Cc1ccc(-c2ccccn2)c(C(=O)N2CCC[C@@H](C)[C@H]2CNc2ncc(C(F)(F)F)cn2)c1]

The title compound was prepared following the same general protocol as described for Example A1, using ((2S,3R)-2-(aminomethyl)-3-methylpiperidin-1-yl)(5-methyl-2-(pyridin-2-yl)phenyl)methanone and 2-chloro-5-(trifluoromethyl)pyrimidine. ESI-MS (m/z): 470 [M+1]⁺.

Example A153

2-((((2S,3R)-3-Methyl-1-(5-methyl-2-(pyridin-2-yl)benzoyl)piperidin-2-yl)methyl)amino)pyrimidine-5-carbonitrile

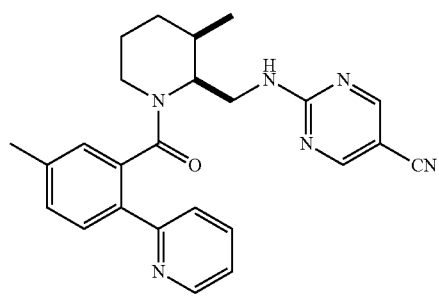 [SMILES: Cc1ccc(-c2ccccn2)c(C(=O)N2CCC[C@@H](C)[C@H]2CNc2ncc(C#N)cn2)c1]

The title compound was prepared following the same general protocol as described for Example A1, using ((2S,3R)-2-(aminomethyl)-3-methylpiperidin-1-yl)(5-methyl-2-(pyridin-2-yl)phenyl)methanone and 2-chloropyrimidine-5-carbonitrile. ESI-MS (m/z): 427 [M+1]⁺.

Example A154

((2S,3R)-3-Methyl-2-(((6-methylpyridazin-3-yl)amino)methyl)piperidin-1-yl)(5-methyl-2-(1H-pyrazol-1-yl)phenyl)methanone

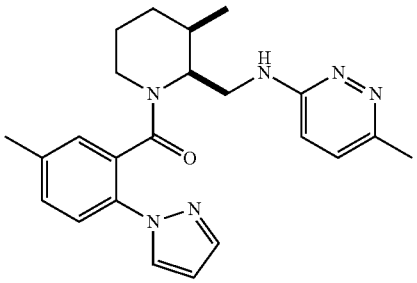

Step 1. ((2S,3R)-2-(Aminomethyl)-3-methylpiperidin-1-yl)(5-methyl-2-(1H-pyrazol-1-yl)phenyl)methanone

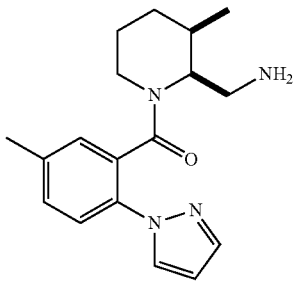 [SMILES: Cc1ccc(-n2cccn2)c(C(=O)N2CCC[C@@H](C)[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A11 using 5-methyl-2-(1H-pyrazol-1-yl)benzoic acid. MS (ESI) 313 (M+H).

Step 2. ((2S,3R)-3-Methyl-2-(((6-methylpyridazin-3-yl)amino)methyl)piperidin-1-yl)(5-methyl-2-(1H-pyrazol-1-yl)phenyl)methanone The title compound was prepared following the same general protocol as described for Example A44 using ((2S,3R)-2-(aminomethyl)-3-methylpiperidin-1-yl)(5-methyl-2-(1H-pyrazol-1-yl)phenyl)methanone and 3-bromo-6-methylpyridazine. MS (ESI) 405 (M+H).

Example A155

6-((((2S,3R)-3-Methyl-1-(5-methyl-2-(1H-pyrazol-1-yl)benzoyl)piperidin-2-yl)methyl)amino)nicotinonitrile

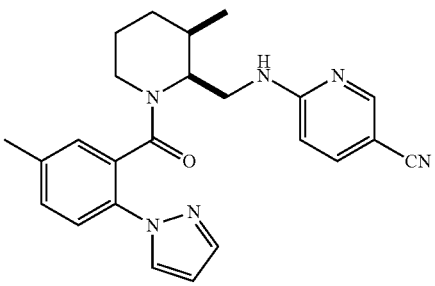 [SMILES: Cc1ccc(-n2cccn2)c(C(=O)N2CCC[C@@H](C)[C@H]2CNc2ccc(C#N)cn2)c1]

The title compound was prepared following the same general protocol as described for Example A45 using ((2S, 3R)-2-(aminomethyl)-3-methylpiperidin-1-yl)(5-methyl-2-(1H-pyrazol-1-yl)phenyl)methanone and 2-bromo-5-cyano-pyridine. MS (ESI) 415 (M+H).

Example A156

6-(((((2S,3R)-3-Methyl-1-(5-methyl-2-(1H-pyrazol-1-yl)benzoyl)piperidin-2-yl)methyl)amino)pyridazine-3-carbonitrile

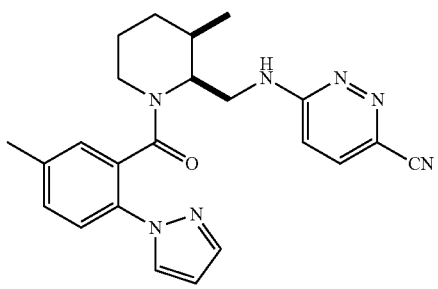 [SMILES: Cc1ccc(-n2cccn2)c(C(=O)N2CCC[C@@H](C)[C@H]2CNc2ccc(C#N)nn2)c1]

The title compound was prepared following the same general protocol as described for Example A45 using ((2S, 3R)-2-(aminomethyl)-3-methylpiperidin-1-yl)(5-methyl-2-(1H-pyrazol-1-yl)phenyl)methanone and 6-chloro-pyridazine-3-carbonitrile. MS (ESI) 416 (M+H).

Example A157

((2S,3R)-3-Methyl-2-(((6-(trifluoromethyl)pyridazin-3-yl)amino)methyl)piperidin-1-yl)(5-methyl-2-(1H-pyrazol-1-yl)phenyl)methanone

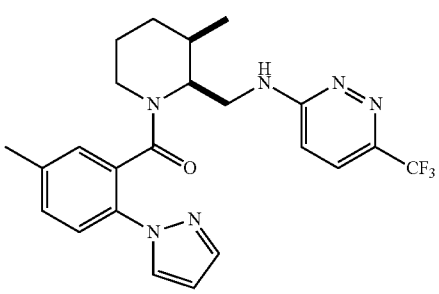 [SMILES: Cc1ccc(-n2cccn2)c(C(=O)N2CCC[C@@H](C)[C@H]2CNc2ccc(C(F)(F)F)nn2)c1]

The title compound was prepared following the same general protocol as described for Example A45 using ((2S, 3R)-2-(aminomethyl)-3-methylpiperidin-1-yl)(5-methyl-2-(1H-pyrazol-1-yl)phenyl)methanone and 3-chloro-6-(trifluoromethyl)pyridazine. MS (ESI) 459 (M+H).

Example A158

((2S,3R)-2-(((5-Chloropyridin-2-yl)amino)methyl)-3-methylpiperidin-1-yl)(5-methyl-2-(5-(trifluoromethyl)pyridin-2-yl)phenyl)methanone

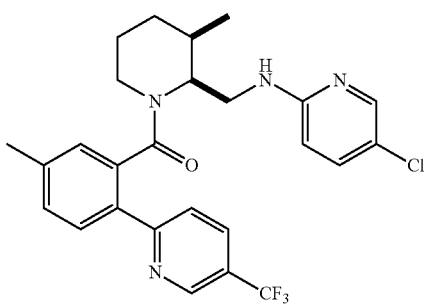 [SMILES: Cc1ccc(-c2ccc(C(F)(F)F)cn2)c(C(=O)N2CCC[C@@H](C)[C@H]2CNc2ccc(Cl)cn2)c1]

Step 1. ((2S,3R)-2-(Aminomethyl)-3-methylpiperidin-1-yl)(5-methyl-2-(5-(trifluoromethyl)pyridin-2-yl)phenyl)methanone

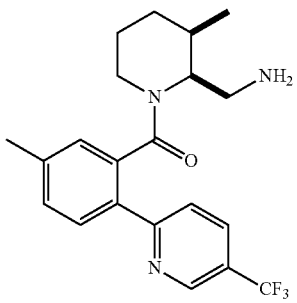 [SMILES: Cc1ccc(-c2ccc(C(F)(F)F)cn2)c(C(=O)N2CCC[C@@H](C)[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-methyl-2-(5-(trifluoromethyl)pyridin-2-yl)benzoic acid. MS (ESI) 392 (M+H).

Step 2. ((2S,3R)-2-(((5-Chloropyridin-2-yl)amino)methyl)-3-methylpiperidin-1-yl)(5-methyl-2-(5-(trifluoromethyl)pyridin-2-yl)phenyl)methanone The title compound was prepared following the same general protocol as described for Example A44 using ((2S, 3R)-2-(aminomethyl)-3-methylpiperidin-1-yl)(5-methyl-2-(5-(trifluoromethyl)pyridin-2-yl)phenyl)methanone and 2-bromo-5-chloropyridine. MS (ESI) 503 (M+H).

Example A159

((2S,3R)-2-(((5-Chloropyridin-2-yl)amino)methyl)-3-methylpiperidin-1-yl)(2-(5-fluoropyridin-2-yl)-5-methylphenyl)methanone

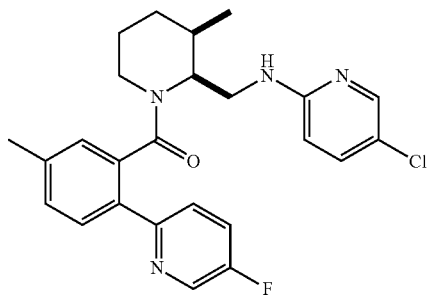 [SMILES: Cc1ccc(-c2ccc(F)cn2)c(C(=O)N2CCC[C@@H](C)[C@H]2CNc2ccc(Cl)cn2)c1]

Step 1. ((2S,3R)-2-(Aminomethyl)-3-methylpiperidin-1-yl)(2-(5-fluoropyridin-2-yl)-5-methylphenyl)methanone

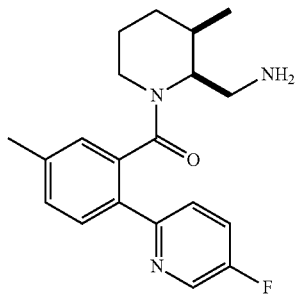 [SMILES: Cc1ccc(-c2ccc(F)cn2)c(C(=O)N2CCC[C@@H](C)[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(5-fluoropyridin-2-yl)-5-methylbenzoic acid. MS (ESI) 342 (M+H).

Step 2. ((2S,3R)-2-(((5-Chloropyridin-2-yl)amino)methyl)-3-methylpiperidin-1-yl)(2-(5-fluoropyridin-2-yl)-5-methylphenyl)methanone The title compound was prepared following the same general protocol as described for Example A44 using ((2S,3R)-2-(aminomethyl)-3-methylpiperidin-1-yl)(2-(5-fluoropyridin-2-yl)-5-methylphenyl)methanone and 2-bromo-5-chloropyridine. MS (ESI) 453 (M+H).

Example A160

(5-Chloro-2-(2H-1,2,3-triazol-2-yl)phenyl)((2S,3R)-3-methyl-2-(((5-(trifluoromethyl)pyrimidin-2-yl)amino)methyl)piperidin-1-yl)methanone

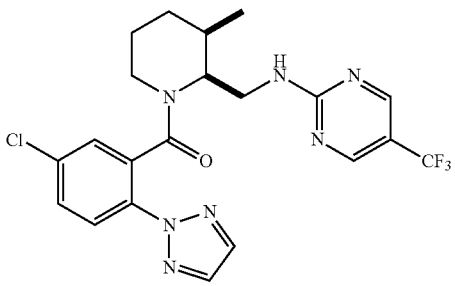 [SMILES: C[C@@H]1CCCN(C(=O)c2cc(Cl)ccc2-n2nccn2)[C@@H]1CNc1ncc(C(F)(F)F)cn1]

Step 1. 5-Chloro-2-(2H-1,2,3-triazol-2-yl)benzoic acid

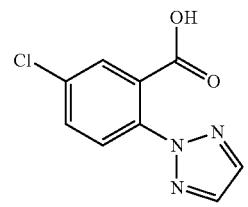 [SMILES: O=C(O)c1cc(Cl)ccc1-n1nccn1]

The title compound was prepared following the same general protocol as described for 5-methyl-2-(2H-1,2,3-triazol-2-yl)benzoic acid in Example A11 using 2-bromo-5-chlorobenzoic acid. MS (ESI) 224 (M+H).

Step 2. ((2S,3R)-2-(Aminomethyl)-3-methylpiperidin-1-yl)(5-chloro-2-(2H-1,2,3-triazol-2-yl)phenyl)methanone

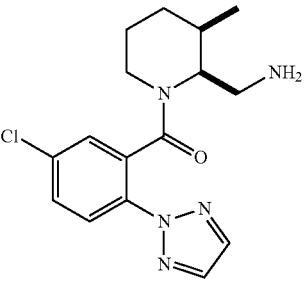 [SMILES: C[C@@H]1CCCN(C(=O)c2cc(Cl)ccc2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-chloro-2-(2H-1,2,3-triazol-2-yl)benzoic acid. MS (ESI) 334 (M+H).

Step 3. (5-Chloro-2-(2H-1,2,3-triazol-2-yl)phenyl) ((2S,3R)-3-methyl-2-(((5-(trifluoromethyl)pyrimidin-2-yl)amino)methyl)piperidin-1-yl)methanone The title compound was prepared following the same general protocol as described for Example A45 using ((2S, 3R)-2-(aminomethyl)-3-methylpiperidin-1-yl)(5-chloro-2-(2H-1,2,3-triazol-2-yl)phenyl)methanone and 2-chloro-5-(trifluoromethyl)pyrimidine. MS (ESI) 480 (M+H).

Example A161

(5-Chloro-2-(2H-1,2,3-triazol-2-yl)phenyl)((2S,3R)-2-(((5-chloropyridin-2-yl)amino)methyl)-3-methyl-piperidin-1-yl)methanone

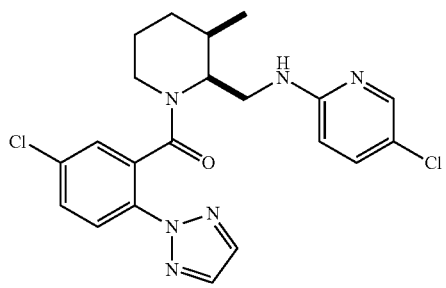 [SMILES: C[C@@H]1CCCN(C(=O)c2cc(Cl)ccc2-n2nccn2)[C@@H]1CNc1ccc(Cl)cn1]

The title compound was prepared following the same general protocol as described for Example A44 using ((2S, 3R)-2-(aminomethyl)-3-methylpiperidin-1-yl)(5-chloro-2-(2H-1,2,3-triazol-2-yl)phenyl)methanone and 2-bromo-5-chloropyridine. MS (ESI) 445 (M+H).

Example A162

(5-Chloro-2-(2H-1,2,3-triazol-2-yl)phenyl)((2S,3R)-3-methyl-2-(((6-(trifluoromethyl)pyridazin-3-yl) amino)methyl)piperidin-1-yl)methanone

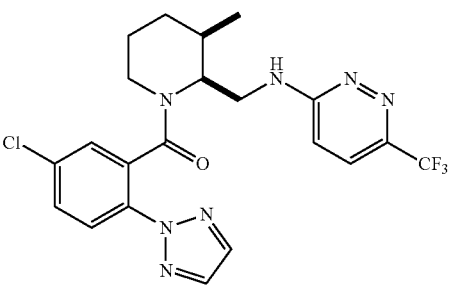 [SMILES: C[C@@H]1CCCN(C(=O)c2cc(Cl)ccc2-n2nccn2)[C@@H]1CNc1ccc(C(F)(F)F)nn1]

The title compound was prepared following the same general protocol as described for Example A45 using ((2S, 3R)-2-(aminomethyl)-3-methylpiperidin-1-yl)(5-chloro-2-(2H-1,2,3-triazol-2-yl)phenyl)methanone and 3-chloro-6-(trifluoromethyl)pyridazine. MS (ESI) 480 (M+H).

Example A163

((2S,3R)-3-Methyl-2-(((4-(trifluoromethyl)pyrimidin-2-yl)amino)methyl)piperidin-1-yl)(5-methyl-2-(2H-1,2,3-triazol-2-yl)phenyl)methanone

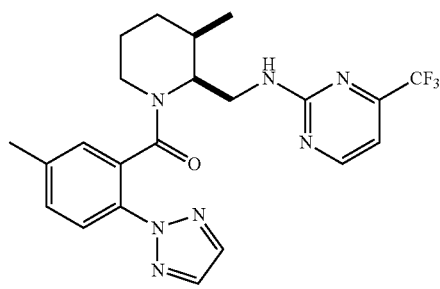 [SMILES: Cc1ccc(-n2nccn2)c(C(=O)N2CCC[C@@H](C)[C@H]2CNc2nccc(C(F)(F)F)n2)c1]

The title compound was prepared following the same general protocol as described for Example A1, using ((2S, 3R)-2-(aminomethyl)-3-methylpiperidin-1-yl)(5-methyl-2-(2H-1,2,3-triazol-2-yl)phenyl)methanone and 2-chloro-4-(trifluoromethyl)pyrimidine. ESI-MS (m/z): 460 [M+1]$^+$.

Example A164

((2S,3R)-3-Methyl-2-(((6-(trifluoromethyl) pyridazin-3-yl)amino)methyl)piperidin-1-yl)(6-methyl-3-(1H-pyrazol-1-yl)pyridin-2-yl)methanone

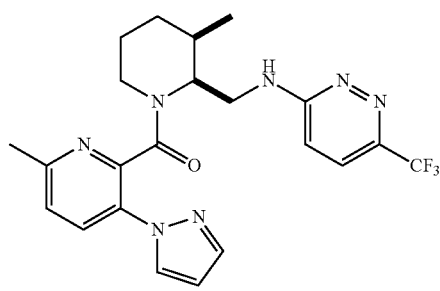

Step 1. 6-Methyl-3-(1H-pyrazol-1-yl)picolinonitrile

A mixture of 3-bromo-6-methylpicolinonitrile (1 g, 5.1 mmol), 1H-pyrazole (0.52 ml, 7.61 mmol), (1S,2S)—N1, N2-dimethylcyclohexane-1,2-diamine (0.97 ml, 6.09 mmol), Cs$_2$CO$_3$ (2.48 g, 7.61 mmol) and CuI (97 mg, 0.51 mmol) in DMF (10 mL) was degassed and heated at 120° C. for 1 h in a microwave reactor. The solvent was removed in vacuo to obtain the crude which was purified by silica gel chromatography (0-100% DCM/EtOAc) to yield the title compound as a yellow oil (600 mg, 64%). MS (ESI) 185 (M+H).

Step 2. 6-Methyl-3-(1H-pyrazol-1-yl)picolinic acid

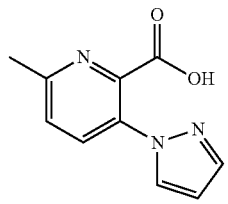

6-Methyl-3-(1H-pyrazol-1-yl)picolinonitrile (0.60 g, 3.26 mmol) and NaOH (1.37 g, 34.2 mmol) were dissolved in methanol (3 ml) and stirred at reflux overnight. The reaction was cooled to RT, diluted with more methanol (5 ml), and acidified with AcOH to pH4~5. The solvent was removed in vacuo to obtain the crude which was purified by silica gel chromatography (0~100% DCM/EtOAc) to yield the title compound as a clear oil (0.62 g, 94%). MS (ESI) 204 (M+H).

Step 3. ((2S,3R)-2-(Aminomethyl)-3-methylpiperidin-1-yl)(6-methyl-3-(1H-pyrazol-1-yl)pyridin-2-yl)methanone

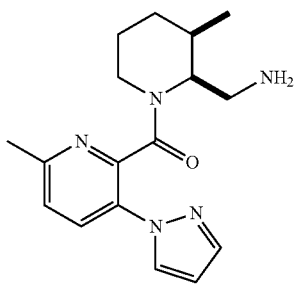

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 6-methyl-3-(1H-pyrazol-1-yl)picolinic acid. MS (ESI) 314 (M+H).

Step 4. ((2S,3R)-3-Methyl-2-(((6-(trifluoromethyl)pyridazin-3-yl)amino)methyl)piperidin-1-yl)(6-methyl-3-(1H-pyrazol-1-yl)pyridin-2-yl)methanone The title compound was prepared following the same general protocol as described for Example A45 using ((2S,3R)-2-(aminomethyl)-3-methylpiperidin-1-yl)(6-methyl-3-(1H-pyrazol-1-yl)pyridin-2-yl)methanone and 3-chloro-6-(trifluoromethyl)pyridazine. MS (ESI) 460 (M+H).

Example A165

((2S,3R)-3-methyl-2-(((6-(trifluoromethyl)pyridazin-3-yl)amino)methyl)piperidin-1-yl)(6'-methyl-[2,3'-bipyridin]-2'-yl)methanone

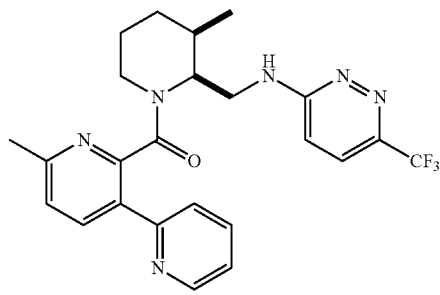 [SMILES: Cc1ccc(-c2ccccn2)c(C(=O)N2CCC[C@@H](C)[C@H]2CNc2ccc(C(F)(F)F)nn2)n1]

Step 1. 6'-Methyl-[2,3'-bipyridine]-2'-carbonitrile

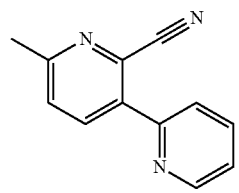

A mixture of 3-bromo-6-methylpicolinonitrile (1 g, 5.1 mmol), 2-(tributylstannyl)pyridine (2.43 ml, 6.60 mmol), cesium fluoride (150 mg, 10.2 mmol), CuI (193 mg, 1.02 mmol) and Pd(PPh$_3$)$_4$ (586 mg, 0.51 mmol) in DMF (10 mL) was degassed and heated at 120° C. for 1 h in a microwave reactor. The solvent was removed in vacuo to obtain the crude which was purified by silica gel chromatography (0-100% DCM/EtOAc) to yield the title compound as a brown oil (0.87 g, 88%). MS (ESI) 196 (M+H).

Step 2. 6'-Methyl-[2,3'-bipyridine]-2'-carboxylic acid

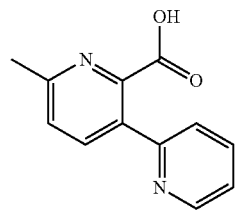 [SMILES: Cc1ccc(-c2ccccn2)c(C(=O)O)n1]

6'-Methyl-[2,3'-bipyridine]-2'-carbonitrile (0.87 g, 4.46 mmol) and NaOH (1.87 g, 46.8 mmol) were dissolved in methanol (3 ml) and stirred at reflux overnight. The reaction was cooled to RT, diluted with more methanol (5 ml), and acidified with AcOH to pH4~5. The solvent was removed in vacuo to obtain the crude which was purified by silica gel chromatography (0~100% DCM/EtOAc) to yield the title compound as a clear oil (0.9 g, 94%).

389

Step 3. ((2S,3R)-2-(Aminomethyl)-3-methylpiperidin-1-yl)(6'-methyl-[2,3'-bipyridin]-2'-yl)methanone

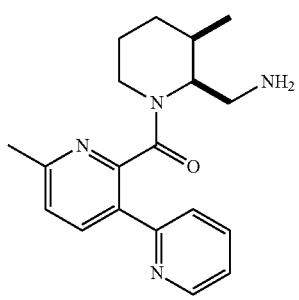 [SMILES: Cc1ccc(-c2ccccn2)c(C(=O)N2CCC[C@@H](C)[C@H]2CN)n1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 6'-methyl-[2,3'-bipyridine]-2'-carboxylic acid. MS (ESI) 325 (M+H).

Step 4. ((2S,3R)-3-Methyl-2-(((6-(trifluoromethyl)pyridazin-3-yl)amino)methyl)piperidin-1-yl)(6'-methyl-[2,3'-bipyridin]-2'-yl)methanone The title compound was prepared following the same general protocol as described for Example A45 using ((2S,3R)-2-(aminomethyl)-3-methylpiperidin-1-yl)(6'-methyl-[2,3'-bipyridin]-2'-yl)methanone and 3-chloro-6-(trifluoromethyl)pyridazine. MS (ESI) 471 (M+H).

Example A166

((2S,3R)-3-Methyl-2-(((5-(trifluoromethyl)pyrimidin-2-yl)amino)methyl)piperidin-1-yl)(6-methyl-3-(1H-pyrazol-1-yl)pyridin-2-yl)methanone

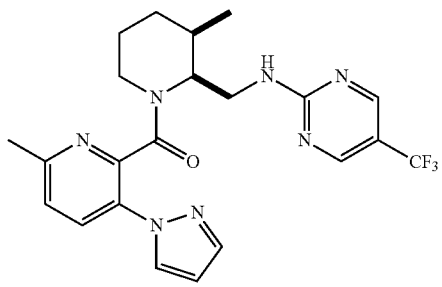

The title compound was prepared following the same general protocol as described for Example A45 using ((2S,3R)-2-(aminomethyl)-3-methylpiperidin-1-yl)(6-methyl-3-(1H-pyrazol-1-yl)pyridin-2-yl)methanone and 2-chloro-5-(trifluoromethyl)pyrimidine. MS (ESI) 460 (M+H).

390

Example A167

((2S,3R)-3-Methyl-2-(((5-(trifluoromethyl)pyrimidin-2-yl)amino)methyl)piperidin-1-yl)(6'-methyl-[2,3'-bipyridin]-2'-yl)methanone

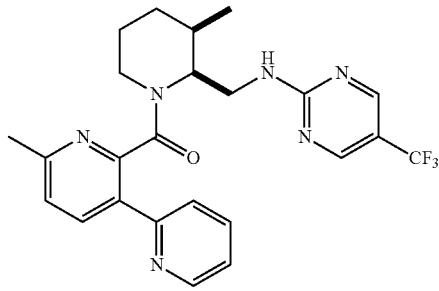 [SMILES: Cc1ccc(-c2ccccn2)c(C(=O)N2CCC[C@@H](C)[C@H]2CNc2ncc(C(F)(F)F)cn2)n1]

The title compound was prepared following the same general protocol as described for Example A45 using ((2S,3R)-2-(aminomethyl)-3-methylpiperidin-1-yl)(5-methyl-2-(1-methyl-1H-pyrazol-4-yl)phenyl)methanone and 2-chloro-5-(trifluoromethyl)pyrimidine. MS (ESI) 471 (M+H).

Example A168

((2S,3R)-2-(((5-Chloropyridin-2-yl)amino)methyl)-3-methylpiperidin-1-yl)(6-methyl-3-(1H-pyrazol-1-yl)pyridin-2-yl)methanone

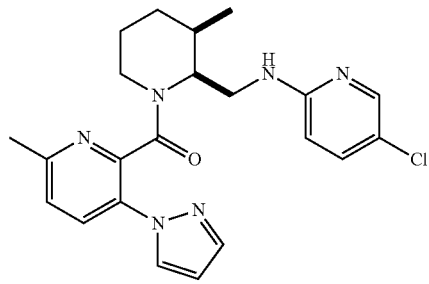

The title compound was prepared following the same general protocol as described for Example A44 using ((2S,3R)-2-(aminomethyl)-3-methylpiperidin-1-yl)(6-methyl-3-(1H-pyrazol-1-yl)pyridin-2-yl)methanone and 2-bromo-5-chloropyridine. MS (ESI) 425 (M+H).

Example A169

((2S,3R)-2-(((5-Chloropyridin-2-yl)amino)methyl)-3-methylpiperidin-1-yl)(6'-methyl-[2,3'-bipyridin]-2'-yl)methanone

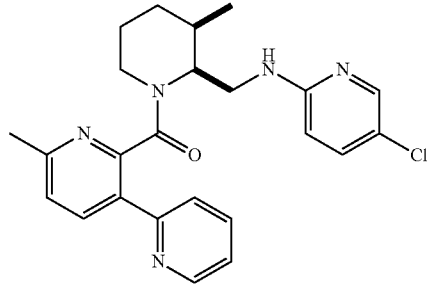

The title compound was prepared following the same general protocol as described for Example A44 using ((2S,3R)-2-(aminomethyl)-3-methylpiperidin-1-yl)(6'-methyl-[2,3'-bipyridin]-2'-yl)methanone and 2-bromo-5-chloropyridine. MS (ESI) 436 (M+H).

Example A170

((2S,3R)-2-(((5-Fluoropyrimidin-2-yl)amino)methyl)-3-methylpiperidin-1-yl)(5-methyl-2-(1H-pyrazol-1-yl)phenyl)methanone

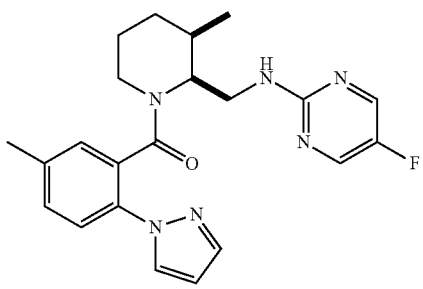

A mixture of ((2S,3R)-2-(aminomethyl)-3-methylpiperidin-1-yl)(5-methyl-2-(1H-pyrazol-1-yl)phenyl)methanone (30 mg, 96 µmol), 2-chloro-5-fluoropyrimidine (18 µl, 144 µmol) and anhydrous DIEA (50 µg, 288 µmol) in CH$_3$CN (2 mL) was heated at 100° C. for 3 days. The mixture was cooled to room temperature and the solvent was removed in vacuo. The crude was dissolved in EtOAc and washed with sat'd NaHCO$_3$, brine, and dried (MgSO$_4$). The solvent was removed and the crude was purified by reverse-phase preparative HPLC to afford the title compound. MS (ESI) 409 (M+H).

Example A171

((2S,3R)-2-(((5-Fluoropyrimidin-2-yl)amino)methyl)-3-methylpiperidin-1-yl)(5-methyl-2-(2H-1,2,3-triazol-2-yl)phenyl)methanone

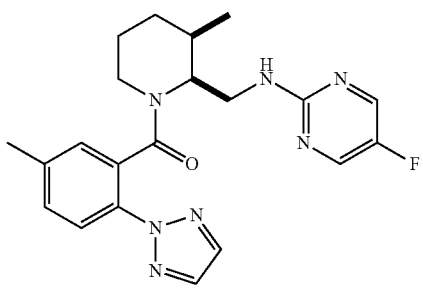 [SMILES: Cc1ccc(-n2nccn2)c(C(=O)N2CCC[C@@H](C)[C@H]2CNc2ncc(F)cn2)c1]

The title compound was prepared following the same general protocol as described for Example A1 using ((2S,3R)-2-(aminomethyl)-3-methylpiperidin-1-yl)(5-methyl-2-(2H-1,2,3-triazol-2-yl)phenyl)methanone and 2-chloro-5-fluoropyrimidine. ESI-MS (m/z): 410, 471 [M+1]$^+$.

Example A172

((2S,3R)-2-(((3,5-Difluoropyridin-2-yl)amino)methyl)-3-methylpiperidin-1-yl)(5-methyl-2-(2H-1,2,3-triazol-2-yl)phenyl)methanone

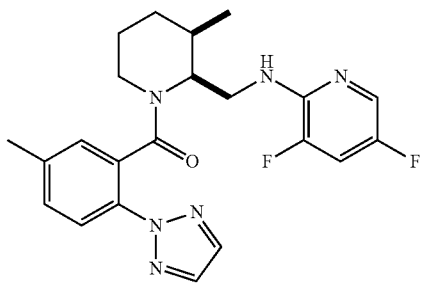 [SMILES: Cc1ccc(-n2nccn2)c(C(=O)N2CCC[C@@H](C)[C@H]2CNc2ncc(F)cc2F)c1]

The title compound was prepared following the same general protocol as described for Example A44 using 2-bromo-3,5-difluoropyridine. ESI-MS (m/z): 427 [M+1]$^+$.

Example A173

((2S,3R)-2-(((5-Chloro-3-fluoropyridin-2-yl)amino)methyl)-3-methylpiperidin-1-yl)(5-methyl-2-(2H-1,2,3-triazol-2-yl)phenyl)methanone

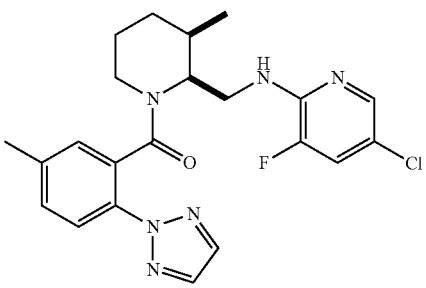

The title compound was prepared following the same general protocol as described for Example A44 using 2-bromo-5-chloro-3-fluoropyridine. ESI-MS (m/z): 443 [M+1]$^+$.

Example A174

((2S,3R)-3-Methyl-2-(((5-(trifluoromethyl)pyridin-2-yl)amino)methyl)piperidin-1-yl)(6-methyl-3-(2H-1,2,3-triazol-2-yl)pyridin-2-yl)methanone

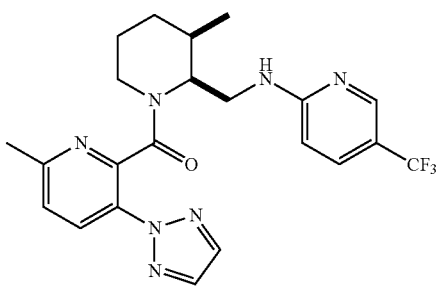

Step 1. 6-Methyl-3-(2H-1,2,3-triazol-2-yl)picolinic acid

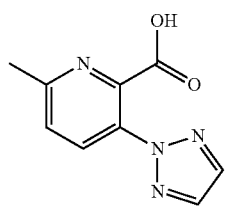

The title compound was prepared following the same general protocol as described for 6-methyl-3-(1H-pyrazol-1-yl)picolinic acid in Example A164, using 2H-1,2,3-triazole. ESI-MS (m/z): 205 [M+1]⁺.

Step 2. ((2S,3R)-2-(Aminomethyl)-3-methylpiperidin-1-yl)(6-methyl-3-(2H-1,2,3-triazol-2-yl)pyridin-2-yl)methanone

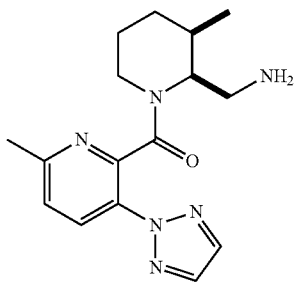

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1, using 6-methyl-3-(2H-1,2,3-triazol-2-yl)picolinic acid. ESI-MS (m/z): 315 [M+1]⁺.

Step 3. ((2S,3R)-3-Methyl-2-(((5-(trifluoromethyl)pyridin-2-yl)amino)methyl)piperidin-1-yl)(6-methyl-3-(2H-1,2,3-triazol-2-yl)pyridin-2-yl)methanone The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 2-fluoro-5-trifluoromethylpyridine. ESI-MS (m/z): 460 [M+1]⁺.

Example A175

((2S,3R)-3-Methyl-2-(((5-(trifluoromethyl)pyrimidin-2-yl)amino)methyl)piperidin-1-yl)(6-methyl-3-(2H-1,2,3-triazol-2-yl)pyridin-2-yl)methanone

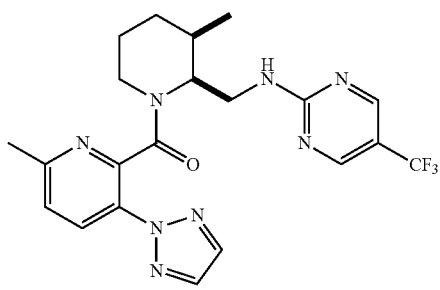

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 2-chloro-5-trifluoromethylpyrimidine. ESI-MS (m/z): 461 [M+1]⁺.

Example A176

((2S,3R)-3-Methyl-2-(((6-(trifluoromethyl)pyridazin-3-yl)amino)methyl)piperidin-1-yl)(6-methyl-3-(2H-1,2,3-triazol-2-yl)pyridin-2-yl)methanone

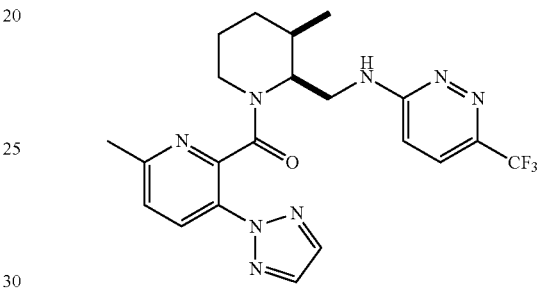

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 3-chloro-6-(trifluoromethyl)pyridazine. ESI-MS (m/z): 461 [M+1]⁺.

Example A177

((2S,3R)-2-(((5-Chloropyrimidin-2-yl)amino)methyl)-3-methylpiperidin-1-yl)(6-methyl-3-(2H-1,2,3-triazol-2-yl)pyridin-2-yl)methanone

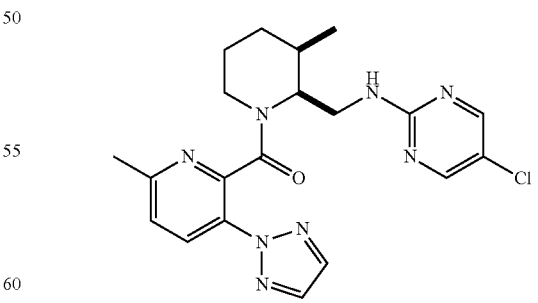

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 2,5-dichloropyrimidine. ESI-MS (m/z): 427 [M+1]⁺.

Example A178

((2S,3R)-2-(((5-Chloropyridin-2-yl)amino)methyl)-3-methylpiperidin-1-yl)(6-methyl-3-(2H-1,2,3-triazol-2-yl)pyridin-2-yl)methanone

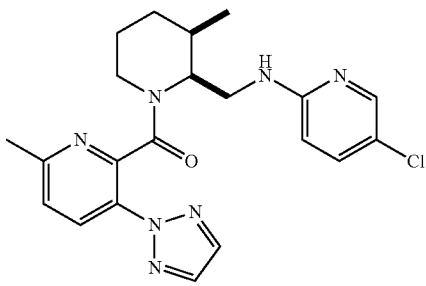 [SMILES: Cc1ccc(-n2nccn2)c(C(=O)N2CCC[C@@H](C)[C@H]2CNc2ccc(Cl)cn2)n1]

The title compound was prepared following the same general protocol as described for Example A44 using ((2S,3R)-2-(aminomethyl)-3-methylpiperidin-1-yl)(6-methyl-3-(2H-1,2,3-triazol-2-yl)pyridin-2-yl)methanone and 2-bromo-5-chloropyridine. ESI-MS (m/z): 426 [M+1]$^+$.

Example A179

((2S,3R)-2-(((5-Fluoropyrimidin-2-yl)amino)methyl)-3-methylpiperidin-1-yl)(5-methyl-2-(pyridin-2-yl)phenyl)methanone

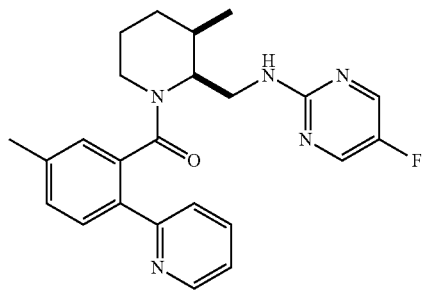 [SMILES: Cc1ccc(-c2ccccn2)c(C(=O)N2CCC[C@@H](C)[C@H]2CNc2ncc(F)cn2)c1]

The title compound was prepared following the same general protocol as described for Example A1, using ((2S,3R)-2-(aminomethyl)-3-methylpiperidin-1-yl)(5-methyl-2-(pyridin-2-yl)phenyl)methanone and 2-chloro-5-fluoropyrimidine. ESI-MS (m/z): 420 [M+1]$^+$.

Example A180

((2S,3R)-2-((Benzo[d]oxazol-2-ylamino)methyl)-3-methylpiperidin-1-yl)(5-methyl-2-(2H-1,2,3-triazol-2-yl)phenyl)methanone

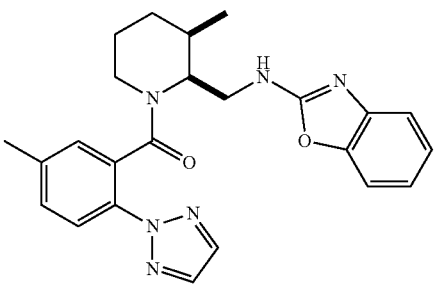 [SMILES: Cc1ccc(-n2nccn2)c(C(=O)N2CCC[C@@H](C)[C@H]2CNc2nc3ccccc3o2)c1]

The title compound was prepared following the same general protocol as described for Example A1 using ((2S,3R)-2-((benzo[d]oxazol-2-ylamino)methyl)-3-methylpiperidin-1-yl)(5-methyl-2-(2H-1,2,3-triazol-2-yl)phenyl)methanone. MS (ESI) 431 (M+H).

Example A181

((2S,3R)-2-(((5-Chloro-3-fluoropyridin-2-yl)amino)methyl)-3-methylpiperidin-1-yl)(5-methyl-2-(pyrimidin-2-yl)phenyl)methanone

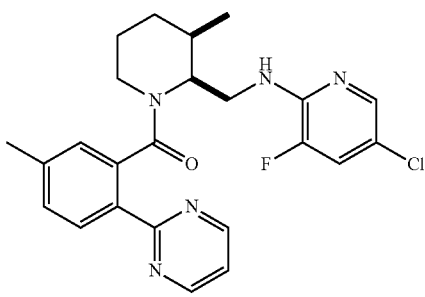 [SMILES: Cc1ccc(-c2ncccn2)c(C(=O)N2CCC[C@@H](C)[C@H]2CNc2ncc(Cl)cc2F)c1]

The title compound was prepared following the same general protocol as described for Example A44 using ((2S,3R)-2-(aminomethyl)-3-methylpiperidin-1-yl)(5-methyl-2-(pyrimidin-2-yl)phenyl)methanone and 2-bromo-5-chloro-3-fluoropyridine. MS (ESI) 454 (M+H).

Example A182

((2S,3R)-2-(((3,5-Difluoropyridin-2-yl)amino)methyl)-3-methylpiperidin-1-yl)(5-methyl-2-(pyrimidin-2-yl)phenyl)methanone

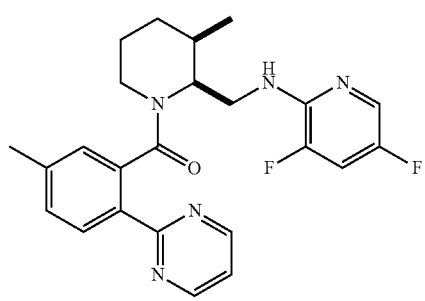 [SMILES: Cc1ccc(-c2ncccn2)c(C(=O)N2CCC[C@@H](C)[C@H]2CNc2ncc(F)cc2F)c1]

The title compound was prepared following the same general protocol as described for Example A44 using ((2S,3R)-2-(aminomethyl)-3-methylpiperidin-1-yl)(5-methyl-2-(pyrimidin-2-yl)phenyl)methanone and 2-bromo-3,5-difluoropyridine. MS (ESI) 438 (M+H).

Example A183

((2S,3R)-3-Methyl-2-(((5-(trifluoromethyl)pyridin-2-yl)amino)methyl)piperidin-1-yl)(6-methyl-3-(pyrimidin-2-yl)pyridin-2-yl)methanone

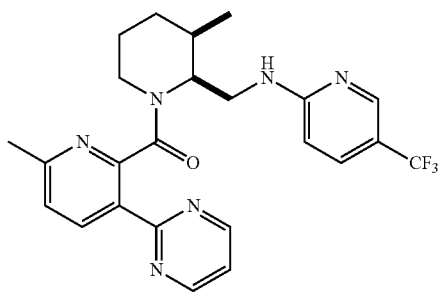

Step 1. 2-(((2S,3R)-1-(3-Bromo-6-methylpicolinoyl)-3-methylpiperidin-2-yl)methyl)isoindoline-1,3-dione

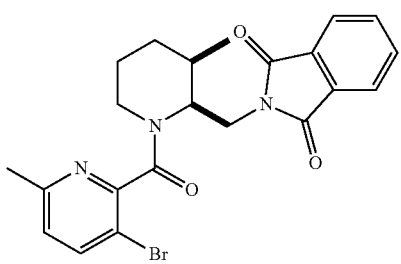 [SMILES: Cc1ccc(Br)c(C(=O)N2CCC[C@@H](C)[C@H]2CN2C(=O)c3ccccc3C2=O)n1]

The title compound was prepared following the same general protocol as described for 2-(((2S,3R)-3-methyl-1-(5-methyl-2-(1-methyl-1H-pyrazol-4-yl)benzoyl)piperidin-2-yl)methyl)isoindoline-1,3-dione in Example A1, using 3-bromo-6-methylpicolinic acid. ESI-MS (m/z): 456, 458 [M]+[M+2]+.

Step 2. 2-(((2S,3R)-3-Methyl-1-(6-methyl-3-(pyrimidin-2-yl)picolinoyl)piperidin-2-yl)methyl)isoindoline-1,3-dione

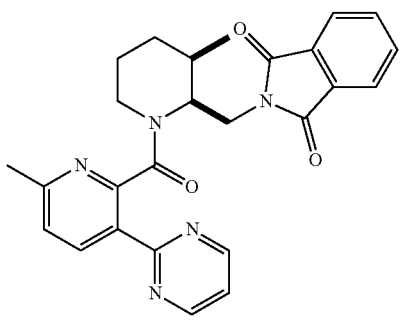 [SMILES: Cc1ccc(-c2ncccn2)c(C(=O)N2CCC[C@@H](C)[C@H]2CN2C(=O)c3ccccc3C2=O)n1]

The title compound was prepared following the same general protocol as described for methyl 5-methyl-2-(pyridin-2-yl)benzoate in Example A9, using 2-(((2S,3R)-1-(3-bromo-6-methylpicolinoyl)-3-methylpiperidin-2-yl)methyl)isoindoline-1,3-dione and 2-(tributylstannyl)pyrimidine. ESI-MS (m/z): 456, [M+1]+.

Step 3. ((2S,3R)-2-(Aminomethyl)-3-methylpiperidin-1-yl)(6-methyl-3-(pyrimidin-2-yl)pyridin-2-yl)methanone

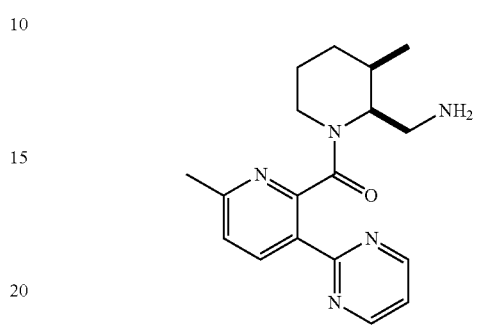

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1, using 2-(((2S,3R)-3-methyl-1-(6-methyl-3-(pyrimidin-2-yl)picolinoyl)piperidin-2-yl)methyl)isoindoline-1,3-dione. ESI-MS (m/z): 326 [M+1]+.

Step 4. ((2S,3R)-3-Methyl-2-(((5-(trifluoromethyl)pyridin-2-yl)amino)methyl)piperidin-1-yl)(6-methyl-3-(pyrimidin-2-yl)pyridin-2-yl)methanone The title compound was prepared following the same general protocol as described for Example A1, using ((2S,3R)-2-(aminomethyl)-3-methylpiperidin-1-yl)(6-methyl-3-(pyrimidin-2-yl)pyridin-2-yl)methanone and 2-fluoro-5-trifluoromethylpyridine. ESI-MS (m/z): 471 [M+1]+.

Example A184

((2S,3R)-3-Methyl-2-(((5-(trifluoromethyl)pyrimidin-2-yl)amino)methyl)piperidin-1-yl)(6-methyl-3-(pyrimidin-2-yl)pyridin-2-yl)methanone

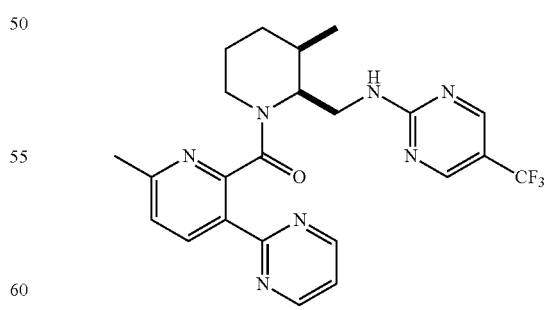

The title compound was prepared following the same general protocol as described for Example A1, using ((2S,3R)-2-(aminomethyl)-3-methylpiperidin-1-yl)(6-methyl-3-(pyrimidin-2-yl)pyridin-2-yl)methanone and 2-chloro-5-trifluoromethylpyrimidine. ESI-MS (m/z): 472 [M+1]+.

Example A185

((2S,3R)-3-Methyl-2-(((6-(trifluoromethyl)
pyridazin-3-yl)amino)methyl)piperidin-1-yl)(6-
methyl-3-(pyrimidin-2-yl)pyridin-2-yl)methanone

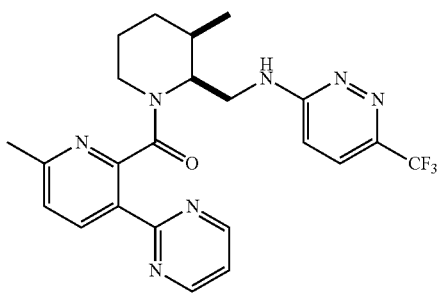

The title compound was prepared following the same general protocol as described for Example A1, using ((2S,3R)-2-(aminomethyl)-3-methylpiperidin-1-yl)(6-methyl-3-(pyrimidin-2-yl)pyridin-2-yl)methanone and 3-chloro-6-(trifluoromethyl)pyridazine. ESI-MS (m/z): 472 [M+1]⁺.

Example A186

((2S,3R)-2-(((5-chloropyridin-2-yl)amino)methyl)-3-
methylpiperidin-1-yl)(6-methyl-3-(pyrimidin-2-yl)
pyridin-2-yl)methanone

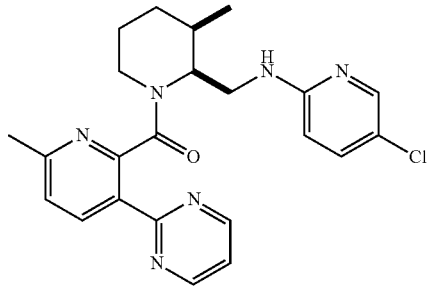 [SMILES: Cc1ccc(-c2ncccn2)c(C(=O)N2CCC[C@@H](C)[C@H]2CNc2ccc(Cl)cn2)n1]

The title compound was prepared following the same general protocol as described for Example A44 using ((2S,3R)-2-(aminomethyl)-3-methylpiperidin-1-yl) (6-methyl-3-(pyrimidin-2-yl)pyridin-2-yl)methanone and 2-bromo-5-chloropyridine. ESI-MS (m/z): 437 [M+1]⁺.

Example A187

((2S,3R)-3-Methyl-2-(((5-(trifluoromethyl)-1,3,4-
thiadiazol-2-yl)amino)methyl)piperidin-1-yl)(6-
methyl-3-(pyrimidin-2-yl)pyridin-2-yl)methanone

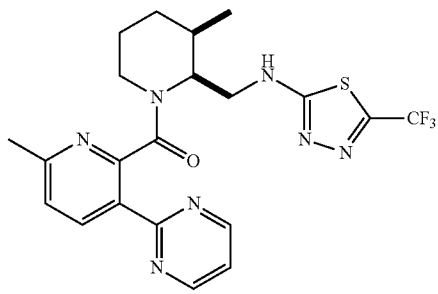 [SMILES: Cc1ccc(-c2ncccn2)c(C(=O)N2CCC[C@@H](C)[C@H]2CNc2nnc(C(F)(F)F)s2)n1]

The title compound was prepared following the same general protocol as described for Example A102 using ((2S,3R)-2-(aminomethyl)-3-methylpiperidin-1-yl)(6-methyl-3-(pyrimidin-2-yl)pyridin-2-yl)methanone. ESI-MS (m/z): 478 [M+1]⁺.

Example A188

((2S,3R)-2-(((3-Fluoro-5-(trifluoromethyl)pyridin-2-
yl)amino)methyl)-3-methylpiperidin-1-yl)(6-methyl-
3-(2H-1,2,3-triazol-2-yl)pyridin-2-yl)methanone

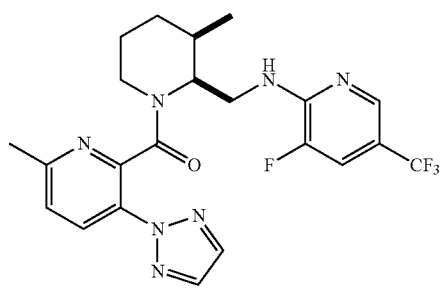 [SMILES: Cc1ccc(-n2nccn2)c(C(=O)N2CCC[C@@H](C)[C@H]2CNc2ncc(C(F)(F)F)cc2F)n1]

The title compound was prepared following the same general protocol as described for Example A44 using ((2S,3R)-2-(aminomethyl)-3-methylpiperidin-1-yl)(6-methyl-3-(2H-1,2,3-triazol-2-yl)pyridin-2-yl)methanone and 2-bromo-3-fluoro-5-(trifluoromethyl)pyridine. ESI-MS (m/z): 478 [M+1]⁺.

Example A189

6-((((2S,3R)-3-Methyl-1-(6-methyl-3-(2H-1,2,3-
triazol-2-yl)picolinoyl)piperidin-2-yl)methyl)amino)
nicotinonitrile

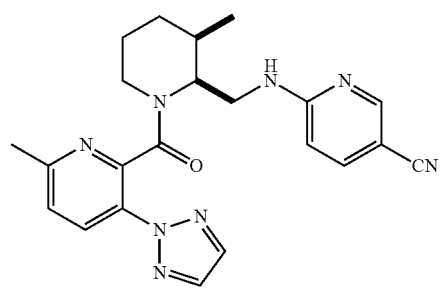 [SMILES: Cc1ccc(-n2nccn2)c(C(=O)N2CCC[C@@H](C)[C@H]2CNc2ccc(C#N)cn2)n1]

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 6-chloronicotinonitrile. ESI-MS (m/z): 417 [M+1]⁺.

Example A190

2-((((2S,3R)-3-Methyl-1-(6-methyl-3-(2H-1,2,3-triazol-2-yl)picolinoyl)piperidin-2-yl)methyl)amino)pyrimidine-5-carbonitrile

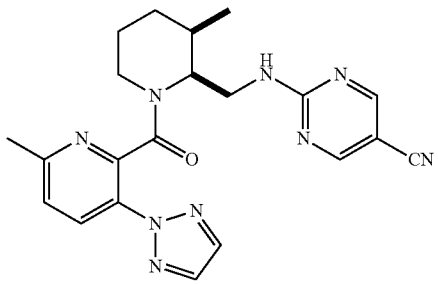

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 2-chloropyrimidine-5-carbonitrile. ESI-MS (m/z): 418 [M+1]⁺.

Example A191

((2S,3R)-3-Methyl-2-(((5-(trifluoromethyl)-1,3,4-thiadiazol-2-yl)amino)methyl)piperidin-1-yl)(6-methyl-3-(2H-1,2,3-triazol-2-yl)pyridin-2-yl)methanone

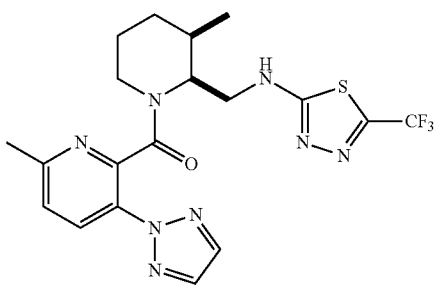 [SMILES: Cc1ccc(-n2nccn2)c(C(=O)N2CCC[C@@H](C)[C@H]2CNc2nnc(C(F)(F)F)s2)n1]

The title compound was prepared following the same general protocol as described for Example A102 using ((2S,3R)-2-(aminomethyl)-3-methylpiperidin-1-yl)(6-methyl-3-(2H-1,2,3-triazol-2-yl)pyridin-2-yl)methanone. ESI-MS (m/z): 467 [M+1]⁺.

Example A192

((2S,3R)-2-(((5-Chloro-3-fluoropyridin-2-yl)amino)methyl)-3-methylpiperidin-1-yl)(6-methyl-3-(2H-1,2,3-triazol-2-yl)pyridin-2-yl)methanone

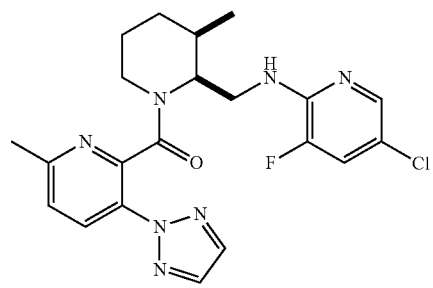 [SMILES: Cc1ccc(-n2nccn2)c(C(=O)N2CCC[C@@H](C)[C@H]2CNc2ncc(Cl)cc2F)n1]

The title compound was prepared following the same general protocol as described for Example A44 using ((2S,3R)-2-(aminomethyl)-3-methylpiperidin-1-yl)(6-methyl-3-(2H-1,2,3-triazol-2-yl)pyridin-2-yl)methanone and 2-bromo-3-fluoro-5-chloropyridine. ESI-MS (m/z): 444 [M+1]⁺.

Example A193

5-Fluoro-6-((((2S,3R)-3-methyl-1-(6-methyl-3-(2H-1,2,3-triazol-2-yl)picolinoyl)piperidin-2-yl)methyl)amino)nicotinonitrile

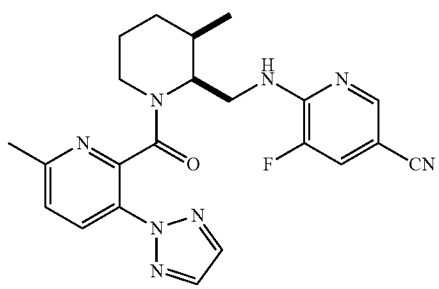

The title compound was prepared following the same general protocol as described for Example A1, using ((2S,3R)-2-(aminomethyl)-3-methylpiperidin-1-yl)(6-methyl-3-(2H-1,2,3-triazol-2-yl)pyridin-2-yl)methanone and 6-chloro-5-fluoronicotinonitrile. ESI-MS (m/z): 435 [M+1]⁺.

Example A194

((2S,3R)-3-Methyl-2-((methyl(5-(trifluoromethyl)pyridin-2-yl)amino)methyl)piperidin-1-yl)(6-methyl-3-(2H-1,2,3-triazol-2-yl)pyridin-2-yl)methanone

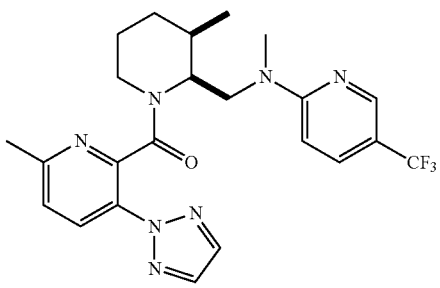 [SMILES: Cc1ccc(-n2nccn2)c(C(=O)N2CCC[C@@H](C)[C@H]2CN(C)c2ccc(C(F)(F)F)cn2)n1]

To a solution of ((2S,3R)-3-methyl-2-(((5-(trifluoromethyl)pyridin-2-yl)amino)methyl)piperidin-1-yl)(6-methyl-3-(2H-1,2,3-triazol-2-yl)pyridin-2-yl)methanone (0.0215 g, 0.047 mmol) in DMF (0.5 mL) at room temperature was added NaH (60%, 0.006 g, 0.141 mmol). The mixture was stirred at rt for 1 h, then MeI (0.013 g, 0.094 mmol) was added. The reaction was stirred at rt for another 1 h. The crude was purified via preparative-HPLC to obtain the title compound. ESI-MS (m/z): 474 [M+1]⁺.

Example A195

((2S,3R)-2-(((5-Chlorobenzo[d]oxazol-2-yl)amino)methyl)-3-methylpiperidin-1-yl)(6-methyl-3-(2H-1,2,3-triazol-2-yl)pyridin-2-yl)methanone

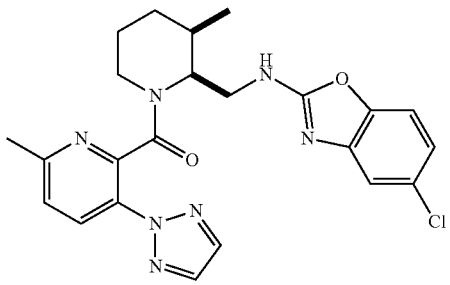 [SMILES: Cc1ccc(-n2nccn2)c(C(=O)N2CCC[C@@H](C)[C@H]2CNc2nc3cc(Cl)ccc3o2)n1]

The title compound was synthesized following the same general protocol as described for (2S,3R)-allyl 2-(((5-chlorobenzo[d]oxazol-2-yl)amino)methyl)-3-methylpiperidine-1-carboxylate in Example A27, using ((2S,3R)-2-(aminomethyl)-3-methylpiperidin-1-yl)(6-methyl-3-(2H-1,2,3-triazol-2-yl)pyridin-2-yl)methanone. ESI-MS (m/z): 466 [M+1]⁺.

Example A196

((2S,3R)-3-Methyl-2-(((5-methylpyridin-2-yl)amino)methyl)piperidin-1-yl)(6-methyl-3-(2H-1,2,3-triazol-2-yl)pyridin-2-yl)methanone

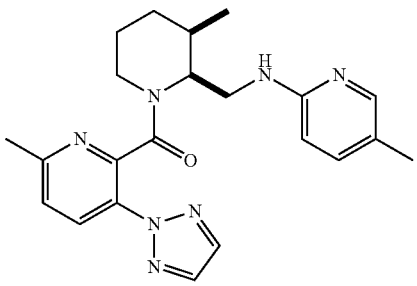

The title compound was prepared following the same general protocol as described for Example A44 using ((2S,3R)-2-(aminomethyl)-3-methylpiperidin-1-yl)(6-methyl-3-(2H-1,2,3-triazol-2-yl)pyridin-2-yl)methanone and 2-bromo-5-methylpyridine. ESI-MS (m/z): 406 [M+1]⁺.

Example A197

((2S,3R)-3-methyl-2-(((5-(trifluoromethyl)pyridin-2-yl)amino)methyl)piperidin-1-yl)(5-methyl-2-(pyridazin-3-yl)phenyl)methanone

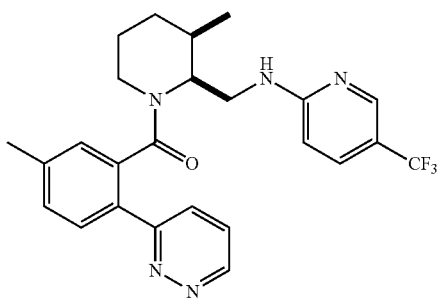 [SMILES: Cc1ccc(-c2cccnn2)c(C(=O)N2CCC[C@@H](C)[C@H]2CNc2ccc(C(F)(F)F)cn2)c1]

Step 1. 5-Methyl-2-(pyridazin-3-yl)benzoic acid

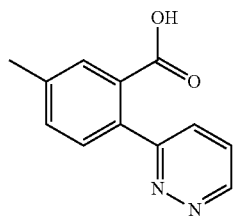 [SMILES: Cc1ccc(-c2cccnn2)c(C(=O)O)c1]

The title compound was prepared following the same general protocol as described for 5-methyl-2-(pyrazin-2-yl)benzoic acid in Example A19, starting with 3-bromopyridazine. ESI-MS (m/z): 215 [M+1]⁺.

Step 2. 2-(((2S,3R)-3-Methyl-1-(5-methyl-2-(pyridazin-3-yl)benzoyl)piperidin-2-yl)methyl)isoindoline-1,3-dione

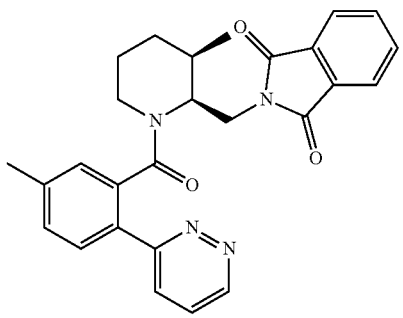 [SMILES: Cc1ccc(-c2cccnn2)c(C(=O)N2CCC[C@@H](C)[C@H]2CN2C(=O)c3ccccc3C2=O)c1]

To a mixture of 2-(((2S,3R)-3-methylpiperidin-2-yl)methyl)isoindoline-1,3-dione (1.09 g, 4.20 mmol), 5-methyl-2-(pyridazin-3-yl)benzoic acid (0.75 g, 3.5 mmol) and DIEA (1.8 mL, 10.5 mmol) in DCM (20 mL) was added propylphosphonic anhydride (T3P) (50% in EtOAc, 4.2 mL, 7.0 mmol). The mixture was heated at 40° C. for 16 h. The mixture was cooled to room temperature and diluted with DCM. The mixture was washed with sat'd NaHCO₃, brine, and dried (MgSO₄). The solvent was removed in vacuo. The crude was purified by chromatography on silica gel (EtOAc/hexanes) to afford the title compound. ESI-MS (m/z): 455 [M+1]⁺.

Step 3. ((2S,3R)-2-(Aminomethyl)-3-methylpiperidin-1-yl)(5-methyl-2-(pyridazin-3-yl)phenyl)methanone

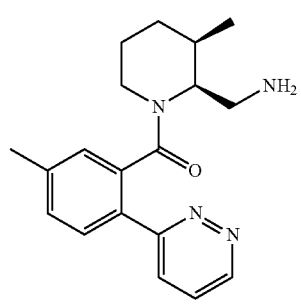 [SMILES: Cc1ccc(-c2cccnn2)c(C(=O)N2CCC[C@@H](C)[C@H]2CN)c1]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, using 2-(((2S,3R)-3-methyl-1-(5-methyl-2-(pyridazin-3-yl)benzoyl)piperidin-2-yl)methyl)isoindoline-1,3-dione. ESI-MS (m/z): 325 [M+1]⁺.

Step 4. ((2S,3R)-3-Methyl-2-(((5-(trifluoromethyl)pyridin-2-yl)amino)methyl)piperidin-1-yl)(5-methyl-2-(pyridazin-3-yl)phenyl)methanone The title compound was prepared following the same general protocol as described for Example A1, using ((2S,3R)-2-(aminomethyl)-3-methylpiperidin-1-yl)(5-methyl-2-(pyridazin-3-yl)phenyl)methanone and 2-fluoro-5-trifluoromethylpyridine. ESI-MS (m/z): 470 [M+1]⁺.

Example A198

((2S,3R)-3-Methyl-2-(((5-(trifluoromethyl)pyrimidin-2-yl)amino)methyl)piperidin-1-yl)(5-methyl-2-(pyridazin-3-yl)phenyl)methanone

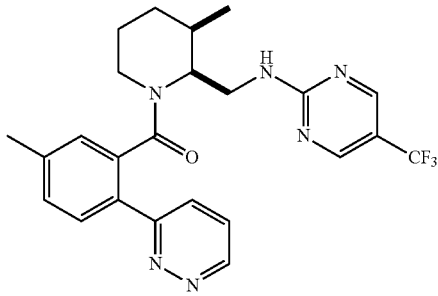

The title compound was prepared following the same general protocol as described for Example A1, using ((2S,3R)-2-(aminomethyl)-3-methylpiperidin-1-yl)(5-methyl-2-(pyridazin-3-yl)phenyl)methanone and 2-chloro-5-(trifluoromethyl)pyrimidine. ESI-MS (m/z): 471 [M+1]⁺.

Example A199

((2S,3R)-2-(((5-Chlorobenzo[d]oxazol-2-yl)amino)methyl)-3-methylpiperidin-1-yl)(6'-methyl-[2,3'-bipyridin]-2'-yl)methanone

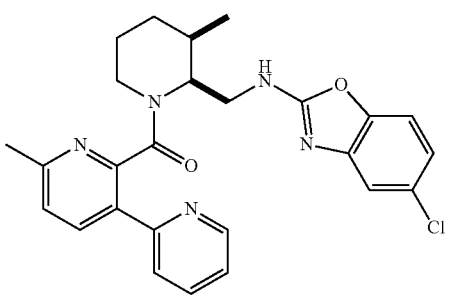 [SMILES: Cc1ccc(-c2ccccn2)c(C(=O)N2CCC[C@@H](C)[C@H]2CNc2nc3cc(Cl)ccc3o2)n1]

The title compound was prepared following the same general protocol as described for Example A2 using ((2S,3R)-2-(aminomethyl)-3-methylpiperidin-1-yl)(6'-methyl-[2,3'-bipyridin]-2'-yl)methanone and 2,5-dichlorobenzoxazole. MS (ESI) 476 (M+H).

Example A200

(5-Chloro-2-(pyrimidin-2-yl)phenyl)((2S,3R)-3-methyl-2-(((6-(trifluoromethyl)pyridazin-3-yl)amino)methyl)piperidin-1-yl)methanone

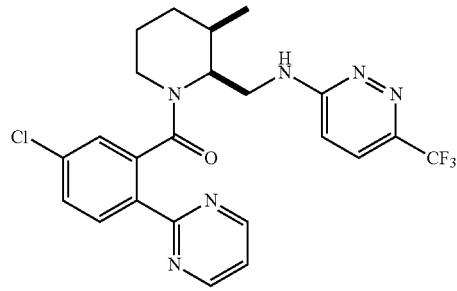 [SMILES: C[C@@H]1CCCN(C(=O)c2cc(Cl)ccc2-c2ncccn2)[C@@H]1CNc1ccc(C(F)(F)F)nn1]

Step 1. 2-(((2S,3R)-1-(5-Chloro-2-iodobenzoyl)-3-methylpiperidin-2-yl)methyl)isoindoline-1,3-dione

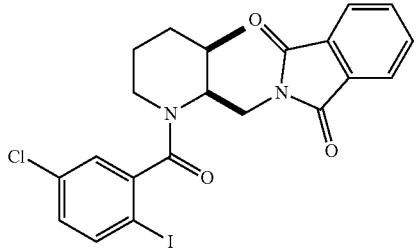 [SMILES: C[C@@H]1CCCN(C(=O)c2cc(Cl)ccc2I)[C@@H]1CN1C(=O)c2ccccc2C1=O]

A mixture of 2-(((2S,3R)-3-methylpiperidin-2-yl)methyl)isoindoline-1,3-dione (0.70 g, 2.71 mmol), 5-chloro-2-iodobenzoic acid (0.66 g, 2.32 mmol), diisopropylethylamine (1.21 mL, 6.97 mmol) and HATU (1.06 g, 2.79 mmol) in DMF (5 ml) was stirred at room temperature for 1 h. The reaction mixture was diluted with ethyl acetate and washed with sat'd NaHCO₃ and brine successively. The organic layer was separated, dried with MgSO₄ and concentrated in vacuo. The crude product was purified by chromatography on silica gel (EtOAc/hex) to afford the title compound. MS (ESI) 523 (M+H).

Step 2. 2-(((2S,3R)-1-(5-Chloro-2-(pyrimidin-2-yl)benzoyl)-3-methylpiperidin-2-yl)methyl)isoindoline-1,3-dione

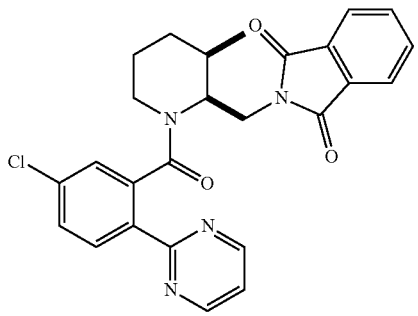 [SMILES: C[C@@H]1CCCN(C(=O)c2cc(Cl)ccc2-c2ncccn2)[C@@H]1CN1C(=O)c2ccccc2C1=O]

A mixture of 2-(((2S,3R)-1-(5-chloro-2-iodobenzoyl)-3-methylpiperidin-2-yl)methyl)isoindoline-1,3-dione (0.22 g, 0.42 mmol), 2-(tributylstannyl)pyrimidine (0.16 ml, 0.51 mmol), cesium fluoride (128 mg, 0.84 mmol), CuI (16 mg, 0.08 mmol) and Pd(PPh₃)₄ (49 mg, 0.04 mmol) in DMF (5 mL) was degassed and heated at 120° C. for 1 h in a microwave reactor. The solvent was removed in vacuo to obtain the crude which was purified by silica gel chromatography (0~100% Hexane/EtOAc) to yield the title compound as a white solid (0.134 g, 67%). MS (ESI) 475 (M+H).

Step 3. ((2S,3R)-2-(Aminomethyl)-3-methylpiperidin-1-yl)(5-chloro-2-(pyrimidin-2-yl)phenyl)methanone

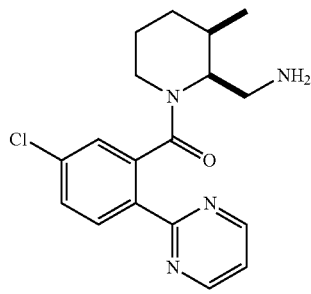 [SMILES: C[C@@H]1CCCN(C(=O)c2cc(Cl)ccc2-c2ncccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(((2S,3R)-1-(5-chloro-2-(pyrimidin-2-yl)benzoyl)-3-methylpiperidin-2-yl)methyl)isoindoline-1,3-dione. MS (ESI) 345 (M+H).

Step 4. (5-Chloro-2-(pyrimidin-2-yl)phenyl)((2S,3R)-3-methyl-2-(((6-(trifluoromethyl)pyridazin-3-yl)amino)methyl)piperidin-1-yl)methanone The title compound was prepared following the same general protocol as described for Example A45 using ((2S,3R)-2-(aminomethyl)-3-methylpiperidin-1-yl)(5-chloro-2-(pyrimidin-2-yl)phenyl)methanone and 3-chloro-6-(trifluoromethyl)pyridazine. MS (ESI) 491 (M+H).

Example A201

(5-Chloro-2-(pyrimidin-2-yl)phenyl)((2S,3R)-3-methyl-2-(((5-(trifluoromethyl)pyrimidin-2-yl)amino)methyl)piperidin-1-yl)methanone

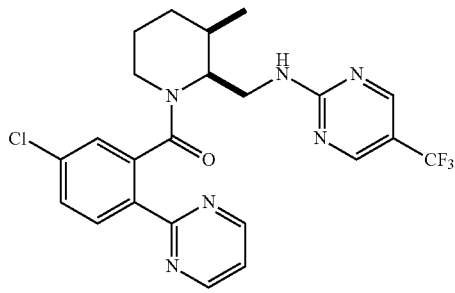 [SMILES: C[C@@H]1CCCN(C(=O)c2cc(Cl)ccc2-c2ncccn2)[C@@H]1CNc1ncc(C(F)(F)F)cn1]

The title compound was prepared following the same general protocol as described for Example A45 using ((2S,3R)-2-(aminomethyl)-3-methylpiperidin-1-yl)(5-chloro-2-(pyrimidin-2-yl)phenyl)methanone and 2-chloro-5-(trifluoromethyl)pyrimidine. MS (ESI) 491 (M+H).

Example A202

(5-Chloro-2-(pyrimidin-2-yl)phenyl)((2S,3R)-2-(((5-chloropyrimidin-2-yl)amino)methyl)-3-methylpiperidin-1-yl)methanone

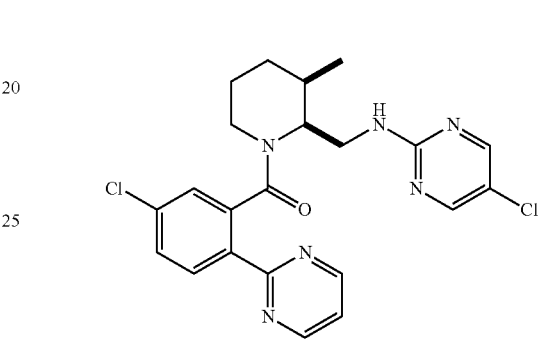

The title compound was prepared following the same general protocol as described for Example A45 using ((2S,3R)-2-(aminomethyl)-3-methylpiperidin-1-yl)(5-chloro-2-(pyrimidin-2-yl)phenyl)methanone and 2,5-dichloropyrimidine. MS (ESI) 457 (M+H).

Example A203

(5-Chloro-2-(pyrimidin-2-yl)phenyl)((2S,3R)-2-(((5-chloropyridin-2-yl)amino)methyl)-3-methylpiperidin-1-yl)methanone

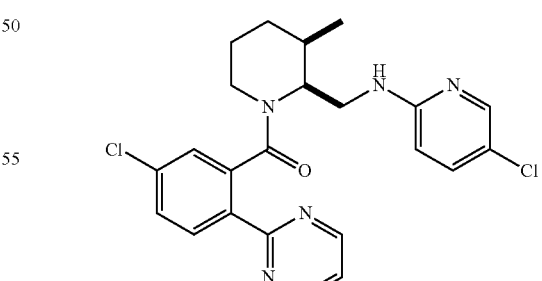

The title compound was prepared following the same general protocol as described for Example A44 using ((2S,3R)-2-(aminomethyl)-3-methylpiperidin-1-yl)(5-chloro-2-(pyrimidin-2-yl)phenyl)methanone and 2-bromo-5-chloropyridine. MS (ESI) 456 (M+H).

Example A204

((2S,3R)-2-((Benzo[d]oxazol-2-ylamino)methyl)-3-methylpiperidin-1-yl)(5-methyl-2-(pyrimidin-2-yl)phenyl)methanone

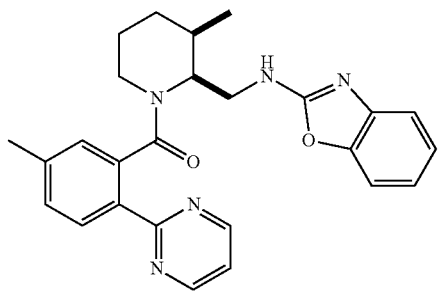 [SMILES: Cc1ccc(-c2ncccn2)c(C(=O)N2CCC[C@@H](C)[C@H]2CNc2nc3ccccc3o2)c1]

The title compound was prepared following the same general protocol as described for Example A2 using ((2S,3R)-2-(aminomethyl)-3-methylpiperidin-1-yl)(5-methyl-2-(pyrimidin-2-yl)phenyl)methanone and 2-chlorobenzoxazole. MS (ESI) 442 (M+H).

Example A205

((2S,3R)-2-(((5-Chlorobenzo[d]oxazol-2-yl)amino)methyl)-3-methylpiperidin-1-yl)(5-methyl-2-(pyrimidin-2-yl)phenyl)methanone

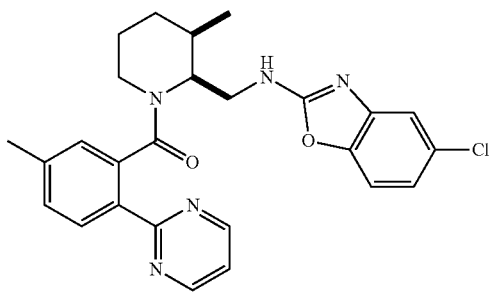 [SMILES: Cc1ccc(-c2ncccn2)c(C(=O)N2CCC[C@@H](C)[C@H]2CNc2nc3cc(Cl)ccc3o2)c1]

The title compound was prepared following the same general protocol as described for Example A2 using ((2S,3R)-2-(aminomethyl)-3-methylpiperidin-1-yl)(5-methyl-2-(pyrimidin-2-yl)phenyl)methanone and 2,6-dichlorobenzoxazole. MS (ESI) 476 (M+H).

Example A206

((2S,3R)-2-(((5-Fluorobenzo[d]oxazol-2-yl)amino)methyl)-3-methylpiperidin-1-yl)(5-methyl-2-(pyrimidin-2-yl)phenyl)methanone

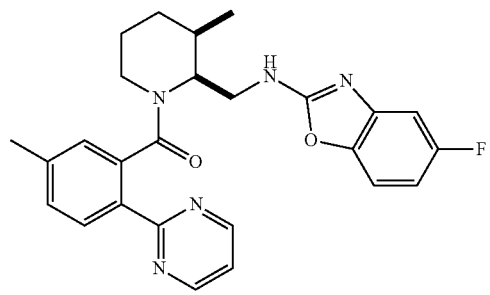 [SMILES: Cc1ccc(-c2ncccn2)c(C(=O)N2CCC[C@@H](C)[C@H]2CNc2nc3cc(F)ccc3o2)c1]

The title compound was prepared following the same general protocol as described for Example A2 using ((2S,3R)-2-(aminomethyl)-3-methylpiperidin-1-yl)(5-methyl-2-(pyrimidin-2-yl)phenyl)methanone and 2-chloro-5-fluorobenzo[d]oxazole. MS (ESI) 460 (M+H).

Example A207

(5-Fluoro-2-(2H-1,2,3-triazol-2-yl)phenyl)((2S,3R)-3-methyl-2-(((5-(trifluoromethyl)pyrimidin-2-yl)amino)methyl)piperidin-1-yl)methanone

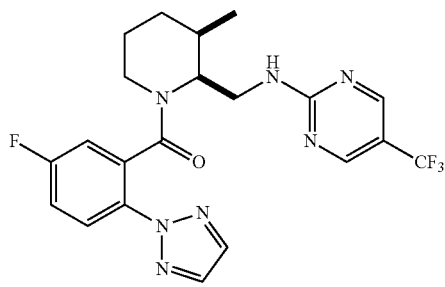

Step 1. 5-Fluoro-2-(2H-1,2,3-triazol-2-yl)benzoic acid

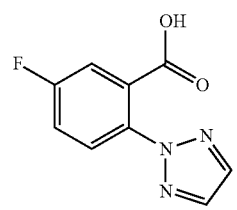 [SMILES: O=C(O)c1cc(F)ccc1-n1nccn1]

The title compound was prepared following the same general protocol as described for 5-methyl-2-(2H-1,2,3-triazol-2-yl)benzoic acid in Example A11 using 2-bromo-5-fluorobenzoic acid. MS (ESI) 208 (M+H).

Step 2. ((2S,3R)-2-(Aminomethyl)-3-methylpiperidin-1-yl)(5-fluoro-2-(2H-1,2,3-triazol-2-yl)phenyl)methanone

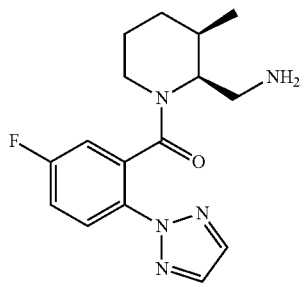 [SMILES: C[C@@H]1CCCN(C(=O)c2cc(F)ccc2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H- pyrazol-4-yl)phenyl)methanone in Example A1 using 5-fluoro-2-(2H-1,2,3-triazol-2-yl)benzoic acid. MS (ESI) 318 (M+H).

Step 3. (5-Fluoro-2-(2H-1,2,3-triazol-2-yl)phenyl) ((2S,3R)-3-methyl-2-(((5-(trifluoromethyl)pyrimidin-2-yl)amino)methyl)piperidin-1-yl)methanone The title compound was prepared following the same general protocol as described for Example A45 using ((2S,3R)-2-(aminomethyl)-3-methylpiperidin-1-yl)(5-fluoro-2-(2H-1,2,3-triazol-2-yl)phenyl)methanone and 2-chloro-5-(trifluoromethyl)pyrimidine. MS (ESI) 464 (M+H).

Example A208

(5-Fluoro-2-(2H-1,2,3-triazol-2-yl)phenyl)((2S,3R)-3-methyl-2-(((6-(trifluoromethyl)pyridazin-3-yl)amino)methyl)piperidin-1-yl)methanone

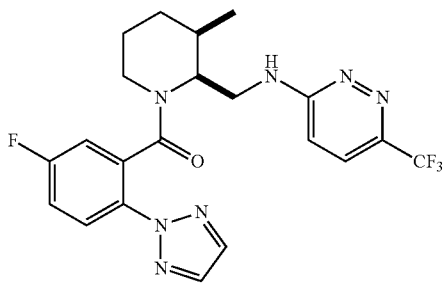

The title compound was prepared following the same general protocol as described for Example A45 using ((2S,3R)-2-(aminomethyl)-3-methylpiperidin-1-yl)(5-fluoro-2-(2H-1,2,3-triazol-2-yl)phenyl)methanone and 3-chloro-6-(trifluoromethyl)pyridazine. MS (ESI) 464 (M+H).

Example A209

((2S,3R)-2-(((5-Chloropyridin-2-yl)amino)methyl)-3-methylpiperidin-1-yl)(5-fluoro-2-(2H-1,2,3-triazol-2-yl)phenyl)methanone

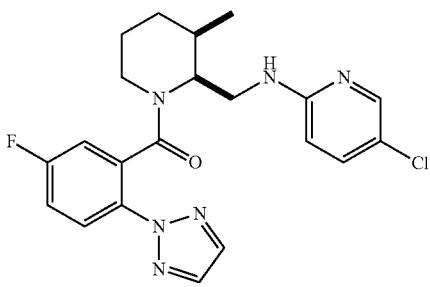

The title compound was prepared following the same general protocol as described for Example A44 using ((2S,3R)-2-(aminomethyl)-3-methylpiperidin-1-yl)(5-fluoro-2-(2H-1,2,3-triazol-2-yl)phenyl)methanone and 2-bromo-5-chloropyridine. MS (ESI) 429 (M+H).

Example A210

(S)-(2-(((5-Chloropyridin-2-yl)amino)methyl)-4,4-difluoropiperidin-1-yl)(5-methyl-2-(2H-1,2,3-triazol-2-yl)phenyl)methanone

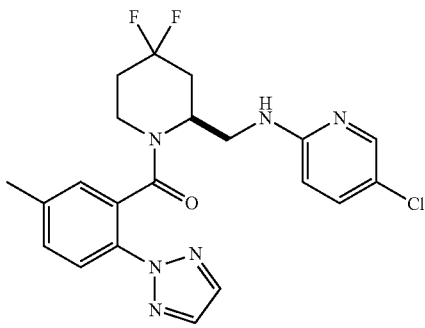 [SMILES: Cc1ccc(-n2nccn2)c(C(=O)N2CCC(F)(F)C[C@H]2CNc2ccc(Cl)cn2)c1]

Step 1. Methyl 4-hydroxy-1-((S)-1-phenylethyl)piperidine-2-carboxylate

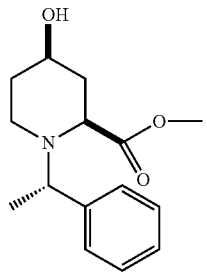 [SMILES: COC(=O)[C@@H]1C[C@H](O)CCN1[C@@H](C)c1ccccc1]

The title compound was prepared from (R)-(+)-α-methylbenzylamine, 4-bromo-1-butene, and Et₃N in CH₃CN using a procedure by Sidles et al. (*Bioorg. Med. Chem. Lett.* 1996, 6(8), 963). MS (ESI) 264 (M+H).

Step 2. Methyl 4-oxo-1-((S)-1-phenylethyl)piperidine-2-carboxylate

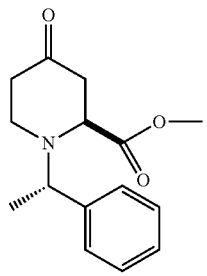 [SMILES: COC(=O)[C@@H]1CC(=O)CCN1[C@@H](C)c1ccccc1]

Methyl 4-hydroxy-1-((S)-1-phenylethyl)piperidine-2-carboxylate (3.4 g, 12.9 mmol), N-methylmorpholine N-oxide (3.0 g, 25.82 mmol) and 4 Å molecular sieves were stirred together in 15 ml of DCM at room temperature under argon. Tetra-n-propylammonium perruthenate (454 mg, 1.29 mmol) was then added slowly and reaction stirred for 5 h. The reaction was then filtered through silica and washed with 10% methanol in DCM and concentrated to give the title compound as a clear oil (3.34 g, 99%). MS (ESI) 262 (M+H).

Step 3. Methyl 4,4-difluoro-1-((S)-1-phenylethyl)piperidine-2-carboxylate

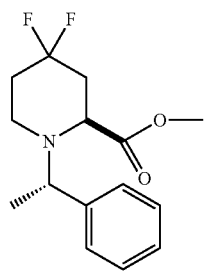 [SMILES: COC(=O)[C@@H]1CC(F)(F)CCN1[C@@H](C)c1ccccc1]

Methyl 4-oxo-1-((S)-1-phenylethyl)piperidine-2-carboxylate (3.0 g, 11.5 mmol) was dissolved in 10 ml DCM and cooled to 0° C. Bis(2-methoxyethyl)aminosulfur trifluoride (4.23 ml, 23.0 mmol) was then added slowly and reaction stirred at room temperature for 2 days. The reaction mixture was cooled to 0° C. and quenched with 20 ml of saturated NaHCO$_3$. The resulting suspension was diluted with more DCM and washed with water, brine, dried (MgSO$_4$), and concentrated. The crude residue was purified by chromatography on silica gel (EtOAc/hex) to give the title compound (1.15 g, 35%). MS (ESI) 284 (M+H).

Step 4. (4,4-Difluoro-1-((S)-1-phenylethyl)piperidin-2-yl)methanol

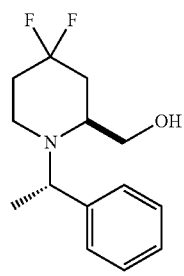 [SMILES: C[C@@H](c1ccccc1)N1CCC(F)(F)C[C@H]1CO]

To a suspension of LiAlH$_4$ (4 equiv.) in THF (40 ml) was added in portions the product from the previous step (1.15 g) in THF at 0° C. The reaction was allowed to stir to room temperature overnight and then refluxed for 2 h. The reaction mixture was then quenched with saturated Na$_2$SO$_4$ at 0° C. and stirred for 1 h. The reaction mixture was filtered and concentrated in vacuo to give the title compound as a clear oil (750 mg, 76%). MS (ESI) 256 (M+H).

Step 5. 2-((4,4-Difluoro-1-((S)-1-phenylethyl)piperidin-2-yl)methyl)isoindoline-1,3-dione

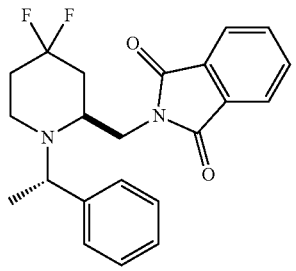 [SMILES: C[C@@H](c1ccccc1)N1CCC(F)(F)C[C@H]1CN1C(=O)c2ccccc2C1=O]

The title compound was prepared following the same general protocol as described for (2S,3R)-benzyl 2-((1,3-dioxoisoindolin-2-yl)methyl)-3-methylpiperidine-1-carboxylate in Example A1 using (4,4-difluoro-1-((S)-1-phenylethyl)piperidin-2-yl)methanol (1.1 g, 97%). MS (ESI) 285 (M+H).

Step 6. 2-((4,4-Difluoropiperidin-2-yl)methyl)isoindoline-1,3-dione

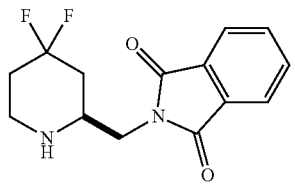 [SMILES: O=C1c2ccccc2C(=O)N1C[C@@H]1CC(F)(F)CCN1]

To a solution of 2-((4,4-difluoro-1-((S)-1-phenylethyl)piperidin-2-yl)methyl)isoindoline-1,3-dione (1.1 g, 2.86 mmol) in acetic acid (10 ml) was added 10% Pd/C (200 mg). The reaction was then stirred under H$_2$ until HPLC indicated complete removal of the phenethyl group. The reaction was the filtered through diatomaceous earth and concentrated. The crude residue was then dissolved in EtOAc and washed with saturated NaHCO$_3$, brine, dried (MgSO$_4$), and concentrated to yield the title compound as an orange oil (720 mg, 90%).

Step 7. (2-(Aminomethyl)-4,4-difluoropiperidin-1-yl)(5-methyl-2-(2H-1,2,3-triazol-2-yl)phenyl)methanone

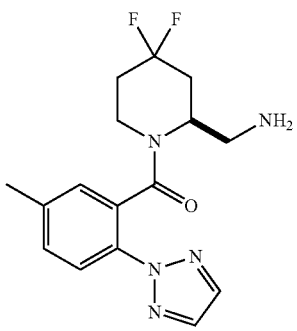 [SMILES: Cc1ccc(-n2nccn2)c(C(=O)N2CCC(F)(F)C[C@H]2CN)c1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 5-methyl-2-(2H-1,2,3-triazol-2-yl)benzoic acid and 2-((4,4-difluoropiperidin-2-yl)methyl)isoindoline-1,3-dione. MS (ESI) 336 (M+H).

Step 8. (2-(((5-Chloropyridin-2-yl)amino)methyl)-4,4-difluoropiperidin-1-yl)(5-methyl-2-(2H-1,2,3-triazol-2-yl)phenyl)methanone The title compound was prepared following the same general protocol as described for Example A44 using (2-(aminomethyl)-4,4-difluoropiperidin-1-yl)(5-methyl-2-(2H-1,2,3-triazol-2-yl)phenyl)methanone and 2-bromo-5-chloropyridine. MS (ESI) 447 (M+H).

Example A211

(S)-(4,4-Difluoro-2-(((5-(trifluoromethyl)pyrimidin-2-yl)amino)methyl)piperidin-1-yl)(5-methyl-2-(2H-1,2,3-triazol-2-yl)phenyl)methanone

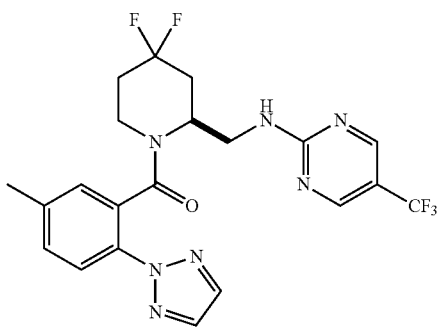 [SMILES: Cc1ccc(-n2nccn2)c(C(=O)N2CCC(F)(F)C[C@H]2CNc2ncc(C(F)(F)F)cn2)c1]

The title compound was prepared following the same general protocol as described for Example A45 using (2-(aminomethyl)-4,4-difluoropiperidin-1-yl)(5-methyl-2-(2H-1,2,3-triazol-2-yl)phenyl)methanone and 2-chloro-5-(trifluoromethyl)pyrimidine. MS (ESI) 482 (M+H).

Example A212

((2S,3R)-3-Methyl-2-(((5-(trifluoromethyl)pyrimidin-2-yl)amino)methyl)piperidin-1-yl)(5-methyl-2-(pyrimidin-2-yl)phenyl)methanone

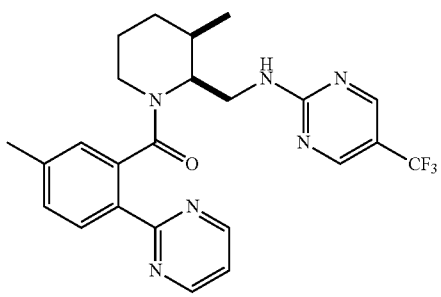 [SMILES: Cc1ccc(-c2ncccn2)c(C(=O)N2CCC[C@@H](C)[C@H]2CNc2ncc(C(F)(F)F)cn2)c1]

The title compound was prepared following the same general protocol as described for Example A45 using ((2S,3R)-2-(aminomethyl)-3-methylpiperidin-1-yl)(5-methyl-2-(pyrimidin-2-yl)phenyl)methanone and 2-chloro-5-(trifluoromethyl)pyrimidine. MS (ESI) 471 (M+H).

Example A213

((2S,3R)-2-(((2,5-Dimethyl-1,2,4]triazolo[1,5-a]pyrimidin-7-yl)amino)methyl)-3-methylpiperidin-1-yl)(5-methyl-2-(2H-1,2,3-triazol-2-yl)phenyl)methanone

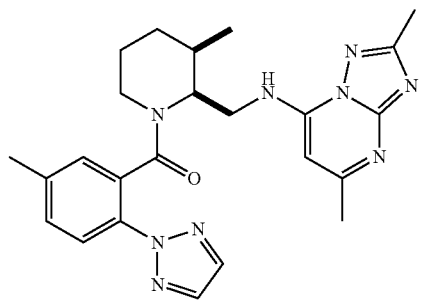

The title compound was prepared following the same general protocol as described for Example A1 using ((2S,3R)-2-(aminomethyl)-3-methylpiperidin-1-yl)(5-methyl-2-(2H-1,2,3-triazol-2-yl)phenyl)methanone and 7-chloro-2,5-dimethyl-[1,2,4]triazolo[1,5-a]pyrimidine. ESI-MS (m/z): 460 [M+1]+.

Example A214

((2S,3R)-3-Methyl-2-(((5-methylquinazolin-2-yl)amino)methyl)piperidin-1-yl)(5-methyl-2-(2H-1,2,3-triazol-2-yl)phenyl)methanone

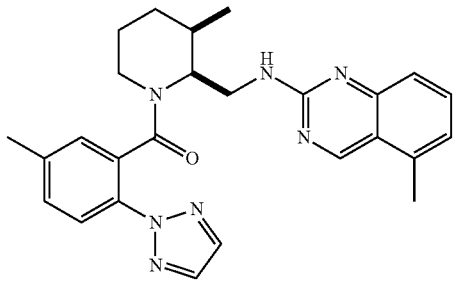 [SMILES: Cc1ccc(-n2nccn2)c(C(=O)N2CCC[C@@H](C)[C@H]2CNc2ncc3c(C)cccc3n2)c1]

Step 1. ((2S,3R)-2-(((5-Bromoquinazolin-2-yl)amino)methyl)-3-methylpiperidin-1-yl)(5-methyl-2-(2H-1,2,3-triazol-2-yl)phenyl)methanone

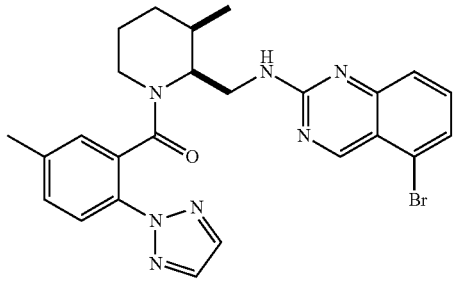 [SMILES: Cc1ccc(-n2nccn2)c(C(=O)N2CCC[C@@H](C)[C@H]2CNc2ncc3c(Br)cccc3n2)c1]

The title compound was prepared following the same general protocol as described for Example A1 using ((2S, 3R)-2-(aminomethyl)-3-methylpiperidin-1-yl)(5-methyl-2-(2H-1,2,3-triazol-2-yl)phenyl)methanone and 5-bromo-2-chloroquinazoline. ESI-MS (m/z): 520, 522 [M]⁺, [M+2]⁺.

Step 2. ((2S,3R)-3-Methyl-2-(((5-methylquinazolin-2-yl)amino)methyl)piperidin-1-yl)(5-methyl-2-(2H-1,2,3-triazol-2-yl)phenyl)methanone The title compound was prepared following the same general protocol as described for methyl 5-methyl-2-(1-methyl-1H-pyrazol-4-yl)benzoate in Example A1, using ((2S,3R)-2-(((5-bromoquinazolin-2-yl)amino)methyl)-3-methylpiperidin-1-yl)(5-methyl-2-(2H-1,2,3-triazol-2-yl)phenyl)methanone and 2,4,6-trimethyl-1,3,5,2,4,6-trioxatriborinane. ESI-MS (m/z): 456 [M+1]⁺.

Example A215

((2S,3R)-3-Methyl-2-(((7-methylquinazolin-2-yl)amino)methyl)piperidin-1-yl)(5-methyl-2-(2H-1,2,3-triazol-2-yl)phenyl)methanone

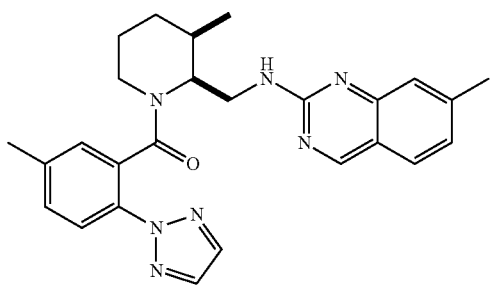

Step 1. ((2S,3R)-2-(((7-bromoquinazolin-2-yl)amino)methyl)-3-methylpiperidin-1-yl)(5-methyl-2-(2H-1,2,3-triazol-2-yl)phenyl)methanone

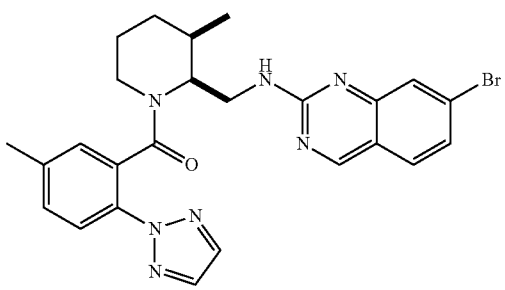 [SMILES: Cc1ccc(-n2nccn2)c(C(=O)N2CCC[C@@H](C)[C@H]2CNc2ncc3ccc(Br)cc3n2)c1]

The title compound was prepared following the same general protocol as described for Example A1 using ((2S, 3R)-2-(aminomethyl)-3-methylpiperidin-1-yl)(5-methyl-2-(2H-1,2,3-triazol-2-yl)phenyl)methanone and 7-bromo-2-chloroquinazoline. ESI-MS (m/z): 520, 522 [M]⁺, [M+2]⁺.

Step 2. ((2S,3R)-3-Methyl-2-(((7-methylquinazolin-2-yl)amino)methyl)piperidin-1-yl)(5-methyl-2-(2H-1,2,3-triazol-2-yl)phenyl)methanone The title compound was prepared following the same general protocol as described for methyl 5-methyl-2-(1-methyl-1H-pyrazol-4-yl)benzoate in Example A1, using ((2S,3R)-2-(((7-bromoquinazolin-2-yl)amino)methyl)-3-methylpiperidin-1-yl)(5-methyl-2-(2H-1,2,3-triazol-2-yl)phenyl)methanone and 2,4,6-trimethyl-1,3,5,2,4,6-trioxatriborinane. ESI-MS (m/z): 456 [M+1]⁺.

Example A216

((2S,3R)-3-Methyl-2-((quinazolin-2-ylamino)methyl)piperidin-1-yl)(5-methyl-2-(2H-1,2,3-triazol-2-yl)phenyl)methanone

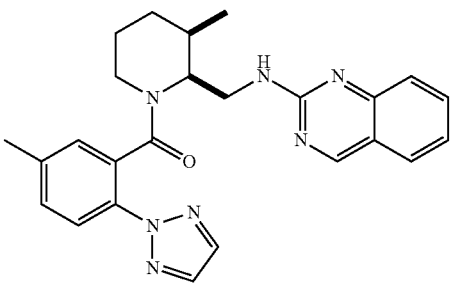 [SMILES: Cc1ccc(-n2nccn2)c(C(=O)N2CCC[C@@H](C)[C@H]2CNc2ncc3ccccc3n2)c1]

A mixture of ((2S,3R)-2-(((5-bromoquinazolin-2-yl)amino)methyl)-3-methylpiperidin-1-yl)(5-methyl-2-(2H-1,2,3-triazol-2-yl)phenyl)methanone (0.057 g, 0.111 mmol), HCOONH₄ (0.14 g, 0.222 mmol) and Pd(PPh₃)₄ (0.026 g, 0.022 mmol) in dioxane and water (4:1, 2 mL) was heated for 2 h at 100° C. The mixture was cooled to room temperature and filtered through diatomaceous earth. The solvent was removed and the crude residue was purified via silica gel chromatography to obtain the title compound. ESI-MS (m/z): 442 [M+1]⁺.

Example A217

((2S,3R)-3-Methyl-2-(((5-(trifluoromethyl)pyridin-2-yl)amino)methyl)piperidin-1-yl)(6'-methyl-[2,3'-bipyridin]-2'-yl)methanone

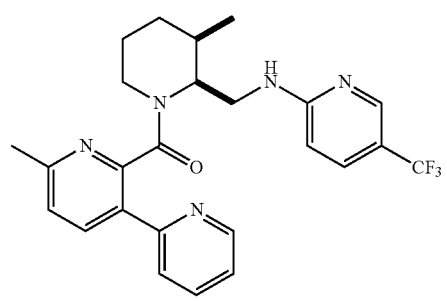 [SMILES: Cc1ccc(-c2ccccn2)c(C(=O)N2CCC[C@@H](C)[C@H]2CNc2ccc(C(F)(F)F)cn2)n1]

The title compound was prepared following the same general protocol as described for Example A1 using ((2S, 3R)-2-(aminomethyl)-3-methylpiperidin-1-yl)(6'-methyl-[2,3'-bipyridin]-2'-yl)methanone. MS (ESI) 470 (M+H).

Example A218

(2-(2H-1,2,3-Triazol-2-yl)phenyl)((2S,3R)-2-((benzo[d]oxazol-2-ylamino)methyl)-3-methylpiperidin-1-yl)methanone

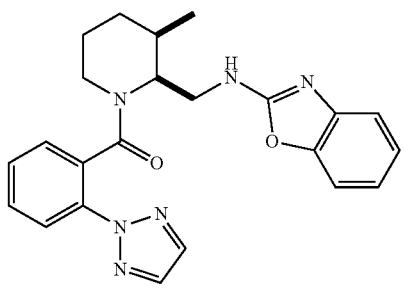 [SMILES: C[C@@H]1CCCN(C(=O)c2ccccc2-n2nccn2)[C@@H]1CNc1nc2ccccc2o1]

Step 1. 2-(2H-1,2,3-Triazol-2-yl)benzoic acid

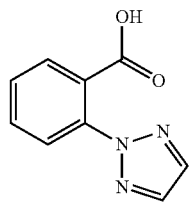 [SMILES: O=C(O)c1ccccc1-n1nccn1]

The title compound was prepared following the same general protocol as described for 5-methyl-2-(2H-1,2,3-triazol-2-yl)benzoic acid in Example A11 using 2-bromobenzoic acid. MS (ESI) 190 (M+H).

Step 2. (2-(2H-1,2,3-Triazol-2-yl)phenyl)((2S,3R)-2-(aminomethyl)-3-methylpiperidin-1-yl)methanone

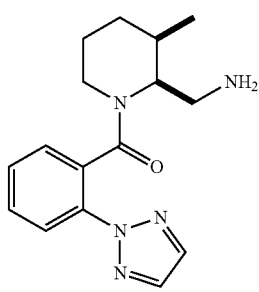 [SMILES: C[C@@H]1CCCN(C(=O)c2ccccc2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(2H-1,2,3-triazol-2-yl)benzoic acid. MS (ESI) 300 (M+H).

Step 3. (2-(2H-1,2,3-Triazol-2-yl)phenyl)((2S,3R)-2-((benzo[d]oxazol-2-ylamino)methyl)-3-methylpiperidin-1-yl)methanone The title compound was prepared following the same general protocol as described for Example A2 using (2-(2H-1,2,3-triazol-2-yl)phenyl)((2S,3R)-2-(aminomethyl)-3-methylpiperidin-1-yl)methanone. MS (ESI) 417 (M+H).

Example A219

(2-(2H-1,2,3-Triazol-2-yl)phenyl)((2S,3R)-2-(((5-chlorobenzo[d]oxazol-2-yl)amino)methyl)-3-methylpiperidin-1-yl)methanone

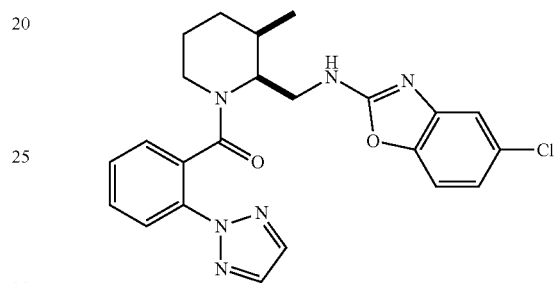

The title compound was prepared following the same general protocol as described for Example A2 using (2-(2H-1,2,3-triazol-2-yl)phenyl)((2S,3R)-2-(aminomethyl)-3-methylpiperidin-1-yl)methanone and 2,5-dichlorobenzoxazole. MS (ESI) 451 (M+H).

Example A220

((2S,3R)-3-Methyl-2-(((6-methylquinazolin-2-yl)amino)methyl)piperidin-1-yl)(5-methyl-2-(2H-1,2,3-triazol-2-yl)phenyl)methanone

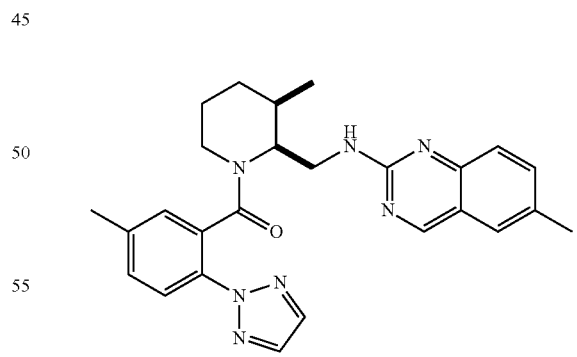

The title compound was prepared following the same general protocol as described for methyl 5-methyl-2-(1-methyl-1H-pyrazol-4-yl)benzoate in Example A1, using ((2S,3R)-2-(((6-bromoquinazolin-2-yl)amino)methyl)-3-methylpiperidin-1-yl)(5-methyl-2-(2H-1,2,3-triazol-2-yl)phenyl)methanone (synthesized in Example A122) and 2,4,6-trimethyl-1,3,5,2,4,6-trioxatriborinane. ESI-MS (m/z): 456 [M+1]$^+$.

Example A221

((2S,3R)-2-(((5-Chloropyrimidin-2-yl)amino)methyl)-3-methylpiperidin-1-yl)(5-fluoro-2-(2H-1,2,3-triazol-2-yl)phenyl)methanone

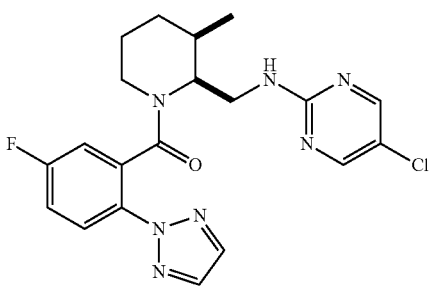

The title compound was prepared following the same general protocol as described for Example A207 using ((2S,3R)-2-(aminomethyl)-3-methylpiperidin-1-yl)(5-fluoro-2-(2H-1,2,3-triazol-2-yl)phenyl)methanone and 2,5-dichloropyridine. MS (ESI) 430 (M+H).

Example A222

((2S,3R)-2-(((5-Chloropyrimidin-2-yl)amino)methyl)-3-methylpiperidin-1-yl)(6-methyl-[3,3'-bipyridin]-2-yl)methanone

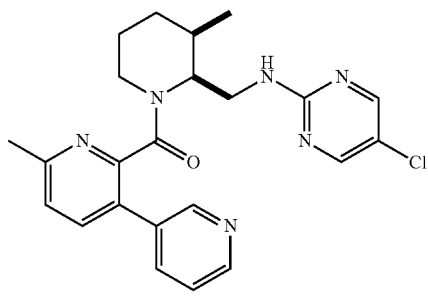 [SMILES: Cc1ccc(-c2cccnc2)c(C(=O)N2CCC[C@@H](C)[C@H]2CNc2ncc(Cl)cn2)n1]

Step 1. ((2S,3R)-2-(aminomethyl)-3-methylpiperidin-1-yl)(6-methyl-[3,3'-bipyridin]-2-yl)methanone

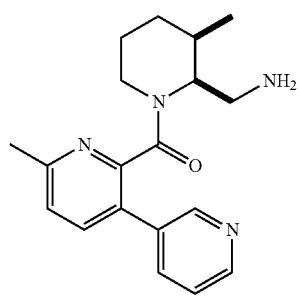 [SMILES: Cc1ccc(-c2cccnc2)c(C(=O)N2CCC[C@@H](C)[C@H]2CN)n1]

The title compound was prepared following the same general protocol as described for ((2S,3R)-2-(aminomethyl)-3-methylpiperidin-1-yl) (3-(4-fluorophenyl)-6-methylpyridin-2-yl)methanone in Example A73 using pyridin-3-ylboronic acid. ESI-MS (m/z): 325 [M+1]$^+$.

Step 2. ((2S,3R)-2-(((5-Chloropyrimidin-2-yl)amino)methyl)-3-methylpiperidin-1-yl)(6-methyl-[3,3'-bipyridin]-2-yl)methanone The title compound was prepared following the same general protocol as described for Example A1, using ((2S,3R)-2-(aminomethyl)-3-methylpiperidin-1-yl)(6-methyl-[3,3'-bipyridin]-2-yl)methanone and 2,5-dichloropyrimidine. ESI-MS (m/z): 437 [M+1]$^+$.

Example A223

((2S,3R)-3-Methyl-2-(((5-(trifluoromethyl)pyrimidin-2-yl)amino)methyl)piperidin-1-yl)(6-methyl-[3,3'-bipyridin]-2-yl)methanone

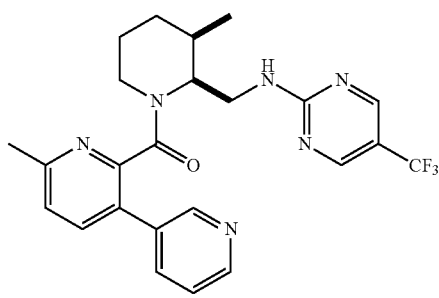

The title compound was prepared following the same general protocol as described for Example A1, using ((2S,3R)-2-(aminomethyl)-3-methylpiperidin-1-yl) (6-methyl-[3,3'-bipyridin]-2-yl)methanone and 2-chloro-5-(trifluoromethyl)pyrimidine. ESI-MS (m/z): 471 [M+1]$^+$.

Example A224

((2S,3R)-2-(((5-Chloropyridin-2-yl)amino)methyl)-3-methylpiperidin-1-yl)(6-methyl-[3,3'-bipyridin]-2-yl)methanone

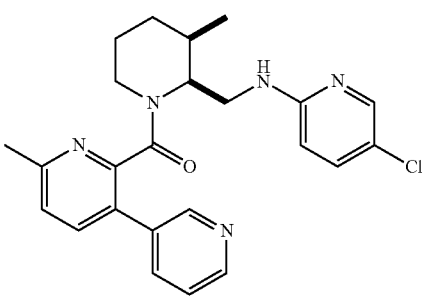 [SMILES: Cc1ccc(-c2cccnc2)c(C(=O)N2CCC[C@@H](C)[C@H]2CNc2ccc(Cl)cn2)n1]

The title compound was prepared following the same general protocol as described for Example A44 using ((2S,3R)-2-(aminomethyl)-3-methylpiperidin-1-yl) (6-methyl-[3, 3'-bipyridin]-2-yl)methanone and 2-bromo-5-chloropyridine. ESI-MS (m/z): 436 [M+1]+.

Example A225

((2S,3R)-2-(((5-Chloropyrimidin-2-yl)amino)methyl)-3-methylpiperidin-1-yl)(isoquinolin-1-yl)methanone

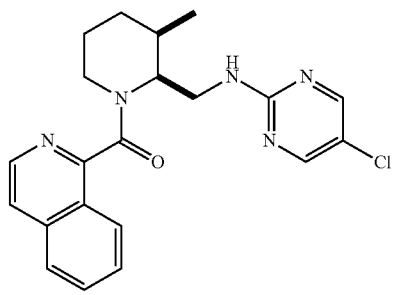 [SMILES: C[C@@H]1CCCN(C(=O)c2nccc3ccccc23)[C@@H]1CNc1ncc(Cl)cn1]

Step 1. 2-(((2S,3R)-1-(Isoquinoline-1-carbonyl)-3-methylpiperidin-2-yl)methyl)isoindoline-1,3-dione

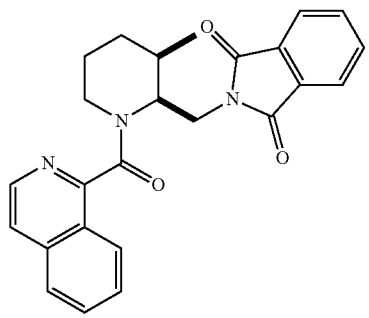 [SMILES: C[C@@H]1CCCN(C(=O)c2nccc3ccccc23)[C@@H]1CN1C(=O)c2ccccc2C1=O]

The title compound was prepared following the same general protocol as described for 2-(((2S,3R)-3-methyl-1-(5-methyl-2-(1-methyl-1H-pyrazol-4-yl)benzoyl)piperidin-2-yl)methyl)isoindoline-1,3-dione in Example A1, using isoquinoline-1-carboxylic acid. ESI-MS (m/z): 414 [M+1]+.

Step 2. ((2S,3R)-2-(Aminomethyl)-3-methylpiperidin-1-yl)(isoquinolin-1-yl)methanone

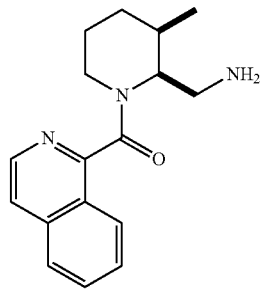 [SMILES: C[C@@H]1CCCN(C(=O)c2nccc3ccccc23)[C@@H]1CN]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, using 2-(((2S,3R)-1-(isoquinoline-1-carbonyl)-3-methylpiperidin-2-yl)methyl)isoindoline-1,3-dione. ESI-MS (m/z): 284 [M+1]+.

Step 3. ((2S,3R)-2-(((5-Chloropyrimidin-2-yl)amino)methyl)-3-methylpiperidin-1-yl)(isoquinolin-1-yl)methanone The title compound was prepared following the same general protocol as described for Example A1, using ((2S,3R)-2-(aminomethyl)-3-methylpiperidin-1-yl)(isoquinolin-1-yl)methanone and 2,5-dichloropyrimidine. ESI-MS (m/z): 396 [M+1]+.

Example A226

((2S,3R)-2-(((5-Chloropyrimidin-2-yl)amino)methyl)-3-methylpiperidin-1-yl)(5-fluoro-2-(pyrimidin-2-yl)phenyl)methanone

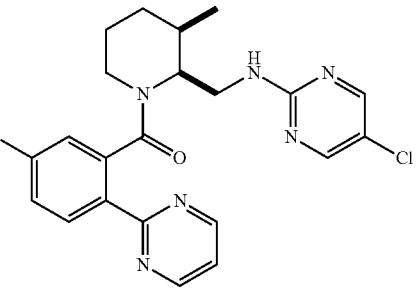

Step 1. 2-(((2S,3R)-1-(2-Bromo-5-fluorobenzoyl)-3-methylpiperidin-2-yl)methyl)isoindoline-1,3-dione

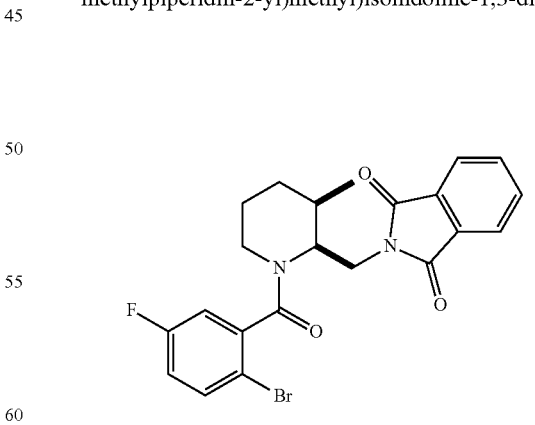

The title compound was prepared following the same general protocol as described for 2-(((2S,3R)-3-methyl-1-(5-methyl-2-(1-methyl-1H-pyrazol-4-yl)benzoyl)piperidin-2-yl)methyl)isoindoline-1,3-dione in Example A1, using 2-bromo-5-fluorobenzoic acid. ESI-MS (m/z): 459, 461 [M]+[M+2]+.

Step 2. 2-(((2S,3R)-1-(5-Fluoro-2-(pyrimidin-2-yl)benzoyl)-3-methylpiperidin-2-yl)methyl)isoindoline-1,3-dione

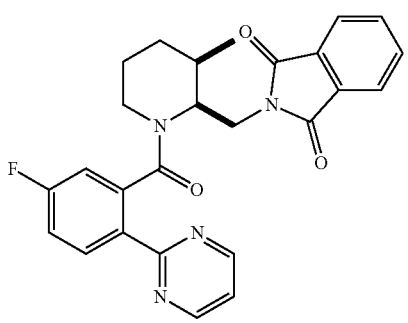

The title compound was prepared following the same general protocol as described for methyl 5-methyl-2-(pyridin-2-yl)benzoate in Example A9, using 2-(((2S,3R)-1-(2-bromo-5-fluorobenzoyl)-3-methylpiperidin-2-yl)methyl)isoindoline-1,3-dione and 2-(tributylstannyl)pyrimidine. ESI-MS (m/z): 445, [M+1]$^+$.

Step 3. ((2S,3R)-2-(Aminomethyl)-3-methylpiperidin-1-yl)(5-fluoro-2-(pyrimidin-2-yl)phenyl)methanone

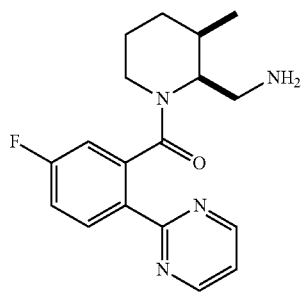 [SMILES: C[C@@H]1CCCN(C(=O)c2cc(F)ccc2-c2ncccn2)[C@@H]1CN]

The title compound was synthesized following the same general protocol as described for ((2S,3R)-2-(aminomethyl)-3-methylpiperidin-1-yl)(5-methyl-2-(1-methyl-1H-pyrazol-4-yl)phenyl)methanone in Example A1, using 2-(((2S,3R)-1-(5-fluoro-2-(pyrimidin-2-yl)benzoyl)-3-methylpiperidin-2-yl)methyl)isoindoline-1,3-dione. ESI-MS (m/z): 329 [M+1]$^+$.

Step 4. ((2S,3R)-2-(((5-Chloropyrimidin-2-yl)amino)methyl)-3-methylpiperidin-1-yl)(5-fluoro-2-(pyrimidin-2-yl)phenyl)methanone The title compound was prepared following the same general protocol as described for Example A1, using ((2S,3R)-2-(aminomethyl)-3-methylpiperidin-1-yl)(5-fluoro-2-(pyrimidin-2-yl)phenyl)methanone and 2,5-dichloropyrimidine. ESI-MS (m/z): 441 [M+1]$^+$.

Example A227

(5-Fluoro-2-(pyrimidin-2-yl)phenyl)((2S,3R)-3-methyl-2-(((5-(trifluoromethyl)pyrimidin-2-yl)amino)methyl)piperidin-1-yl)methanone

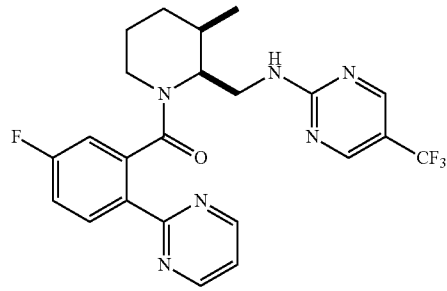

The title compound was prepared following the same general protocol as described for Example A1, using ((2S,3R)-2-(aminomethyl)-3-methylpiperidin-1-yl)(5-fluoro-2-(pyrimidin-2-yl)phenyl)methanone and 2-chloro-5-(trifluoromethyl)pyrimidine. ESI-MS (m/z): 475 [M+1]$^+$.

Example A228

(5-Fluoro-2-(pyrimidin-2-yl)phenyl)((2S,3R)-3-methyl-2-(((5-(trifluoromethyl)pyridin-2-yl)amino)methyl)piperidin-1-yl)methanone

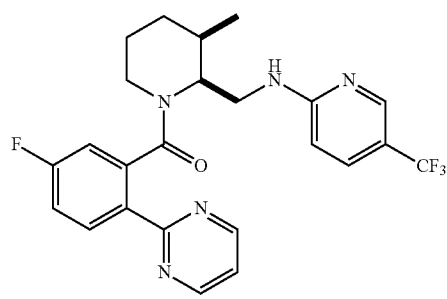

The title compound was prepared following the same general protocol as described for Example A1, using ((2S,3R)-2-(aminomethyl)-3-methylpiperidin-1-yl)(5-fluoro-2-(pyrimidin-2-yl)phenyl)methanone and 2-fluoro-5-(trifluoromethyl)pyridine. ESI-MS (m/z): 474 [M+1]$^+$.

Example A229

((2S,3R)-2-(((5-Chloropyridin-2-yl)amino)methyl)-3-methylpiperidin-1-yl)(5-fluoro-2-(pyrimidin-2-yl)phenyl)methanone

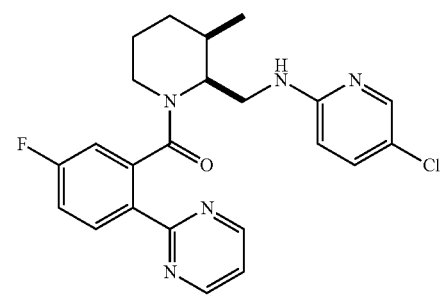

The title compound was prepared following the same general protocol as described for Example A44 using ((2S, 3R)-2-(aminomethyl)-3-methylpiperidin-1-yl)(5-fluoro-2-(pyrimidin-2-yl)phenyl)methanone and 2-bromo-5-chloropyridine. ESI-MS (m/z): 440 [M+1]⁺.

Example A230

(3-Fluoro-2-(pyrimidin-2-yl)phenyl)((2S,3R)-3-methyl-2-(((5-(trifluoromethyl)pyrimidin-2-yl)amino)methyl)piperidin-1-yl)methanone

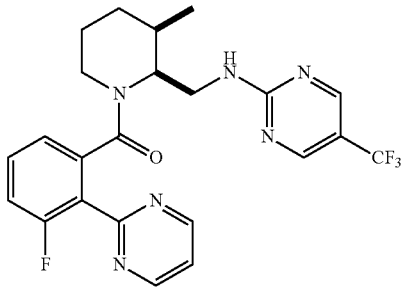

Step 1. 2-(((2S,3R)-1-(3-fluoro-2-iodobenzoyl)-3-methylpiperidin-2-yl)methyl)isoindoline-1,3-dione

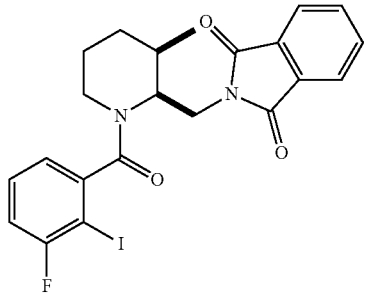 [SMILES: C[C@@H]1CCCN(C(=O)c2cccc(F)c2I)[C@@H]1CN1C(=O)c2ccccc2C1=O]

A mixture of 2-(((2S,3R)-3-methylpiperidin-2-yl)methyl)isoindoline-1,3-dione (0.4 g, 1.55 mmol), 3-fluoro-2-iodobenzoic acid (0.37 g, 1.4 mmol), diisopropylethylamine (0.49 mL, 2.8 mmol) and HATU (0.53 g, 1.4 mmol) in DMF (10 ml) was stirred at room temperature for 1 h. The reaction mixture was diluted with ethyl acetate and washed with sat'd NaHCO₃ and brine successively. The organic layer was separated, dried with MgSO₄ and concentrated in vacuo. The crude product was purified by chromatography on silica gel (EtOAc/hex) to afford the title compound. MS (ESI) 507 (M+H).

Step 2. 2-(((2S,3R)-1-(3-fluoro-2-(pyrimidin-2-yl)benzoyl)-3-methylpiperidin-2-yl)methyl)isoindoline-1,3-dione

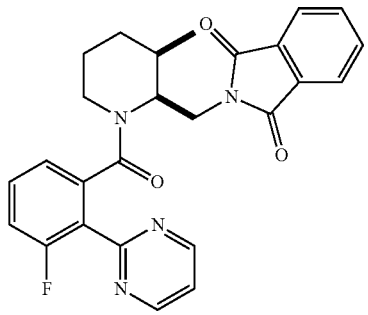 [SMILES: C[C@@H]1CCCN(C(=O)c2cccc(F)c2-c2ncccn2)[C@@H]1CN1C(=O)c2ccccc2C1=O]

A mixture of 2-(((2S,3R)-1-(3-fluoro-2-iodobenzoyl)-3-methylpiperidin-2-yl)methyl)isoindoline-1,3-dione (0.493 g, 0.974 mmol), 2-(tributylstannyl)pyrimidine (0.4 g, 1.07 mmol), cesium fluoride (0.3 g, 1.948 mmol), CuI (0.0185 g, 0.098 mmol) and Pd(PPh₃)₄ (0.112 g, 0.098 mmol) in DMF (5 mL) was degassed and heated at 100° C. oil bath for 16 h. The solvent was removed in vacuo to obtain the crude which was purified by silica gel chromatography (0~100% Hexane/EtOAc) to yield the title compound as a white solid (0.331 g, 75%). MS (ESI) 459 (M+H).

Step 3. ((2S,3R)-2-(aminomethyl)-3-methylpiperidin-1-yl)(3-fluoro-2-(pyrimidin-2-yl)phenyl)methanone

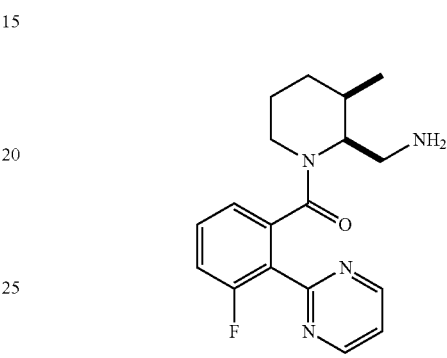

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(((2S,3R)-1-(3-fluoro-2-(pyrimidin-2-yl)benzoyl)-3-methylpiperidin-2-yl)methyl)isoindoline-1,3-dione. MS (ESI) 329 (M+H).

Step 4: (3-Fluoro-2-(pyrimidin-2-yl)phenyl)((2S,3R)-3-methyl-2-(((5-(trifluoromethyl)pyrimidin-2-yl)amino)methyl)piperidin-1-yl)methanone The title compound was prepared following the same general protocol as described for Example A1 using ((2S,3R)-2-(aminomethyl)-3-methylpiperidin-1-yl)(3-fluoro-2-(pyrimidin-2-yl)phenyl)methanone and 2-chloro-5-(trifluoromethyl)pyrimidine. ESI-MS (m/z): 475 [M+1]⁺.

Example A231

(3-Fluoro-2-(pyrimidin-2-yl)phenyl)((2S,3R)-3-methyl-2-(((5-chloropyrimidin-2-yl)amino)methyl)piperidin-1-yl)methanone

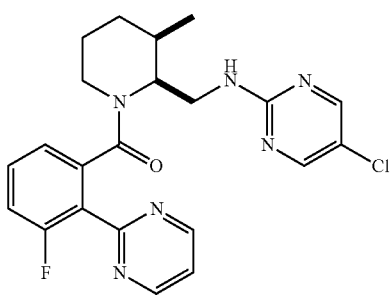 [SMILES: C[C@@H]1CCCN(C(=O)c2cccc(F)c2-c2ncccn2)[C@@H]1CNc1ncc(Cl)cn1]

The title compound was prepared following the same general protocol as described for Example A1 using ((2S,3R)-2-(aminomethyl)-3-methylpiperidin-1-yl)(3-fluoro-2-(pyrimidin-2-yl)phenyl)methanone and 2,5-dichloropyrimidine. ESI-MS (m/z): 441 [M+1]⁺.

Example A232

((2S,3R)-2-(((5-chloropyridin-2-yl)amino)methyl)-3-methylpiperidin-1-yl)(3-fluoro-2-(pyrimidin-2-yl)phenyl)methanone

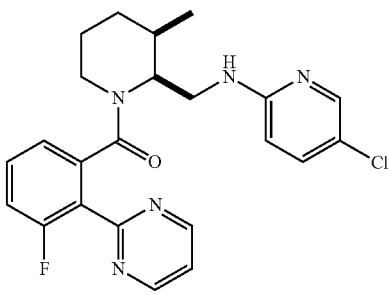 [SMILES: C[C@@H]1CCCN(C(=O)c2cccc(F)c2-c2ncccn2)[C@@H]1CNc1ccc(Cl)cn1]

The title compound was prepared following the same general protocol as described for Example A44 using ((2S,3R)-2-(aminomethyl)-3-methylpiperidin-1-yl)(3-fluoro-2-(pyrimidin-2-yl)phenyl)methanone and 2-bromo-5-chloropyridine. ESI-MS (m/z): 440 [M+1]⁺.

Example A233

(3-Fluoro-2-(pyrimidin-2-yl)phenyl)((2S,3R)-3-methyl-2-(((5-(trifluoromethyl)pyridin-2-yl)amino)methyl)piperidin-1-yl)methanone

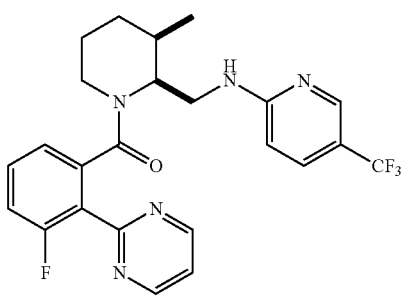

The title compound was prepared following the same general protocol as described for Example A1 using ((2S,3R)-2-(aminomethyl)-3-methylpiperidin-1-yl)(3-fluoro-2-(pyrimidin-2-yl)phenyl)methanone and 2-fluoro-5-(trifluoromethyl)pyridine. ESI-MS (m/z): 474 [M+1]⁺.

Example A234

(4-Fluoro-2-(pyrimidin-2-yl)phenyl)((2S,3R)-3-methyl-2-(((5-(trifluoromethyl)pyridin-2-yl)amino)methyl)piperidin-1-yl)methanone

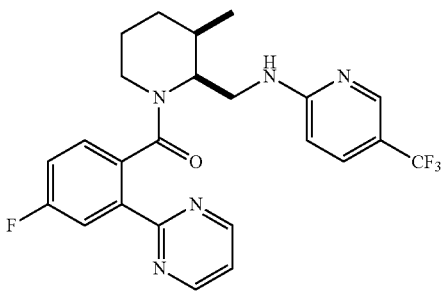 [SMILES: C[C@@H]1CCCN(C(=O)c2ccc(F)cc2-c2ncccn2)[C@@H]1CNc1ccc(C(F)(F)F)cn1]

Step 1. 2-(((2S,3R)-1-(4-fluoro-2-iodobenzoyl)-3-methylpiperidin-2-yl)methyl)isoindoline-1,3-dione

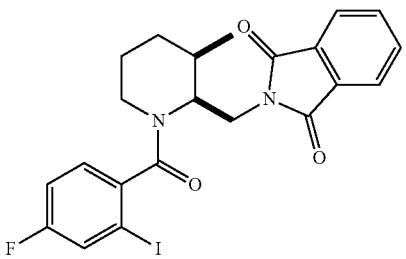 [SMILES: C[C@@H]1CCCN(C(=O)c2ccc(F)cc2I)[C@@H]1CN1C(=O)c2ccccc2C1=O]

A mixture of 2-(((2S,3R)-3-methylpiperidin-2-yl)methyl)isoindoline-1,3-dione (0.4 g, 1.549 mmol), 4-fluoro-2-iodobenzoic acid (0.374 g, 1.4 mmol), diisopropylethylamine (0.49 mL, 2.8 mmol) and HATU (0.53 g, 1.4 mmol) in DMF (10 ml) was stirred at room temperature for 1 h. The reaction mixture was diluted with ethyl acetate and washed with sat'd NaHCO₃ and brine successively. The organic layer was separated, dried with MgSO₄ and concentrated in vacuo. The crude product was purified by chromatography on silica gel (EtOAc/hex) to afford the title compound. MS (ESI) 507 (M+H).

Step 2. 2-(((2S,3R)-1-(4-fluoro-2-(pyrimidin-2-yl)benzoyl)-3-methylpiperidin-2-yl)methyl)isoindoline-1,3-dione

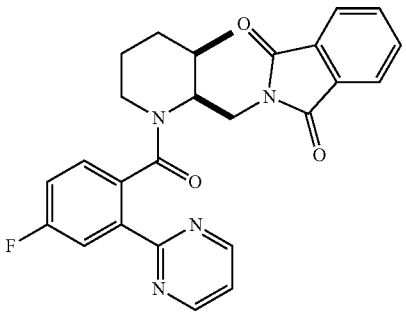

A mixture of 2-(((2S,3R)-1-(4-fluoro-2-iodobenzoyl)-3-methylpiperidin-2-yl)methyl)isoindoline-1,3-dione (0.51 g, 1.0 mmol), 2-(tributylstannyl)pyrimidine (0.406 g, 1.1 mmol), cesium fluoride (0.304 g, 2.0 mmol), CuI (0.019 g, 0.1 mmol) and Pd(PPh₃)₄ (0.116 g, 0.1 mmol) in DMF (5 mL) was degassed and heated at 100° C. oil bath for 16 h. The solvent was removed in vacuo to obtain the crude which was purified by silica gel chromatography (0~100% Hexane/EtOAc) to yield the title compound as a white solid (0.370 g, 81%). MS (ESI) 459 (M+H).

Step 3. ((2S,3R)-2-(aminomethyl)-3-methylpiperidin-1-yl)(4-fluoro-2-(pyrimidin-2-yl)phenyl)methanone

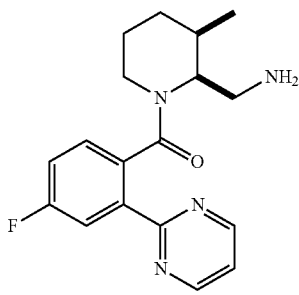 [SMILES: C[C@@H]1CCCN(C(=O)c2ccc(F)cc2-c2ncccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(((2S,3R)-1-(4-fluoro-2-(pyrimidin-2-yl)benzoyl)-3-methylpiperidin-2-yl)methyl)isoindoline-1,3-dione. MS (ESI) 329 (M+H).

Step 4: (4-Fluoro-2-(pyrimidin-2-yl)phenyl)((2S,3R)-3-methyl-2-(((5-(trifluoromethyl)pyridin-2-yl)amino)methyl)piperidin-1-yl)methanone The title compound was prepared following the same general protocol as described for Example A1 using ((2S,3R)-2-(aminomethyl)-3-methylpiperidin-1-yl)(4-fluoro-2-(pyrimidin-2-yl)phenyl)methanone and 2-fluoro-5-(trifluoromethyl)pyridine. ESI-MS (m/z): 474 [M+1]⁺.

Example A235

(4-Fluoro-2-(pyrimidin-2-yl)phenyl)((2S,3R)-3-methyl-2-(((5-(trifluoromethyl)pyrimidin-2-yl)amino)methyl)piperidin-1-yl)methanone

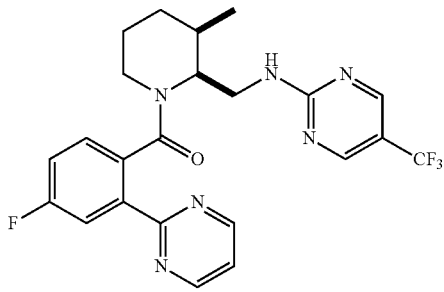 [SMILES: C[C@@H]1CCCN(C(=O)c2ccc(F)cc2-c2ncccn2)[C@@H]1CNc1ncc(C(F)(F)F)cn1]

The title compound was prepared following the same general protocol as described for Example A1 using ((2S,3R)-2-(aminomethyl)-3-methylpiperidin-1-yl)(4-fluoro-2-(pyrimidin-2-yl)phenyl)methanone and 2-chloro-5-(trifluoromethyl)pyrimidine. ESI-MS (m/z): 475 [M+1]⁺.

Example A236

((2S,3R)-2-(((5-chloropyrimidin-2-yl)amino)methyl)-3-methylpiperidin-1-yl)(4-fluoro-2-(pyrimidin-2-yl)phenyl)methanone

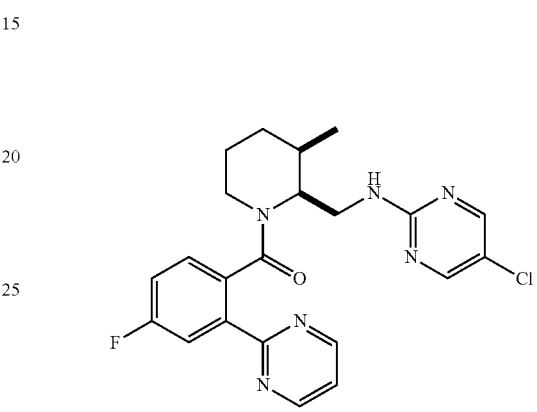

The title compound was prepared following the same general protocol as described for Example A44 using ((2S,3R)-2-(aminomethyl)-3-methylpiperidin-1-yl)(4-fluoro-2-(pyrimidin-2-yl)phenyl)methanone and 2,5-dichloropyrimidine. ESI-MS (m/z): 441 [M+1]⁺.

Example A237

((2S,3R)-2-(((5-chloropyridin-2-yl)amino)methyl)-3-methylpiperidin-1-yl)(4-fluoro-2-(pyrimidin-2-yl)phenyl)methanone

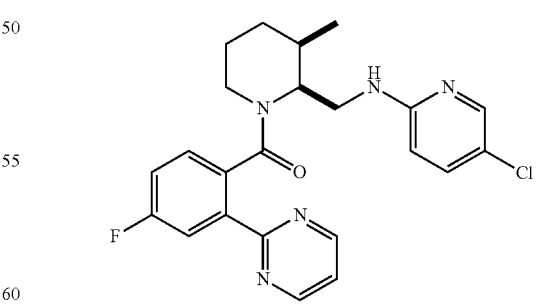

The title compound was prepared following the same general protocol as described for Example A1 using ((2S,3R)-2-(aminomethyl)-3-methylpiperidin-1-yl)(4-fluoro-2-(pyrimidin-2-yl)phenyl)methanone and 2-bromo-5-chloropyridine. ESI-MS (m/z): 440 [M+1]⁺.

Example A239

((2S,3R)-2-(((5-chloropyrimidin-2-yl)amino)methyl)-3-methylpiperidin-1-yl)(2-fluoro-6-(pyrimidin-2-yl)phenyl)methanone

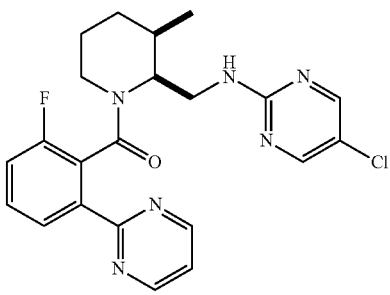 [SMILES: C[C@@H]1CCCN(C(=O)c2c(F)cccc2-c2ncccn2)[C@@H]1CNc1ncc(Cl)cn1]

Step 1. 2-(((2S,3R)-1-(2-fluoro-6-iodobenzoyl)-3-methylpiperidin-2-yl)methyl)isoindoline-1,3-dione

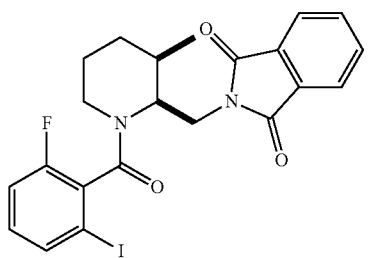 [SMILES: C[C@@H]1CCCN(C(=O)c2c(F)cccc2I)[C@@H]1CN1C(=O)c2ccccc2C1=O]

A mixture of 2-(((2S,3R)-3-methylpiperidin-2-yl)methyl)isoindoline-1,3-dione (0.4 g, 1.549 mmol), 2-fluoro-6-iodobenzoic acid (0.374 g, 1.4 mmol), diisopropylethylamine (0.49 mL, 2.8 mmol) and HATU (0.53 g, 1.4 mmol) in DMF (10 ml) was stirred at room temperature for 1 h. The reaction mixture was diluted with ethyl acetate and washed with sat'd NaHCO₃ and brine successively. The organic layer was separated, dried with MgSO₄ and concentrated in vacuo. The crude product was purified by chromatography on silica gel (EtOAc/hex) to afford the title compound. MS (ESI) 507 (M+H).

Step 2. 2-(((2S,3R)-1-(2-fluoro-6-(pyrimidin-2-yl)benzoyl)-3-methylpiperidin-2-yl)methyl)isoindoline-1,3-dione

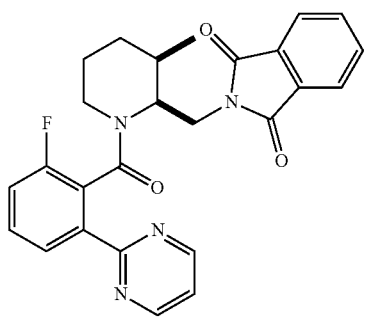 [SMILES: C[C@@H]1CCCN(C(=O)c2c(F)cccc2-c2ncccn2)[C@@H]1CN1C(=O)c2ccccc2C1=O]

A mixture of 2-(((2S,3R)-1-(2-fluoro-6-iodobenzoyl)-3-methylpiperidin-2-yl)methyl)isoindoline-1,3-dione (0.6 g, 1.185 mmol), 2-(tributylstannyl)pyrimidine (0.437 g, 1.185 mmol), cesium fluoride (0.36 g, 2.37 mmol), CuI (0.023 g, 0.119 mmol) and Pd(PPh₃)₄ (0.14 g, 0.119 mmol) in DMF (5 mL) was degassed and heated at 100° C. oil bath for 16 h. The solvent was removed in vacuo to obtain the crude which was purified by silica gel chromatography (0~100% Hexane/EtOAc) to yield the title compound as a white solid. MS (ESI) 459 (M+H).

Step 3. ((2S,3R)-2-(aminomethyl)-3-methylpiperidin-1-yl)(2-fluoro-6-(pyrimidin-2-yl)phenyl)methanone

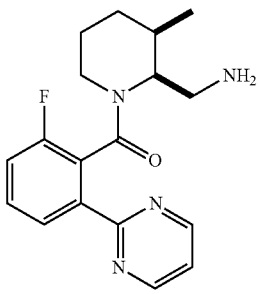 [SMILES: C[C@@H]1CCCN(C(=O)c2c(F)cccc2-c2ncccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(((2S,3R)-1-(2-fluoro-6-(pyrimidin-2-yl)benzoyl)-3-methylpiperidin-2-yl)methyl)isoindoline-1,3-dione. MS (ESI) 329 (M+H).

Step 4: ((2S,3R)-2-(((5-chloropyrimidin-2-yl)amino)methyl)-3-methylpiperidin-1-yl)(2-fluoro-6-(pyrimidin-2-yl)phenyl)methanone The title compound was prepared following the same general protocol as described for Example A1 using ((2S,3R)-2-(aminomethyl)-3-methylpiperidin-1-yl)(6-fluoro-2-(pyrimidin-2-yl)phenyl)methanone and 2,5-dichloropyrimidine. ESI-MS (m/z): 441 [M+1]⁺.

Example A240

(2-Fluoro-6-(pyrimidin-2-yl)phenyl)((2S,3R)-3-methyl-2-(((5-(trifluoromethyl)pyrimidin-2-yl)amino)methyl)piperidin-1-yl)methanone

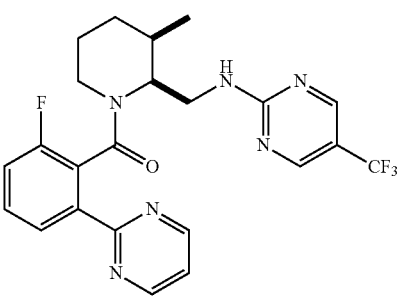

The title compound was prepared following the same general protocol as described for Example A1 using ((2S,3R)-2-(aminomethyl)-3-methylpiperidin-1-yl)(6-fluoro-2-(pyrimidin-2-yl)phenyl)methanone and 2-chloro-5-(trifluoromethyl)pyrimidine. ESI-MS (m/z): 475 [M+1]+.

Example A241

(2-Fluoro-6-(pyrimidin-2-yl)phenyl)((2S,3R)-3-methyl-2-(((5-(trifluoromethyl)pyridin-2-yl)amino)methyl)piperidin-1-yl)methanone

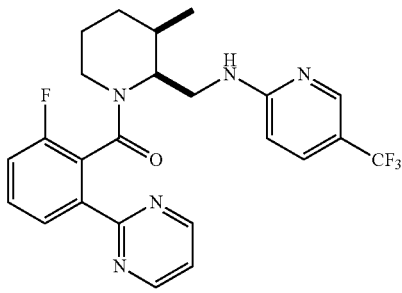 [SMILES: C[C@@H]1CCCN(C(=O)c2c(F)cccc2-c2ncccn2)[C@@H]1CNc1ccc(C(F)(F)F)cn1]

The title compound was prepared following the same general protocol as described for Example A1 using ((2S,3R)-2-(aminomethyl)-3-methylpiperidin-1-yl)(6-fluoro-2-(pyrimidin-2-yl)phenyl)methanone and 2-fluoro-5-(trifluoromethyl)pyridine. ESI-MS (m/z): 474 [M+1]+.

Example A242

(4,5-difluoro-2-(pyrimidin-2-yl)phenyl)((2S,3R)-3-methyl-2-(((5-(trifluoromethyl)pyridin-2-yl)amino)methyl)piperidin-1-yl)methanone

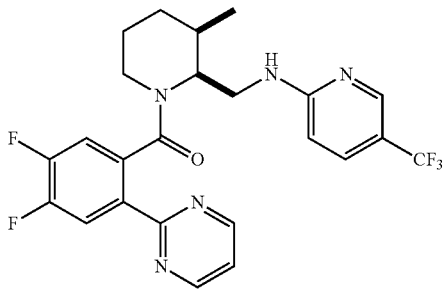 [SMILES: C[C@@H]1CCCN(C(=O)c2cc(F)c(F)cc2-c2ncccn2)[C@@H]1CNc1ccc(C(F)(F)F)cn1]

Step 1. 2-(((2S,3R)-1-(4,5-difluoro-2-iodobenzoyl)-3-methylpiperidin-2-yl)methyl)isoindoline-1,3-dione

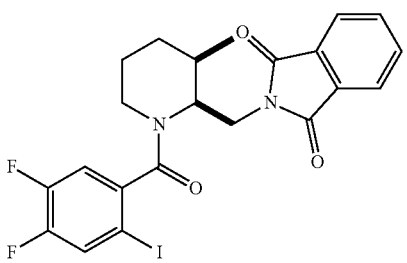 [SMILES: C[C@@H]1CCCN(C(=O)c2cc(F)c(F)cc2I)[C@@H]1CN1C(=O)c2ccccc2C1=O]

A mixture of 2-(((2S,3R)-3-methylpiperidin-2-yl)methyl)isoindoline-1,3-dione (1.89 g, 3.38 mmol), 4,5-difluoro-2-iodobenzoic acid (0.8 g, 2.817 mmol), diisopropylethylamine (1.5 mL, 8.45 mmol) and HATU (1.07, 2.817 mmol) in DMF (15 ml) was stirred at room temperature for 1 h. The reaction mixture was diluted with ethyl acetate and washed with sat'd NaHCO₃ and brine successively. The organic layer was separated, dried with MgSO₄ and concentrated in vacuo. The crude product was purified by chromatography on silica gel (EtOAc/hex) to afford the title compound. MS (ESI) 525 (M+H).

Step 2. 2-(((2S,3R)-1-(4,5-difluoro-2-(pyrimidin-2-yl)benzoyl)-3-methylpiperidin-2-yl)methyl)isoindoline-1,3-dione

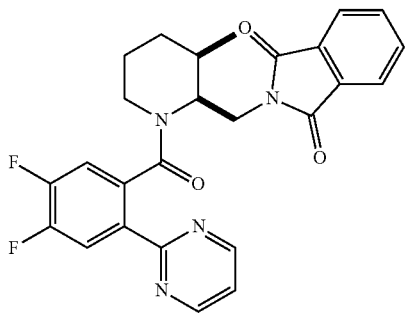 [SMILES: C[C@@H]1CCCN(C(=O)c2cc(F)c(F)cc2-c2ncccn2)[C@@H]1CN1C(=O)c2ccccc2C1=O]

A mixture of 2-(((2S,3R)-1-(4,5-difluoro-2-iodobenzoyl)-3-methylpiperidin-2-yl)methyl)isoindoline-1,3-dione (0.738 g, 1.409 mmol), 2-(tributylstannyl)pyrimidine (0.52, 1.409 mmol), cesium fluoride (0.43 g, 2.818 mmol), CuI (0.027 g, 0.14 mmol) and Pd(PPh₃)₄ (0.16 g, 0.14 mmol) in DMF (15 mL) was degassed and heated at 100° C. oil bath for 16 h. The solvent was removed in vacuo to obtain the crude which was purified by silica gel chromatography (0~100% Hexane/EtOAc) to yield the title compound as a white solid. MS (ESI) 477 (M+H).

Step 3. ((2S,3R)-2-(aminomethyl)-3-methylpiperidin-1-yl)(4,5-difluoro-2-(pyrimidin-2-yl)phenyl)methanone

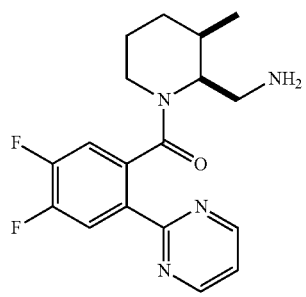 [SMILES: C[C@@H]1CCCN(C(=O)c2cc(F)c(F)cc2-c2ncccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-(((2S,3R)-1-(4,5-difluoro-2-(pyrimidin-2-yl)benzoyl)-3-methylpiperidin-2-yl)methyl)isoindoline-1,3-dione. MS (ESI) 347 (M+H).

437

Step 4: (4,5-difluoro-2-(pyrimidin-2-yl)phenyl)((2S,3R)-3-methyl-2-(((5-(trifluoromethyl)pyridin-2-yl)amino)methyl)piperidin-1-yl)methanone The title compound was prepared following the same general protocol as described for Example A1 using ((2S,3R)-2-(aminomethyl)-3-methylpiperidin-1-yl)(4,5-difluoro-2-(pyrimidin-2-yl)phenyl)methanone and 2-fluoro-5-(trifluoromethyl)pyridine. ESI-MS (m/z): 492 [M+1]+.

Example A243

(4,5-difluoro-2-(pyrimidin-2-yl)phenyl)((2S,3R)-3-methyl-2-(((5-(trifluoromethyl)pyrimidin-2-yl)amino)methyl)piperidin-1-yl)methanone

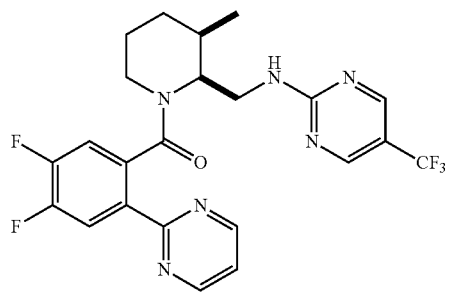 [SMILES: C[C@@H]1CCCN(C(=O)c2cc(F)c(F)cc2-c2ncccn2)[C@@H]1CNc1ncc(C(F)(F)F)cn1]

The title compound was prepared following the same general protocol as described for Example A1 using ((2S,3R)-2-(aminomethyl)-3-methylpiperidin-1-yl)(4,5-difluoro-2-(pyrimidin-2-yl)phenyl)methanone and 2-chloro-5-(trifluoromethyl)pyrimidine. ESI-MS (m/z): 493 [M+1]+.

Example A244

((2S,3R)-2-(((5-chloropyrimidin-2-yl)amino)methyl)-3-methylpiperidin-1-yl)(4,5-difluoro-2-(pyrimidin-2-yl)phenyl)methanone

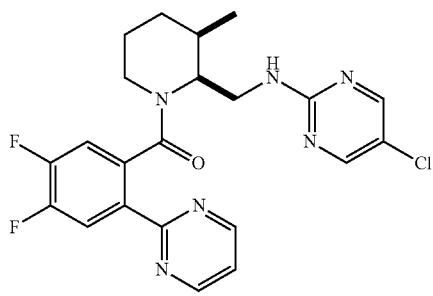 [SMILES: C[C@@H]1CCCN(C(=O)c2cc(F)c(F)cc2-c2ncccn2)[C@@H]1CNc1ncc(Cl)cn1]

The title compound was prepared following the same general protocol as described for Example A1 using ((2S,3R)-2-(aminomethyl)-3-methylpiperidin-1-yl)(4,5-difluoro-2-(pyrimidin-2-yl)phenyl)methanone and 2,5-dichloropyrimidine. ESI-MS (m/z): 459 [M+1]+.

438

Example A246

((2S,3R)-2-(((5-chloropyridin-2-yl)amino)methyl)-3-methylpiperidin-1-yl)(4,5-difluoro-2-(2H-1,2,3-triazol-2-yl)phenyl)methanone

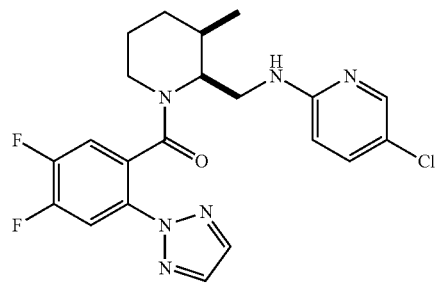

Step 1: 4,5-difluoro-2-(2H-1,2,3-triazol-2-yl)benzoic acid

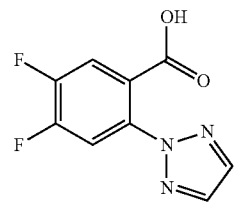 [SMILES: O=C(O)c1cc(F)c(F)cc1-n1nccn1]

The title compound was prepared following the same general protocol as described for 5-methyl-2-(2H-1,2,3-triazol-2-yl)benzoic acid in Example A11 using 4,5-difluoro-2-iodobenzoic acid and 1,2,3-triazole. ESI-MS (m/z): 226 [M+1]+.

Step 2. ((2S,3R)-2-(aminomethyl)-3-methylpiperidin-1-yl)(4,5-difluoro-2-(2H-1,2,3-triazol-2-yl)phenyl)methanone

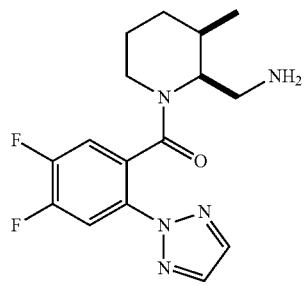 [SMILES: C[C@@H]1CCCN(C(=O)c2cc(F)c(F)cc2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 4,5-difluoro-2-(2H-1,2,3-triazol-2-yl)benzoic acid. MS (ESI) 336, (M+H).

Step 3: ((2S,3R)-2-(((5-chloropyridin-2-yl)amino)methyl)-3-methylpiperidin-1-yl)(4,5-difluoro-2-(2H-1,2,3-triazol-2-yl)phenyl)methanone The title compound was prepared following the same general protocol as described for Example A44 using ((2S,3R)-2-(aminomethyl)-3-methylpiperidin-1-yl)(4,5-difluoro-2-(2H-1,2,3-triazol-2-yl)phenyl)methanone and 2-bromo-5-chloropyridine. ESI-MS (m/z): 447 [M+1]$^+$.

Example A247

((2S,3R)-2-(((5-chloropyrimidin-2-yl)amino)methyl)-3-methylpiperidin-1-yl)(4,5-difluoro-2-(2H-1,2,3-triazol-2-yl)phenyl)methanone

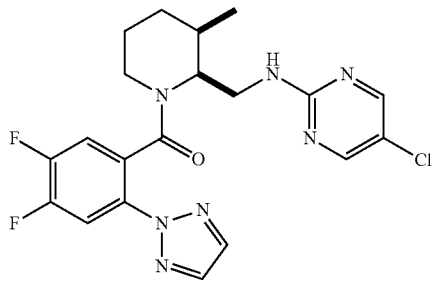

The title compound was prepared following the same general protocol as described for Example A1 using ((2S,3R)-2-(aminomethyl)-3-methylpiperidin-1-yl)(4,5-difluoro-2-(2H-1,2,3-triazol-2-yl)phenyl)methanone and 2,5-dichloropyrimidine. ESI-MS (m/z): 448 [M+1]$^+$.

Example A248

(4,5-difluoro-2-(2H-1,2,3-triazol-2-yl)phenyl)((2S,3R)-3-methyl-2-(((5-(trifluoromethyl)pyrimidin-2-yl)amino)methyl)piperidin-1-yl)methanone

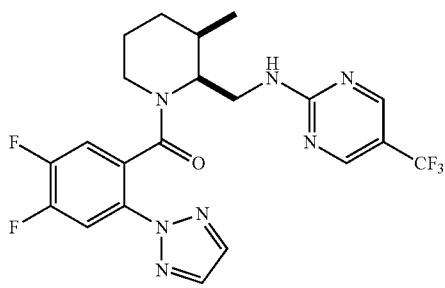 [SMILES: C[C@@H]1CCCN(C(=O)c2cc(F)c(F)cc2-n2nccn2)[C@@H]1CNc1ncc(C(F)(F)F)cn1]

The title compound was prepared following the same general protocol as described for Example A1 using ((2S,3R)-2-(aminomethyl)-3-methylpiperidin-1-yl)(4,5-difluoro-2-(2H-1,2,3-triazol-2-yl)phenyl)methanone and 2-chloro-5-(trifluoromethyl)pyrimidine. ESI-MS (m/z): 482 [M+1]$^+$.

Example A249

(4,5-difluoro-2-(2H-1,2,3-triazol-2-yl)phenyl)((2S,3R)-3-methyl-2-(((5-(trifluoromethyl)pyridin-2-yl)amino)methyl)piperidin-1-yl)methanone

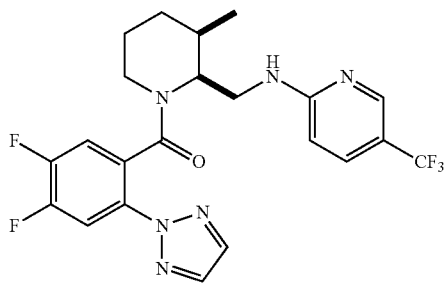 [SMILES: C[C@@H]1CCCN(C(=O)c2cc(F)c(F)cc2-n2nccn2)[C@@H]1CNc1ccc(C(F)(F)F)cn1]

The title compound was prepared following the same general protocol as described for Example A1 using ((2S,3R)-2-(aminomethyl)-3-methylpiperidin-1-yl)(4,5-difluoro-2-(2H-1,2,3-triazol-2-yl)phenyl)methanone and 2-fluoro-5-(trifluoromethyl)pyridine. ESI-MS (m/z): 481 [M+1]$^+$.

Example A250

(4-fluoro-2-(2H-1,2,3-triazol-2-yl)phenyl)((2S,3R)-3-methyl-2-(((5-(trifluoromethyl)pyridin-2-yl)amino)methyl)piperidin-1-yl)methanone

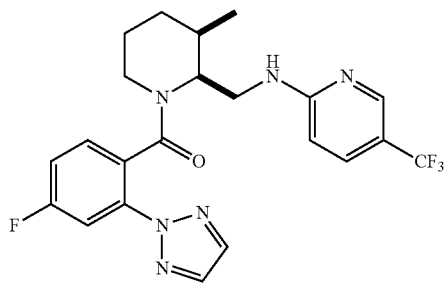 [SMILES: C[C@@H]1CCCN(C(=O)c2ccc(F)cc2-n2nccn2)[C@@H]1CNc1ccc(C(F)(F)F)cn1]

Step 1: 4-fluoro-2-(2H-1,2,3-triazol-2-yl)benzoic acid

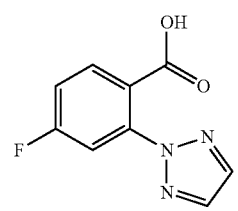 [SMILES: O=C(O)c1ccc(F)cc1-n1nccn1]

The title compound was prepared following the same general protocol as described for 5-methyl-2-(2H-1,2,3-triazol-2-yl)benzoic acid in Example A11 using 4-fluoro-2-iodobenzoic acid and 1,2,3-triazole. ESI-MS (m/z): 208.2 [M+1]$^+$.

Step 2. ((2S,3R)-2-(aminomethyl)-3-methylpiperi-
din-1-yl)(4-fluoro-2-(2H-1,2,3-triazol-2-yl)phenyl)
methanone

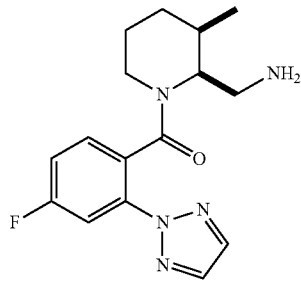 [SMILES: C[C@@H]1CCCN(C(=O)c2ccc(F)cc2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 4,5-difluoro-2-(2H-1,2,3-triazol-2-yl)benzoic acid. MS (ESI) 318.4 (M+H).

Step 3: (4-fluoro-2-(2H-1,2,3-triazol-2-yl)phenyl)
((2S,3R)-3-methyl-2-(((5-(trifluoromethyl)pyridin-2-
yl)amino)methyl)piperidin-1-yl)methanone The title compound was prepared following the same general protocol as described for Example A1 using ((2S,3R)-2-(aminomethyl)-3-methylpiperidin-1-yl)(4-fluoro-2-(2H-1,2,3-triazol-2-yl)phenyl)methanone and 2-fluoro-5-(trifluoromethyl)pyridine. ESI-MS (m/z): 463.4 [M+1]$^+$.

Example A251

(4-fluoro-2-(2H-1,2,3-triazol-2-yl)phenyl)((2S,3R)-
3-methyl-2-(((5-(trifluoromethyl)pyrimidin-2-yl)
amino)methyl)piperidin-1-yl)methanone

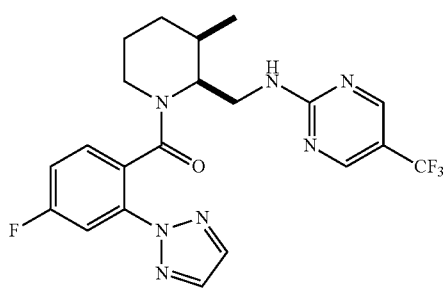 [SMILES: C[C@@H]1CCCN(C(=O)c2ccc(F)cc2-n2nccn2)[C@@H]1CNc1ncc(C(F)(F)F)cn1]

The title compound was prepared following the same general protocol as described for Example A1 using ((2S,3R)-2-(aminomethyl)-3-methylpiperidin-1-yl)(4-fluoro-2-(2H-1,2,3-triazol-2-yl)phenyl)methanone and 2-chloro-5-(trifluoromethyl)pyrimidine. ESI-MS (m/z): 464.4 [M+1]$^+$.

Example A254

((2S,3R)-2-(((5-chloropyridin-2-yl)amino)methyl)-3-
methylpiperidin-1-yl)(3-fluoro-2-(2H-1,2,3-triazol-
2-yl)phenyl)methanone

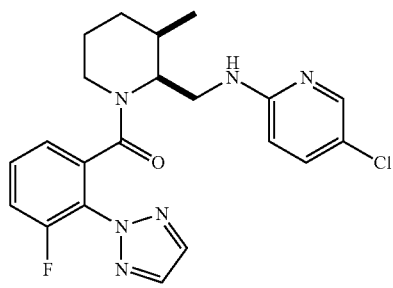 [SMILES: C[C@@H]1CCCN(C(=O)c2cccc(F)c2-n2nccn2)[C@@H]1CNc1ccc(Cl)cn1]

Step 1: 3-fluoro-2-(2H-1,2,3-triazol-2-yl)benzoic
acid

The title compound was prepared following the same general protocol as described for 5-methyl-2-(2H-1,2,3-triazol-2-yl)benzoic acid in Example A11 using 3-fluoro-2-iodobenzoic acid and 1,2,3-triazole. ESI-MS (m/z): 208 [M+1]$^+$.

Step 2. ((2S,3R)-2-(aminomethyl)-3-methylpiperi-
din-1-yl)(3-fluoro-2-(2H-1,2,3-triazol-2-yl)phenyl)
methanone

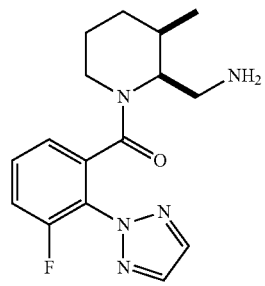 [SMILES: C[C@@H]1CCCN(C(=O)c2cccc(F)c2-n2nccn2)[C@@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 3-fluoro-2-(2H-1,2,3-triazol-2-yl)benzoic acid. MS (ESI) 318 (M+H).

Step 3: ((2S,3R)-2-(((5-chloropyridin-2-yl)amino)
methyl)-3-methylpiperidin-1-yl)(3-fluoro-2-(2H-1,2,
3-triazol-2-yl)phenyl)methanone The title compound was prepared following the same general protocol as described for Example A44 using ((2S,3R)-2-(aminomethyl)-3-methylpiperidin-1-yl)(3-fluoro-2-(2H-1,2,3-triazol-2-yl)phenyl)methanone and 2-bromo-5-chloropyridine. ESI-MS (m/z): 429 [M+1]$^+$.

Example A255

((2S,3R)-2-(((5-chloropyrimidin-2-yl)amino)
methyl)-3-methylpiperidin-1-yl)(3-fluoro-2-(2H-1,2,
3-triazol-2-yl)phenyl)methanone

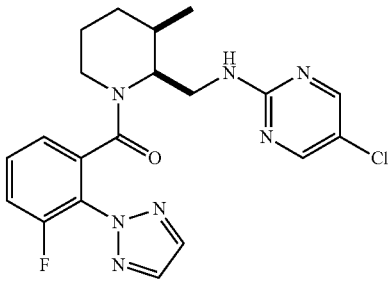

The title compound was prepared following the same general protocol as described for Example A1 using ((2S,3R)-2-(aminomethyl)-3-methylpiperidin-1-yl)(3-fluoro-2-(2H-1,2,3-triazol-2-yl)phenyl)methanone and 2,5-dichloropyrimidine. ESI-MS (m/z): 430 [M+1]$^+$.

Example A256

(3-fluoro-2-(2H-1,2,3-triazol-2-yl)phenyl)((2S,3R)-
3-methyl-2-(((5-(trifluoromethyl)pyrimidin-2-yl)
amino)methyl)piperidin-1-yl)methanone

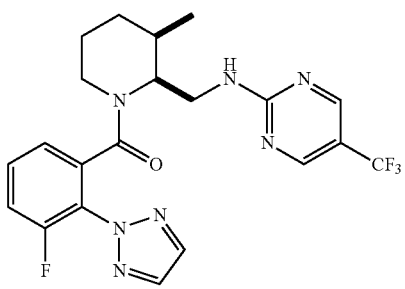

The title compound was prepared following the same general protocol as described for Example A1 using ((2S,3R)-2-(aminomethyl)-3-methylpiperidin-1-yl)(3-fluoro-2-(2H-1,2,3-triazol-2-yl)phenyl)methanone and 2-chloro-5-(trifluoromethyl)pyrimidine. ESI-MS (m/z): 464 [M+1]$^+$.

Example A257

(3-fluoro-2-(2H-1,2,3-triazol-2-yl)phenyl)((2S,3R)-
3-methyl-2-(((5-(trifluoromethyl)pyridin-2-yl)
amino)methyl)piperidin-1-yl)methanone

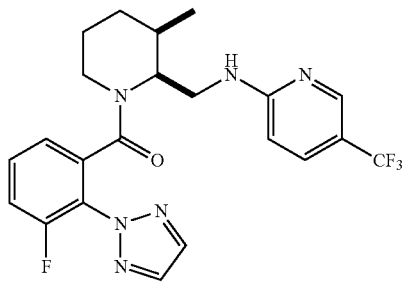

The title compound was prepared following the same general protocol as described for Example A1 using ((2S,3R)-2-(aminomethyl)-3-methylpiperidin-1-yl)(3-fluoro-2-(2H-1,2,3-triazol-2-yl)phenyl)methanone and 2-fluoro-5-(trifluoromethyl)pyridine. ESI-MS (m/z): 463 [M+1]$^+$.

Example A258

(2-fluoro-6-(2H-1,2,3-triazol-2-yl)phenyl)((2S,3R)-
3-methyl-2-(((5-(trifluoromethyl)pyridin-2-yl)
amino)methyl)piperidin-1-yl)methanone

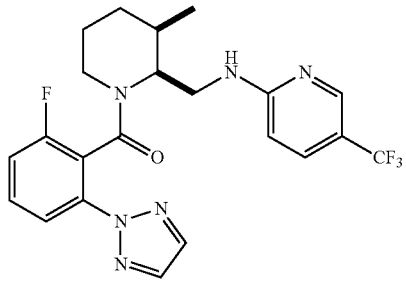 [SMILES: C[C@@H]1CCCN(C(=O)c2c(F)cccc2-n2nccn2)[C@@H]1CNc1ccc(C(F)(F)F)cn1]

Step 1: 2-fluoro-6-(2H-1,2,3-triazol-2-yl)benzoic
acid

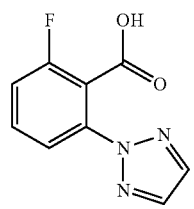 [SMILES: O=C(O)c1c(F)cccc1-n1nccn1]

The title compound was prepared following the same general protocol as described for 5-methyl-2-(2H-1,2,3-triazol-2-yl)benzoic acid in Example A11 using 2-fluoro-6-iodobenzoic acid and 1,2,3-triazole. ESI-MS (m/z): 208 [M+1]$^+$.

Step 2. ((2S,3R)-2-(aminomethyl)-3-methylpiperi-din-1-yl)(2-fluoro-6-(2H-1,2,3-triazol-2-yl)phenyl)methanone

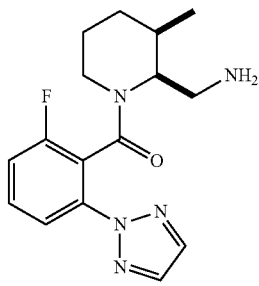

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-fluoro-6-(2H-1,2,3-triazol-2-yl)benzoic acid. MS (ESI) 318 (M+H).

Step 3: (2-fluoro-6-(2H-1,2,3-triazol-2-yl)phenyl)((2S,3R)-3-methyl-2-(((5-(trifluoromethyl)pyridin-2-yl)amino)methyl)piperidin-1-yl)methanone The title compound was prepared following the same general protocol as described for Example A44 using ((2S,3R)-2-(aminomethyl)-3-methylpiperidin-1-yl)(2-fluoro-6-(2H-1,2,3-triazol-2-yl)phenyl)methanone and 2-fluoro-5-(trifluoromethyl)pyridine. ESI-MS (m/z): 463 [M+1]$^+$.

Example A259

(2-fluoro-6-(2H-1,2,3-triazol-2-yl)phenyl)((2S,3R)-3-methyl-2-(((5-(trifluoromethyl)pyrimidin-2-yl)amino)methyl)piperidin-1-yl)methanone

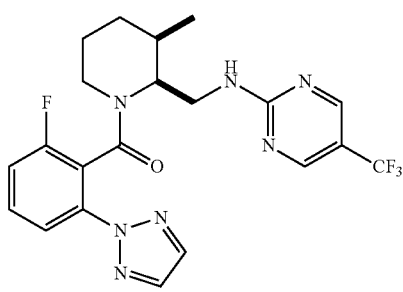 [SMILES: C[C@@H]1CCCN(C(=O)c2c(F)cccc2-n2nccn2)[C@@H]1CNc1ncc(C(F)(F)F)cn1]

The title compound was prepared following the same general protocol as described for Example A1 using ((2S,3R)-2-(aminomethyl)-3-methylpiperidin-1-yl)(2-fluoro-6-(2H-1,2,3-triazol-2-yl)phenyl)methanone and 2-chloro-5-(trifluoromethyl)pyrimidine. ESI-MS (m/z): 464 [M+1]$^+$.

Example A260

((2S,3R)-2-(((5-chloropyrimidin-2-yl)amino)methyl)-3-methylpiperidin-1-yl)(2-fluoro-6-(2H-1,2,3-triazol-2-yl)phenyl)methanone

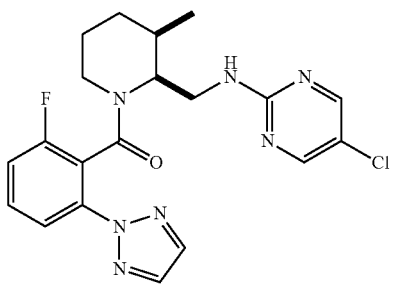 [SMILES: C[C@@H]1CCCN(C(=O)c2c(F)cccc2-n2nccn2)[C@@H]1CNc1ncc(Cl)cn1]

The title compound was prepared following the same general protocol as described for Example A1 using ((2S,3R)-2-(aminomethyl)-3-methylpiperidin-1-yl)(2-fluoro-6-(2H-1,2,3-triazol-2-yl)phenyl)methanone and 2,5-dichloropyrimidine. ESI-MS (m/z): 430 [M+1]$^+$.

Example A261

((2S,3R)-2-(((5-chloropyridin-2-yl)amino)methyl)-3-methylpiperidin-1-yl)(2-fluoro-6-(2H-1,2,3-triazol-2-yl)phenyl)methanone

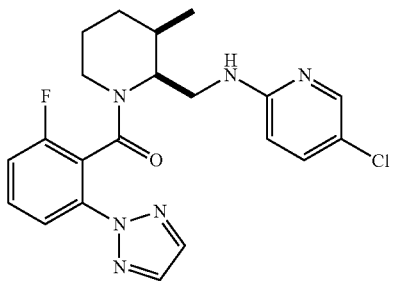 [SMILES: C[C@@H]1CCCN(C(=O)c2c(F)cccc2-n2nccn2)[C@@H]1CNc1ccc(Cl)cn1]

The title compound was prepared following the same general protocol as described for Example A1 using ((2S,3R)-2-(aminomethyl)-3-methylpiperidin-1-yl)(2-fluoro-6-(2H-1,2,3-triazol-2-yl)phenyl)methanone and 2-bromo-5-chloropyridine. ESI-MS (m/z): 429 [M+1]$^+$.

Example 264

((2S,3R)-3-methyl-2-(((5-(trifluoromethyl)pyrimidin-2-yl)amino)methyl)piperidin-1-yl)(2-methyl-6-(2H-1,2,3-triazol-2-yl)phenyl)methanone

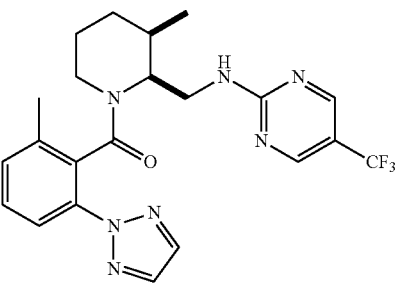 [SMILES: Cc1cccc(-n2nccn2)c1C(=O)N1CCC[C@@H](C)[C@H]1CNc1ncc(C(F)(F)F)cn1]

Step 1: 2-methyl-6-(2H-1,2,3-triazol-2-yl)benzoic acid

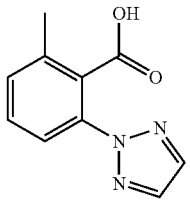

The title compound was prepared following the same general protocol as described for 5-methyl-2-(2H-1,2,3-triazol-2-yl)benzoic acid in Example A11 using 6-methyl-2-iodobenzoic acid and 1,2,3-triazole. ESI-MS (m/z): 204 [M+1]$^+$.

Step 2: ((2S,3R)-2-(aminomethyl)-3-methylpiperidin-1-yl)(2-methyl-6-(2H-1,2,3-triazol-2-yl)phenyl)methanone

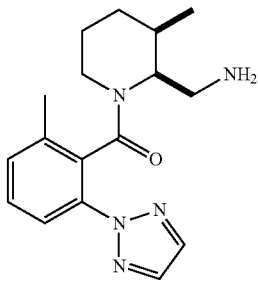 [SMILES: Cc1cccc(-n2nccn2)c1C(=O)N1CCC[C@@H](C)[C@H]1CN]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 2-methyl-6-(2H-1,2,3-triazol-2-yl)benzoic acid. ESI-MS m/z: 314 [M+1]$^+$.

Step 3: ((2S,3R)-3-methyl-2-(((5-(trifluoromethyl)pyrimidin-2-yl)amino)methyl)piperidin-1-yl)(2-methyl-6-(2H-1,2,3-triazol-2-yl)phenyl)methanone The title compound was prepared following the same general protocol as described for Example A1 using ((2S,3R)-2-(aminomethyl)-3-methylpiperidin-1-yl)(2-methyl-6-(2H-1,2,3-triazol-2-yl)phenyl)methanone and 2-chloro-5-(trifluoromethyl)pyrimidine. ESI-MS (m/z): 460 [M+1]$^+$.

Example 265

((2S,3R)-3-methyl-2-(((5-(trifluoromethyl)pyridin-2-yl)amino)methyl)piperidin-1-yl)(2-methyl-6-(2H-1,2,3-triazol-2-yl)phenyl)methanone

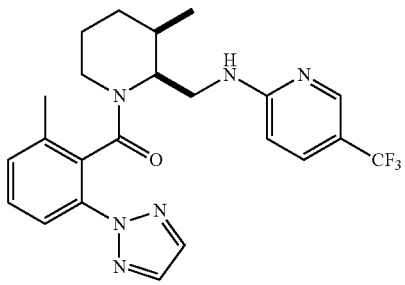 [SMILES: Cc1cccc(-n2nccn2)c1C(=O)N1CCC[C@@H](C)[C@H]1CNc1ccc(C(F)(F)F)cn1]

The title compound was prepared following the same general protocol as described for Example A264 using ((2S,3R)-2-(aminomethyl)-3-methylpiperidin-1-yl)(2-methyl-6-(2H-1,2,3-triazol-2-yl)phenyl)methanone and 2-fluoro-5-(trifluoromethyl)pyridine. ESI-MS (m/z): 459 [M+1]$^+$.

Example A266

((2S,3R)-3-methyl-2-(((5-(trifluoromethyl)pyridin-2-yl)amino)methyl)piperidin-1-yl)(3-methyl-2-(2H-1,2,3-triazol-2-yl)phenyl)methanone

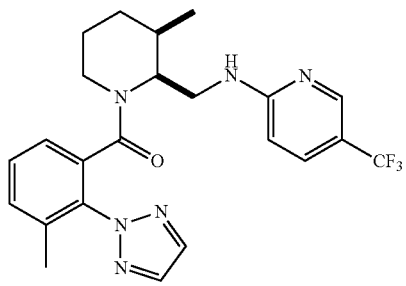 [SMILES: Cc1cccc(C(=O)N2CCC[C@@H](C)[C@H]2CNc2ccc(C(F)(F)F)cn2)c1-n1nccn1]

Step 1: 3-methyl-2-(2H-1,2,3-triazol-2-yl)benzoic acid

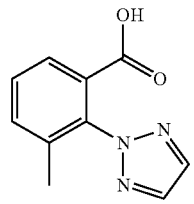

The title compound was prepared following the same general protocol as described for 5-methyl-2-(2H-1,2,3-triazol-2-yl)benzoic acid in Example A11 using 3-methyl-2-iodobenzoic acid and 1,2,3-triazole. ESI-MS (m/z): 204 [M+1]$^+$.

Step 2. ((2S,3R)-2-(aminomethyl)-3-methylpiperidin-1-yl)(3-methyl-2-(2H-1,2,3-triazol-2-yl)phenyl)methanone

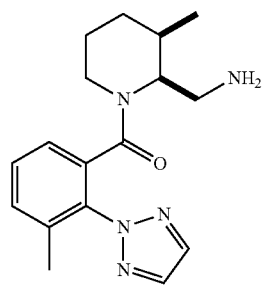 [SMILES: Cc1cccc(C(=O)N2CCC[C@@H](C)[C@H]2CN)c1-n1nccn1]

The title compound was prepared following the same general protocol as described for ((2S,3R)-2-(aminomethyl)-3-methylpiperidin-1-yl)(5-methyl-2-(1-methyl-1H-pyrazol-4-yl)phenyl)methanone in Example A1 using 3-methyl-2-(2H-1,2,3-triazol-2-yl)benzoic acid. MS (ESI) 314(M+H).

Step 3: ((2S,3R)-3-methyl-2-(((5-(trifluoromethyl)pyridin-2-yl)amino)methyl)piperidin-1-yl)(3-methyl-2-(2H-1,2,3-triazol-2-yl)phenyl)methanone The title compound was prepared following the same general protocol as described for Example A1 using ((2S,3R)-2-(aminomethyl)-3-methylpiperidin-1-yl)(3-methyl-2-(2H-1,2,3-triazol-2-yl)phenyl)methanone and 2-fluoro-5-(trifluoromethyl)pyridine. ESI-MS (m/z): 459 [M+1]$^+$.

Example A267

((2S,3R)-3-methyl-2-(((5-(trifluoromethyl)pyrimidin-2-yl)amino)methyl)piperidin-1-yl)(3-methyl-2-(2H-1,2,3-triazol-2-yl)phenyl)methanone

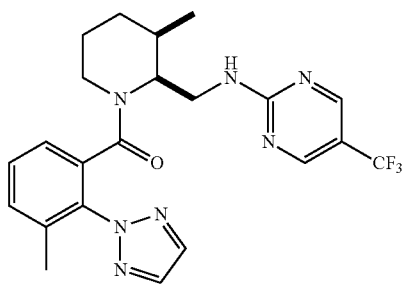 [SMILES: Cc1cccc(C(=O)N2CCC[C@@H](C)[C@H]2CNc2ncc(C(F)(F)F)cn2)c1-n1nccn1]

The title compound was prepared following the same general protocol as described for Example A1 using ((2S,3R)-2-(aminomethyl)-3-methylpiperidin-1-yl)(2-fluoro-6-(2H-1,2,3-triazol-2-yl)phenyl)methanone and 2-chloro-5-(trifluoromethyl)pyrimidine. ESI-MS (m/z): 460 [M+1]$^+$.

Example A268

((2S,3R)-2-(((5-chloropyrimidin-2-yl)amino)methyl)-3-methylpiperidin-1-yl)(3-methyl-2-(2H-1,2,3-triazol-2-yl)phenyl)methanone

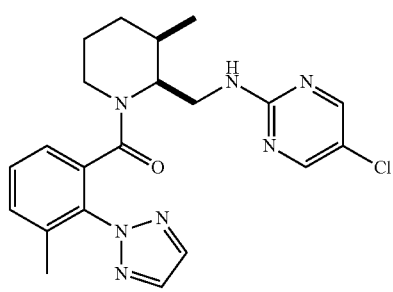 [SMILES: Cc1cccc(C(=O)N2CCC[C@@H](C)[C@H]2CNc2ncc(Cl)cn2)c1-n1nccn1]

The title compound was prepared following the same general protocol as described for Example A1 using ((2S,3R)-2-(aminomethyl)-3-methylpiperidin-1-yl)(2-fluoro-6-(2H-1,2,3-triazol-2-yl)phenyl)methanone and 2,5-dichloropyrimidine. ESI-MS (m/z): 426 [M+1]$^+$.

Example A271

((2S,3R)-2-(((5-chloropyrimidin-2-yl)amino)methyl)-3-methylpiperidin-1-yl)(4-methyl-2-(2H-1,2,3-triazol-2-yl)phenyl)methanone

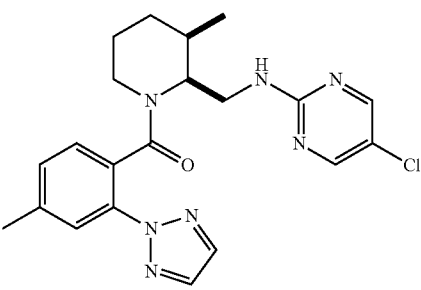 [SMILES: Cc1ccc(C(=O)N2CCC[C@@H](C)[C@H]2CNc2ncc(Cl)cn2)c(-n2nccn2)c1]

The title compound was prepared following the same general protocol as described for Example A89 using ((2S,3R)-2-(aminomethyl)-3-methylpiperidin-1-yl)(4-methyl-2-(2H-1,2,3-triazol-2-yl)phenyl)methanone and 2,5-dichloropyrimidine. ESI-MS (m/z): 426 [M+1]$^+$.

Example A272

((2S,3R)-3-methyl-2-(((5-(trifluoromethyl)pyrimidin-2-yl)amino)methyl)piperidin-1-yl)(4-methyl-2-(2H-1,2,3-triazol-2-yl)phenyl)methanone

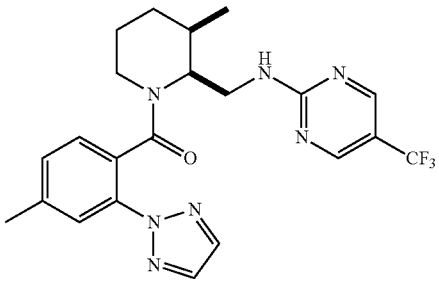 [SMILES: Cc1ccc(C(=O)N2CCC[C@@H](C)[C@H]2CNc2ncc(C(F)(F)F)cn2)c(-n2nccn2)c1]

The title compound was prepared following the same general protocol as described for Example A89 using ((2S,3R)-2-(aminomethyl)-3-methylpiperidin-1-yl)(4-methyl-2-(2H-1,2,3-triazol-2-yl)phenyl)methanone and 2-chloro-5-(trifluoromethyl)pyrimidine. ESI-MS (m/z): 460.2 [M+1]$^+$.

Example A273

((2S,3R)-3-methyl-2-(((5-(trifluoromethyl)pyridin-2-yl)amino)methyl)piperidin-1-yl)(4-methyl-2-(2H-1,2,3-triazol-2-yl)phenyl)methanone

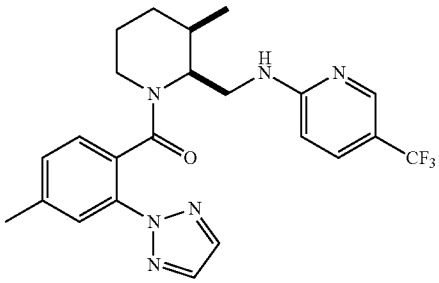 [SMILES: Cc1ccc(C(=O)N2CCC[C@@H](C)[C@H]2CNc2ccc(C(F)(F)F)cn2)c(-n2nccn2)c1]

The title compound was prepared following the same general protocol as described for Example A89 using ((2S,3R)-2-(aminomethyl)-3-methylpiperidin-1-yl)(4-methyl-2-(2H-1,2,3-triazol-2-yl)phenyl)methanone and 2-fluoro-5-(trifluoromethyl)pyrimidine. ESI-MS (m/z): 459 [M+1]⁺.

Example A298

((2S,3R)-3-methyl-2-(((5-(trifluoromethyl)pyridin-2-yl)amino)methyl)piperidin-1-yl)(3-methyl-2-(pyrimidin-2-yl)phenyl)methanone

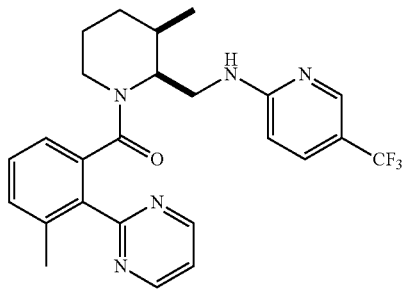 [SMILES: Cc1cccc(C(=O)N2CCC[C@@H](C)[C@H]2CNc2ccc(C(F)(F)F)cn2)c1-c1ncccn1]

The title compound was prepared following the same general protocol as described for Example A230 using 2-iodo-3-methylbenzoic acid to make ((2S,3R)-2-(aminomethyl)-3-methylpiperidin-1-yl)(3-methyl-2-(pyrimidin-2-yl)phenyl)methanone and 2-fluoro-5-(trifluoromethyl)pyridine. ESI-MS (m/z): 470 [M+1]⁺.

Example A299

((2S,3R)-3-methyl-2-(((5-(trifluoromethyl)pyrimidin-2-yl)amino)methyl)piperidin-1-yl)(3-methyl-2-(pyrimidin-2-yl)phenyl)methanone

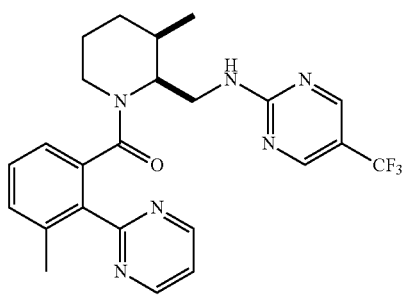 [SMILES: Cc1cccc(C(=O)N2CCC[C@@H](C)[C@H]2CNc2ncc(C(F)(F)F)cn2)c1-c1ncccn1]

The title compound was prepared following the same general protocol as described for Example A298 using ((2S,3R)-2-(aminomethyl)-3-methylpiperidin-1-yl)(3-methyl-2-(pyrimidin-2-yl)phenyl)methanone and 2-chloro-5-(trifluoromethyl)pyrimidine. ESI-MS (m/z): 471 [M+1]⁺.

Example A306

((2S,3R)-3-methyl-2-(((5-(trifluoromethyl)pyridin-2-yl)amino)methyl)piperidin-1-yl)(2-methyl-6-(pyrimidin-2-yl)phenyl)methanone

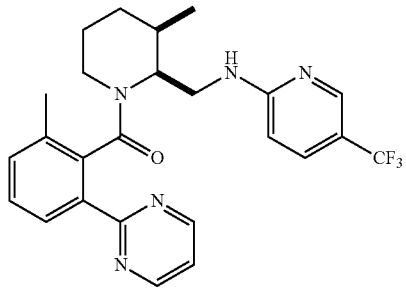 [SMILES: Cc1cccc(-c2ncccn2)c1C(=O)N1CCC[C@@H](C)[C@H]1CNc1ccc(C(F)(F)F)cn1]

The title compound was prepared following the same general protocol as described for Example A230 using 2-iodo-6-methylbenzoic acid to make ((2S,3R)-2-(aminomethyl)-3-methylpiperidin-1-yl)(2-methyl-6-(pyrimidin-2-yl)phenyl)methanone and 2-fluoro-5-(trifluoromethyl)pyridine. ESI-MS (m/z): 470 [M+1]⁺.

Example A307

((2S,3R)-3-methyl-2-(((5-(trifluoromethyl)pyrimidin-2-yl)amino)methyl)piperidin-1-yl)(2-methyl-6-(pyrimidin-2-yl)phenyl)methanone

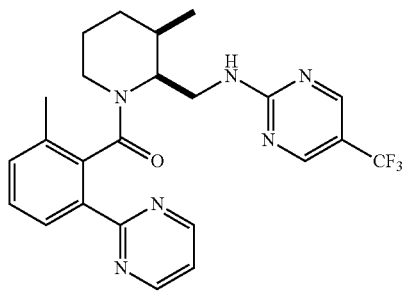

The title compound was prepared following the same general protocol as described for Example A306 using ((2S,3R)-2-(aminomethyl)-3-methylpiperidin-1-yl)(2-methyl-6-(pyrimidin-2-yl)phenyl)methanone and 2-chloro-5-(trifluoromethyl)pyrimidine. ESI-MS (m/z): 471 [M+1]⁺.

Example A310

((2S,3R)-2-(((5-chloropyrimidin-2-yl)amino)methyl)-3-methylpiperidin-1-yl)(3-methyl-2-(2H-1,2,3-triazol-2-yl)phenyl)methanone

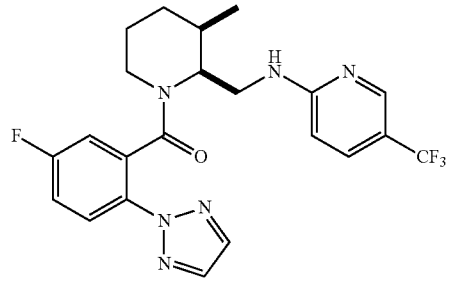

The title compound was prepared following the same general protocol as described for Example A1 using ((2S, 3R)-2-(aminomethyl)-3-methylpiperidin-1-yl)(5-fluoro-2-(2H-1,2,3-triazol-2-yl)phenyl)methanone and 2-fluoro-5-(trifluoromethyl)pyridine. ESI-MS (m/z): 463 [M+1]$^+$.

Example A311

(5-(4-fluorophenyl)-2-methylthiazol-4-yl)((2S,3S)-3-methyl-2-(((5-(trifluoromethyl)pyrimidin-2-yl)amino)methyl)piperidin-1-yl)methanone

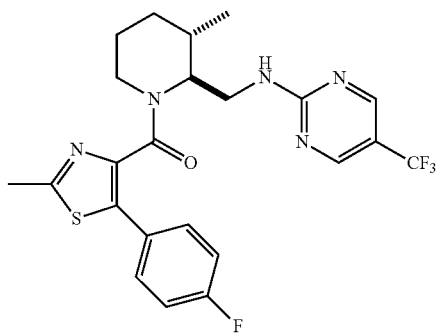 [SMILES: Cc1nc(C(=O)N2CCC[C@H](C)[C@H]2CNc2ncc(C(F)(F)F)cn2)c(-c2ccc(F)cc2)s1]

The title compound was prepared following the same general protocol as described for Example A1 using ((2S, 3S)-2-(aminomethyl)-3-methylpiperidin-1-yl)(5-(4-fluorophenyl)-2-methylthiazol-4-yl)methanone and 2-chloro-5-(trifluoromethyl)pyrimidine. ESI-MS (m/z): 494 [M+1]$^+$.

Example A312

(S)-(4,4-difluoro-2-(((5-(trifluoromethyl)pyrimidin-2-yl)amino)methyl)piperidin-1-yl)(5-methyl-2-(pyrimidin-2-yl)phenyl)methanone

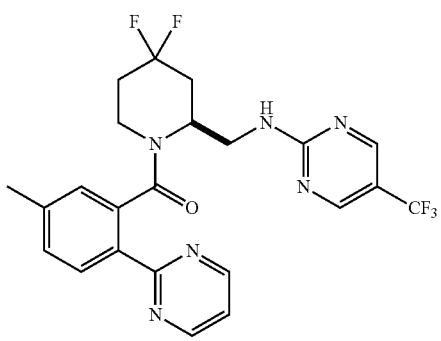 [SMILES: Cc1ccc(-c2ncccn2)c(C(=O)N2CCC(F)(F)C[C@H]2CNc2ncc(C(F)(F)F)cn2)c1]

The title compound was prepared following the same general protocol as described for Example A210 using 2-((4,4-difluoropiperidin-2-yl)methyl)isoindoline-1,3-dione and 5-methyl-2-(pyrimidin-2-yl)benzoic acid and Example A45 using 2-chloro-5-(trifluoromethyl)pyrimidine. ESI-MS (m/z): 493 (M+H).

Example A313

(2-(2H-1,2,3-triazol-2-yl)phenyl)((2S,3R)-3-methyl-2-(((5-(trifluoromethyl)pyrimidin-2-yl)amino)methyl)piperidin-1-yl)methanone

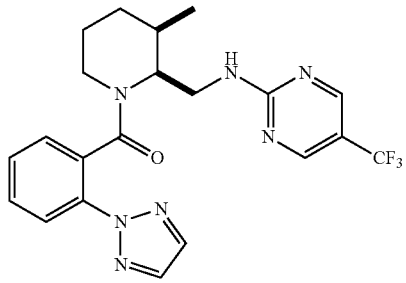 [SMILES: C[C@@H]1CCCN(C(=O)c2ccccc2-n2nccn2)[C@@H]1CNc1ncc(C(F)(F)F)cn1]

The title compound was prepared following the same general protocol as described for Example A1 using (2-(2H-1,2,3-triazol-2-yl)phenyl)((2S,3R)-2-(aminomethyl)-3-methylpiperidin-1-yl)methanone and 2-chloro-5-(trifluoromethyl)pyrimidine. ESI-MS (m/z): 446 [M+1]$^+$.

Example A314

(2-(2H-1,2,3-triazol-2-yl)phenyl)((2S,3R)-3-methyl-2-(((5-(trifluoromethyl)pyridin-2-yl)amino)methyl)piperidin-1-yl)methanone

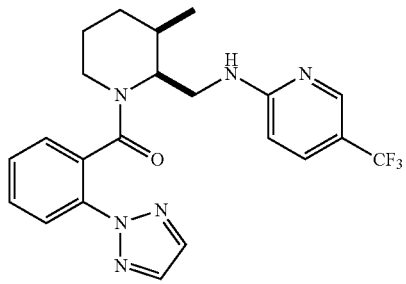

The title compound was prepared following the same general protocol as described for Example A1 using (2-(2H-1,2,3-triazol-2-yl)phenyl)((2S,3R)-2-(aminomethyl)-3-methylpiperidin-1-yl)methanone and 2-fluoro-5-(trifluoromethyl)pyridine. ESI-MS (m/z): 445 [M+1]$^+$.

Example A315

((2R,3S)-3-methyl-2-(((5-(trifluoromethyl)pyridin-2-yl)amino)methyl)piperidin-1-yl)(5-methyl-2-(1-methyl-1H-pyrazol-4-yl)phenyl)methanone

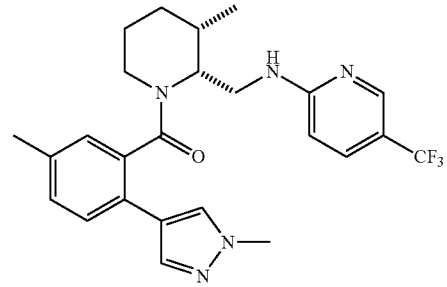 [SMILES: Cc1ccc(-c2cnn(C)c2)c(C(=O)N2CCC[C@H](C)[C@@H]2CNc2ccc(C(F)(F)F)cn2)c1]

The title compound is the (+)-enantiomer of Example A1 and was prepared following the same general protocol as

Example A316

((2S,3R)-3-methyl-2-(((5-(trifluoromethyl)pyridin-2-yl)amino)methyl)piperidin-1-yl)(2-(pyrimidin-2-yl)phenyl)methanone

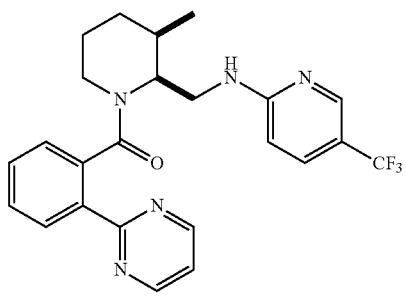 [SMILES: C[C@@H]1CCCN(C(=O)c2ccccc2-c2ncccn2)[C@@H]1CNc1ccc(C(F)(F)F)cn1]

The title compound was prepared following the same general protocol as described for Example A230 using 2-iodobenzoic acid to make ((2S,3R)-2-(aminomethyl)-3-methylpiperidin-1-yl)(2-(pyrimidin-2-yl)phenyl)methanone and 2-fluoro-5-(trifluoromethyl)pyridine. ESI-MS (m/z): 456 [M+1]+.

Example A317

((2S,3R)-3-methyl-2-(((5-(trifluoromethyl)pyrimidin-2-yl)amino)methyl)piperidin-1-yl)(2-(pyrimidin-2-yl)phenyl)methanone

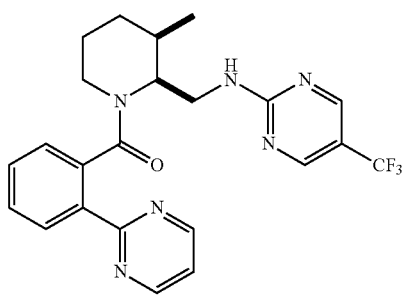 [SMILES: C[C@@H]1CCCN(C(=O)c2ccccc2-c2ncccn2)[C@@H]1CNc1ncc(C(F)(F)F)cn1]

The title compound was prepared following the same general protocol as described for Example A316 using ((2S,3R)-2-(aminomethyl)-3-methylpiperidin-1-yl)(2-(pyrimidin-2-yl)phenyl)methanone and 2-chloro-5-(trifluoromethyl)pyrimidine. ESI-MS (m/z): 457 [M+1]+.

Example A318

(2-fluoro-3-methyl-6-(2H-1,2,3-triazol-2-yl)phenyl)((2S,3R)-3-methyl-2-(((5-(trifluoromethyl)pyridin-2-yl)amino)methyl)piperidin-1-yl)methanone

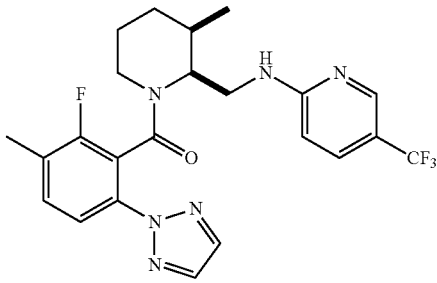 [SMILES: Cc1ccc(-n2nccn2)c(C(=O)N2CCC[C@@H](C)[C@H]2CNc2ccc(C(F)(F)F)cn2)c1F]

Step 1. 2-fluoro-3-methyl-6-(2H-1,2,3-triazol-2-yl)benzoic acid

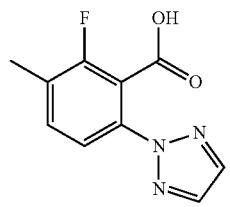 [SMILES: Cc1ccc(-n2nccn2)c(C(=O)O)c1F]

The title compound was synthesized following the same general protocol as described in Example A11 using 2-fluoro-6-iodo-3-methylbenzoic acid and 2H-1,2,3-triazole. ESI-MS (m/z): 222 [M+1]+.

Step 2: (2-fluoro-3-methyl-6-(2H-1,2,3-triazol-2-yl)phenyl)((2S,3R)-3-methyl-2-(((5-(trifluoromethyl)pyridin-2-yl)amino)methyl)piperidin-1-yl)methanone The title compound was prepared following the same general protocol as described in Example A1, using 2-fluoro-3-methyl-6-(2H-1,2,3-triazol-2-yl)benzoic acid, 2-(((2S,3R)-3-methylpiperidin-2-yl)methyl)isoindoline-1,3-dione and 2-fluoro-5-(trifluoromethyl)pyridine. ESI-MS (m/z): 477 [M+1]+.

Example A319

(2-fluoro-3-methyl-6-(2H-1,2,3-triazol-2-yl)phenyl)((2S,3R)-3-methyl-2-(((5-(trifluoromethyl)pyrimidin-2-yl)amino)methyl)piperidin-1-yl)methanone

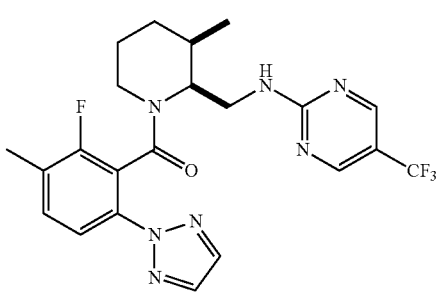 [SMILES: Cc1ccc(-n2nccn2)c(C(=O)N2CCC[C@@H](C)[C@H]2CNc2ncc(C(F)(F)F)cn2)c1F]

The title compound was prepared following the same general protocol as described in Example A318, using 2-fluoro-3-methyl-6-(2H-1,2,3-triazol-2-yl)benzoic acid, 2-(((2S,3R)-3-methylpiperidin-2-yl)methyl)isoindoline-1,3-dione and 2-fluoro-5-(trifluoromethyl)pyrimidine. ESI-MS (m/z): 478 [M+1]+.

Example A322

3-((2S,3R)-3-methyl-2-(((5-(trifluoromethyl)pyrimidin-2-yl)amino)methyl)piperidine-1-carbonyl)-4-(2H-1,2,3-triazol-2-yl)benzonitrile

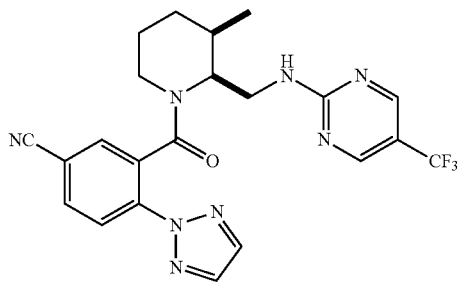 [SMILES: C[C@@H]1CCCN(C(=O)c2cc(C#N)ccc2-n2nccn2)[C@@H]1CNc1ncc(C(F)(F)F)cn1]

Step 1: 5-cyano-2-(2H-1,2,3-triazol-2-yl)benzoic acid

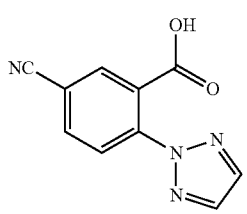 [SMILES: N#Cc1ccc(-n2nccn2)c(C(=O)O)c1]

The title compound was synthesized following the protocol as described in Boss, C. et al., WO2012/085852. ESI-MS (m/z): 215 [M+H]+.

Step 2: 3-((2S,3R)-3-methyl-2-(((5-(trifluoromethyl)pyrimidin-2-yl)amino)methyl)piperidine-1-carbonyl)-4-(2H-1,2,3-triazol-2-yl)benzonitrile The title compound was prepared following the same general protocol as described in Example A1, using 5-cyano-2-(2H-1,2,3-triazol-2-yl)benzoic acid, 2-(((2S,3R)-3-methylpiperidin-2-yl)methyl)isoindoline-1,3-dione and 2-fluoro-5-(trifluoromethyl)pyrimidine. ESI-MS (m/z): 471 [M+1]+.

Example A323

3-((2S,3R)-3-methyl-2-(((5-(trifluoromethyl)pyrimidin-2-yl)amino)methyl)piperidine-1-carbonyl)-4-(pyrimidin-2-yl)benzonitrile

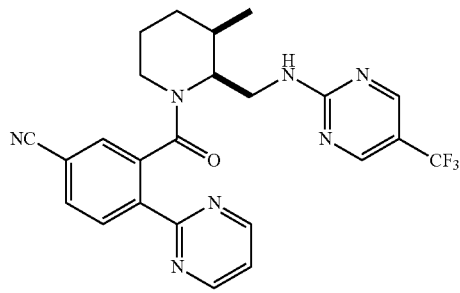 [SMILES: C[C@@H]1CCCN(C(=O)c2cc(C#N)ccc2-c2ncccn2)[C@@H]1CNc1ncc(C(F)(F)F)cn1]

The title compound was prepared following the same general protocol as described for Example A230 using 5-cyano-2-iodobenzoic acid to make 3-((2S,3R)-2-(aminomethyl)-3-methylpiperidine-1-carbonyl)-4-(pyrimidin-2-yl)benzonitrile and 2-chloro-5-(trifluoromethyl)pyrimidine. ESI-MS (m/z): 482 [M+1]+.

Example A336

(2,3-difluoro-6-(2H-1,2,3-triazol-2-yl)phenyl)((2S,3R)-3-methyl-2-(((5-(trifluoromethyl)pyridin-2-yl)amino)methyl)piperidin-1-yl)methanone

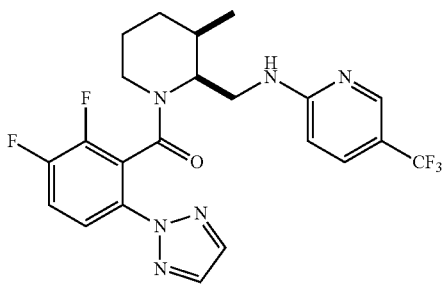 [SMILES: C[C@@H]1CCCN(C(=O)c2c(-n3nccn3)ccc(F)c2F)[C@@H]1CNc1ccc(C(F)(F)F)cn1]

Step 1: 2,3-difluoro-6-(2H-1,2,3-triazol-2-yl)benzoic acid

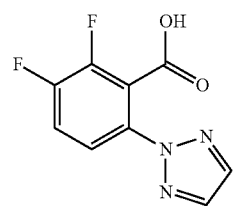 [SMILES: O=C(O)c1c(-n2nccn2)ccc(F)c1F]

The title compound was synthesized following the same general protocol as described in Example A11 using 2,3-difluoro-6-iodobenzoic acid and 2H-1,2,3-triazole. ESI-MS (m/z): 226 [M+1]+.

Step 2: (2,3-difluoro-6-(2H-1,2,3-triazol-2-yl)phenyl)((2S,3R)-3-methyl-2-(((5-(trifluoromethyl)pyridin-2-yl)amino)methyl)piperidin-1-yl)methanone The title compound was prepared following the same general protocol as described in Example A1, using 2,3-difluoro-6-(2H-1,2,3-triazol-2-yl)benzoic acid, 2-(((2S,3R)-3-methylpiperidin-2-yl)methyl)isoindoline-1,3-dione and 2-fluoro-5-(trifluoromethyl)pyridine. ESI-MS (m/z): 481 [M+1]⁺.

Example A337

(2,3-difluoro-6-(2H-1,2,3-triazol-2-yl)phenyl)((2S,3R)-3-methyl-2-(((5-(trifluoromethyl)pyrimidin-2-yl)amino)methyl)piperidin-1-yl)methanone

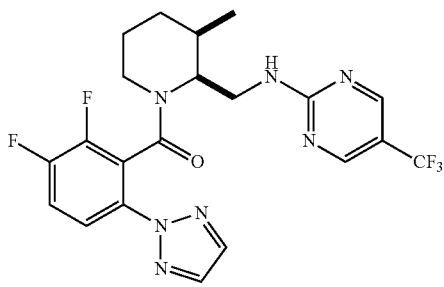 [SMILES: C[C@@H]1CCCN(C(=O)c2c(-n3nccn3)ccc(F)c2F)[C@@H]1CNc1ncc(C(F)(F)F)cn1]

The title compound was prepared following the same general protocol as described in Example A1, using 2,3-difluoro-6-(2H-1,2,3-triazol-2-yl)benzoic acid, 2-(((2S,3R)-3-methylpiperidin-2-yl)methyl)isoindoline-1,3-dione and 2-chloro-5-(trifluoromethyl)pyrimidine. ESI-MS (m/z): 482 [M+1]⁺.

Example A338

(2-fluoro-3-methoxy-6-(2H-1,2,3-triazol-2-yl)phenyl)((2S,3R)-3-methyl-2-(((5-(trifluoromethyl)pyridin-2-yl)amino)methyl)piperidin-1-yl)methanone

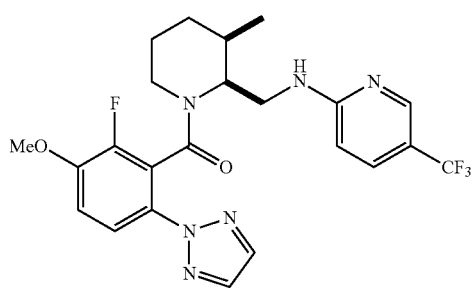 [SMILES: COc1ccc(-n2nccn2)c(C(=O)N2CCC[C@@H](C)[C@H]2CNc2ccc(C(F)(F)F)cn2)c1F]

Step 1: 2-fluoro-3-methoxy-6-(2H-1,2,3-triazol-2-yl)benzoic acid

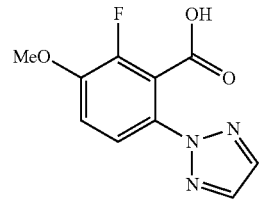 [SMILES: COc1ccc(-n2nccn2)c(C(=O)O)c1F]

The title compound was synthesized following the same general protocol as described in Example A11 using 2-fluoro-6-iodo-3-methoxybenzoic acid and 2H-1,2,3-triazole. ESI-MS (m/z): 238 [M+1]⁺.

Step 2: (2-fluoro-3-methoxy-6-(2H-1,2,3-triazol-2-yl)phenyl)((2S,3R)-3-methyl-2-(((5-(trifluoromethyl)pyridin-2-yl)amino)methyl)piperidin-1-yl)methanone The title compound was prepared following the same general protocol as described in Example A1, using 2-fluoro-3-methoxy-6-(2H-1,2,3-triazol-2-yl)benzoic acid, 2-(((2S,3R)-3-methylpiperidin-2-yl)methyl)isoindoline-1,3-dione and 2-fluoro-5-(trifluoromethyl)pyridine. ESI-MS (m/z): 493 [M+1]⁺.

Example A339

(2-fluoro-3-methoxy-6-(2H-1,2,3-triazol-2-yl)phenyl)((2S,3R)-3-methyl-2-(((5-(trifluoromethyl)pyrimidin-2-yl)amino)methyl)piperidin-1-yl)methanone

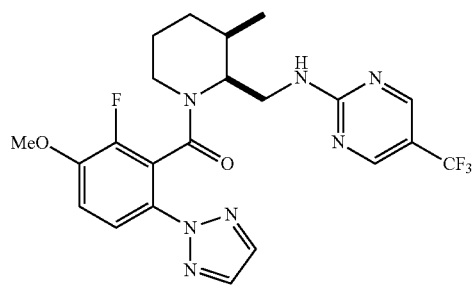 [SMILES: COc1ccc(-n2nccn2)c(C(=O)N2CCC[C@@H](C)[C@H]2CNc2ncc(C(F)(F)F)cn2)c1F]

The title compound was prepared following the same general protocol as described in Example A1, using 2-fluoro-3-methoxy-6-(2H-1,2,3-triazol-2-yl)benzoic acid, 2-(((2S,3R)-3-methylpiperidin-2-yl)methyl)isoindoline-1,3-dione and 2-chloro-5-(trifluoromethyl)pyrimidine. ESI-MS (m/z): 494 [M+1]⁺.

Compounds A238P, A245P, A252P-A253P, A262P-A263P, A269P-A270P, A274P-A297P, A300P-A305P, A308P-A309P, A320P-A321P, A324P-A335P, and A340P-A389P (shown in Table 1A) are prepared using methods analogous to those described in the preceding examples.

Orexin Receptor Cell-based Functional Assay.

Measurement of $[Ca^{2+}]i$ using a FLIPR: CHO—$OX_1$ or CHO—$OX_2$ cells are seeded into black-walled clear-base 384-well plates (Costar) at a density of 20,000 cells per well in F12-K medium supplemented with 10% FBS and selection antibiotic (500 ug/ml G418 or 15 ug/ml Blasticidin) and cultured overnight. The cells are incubated with equal volume of calcium 4 loading buffer (Molecular Devices, Inc.) containing 2.5 mM probenecid at 37° C. for 30 min, followed by putative $OX_1$ or $OX_2$ receptor antagonists (dose-range 0.1 nM-10 µM) for another 30 min. The plates are then placed into a FLIPR (Molecular Devices, Inc.) to monitor fluorescence (1 excitation 488 nm, 1 emission 540 nm) before and after the addition of $EC_{90}$ of [OXA]. Data for compounds tested in this assay are presented in Tables 2 and 2A.

TABLE 2

$IC_{50}$ Bioactivity of Exemplary Compounds of the Invention with Respect to $OX_1$ and $OX_2$

| Compound | $OX_1(\mu M)$ | $OX_2(\mu M)$ |
| --- | --- | --- |
| 1 | 0.001 | 0.008 |
| 2 | 0.001 | 0.007 |
| 3 | 0.002 | 0.036 |
| 4 | 0.088 | 1.0 |
| 5 | 0.006 | 0.040 |
| 6 | 0.030 | 0.70 |
| 7 | 0.15 | 0.075 |
| 8 | 0.003 | 0.060 |
| 9 | 0.015 | 0.085 |
| 10 | <3.0 | NT |
| 11 | 0.008 | 4.9 |
| 12 | 0.004 | 0.45 |
| 13 | 0.009 | 0.22 |
| 14 | 0.009 | 0.46 |
| 15 | 0.001 | >5.0 |
| 16 | 0.008 | >10.0 |
| 17 | 0.052 | 1.8 |
| 18 | 0.016 | 1.5 |
| 19 | 0.27 | >10 |
| 20 | 1.3 | >10 |
| 21 | 0.024 | 0.52 |
| 22 | 0.082 | >10 |
| 23 | 0.06 | 1.4 |
| 24 | 0.004 | 0.34 |
| 25 | 0.008 | 0.13 |
| 26 | 0.018 | 0.091 |
| 27 | <0.10 | NT |
| 28 | <0.01 | NT |
| 29 | 0.20 | NT |
| 30 | 0.22 | NT |
| 31 | 0.010 | NT |
| 32 | 0.002 | 0.014 |
| 33 | 0.020 | NT |
| 34 | 0.005 | 0.005 |
| 35 | 0.002 | 0.004 |
| 36 | 0.002 | 0.002 |
| 37 | 0.001 | 0.003 |
| 38 | 0.004 | NT |
| 39 | 0.030 | 0.16 |
| 40 | 0.60 | 1.5 |
| 41 | 1.5 | NT |
| 42 | 0.027 | 0.14 |
| 43 | 2.0 | NT |
| 44 | NT | 1.0 |
| 45 | <10 | NT |
| 46 | <10 | NT |
| 47 | <10 | NT |
| 48 | <10 | NT |
| 49 | 0.025 | 0.6 |
| 50 | 0.007 | 0.025 |
| 51 | 0.010 | 0.075 |
| 52 | 0.001 | 0.010 |
| 53 | 0.065 | 0.75 |
| 54 | 0.18 | 1.2 |
| 55 | 0.12 | 2.0 |
| 56 | <0.10 | NT |
| 57 | <0.10 | NT |
| 58 | 0.001 | 0.008 |
| 59 | 0.040 | 1.2 |
| 60 | 0.001 | 0.37 |
| 61 | 0.007 | 0.38 |
| 62 | 0.001 | 0.008 |
| 63 | 0.002 | 0.048 |
| 64 | 3.0 | NT |
| 65 | >2.0 | NT |
| 66 | 0.35 | NT |
| 67 | 1.0 | NT |
| 68 | 0.12 | NT |
| 69 | 0.13 | NT |
| 70 | 0.17 | NT |
| 71 | 0.04 | NT |
| 72 | 0.006 | >4.0 |
| 73 | <0.010 | >3.0 |
| 74 | 0.058 | >5.0 |
| 75 | 0.003 | 3.3 |
| 76 | 0.30 | >4.0 |
| 77 | 0.070 | >10 |
| 78 | 0.002 | >10 |
| 79 | 0.001 | >10 |
| 80 | 0.14 | >10 |
| 81 | <0.010 | >10 |
| 82 | 0.004 | >10 |
| 83 | 0.030 | >10 |
| 84 | 0.035 | >10 |
| 85 | 0.100 | >10 |
| 86 | 0.022 | >10 |
| 87 | 0.22 | 0.070 |
| 88 | 0.042 | >10 |
| 89 | NT | NT |
| 90 | NT | NT |
| 91 | 0.14 | >10 |
| 92 | 0.56 | >4.0 |
| 93 | 0.100 | >1.0 |
| 94 | 0.076 | 1.0 |
| 95 | 0.029 | 0.253 |
| 96 | 0.018 | 1.4 |
| 97 | 0.009 | >10 |
| 98 | 0.006 | >10 |
| 99 | 0.082 | 5.0 |
| 100 | 0.008 | >10 |
| 101 | 3.0 | >10 |
| 102 | >1.0 | NT |
| 103 | 0.004 | 6.0 |
| 104 | 0.001 | 8.8 |
| 105 | 0.109 | 1.6 |
| 106 | 0.040 | >1.0 |
| 107 | 0.078 | >10 |
| 108 | 0.013 | >10 |
| 109 | >1.0 | NT |
| 110 | >1.0 | NT |
| 111 | >1.0 | NT |
| 112 | 0.017 | >10 |
| 113 | 0.025 | 0.190 |
| 114 | 0.003 | >10 |
| 115 | 0.010 | >10 |
| 116 | <0.10 | NT |
| 117 | 0.038 | >10 |
| 118 | 0.262 | >10 |
| 119 | 0.400 | >10 |
| 120 | 0.003 | 0.50 |
| 121 | >1.0 | NT |
| 122 | 3.5 | 5 |
| 123 | 3.6 | 3.2 |
| 124 | 0.015 | 0.237 |
| 125 | 0.010 | 0.095 |
| 126 | 0.006 | 0.008 |
| 127 | 0.008 | 0.025 |
| 128 | 0.035 | 0.030 |
| 129 | 0.12 | 0.32 |
| 130 | 0.006 | NT |
| 131 | 0.053 | 0.040 |
| 132 | 0.23 | 1.4 |
| 133 | 0.012 | 1.4 |
| 134 | 0.005 | >10 |

TABLE 2-continued

IC$_{50}$ Bioactivity of Exemplary Compounds of the Invention with Respect to OX$_1$ and OX$_2$

| Compound | OX$_1$ (μM) | OX$_2$ (μM) |
| --- | --- | --- |
| 135 | NT | NT |
| 136 | <1.0 | NT |
| 137 | 0.003 | 0.10 |
| 138 | 0.008 | 0.040 |
| 139 | 0.003 | 0.017 |
| 140 | <0.1 | NT |
| 141 | 0.002 | NT |

NT = not tested

TABLE 2A

Bioactivity with Respect to OX$_1$ and OX$_2$

| Compound | OX$_1$ (μM) | OX$_2$ (μM) |
| --- | --- | --- |
| A1 | 0.002 | 4.0 |
| A2 | 0.061 | >4.0 |
| A3 | 0.006 | >4.0 |
| A4 | 0.025 | >4.0 |
| A5 | 0.006 | 3.5 |
| A6 | 0.013 | >4.0 |
| A7 | NT | NT |
| A8 | 0.058 | >4.0 |
| A9 | 0.009 | 3.7 |
| A10 | 0.081 | >4.0 |
| A11 | 0.003 | 0.045 |
| A12 | 0.020 | 0.8 |
| A13 | 0.003 | >4.0 |
| A14 | 0.010 | 0.62 |
| A15 | NT | NT |
| A16 | 0.26 | >5.0 |
| A17 | 0.020 | >4.0 |
| A18 | 0.007 | >4.0 |
| A19 | 0.004 | 0.23 |
| A20 | 0.037 | >4.0 |
| A21 | 0.013 | >4.0 |
| A22 | NT | NT |
| A23 | >1.0 | NT |
| A24 | 0.011 | 0.41 |
| A25 | 0.005 | >4.0 |
| A26 | NT | NT |
| A27 | NT | NT |
| A28 | NT | NT |
| A29 | 0.087 | >5.0 |
| A30 | NT | NT |
| A31 | NT | NT |
| A32 | 0.009 | 0.42 |
| A33 | NT | NT |
| A34 | NT | NT |
| A35 | NT | NT |
| A36 | NT | NT |
| A37 | 0.004 | NT |
| A38 | 0.100 | >5.0 |
| A39 | NT | NT |
| A40 | NT | NT |
| A41 | 0.004 | >4.0 |
| A42 | >1.0 | NT |
| A43 | 0.67 | >4.0 |
| A44 | 0.011 | >5.0 |
| A45 | >1.0 | NT |
| A46 | 0.005 | >5.0 |
| A47 | 0.15 | >5.0 |
| A48 | 0.025 | >5.0 |
| A49 | 0.50 | >5.0 |
| A50 | 0.23 | >5.0 |
| A51 | >1.0 | NT |
| A52 | NT | NT |
| A53 | 0.67 | >5.0 |
| A54 | NT | NT |
| A55 | NT | NT |
| A56 | >1.0 | NT |
| A57 | >1.0 | NT |
| A58 | 0.23 | 2.4 |
| A59 | 0.050 | >2.0 |
| A60 | 0.49 | >5.0 |
| A61 | 1.1 | >5.0 |
| A62 | NT | NT |
| A63 | NT | NT |
| A64 | >1.0 | NT |
| A65 | 0.007 | 0.038 |
| A66 | 0.15 | 2.5 |
| A67 | 0.006 | 0.13 |
| A68 | NT | NT |
| A69 | 0.021 | 1.4 |
| A70 | NT | NT |
| A71 | 0.070 | 3.6 |
| A72 | NT | NT |
| A73 | NT | NT |
| A74 | NT | NT |
| A75 | 1.3 | >5.0 |
| A76 | >1.0 | NT |
| A77 | >1.0 | NT |
| A78 | 0.007 | 2.9 |
| A79 | 0.31 | >4.0 |
| A80 | 1.87 | >4.0 |
| A81 | NT | NT |
| A82 | 0.008 | 0.84 |
| A83 | NT | NT |
| A84 | 0.003 | >4.0 |
| A85 | 0.002 | >5.0 |
| A86 | NT | NT |
| A87 | 0.22 | >4.0 |
| A88 | 0.60 | 1.8 |
| A89 | NT | NT |
| A90 | 0.36 | >5.0 |
| A91 | NT | NT |
| A92 | 0.001 | >5.0 |
| A93 | 0.46 | >5.0 |
| A94 | NT | NT |
| A95 | >1.0 | NT |
| A96 | NT | NT |
| A97 | NT | NT |
| A98 | 0.27 | >5.0 |
| A99 | 0.34 | >5.0 |
| A100 | 1.3 | 1.2 |
| A101 | NT | NT |
| A102 | 0.061 | >5.0 |
| A103 | NT | NT |
| A104 | 0.003 | 1.9 |
| A105 | NT | NT |
| A106 | 0.007 | 2.3 |
| A107 | 0.004 | 0.14 |
| A108 | 0.002 | 1.8 |
| A109 | <0.010 | >4.0 |
| A110 | 0.016 | 0.69 |
| A111 | 0.017 | 0.86 |
| A112 | 0.002 | 0.25 |
| A113 | NT | NT |
| A114 | >1.0 | NT |
| A115 | 0.016 | >4.0 |
| A116 | 0.004 | 1.1 |
| A117 | 0.037 | >5.0 |
| A118 | 0.015 | 2.2 |
| A119 | 0.019 | >5.0 |
| A120 | 0.021 | >5.0 |
| A121 | 0.005 | >5.0 |
| A122 | 0.096 | >5.0 |
| A123 | 0.41 | >5.0 |
| A124 | NT | NT |
| A125 | 0.025 | >5.0 |
| A126 | 0.043 | >5.0 |
| A127 | 0.005 | >5.0 |
| A128 | NT | NT |
| A129 | 0.003 | 0.10 |
| A130 | 0.021 | >5.0 |
| A131 | 0.020 | >5.0 |
| A132 | 0.16 | >5.0 |
| A133 | 0.093 | >5.0 |

TABLE 2A-continued

Bioactivity with Respect to OX$_1$ and OX$_2$

| Compound | OX$_1$ (μM) | OX$_2$ (μM) |
|---|---|---|
| A134 | 0.15 | >5.0 |
| A135 | 0.021 | >5.0 |
| A136 | 0.004 | 0.59 |
| A137 | 0.031 | >5.0 |
| A138 | 0.012 | 3.4 |
| A139 | 0.14 | >5.0 |
| A140 | 0.013 | 0.79 |
| A141 | 0.003 | 0.086 |
| A142 | 0.051 | >5.0 |
| A143 | 0.026 | >5.0 |
| A144 | NT | NT |
| A145 | >1.0 | NT |
| A146 | >1.0 | NT |
| A147 | 0.008 | >5.0 |
| A148 | 0.083 | >5.0 |
| A149 | 0.003 | >5.0 |
| A150 | 0.130 | 4.0 |
| A151 | 0.083 | >5.0 |
| A152 | 0.004 | 2.0 |
| A153 | 0.14 | >5.0 |
| A154 | >1.0 | NT |
| A155 | 0.50 | >5.0 |
| A156 | >1.0 | NT |
| A157 | 0.11 | >5.0 |
| A158 | 0.22 | >5.0 |
| A159 | 0.17 | >5.0 |
| A160 | 0.001 | 1.3 |
| A161 | 0.013 | >5.0 |
| A162 | 0.015 | >5.0 |
| A163 | 0.071 | 1.2 |
| A164 | 0.075 | >5.0 |
| A165 | 0.027 | >5.0 |
| A166 | 0.008 | >5.0 |
| A167 | 0.005 | >5.0 |
| A168 | 0.010 | >5.0 |
| A169 | 0.008 | >5.0 |
| A170 | NT | NT |
| A171 | 0.37 | >5.0 |
| A172 | 0.064 | >5.0 |
| A173 | 0.001 | >5.0 |
| A174 | 0.001 | >5.0 |
| A175 | 0.001 | >5.0 |
| A176 | 0.006 | >5.0 |
| A177 | 0.005 | >5.0 |
| A178 | 0.004 | >5.0 |
| A179 | 0.49 | >5.0 |
| A180 | 0.004 | 0.16 |
| A181 | 0.004 | >5.0 |
| A182 | 0.14 | 4.0 |
| A183 | 0.003 | 4.0 |
| A184 | 0.005 | 2.5 |
| A185 | 0.046 | >5.0 |
| A186 | 0.005 | >5.0 |
| A187 | 0.20 | >5.0 |
| A188 | 0.001 | 2.3 |
| A189 | 0.12 | >5.0 |
| A190 | 2.0 | >5.0 |
| A191 | 0.043 | >5.0 |
| A192 | NT | NT |
| A193 | 0.10 | >5.0 |
| A194 | 0.006 | >5.0 |
| A195 | 0.004 | 0.389 |
| A196 | 0.017 | >5.0 |
| A197 | 0.007 | >5.0 |
| A198 | 0.005 | >5.0 |
| A199 | 0.015 | 2.6 |
| A200 | 0.054 | >5.0 |
| A201 | 0.004 | 2.8 |
| A202 | 0.018 | >5.0 |
| A203 | 0.021 | >5.0 |
| A204 | 0.003 | 0.26 |
| A205 | 0.011 | 0.35 |
| A206 | 0.006 | 0.14 |
| A207 | 0.011 | >5.0 |
| A208 | 0.20 | >5.0 |
| A209 | 0.045 | >5.0 |
| A210 | 0.14 | >5.0 |
| A211 | 0.14 | >5.0 |
| A212 | 0.005 | 3.3 |
| A213 | NT | NT |
| A214 | NT | NT |
| A215 | 0.010 | 1.3 |
| A216 | 0.005 | 2.0 |
| A217 | 0.15 | >5.0 |
| A218 | 0.13 | >5.0 |
| A219 | 2.6 | >5.0 |
| A220 | 0.011 | 2.5 |
| A221 | 0.032 | >5.0 |
| A222 | 0.082 | >5.0 |
| A223 | 0.037 | >5.0 |
| A224 | 0.013 | >5.0 |
| A225 | 0.34 | >5.0 |
| A226 | 0.011 | >5.0 |
| A227 | 0.002 | >5.0 |
| A228 | 0.001 | >5.0 |
| A229 | 0.004 | >5.0 |
| A230 | 0.005 | >5.0 |
| A231 | 0.017 | >5.0 |
| A232 | 0.008 | >5.0 |
| A233 | 0.005 | 0.81 |
| A234 | NT | NT |
| A235 | NT | NT |
| A236 | NT | NT |
| A237 | NT | NT |
| A239 | 0.083 | >5.0 |
| A240 | 0.003 | >5.0 |
| A241 | 0.009 | >5.0 |
| A242 | 0.024 | >5.0 |
| A243 | 0.075 | >5.0 |
| A244 | 1.3 | >5.0 |
| A246 | >0.10 | >5.0 |
| A247 | >0.10 | >5.0 |
| A248 | 0.020 | >5.0 |
| A249 | 0.018 | >5.0 |
| A250 | 0.047 | >5.0 |
| A251 | 0.058 | >5.0 |
| A254 | 0.037 | >5.0 |
| A255 | 0.041 | >5.0 |
| A256 | 0.005 | >5.0 |
| A257 | 0.004 | >5.0 |
| A258 | 0.004 | >5.0 |
| A259 | 0.009 | >5.0 |
| A260 | 0.085 | >5.0 |
| A261 | 0.005 | >5.0 |
| A266 | 0.004 | 1.1 |
| A267 | 0.006 | 2.6 |
| A268 | 0.003 | 1.7 |
| A271 | 0.086 | 9.4 |
| A272 | 0.014 | 8.5 |
| A273 | 0.006 | 4.4 |
| A298 | 0.005 | 0.483 |
| A299 | 0.003 | 2.35 |
| A306 | NT | NT |
| A307 | 0.25 | >5.0 |
| A310 | 0.003 | >5.0 |
| A311 | 0.027 | 3.1 |
| A312 | 0.144 | >5.0 |
| A313 | 0.005 | 3.6 |
| A314 | 0.002 | 2.7 |
| A315 | 2.5 | >5.0 |
| A316 | 0.004 | >5.0 |
| A317 | 0.001 | >1.0 |
| A318 | 0.007 | 2.5 |
| A319 | 0.006 | 4.5 |
| A322 | 0.011 | >5.0 |
| A323 | 0.010 | >5.0 |
| A336 | 0.010 | >5.0 |
| A337 | 0.009 | >5.0 |
| A338 | <0.010 | >5.0 |
| A339 | 0.005 | >5.0 |

NT = not tested

Cytochrome P450 Inhibition Assay.

Compounds were tested for the potential to induce drug-drug interactions by inhibition of the cytochrome P450 3A4 isoform. The assay evaluated the metabolism of a specific marker substrate (CYP3A4, midazolam hydroxylation to 1'-hydroxymidazolam) in the presence or absence of 10 μM test compound. The concentration of the marker substrate was approximately its $K_m$ (Dixit, Hariparsad et al. 2007). A specific inhibitor for the isoform was included in each run to validate the system. An appropriate positive control inhibitor was used. Mechanism-based inhibition was investigated where warranted using a classical method. To evaluate time-dependent inhibition, parallel samples may have been included where 10 μM probe compound was pre-incubated with human liver microsomes and NADPH for 30 minutes prior to the addition of the P450 substrate. The percent inhibition of the pre-incubated and non-pre-incubated samples were compared as a preliminary evaluation of time-dependent inhibition.

TABLE 3

Percent Inhibition of CYP3A4

| Compound | % CYP3A4 Inhibition |
|---|---|
| Ketoconazole | 98 |
| A1 | 98 |
| A2 | 93 |
| A3 | 98 |
| A4 | 96 |
| A5 | 98 |
| A6 | 85 |
| A7 | 93 |
| A8 | 99 |
| A9 | 89 |
| A10 | 98 |
| A11 | 78 |
| A12 | 98 |
| A13 | 83 |
| A14 | 80 |
| A15 | 78 |
| A16 | 96 |
| A17 | 95 |
| A18 | 95 |
| A19 | 96 |
| A20 | 83 |
| A21 | 89 |
| A22 | 72 |
| A23 | 75 |
| A24 | 97 |
| A25 | 99 |
| A26 | 99 |
| A27 | 95 |
| A28 | 95 |
| A29 | 91 |
| A30 | 97 |
| A31 | 98 |
| A32 | 92 |
| A33 | 98 |
| A34 | 99 |
| A35 | 92 |
| A36 | 97 |
| A37 | 96 |
| A38 | 96 |
| A39 | 96 |
| A40 | 96 |
| A41 | 52 |
| A43 | 55 |
| A46 | 53 |
| A47 | 56 |
| A48 | 74 |
| A59 | 87 |
| A60 | 69 |
| A73 | 76 |
| A74 | 74 |
| A78 | 84 |
| A79 | 5 |
| A80 | 28 |
| A81 | 67 |
| A82 | 68 |
| A83 | 97 |
| A84 | 50 |
| A85 | 9 |
| A86 | 95 |
| A87 | 73 |
| A88 | 75 |
| A89 | 92 |
| A90 | 33 |
| A91 | 58 |
| A92 | 91 |
| A93 | 96 |
| A94 | 99 |
| A95 | 88 |
| A96 | 92 |
| A97 | 98 |
| A98 | 48 |
| A99 | 52 |
| A100 | 85 |
| A101 | 83 |
| A102 | 48 |
| A103 | 95 |
| A104 | 91 |
| A105 | 96 |
| A106 | 54 |
| A107 | 91 |
| A108 | 88 |
| A110 | 95 |
| A111 | 96 |
| A112 | 84 |
| A113 | 98 |
| A115 | 90 |
| A116 | 75 |
| A117 | 92 |
| A118 | 95 |
| A119 | 59 |
| A120 | 90 |
| A121 | 84 |
| A122 | 72 |
| A123 | 97 |
| A124 | 55 |
| A125 | 75 |
| A126 | 56 |
| A127 | 57 |
| A128 | 88 |
| A129 | 64 |
| A130 | 86 |
| A131 | 84 |
| A132 | 81 |
| A133 | 89 |
| A134 | 50 |
| A135 | 80 |
| A136 | 91 |
| A137 | 47 |
| A138 | 75 |
| A139 | 41 |
| A140 | 64 |
| A141 | 72 |
| A142 | 74 |
| A143 | 75 |
| A144 | 87 |
| A145 | 48 |
| A146 | 29 |
| A147 | 66 |
| A148 | 81 |
| A149 | 60 |
| A150 | 74 |
| A151 | 86 |
| A152 | 86 |
| A153 | 66 |
| A154 | 43 |

TABLE 3-continued

Percent Inhibition of CYP3A4

| Compound | % CYP3A4 Inhibition |
|---|---|
| A155 | 72 |
| A156 | 53 |
| A157 | 77 |
| A158 | 83 |
| A159 | 88 |
| A160 | 59 |
| A161 | 68 |
| A162 | 76 |
| A163 | 90 |
| A164 | 37 |
| A165 | 42 |
| A166 | 44 |
| A167 | 45 |
| A168 | 59 |
| A169 | 60 |
| A170 | 66 |
| A171 | 36 |
| A172 | 76 |
| A173 | 81 |
| A174 | 51 |
| A175 | 33 |
| A176 | 37 |
| A177 | 39 |
| A178 | 64 |
| A179 | 67 |
| A181 | 76 |
| A182 | 65 |
| A183 | 49 |
| A184 | 34 |
| A185 | 33 |
| A186 | 53 |
| A187 | 40 |
| A188 | 59 |
| A189 | 37 |
| A190 | 24 |
| A191 | 44 |
| A192 | 51 |
| A193 | 45 |
| A194 | 79 |
| A195 | 57 |
| A196 | 50 |
| A197 | 83 |
| A198 | 51 |
| A199 | 62 |
| A200 | 73 |
| A201 | 38 |
| A202 | 44 |
| A203 | 70 |
| A204 | 60 |
| A205 | 72 |
| A206 | 58 |
| A207 | 44 |
| A208 | 59 |
| A209 | 69 |
| A210 | 76 |
| A211 | 60 |
| A212 | 49 |
| A213 | 19 |
| A214 | 69 |
| A215 | 67 |
| A216 | 67 |
| A217 | NT |
| A218 | 75 |
| A219 | 84 |
| A220 | 68 |
| A221 | 53 |
| A222 | NT |
| A223 | 93 |
| A224 | NT |
| A225 | NT |
| A226 | 60 |
| A227 | 59 |
| A228 | 72 |
| A229 | 72 |
| A230 | 50 |
| A231 | 54 |
| A232 | 65 |
| A233 | 72 |
| A234 | NT |
| A235 | NT |
| A236 | NT |
| A237 | NT |
| A238 | NT |
| A239 | 50 |
| A240 | 42 |
| A241 | 62 |
| A242 | 87 |
| A243 | 68 |
| A244 | 70 |
| A245 | NT |
| A246 | 69 |
| A247 | 65 |
| A248 | 67 |
| A249 | 83 |
| A250 | NT |
| A251 | NT |
| A252 | NT |
| A253 | NT |
| A254 | 63 |
| A255 | 41 |
| A256 | 52 |
| A257 | 69 |
| A258 | 69 |
| A259 | 37 |
| A260 | 53 |
| A261 | 77 |
| A264 | NT |
| A265 | NT |
| A266 | 76 |
| A267 | 65 |
| A268 | 60 |
| A271 | NT |
| A298 | 75 |
| A299 | 51 |
| A306 | NT |
| A307 | 46 |
| A310 | 75 |
| A311 | 57 |
| A312 | 40 |
| A313 | 60 |
| A314 | 76 |
| A315 | NT |
| A316 | 63 |
| A317 | 46 |
| A318 | 79 |
| A319 | 53 |
| A322 | 40 |
| A323 | 39 |

NT = not tested

Compounds as shown in Table 1A (e.g., A201, A207, A207, and A259) show improved selectivity for OX$_1$ over OX$_2$ as well as reduced inhibition of CYP3A4 relative to Examples 112 and 114, as shown in Table 4. The difference in CYP3A4 activity is particularly improved with regards to time-dependence inhibition.

TABLE 4

| Example | OX$_1$ IC$_{50}$ (µM) | OX$_2$ IC$_{50}$ (µM) | CYP3A4 % inh (10 µM, 5 min) | CYP3A4 % inh (10 µM, 30 min) |
|---|---|---|---|---|
| 112 | 0.042 | 2.9 | 72 | 94 |
| A201 | 0.004 | 2.8 | 38 | 59 |
| A227 | 0.002 | >5.0 | 59 | 58 |
| 114 | 0.005 | 0.27 | 78 | 93 |

TABLE 4-continued

| Example | OX$_1$ IC$_{50}$ (μM) | OX$_2$ IC$_{50}$ (μM) | CYP3A4 % inh (10 μM, 5 min) | CYP3A4 % inh (10 μM, 30 min) |
|---|---|---|---|---|
| A207 | 0.011 | >5.0 | 44 | 52 |
| A259 | 0.009 | >5.0 | 37 | 41 |

The 3-methylpiperidine substituent has a marked effect on OX$_1$/OX$_2$ selectivity. As shown in Table 5, reference compound SR-12376, which lacks any 3-methyl substituent on the central piperidine ring, shows approximately five-fold selectivity for OX1. Reference compound SR-12365, which includes a dimethyl substituent at that position, has a selectivity ratio of approximately 20. Comparative Example A311 with a "alpha" methyl group, has a selectivity ratio of approximately 110, while Example 75, with an "beta" methyl group has a selectivity ratio of over 1000.

TABLE 5

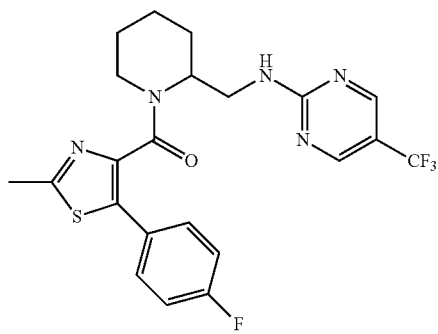 [SMILES: Cc1nc(C(=O)N2CCCCC2CNc2ncc(C(F)(F)F)cn2)c(-c2ccc(F)cc2)s1]

SR-12376
(reference compound)
OX$_1$ IC$_{50}$: 13 nM
OX$_2$ IC$_{50}$: 70 nM

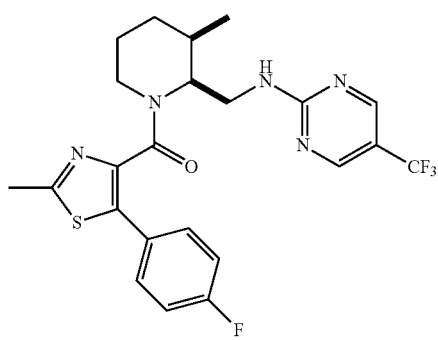 [SMILES: Cc1nc(C(=O)N2CCC[C@@H](C)[C@H]2CNc2ncc(C(F)(F)F)cn2)c(-c2ccc(F)cc2)s1]

Ex. 75
OX$_1$ IC$_{50}$: 3 nM
OX$_2$ IC$_{50}$: 3279 nM

TABLE 5-continued

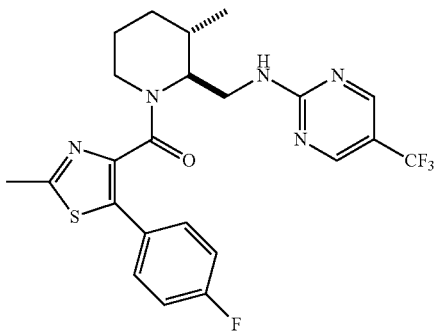 [SMILES: Cc1nc(C(=O)N2CCC[C@H](C)[C@H]2CNc2ncc(C(F)(F)F)cn2)c(-c2ccc(F)cc2)s1]

Ex. A311
OX$_1$ IC$_{50}$: 27 nM
OX$_2$ IC$_{50}$: 3092 nM

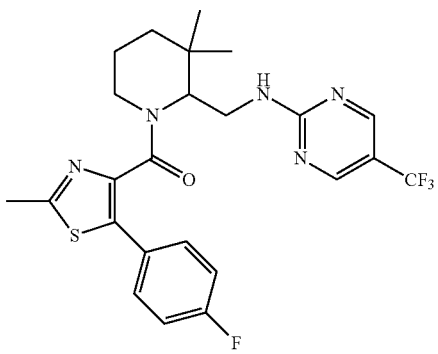 [SMILES: Cc1nc(C(=O)N2CCCC(C)(C)C2CNc2ncc(C(F)(F)F)cn2)c(-c2ccc(F)cc2)s1]

SR-12364
(reference compound)
OX$_1$ IC$_{50}$: 137 nM
OX$_2$ IC$_{50}$: 2637 nM The (−)-enantiomer retains most to all of the potency against OX1 as shown in Table 6. Individual enantiomers of both Example 11 and Example 103 were prepared. In both cases, the (−)-enantiomer is the more potent and selective of the two.

TABLE 6

| Example | Enantiomer | OX$_1$ IC$_{50}$ (μM) | OX$_2$ IC$_{50}$ (μM) |
|---|---|---|---|
| 11 | (+/−) | 0.008 | 4.9 |
| A85 | (−) | 0.002 | >5.0 |
| A43 | (+) | 0.67 | 4.0 |
| 103 | (+/−) | 0.004 | 6.0 |
| A1 | (−) | 0.002 | 4.0 |
| A315 | (+) | 2.5 | >5.0 |

Compounds of the invention are found to have bioactivity as modulators, e.g, as antagonists of both OX$_1$ and OX$_2$. Certain compounds, e.g., compound A1, are seen to be selective inhibitors of the OX$_1$ receptor (~2000-fold selectivity). In some embodiments, compounds of the generic formulae presented herein have greater than 50, greater than 100, greater than 200, greater than 300, greater than 500, greater than 1000, or greater than 2000-fold selectivity for OX$_1$ over OX$_2$ in the cell-based functional assay described above.

Nicotine Self-Administration Assay

Development of Animal Subjects.

To generate Hcrt-R1$^{+/+}$ and Hcrt-R$^{−/1}$ mice, breeding pairs of male and female Hcrt-R1$^{+/−}$ mice that were backcrossed >10 generations on a C57BL/6 background were obtained from Jackson Laboratory (Bar Harbor, Me.). For all experiments, mice weighing 25-35 g were housed in groups of 2-3 per cage, in a temperature-controlled vivarium under a reversed 12-h light/dark cycle (lights off at 8 am). Food and water were provided ad libitum until behavioral training commenced. During training, mice were food-restricted to maintain ~85-90% of their free-feeding body weight. Behavioral testing occurred during the dark portion of the light/dark cycle between the hours of 9 am-1 pm, during the early portion of the dark phase of the cycle. All procedures were conducted in strict adherence with the National Institutes of Health Guide for the Care and Use of Laboratory Animals and were approved by the Institutional Animal Care and Use Committee of The Scripps Research Institute.

Assay Protocol.

Mice were anesthetized by inhalation of 1-3% isoflurane in oxygen and silastic catheters were inserted into the jugular veins. Briefly, the catheters consisted of a 6 cm length of silastic tubing fitted to a guide cannula (Plastics One, Wallingford, Conn.), bent at a curved right angle and encased in dental acrylic. The catheter tubing was passed subcutaneously from each animal's back to the right jugular vein, and 1 cm length of the catheter tip was inserted into the vein. After surgery, catheters were flushed daily with 0.1 ml of a heparinized (30 USP units/ml) sterile saline solution. Following 7 d of surgical recovery, mice were mildly food restricted to 85-90% of their free-feeding body weight and trained to press a lever in an operant chamber (Med Associates, St. Albans, Vt.) for food pellets (20 mg; TestDiet, Richmond, Ind.) under a fixed-ratio 5, time out 20-s (FR5TO20 s) schedule of reinforcement prior to catheter implantation. Once stable responding was achieved (>25 pellets per session), mice were permitted to acquire IV nicotine self-administration by autoshaping during 1-h daily sessions, 7 days per week. Nicotine was delivered through the tubing into the IV catheter by a Razel syringe pump (Med Associates). Each nicotine self-administration session was performed using two retractable levers (1 active; 1 inactive). Completion of the response criteria on the active lever resulted in the delivery of an IV nicotine infusion (0.03 mg/kg/infusion). After 1 week, the nicotine dose was increased to 0.1 mg/kg/inf for the remainder of the experiment, including subsequent training and test sessions. Delivery of all nicotine infusions coincided with the initiation of a 20-s time-out (TO) period, signaled by a light cue located above the lever. During the TO period, responding on the lever was recorded but without scheduled consequence. Catheter integrity was tested with the ultra short-acting barbiturate Brevital (methohexital sodium; Eli Lilly) at the end of the experiment.

Generation of Lentivirus and Titer Estimation.

For Hcrt-R1 re-expression studies, the human Hcrt-R1 gene was cloned into the pCDF1 lentivirus expression vector containing copGFP (GFP cloned from copepod *Pontellina plumata*) from Systems Biosciences. To generate lentivirus supernatant, HEK293FT packaging cells ($3.75 \times 10^6$ 293TN cells per 10-cm plate) were transfected with the vectors, along with the pPACLF1™ Lentiviral Packaging Kit using lipofectamine reagent and plus reagent (Invitrogen) according to the manufacturer's instructions. Medium containing virus particles (~10 ml) was harvested 48-60 h after transfection by centrifugation at 76,755 g at room temperature (22° C.) for 5 min to pellet cell debris and was filtered through 0.45 mm PVDF (polyvinylidene difluoride) filters (Millex-HV). To concentrate the viral supernatant for intrastriatal administration, supernatants were centrifuged at 32,000 g for 90 min at 4° C., and the precipitate re-suspended in 100 µl cold PBS. Supernatants were aliquoted into 100 µl volumes and stored at −80° C. until use. Viral supernatant titres were determined using the Lentivector Rapid Titer Kit from System Biosciences, according to the manufacturer's instructions. The number of infectious units per ml of supernatant (IFU ml$^{-1}$) was calculated as follows: multiplicity of infection (MOI) of the sample× the number of cells in the well upon infection×1,000/µl of viral supernatant used.

Results.

Results of the assay are shown in FIG. 1. As shown in FIG. 1A, knock-out (KO) and wild-type (WT) mice showed very stable acquisition of learning to lever press for food pellets, demonstrating that genetic deletion of the Hcrt-1R had no effect on learning the task. As shown in FIG. 1B, systemic administration (i.p.) of Example 1130 min prior to the self administration (SA) session had no effect on food SA in KO and WT mice. As shown in FIG. 1C, WT (n=12) and KO (n=10) were evenly divided and were given a virus to site-specifically restore Hcrt-1R expression or an empty vector (control) in the dorsal thalamus three weeks prior to the initiation of the experiment. There were no effects on food SA in any group. As shown in FIG. 1D, lentiviral restoration of Hcrt-1R expression in the dorsal thalamus of KO mice restored nicotine SA. Mice that received systemic pretreatment of Example 11 (7.5 and 15.0 mg/kg) exhibited decreased nicotine SA in the WT and virally-rescued mice, with no significant reduction in KO mice that received the control virus.

Comparison of Results to Orexin-2 Selective Agent.

Figure 2:
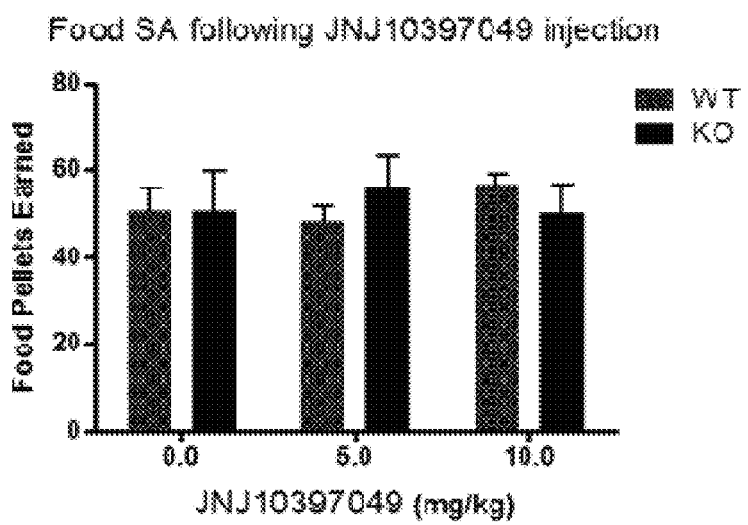
FIG. 2 shows the results of the nicotine self-administration assay for an orexin-2 selective antagonist, JNJ10397049 at 5 mg/kg and 10 mg/kg.
Figure 2:
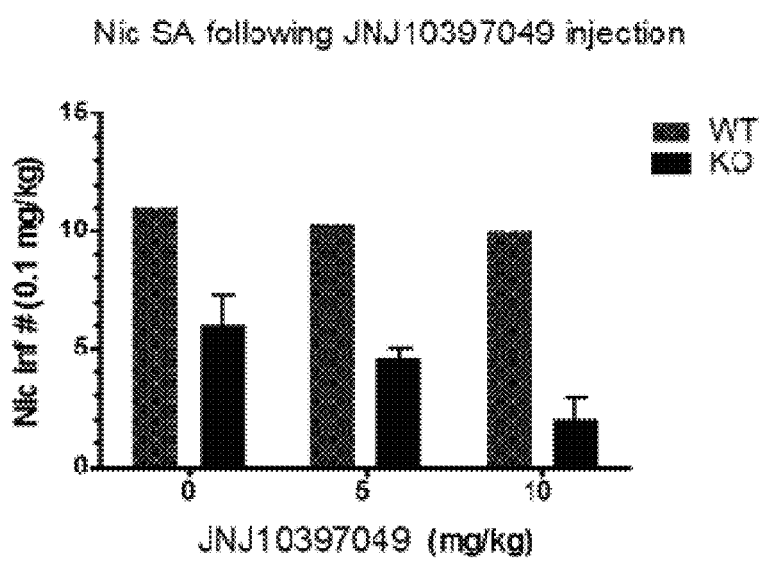

The assay was repeated with JNJ10397049, a commercially available orexin-2 selective receptor antagonist. Results of this assay are shown in FIG. 2. FIG. 2A shows that systemic administration of JNJ 10397049 30 min prior to the experimental session had no effect on SA of food pellets in both WT (n=6) and KO (n=6) mice. FIG. 2B shows that JNJ 10397049 had no effect on nicotine SA at any of the doses tested (0, 5 and 10 mg/kg) in the WT mice. JNJ 10397049 induced a marginal decrease in nicotine SA in KO mice.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of Formula (VI):

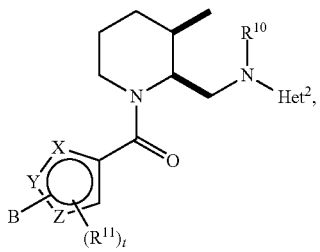

(VI)

wherein $R^{10}$ is H or methyl;

$Het^2$ is selected from the group consisting of pyrrolyl, pyrazolyl, imidazolyl, oxazolyl, isoxazolyl, thiazolyl, isothiazolyl, oxadiazolyl, thiadiazolyl, triazolyl, tetrazolyl, pyridyl, pyrimidinyl, pyridazinyl, and pyrazinyl, each optionally fused to phenyl or a monocyclic heteroaryl, and each optionally substituted with one or two substituents $R_x$; wherein each $R_x$ is independently selected from the group consisting of —F, —Cl, —Br, methyl, methoxy, —CN, —CF$_3$, cyclopropyl, and cyano-cyclopropyl;

X, Y, and Z are defined as in (a), (b), or (c), wherein:

(a) X is N, Y is CH, and Z is S;

(b) X is N, Y is CHCH, and Z is CH; and (c) X is CH, Y is CHCH, and Z is CH;

each $R^{11}$ is independently selected from the group consisting of methyl, cyano, chloro, fluoro, and methoxy; t is 0, 1, or 2;

and B is selected from the group consisting of phenyl, pyrrolyl, pyrazolyl, imidazolyl, oxazolyl, isoxazolyl, thiazolyl, isothiazolyl, oxadiazolyl, thiadiazolyl, triazolyl, tetrazolyl, pyridyl, pyrimidinyl, pyridazinyl, and pyrazinyl, each optionally substituted with one or two substituents $R_y$; wherein $R_y$ is independently selected from the group consisting of methyl, ethyl, propyl, isopropyl, butyl, isobutyl, methoxy, ethoxy, isopropoxy, —F, —Cl, —Br, —CN, and —CF$_3$, or a pharmaceutically acceptable salt thereof;

provided that the compound is not:

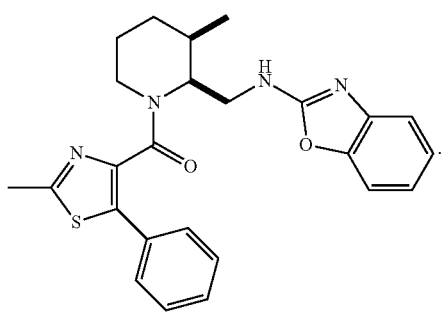 [SMILES: Cc1nc(C(=O)N2CCC[C@@H](C)[C@H]2CNc2nc3ccccc3o2)c(-c2ccccc2)s1]

2. The compound of claim 1, wherein the compound is a compound of Formula (VIA):

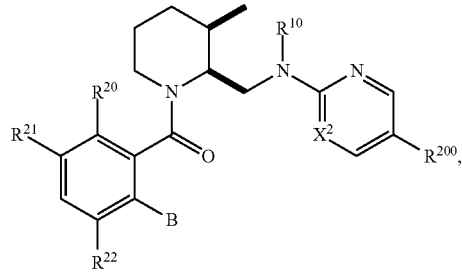

wherein

B is selected from the group consisting of phenyl, pyridyl, and pyrimidinyl, each unsubstituted or substituted with one or two substituents selected from the group consisting of methyl, cyano, chloro, fluoro, and methoxy;

$X^2$ is CH or N;

$R^{10}$ is H or methyl;

$R^{200}$ is H, —CF$_3$, or chloro; and (a) one of $R^{20}$ and $R^{22}$ is methyl, chloro, or fluoro, the other of $R^{20}$ and $R^{22}$ is H, and $R^{21}$ is H; or (b) $R^{21}$ is H, chloro, or fluoro, and $R^{20}$ and $R^{22}$ are both H;

or a pharmaceutically acceptable salt thereof.

3. The compound of claim 1, wherein $Het^2$ is selected from the group consisting of pyrrolyl, pyrazolyl, imidazolyl, isoxazolyl, thiazolyl, isothiazolyl, oxadiazolyl, thiadiazolyl, triazolyl, tetrazolyl, pyridyl, pyrimidinyl, pyridazinyl, and pyrazinyl, each optionally fused to phenyl or a monocyclic heteroaryl, and each optionally substituted with one or two substituents $R_x$, wherein each $R_x$ is independently selected from the group consisting of —F, —Cl, —Br, methyl, methoxy, —CN, —CF$_3$, cyclopropyl, and cyano-cyclopropyl.

4. The compound of claim 1, wherein $Het^2$ is selected from the group consisting of thiazolyl, thiadiazolyl, pyridyl, pyrimidinyl, pyridazinyl, benzoxazolyl, quinazolinyl, and triazolo-pyrimidinyl, each optionally substituted with one or two substituents $R_x$, wherein each $R_x$ is independently selected from the group consisting of —F, —Cl, —Br, methyl, methoxy, —CN, —CF$_3$, cyclopropyl, and cyano-cyclopropyl.

5. The compound of claim 1, wherein X is N, Y is CHCH, and Z is CH; or X is CH, Y is CHCH, and Z is CH.

6. The compound of claim 1, wherein ring B is selected from the group consisting of pyrrolyl, pyrazolyl, imidazolyl, oxazolyl, isoxazolyl, thiazolyl, isothiazolyl, oxadiazolyl, thiadiazolyl, triazolyl, tetrazolyl, pyridyl, pyrimidinyl, pyridazinyl, and pyrazinyl, each optionally substituted with one or two substituents $R_y$, wherein each $R_y$ is independently selected from the group consisting of methyl, ethyl, propyl, isopropyl, butyl, isobutyl, methoxy, ethoxy, isopropoxy, —F, —Cl, —Br, —CN, and —CF$_3$.

7. The compound of claim 1, wherein ring B is pyrazolyl or triazolyl.

8. The compound of claim 1, wherein ring B is pyridyl or pyrimidinyl.

9. The compound of claim 1, wherein each $R^{11}$ is independently selected from the group consisting of methyl, chloro, fluoro, and —CN.

10. The compound of claim 1, wherein the group (XX):

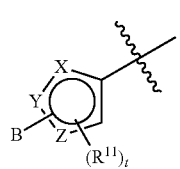
(XX)

is a group of Formula (Xa), or is a group of Formula (Xb), or is a group of Formula (Xc):

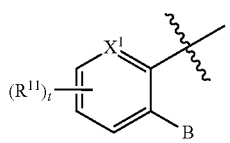
(Xa)

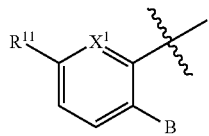
(Xb)

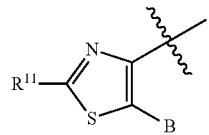
(Xc)

wherein $X^1$ is CH or N; and
B is unsubstituted or is substituted as described in claim 1.

11. The compound of claim 1, wherein the group (XX)

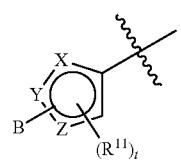
(XX)

is a group of Formula (Xd):

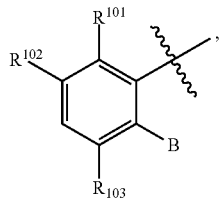
(Xd)

where (a) one of $R^{101}$ and $R^{103}$ is methyl, chloro, or fluoro, the other of $R^{101}$ and $R^{103}$ is H, and $R^{102}$ is H; or (b) $R^{102}$ is H, chloro, or fluoro, and $R^{101}$ and $R^{103}$ are both H.

12. A pharmaceutical composition comprising a compound of claim 1 or a pharmaceutically acceptable salt thereof, and a pharmaceutically acceptable excipient.

* * * * *